US012655127B2

(12) United States Patent
Xie et al.

(10) Patent No.: US 12,655,127 B2
(45) Date of Patent: Jun. 16, 2026

(54) FUSED RING COMPOUND AS WEE-1 INHIBITOR

(71) Applicant: WIGEN BIOMEDICINE TECHNOLOGY (SHANGHAI) CO., LTD., Shanghai (CN)

(72) Inventors: Yuli Xie, Shanghai (CN); Yingming Wu, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanhai (CN)

( * ) Notice: Subject to any disclaimer, the term of this patent is extended or adjusted under 35 U.S.C. 154(b) by 417 days.

(21) Appl. No.: 18/277,987

(22) PCT Filed: Feb. 15, 2022

(86) PCT No.: PCT/CN2022/076366
§ 371 (c)(1),
(2) Date: Aug. 19, 2023

(87) PCT Pub. No.: WO2022/174765
PCT Pub. Date: Aug. 25, 2022

(65) Prior Publication Data

US 2024/0182447 A1 Jun. 6, 2024

(30) Foreign Application Priority Data

Feb. 19, 2021 (CN) ......................... 202110195821.5
Feb. 9, 2022 (CN) ......................... 202210122682.8

(51) Int. Cl.

| | |
|---|---|
| ***C07D 401/14*** | (2006.01) |
| ***A61P 35/00*** | (2006.01) |
| ***C07D 471/04*** | (2006.01) |
| ***C07D 491/044*** | (2006.01) |
| ***C07D 495/04*** | (2006.01) |
| ***C07F 9/6558*** | (2006.01) |
| ***C07F 9/6568*** | (2006.01) |

(52) U.S. Cl.
CPC ............ *C07D 401/14* (2013.01); *A61P 35/00* (2018.01); *C07D 471/04* (2013.01); *C07D 491/044* (2013.01); *C07D 495/04* (2013.01); *C07F 9/65586* (2013.01); *C07F 9/6568* (2013.01)

(58) Field of Classification Search
CPC ........................... C07D 401/14; C07D 471/04; C07D 491/044; C07D 495/04; C07D 401/12; A61P 35/00; C07F 9/65586; C07F 9/6568; A61K 31/519
See application file for complete search history.

(56) References Cited

FOREIGN PATENT DOCUMENTS

| | | | |
|---|---|---|---|
| CN | 101784551 | A | 7/2010 |
| CN | 103703005 | A | 4/2014 |
| CN | 110621316 | A | 12/2019 |
| CN | 112442049 | A | 3/2021 |

OTHER PUBLICATIONS

CAS Registry No. 2055221-10-6 (which entered STN database on Dec. 30, 2016). (Year: 2016).*
Yang, Yueqian et al., "Research Progress in WEE1 Kinase and Its Inhibitor" Progress in Pharmaceutical Sciences, vol. 46, No. 1, pp. 71-80 (Jan. 25, 2022).

* cited by examiner

*Primary Examiner* — Kamal A Saeed
*Assistant Examiner* — Meghan C Heasley
(74) *Attorney, Agent, or Firm* — SZDC Law PC

(57) ABSTRACT

The present invention discloses a fused cyclic compound as a Wee-1 inhibitor. Specifically, the present invention relates to a compound of general formula (1), a method for preparing same, and use of the compound of general formula (1) or an isomer, a crystalline form, a pharmaceutically acceptable salt, a hydrate or a solvate thereof as a Wee-1 inhibitor in the preparation of an anti-tumor drug.

(1)

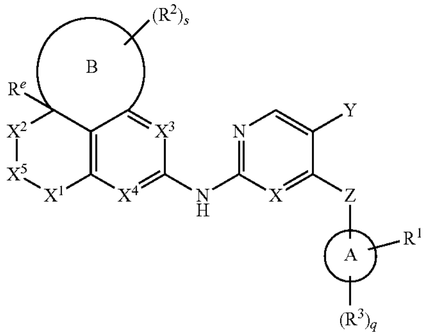

19 Claims, No Drawings

FUSED RING COMPOUND AS WEE-1 INHIBITOR

The present application is the national stage application of PCT/CN2022/076366, filed on Feb. 15, 2022, which claims priority to Chinese Patent Application No. 2021101958215 filed on Feb. 19, 2021 and Chinese Patent Application No. 2022101226828 filed on Feb. 9, 2022, which are incorporated herein by reference in their entirety.

TECHNICAL FIELD

The present invention relates to the field of pharmaceutical chemistry, and particularly to a fused cyclic compound with an inhibitory effect on the Weel kinase, a method for preparing same and use of such compounds in the preparation of anti-tumor drugs.

BACKGROUND

Wee-1 protein kinase is an important negative regulatory protein in cell cycle checkpoints. The cell cycle checkpoints include a G1 checkpoint for the transition from G1 phase (cell resting phase) to S phase (DNA synthesis phase), a G2 checkpoint for the transition from G2 phase (cell division preparation phase) to M phase (cell division phase), and a spindle checkpoint for the transition from metaphase (cell division metaphase) to anaphase (cell division anaphase) of the M phase. The Wee-1 protein kinase plays an important role in the G2 phase checkpoint. Cell entry into M phase depends on CDK1 kinase activity, and Wee-1 inhibits the activity of CDK1 by phosphorylating Tyr 15 of CDK1 protein, preventing cells from entering M phase (cell division phase). In contrast, polo kinase phosphorylates Wee-1 and activates the degradation of Wee-1 protein, promoting the start of M phase. Thus, Wee-1 kinase activity determines the activity of G2 checkpoint and regulates the G2-to-M transition of cells [Cell Cycle, 2013.12(19): p. 3159-3164].

The cell cycle checkpoints are activated primarily following DNA damage and play an important role in the repair of DNA in cells. The normal activation of the cell cycle checkpoints blocks the cell cycle and promotes DNA repair. If the functions of the checkpoints are inhibited, the DNA damage is unable to be repaired, and the cells undergo apoptosis. Compared with normal cells, a variety of tumor cells repair DNA damage and avoid apoptosis mainly depending on the activation of the G2 phase checkpoint due to the impaired function of the important protein p53 protein of the G1 phase checkpoint. Therefore, tumor cells can be selectively killed by inhibiting the G2 phase checkpoint. The important role of Wee-1 kinase activity in the G2 phase checkpoint suggests that Wee-1 kinase determines the repair or death of tumor cells after DNA damage, and the inhibition of Wee-1 activity can promote the start of M phase in unrepaired tumor cells after DNA damage and induce apoptosis [Curr Clin Pharmacol, 2010.5(3): p. 186-191].

Studies have shown that in addition to the role in the G2 checkpoint, Wee-1 is involved in DNA synthesis, DNA homologous repair, post-translational modification of chromosomal histones, and other functions closely related to the development and progression of tumors [J Cell Biol, 2011.194(4): p. 567-579]. Wee-1 expression is greatly increased in many tumors including liver cancer, breast cancer, cervical cancer, melanoma and lung cancer [PLoS One, 2009.4(4): p.e5120; Hepatology, 2003.37(3): p. 534-543; Mol Cancer, 2014.13: p. 72]. The high expression of Wee-1 is in a positive correlation with the progression and poor prognosis of tumors, suggesting that Wee-1 kinase may be involved in the development and progression of tumors. Studies on in vitro cell models and in vivo animal models have shown that inhibiting Wee-1 activity while inducing DNA damage can significantly inhibit the growth of a variety of tumors [Cancer Biol Ther, 2010.9(7): p. 514-522; Mol Cancer Ther, 2009.8(11): p. 2992-3000]. Therefore, the development of specific and highly active small-molecule inhibitors against Wee-1 kinase would be of important clinical value for tumor treatment, especially targeting tumors with impaired G1 checkpoints such as P53 deletion.

SUMMARY

The present invention provides a compound of general formula (1) or an isomer, a crystalline form, a pharmaceutically acceptable salt, a hydrate or a solvate thereof:

(1)

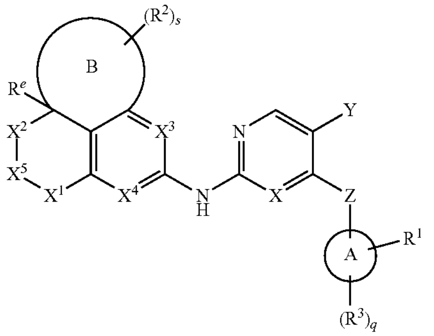

wherein in general formula (1):

X is CH or N;

Y is —H, a halogen, —CN, —$S(O)_2R^6$, —$P(O)(R^7)_2$, —$C(O)NR^8R^9$, (C1-C6) alkyl, (C1-C6) haloalkyl, (C2-C6) alkynyl, (C3-C14) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkynyl, (C3-C14) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_nOR^8$—, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$;

Z is a chemical bond, —$CH_2$—, —O— or —NH—;

ring A is (C6-C14) aryl, (5-14 membered) heteroaryl or (3-14 membered) heterocycloalkyl;

$R^1$ is

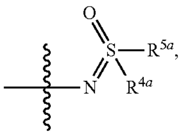
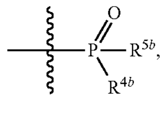

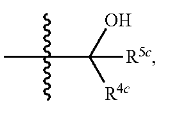
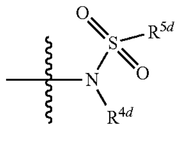
,

-continued

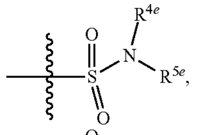

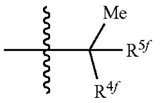

or

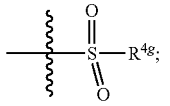

$R^{4a}$ and $R^{5a}$ are each independently (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or $R^{4a}$ and $R^{5a}$, together with the S atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4b}$ and $R^{5b}$ are each independently (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^8S(O)_2R^8$, —$S(O)_pR^8$ and —$S(O)_2NR^8R^9$; or $R^{4b}$ and $R^{5b}$, together with the P atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4c}$ and $R^{5c}$ are each independently —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or $R^{4c}$ and $R^{5c}$, together with the carbon atom to which they are attached, can form (3-7 membered) cycloalkyl, wherein the (3-7 membered) cycloalkyl may be optionally substituted with 1, 2, 3 or 4 of the following groups: —H, halogen, $R^8$, —$OR^8$, —$NR^8R^9$ and —CN;

$R^{4d}$ is —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; and $R^{5d}$ is (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl, or (C3-C6) cycloalkyl may be each independently and optionally substituted with 1, 2, 3 or 4 of the following groups: —H, -D, halogen, $R^1$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or $R^{4d}$ and $R^{5d}$ together with the atoms to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4e}$ and $R^{5e}$ are each independently —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or $R^{4e}$ and $R^{5e}$, together with the N atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4f}$ and $R^{5f}$ are each independently —H, a halogen, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or $R^{4f}$ and $R^{5f}$, together with the carbon atom to which they are attached, can form (3-7 membered) cycloalkyl, wherein the (3-7 membered) cycloalkyl may be optionally substituted with 1, 2, 3 or 4 of the following groups: —H, halogen, $R^8$, —$OR^8$, —$NR^8R^9$ and —CN;

$R^{4g}$ is (C1-C3) alkyl or (C3-C6) cycloalkyl, wherein the (C1-C3) alkyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$;

each $R^3$ is independently —H, -D, a halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^8$, —$NR^9S(O)_2R^8$, —$S(O)_pR^8$ and —$S(O)_2NR^8R^9$; or 2 adjacent $R^3$, together with the atoms to which they are attached, can form (5-9 membered) heterocycloalkyl or (C5-C9) cycloalkyl, wherein the (5-9 membered) heterocycloalkyl or (C5-C9) cycloalkyl may be optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$; ring B is (C5-C11) partially unsaturated cycloalkyl or (5-11 membered) partially unsaturated heterocycloalkyl;

$X^1$ is

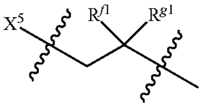
,
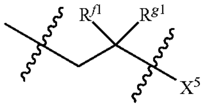
or
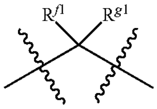
;

$X^2$ is a chemical bond,

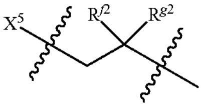
,
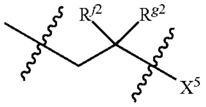
or
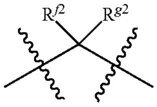
;

$X^3$ is CH, N or $C—R^c$;

$X^4$ is CH, N or $C—R^d$;

$X^5$ is $N—R^a$ or $CH—R^b$;

each $R^2$ is independently —H, -D, a halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$; or 2 adjacent $R^2$, together with the atoms to which they are attached, can form (5-7 membered) heterocycloalkyl or (C3-C9) cycloalkyl, wherein the (5-7 membered) heterocycloalkyl or (C3-C9) cycloalkyl may be optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$; or 2 $R^2$ on the same carbon atom of ring B, together with the carbon atom to which they are attached, can form (4-7 membered) heterocycloalkyl or (C3-C6) cycloalkyl, wherein the (4-7 membered) heterocycloalkyl or (C3-C6) cycloalkyl may be optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$; or $R^2$ and an adjacent $R^e$, together with the atoms to which they are attached, can form (5-7 membered) heterocycloalkyl or (C3-C9) cycloalkyl, wherein the (5-7 membered) heterocycloalkyl or (C3-C9) cycloalkyl may be optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$;

$R^a$ is —H, $R^8$, $—(CH_2)_mOR^8$, $—(CH_2)_mNR^8R^9$, (C1-C6) alkyl, (C1-C6) haloalkyl, (C3-C14) cycloalkyl or (3-15 membered) heterocycloalkyl, wherein the (C1-C6) alkyl, (C1-C6) haloalkyl, (C3-C14) cycloalkyl or (3-15 membered) heterocycloalkyl may be optionally substituted with 1, 2, 3 or 4 of the following groups: —H, -D, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$;

$R^b$ is —H, $R^8$, $—(CH_2)_nOR^8$, $—(CH_2)_nNR^8R^9$, (C1-C6) alkyl, (C1-C6) haloalkyl, (C3-C14) cycloalkyl or (3-15 membered) heterocycloalkyl, wherein the $R^8$, $R^9$, (C1-C6) alkyl, (C1-C6) haloalkyl, (C3-C14) cycloalkyl or (3-15 membered) heterocycloalkyl may be optionally substituted with 1, 2, 3 or 4 of the following groups: —H, -D, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$;

$R^c$ and $R^d$ are each independently —H, a halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$, $—S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, $—(CH_2)_nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$;

$R^e$ is —H, -D, (C1-C6) alkyl, (C1-C6) haloalkyl, (C2-C6) alkenyl, (C2-C6) alkynyl, (C1-C6) alkoxy, (C1-C6) haloalkoxy, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C1-C6) alkoxy, (C1-C6) haloalkoxy, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, $—(CH_2)^nOR^8$, $—(CH_2)_nNR^8R^9$, $—OR^8$, $—NR^8R^9$, —CN, $—C(O)NR^8R^9$, $—NR^9C(O)R^8$, $—NR^9S(O)_2R^8$, $—S(O)_pR^8$ and $—S(O)_2NR^8R^9$;

$R^{f1}$, $R^{f2}$, $R^{g1}$ and $R^{g2}$ are each independently —H, -D, $R^8$, $—(CH_2)_nOR^8$, $—(CH_2)_nNR^8R^9$, —CN, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_n OR^8$, —$(CH_2)_n NR^8R^9$, —$OR^8$, —$NR^8R^9$, —CN, —C(O)$NR^8R^9$, —$NR^9C(O)R^1$, —$NR^9S(O)_2R^8$, —$S(O)_pR^8$ and —$S(O)_2NR^8R^9$; or $R^2$ and an adjacent $R^e$, together with the atoms to which they are attached, can form (C3-C9) cycloalkyl or (3-11 membered) heterocycloalkyl, wherein the (C3-C9) cycloalkyl or (3-11 membered) heterocycloalkyl may be each independently and optionally substituted with 1, 2, 3 or 4 of the following groups: —H, halogen, $R^8$, —OH, —$(CH_2)_n OR^8$, —$(CH_2)_n NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^6$ is (C1-C3) alkyl or (C3-C6) cycloalkyl;

$R^7$ is (C1-C3) alkyl;

$R^8$ and $R^9$ are each independently —H, (C1-C6) alkyl or (C3-C14) cycloalkyl, or $R^8$ and $R^9$ on the same nitrogen atom, together with the N atom to which they are attached, can form (3-11 membered) heterocycloalkyl, wherein the (3-11 membered) heterocycloalkyl may be optionally substituted with 1, 2, 3 or 4 of the following groups: —H, halogen, $R^{10}$ and —$OR^{10}$;

$R^{10}$ is —H, (C1-C6) alkyl or (C3-C14) cycloalkyl;

$R^{11}$ and $R^{12}$ are each independently —H, (C1-C3) alkyl, (C1-C3) haloalkyl or (C3-C6) cycloalkyl, or $R^{11}$ and $R^{12}$ on the same nitrogen atom, together with the N atom to which they are attached, can form (4-6 membered) heterocycloalkyl; and p is an integer of 0, 1 or 2, q is an integer of 1, 2, 3 or 4, s is an integer of 1, 2, 3 or 4, n is an integer of 0, 1, 2 or 3, and m is an integer of 1, 2 or 3.

In another preferred embodiment, in general formula (1), Z is —NH— or a chemical bond.

In another preferred embodiment, in general formula (1), Y is —H, —F, —Cl, —Br, —I, —CN, —$S(O)_2CH_3$, —P(O)$(CH_3)_2$, —C(O)$NH_2$, (C1-C3) alkyl, (C1-C3) haloalkyl, (C3-C5) cycloalkyl, (C2-C3) alkynyl or (5-6 membered) heteroaryl, wherein the (C1-C3) alkyl, (C1-C3) haloalkyl, (C3-C5) cycloalkyl, (C2-C3) alkynyl or (5-6 membered) heteroaryl may be each independently and optionally substituted with 1, 2, 3 or 4 of the following groups: —H, —F, —CN, —$CH_3$ and —$OCH_3$.

In another preferred embodiment, in general formula (1), Y is —H, —F, —Cl, —Br, —I, —CN, —$S(O)_2CH_3$, —P(O)$(CH_3)_2$, —C(O)$NH_2$, —$CH_3$,

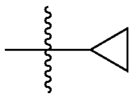, 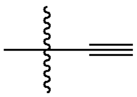, 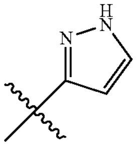, 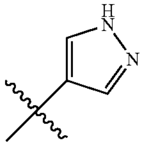, 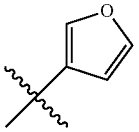, 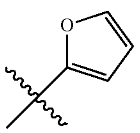 or 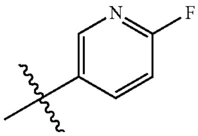;

Y is preferably —Br, —CN, —$S(O)_2CH_3$, —P(O)$(CH_3)_2$, —C(O)$NH_2$, —$CF_3$,

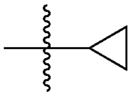 or 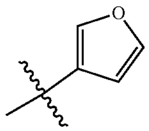;

Y is more preferably —CN.

In another preferred embodiment, in general formula (1), ring A is (C6-C10) aryl, (5-10 membered) heteroaryl or (5-10 membered) heterocycloalkyl.

In another preferred embodiment, in general formula (1), ring A is

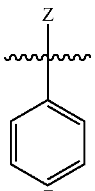, 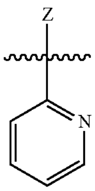, 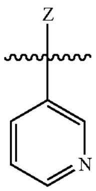, 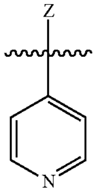, 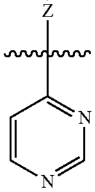, 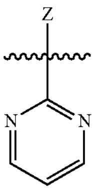, 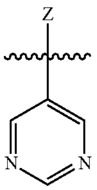, 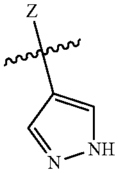, 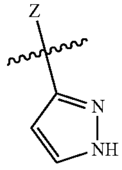, 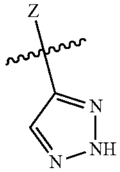, 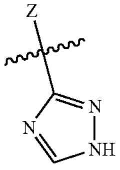, 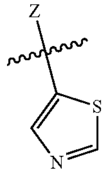, 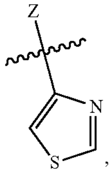, 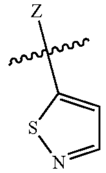, 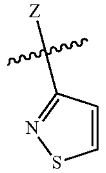, 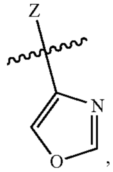, 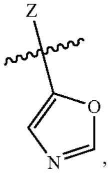, 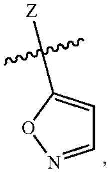, 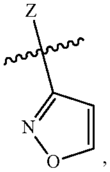, 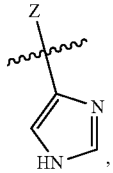, 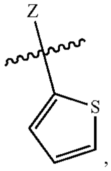, 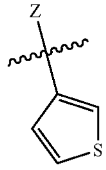, 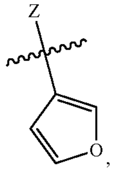, 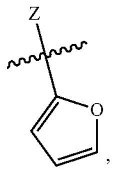, 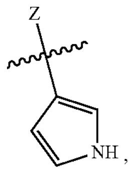, 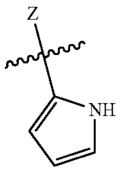, -continued
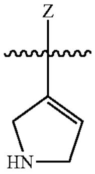, 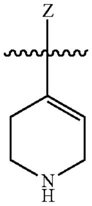, 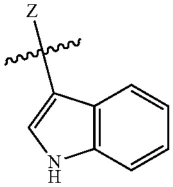,
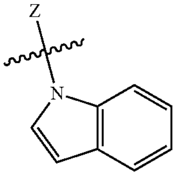, 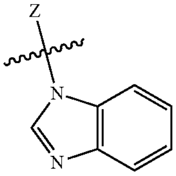,
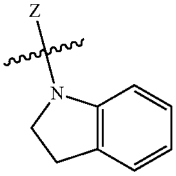, 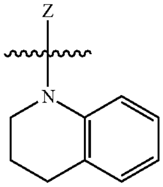,
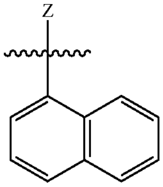, 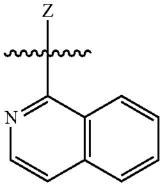,
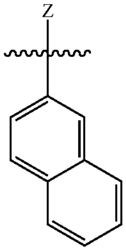, 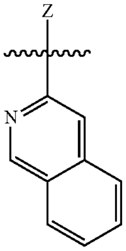, 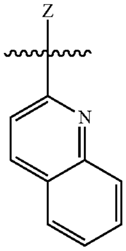,
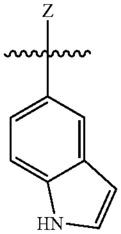, 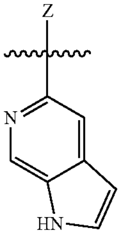, 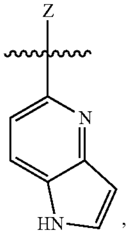,
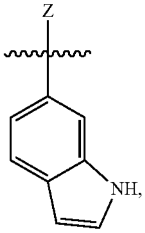 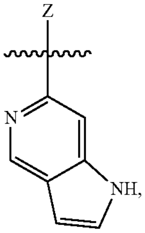 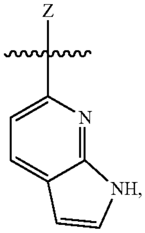
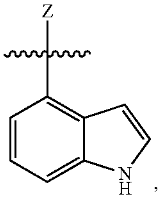, 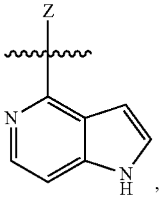, 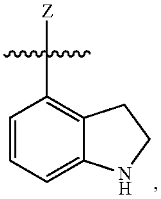,
-continued
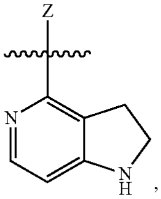, 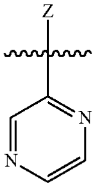 or 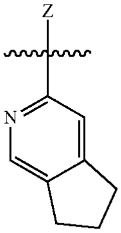;
ring A is preferably
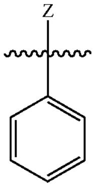, 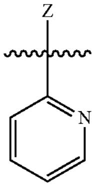, 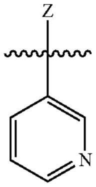,
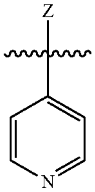, 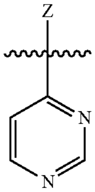, 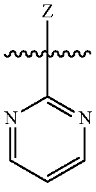,
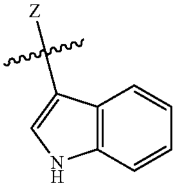, 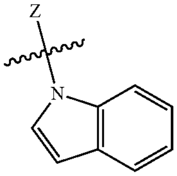,
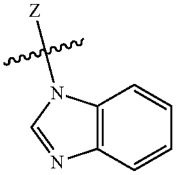, 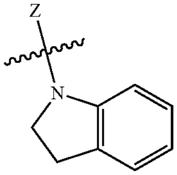,
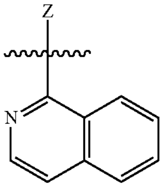, 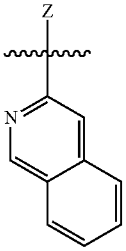,
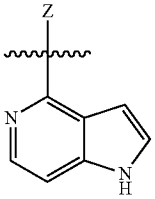, 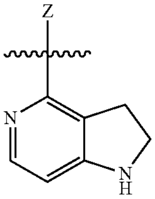, -continued

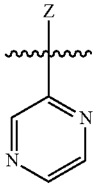

or

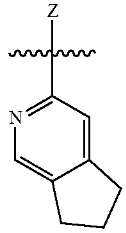

;

ring A is more preferably

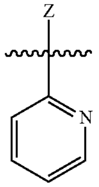

,

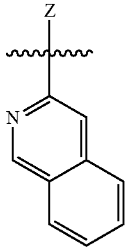

or

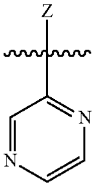

;

ring A is more preferably

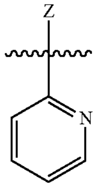

.

In another preferred embodiment, in general formula (1), when $R^1$ is

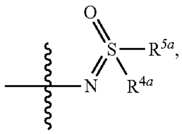

$R^{4a}$ and $R^{5a}$ are each independently (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, $—CH_3$, —OH, $—CH_2OCH_3$, $—CH_2N(CH_3)_2$, $—OCH_3$, $—N(CH_3)_2$ and —CN; or $R^{4a}$ and $R^{5a}$, together with the S atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, $—CH_3$, —OH, $—CH_2OCH_3$, $—CH_2N(CH_3)_2$, $—OCH_3$, $—N(CH_3)_2$ and —CN.

In another preferred embodiment, in general formula (1), when $R^1$ is

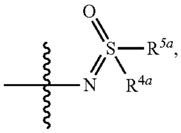

the structural unit

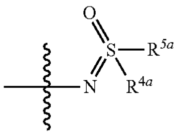

is

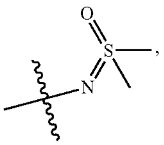

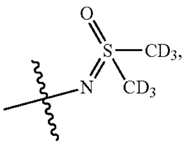

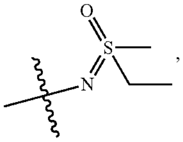

,

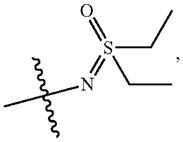

,

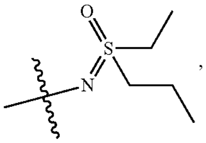

,

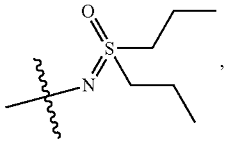

,

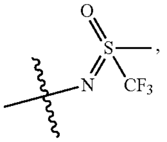

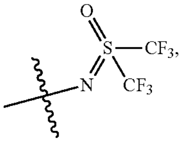

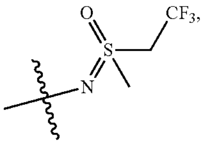

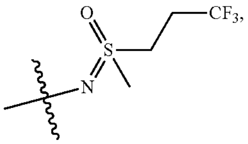

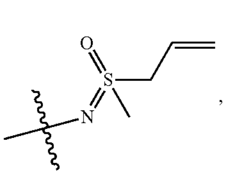

,

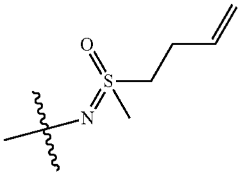

,

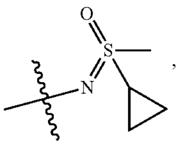

,

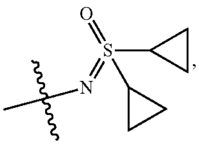

,

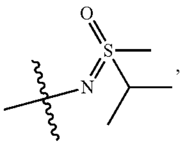

,

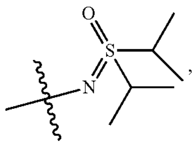

,

-continued

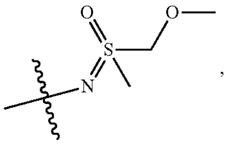,
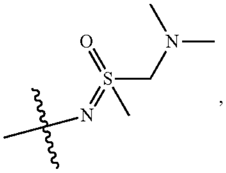,
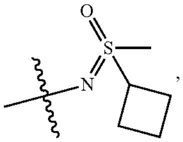,
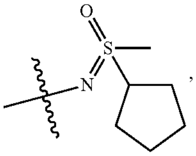,
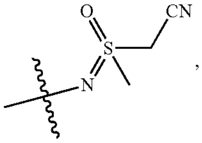,
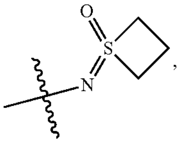,
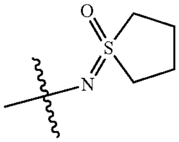
or
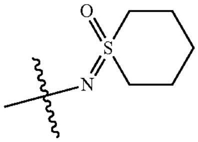;

preferably

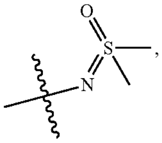,
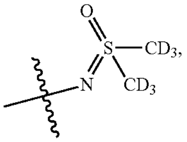
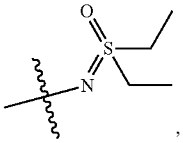,
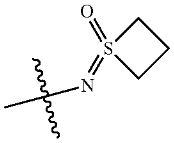
or
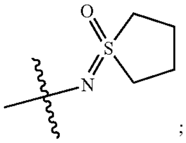;

more preferably

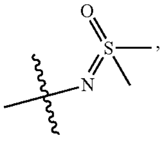,
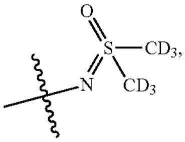
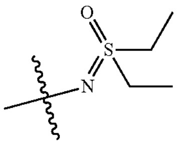,
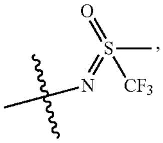,
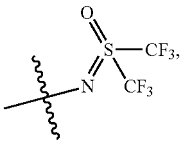
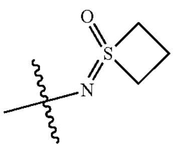
or

-continued

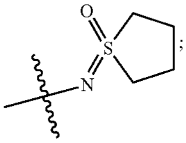;

and more preferably

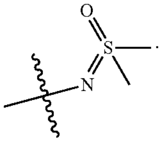 [SMILES: *N=S(C)(C)=O].

In another preferred embodiment, in general formula (1), when $R^1$ is

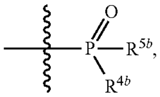

$R^{4b}$ and $R^{5b}$ are each independently (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4b}$ and $R^{5b}$, together with the P atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

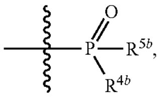

the structural unit

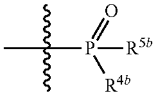

is:

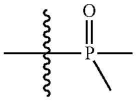,
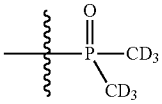,
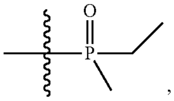,

-continued

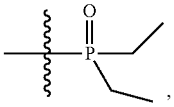, 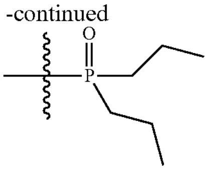, 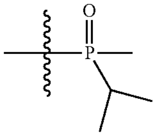, 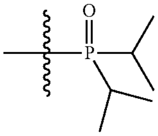, 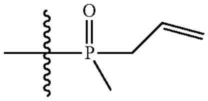, 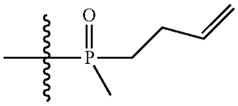, 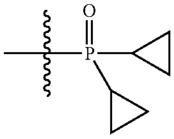, 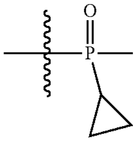, 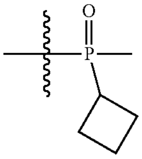, 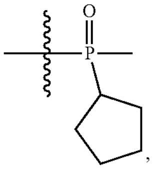, 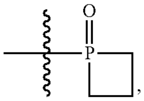, 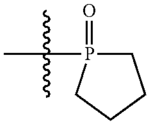 or 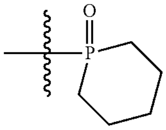;

preferably

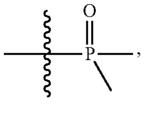 [SMILES: *P(C)(C)=O], 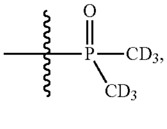, 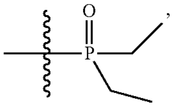, 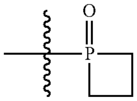 or 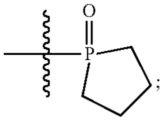;

and more preferably

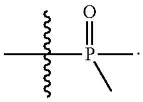.

In another preferred embodiment, in general formula (1), when $R^1$ is

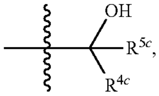, $R^{4c}$ and $R^{5c}$ are each independently —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4c}$ and $R^{5c}$, together with the carbon atom to which they are attached, can form (3-6 membered) cycloalkyl, wherein the (3-6 membered) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

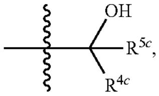, the structural unit

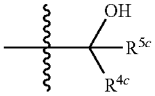

is:

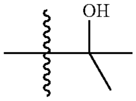, 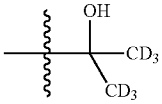, 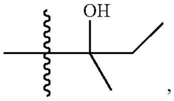, 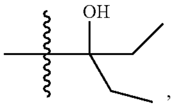, 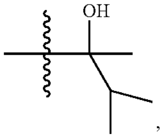, 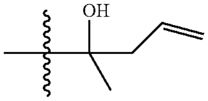, 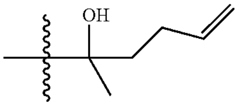, 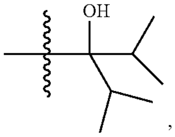, 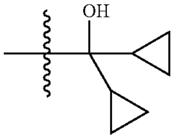, 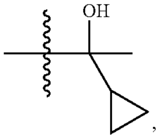, 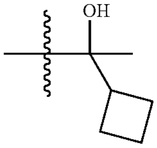, 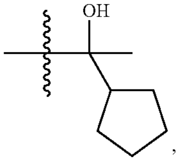, 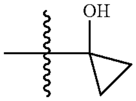, 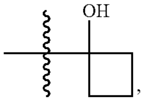, -continued

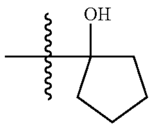
or
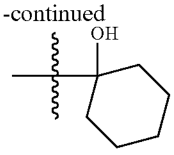
;

preferably

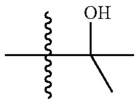
or
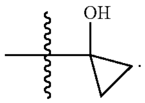

In another preferred embodiment, in general formula (1), when $R^1$ is

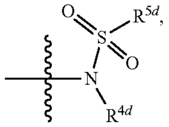

$R^{4d}$ is —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; and $R^{5d}$ is (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4d}$ and $R^{5d}$, together with the atoms to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

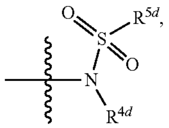

the structural unit

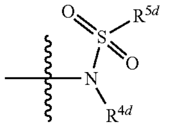

is:

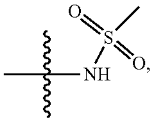
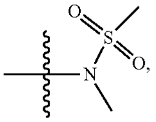
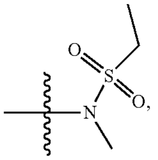
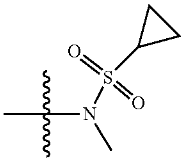
,
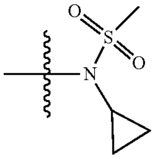
,
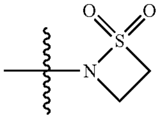
or
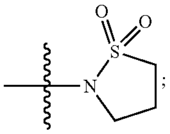
;

preferably

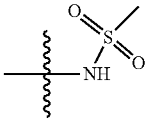
or
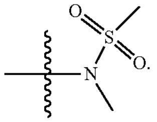

In another preferred embodiment, in general formula (1), when $R^1$ is

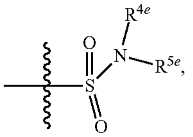

$R^{4e}$ and $R^{5e}$ are each independently —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4e}$ and $R^{5e}$, together with the N atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

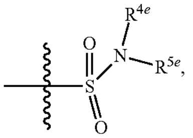

the structural unit

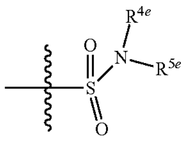

is:

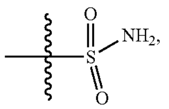 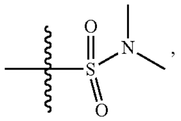

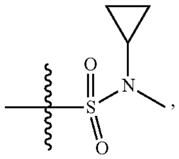 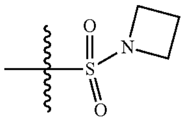 or

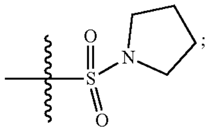

preferably

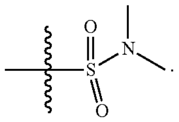 [SMILES: *S(=O)(=O)N(C)C]

In another preferred embodiment, in general formula (1), when $R^1$ is

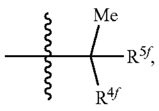

$R^{4f}$ and $R^{5f}$ are each independently —H, a halogen, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4f}$ and $R^{5f}$, together with the carbon atom to which they are attached, can form (3-6 membered) cycloalkyl, wherein the (3-6 membered) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

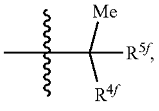

the structural unit

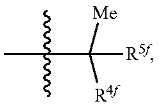

is:

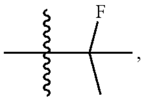, 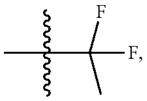 or 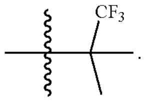.

In another preferred embodiment, in general formula (1), when $R^1$ is

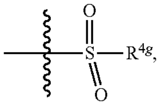

$R^{4g}$ is (C1-C3) alkyl or (C3-C5) cycloalkyl, wherein the (C1-C3) alkyl or (C3-C5) cycloalkyl may be each independently and optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), when $R^1$ is

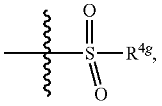

the structural unit

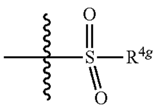

is:

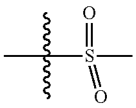 or 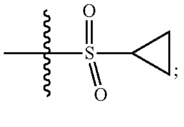;

preferably

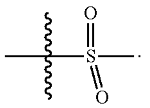

In another preferred embodiment, in general formula (1), each $R^3$ is independently —H, -D, —F, —Cl, —Br, —I, —OH, —$CH_2OR^{11}$, —$CH_2NR^{11}R^{12}$, —$OR^{11}$, —$NR^{11}R^{12}$, —CN, —$C(O)NR^{11}R^{12}$, —$NR^{12}C(O)R^{11}$, —$NR^{12}S(O)_2R^{11}$, —$SR^{11}$, —$S(O)_2R^{11}$, —$S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl, wherein the (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl may be each independently and optionally substituted with 1, 2, 3 or 4 of the following groups: —H, —F, —Cl, —Br, —I, —OH, —$OCH_3$, —$N(CH_3)_2$ and —CN; or 2 adjacent $R^3$, together with the atoms to which they are attached, can form (5-7 membered) heterocycloalkyl or (C5-C7) cycloalkyl, wherein the (5-7 membered) heterocycloalkyl or (C5-C7) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), each $R^3$ is independently: —H, -D, —F, —Cl, —Br, —I, —OH, —$CH_2OCH_3$, —$CH_2N(CH_3)_2$, —$OCH_3$, —$OCF_3$, —$N(CH_3)_2$, —CN, —$C(O)NH_2$, —$C(O)NH(CH_3)$, —$C(O)N(CH_3)_2$, —$NHC(O)CH_3$, —$N(CH_3)$—$C(O)CH_3$, —$NHS(O)_2CH_3$, —$NCH_3S(O)_2CH_3$, —$SCH_3$, —$S(O)_2CH_3$ 和 —$S(O)_2NH_2$, —$S(O)_2NH(CH_3)$, —$S(O)_2N(CH_3)_2$,

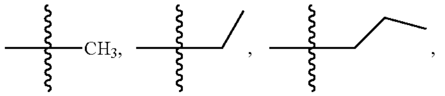
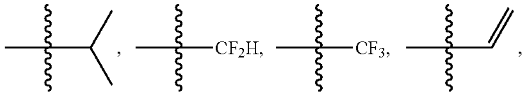
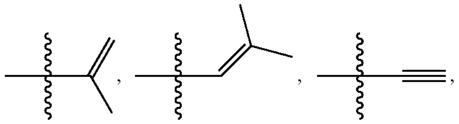
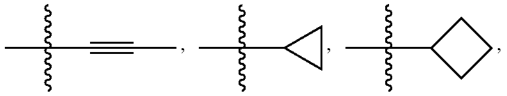
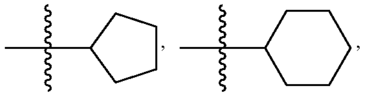
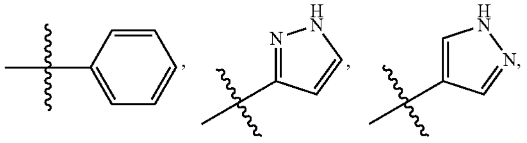
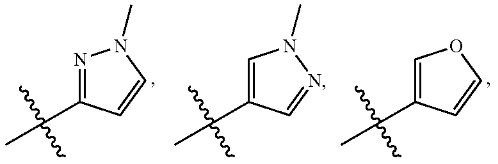

-continued

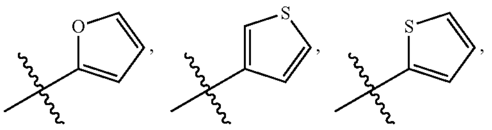
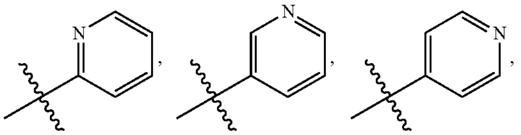
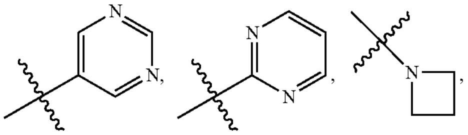
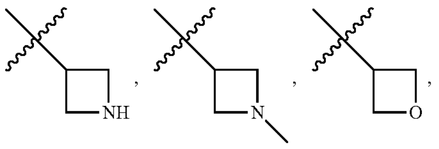
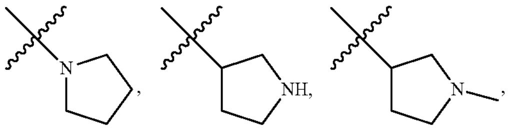
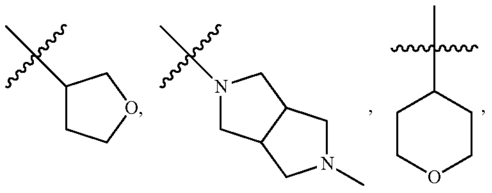
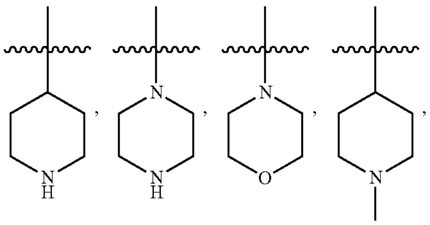
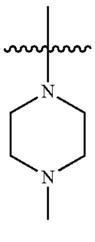

or

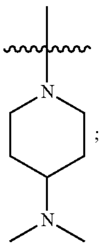

; $R^3$ is preferably —H, -D, —F, —Cl, —Br, —$OCH_3$, —$OCF_3$,

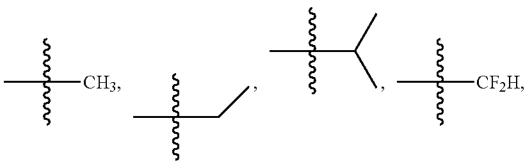

-continued
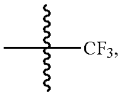, 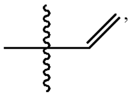, 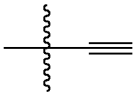 or 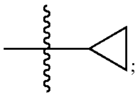;
$R^3$ is more preferably —H, -D, —F, —Cl, —$OCH_3$,
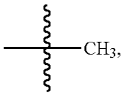, 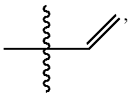, 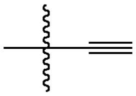 or 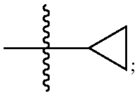;
$R^3$ is more preferably —H, -D, —F, —Cl, —$OCH_3$,
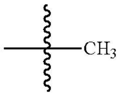 or 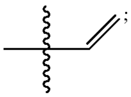;
q is preferably 1 or 2; q is more preferably 1.
In another preferred embodiment, in general formula (1), the structural unit
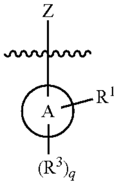
is:
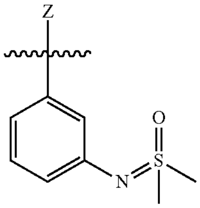,
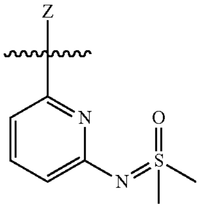,
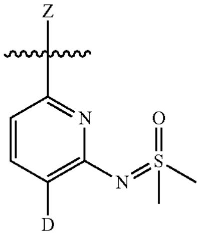,
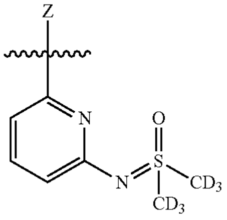,
-continued
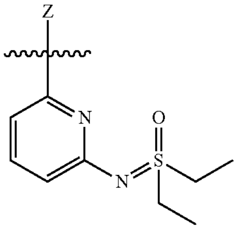,
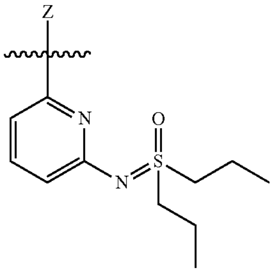,
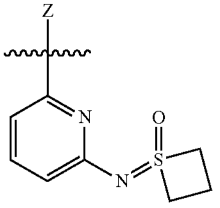,
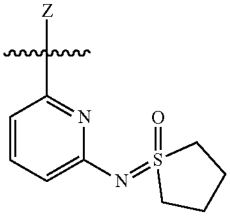,
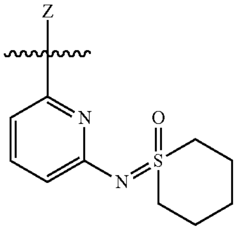,
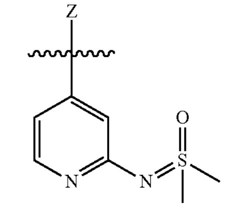,
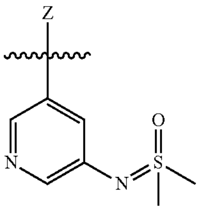,
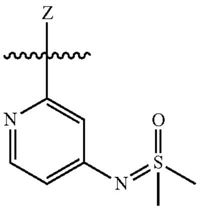,
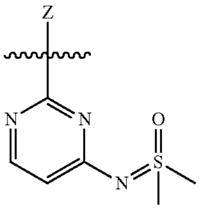,
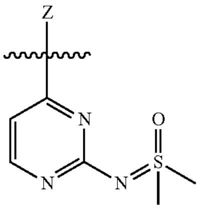,
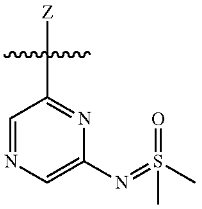,
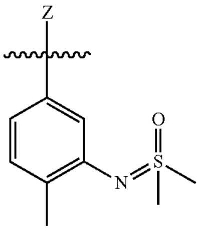, -continued
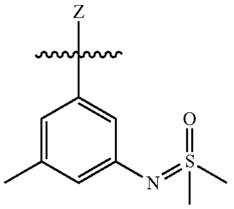,
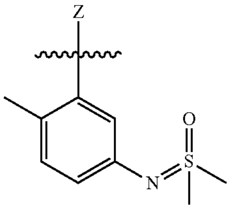,
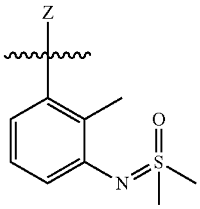,
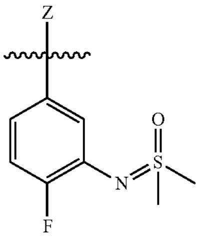,
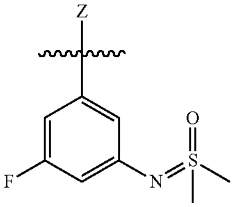,
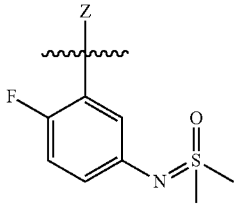,
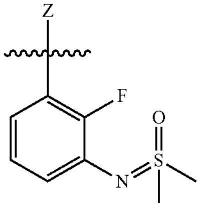,
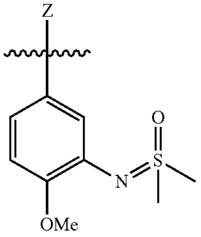,
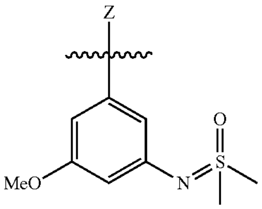,
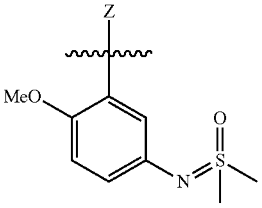,
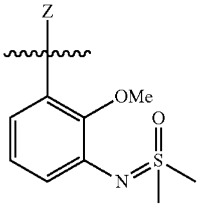,
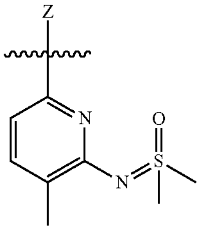,
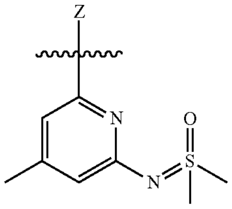,
-continued
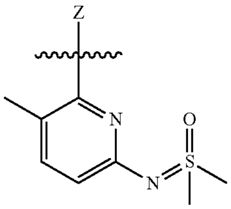,
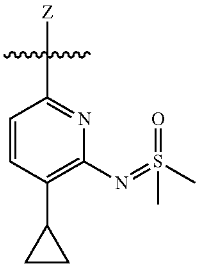,
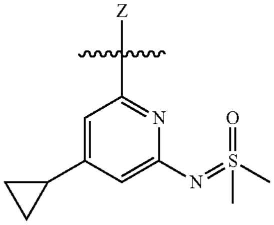,
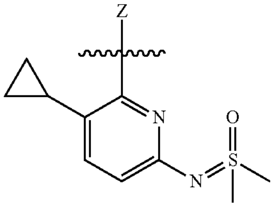,
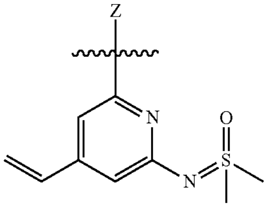,
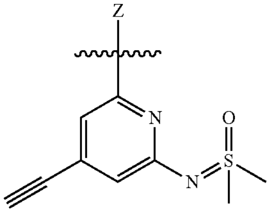,
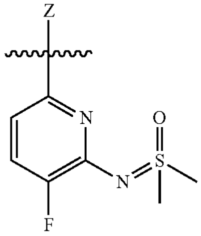,
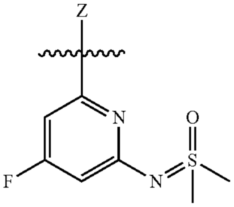,
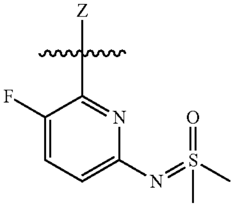,
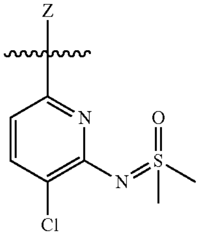,
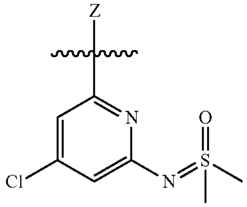, -continued
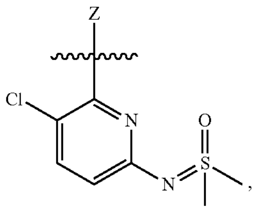,
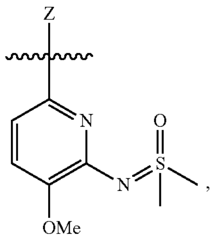,
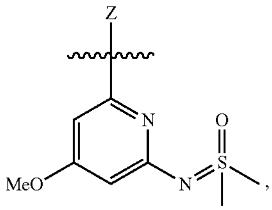,
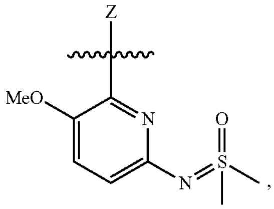,
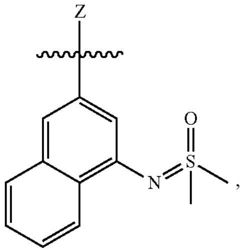,
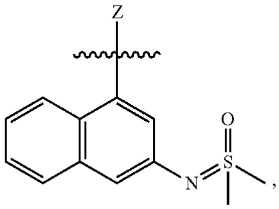,
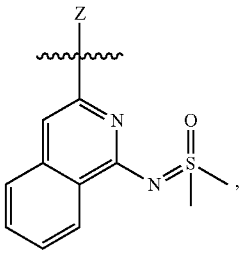,
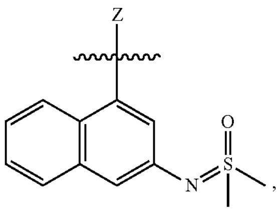,
-continued
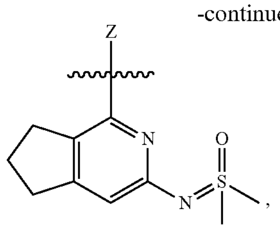,
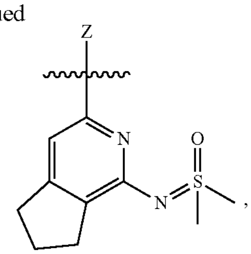,
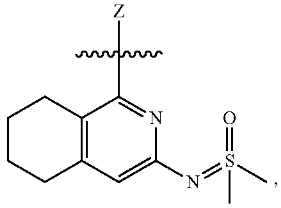,
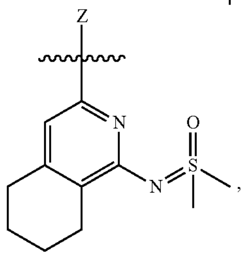,
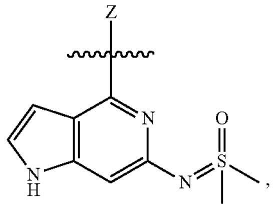,
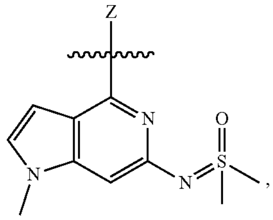,
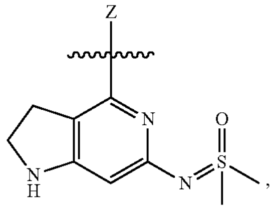,
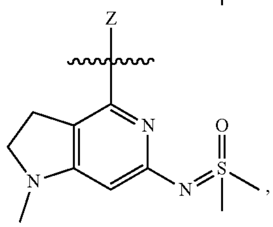,
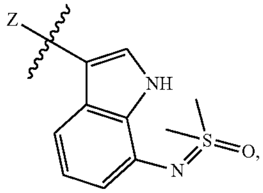,
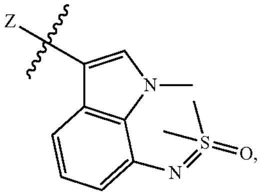, -continued
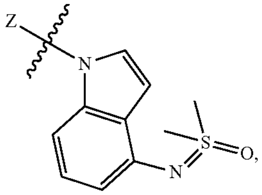 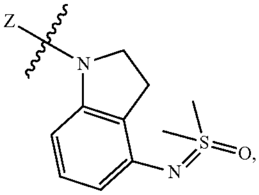
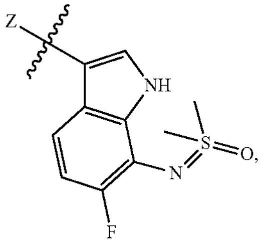 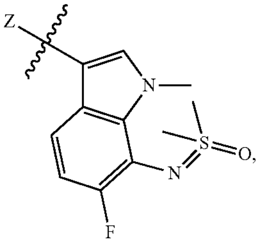
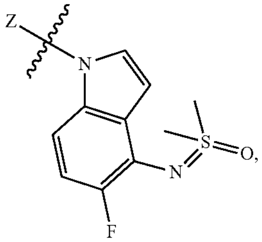 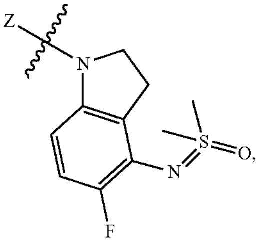
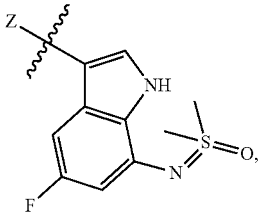 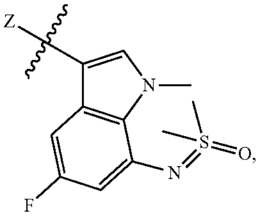
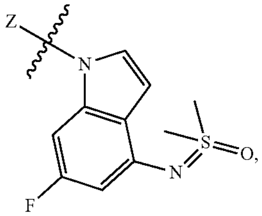 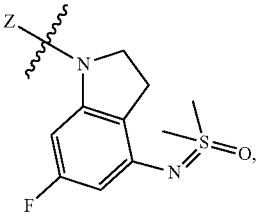
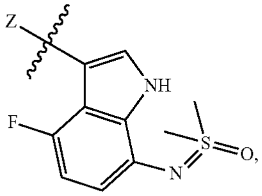 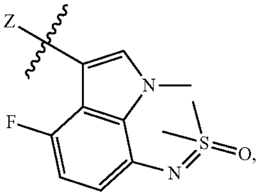
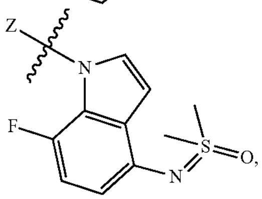 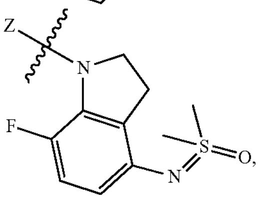
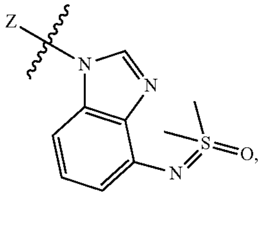 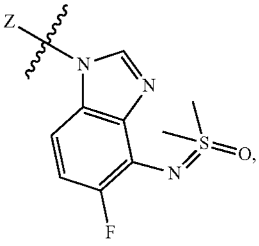
-continued
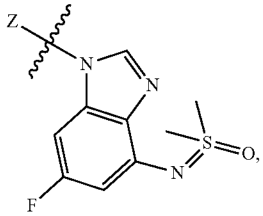 , 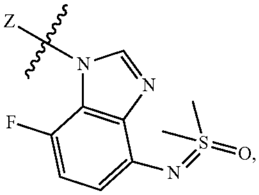 ,
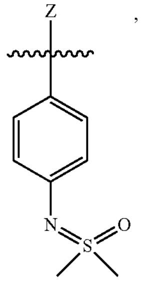 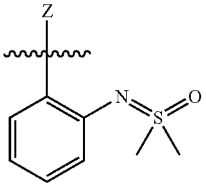
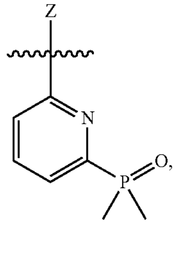 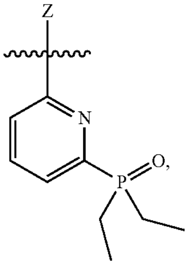
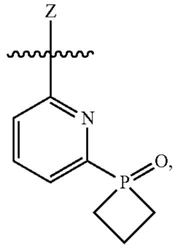 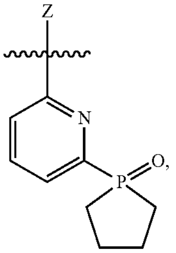
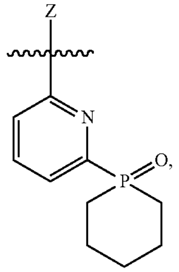 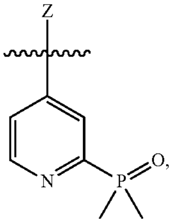
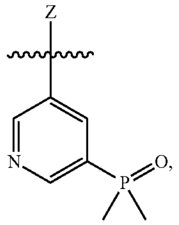 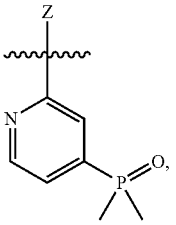
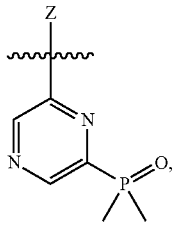 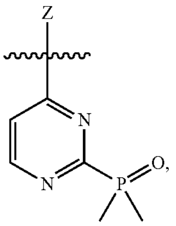

-continued
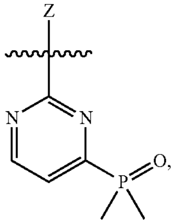
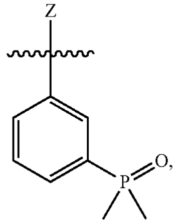
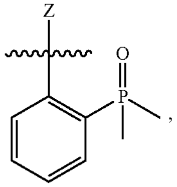
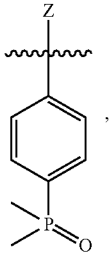
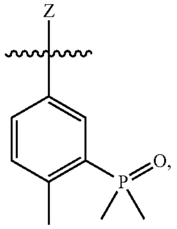
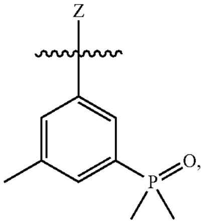
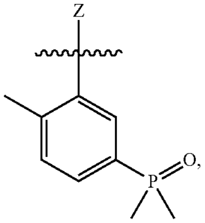
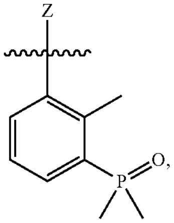
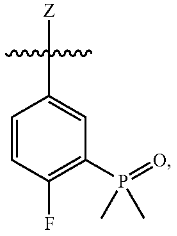
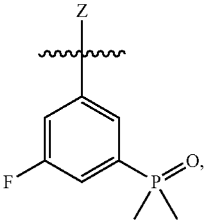
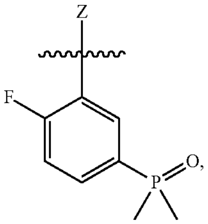
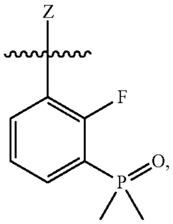
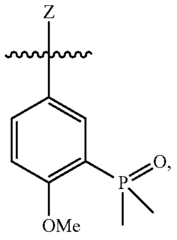
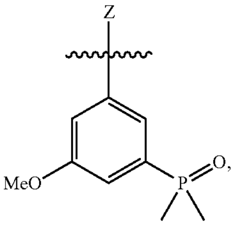
-continued
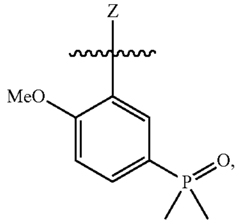
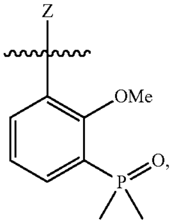
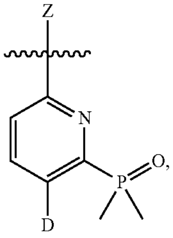
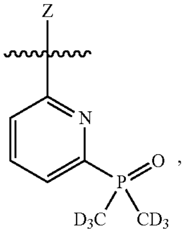
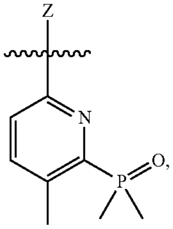
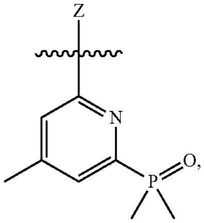
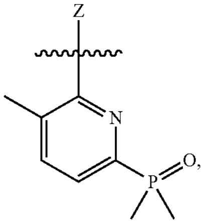
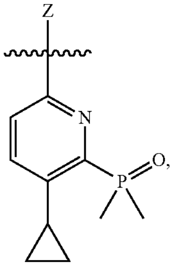
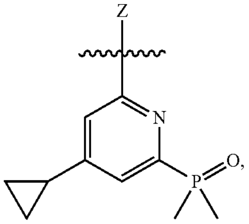
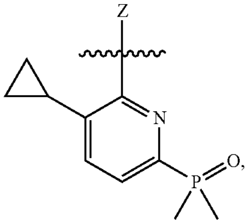
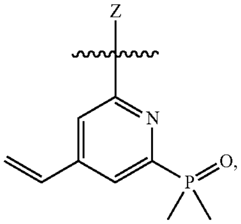
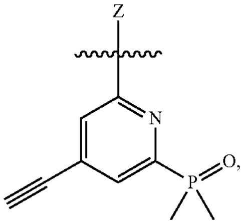
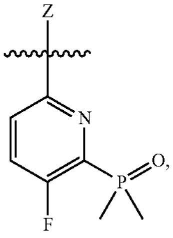
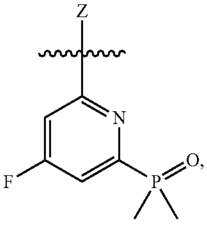

-continued
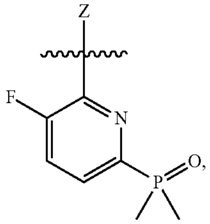
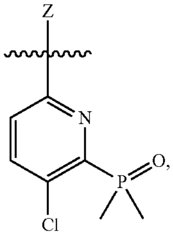
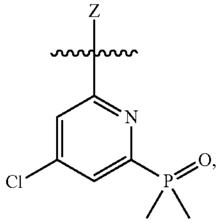
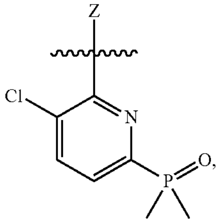
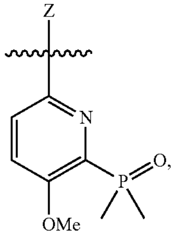
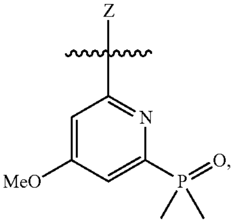
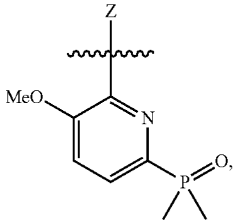
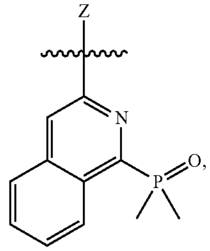
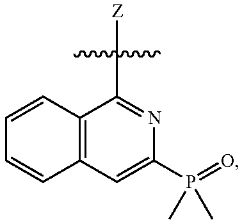
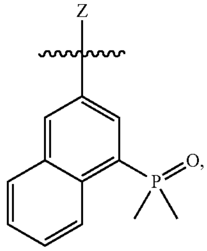
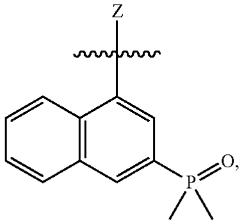
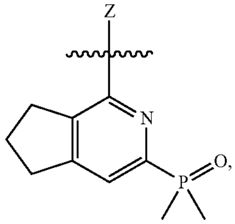
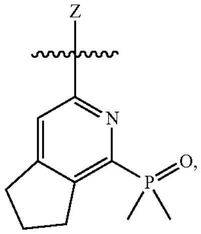
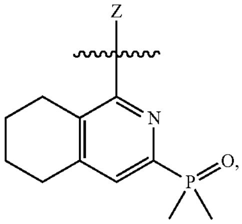
-continued
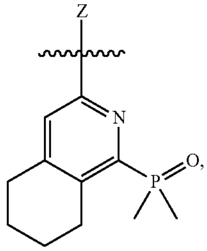
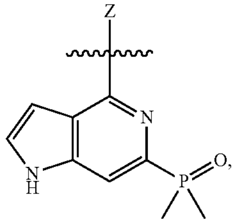
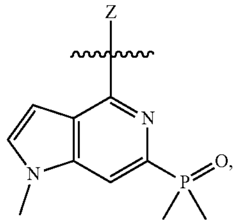
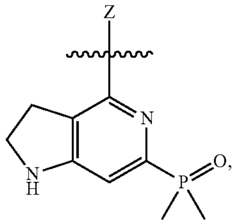
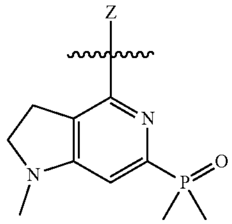
,
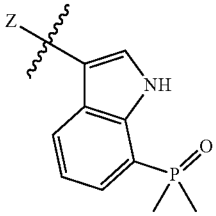
,
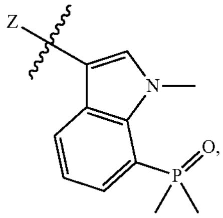
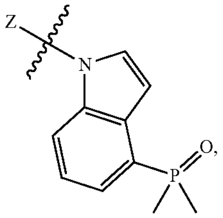
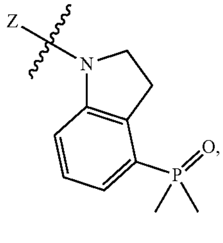
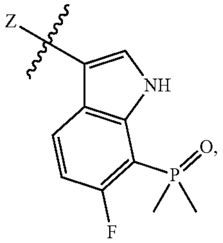
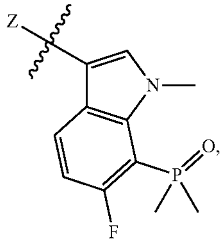
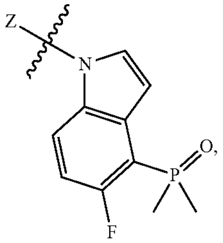
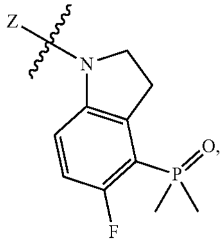
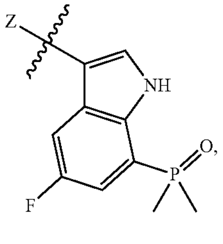

-continued
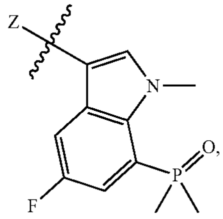
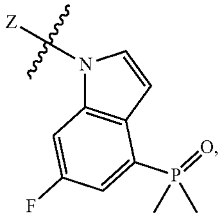
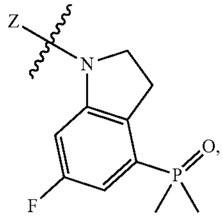
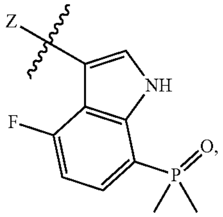
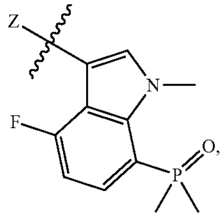
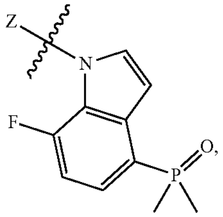
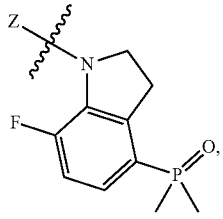
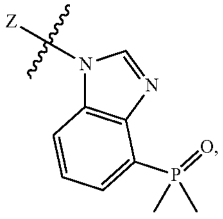
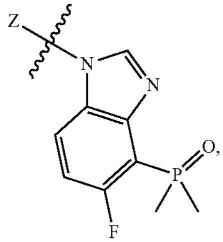
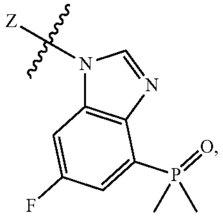
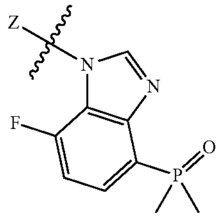
,
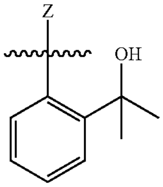
,
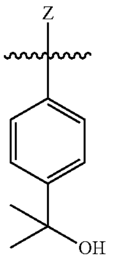
,
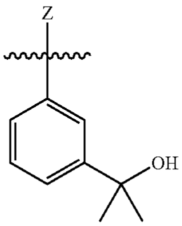
,
-continued
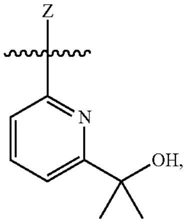
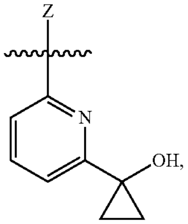
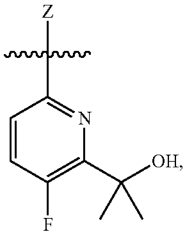
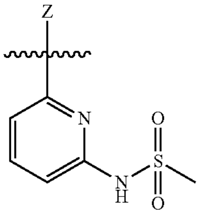
,
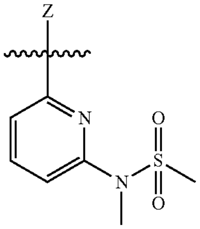
,
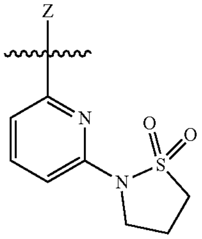
,
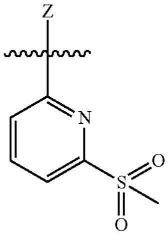
,
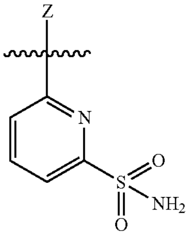
,
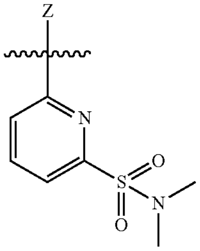
,
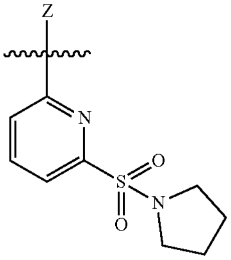
,
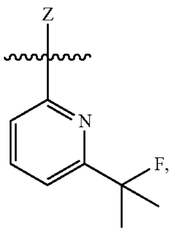
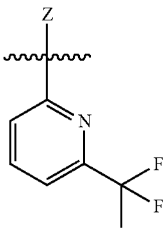
or
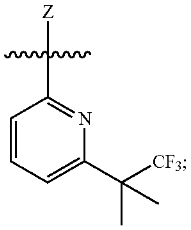

preferably
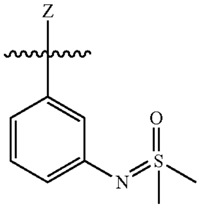
,
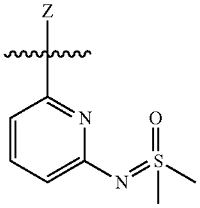
,
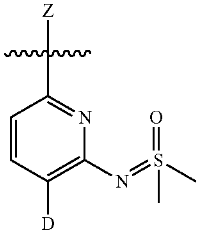
,
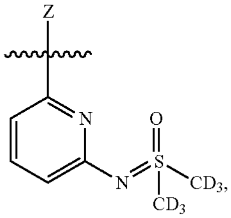
,
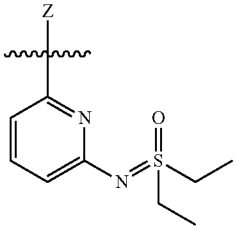
,
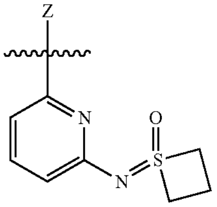
,
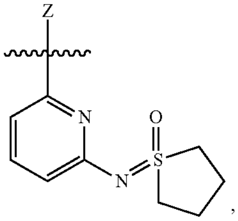
,
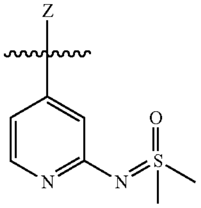
,
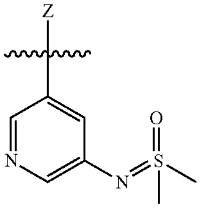
,
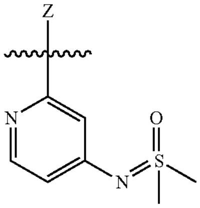
,
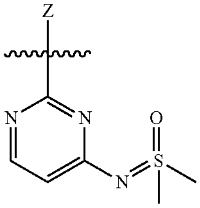
,
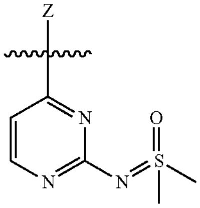
,
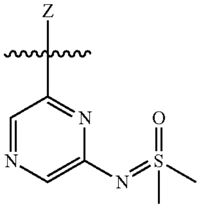
,
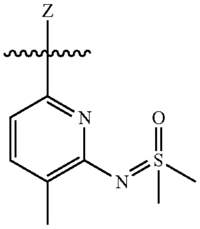
,
-continued
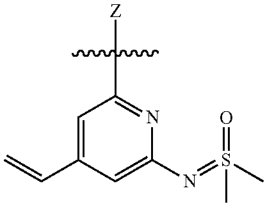
,
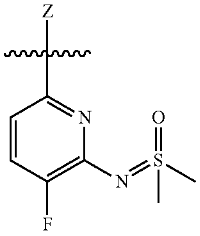
,
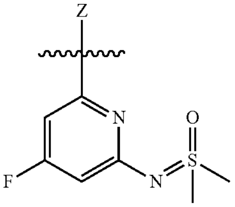
,
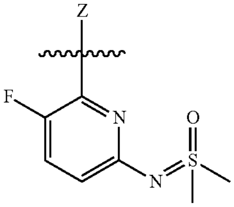
,
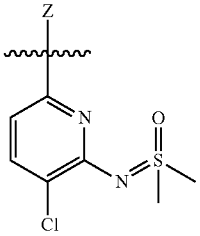
,
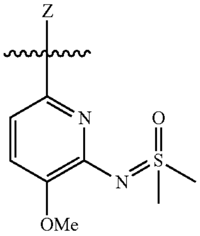
,
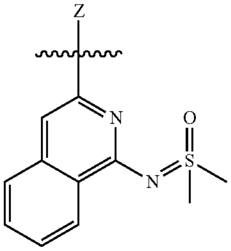
,
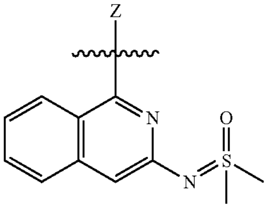
,
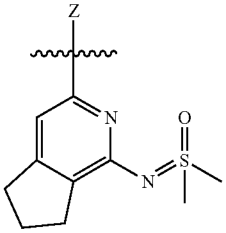
,
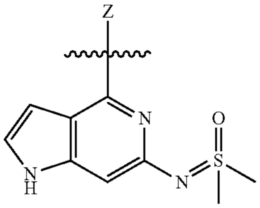
, -continued
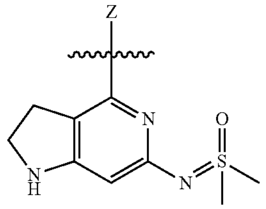
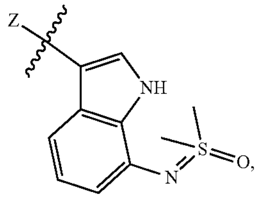
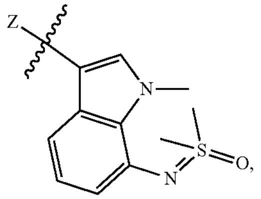
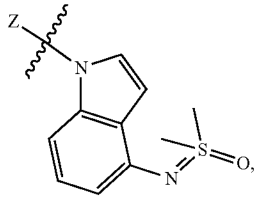
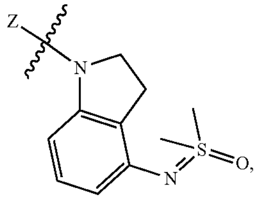
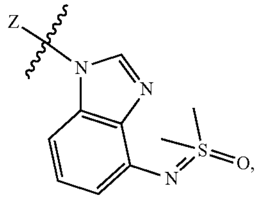
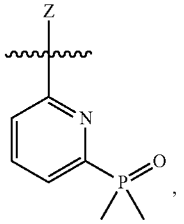
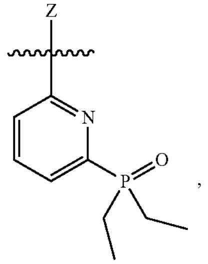
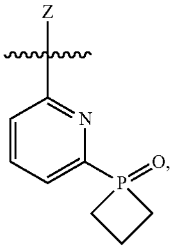
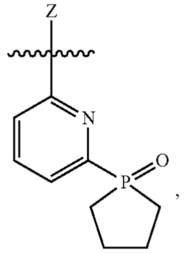
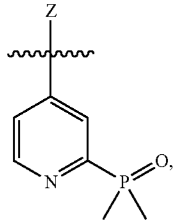
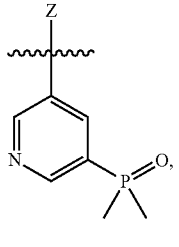
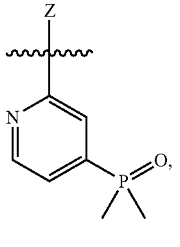
-continued
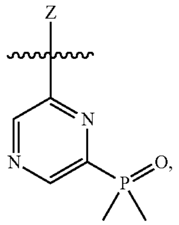
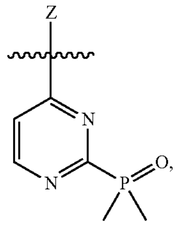
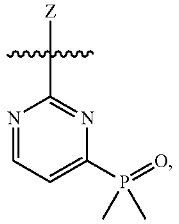
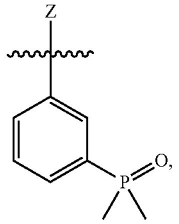
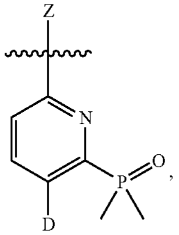
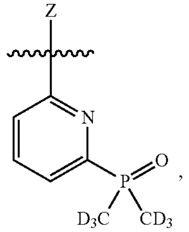
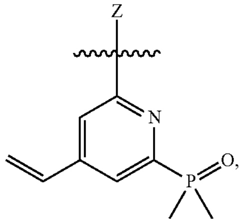
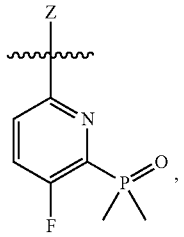
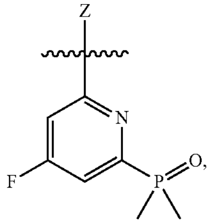
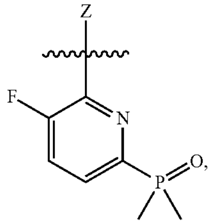
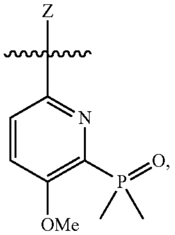
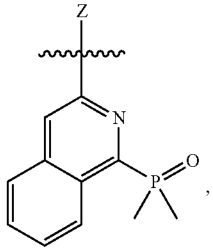
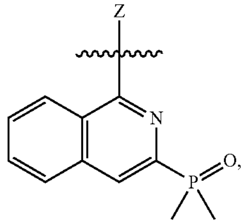

-continued
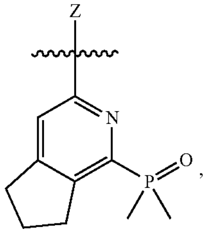,
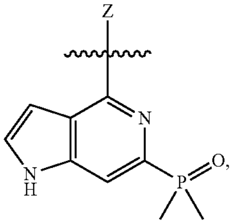,
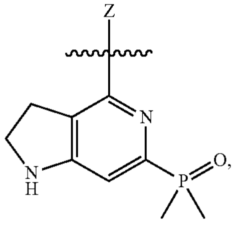,
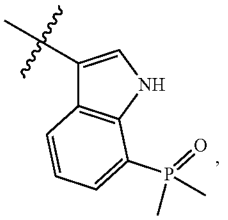,
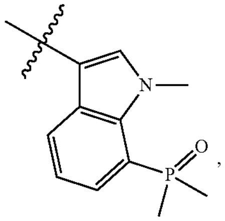,
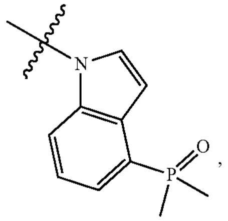,
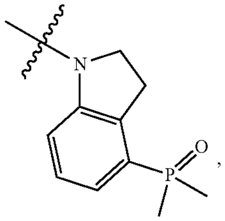,
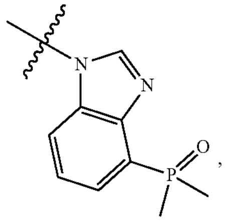,
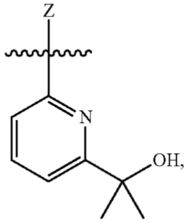,
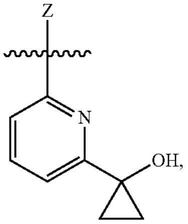,
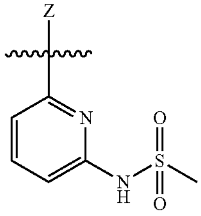,
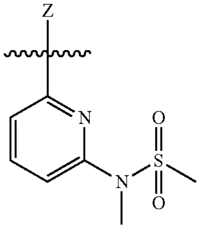,
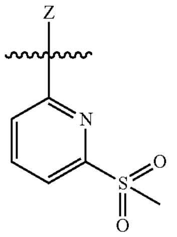,
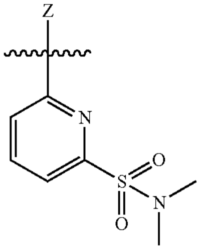,
-continued
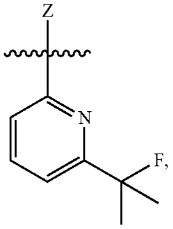,
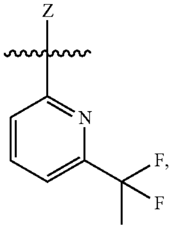, or
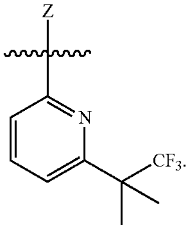.
In another preferred embodiment, in general formula (1), ring B is (C5-C8) partially unsaturated cycloalkyl or (5-8 membered) partially unsaturated heterocycloalkyl; and $R^c$ is: —H, -D, —$CH_3$, —$OCH_3$ or —$CH_2CH_3$.
In another preferred embodiment, in general formula (1), the structural unit
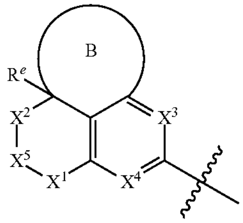
is
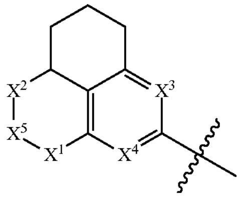,
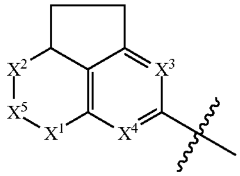,
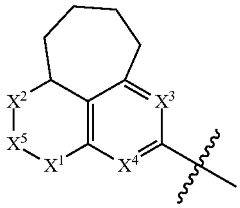,
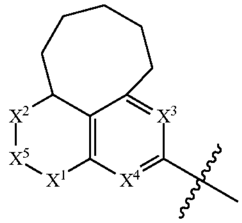,
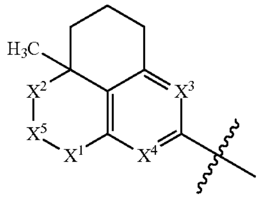, -continued
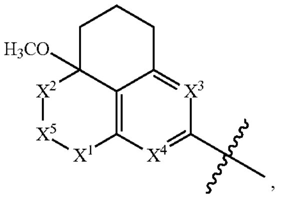
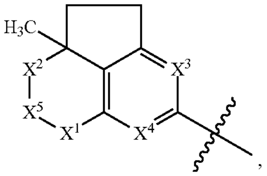
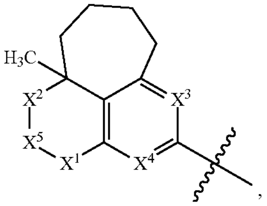
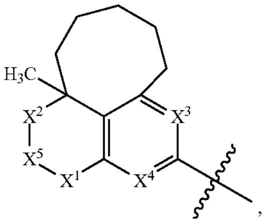
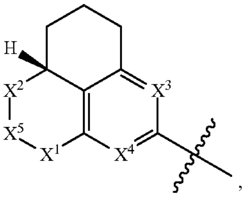
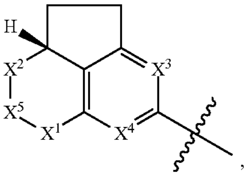
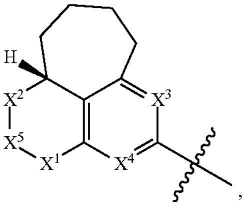
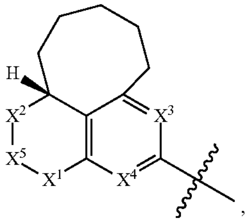
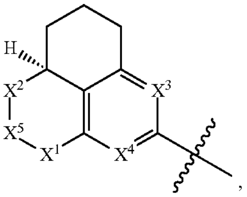
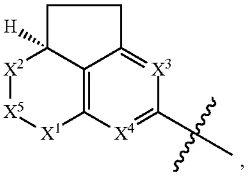
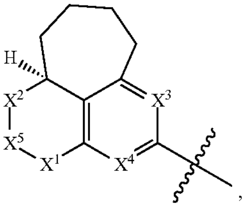
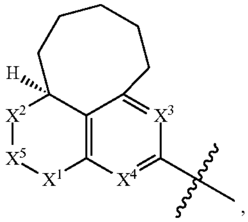
-continued
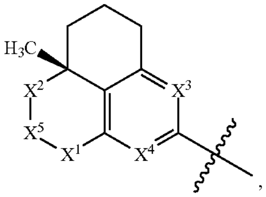
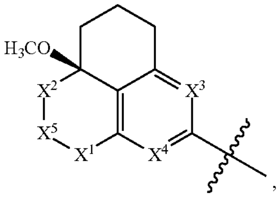
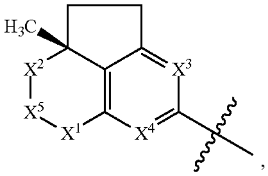
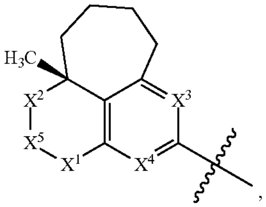
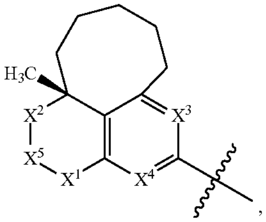
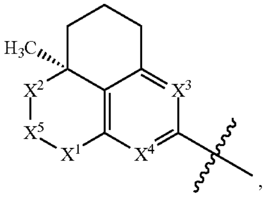
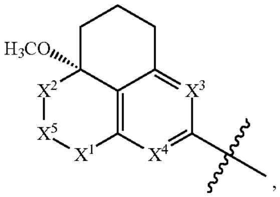
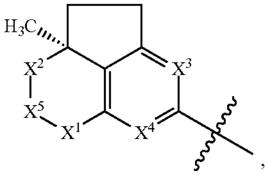

-continued
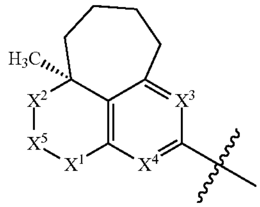
,
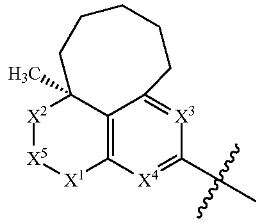
,
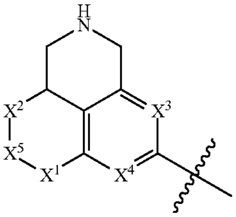
,
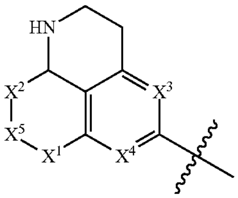
,
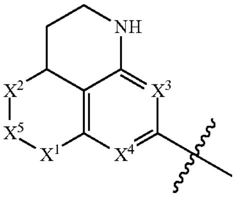
,
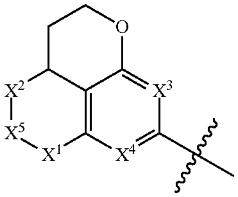
,
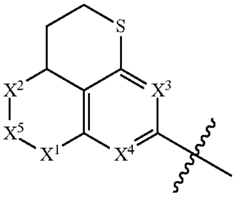
,
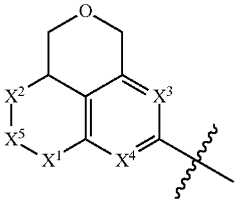
,
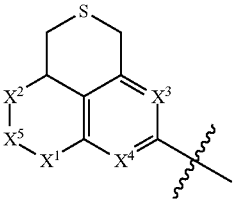
,
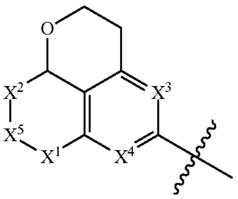
,
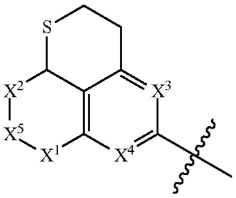
,
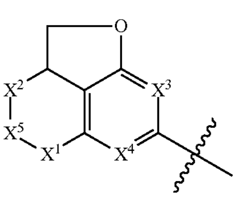
,
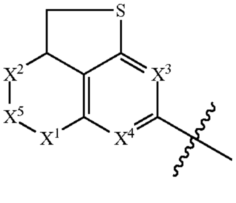
,
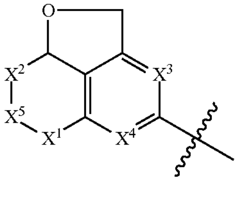
,
-continued
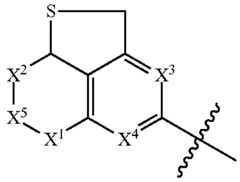
,
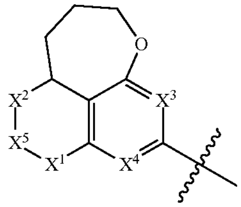
,
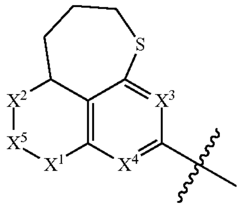
,
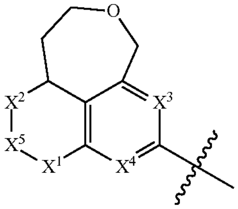
,
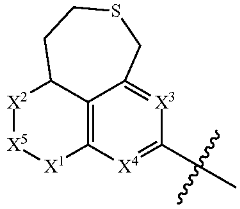
,
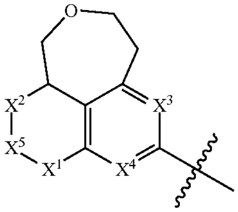
,
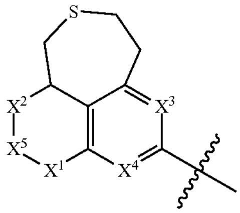
,
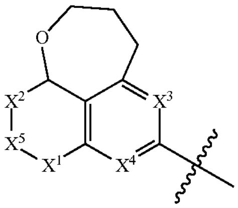
,
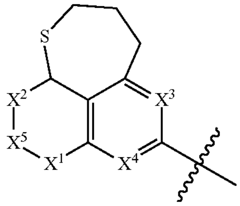
,
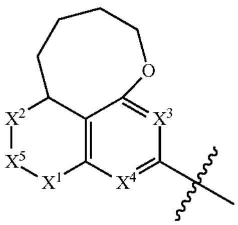
,
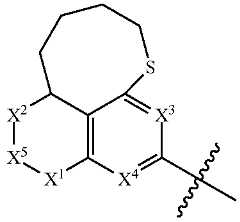
,
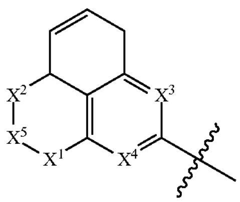
,
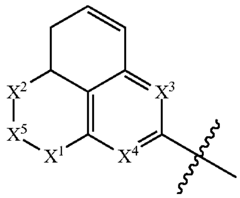
,
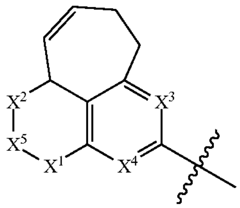
,
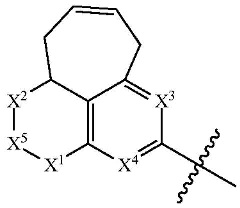
, or -continued
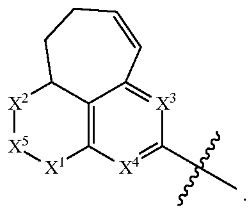
In another preferred embodiment in general formula (1), X is:
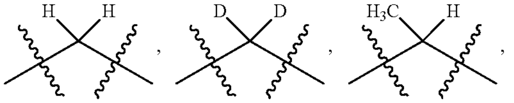
,
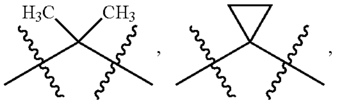
,
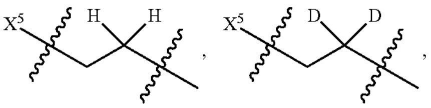
,
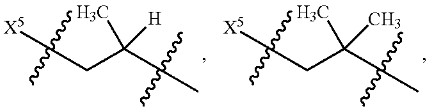
,
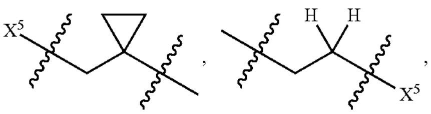
,
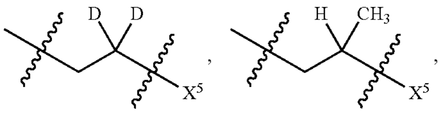
,
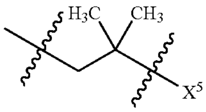
or
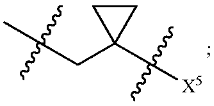
;
preferably,
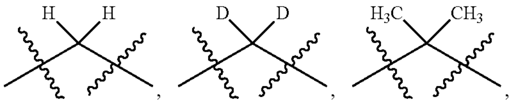
,
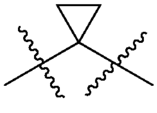
or
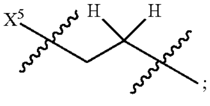
;
more preferably
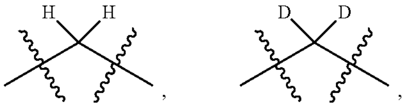
,
-continued
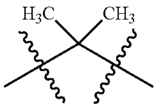
or
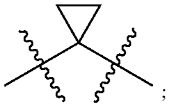
;
and more preferably.
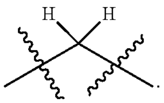 [SMILES: *C*]
In another preferred embodiment, in general formula (1), $X^2$ is: a chemical bond
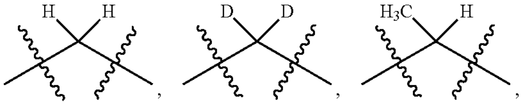
,
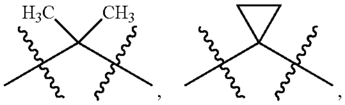
,
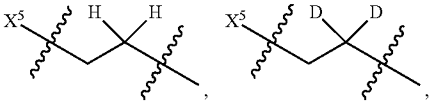
,
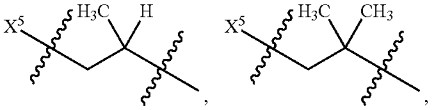
,
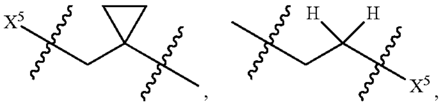
,
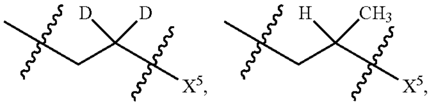
,
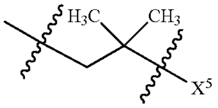
or
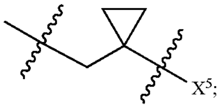
preferably a chemical bond,
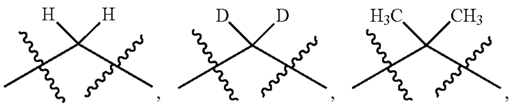
,
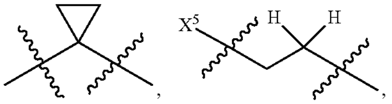
,
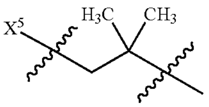
or
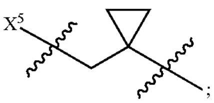
;

more preferably a chemical bond,

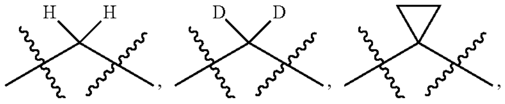

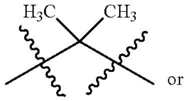

or

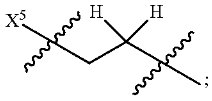

and more preferably a chemical bond or

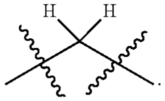 [SMILES: *C*]

In another preferred embodiment, in general formula (1), when $X^5$ is N—$R^a$, $R^a$ is —H, —$(CH_2)_2OR^{11}$, —$(CH_2)_2NR^{11}R^{12}$, (C1-C3) alkyl, (C1-C3) haloalkyl, (C3-C6) cycloalkyl or (4-7 membered) heterocycloalkyl, wherein the (C1-C3) alkyl, (C1-C3) haloalkyl, (C3-C6) cycloalkyl or (4-7 membered) heterocycloalkyl may be optionally substituted with 1, 2, 3 or 4 of the following groups: —H, -D, —F, —OH, —$CH_3$, —$CH_2OCH_3$, —$(CH_2)_2OCH_3$, —$OCH_3$, —$OCH_2CH_3$, —$OCH(CH_3)_2$,

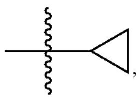

—$OCF_3$, —$CH_2N(CH_3)_2$, —$(CH_2)_2N(CH_3)_2$, —$N(CH_3)_2$ and —CN.

In another preferred embodiment, in general formula (1), when $X^5$ is N—$R^a$, $R^a$ is: —H, —$(CH_2)_2OCH_3$, —$(CH_2)_2OH$, —$(CH_2)_2N(CH_3)_2$,

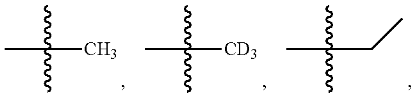

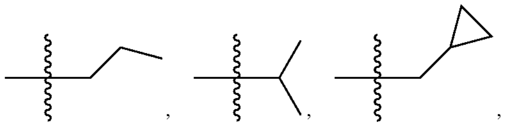

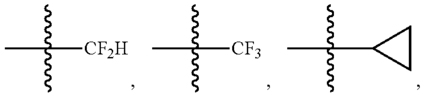

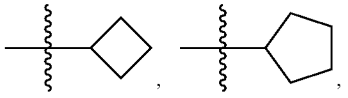

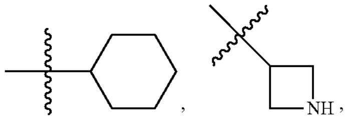

-continued

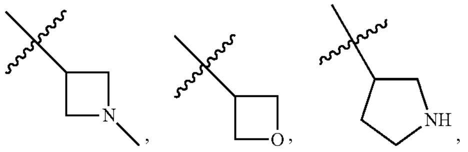

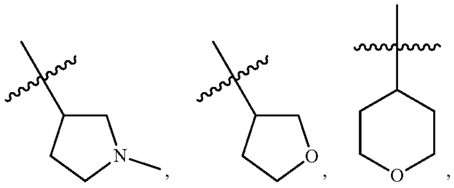

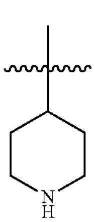

or

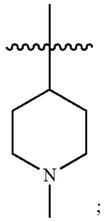

preferably —$(CH_2)_2OH$, —$(CH_2)_2N(CH_3)_2$,

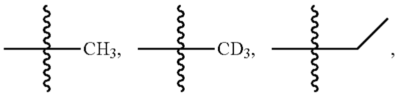

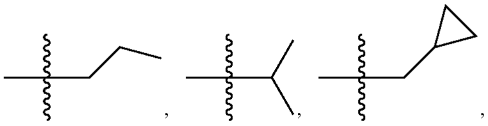

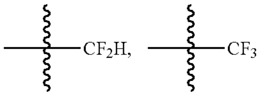

or

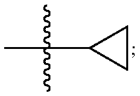

more preferably —$(CH_2)_2OH$, —$(CH_2)_2N(CH_3)_2$,

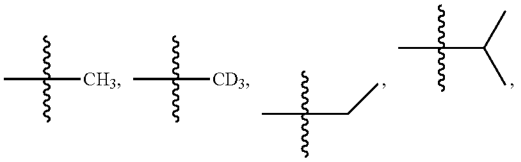

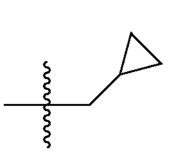

or

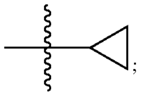

more preferably

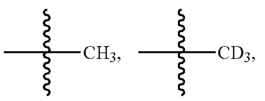

or

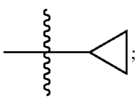 [SMILES: *C1CC1]

and more preferably

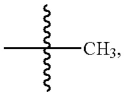

In another preferred embodiment, in general formula (1), when $X^5$ is CH—$R^b$, $R^b$ is —H, —$(CH_2)_2OR^{11}$, —$NR^{11}R^{12}$, —$(CH_2)_2NR^{11}R^{12}$, (C1-C3) alkyl, (C1-C3) haloalkyl, (C3-C6) cycloalkyl or (4-7 membered) heterocycloalkyl, wherein the $R^{11}$, $R^{12}$, (C1-C3) alkyl, (C1-C3) haloalkyl, (C3-C6) cycloalkyl or (4-7 membered) heterocycloalkyl may be optionally substituted with 1, 2, 3 or 4 of the following groups: —H, -D, —F, —OH, —$CH_3$, —$CH_2OCH_3$, —$(CH_2)_2OCH_3$, —$OCH_3$, —$OCH_2CH_3$, —$OCH(CH_3)_2$,

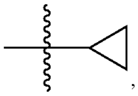
,

—$OCF_3$, —$CH_2N(CH_3)_2$, —$(CH_2)_2N(CH_3)_2$, —$N(CH_3)_2$ and —CN.

In another preferred embodiment, in general formula (1), when $X^5$ is CH—$R^b$, $R^b$ is: —H, —$N(CH_3)_2$, —$N(CD_3)_2$, —$(CH_2)_2OCH_3$, —$(CH_2)_2OH$, —$(CH_2)_2N(CH_3)_2$,

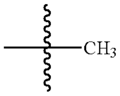 , 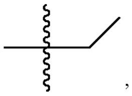 , 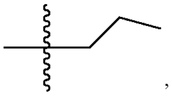 ,

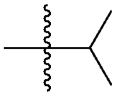 , 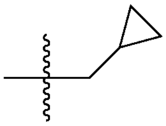 , 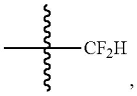 ,

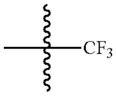 , 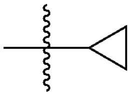 , 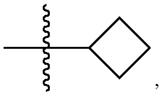 ,

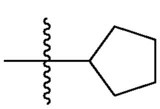 , 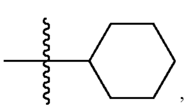 , 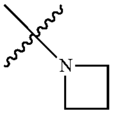 ,

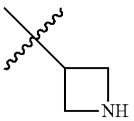 , 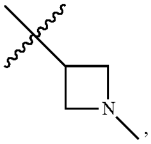 , 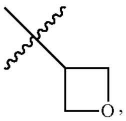 ,

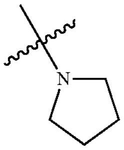 , 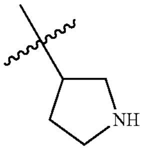 , 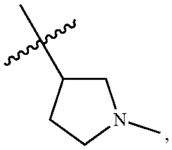 ,

-continued

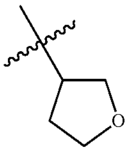 , 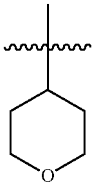 , 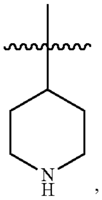 , 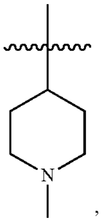 ,

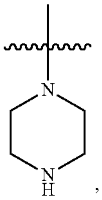 , 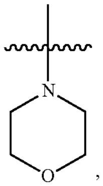 , 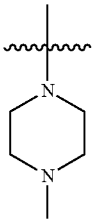 or 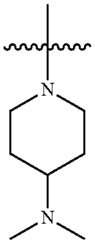 ;

preferably —$N(CH_3)_2$, —$N(CD_3)_2$ or

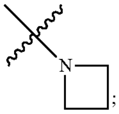 [SMILES: *N1CCC1] ;

and more preferably —$N(CH_3)_2$.

In another preferred embodiment, in general formula (1), $X^3$ is: CH, N or C—$R^c$, wherein the $R^c$ is: —H, —F, —Cl, —Br, —I, —OH, —$CH_3$, —$CH_2OCH_3$,

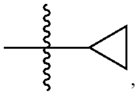
,

—$(CH_2)_2OCH_3$, —$OCH_3$, —$OCH_2CH_3$, —$OCH(CH_3)_2$, —$OCF_3$, —$CH_2N(CH_3)_2$, —$(CH_2)_2N(CH_3)_2$, —$N(CH_3)_2$ or —CN; preferably —H, —F, —Cl, —$CH_3$,

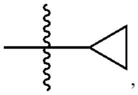
,

—$OCH_3$, —$OCF_3$, —$N(CH_3)_2$ or —CN; and more preferably —H, —F, —$CH_3$,

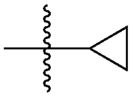

or —$OCH_3$.

In another preferred embodiment, in general formula (1), $X^4$ is: CH, N or C—$R^d$, wherein the $R^d$ is: —H, —F, —Cl, —Br, —I, —OH, —$CH_3$, —$CH_2OCH_3$,

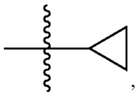,

—$(CH_2)_2OCH_3$, —$OCH_3$, —$OCH_2CH_3$, —$OCH(CH_3)_2$, —$OCF_3$, —$CH_2N(CH_3)_2$, —$(CH_2)_2N(CH_3)_2$, —$N(CH_3)_2$ or —CN; preferably —H, —F, —Cl, —$CH_3$,

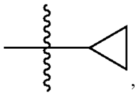,

—$OCH_3$, —$OCF_3$, —$N(CH_3)_2$ or —CN; and more preferably —H, —F, —$CH_3$,

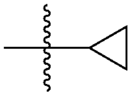

or —$OCH_3$.

In another preferred embodiment, in general formula (1), each $R^2$ is independently —H, -D, —F, —Cl, —Br, —I, —OH, —$CH_2OR_3$, —$CH_2NR^{11}R^{12}$, —$OR^{11}$, —$NR^{11}R^{12}$, —CN, —$C(O)NR^{11}R^{12}$, —$NR^{12}C(O)R^{11}$, —$NR^{12}S(O)_2R^{11}$, —$SR^{11}$, —$S(O)_2R^{11}$, —$S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl, wherein the (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl may be each independently and optionally substituted with 1, 2, 3 or 4 of the following groups: —H, —F, —Cl, —Br, —I, —$CH_3$, —OH, —$OCH_3$, —$N(CH_3)_2$ and —CN; or 2 adjacent $R^2$, together with the atoms to which they are attached, can form (5-7 membered) heterocycloalkyl or (C3-C6) cycloalkyl, wherein the (5-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or 2 $R^2$ on the same carbon atom of ring B, together with the carbon atom to which they are attached, can form (4-7 membered) heterocycloalkyl or (C3-C6) cycloalkyl, wherein the (4-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or $R^2$ and an adjacent $R^e$, together with the atoms to which they are attached, can form (5-7 membered) heterocycloalkyl or (C3-C6) cycloalkyl, wherein the (5-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN.

In another preferred embodiment, in general formula (1), each $R^2$ is independently: —H, -D, —F, —Cl, —Br, —I, —OH, —$CH_2OCH_3$, —$CH_2N(CH_3)_2$, —$OCH_3$, —$OCF_3$, —$NH_2$, —$N(CH_3)_2$, —CN, —$C(O)NH_2$, —$C(O)NH(CH_3)$, —$C(O)N(CH_3)_2$, —$NHC(O)CH_3$, —$N(CH_3)$—$C(O)CH_3$, —$NHS(O)_2CH_3$, —$NCH_3S(O)_2CH_3$, —$SCH_3$, —$S(O)_2CH_3$ 和 —$S(O)_2NH_2$, —$S(O)_2NH(CH_3)$, —$S(O)_2N(CH_3)_2$,

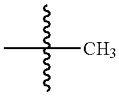, 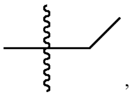, 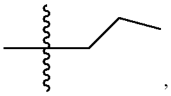,

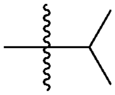, 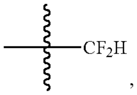, 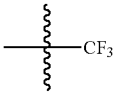,

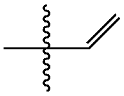, 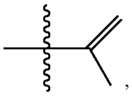, 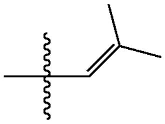,

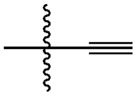, 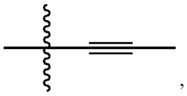, 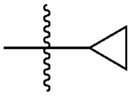,

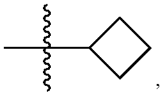, 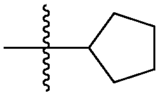,

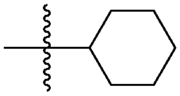, 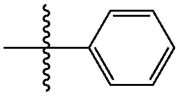,

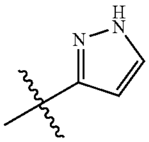, 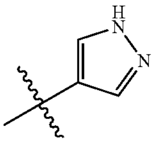, 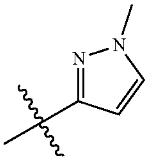,

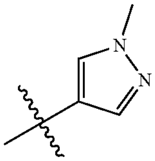, 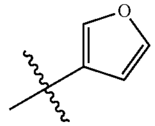, 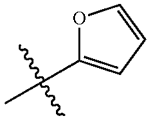,

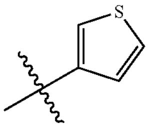, 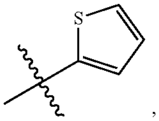, 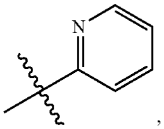,

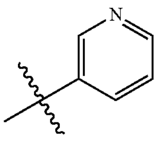, 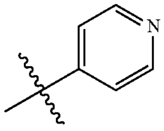, 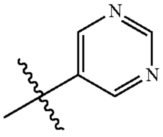,

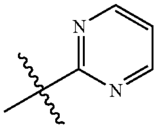, 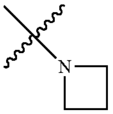, 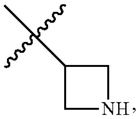,

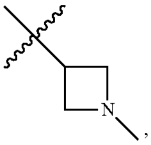, 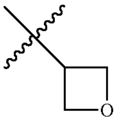, 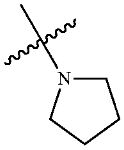,

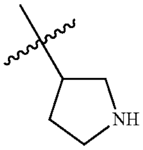, 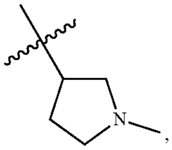, 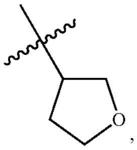,

-continued
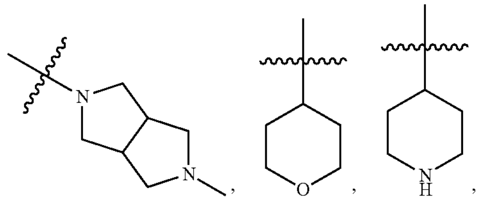
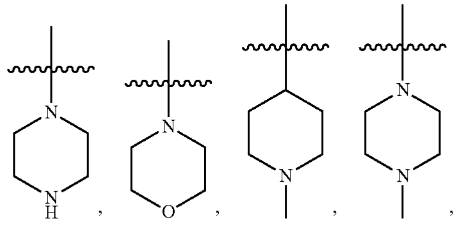
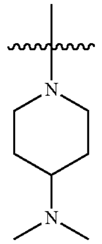
or
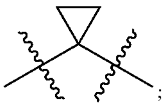
preferably —H, -D, —F, —Cl, —OH, —$OCH_3$, —$OCF_3$, —$NH_2$, —$N(CH_3)_2$, —CN,
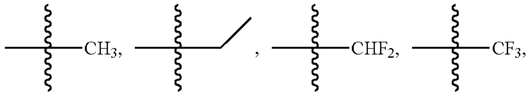
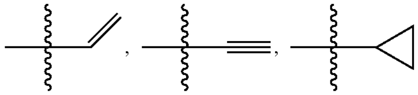
or
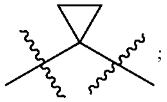
and more preferably —H, —F, —OH, —$NH_2$,
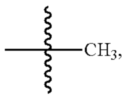
or
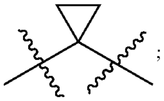
s is preferably 1 or 2; s is more preferably 1; s is more preferably 2.
In another preferred embodiment in general formula (1), the structural unit
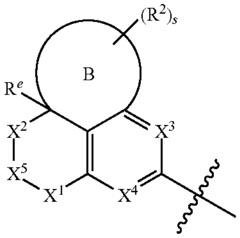
is:
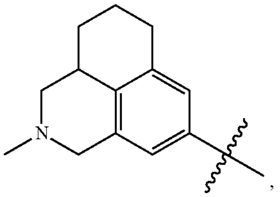
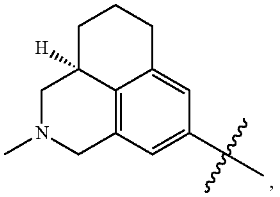
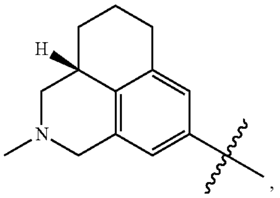
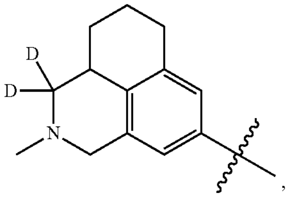
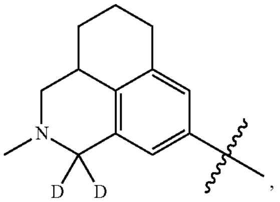
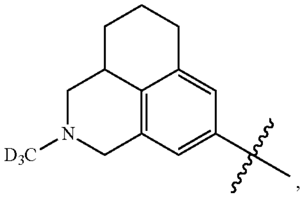
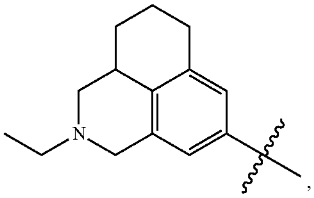

-continued
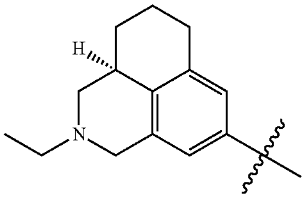
,
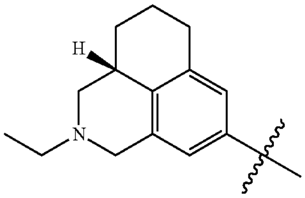
,
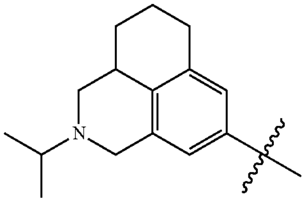
,
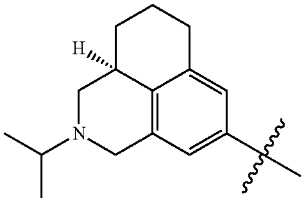
,
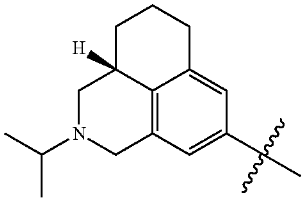
,
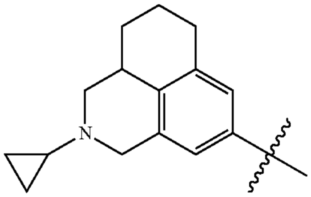
,
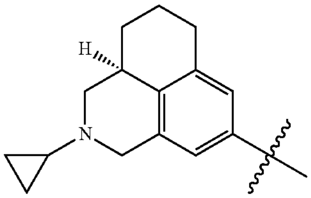
,
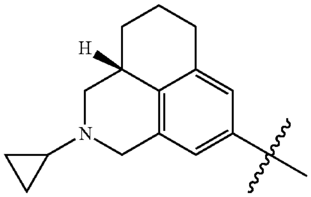
,
-continued
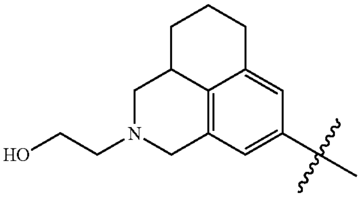
,
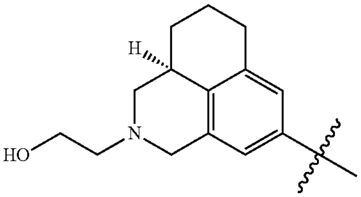
,
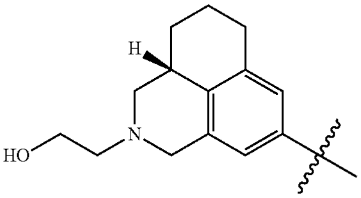
,
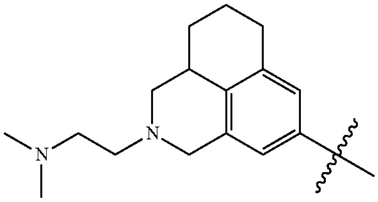
,
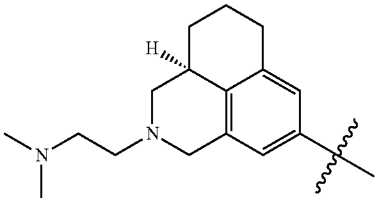
,
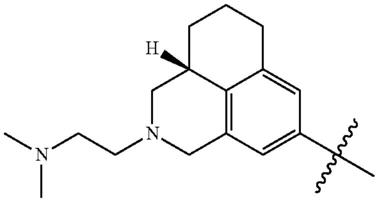
,
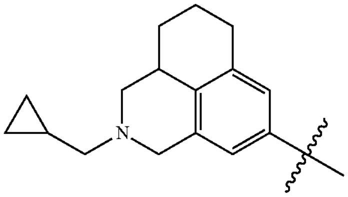
,
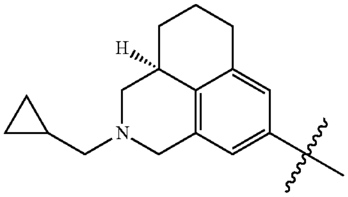
,

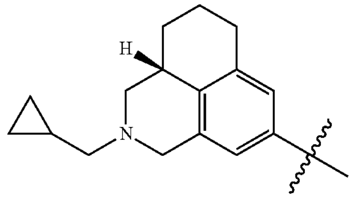
,
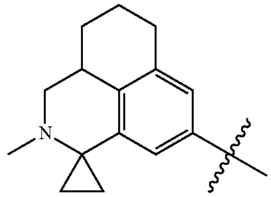
,
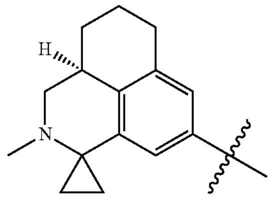
,
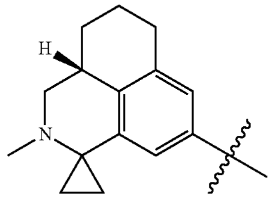
,
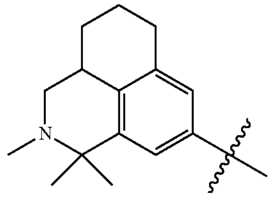
,
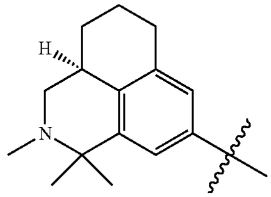
,
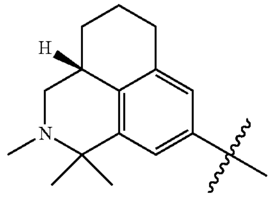
,
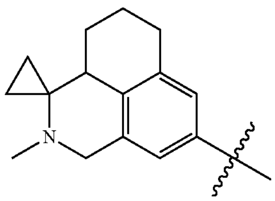
,
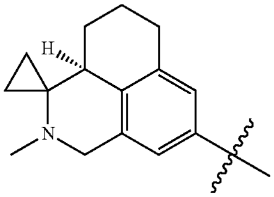
,
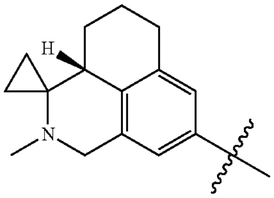
,
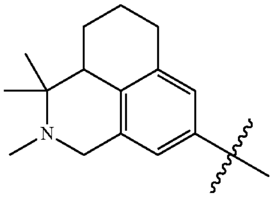
,
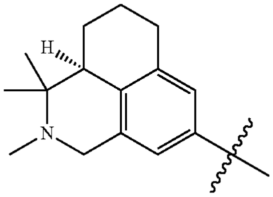
,
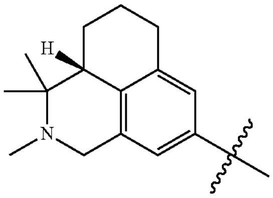
,
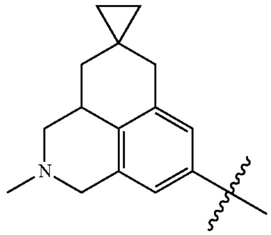
,
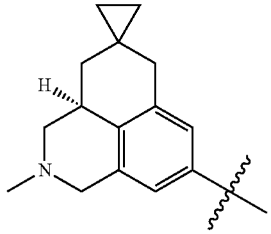
,
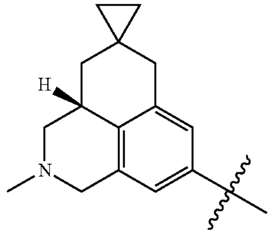
, -continued
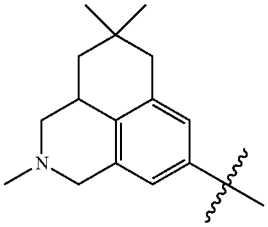
,
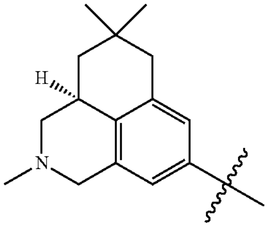
,
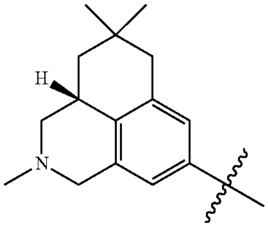
,
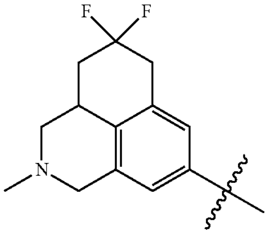
,
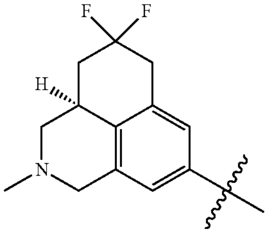
,
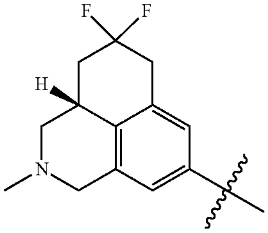
,
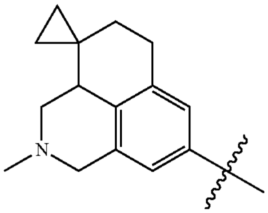
,
-continued
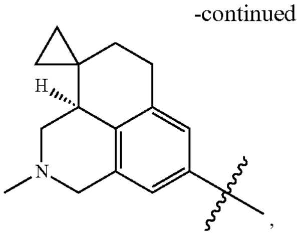
,
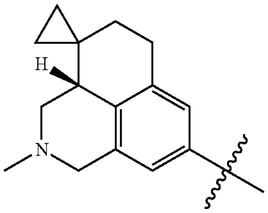
,
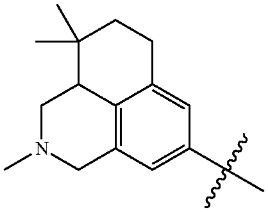
,
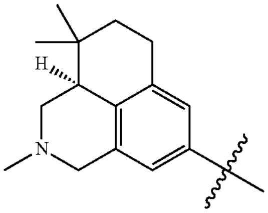
,
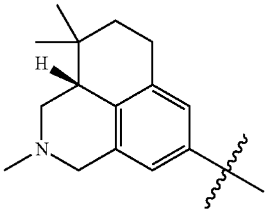
,
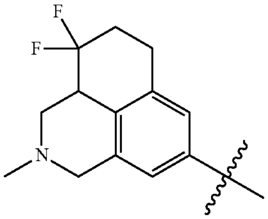
,
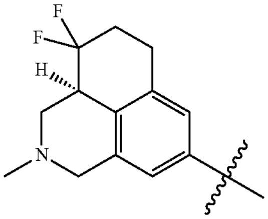
,
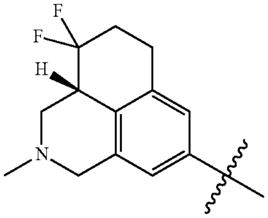
, -continued
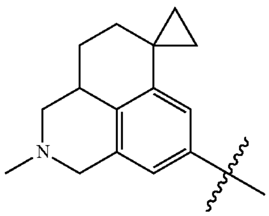
,
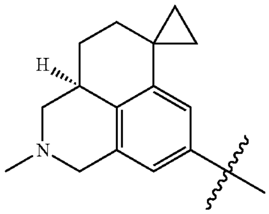
,
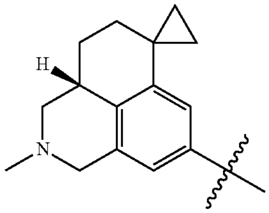
,
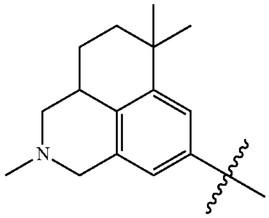
,
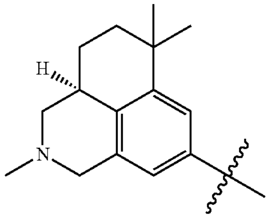
,
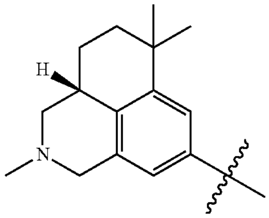
,
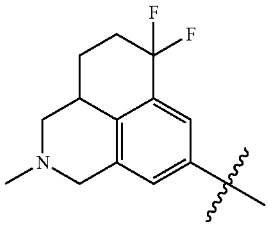
,
-continued
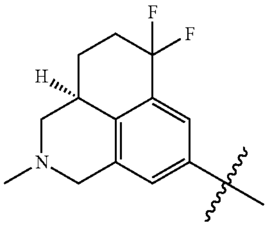
,
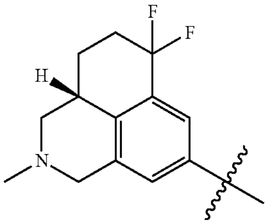
,
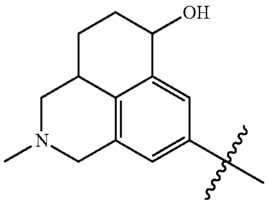
,
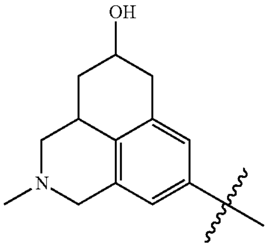
,
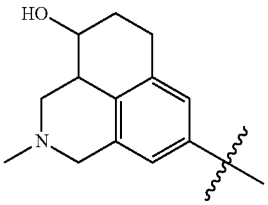
,
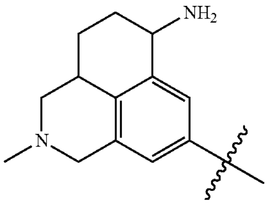
,
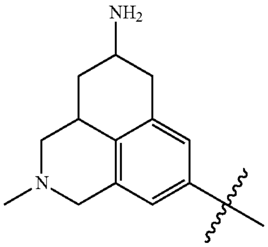
, -continued
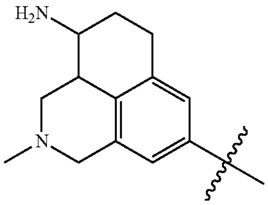,
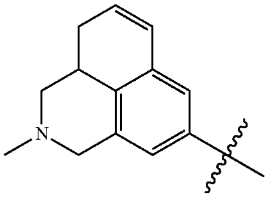,
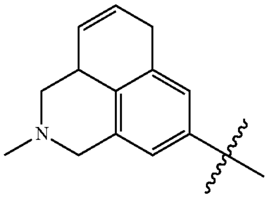,
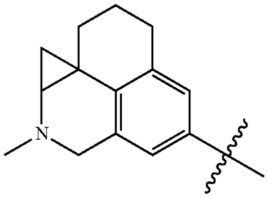,
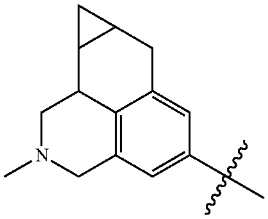,
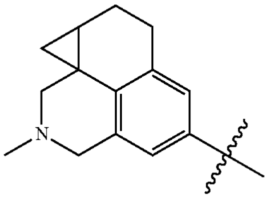,
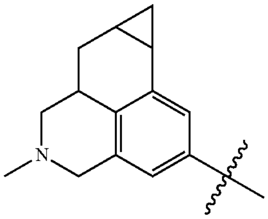,
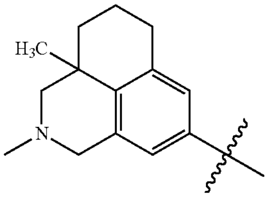,
-continued
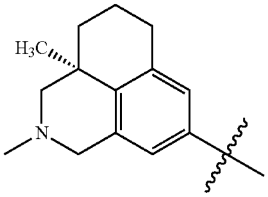,
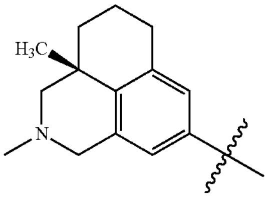,
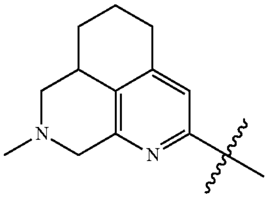,
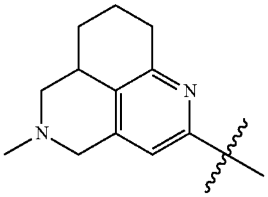,
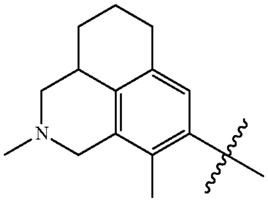,
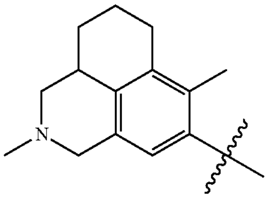,
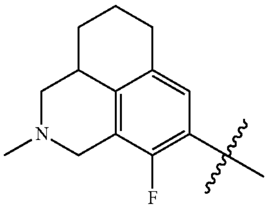,
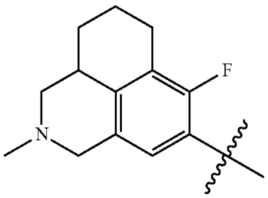, -continued
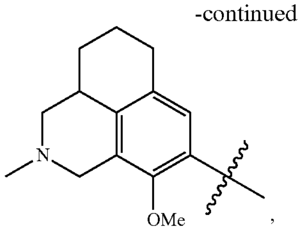,
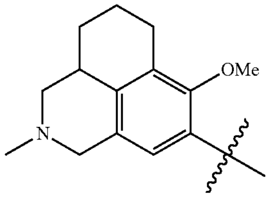,
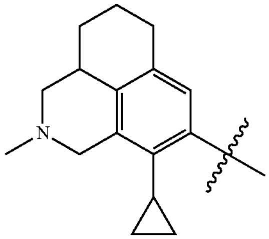,
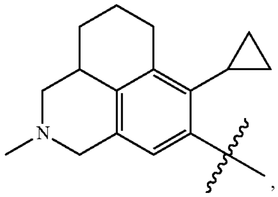,
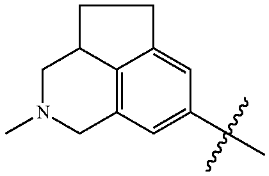,
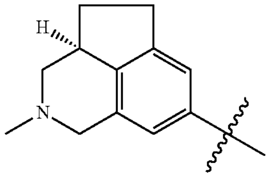,
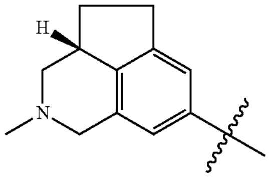,
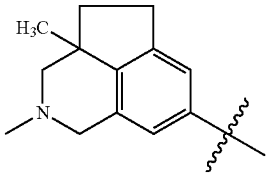,
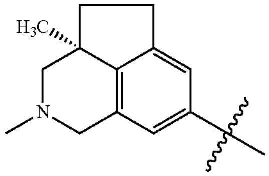,
-continued
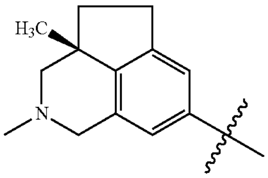,
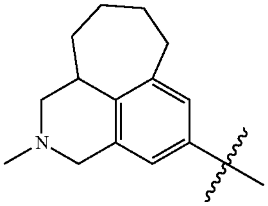,
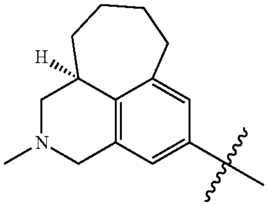,
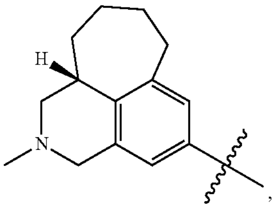,
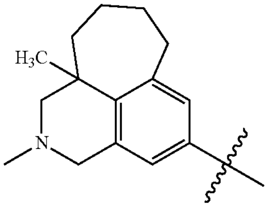,
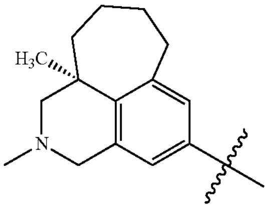,
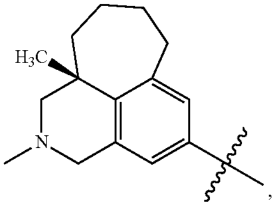,
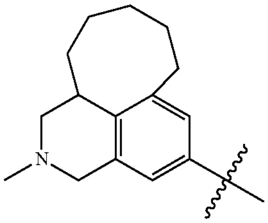, -continued
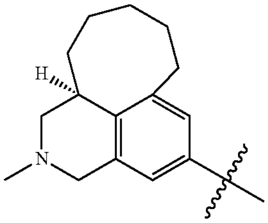
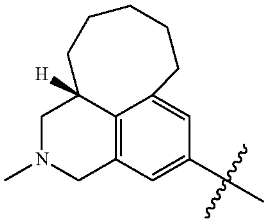
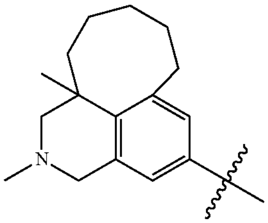
,
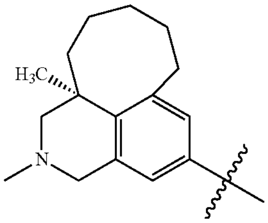
,
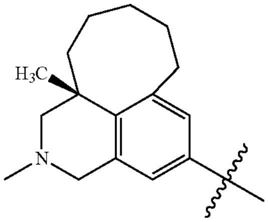
,
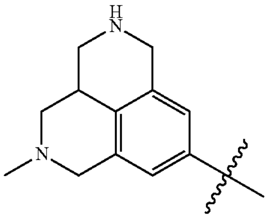
,
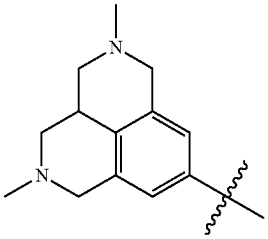
,
-continued
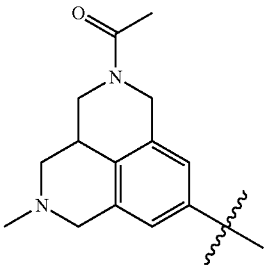
,
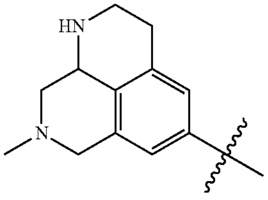
,
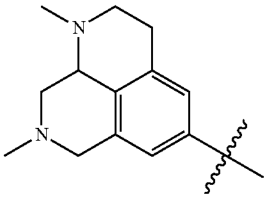
,
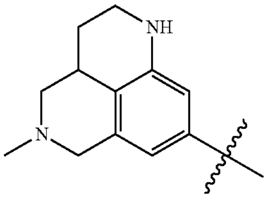
,
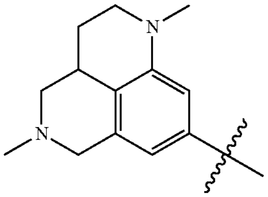
,
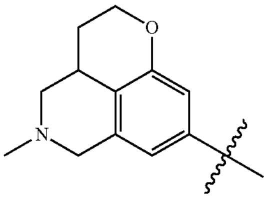
,
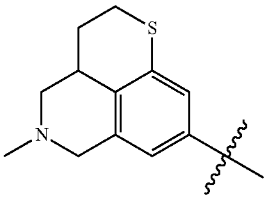
,
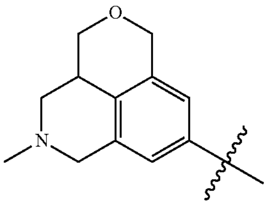
, -continued
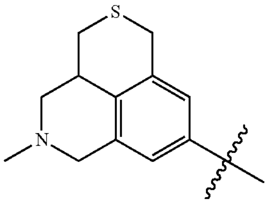
,
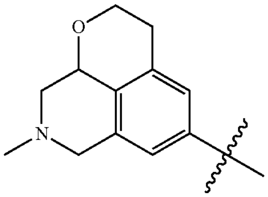
,
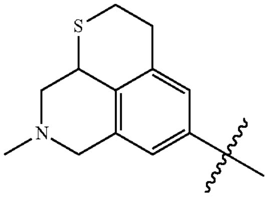
,
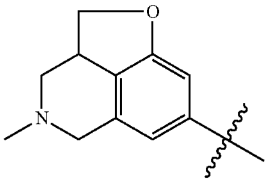
,
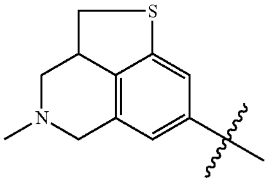
,
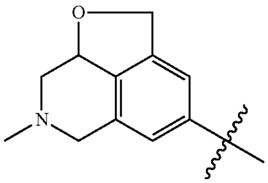
,
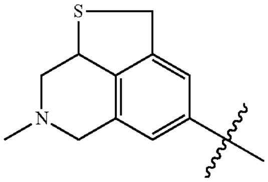
,
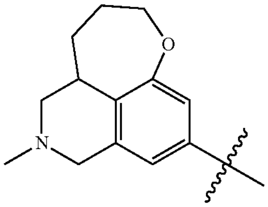
,
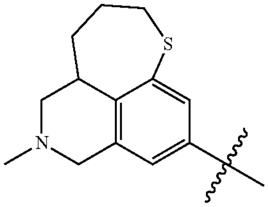
,
-continued
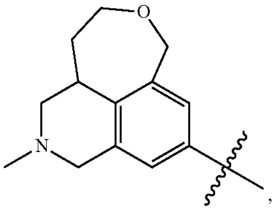
,
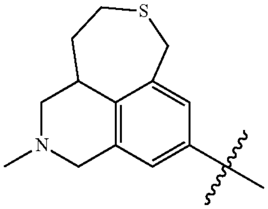
,
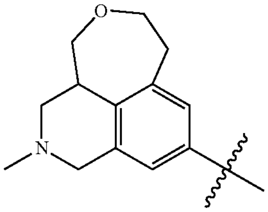
,
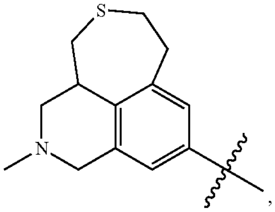
,
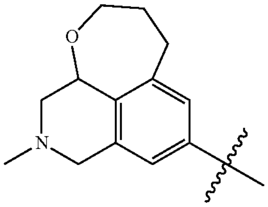
,
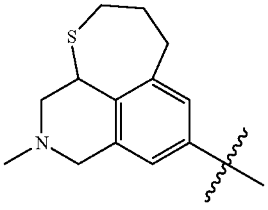
,
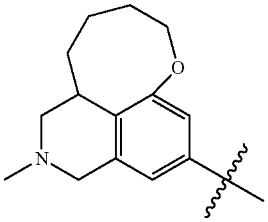
,
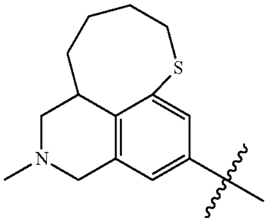
, -continued
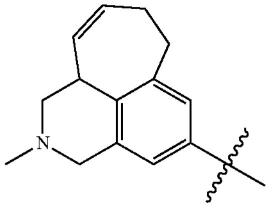
,
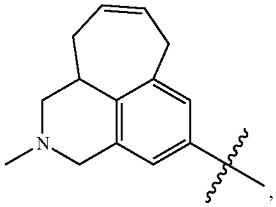
,
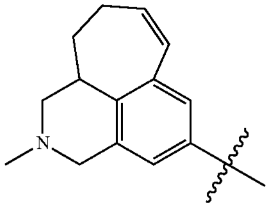
,
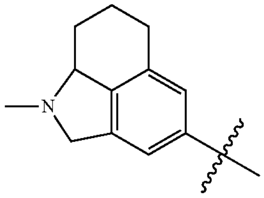
,
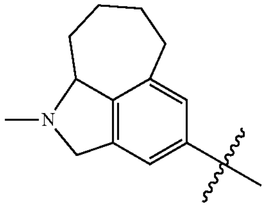
,
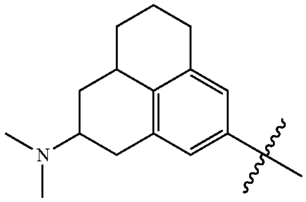
,
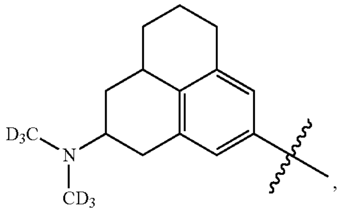
,
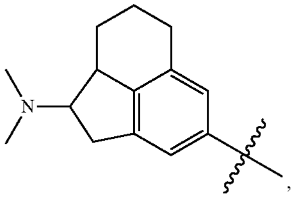
,
-continued
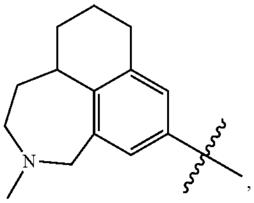
,
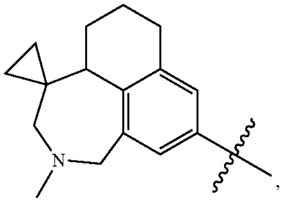
,
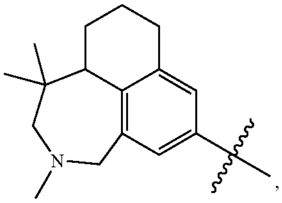
,
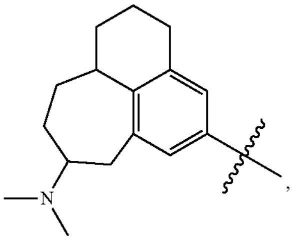
,
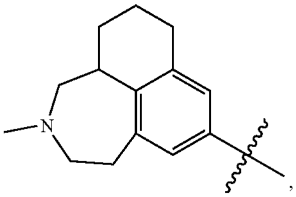
,
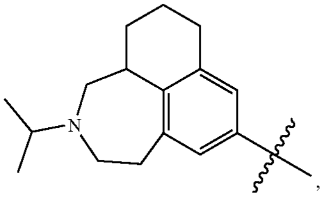
,
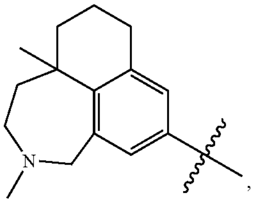
,
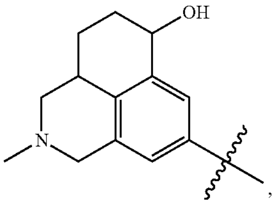
, -continued
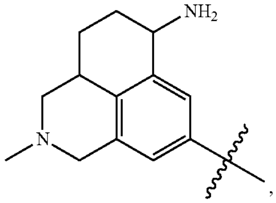
,
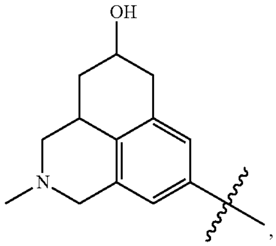
,
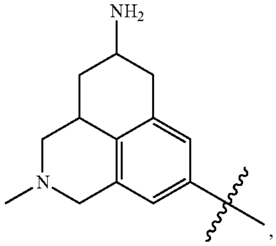
,
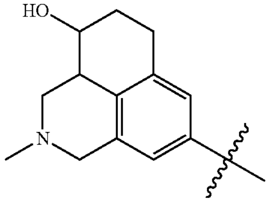
or
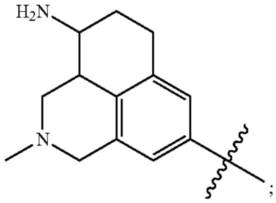
;
preferably
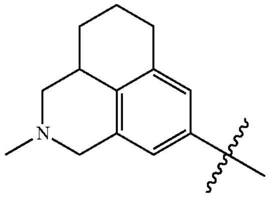
,
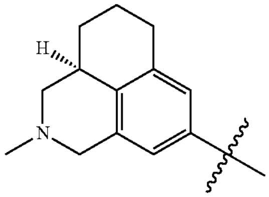
,
-continued
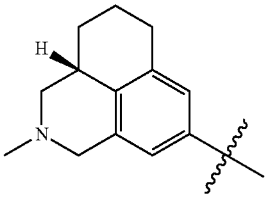
,
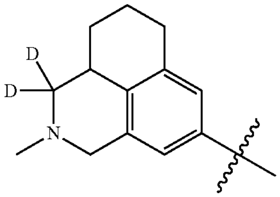
,
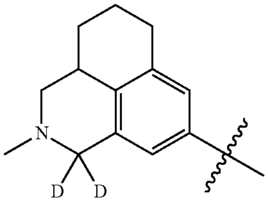
,
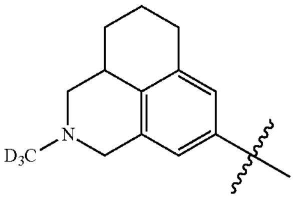
,
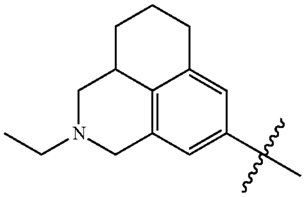
,
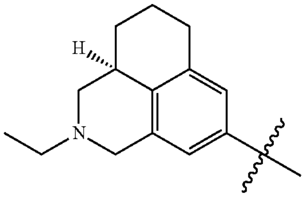
,
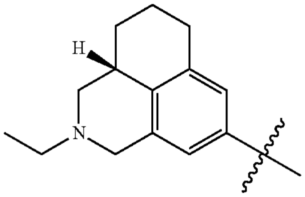
,
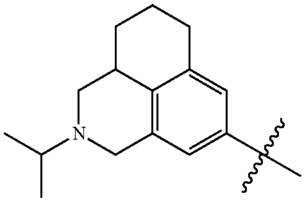
, -continued
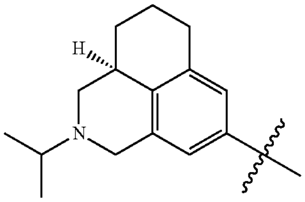
,
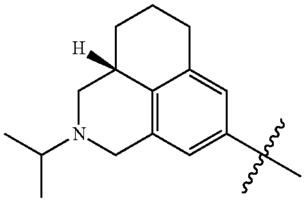
,
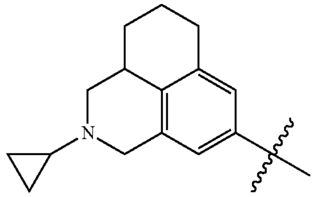
,
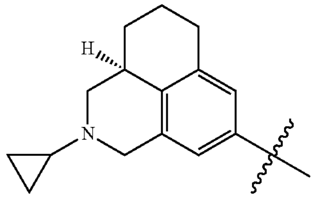
,
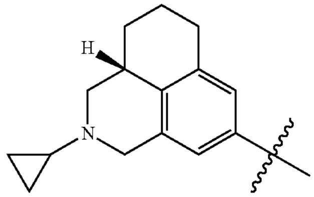
,
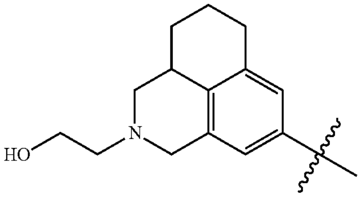
,
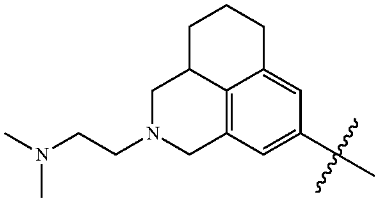
,
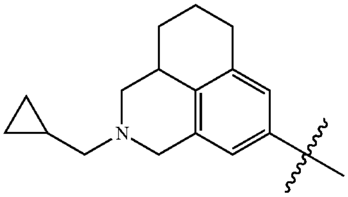
,
-continued
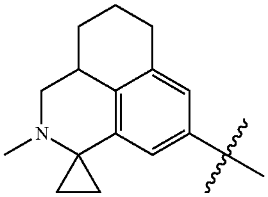
,
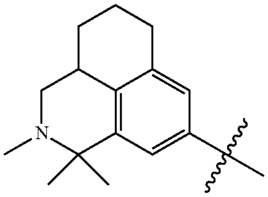
,
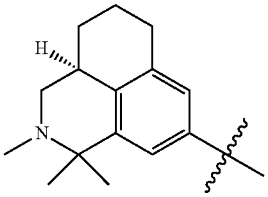
,
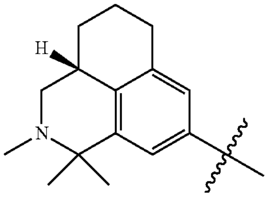
,
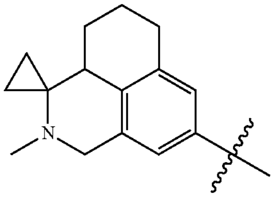
,
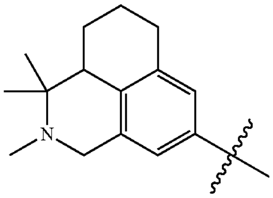
,
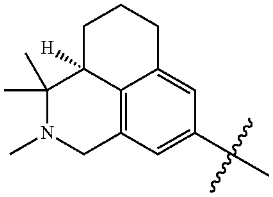
,
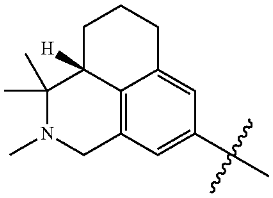
, -continued
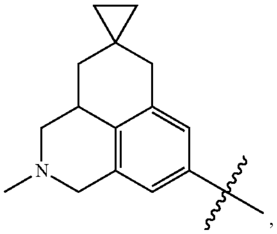
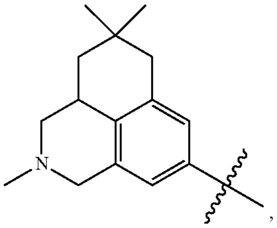
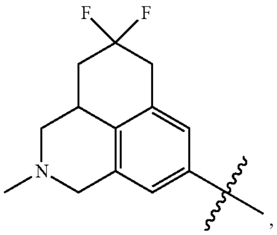
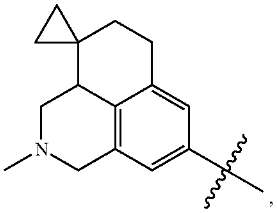
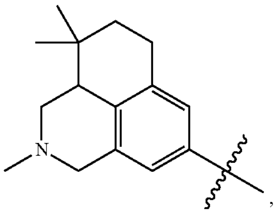
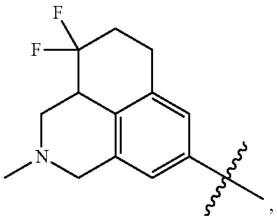
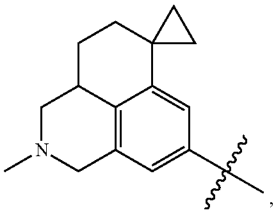
-continued
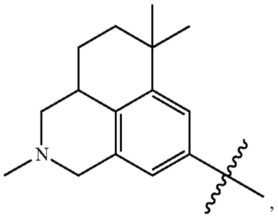
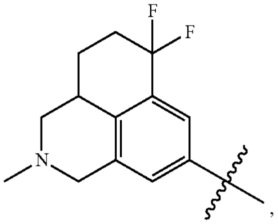
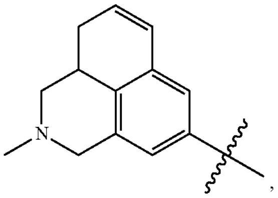
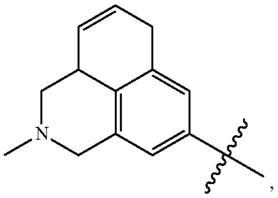
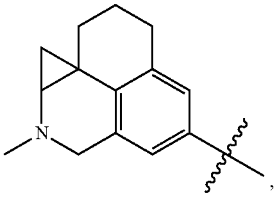
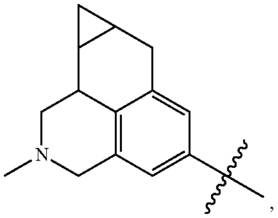
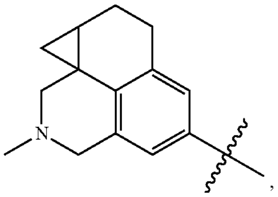
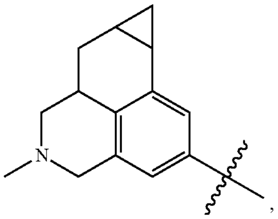

-continued
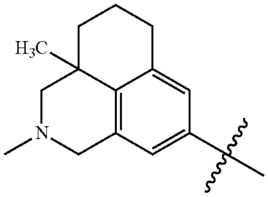
,
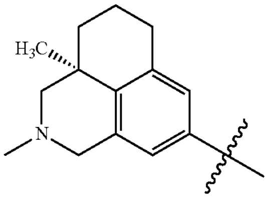
,
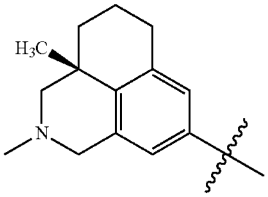
,
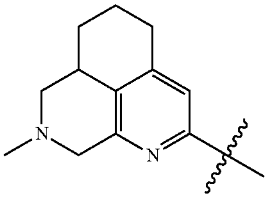
,
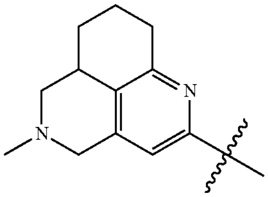
,
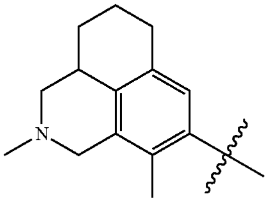
,
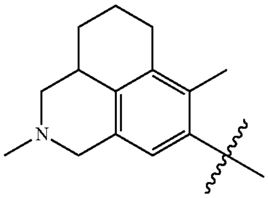
,
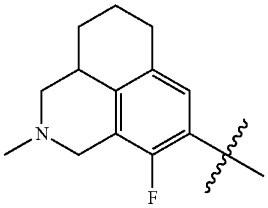
,
-continued
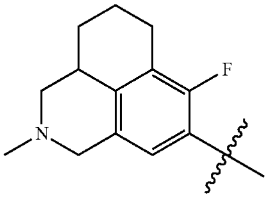
,
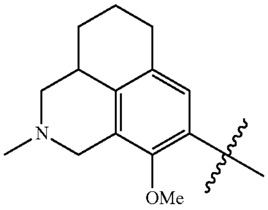
,
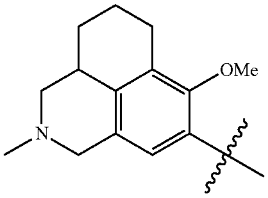
,
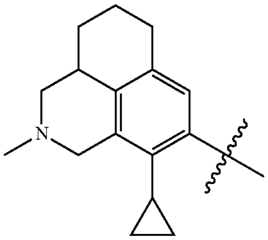
,
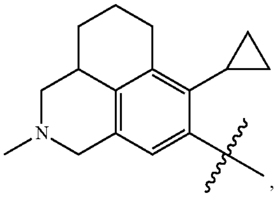
,
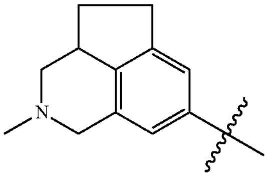
,
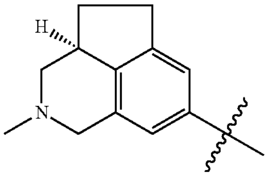
,
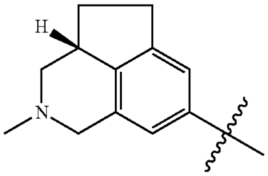
, -continued
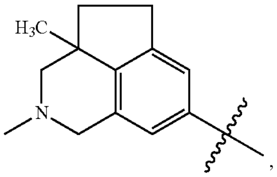
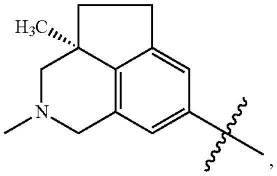
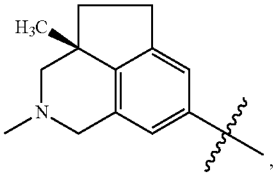
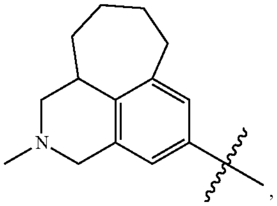
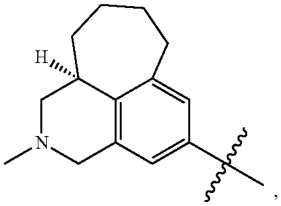
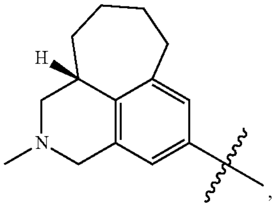
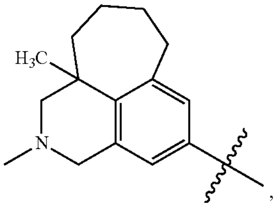
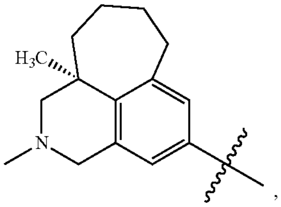
-continued
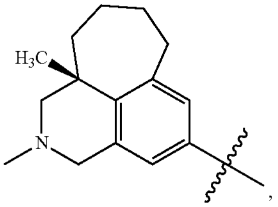
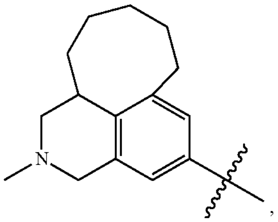
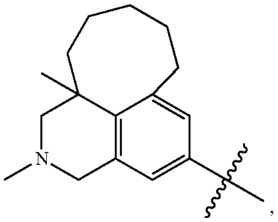
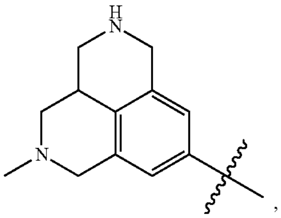
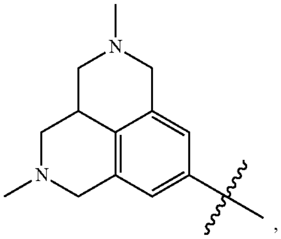
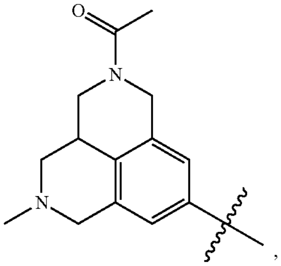
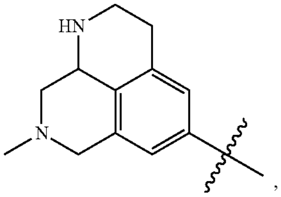

-continued
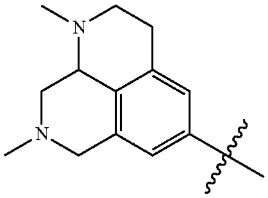,
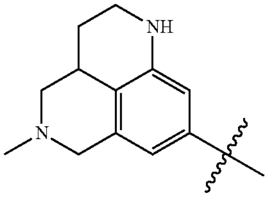,
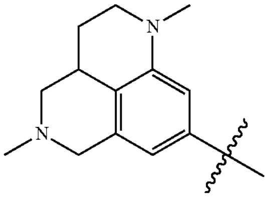,
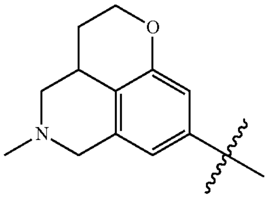,
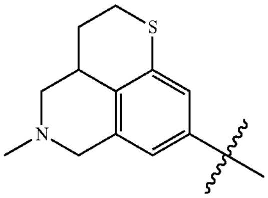,
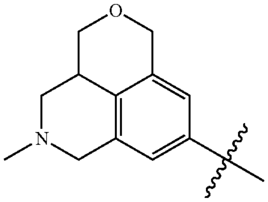,
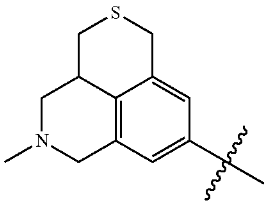,
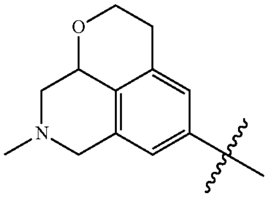,
-continued
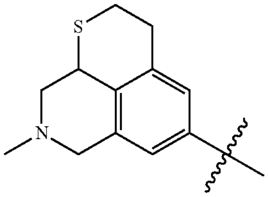,
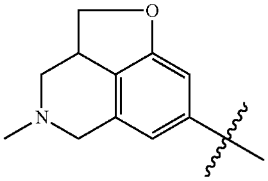,
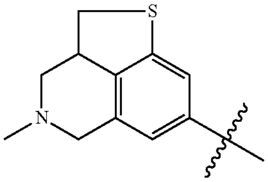,
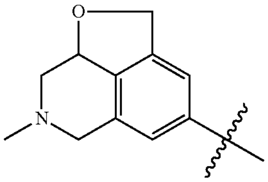,
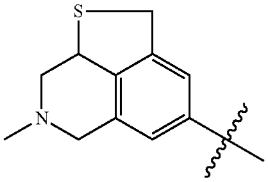,
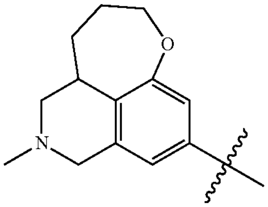,
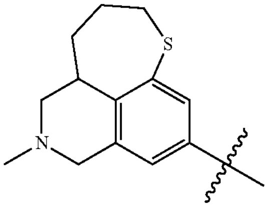,
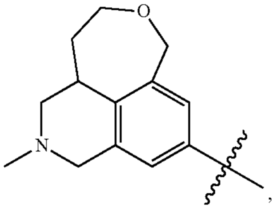, -continued
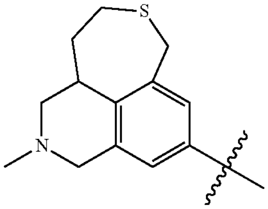
,
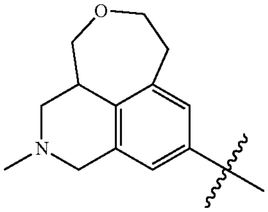
,
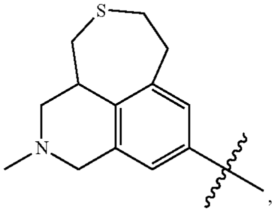
,
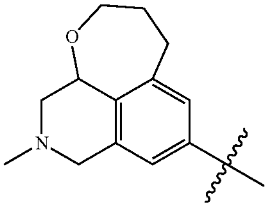
,
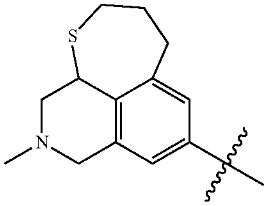
,
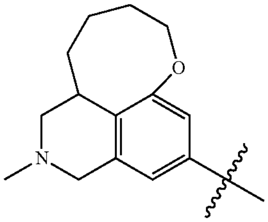
,
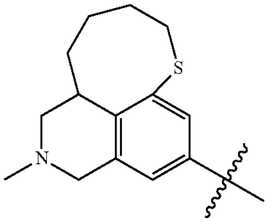
,
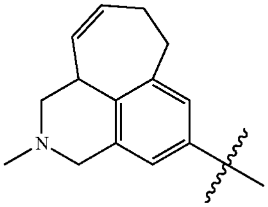
,
-continued
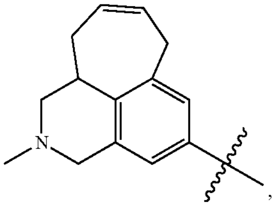
,
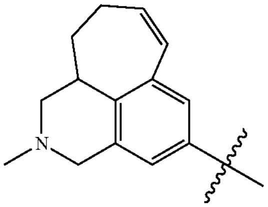
,
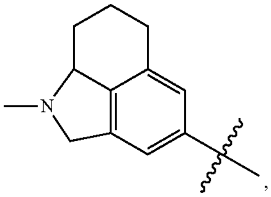
,
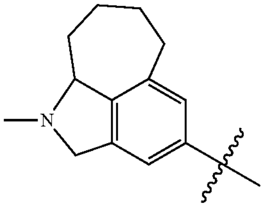
,
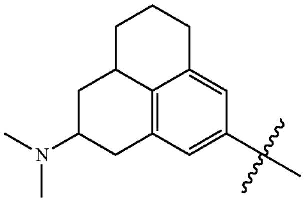
,
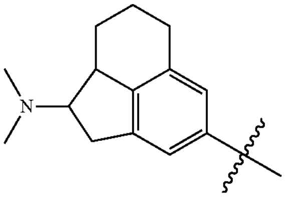
,
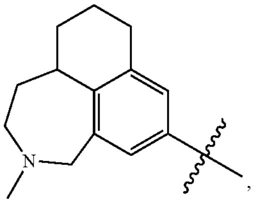
,
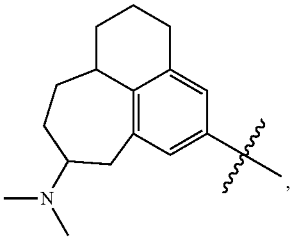
, -continued

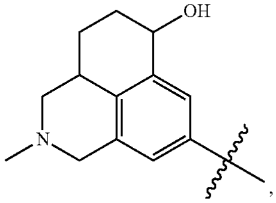
,

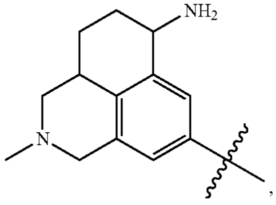
,

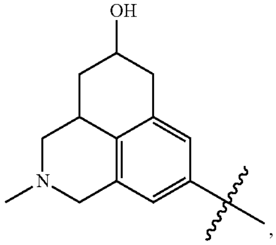
,

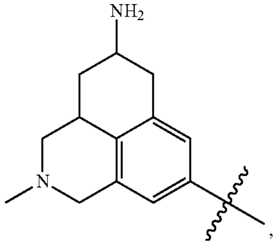
,

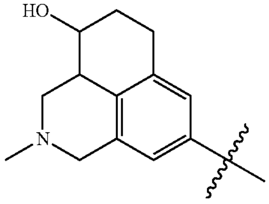
or

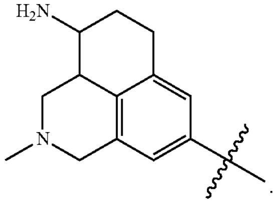
.

In some embodiments of the present invention, the present invention provides a compound of general formula (2) or an isomer, a crystalline form, a pharmaceutically acceptable salt, a hydrate or a solvate thereof:

(2)

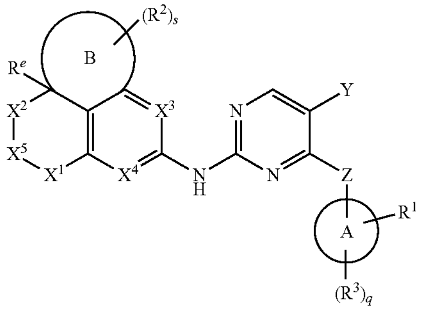

wherein A, B, Y, Z, $R^1$, $R^2$, $R^3$, $R^e$, $X^1$, $X^2$, $X^3$, $X^4$, $X^5$, q and s are as defined above and exemplified in specific embodiments.

In some embodiments of the present invention, the present invention provides a compound of general formula (3a) or general formula (3b) or an isomer, a crystalline form, a pharmaceutically acceptable salt, a hydrate or a solvate thereof:

(3a)

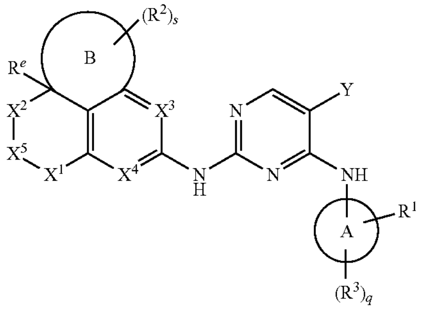

(3b)

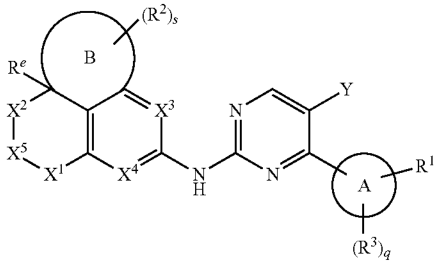

wherein A, B, Y, $R^1$, $R^2$, $R^3$, $R^e$, $X^1$, $X^2$, $X^3$, $X^4$, $X^5$, q and s are as defined above and exemplified in specific embodiments.

In some embodiments of the present invention, the present invention provides a compound of general formula (4a), general formula (4b) or general formula (4c) or an isomer, a crystalline form, a pharmaceutically acceptable salt, a hydrate or a solvate thereof:

(4a)

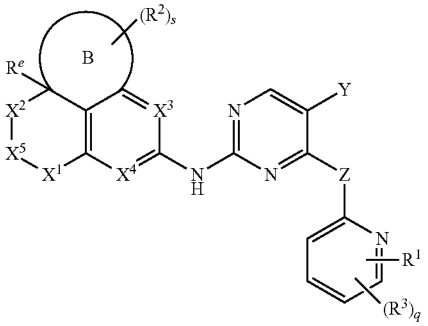

(4b)

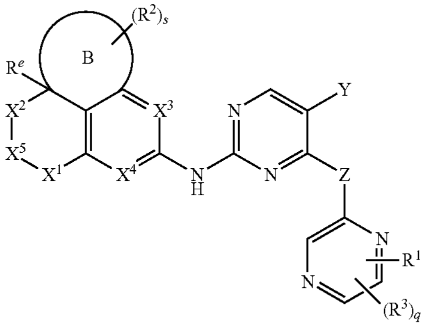

(4c)

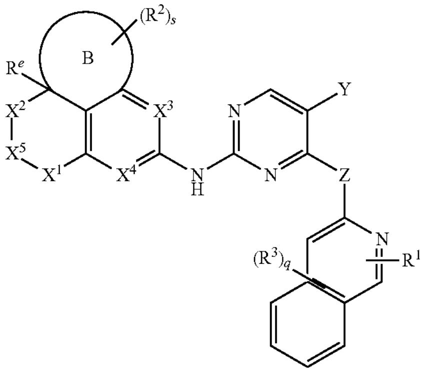

wherein B, Y, Z, $R^1$, $R^2$, $R^3$, $R^e$, $X^1$, $X^2$, $X^3$, $X^4$, $X^5$, q and s are as defined above and exemplified in specific embodiments.

In some embodiments of the present invention, the present invention provides a compound of general formula (5a), general formula (5b) or general formula (5c) or an isomer, a crystalline form, a pharmaceutically acceptable salt, a hydrate or a solvate thereof:

(5a)

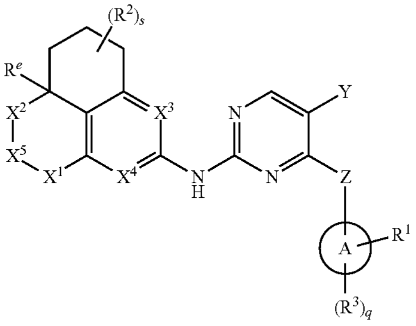

-continued (5b)

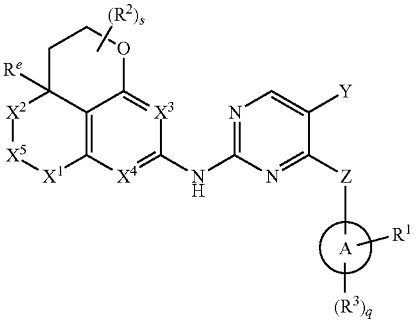

(5c)

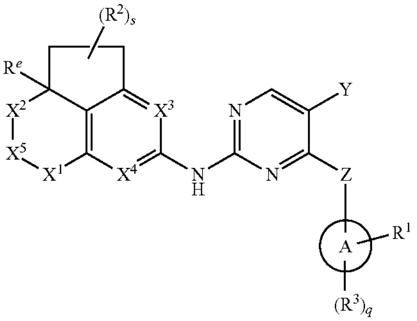

wherein A, Y, Z, $R^1$, $R^2$, $R^3$, $R^e$, $X^1$, $X^2$, $X^3$, $X^4$, $X^5$, q and s are as defined above and exemplified in specific embodiments.

In some embodiments of the present invention, the present invention provides a compound of general formula (6a), general formula (6b) or general formula (6c) or an isomer, a crystalline form, a pharmaceutically acceptable salt, a hydrate or a solvate thereof:

(6a)

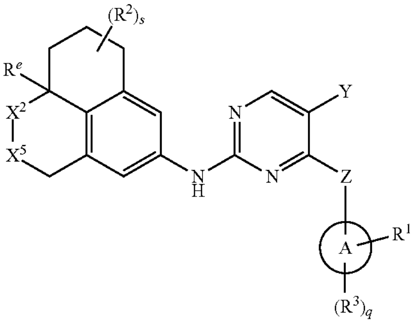

(6b)

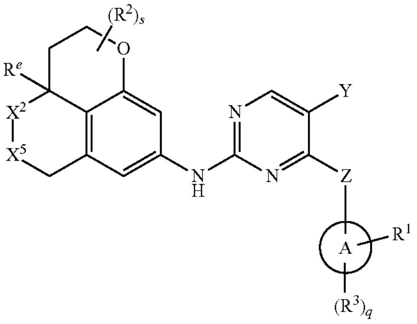

-continued (6c)

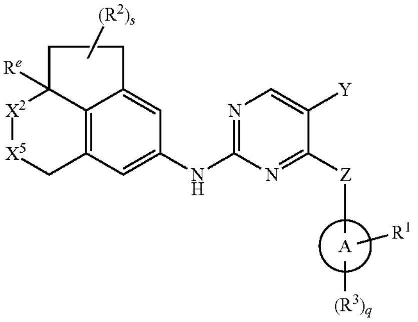

wherein A, Y, Z, $R^1$, $R^2$, $R^3$, $R^e$, $X^2$, $X^5$, q and s are as defined above and exemplified in specific embodiments.

In some embodiments of the present invention, the present invention provides a compound of general formula (7a), general formula (7b), general formula (7c), general formula (7d), general formula (7e) or general formula (7f) or an isomer, a crystalline form, a pharmaceutically acceptable salt, a hydrate or a solvate thereof:

(6a)

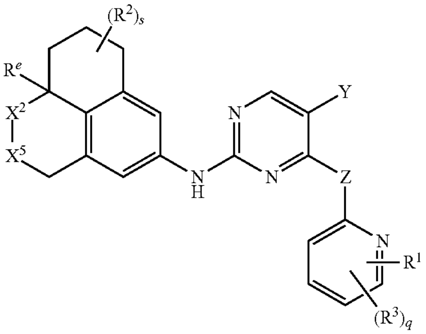

(6b)

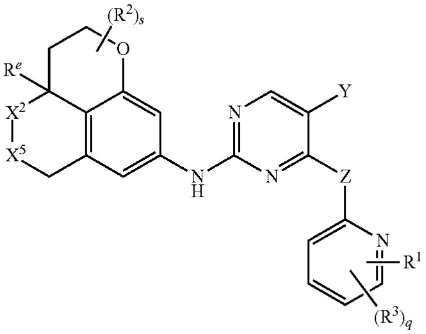

(6c)

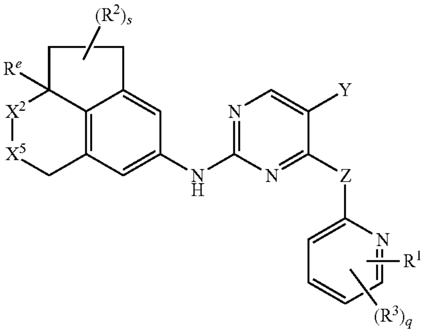

-continued (6d)

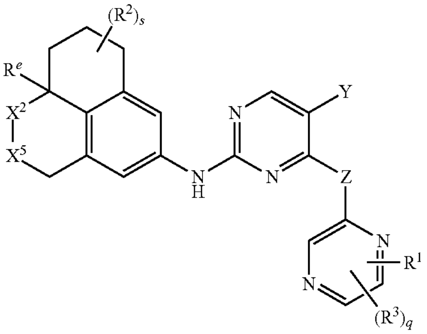

(6e)

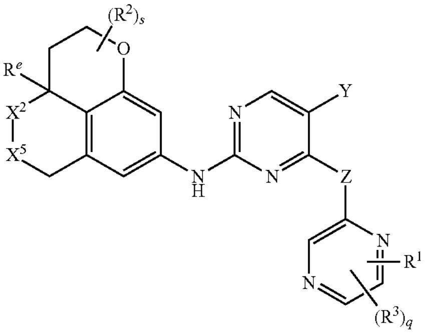

(6f)

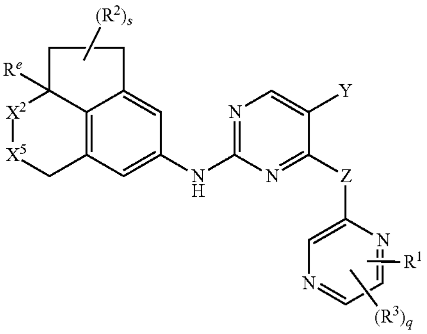

wherein Y, Z, $R^1$, $R^2$, $R^3$, $R^e$, $X^2$, $X^5$, q and s are as defined above and exemplified in specific embodiments.

In various embodiments, representative compounds of the present invention have one of the following structures:

1

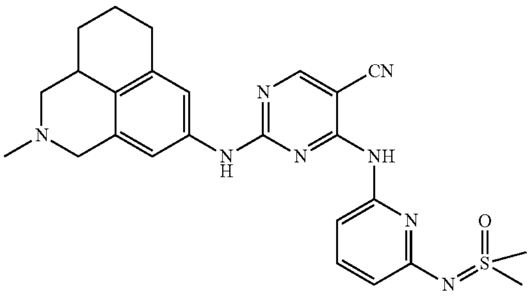

-continued
2
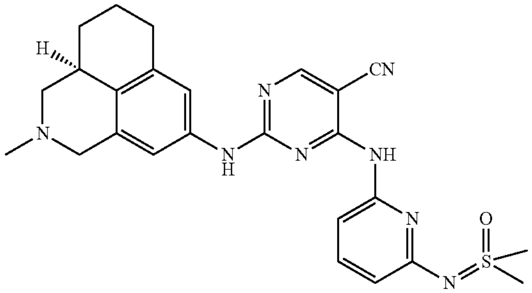
3
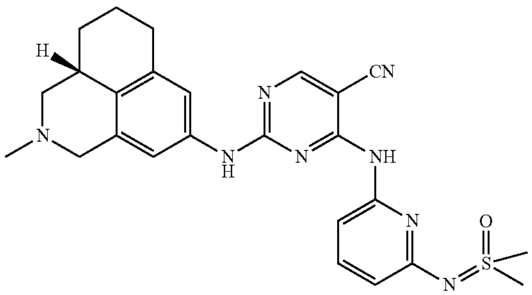
4
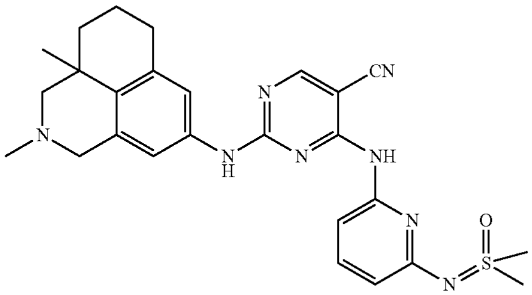
5
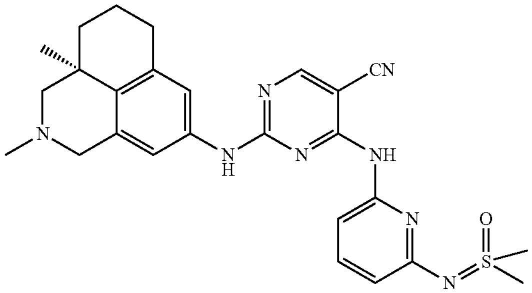
6
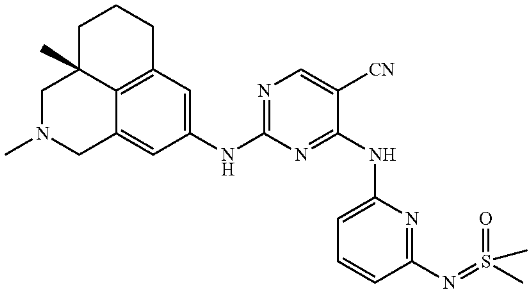
-continued
7
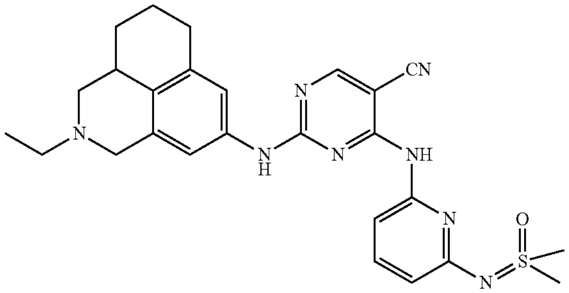 [SMILES: CCN1Cc2cc(Nc3ncc(C#N)c(Nc4cccc(N=S(C)(C)=O)n4)n3)cc3c2C(CCC3)C1]
8
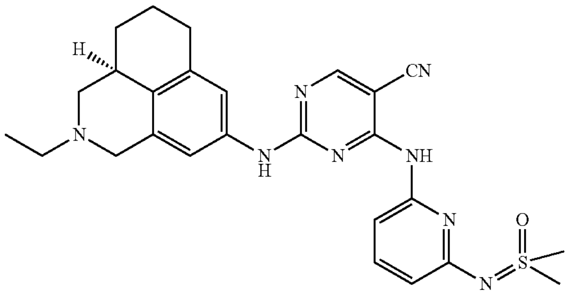 [SMILES: CCN1Cc2cc(Nc3ncc(C#N)c(Nc4cccc(N=S(C)(C)=O)n4)n3)cc3c2[C@H](CCC3)C1]
9
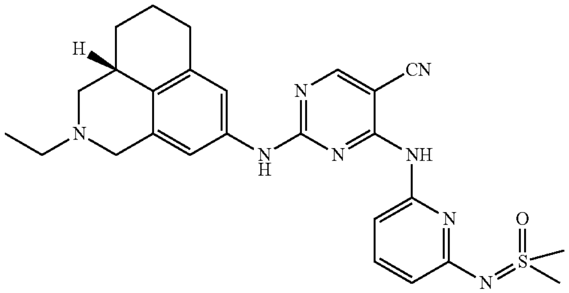 [SMILES: CCN1Cc2cc(Nc3ncc(C#N)c(Nc4cccc(N=S(C)(C)=O)n4)n3)cc3c2[C@@H](CCC3)C1]
10
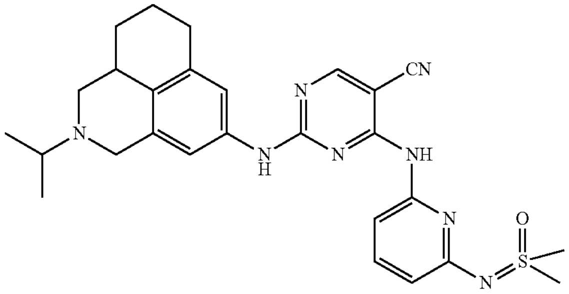 [SMILES: CC(C)N1Cc2cc(Nc3ncc(C#N)c(Nc4cccc(N=S(C)(C)=O)n4)n3)cc3c2C(CCC3)C1]
11
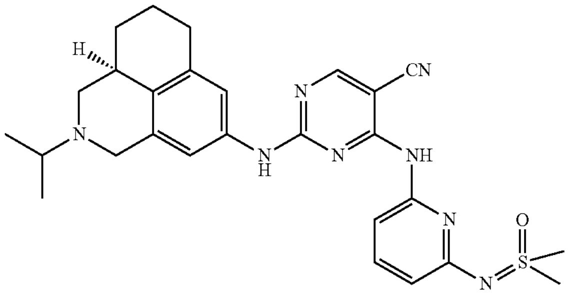 [SMILES: CC(C)N1Cc2cc(Nc3ncc(C#N)c(Nc4cccc(N=S(C)(C)=O)n4)n3)cc3c2[C@H](CCC3)C1]

12
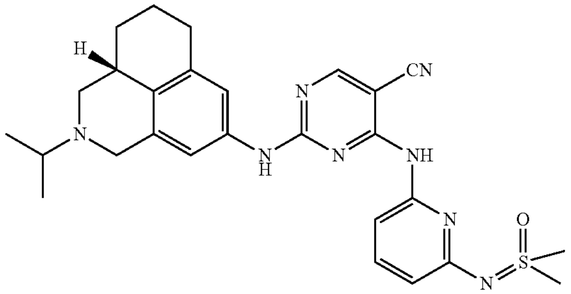 [SMILES: CC(C)N1Cc2cc(Nc3ncc(C#N)c(Nc4cccc(N=S(C)(C)=O)n4)n3)cc3c2[C@@H](CCC3)C1]
13
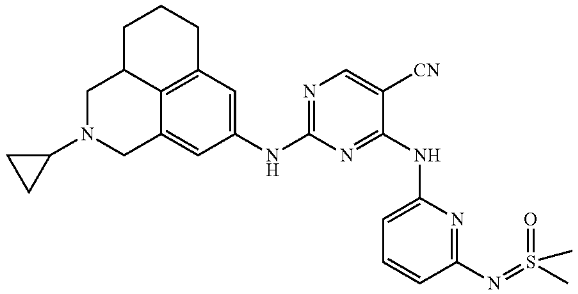 [SMILES: CS(C)(=O)=Nc1cccc(Nc2nc(Nc3cc4c5c(c3)CN(C3CC3)CC5CCC4)ncc2C#N)n1]
14
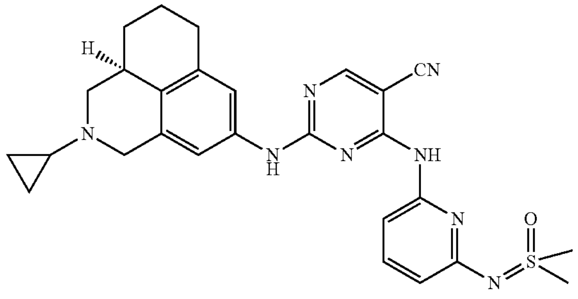 [SMILES: CS(C)(=O)=Nc1cccc(Nc2nc(Nc3cc4c5c(c3)CN(C3CC3)C[C@H]5CCC4)ncc2C#N)n1]
15
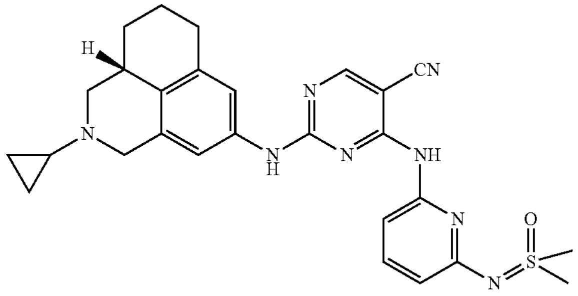 [SMILES: CS(C)(=O)=Nc1cccc(Nc2nc(Nc3cc4c5c(c3)CN(C3CC3)C[C@@H]5CCC4)ncc2C#N)n1]
16
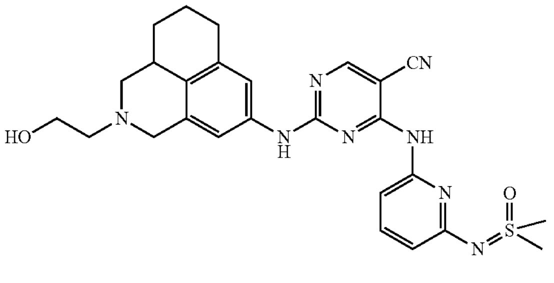 [SMILES: CS(C)(=O)=Nc1cccc(Nc2nc(Nc3cc4c5c(c3)CN(CCO)CC5CCC4)ncc2C#N)n1]
17
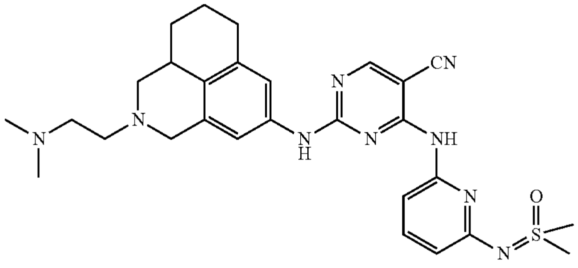
18
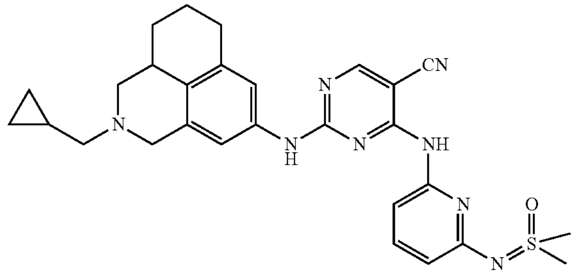 [SMILES: CS(C)(=O)=Nc1cccc(Nc2nc(Nc3cc4c5c(c3)CN(CC3CC3)CC5CCC4)ncc2C#N)n1]
19
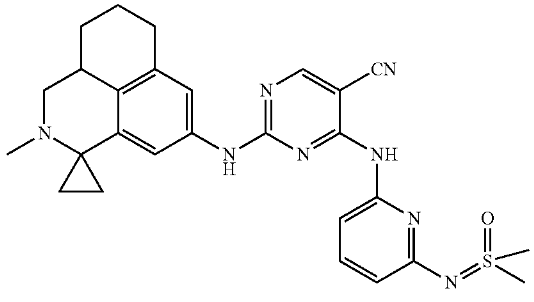
20
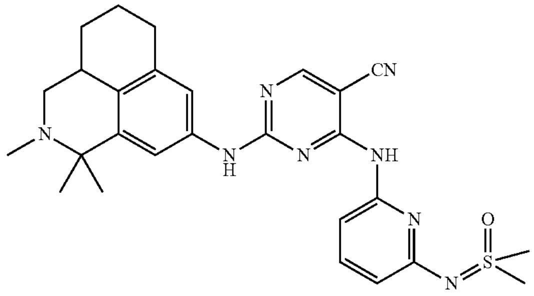
21
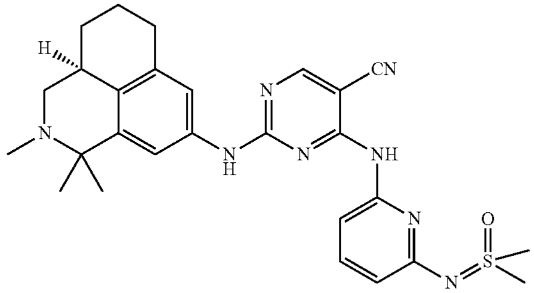

-continued
22
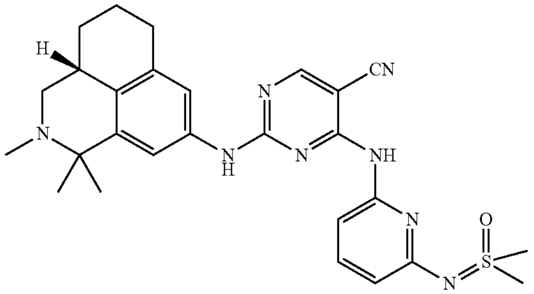
23
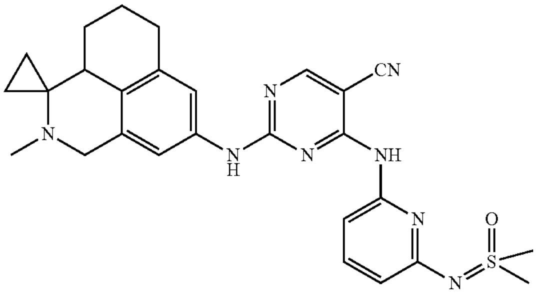 [SMILES: CN1Cc2cc(Nc3ncc(C#N)c(Nc4cccc(N=S(C)(C)=O)n4)n3)cc3c2C(CCC3)C12CC2]
24
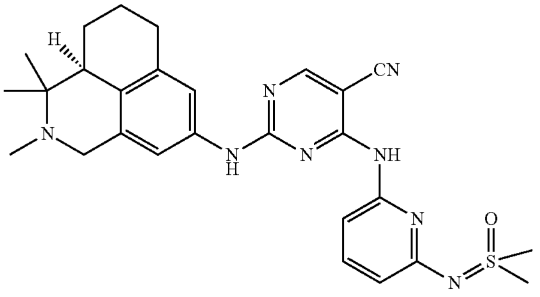
25
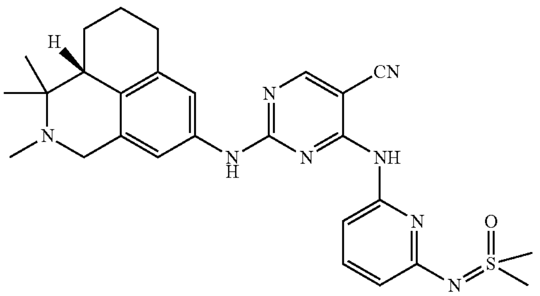
26
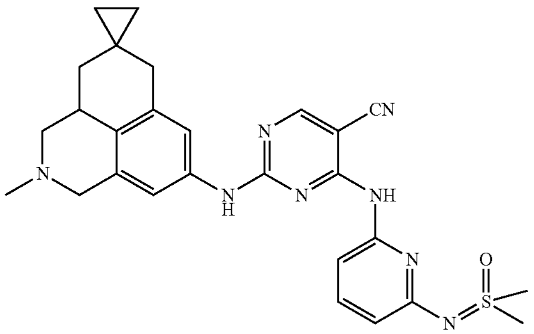
-continued
27
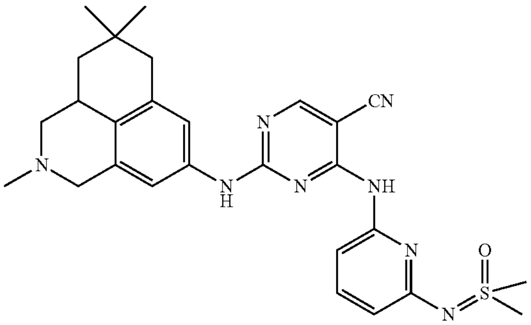
28
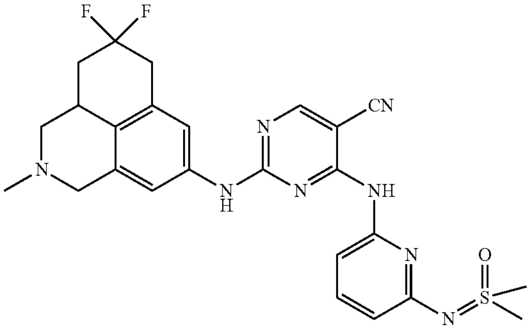
29
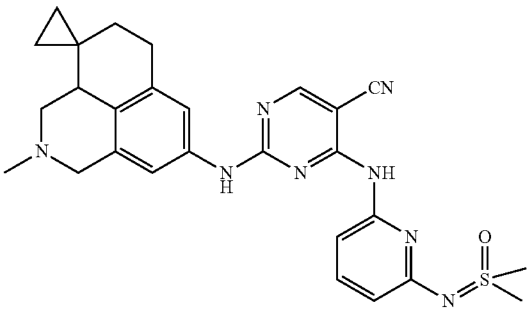
30
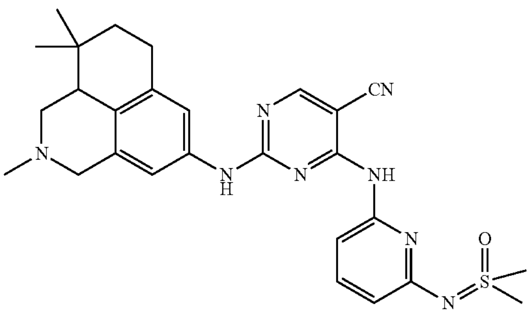

-continued
31
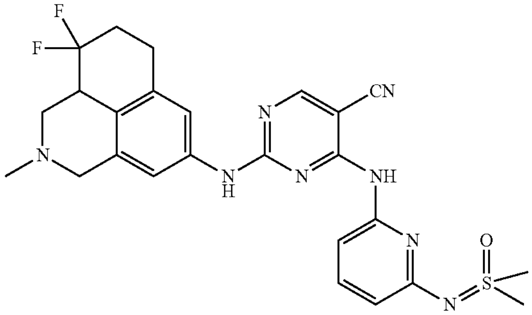
32
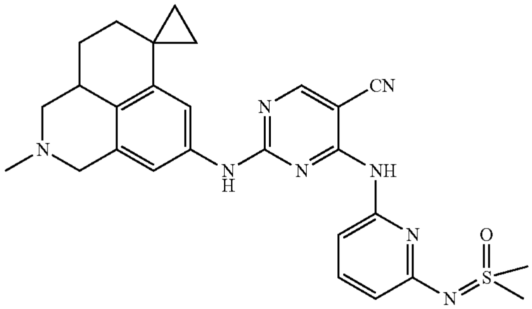
33
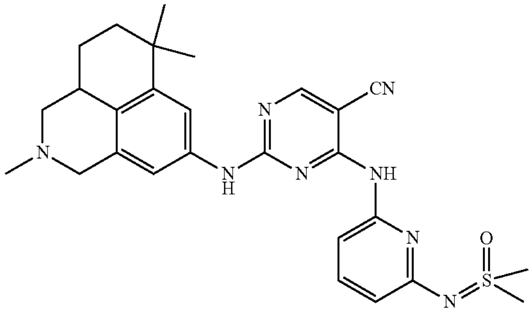
34
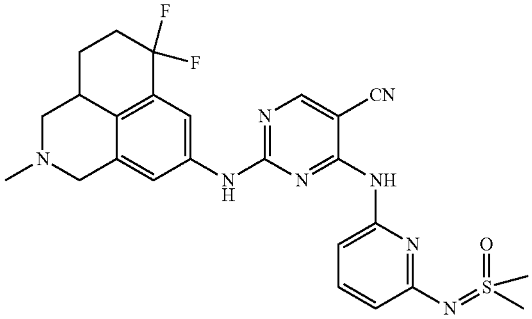
-continued
35
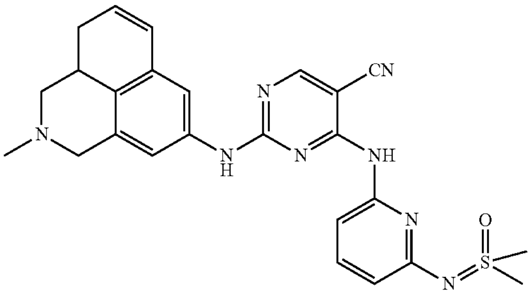
36
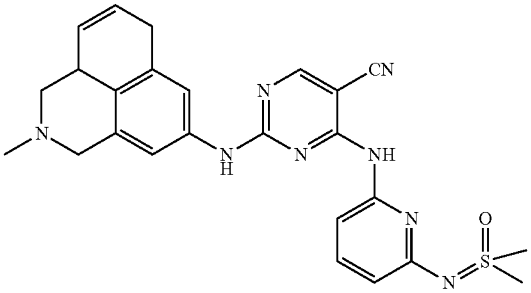
37
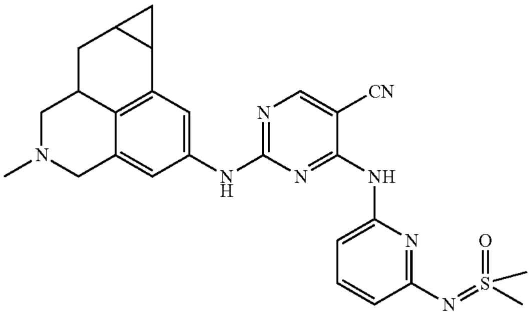
38
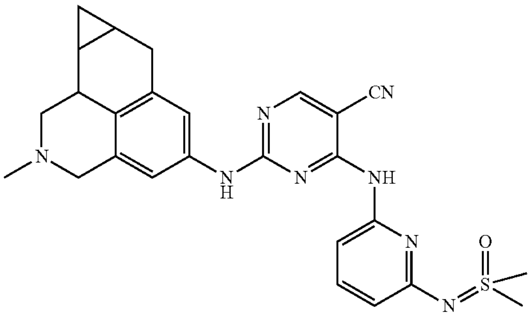
39
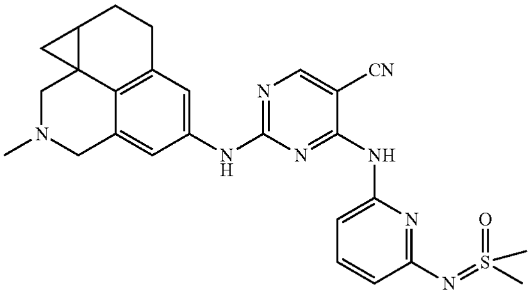

-continued
40
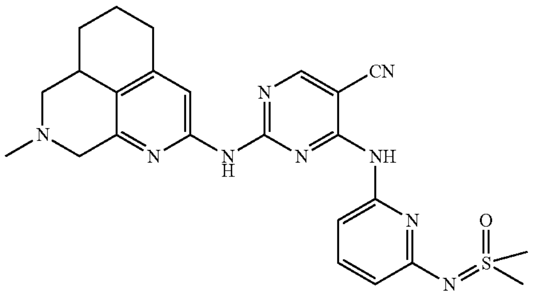
41
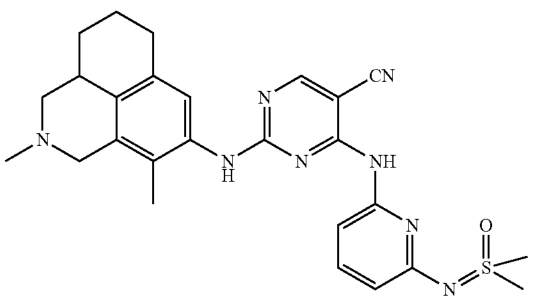
42
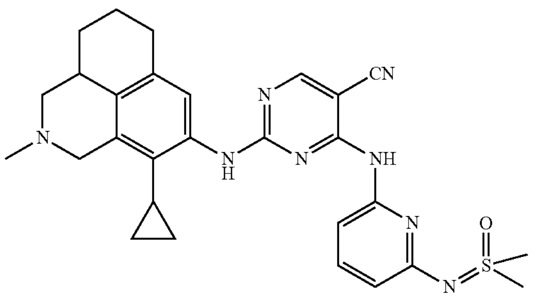
43
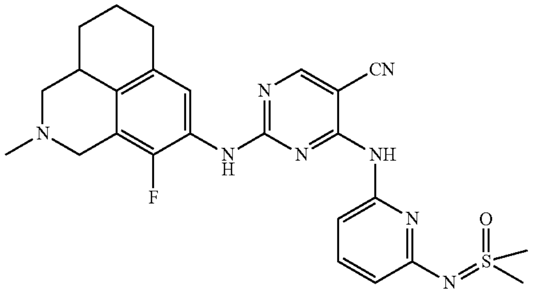
44
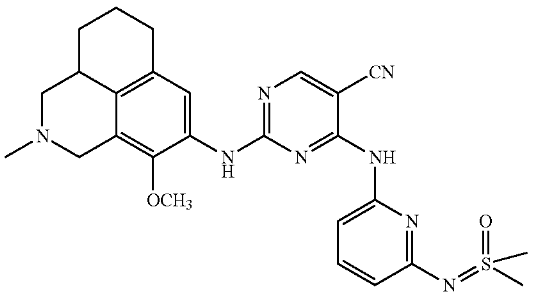
-continued
45
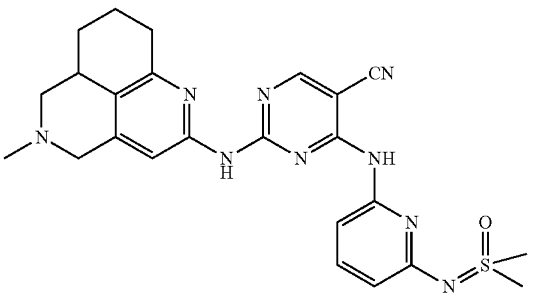
46
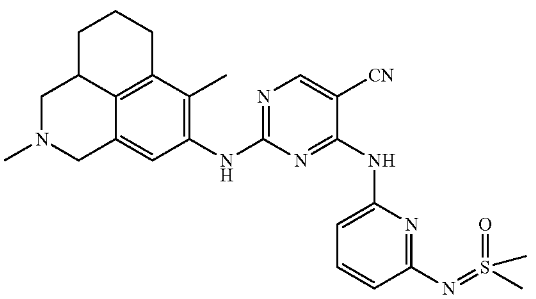
47
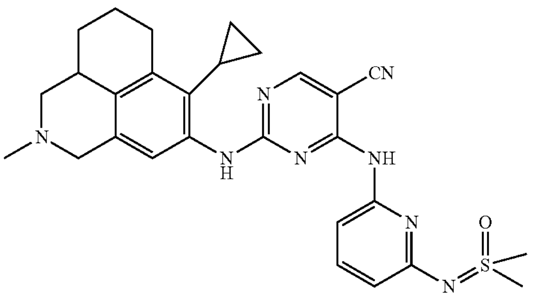
48
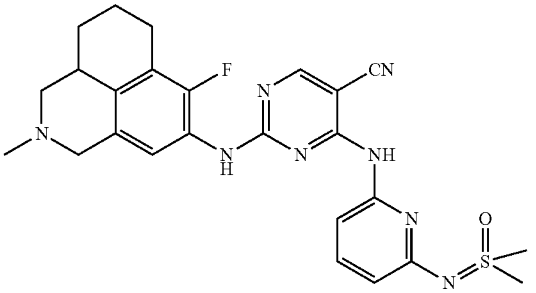
49
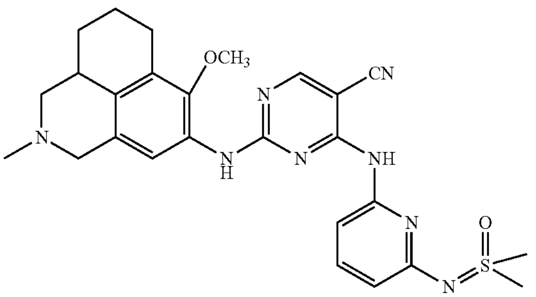

-continued
50
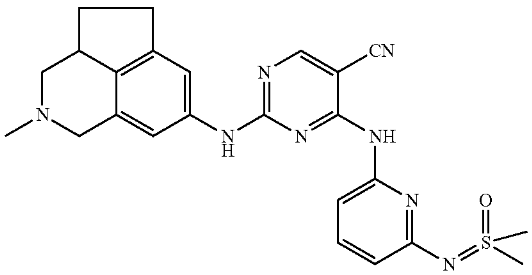
51
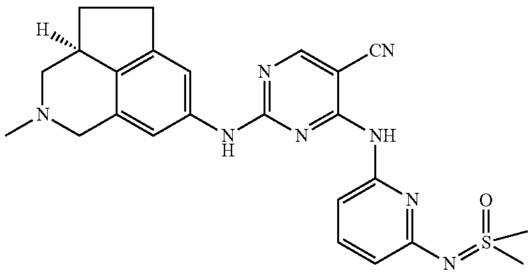
52
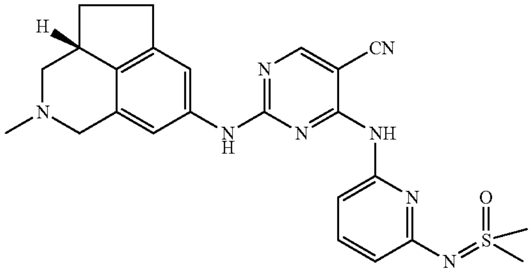
53
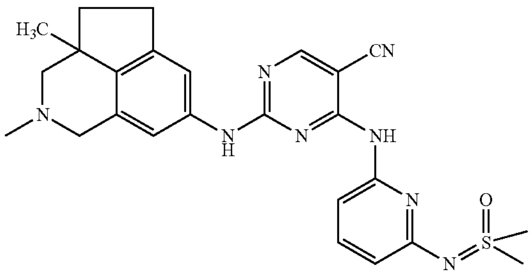
54
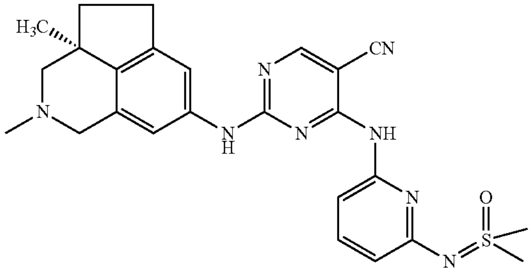
-continued
55
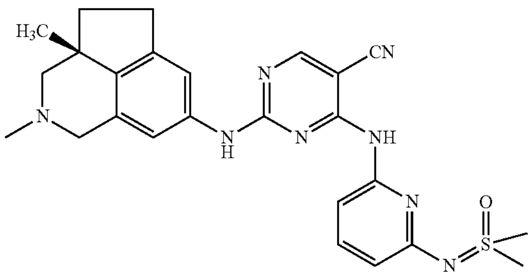
56
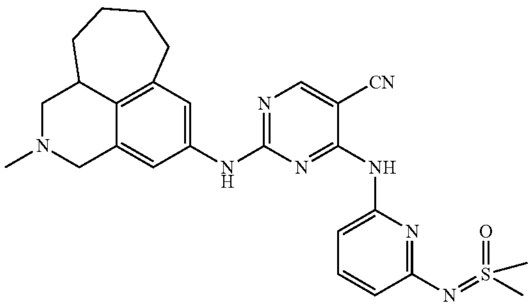
57
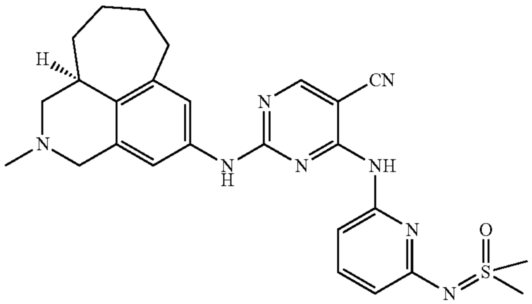
58
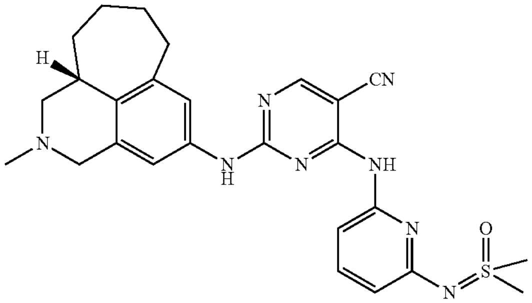
59
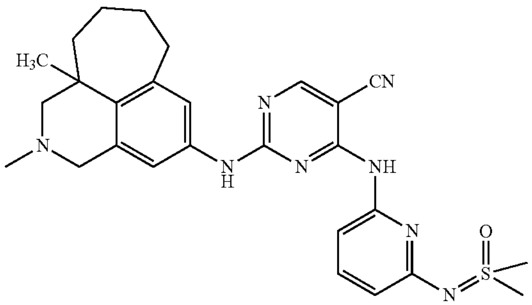

-continued
60
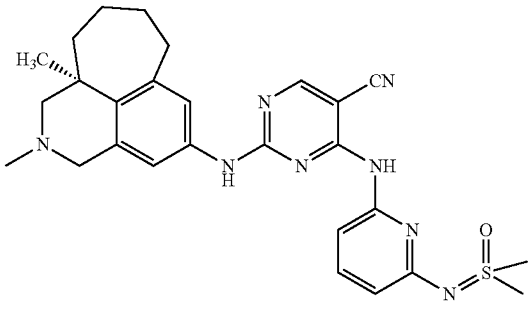
61
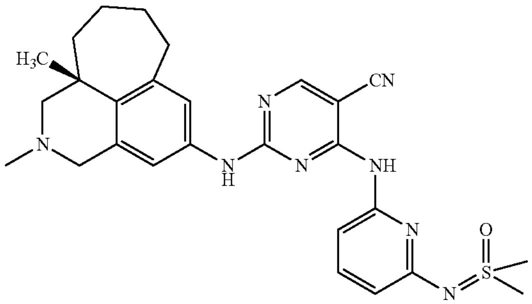
62
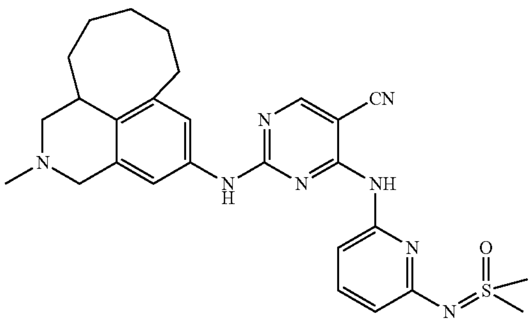
63
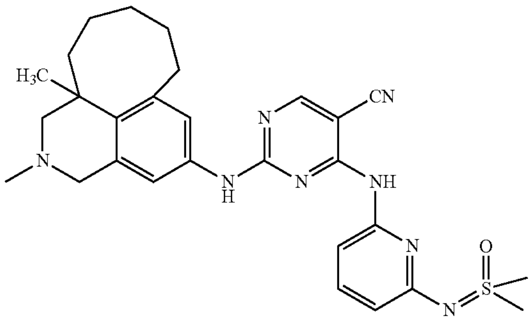
-continued
64
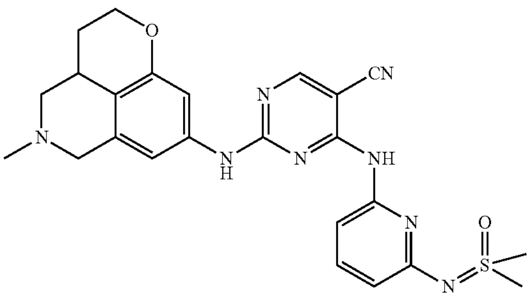
65
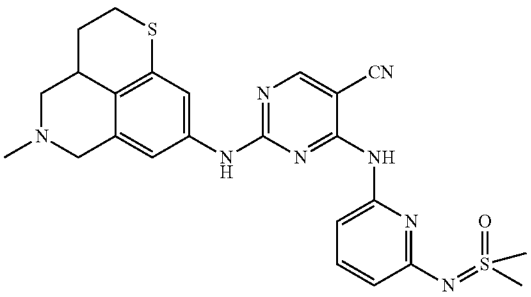
66
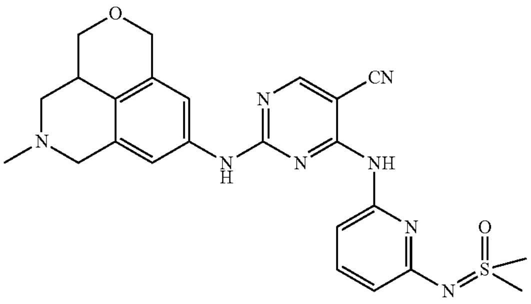
67
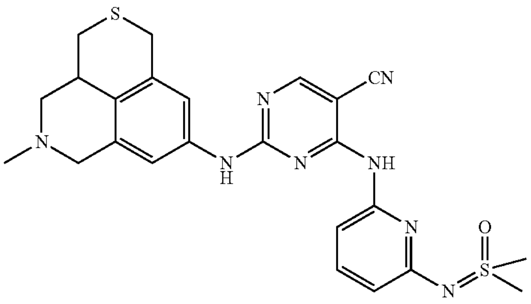
68
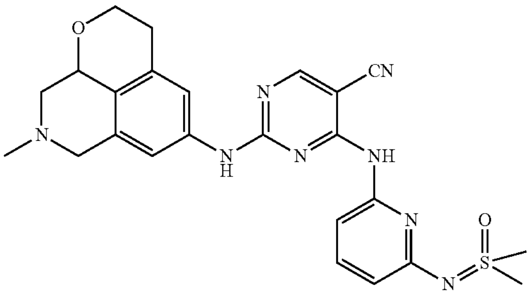

-continued
69
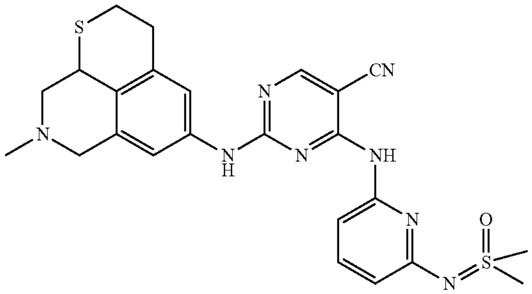
70
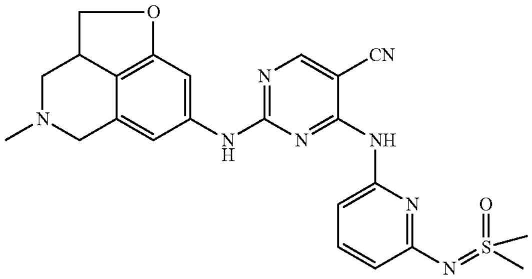
71
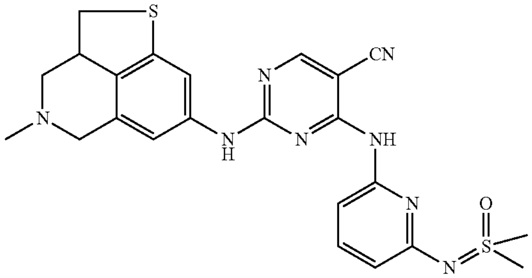
72
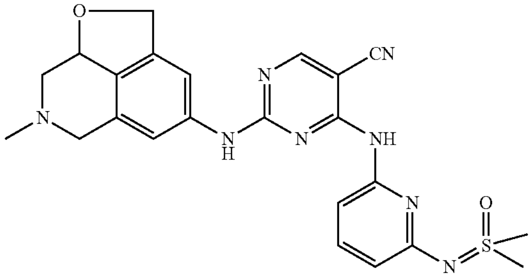
73
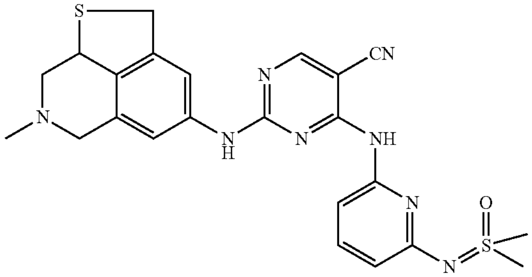
-continued
74
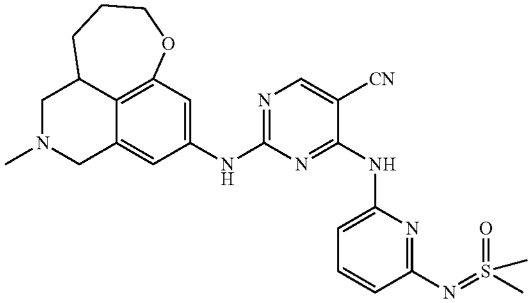
75
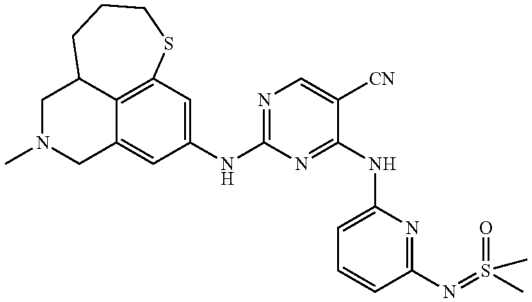
76
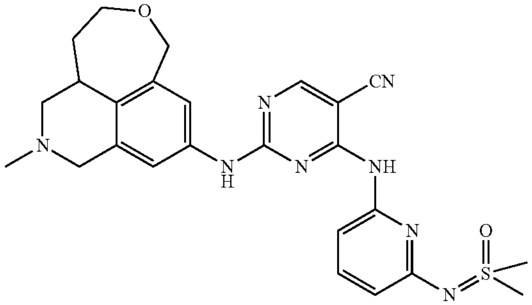
77
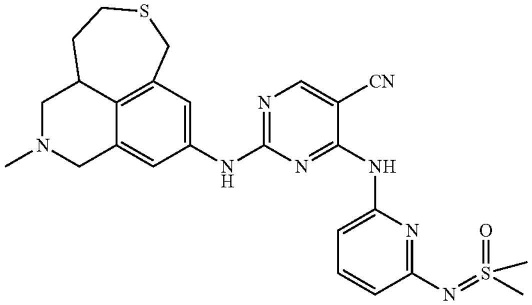
78
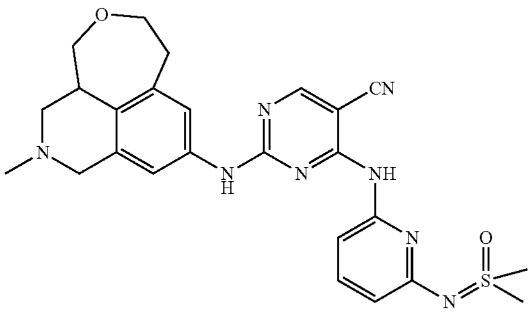

-continued
79
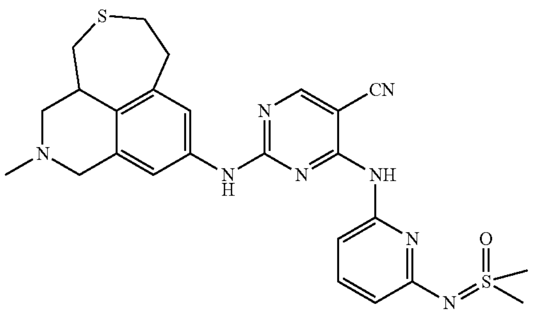
80
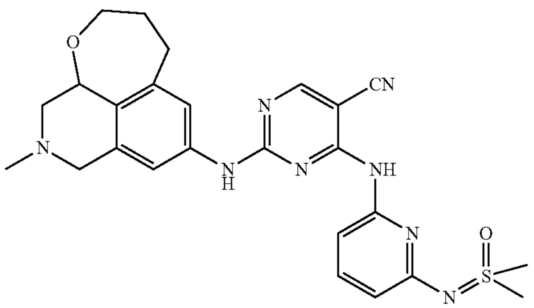
81
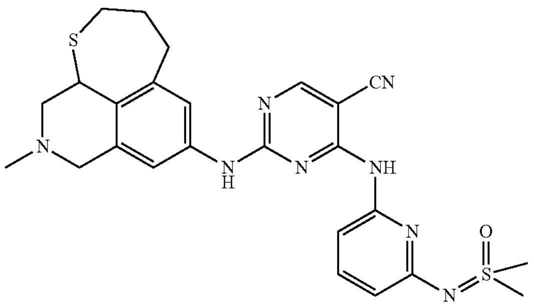
82
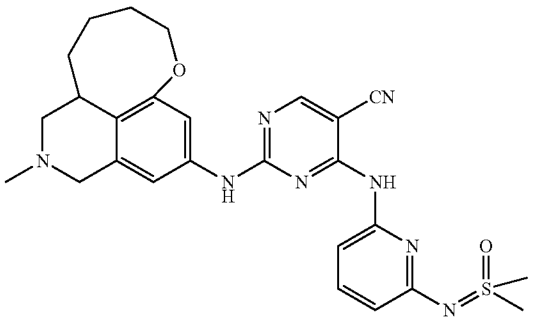
-continued
83
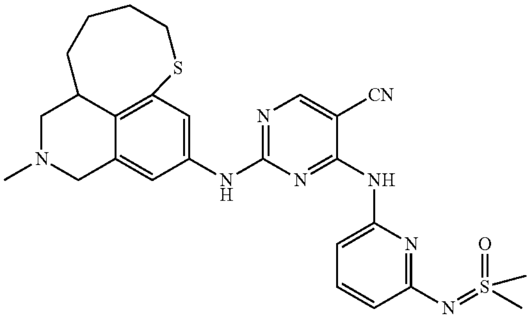
84
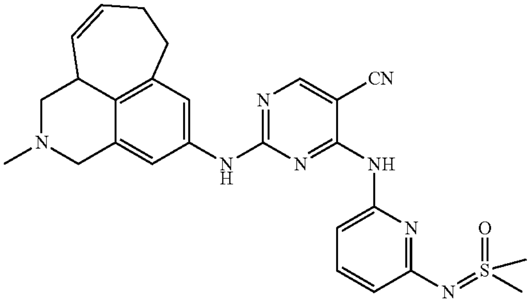
85
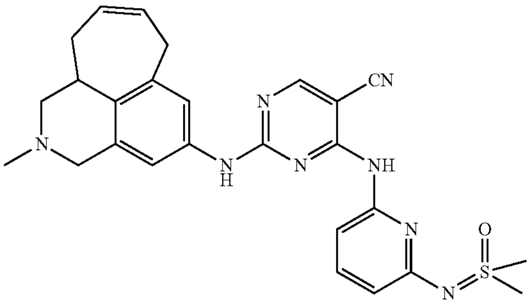
86
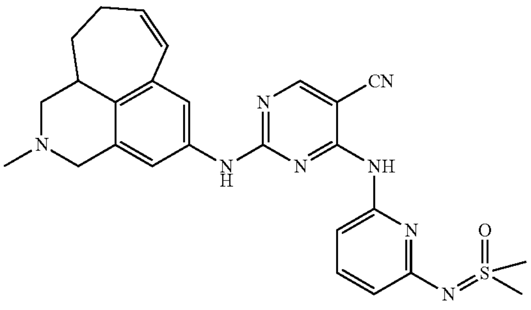
87
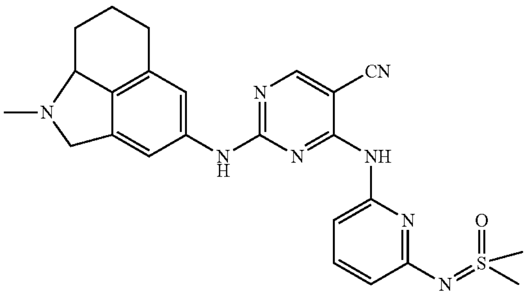

88
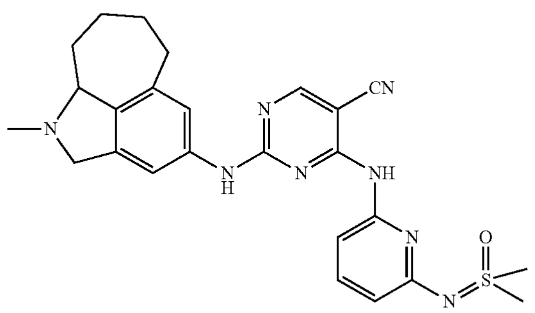
89
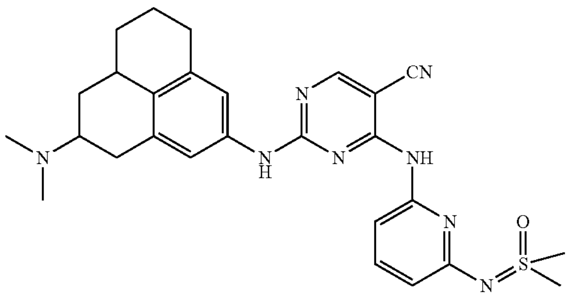
90
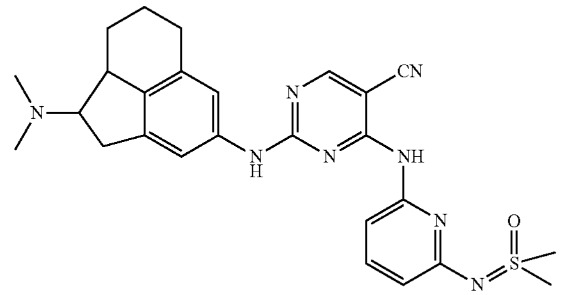
91
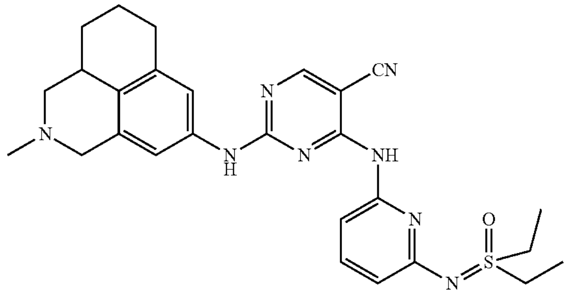
92
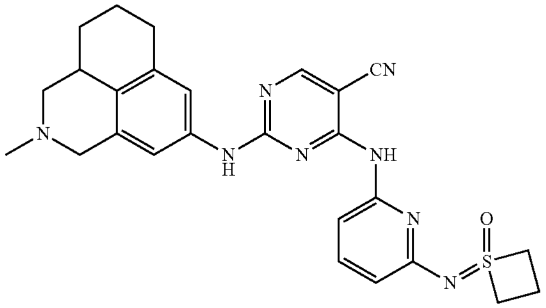
93
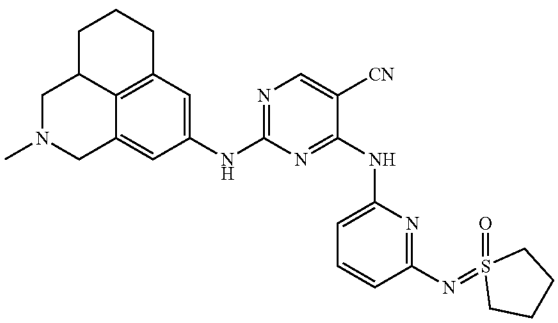
94
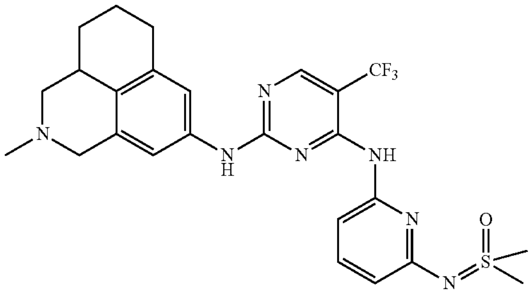
95
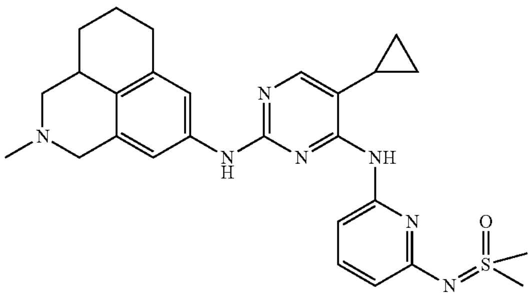
96
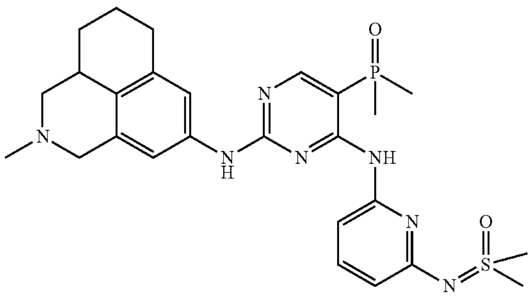
97
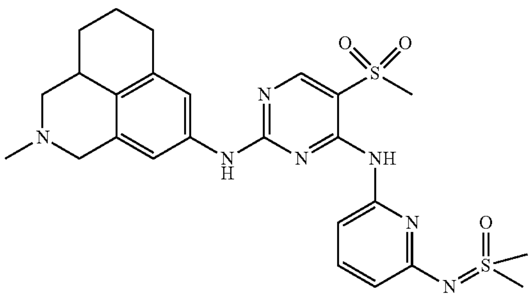

-continued
98
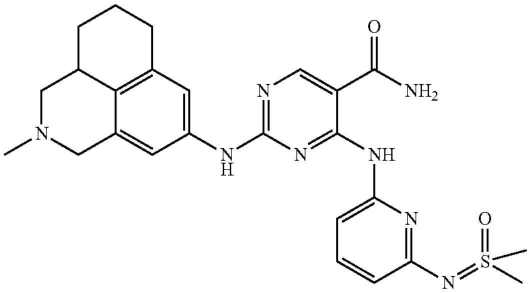
99
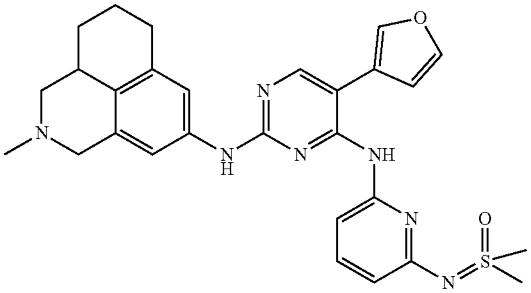
100
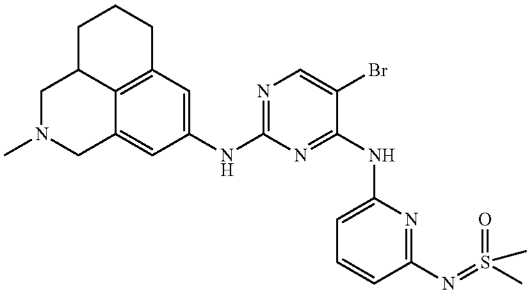
101
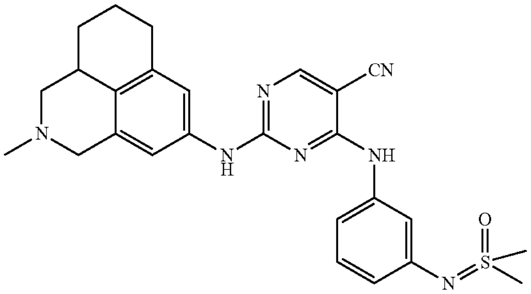
102
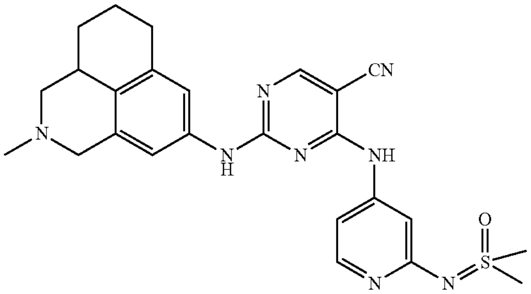
-continued
103
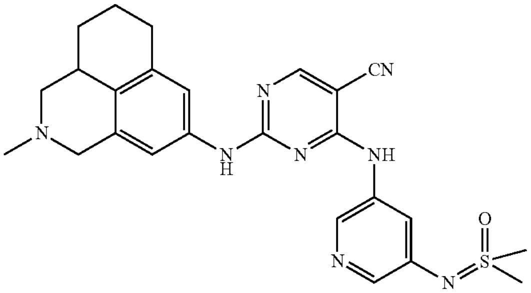
104
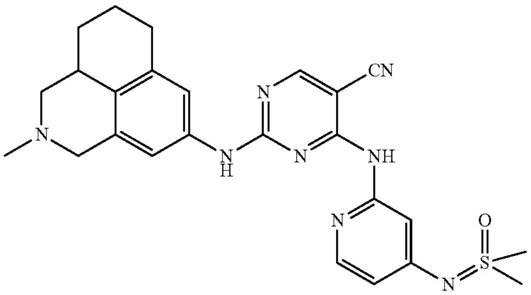
105
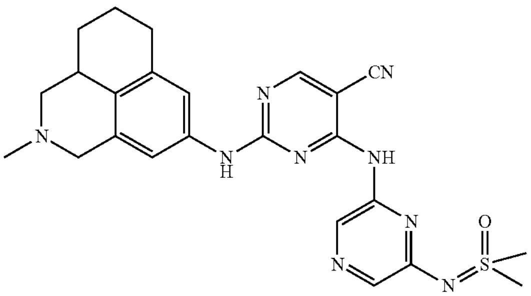
106
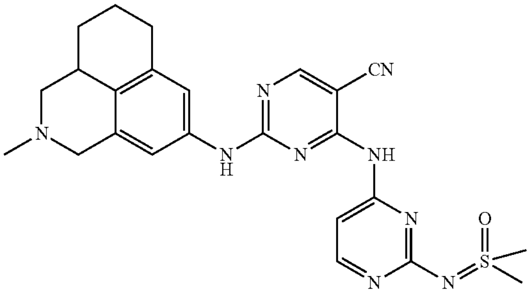
107
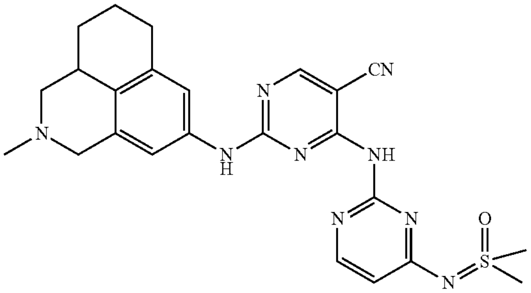

-continued
108
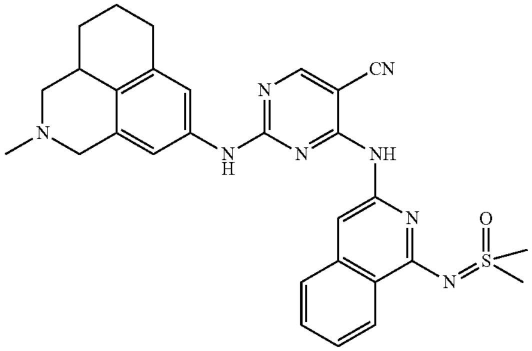
109
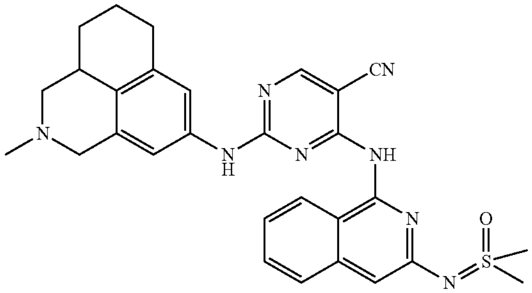
110
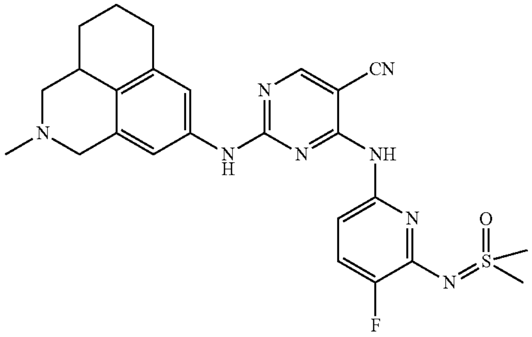
111
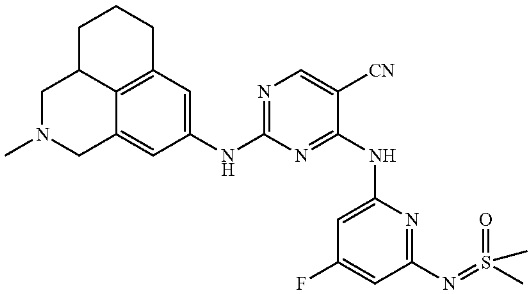
-continued
112
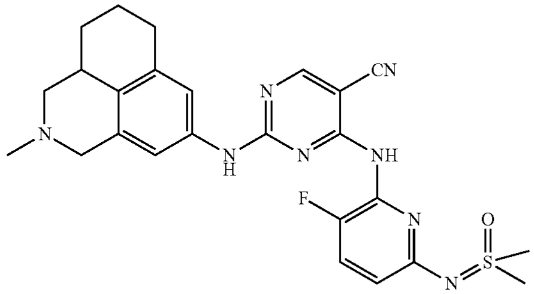
113
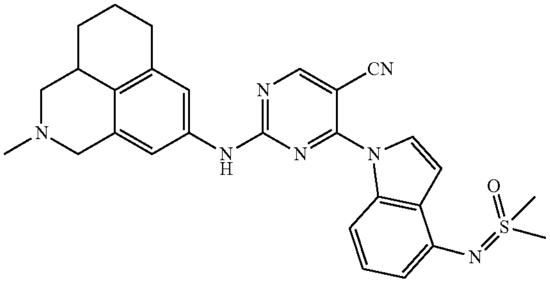
114
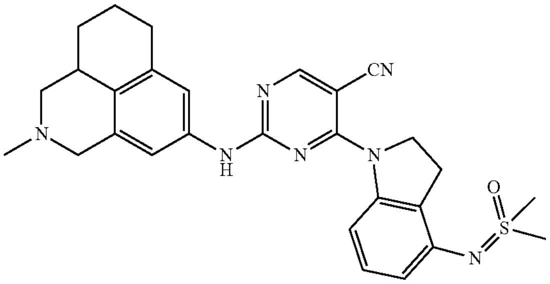
115
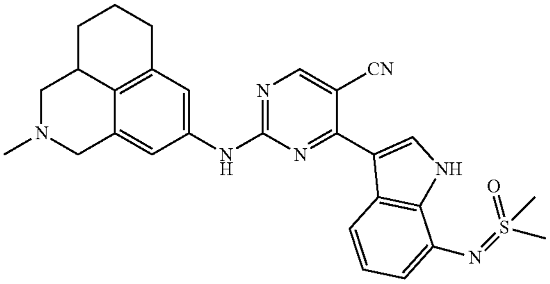
116
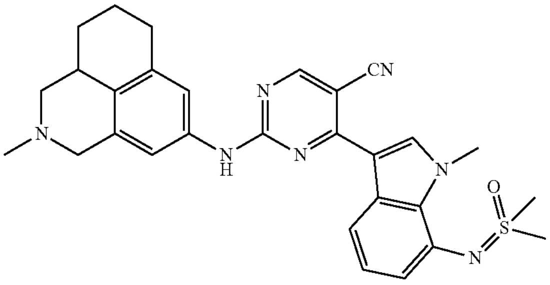

-continued
117
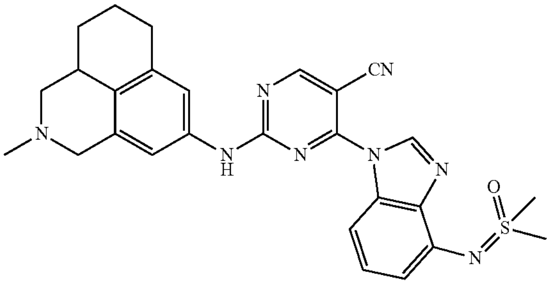
118
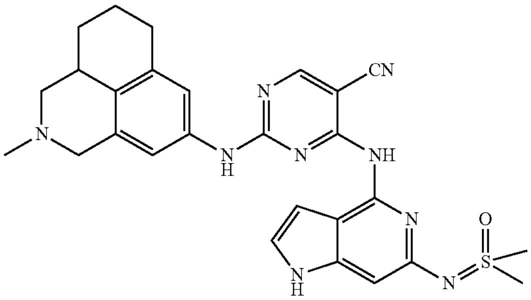
119
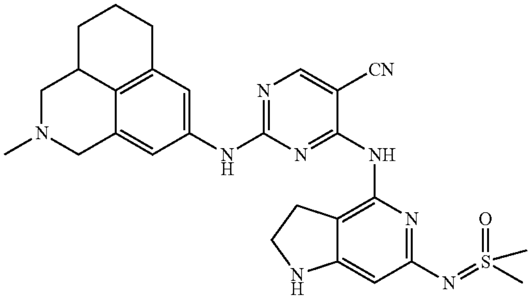
120
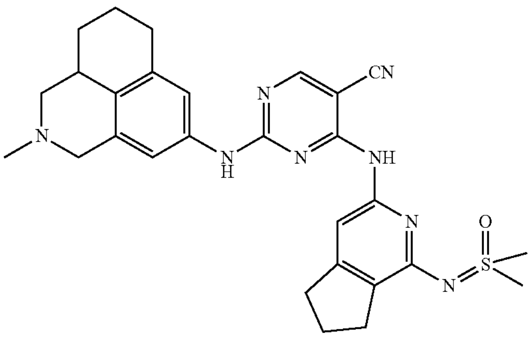
-continued
121
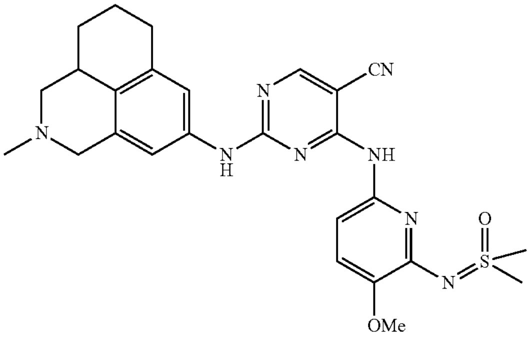
122
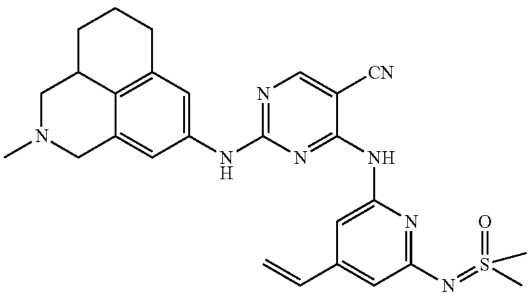
123
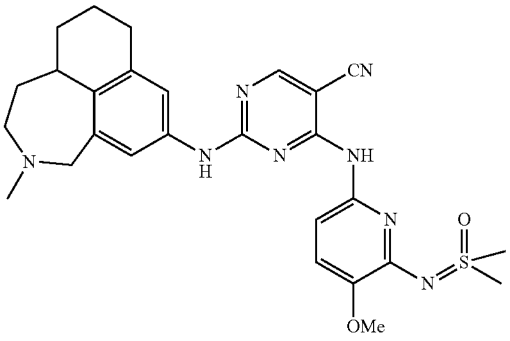
124
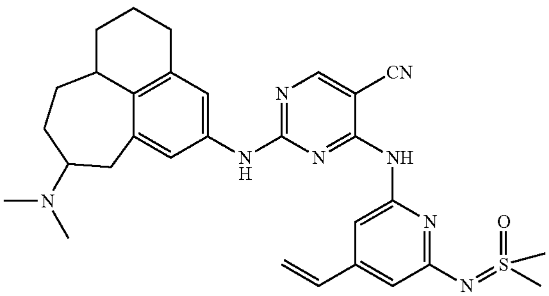

-continued
125
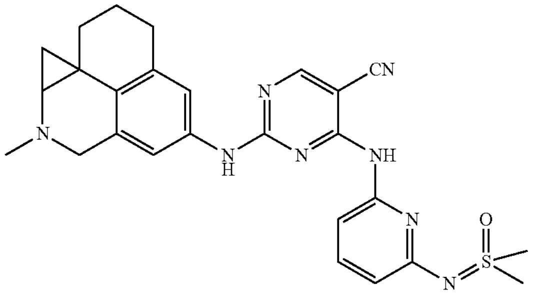
126
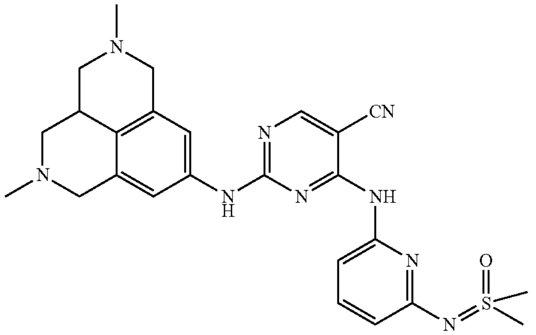
127
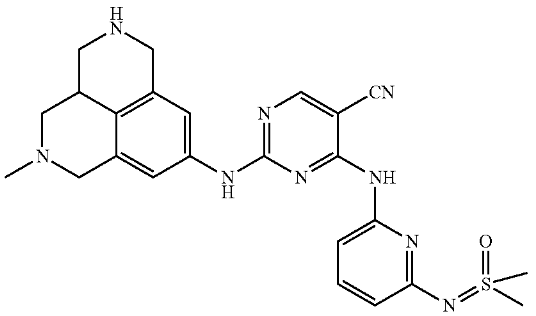
128
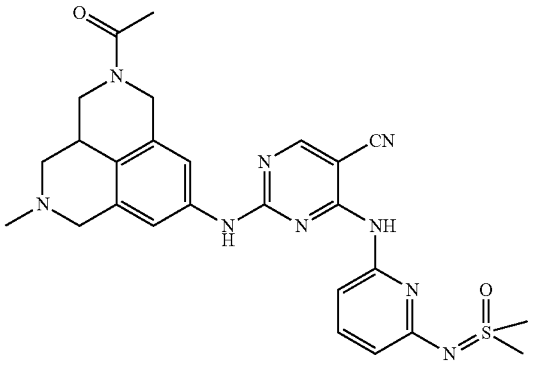
-continued
129
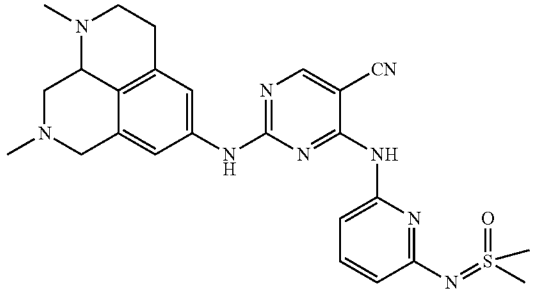
130
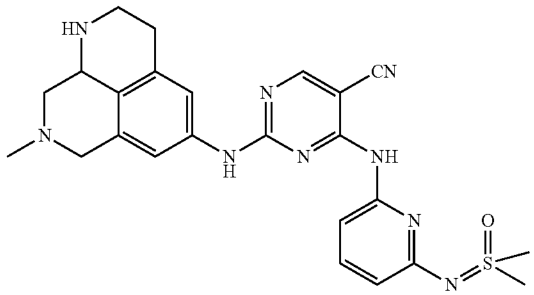
131
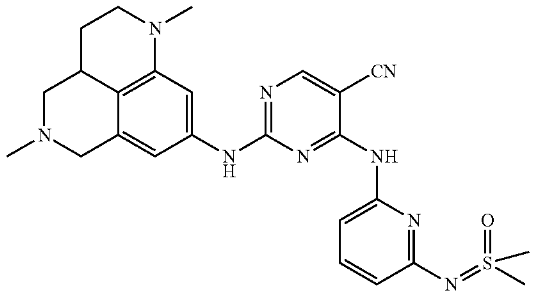
132
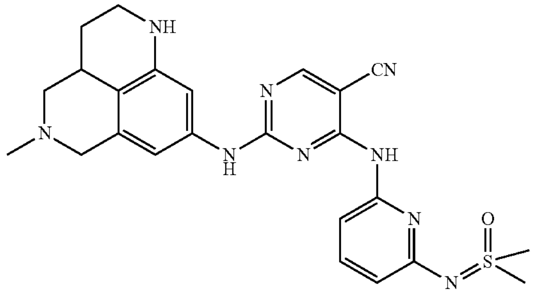
133
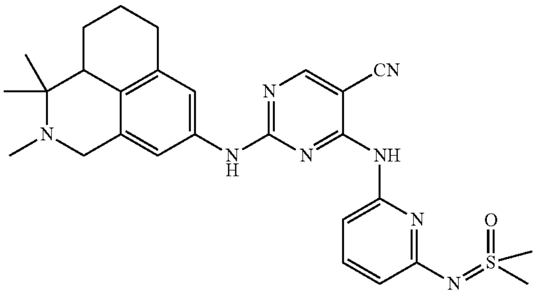

-continued
134
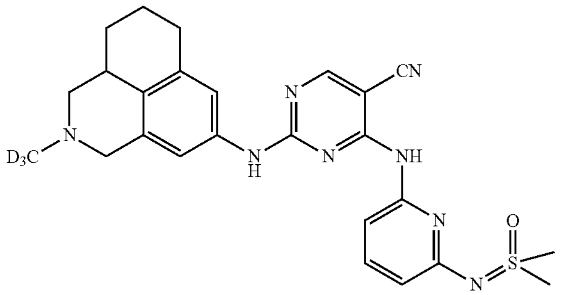
135
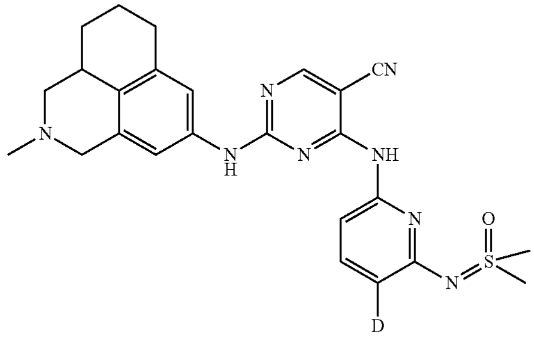
136
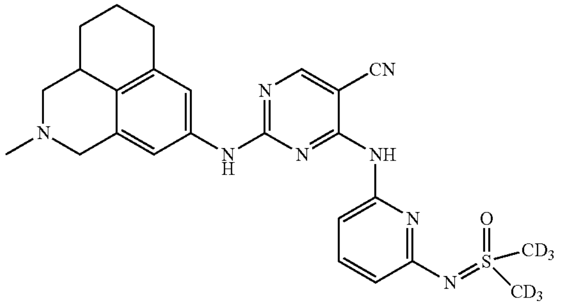
137
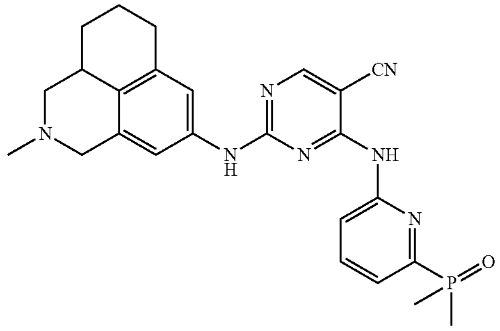
-continued
138
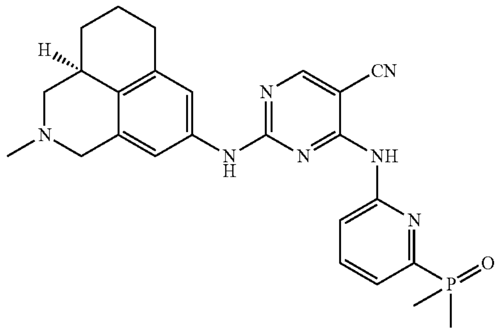
139
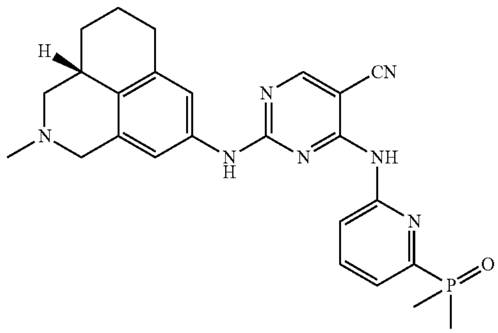
140
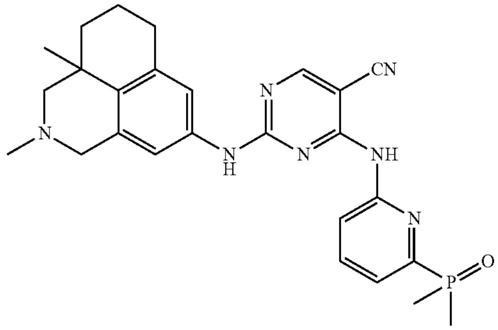
141
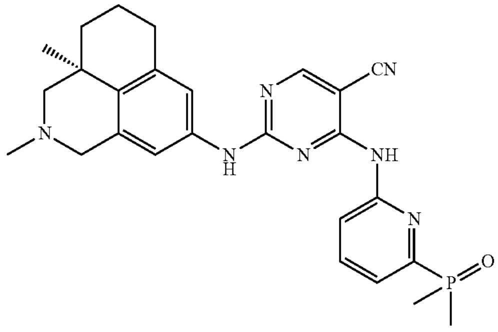

-continued
142
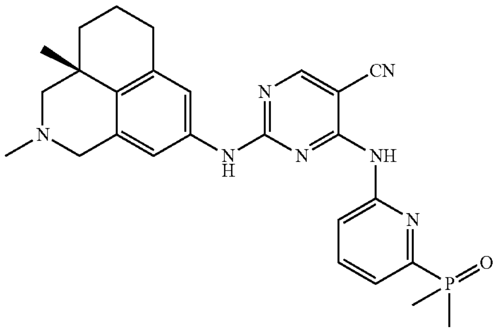
143
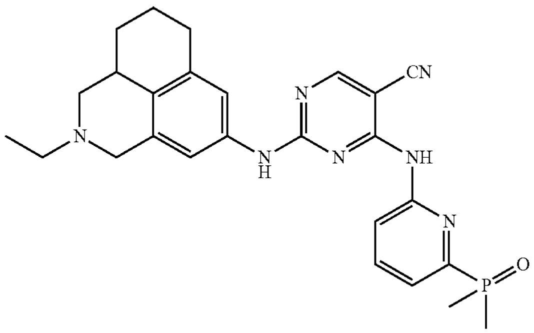
144
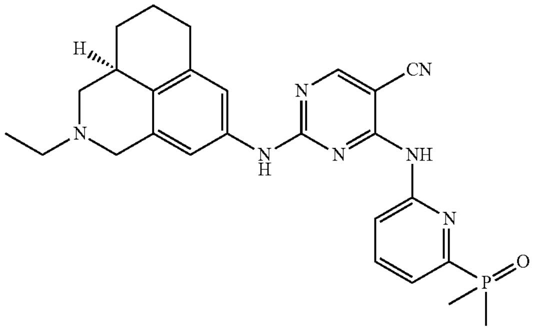
145
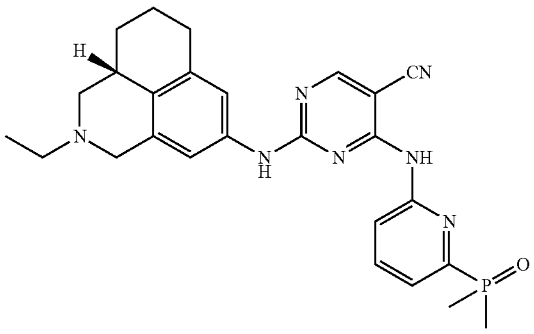
-continued
146
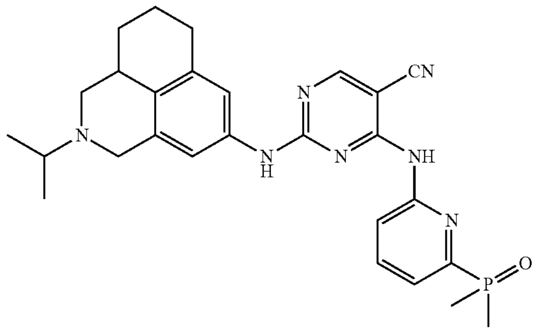
147
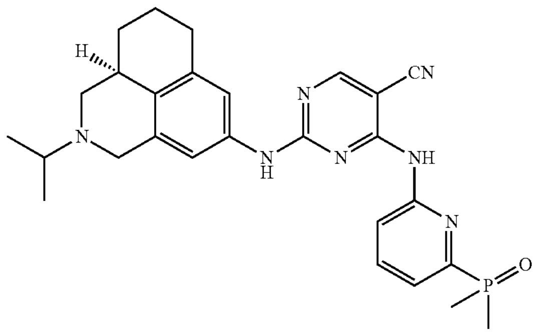
148
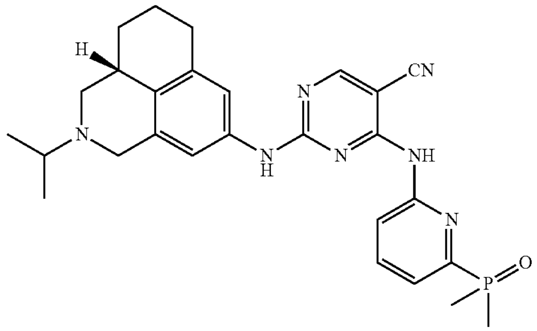
149
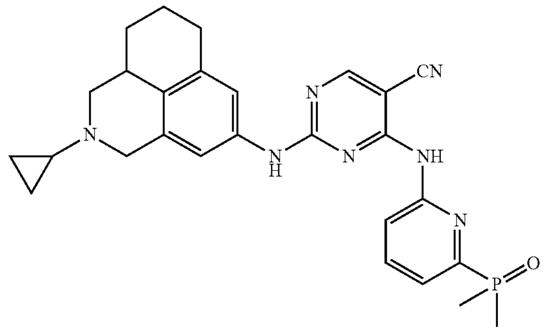

-continued
150
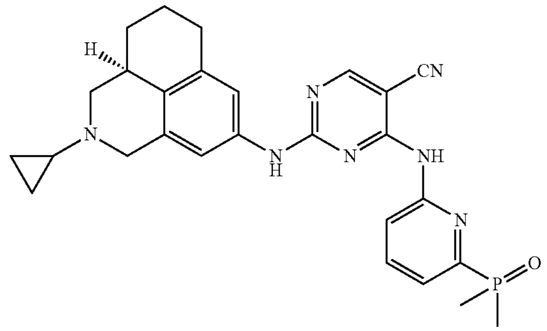
151
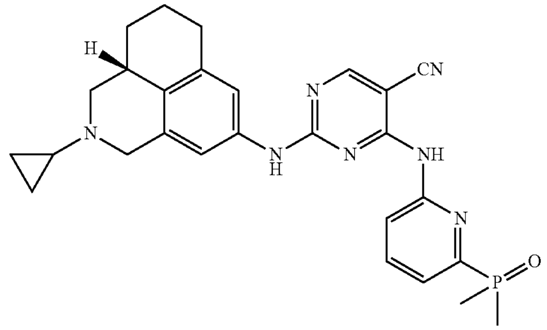
152
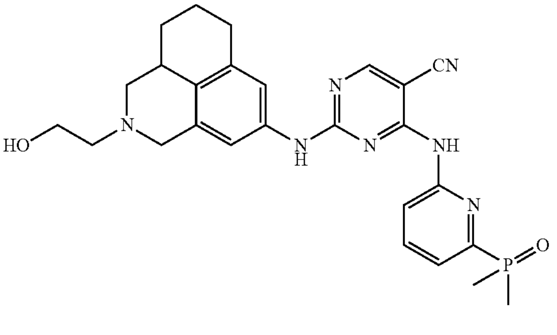
153
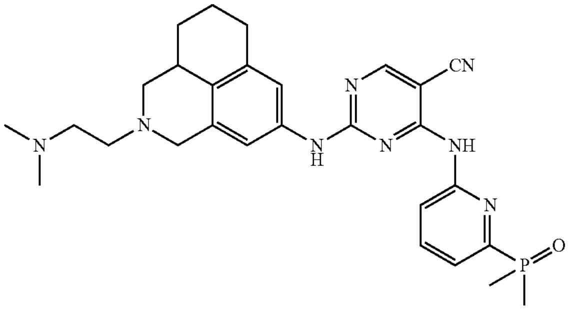
-continued
154
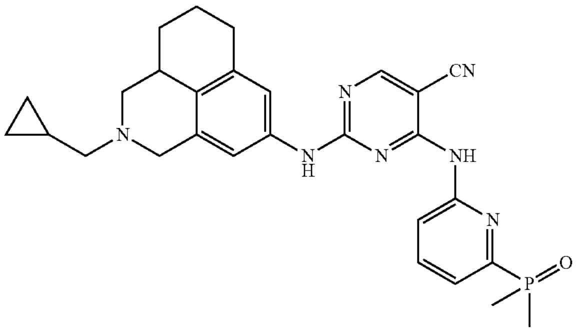
155
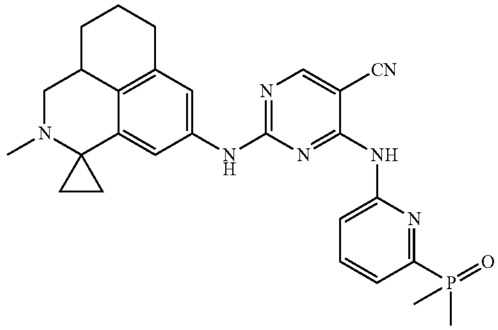
156
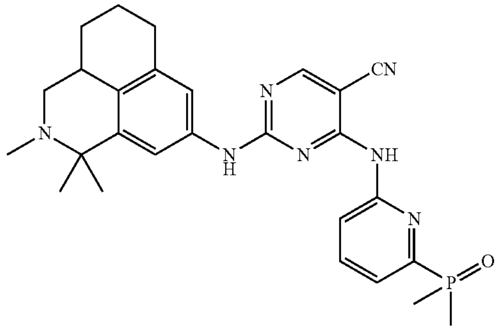
157
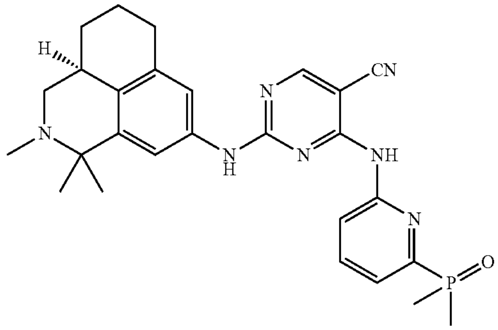

-continued
158
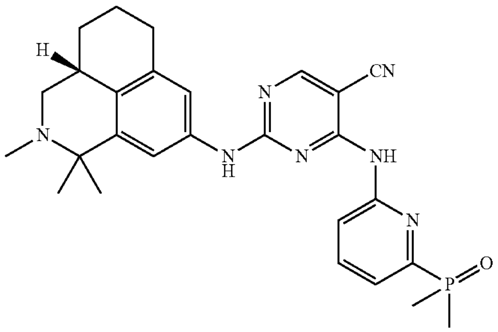
159
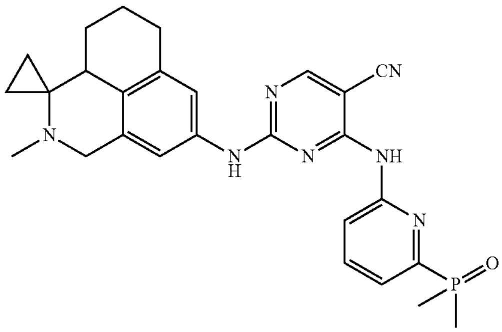
160
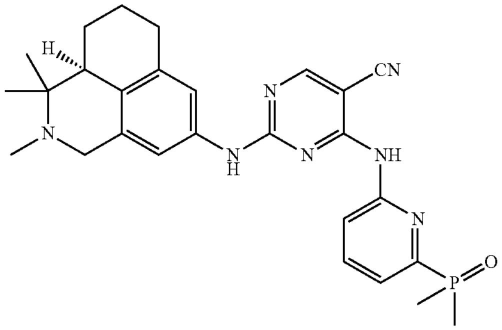
161
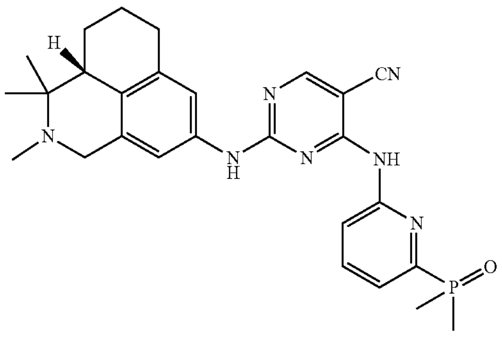
-continued
162
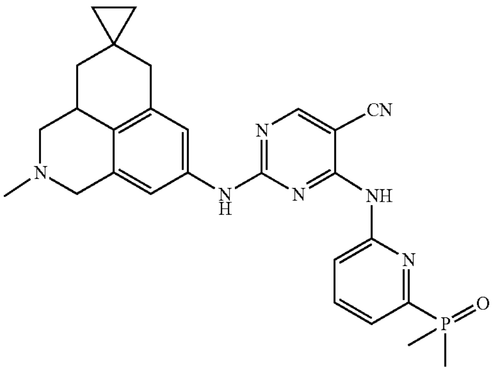
163
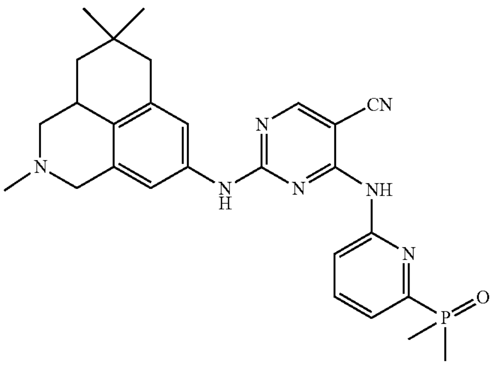
164
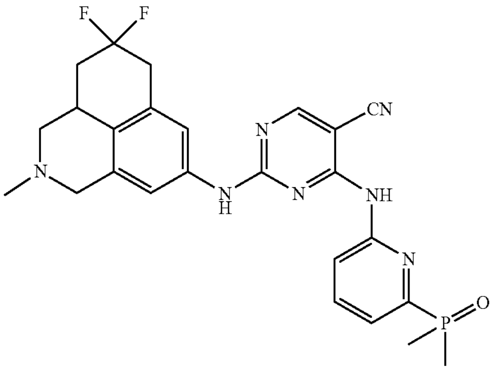
165
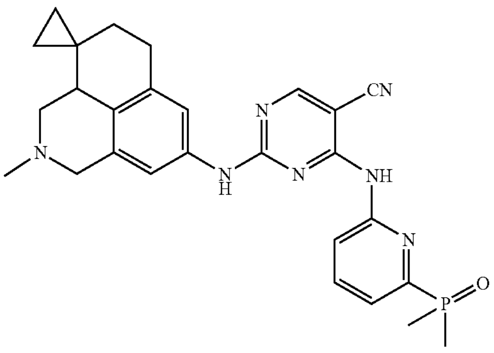

166
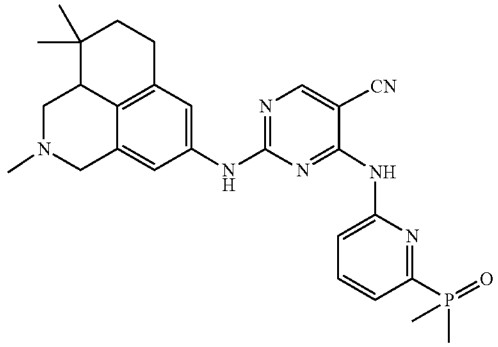
167
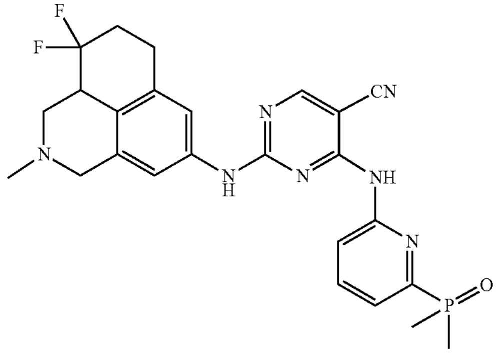
168
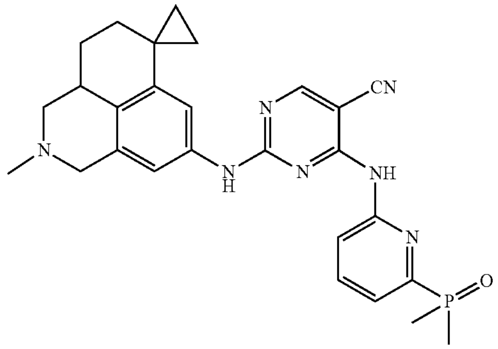
169
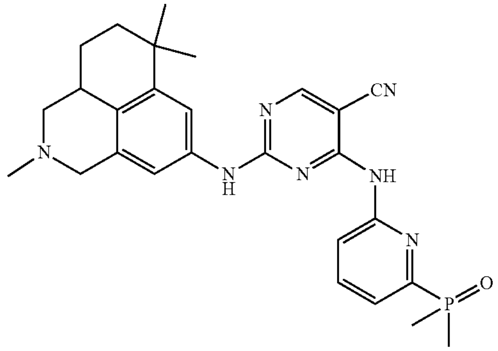
170
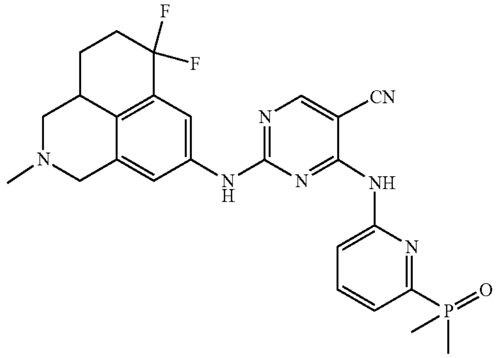
171
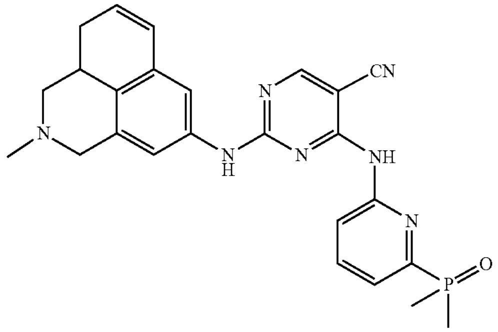
172
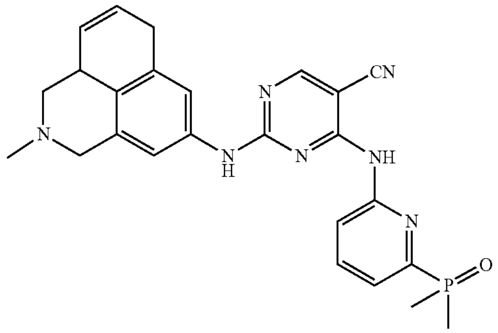
173
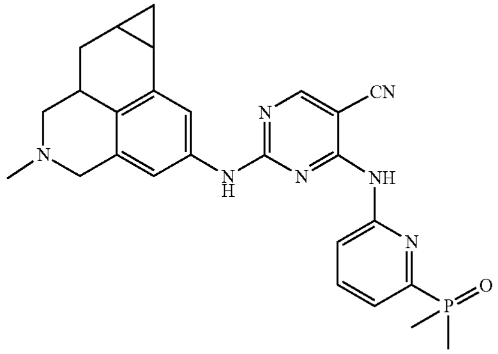

174
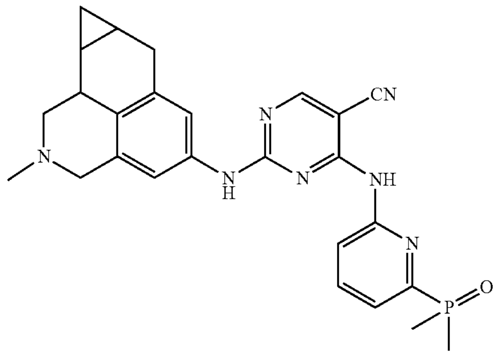
175
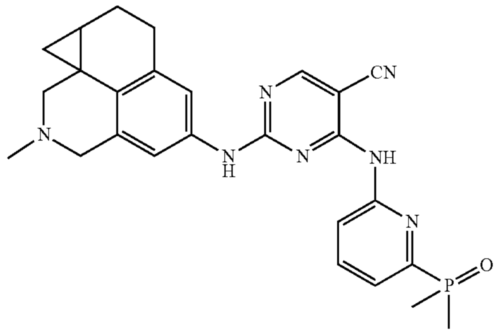
176
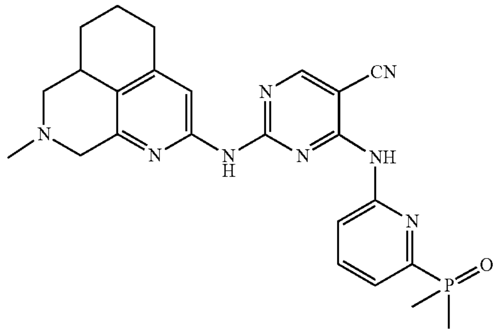
177
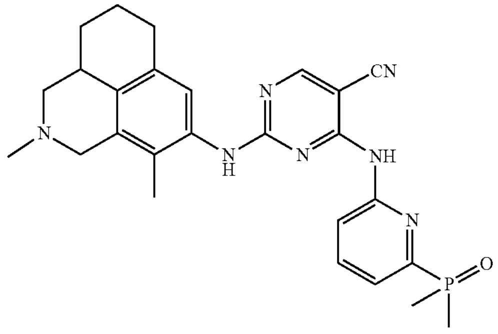
178
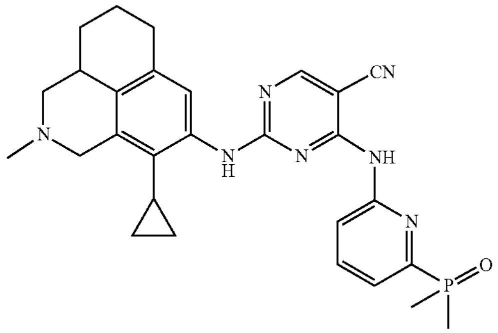
179
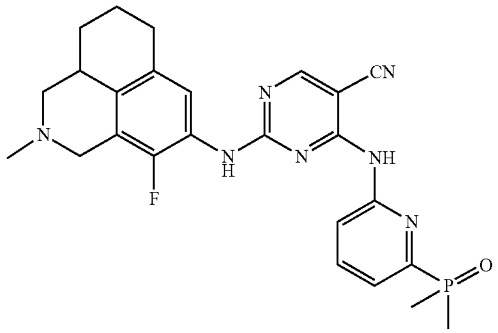
180
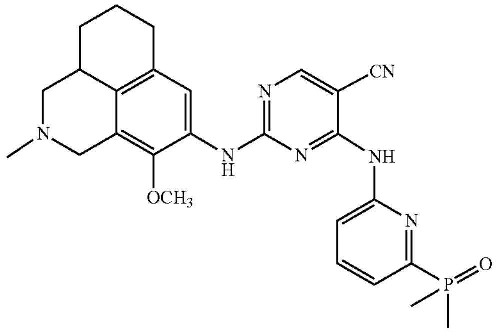
181
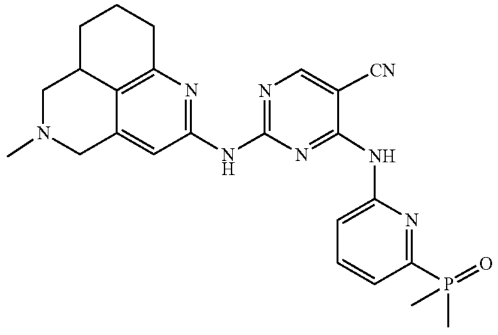

-continued
182
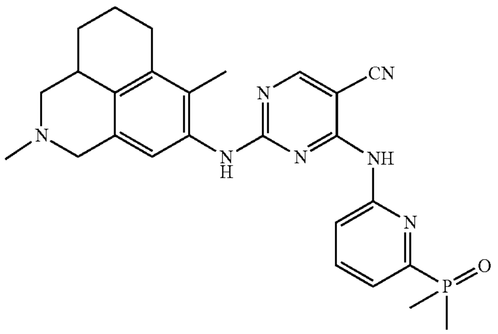
183
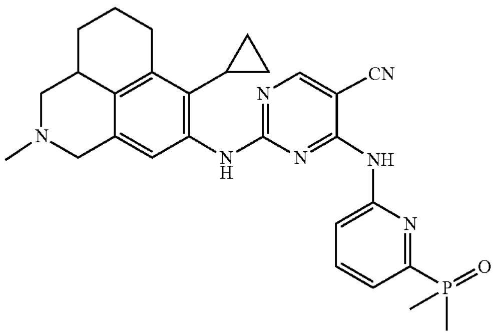
184
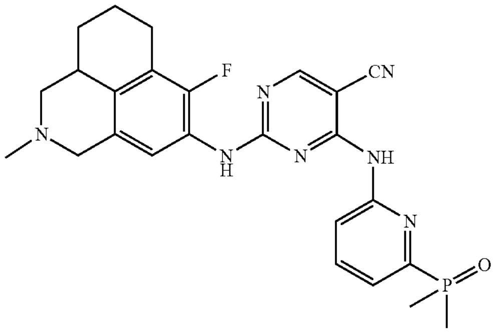
185
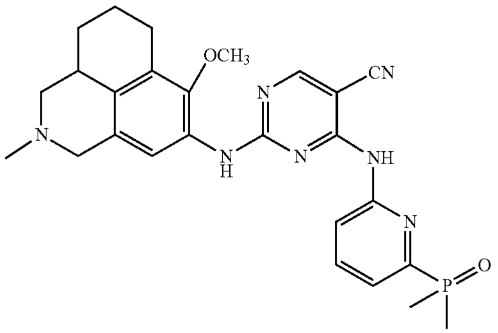
-continued
186
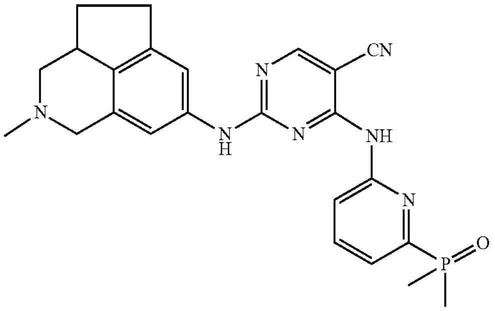
187
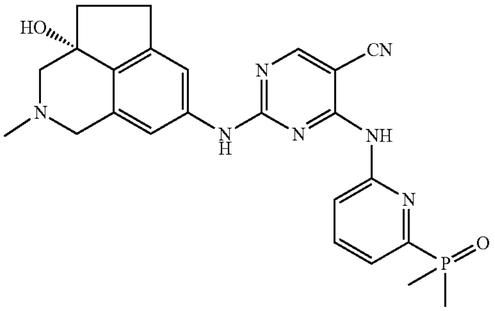
188
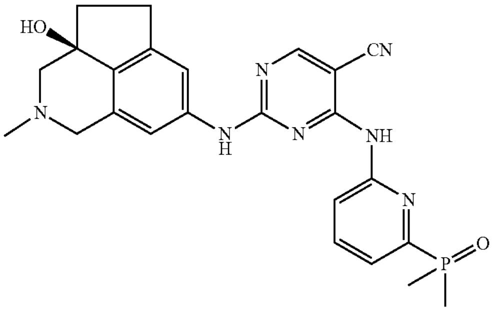
189
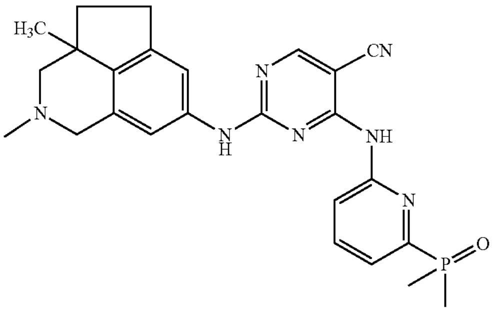

-continued
190
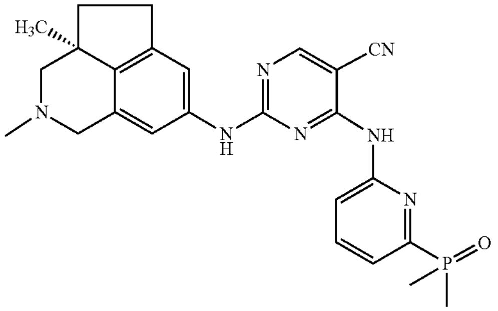
191
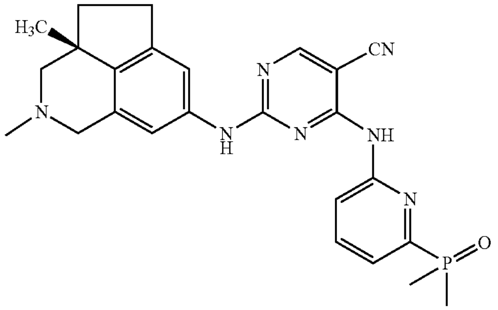
192
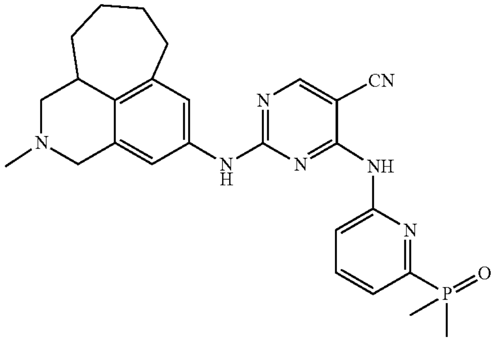
193
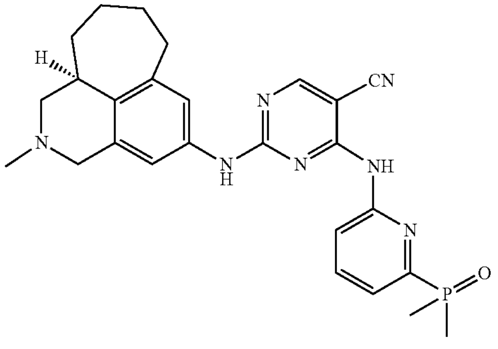
-continued
194
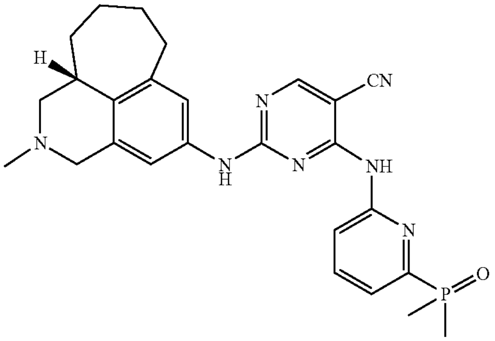
195
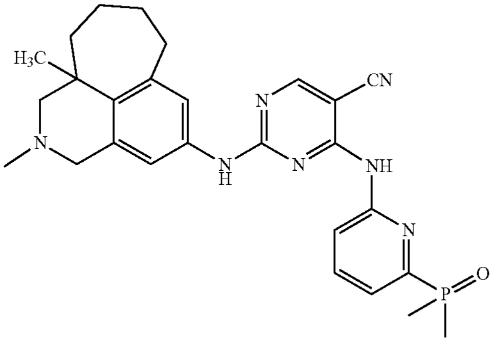
196
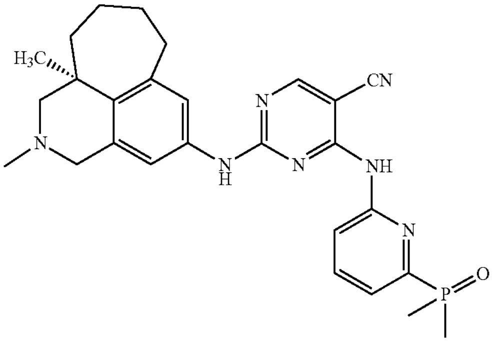
197
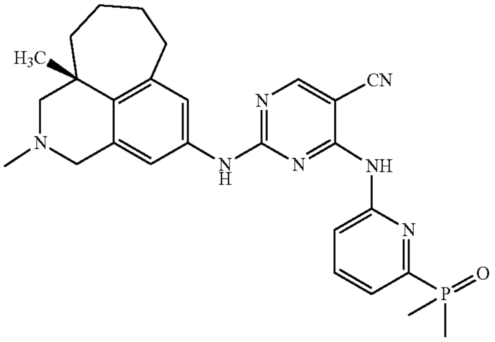

-continued
198
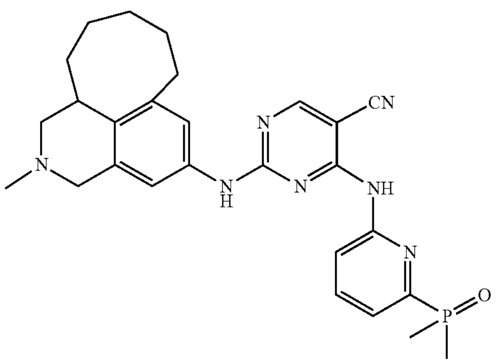
199
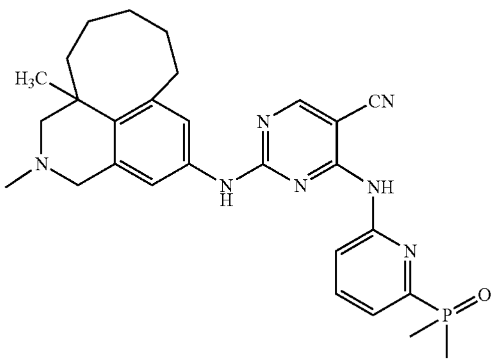
200
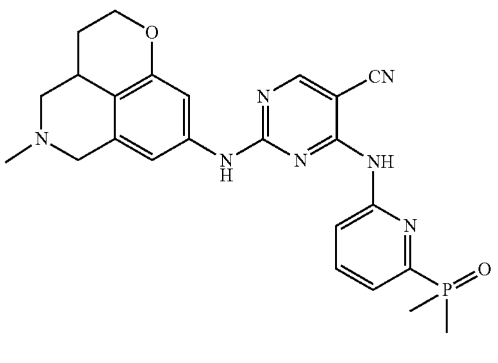
201
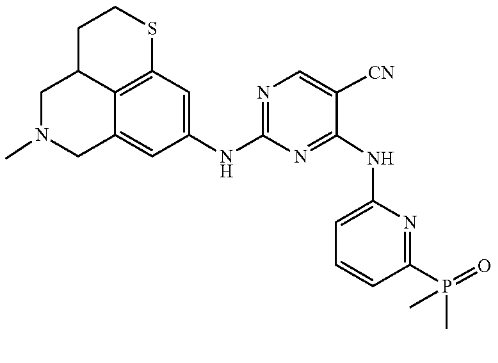
-continued
202
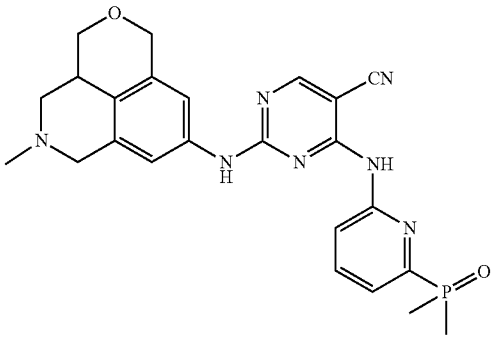
203
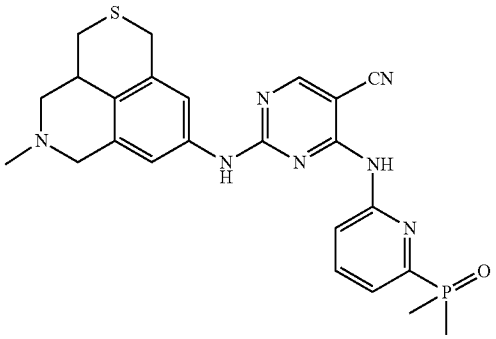
204
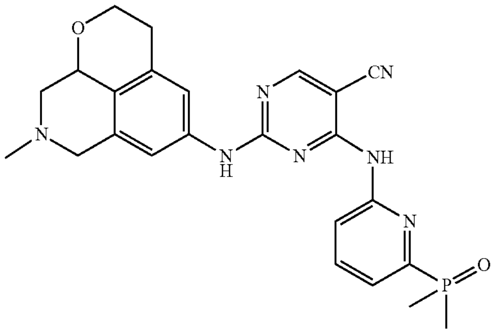
205
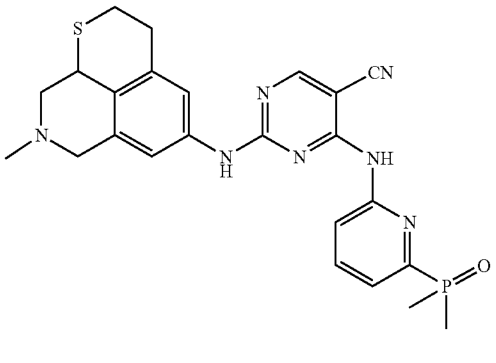

-continued
206
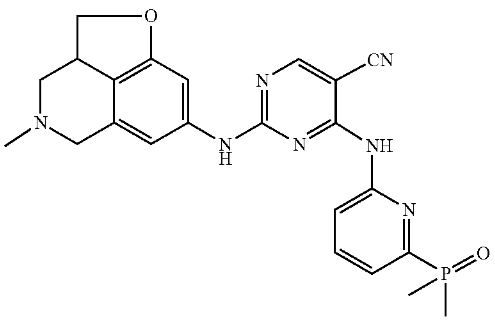
207
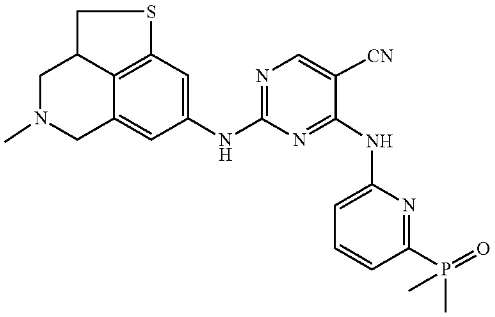
208
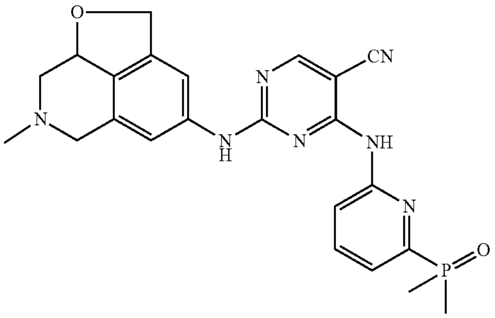
209
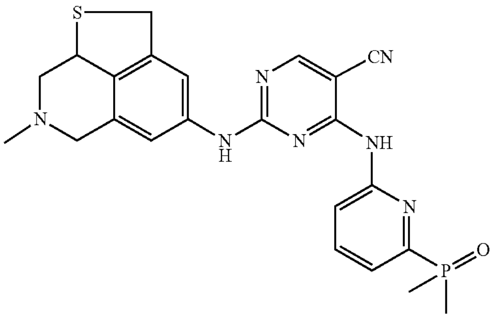
-continued
210
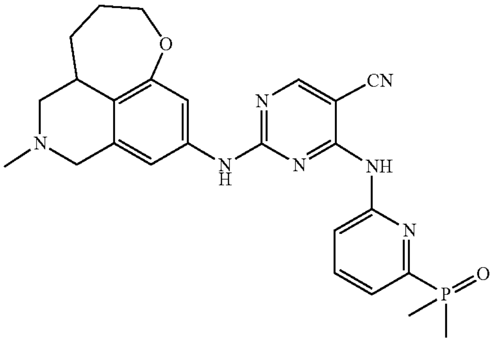
211
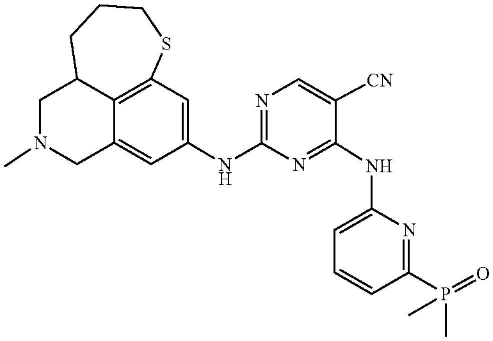
212
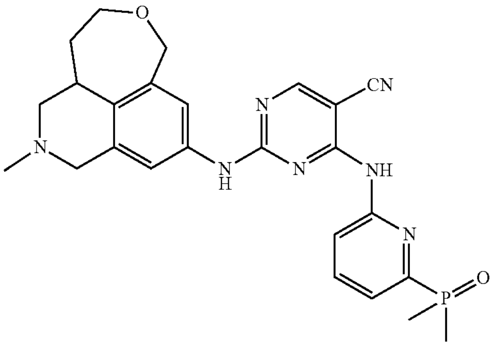
213
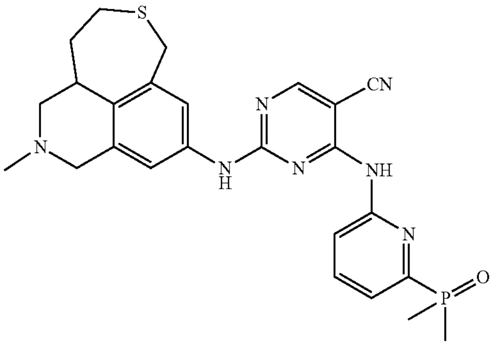

-continued
214
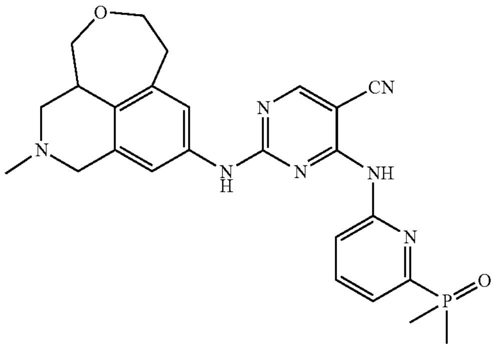
215
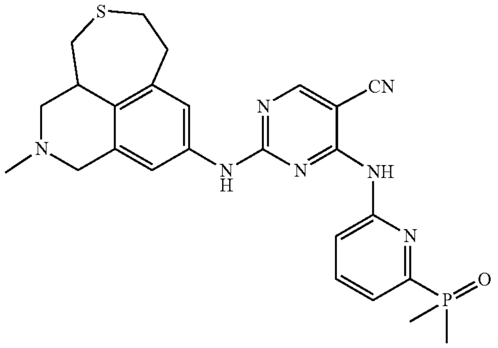
216
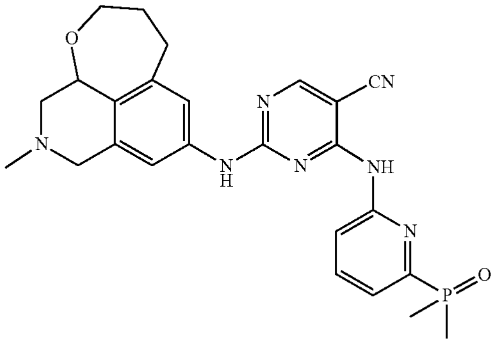
217
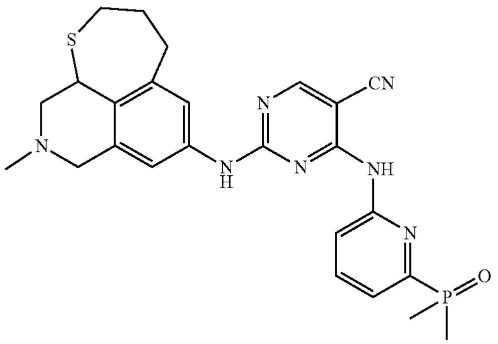
-continued
218
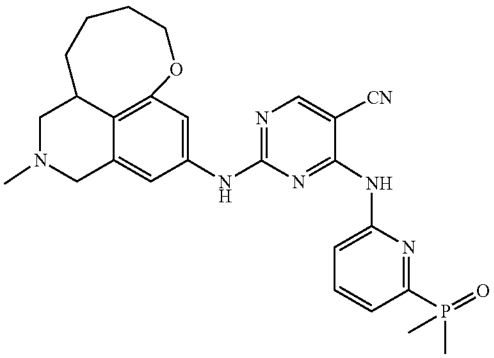
219
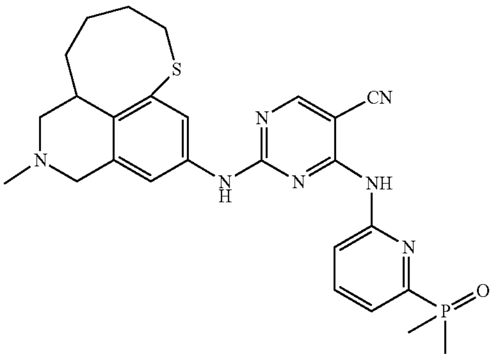
220
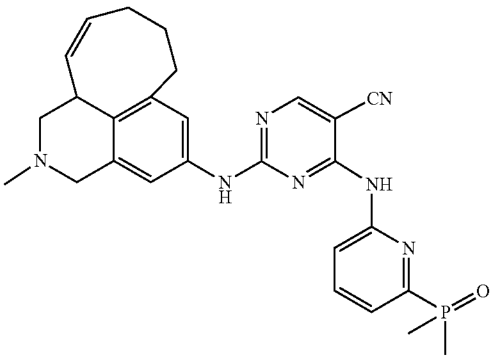
221
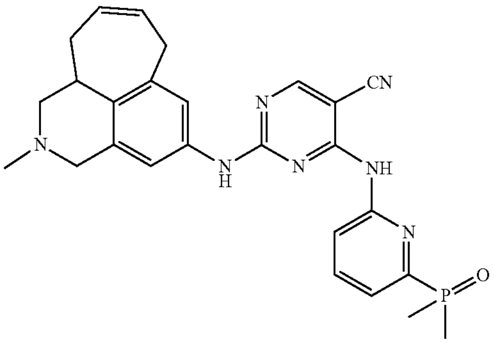

-continued
222
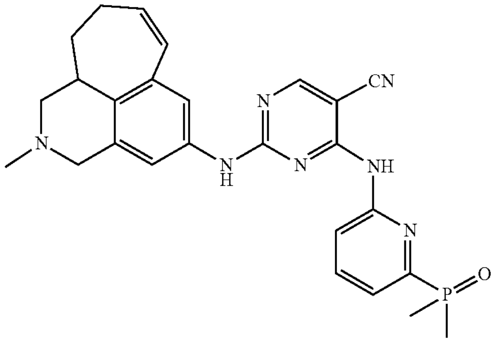
223
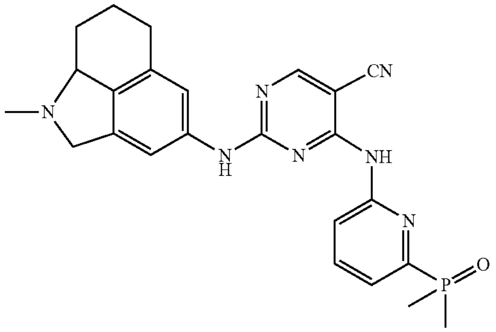
224
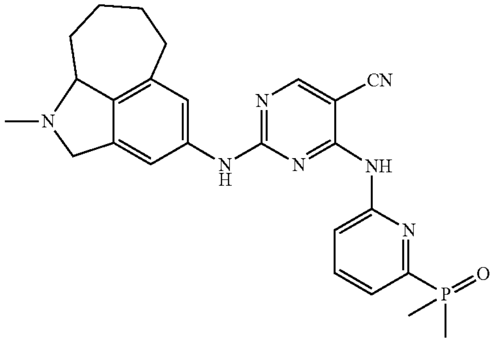
225
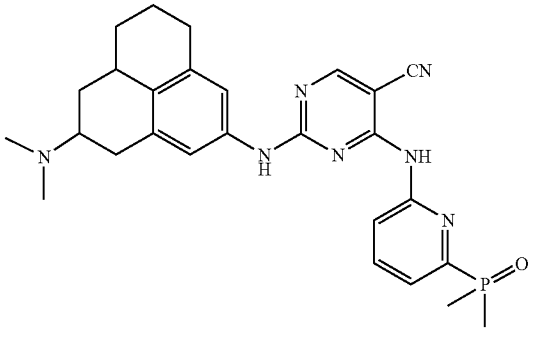
-continued
226
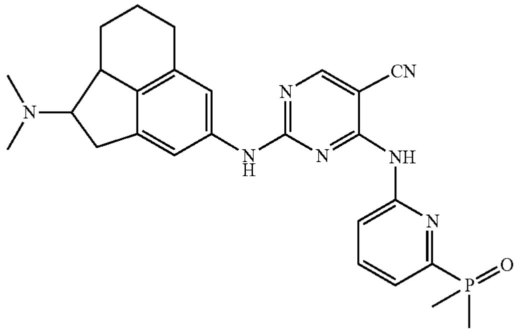
227
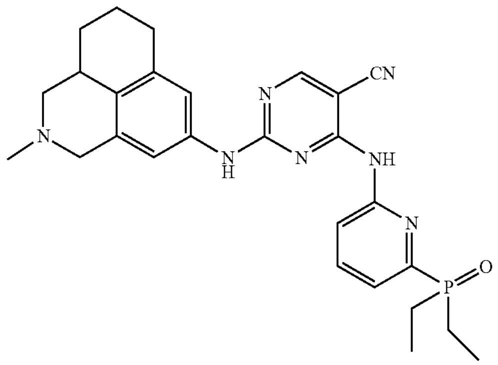
228
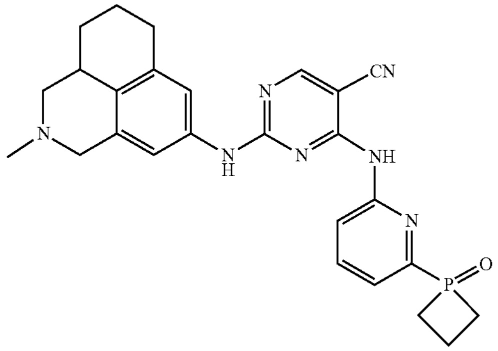
229
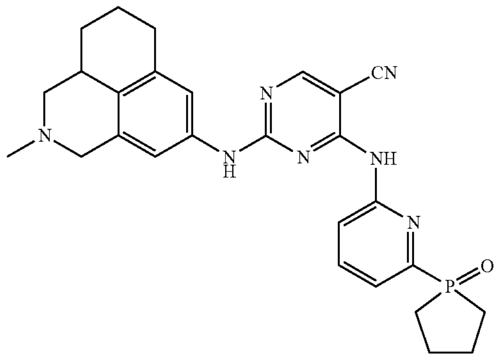

-continued
230
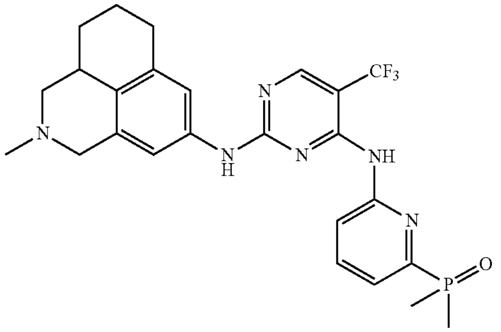
231
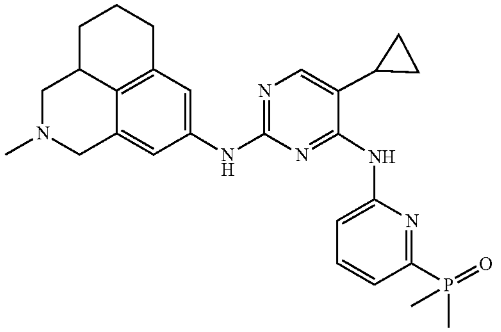
232
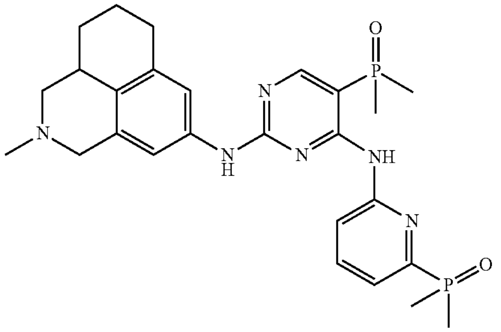
233
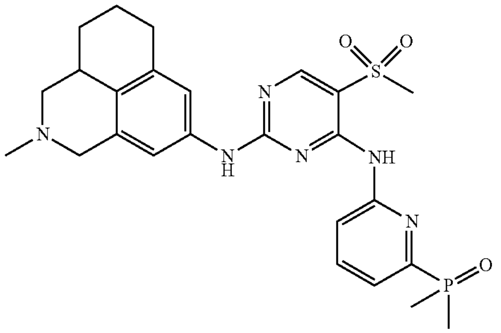
-continued
234
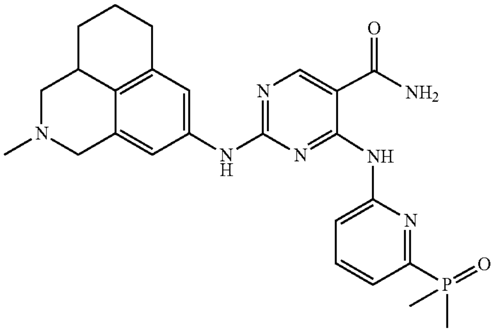
235
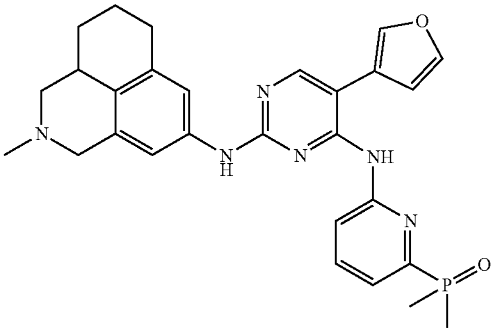
236
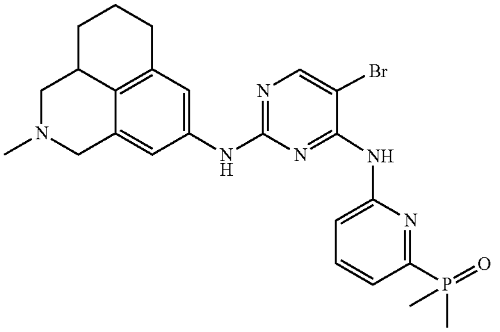
237
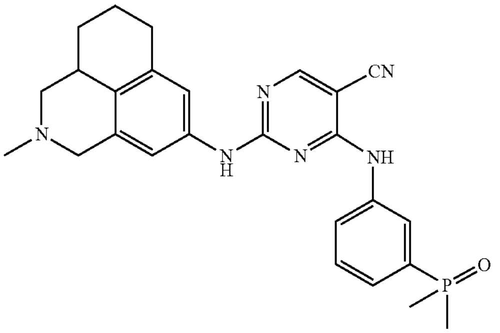

-continued
238
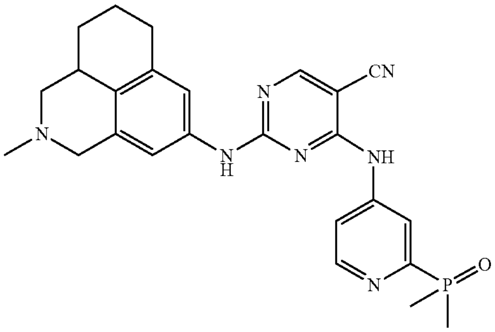
239
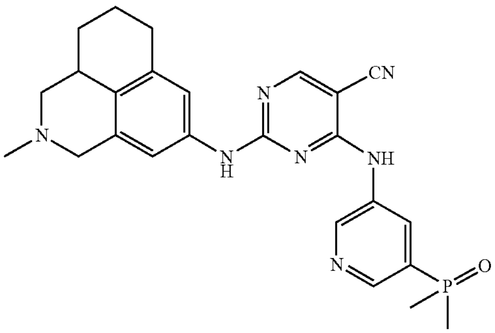
240
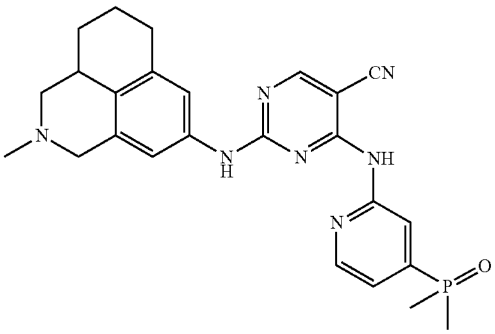
241
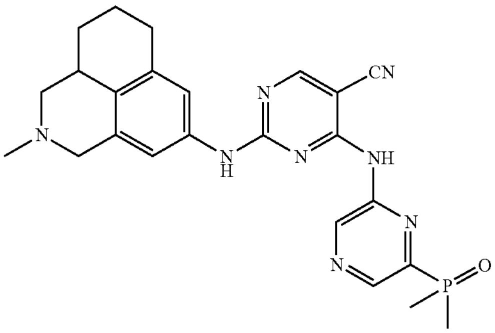
-continued
242
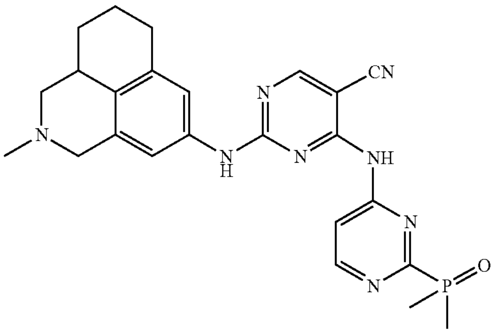
243
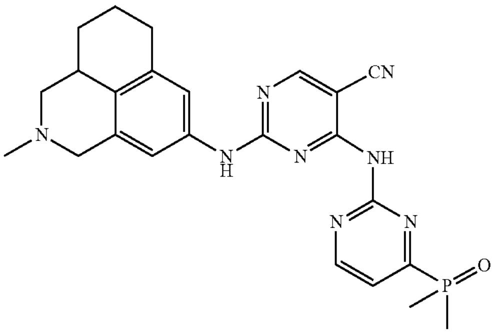
244
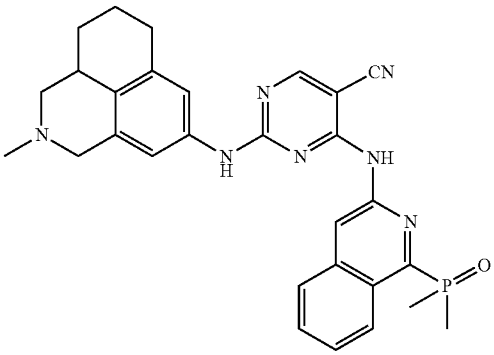
245
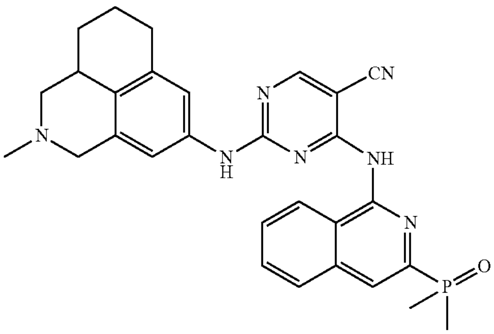

-continued
246
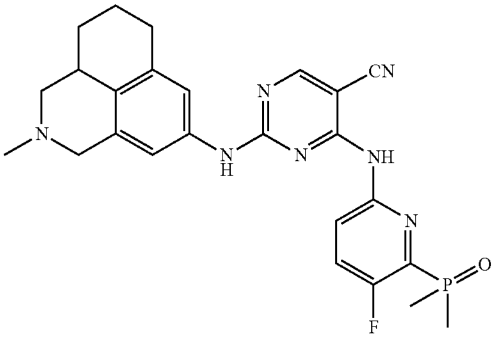
247
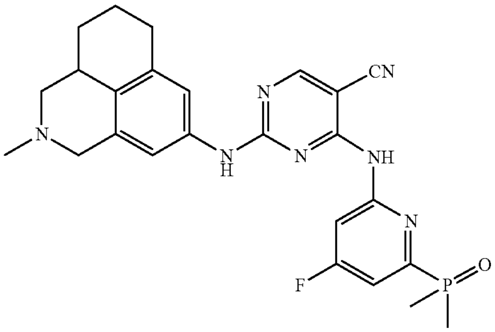
248
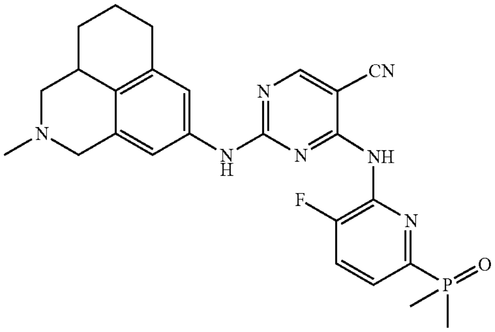
249
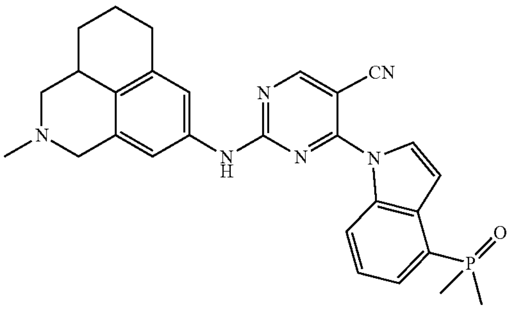
-continued
250
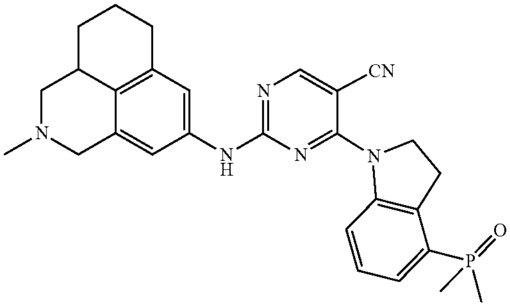
251
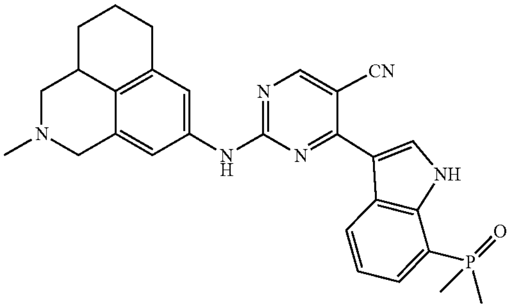
252
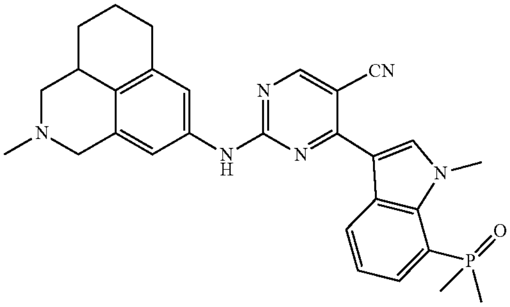
253
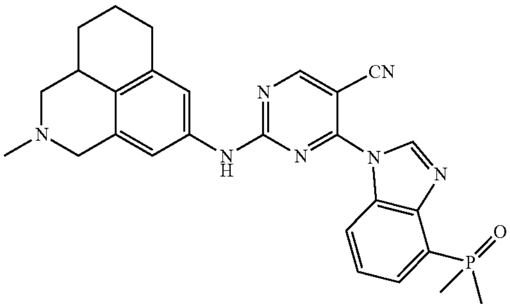

-continued
254
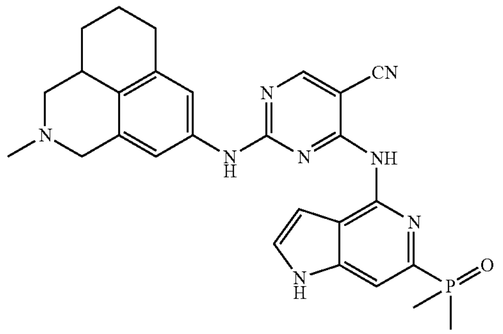
255
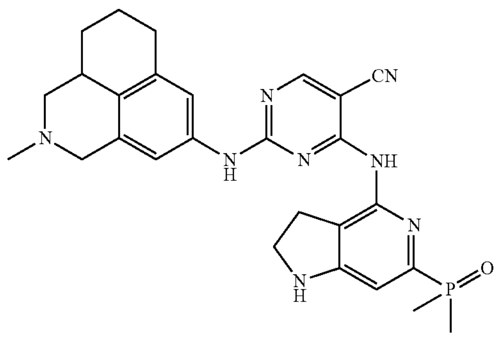
256
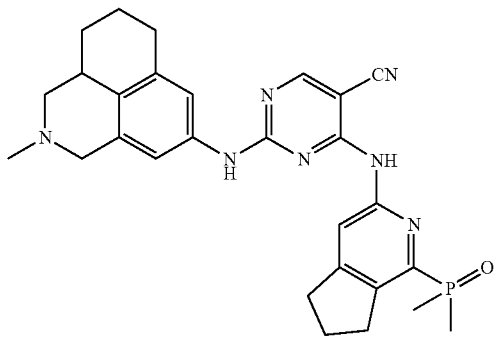
257
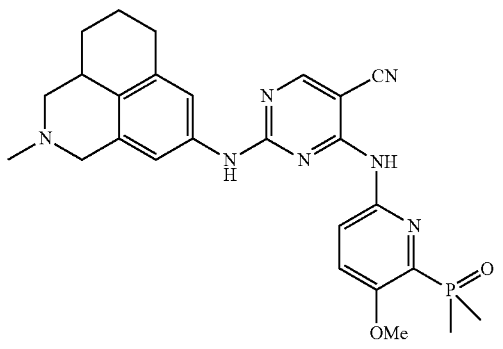
-continued
258
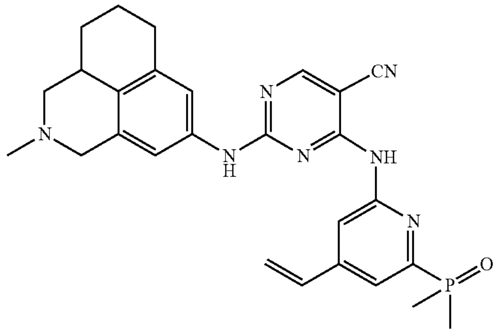
259
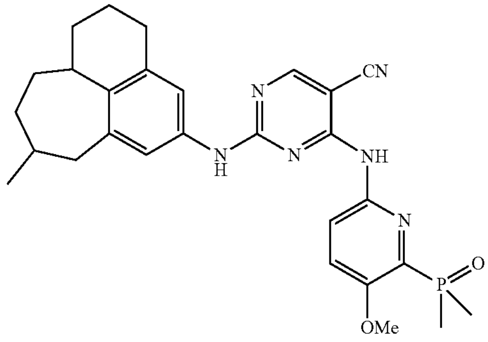
260
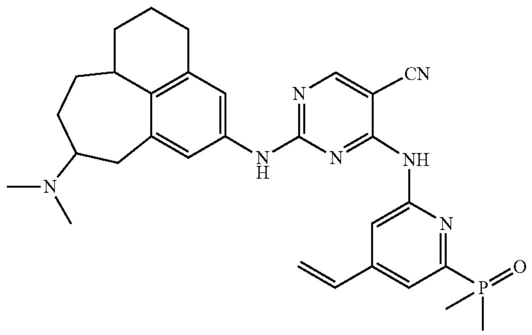
261
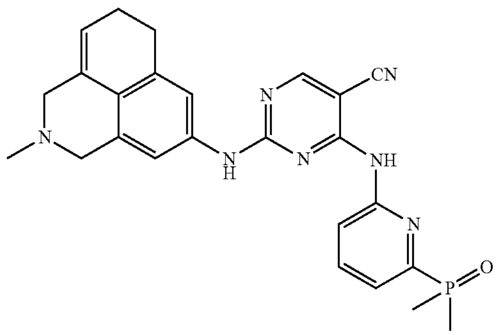

262
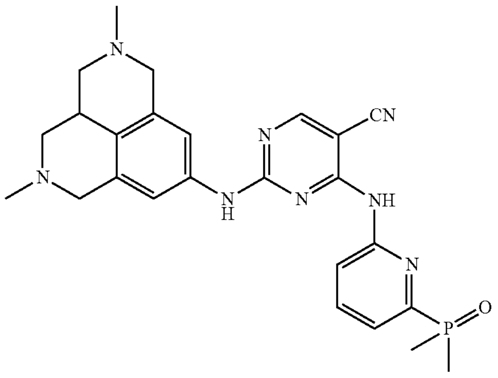
263
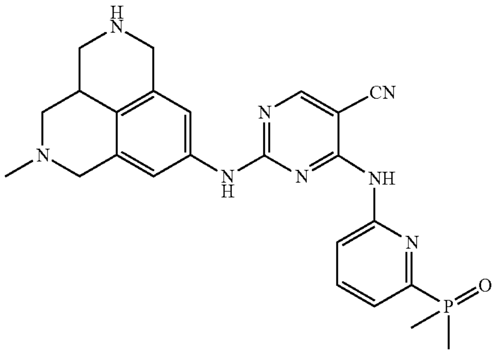
264
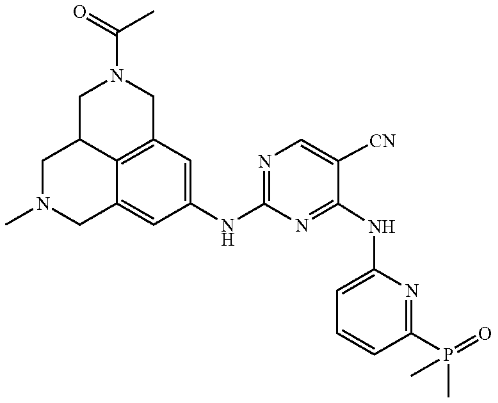
265
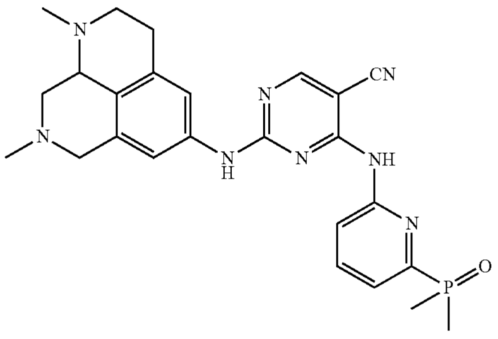
266
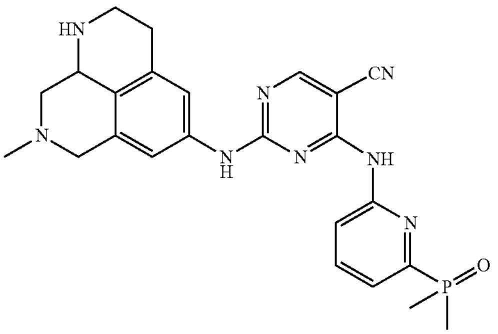
267
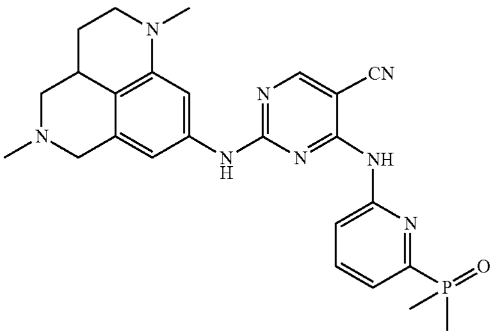
268
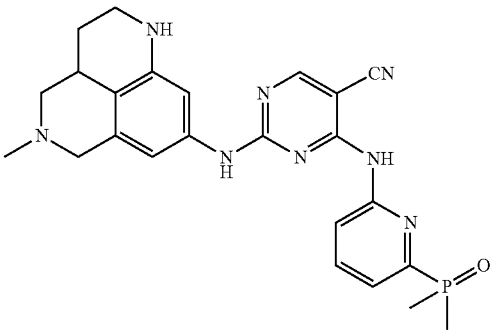
269
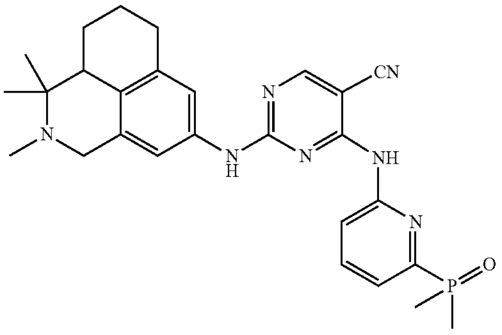

-continued
270
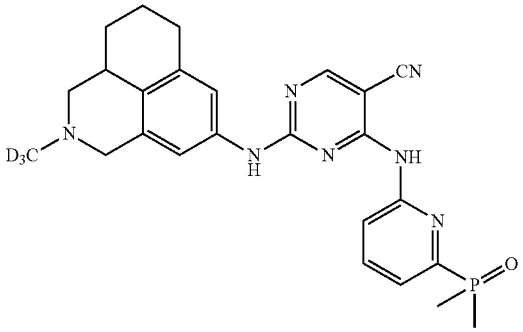
271
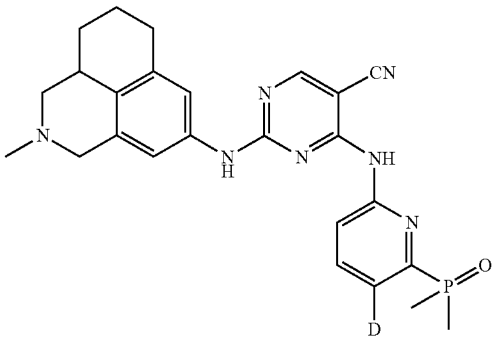
272
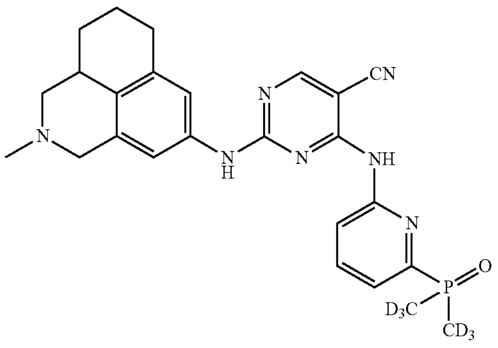
273
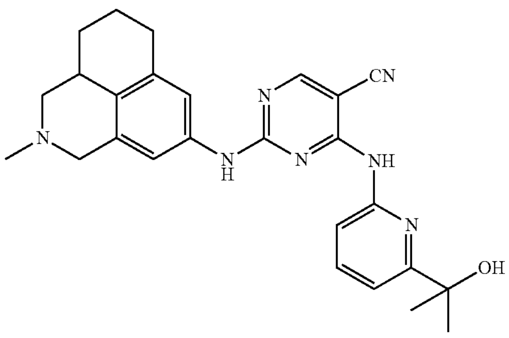
-continued
274
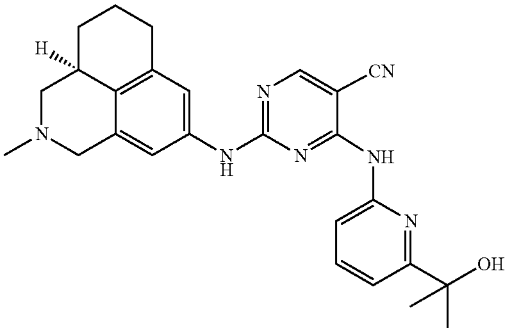
275
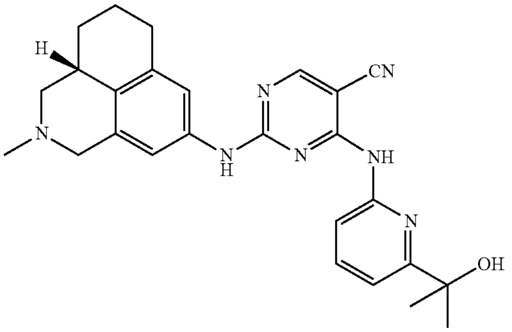
276
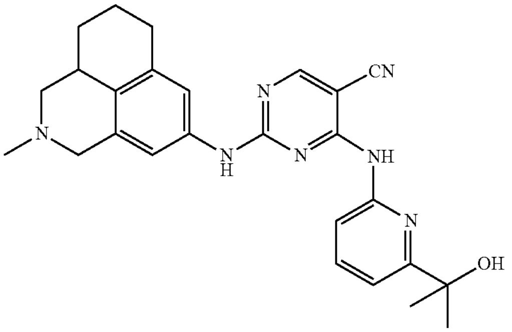
277
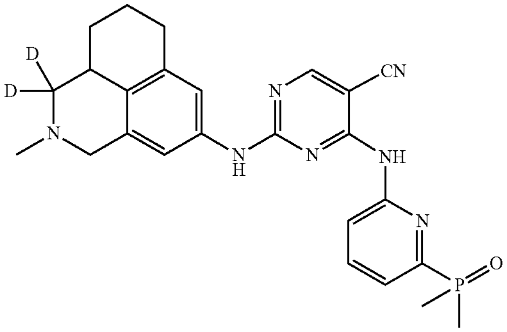

-continued
278
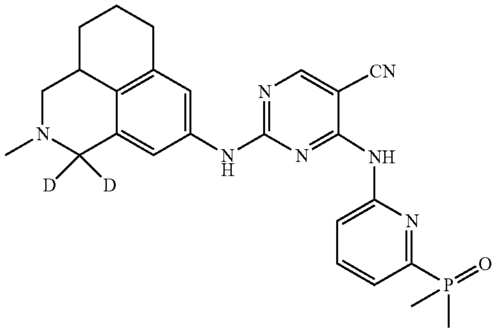
279
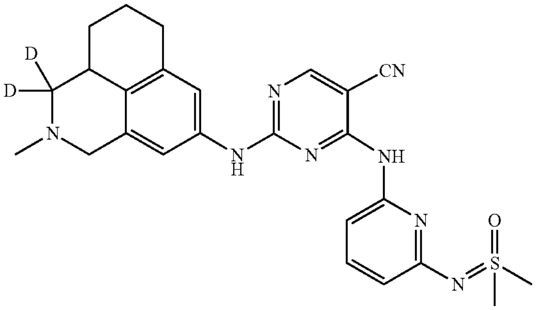
280
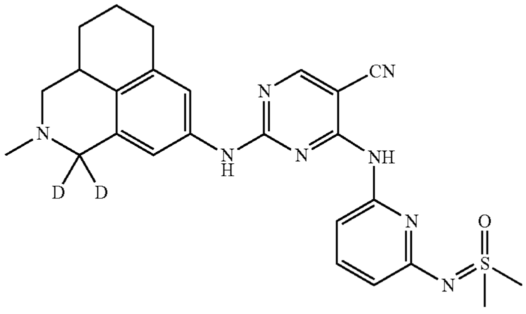
281
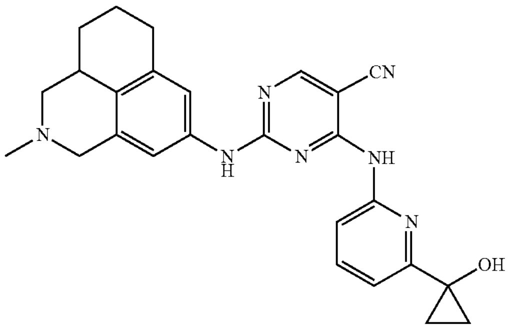
-continued
282
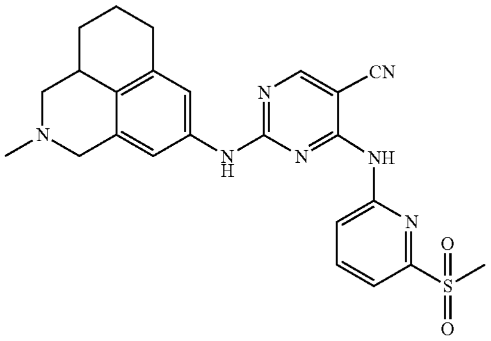
283
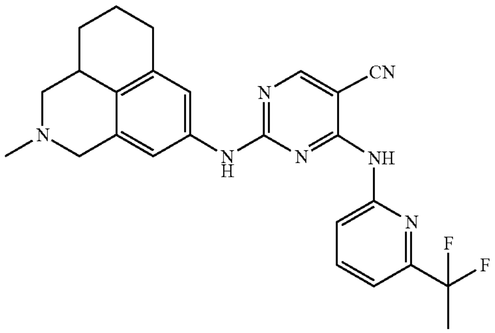
284
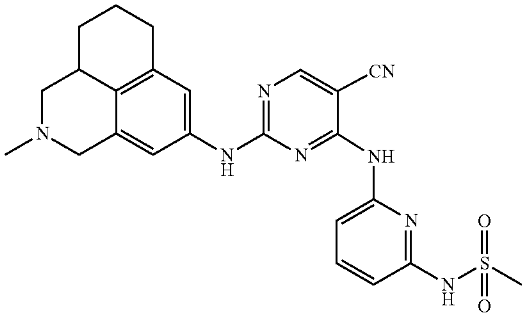
285
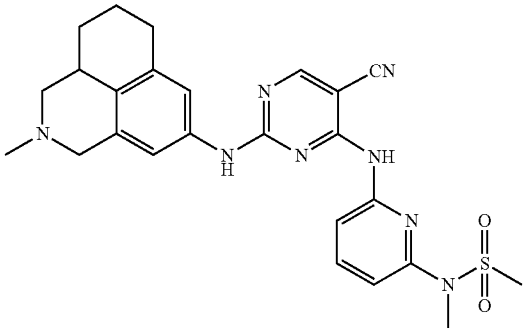

-continued
286
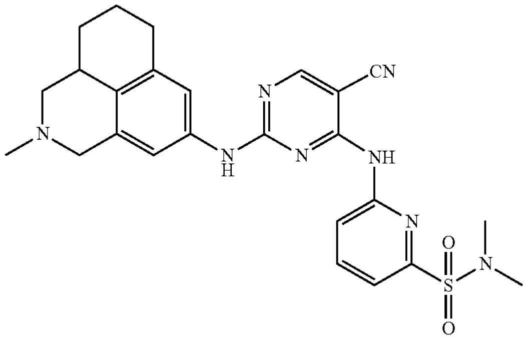
287
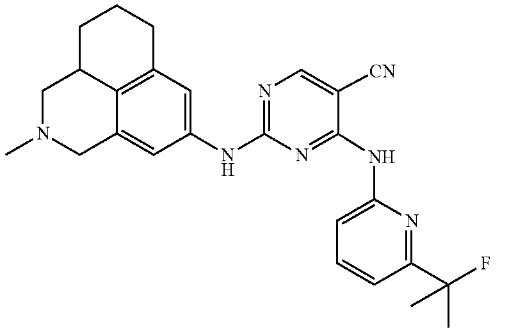
288
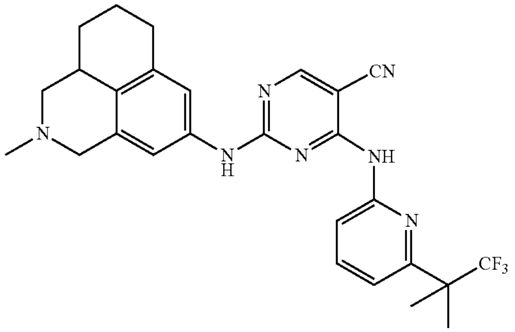
289
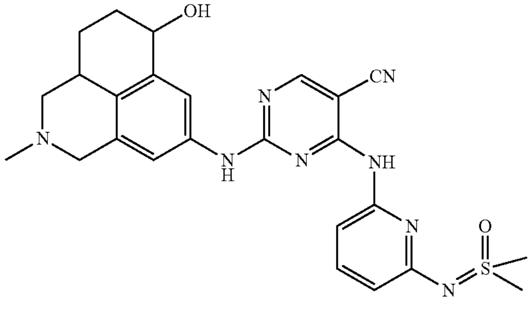
290
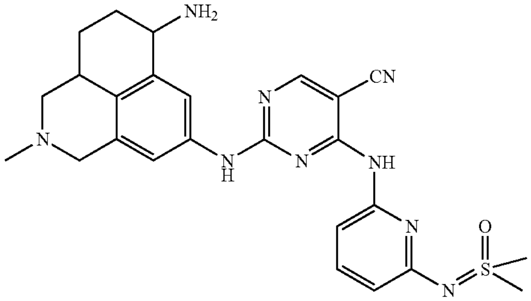
291
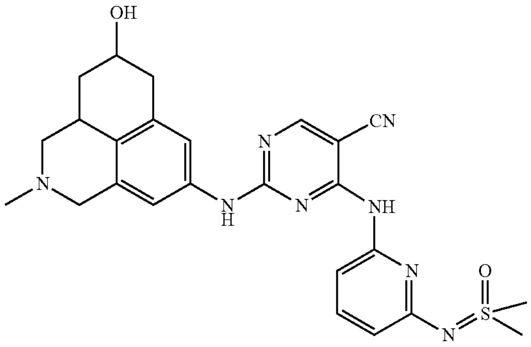
292
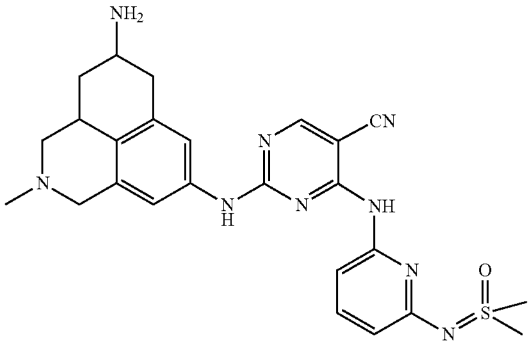
293
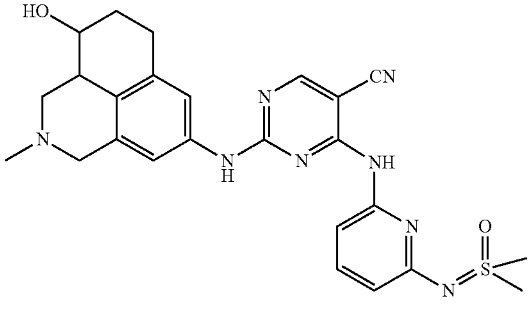

-continued

294

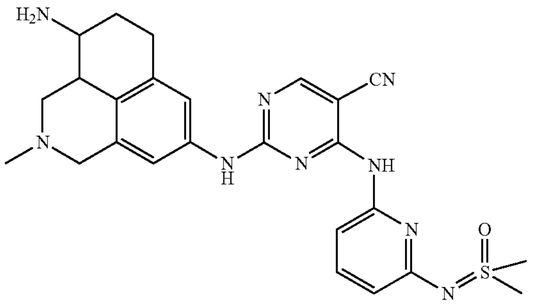

295

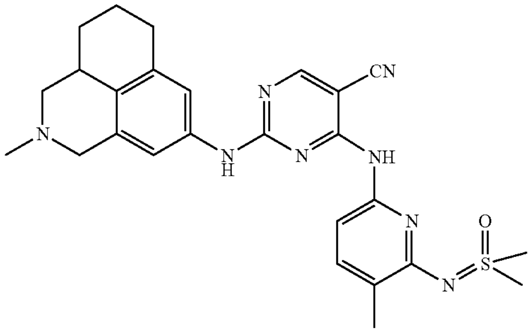

296

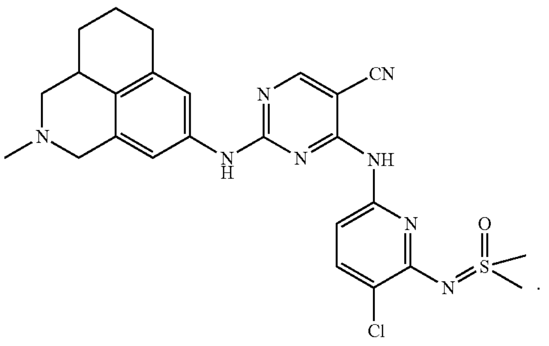

Another objective of the present invention is to provide a pharmaceutical composition including a pharmaceutically acceptable carrier, a diluent and/or an excipient and including the compound of general formula (1) or the isomer, the crystalline form, the pharmaceutically acceptable salt, the hydrate or the solvate thereof of the present invention as an active ingredient.

Yet another objective of the present invention is to provide use of the compound of general formula (1) or the isomer, the crystalline form, the pharmaceutically acceptable salt, the hydrate or the solvate thereof of the present invention or the pharmaceutical composition described above in the preparation of a medicament for treating, regulating or preventing diseases associated with the Wee-1 protein.

Yet another objective of the present invention is to provide a method for treating, regulating or preventing related diseases mediated by the Wee-1 protein, the method including administering to a subject a therapeutically effective amount of the compound of general formula (1) or the isomer, the crystalline form, the pharmaceutically acceptable salt, the hydrate or the solvate thereof of the present invention or the pharmaceutical composition described above.

Through synthesis and careful studies of various classes of new compounds with inhibitory effects on Wee-1, the inventors found that the compound of general formula (1) has surprisingly strong inhibitory activity against Wee-1.

It should be understood that both the above general description and the following detailed description of the present invention are exemplary and explanatory, and are intended to provide further explanation of the present invention claimed.

Synthesis of the Compounds

Methods for preparing the compounds of general formula (1) of the present invention are specifically described below, but these specific methods do not limit the present invention in any way.

The compounds of general formula (1) described above can be synthesized using standard synthetic techniques or well-known techniques in combination with the methods described herein. In addition, the solvents, temperatures and other reaction conditions mentioned herein may vary. Starting materials for the synthesis of the compounds can be obtained synthetically or commercially. The compounds described herein and other related compounds with different substituents can be synthesized using well-known techniques and starting materials, including the methods found in March, Advanced Organic Chemistry, 4$^{th}$ Ed., (Wiley 1992); Carey and Sundberg, Advanced Organic Chemistry, 4$^{th}$ Ed., Vols. A and B (Plenum 2000, 2001); and Green and Wuts, Protective Groups in Organic Synthesis, 3$^{rd}$ Ed., (Wiley 1999). General methods for preparing the compounds can be modified by using appropriate reagents and conditions provided herein for introducing different groups into the formula.

In one aspect, the compounds described herein are prepared according to methods well known in the art. However, the conditions of the methods, such as reactants, solvents, bases, the amount of a compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention further provides a method for preparing the compound of general formula (1), wherein the compound of general formula (1) can be prepared by general reaction scheme 1, 2, 3 or 4 as follows:

General Reaction Scheme 1

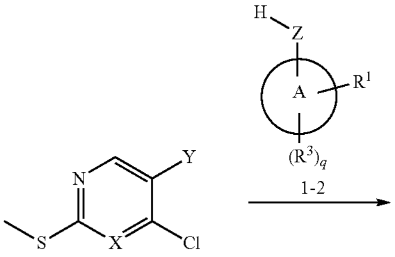

1-2

1-1

-continued

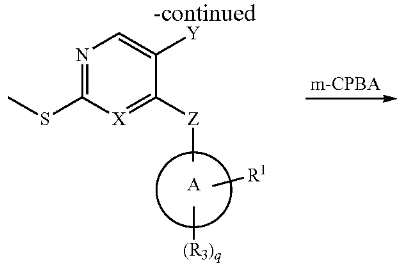

1-3

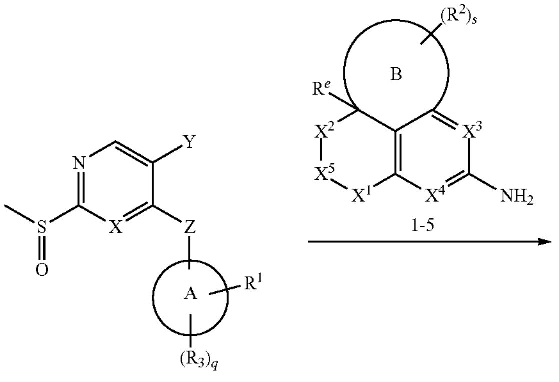

1-4

1-5

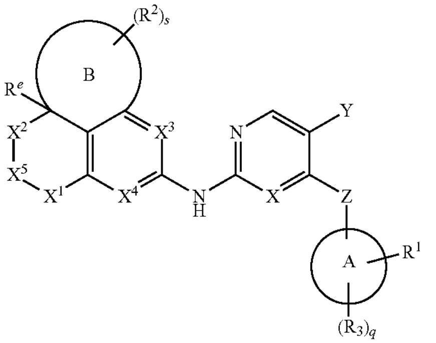

1-6

Embodiments of the compound of general formula (1) can be prepared according to general reaction scheme 1, wherein $R^1$, $R^2$, $R^3$, $R^e$, $X^1$, $X^2$, $X^3$, $X^4$, $X^5$, X, Y, Z, s, q, ring A and ring B are as defined above; H stands for hydrogen, N for nitrogen, Cl for chlorine, S for sulfur, and O for oxygen. As shown in general reaction scheme 1, compound 1-1 undergoes a substitution reaction with compound 1-2 under alkaline conditions to produce compound 1-3, compound 1-3 reacts with m-CPBA to produce compound 1-4, and compound 1-4 undergoes a substitution reaction with compound 1-5 to produce the target compound 1-6.

General Reaction Scheme 2

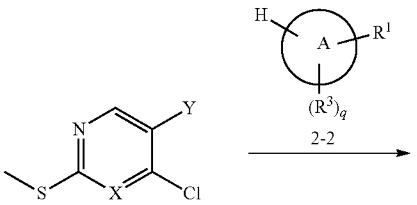

2-1

2-2

-continued

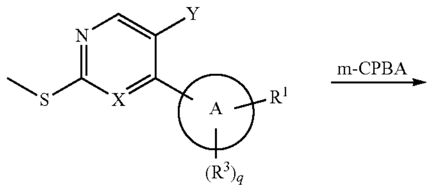

2-3

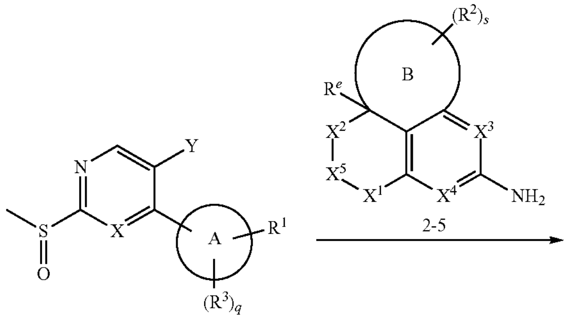

2-4

2-5

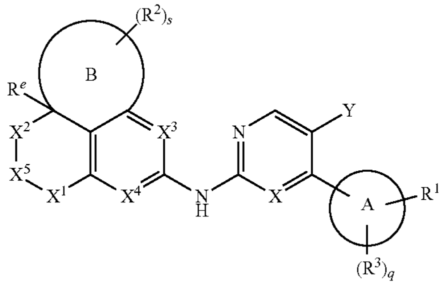

2-6

Embodiments of the compound of general formula (1) can be prepared according to general reaction scheme 2, wherein $R^1$, $R^2$, $R^3$, $R^e$, $X^1$, $X^2$, $X^3$, $X^4$, $X^5$, X, Y, s, q, ring A and ring B are as defined above; H stands for hydrogen, N for nitrogen, Cl for chlorine, S for sulfur, and O for oxygen. As shown in general reaction scheme 2, compound 2-1 undergoes a substitution reaction with compound 2-2 under alkaline conditions to produce compound 2-3, compound 2-3 reacts with m-CPBA to produce compound 2-4, and compound 2-4 undergoes a substitution reaction with compound 2-5 to produce the target compound 2-6.

General Reaction Scheme 3

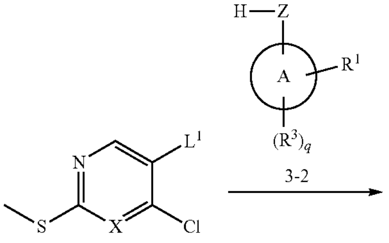

3-1

3-2

-continued

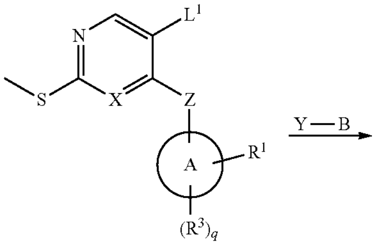

3-3

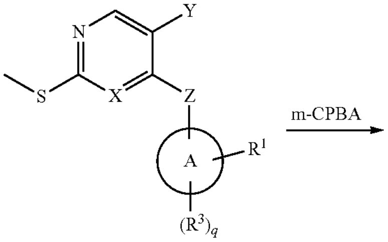

3-4

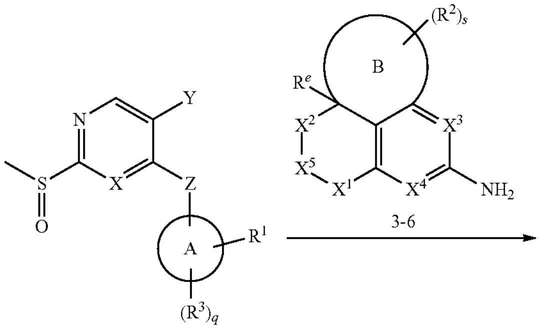

3-6

3-5

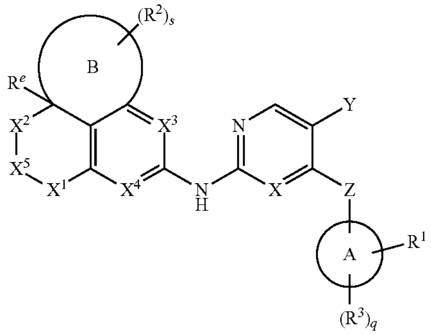

3-7

Embodiments of the compound of general formula (1) can be prepared according to general reaction scheme 3, wherein $R^1$, $R^2$, $R^3$, $R^e$, $X^1$, $X^2$, $X^3$, $X^4$, $X^5$, X, Y, Z, s, q, ring A and ring B are as defined above; H stands for hydrogen, N for nitrogen, Cl for chlorine, S for sulfur, O for oxygen, B for boronic acid, a boronic ester or a trifluoroborate, and $L^1$ for bromine or iodine. As shown in general reaction scheme 3, compound 3-1 undergoes a substitution reaction with compound 3-2 under alkaline conditions to produce compound 3-3, compound 3-3 undergoes a coupling reaction with Y-B to produce the target compound 3-4, compound 3-4 reacts with m-CPBA to produce compound 3-5, and compound 3-5 undergoes a substitution reaction with compound 3-6 to produce the target compound 3-7.

General Reaction Scheme 4

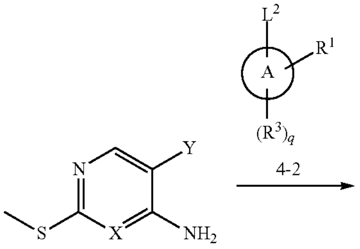

4-2

4-1

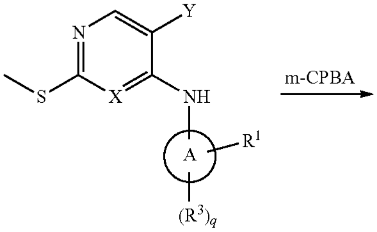

4-3

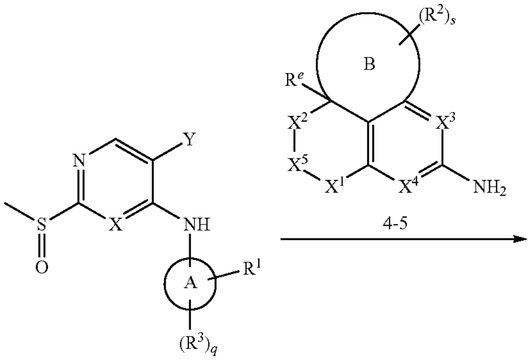

4-5

4-4

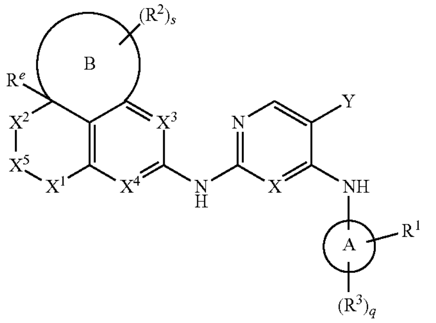

4-6

Embodiments of the compound of general formula (1) can be prepared according to general reaction scheme 4, wherein $R^1$, $R^2$, $R^3$, $R^e$, $X^1$, $X^2$, $X^3$, $X^4$, $X^5$, X, Y, s, q, ring A and ring B are as defined above; H stands for hydrogen, N for nitrogen, Cl for chlorine, S for sulfur, O for oxygen, and $L^2$ for bromine or chlorine. As shown in general reaction scheme 4, compound 4-1 undergoes a substitution reaction with compound 4-2 under alkaline conditions to produce compound 4-3, compound 4-3 reacts with m-CPBA to produce compound 4-4, and compound 4-4 undergoes a substitution reaction with compound 4-5 to produce the target compound 4-6.

Further Forms of the Compounds

"Pharmaceutically acceptable" herein refers to a substance, such as a carrier or diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" refers to a form of a compound that does not cause significant irritation to the organism receiving the administration or eliminate the biological activity and properties of the compound. In certain specific aspects, the pharmaceutically acceptable salt is obtained by subjecting the compound of general formula (1) to a reaction with acids, e.g., inorganic acids such as hydrochloric acid, hydrobromic acid, hydrofluoric acid, sulfuric acid, phosphoric acid, nitric acid, phosphoric acid and the like, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like, and acidic amino acids such as aspartic acid, glutamic acid and the like.

It should be understood that references to pharmaceutically acceptable salts include solvent addition forms or crystalline forms, especially solvates or polymorphs. A solvate contains an either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to the methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol, or methanol. Furthermore, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized, and nanoparticle forms. In addition, the compound of general formula (1) includes crystalline forms, but may also be polymorphs. Polymorphs include different lattice arrangements of the same elements of a compound. Polymorphs generally have different X-ray diffraction spectra, infrared spectra, melting points, density, hardness, crystalline forms, optical and electrical properties, stability, and solubility. Different factors such as recrystallization solvent, crystallization rate, and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer, and a cis-trans isomer. Each chiral center or axial chirality will independently produce two optical isomers, and all possible optical isomers, diastereomeric mixtures, and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium (3H), iodine-125 ($^{125}I$), and C-14 ($^{14}C$). For another example, deuterium can be used to substitute a hydrogen atom to form a deuterated compound. The bond formed by deuterium and carbon is stronger than that formed by common hydrogen and carbon, and compared with an undeuterated medicament, the deuterated medicament generally has the advantages of reduced adverse effects, increased medicament stability, enhanced efficacy, prolonged in vivo half-life, and the like. All isotopic variations of the compound of the present invention, whether radioactive or not, are intended to be encompassed within the scope of the present invention.

Terminology

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA technology and pharmacology are used. As used herein, "or" or "and" refers to "and/or" unless otherwise stated.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl, or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^iPr$, $^nPr$, $^iBu$, $^nBu$ or $^tBu$.

Unless otherwise specified, "alkylene" refers to a divalent alkyl as defined above. Examples of alkylene include, but are not limited to, methylene and ethylene.

Unless otherwise specified, "alkenyl" refers to an unsaturated aliphatic hydrocarbon group containing carbon-carbon double bonds, including linear or branched groups containing 1 to 14 carbon atoms. Lower alkenyl groups containing 1 to 4 carbon atoms, such as vinyl, 1-propenyl, 1-butenyl, or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkynyl groups containing 1 to 4 carbon atoms, such as ethynyl, 1-propynyl, or 1-butynyl, are preferred.

Unless otherwise specified, "cycloalkyl" refers to a non-aromatic hydrocarbon ring system (monocyclic, bicyclic, or polycyclic), and partially unsaturated cycloalkyl may be referred to as "cycloalkenyl" if the carbocyclic ring contains at least one double bond, or "cycloalkynyl" if the carbocyclic ring contains at least one triple bond. Cycloalkyl may include monocyclic or polycyclic groups and spiro rings (e.g., having 2, 3 or 4 fused rings). In some embodiments, cycloalkyl is monocyclic. In some embodiments, cycloalkyl is monocyclic or bicyclic. The ring carbon atoms of cycloalkyl may optionally be oxidized to form an oxo or sulfido group. Cycloalkyl further includes cycloalkylene. In some embodiments, cycloalkyl contains 0, 1, or 2 double bonds. In some embodiments, cycloalkyl contains 1 or 2 double bonds (partially unsaturated cycloalkyl). In some embodiments, cycloalkyl may be fused to aryl, heteroaryl, cycloalkyl, and heterocycloalkyl. In some embodiments, cycloalkyl may be fused to aryl, cycloalkyl, and heterocycloalkyl. In some embodiments, cycloalkyl may be fused to aryl and heterocycloalkyl. In some embodiments, cycloalkyl may be fused to aryl and cycloalkyl. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo [1.1.1]pentyl, bicyclo[2.1.1]hexyl, and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}$PrO, $^{n-}$PrO, $^{n-}$BuO, $^{n-}$BuO or $^{t-}$BuO.

Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "heteroaryl" refers to an aromatic group containing one or more heteroatoms (O, S, or N), and the "heteroaryl" is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, pyrrolyl, indolyl, benzimidazolyl, benzofuranyl, benzothiazolyl, benzothienyl, benzoxazolyl, benzopyridinyl, pyrrolopyrimidinyl, 1H-pyrrolo[3,2-b]pyridinyl, 1H-pyrrolo[2,3-c]pyridinyl, 1H-pyrrolo[3,2-c]pyridinyl, 1H-pyrrolo[2,3-b]pyridinyl,

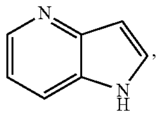,
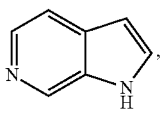,
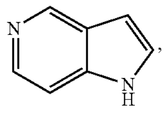, and
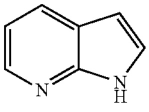.

Unless otherwise specified, "heterocycloalkyl" refers to a non-aromatic ring or ring system, which may optionally contain one or more alkenylene as part of the ring structure, having at least one heteroatom ring member independently selected from boron, phosphorus, nitrogen, sulfur, oxygen, and phosphorus. Partially unsaturated heterocycloalkyl may be referred to as "heterocycloalkenyl" if heterocycloalkyl contains at least one double bond, or "heterocycloalkynyl" if the heterocycloalkyl contains at least one triple bond. Heterocycloalkyl may include monocyclic, bicyclic, spiro ring, or polycyclic systems (e.g., having two fused or bridged rings). In some embodiments, heterocycloalkyl is a monocyclic group having 1, 2, or 3 heteroatoms independently selected from nitrogen, sulfur, and oxygen. The ring carbon atoms and heteroatoms of heterocycloalkyl may optionally be oxidized to form oxo or sulfido groups or other oxidized bonds (e.g., C(O), S(O), C(S) or $S(O)_2$, N-oxides, etc.), or the nitrogen atoms may be quaternized. Heterocycloalkyl may be attached via a ring carbon atom or a ring heteroatom. In some embodiments, heterocycloalkyl contains 0 to 3 double bonds. In some embodiments, heterocycloalkyl contains 0 to 2 double bonds. The definition of heterocycloalkyl further includes moieties having one or more aromatic rings fused to (i.e., sharing a bond with) the heterocycloalkyl ring, for example, benzo-derivatives of piperidine, morpholine, azepin, thienyl, or the like. Heterocycloalkyl containing a fused aromatic ring may be attached via any ring atom, including ring atoms of the fused aromatic ring. Examples of heterocycloalkyl include, but are not limited to, azetidinyl, azepinyl, dihydrobenzofuranyl, dihydrofuranyl, dihydropyranyl, N-morpholinyl, 3-oxa-9-azaspiro[5.5]undecyl, 1-oxa-8-azaspiro[4.5]decyl, piperidinyl, piperazinyl, oxopiperazinyl, pyranyl, pyrrolidinyl, quininyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c] pyridine, N-methylpiperidinyl, tetrahydroimidazolyl, pyrazolidinyl, butyrolactam, valerolactam, imidazolidinonyl, hydantoinyl, dioxolanyl, phthalimidyl, pyrimidine-2,4(1H,3H)-dione, 1,4-dioxanyl, morpholinyl, thiomorpholinyl, thiomorpholinyl-S-oxide, thiomorpholinyl-S,S-oxide, piperazinyl, pyranyl, pyridonyl, 3-pyrrolinyl, thiopyranyl, pyronyl, tetrahydrothienyl, 2-azaspiro[3.3]heptanyl, indolinyl,

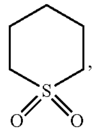,
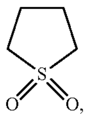,
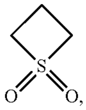,
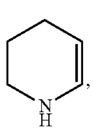,
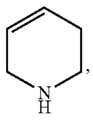,
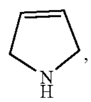, and
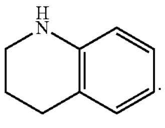.

Unless otherwise specified, "halogen" (or halo) refers to fluorine, chlorine, bromine, or iodine. The term "halo" (or "halogenated") before a group name indicates that the group is partially or fully halogenated, that is, substituted in any combination with F, Cl, Br, or I, preferably with F or Cl.

"Optional" or "optionally" means that the subsequently described event or circumstance may, but does not necessarily, occur, and the description includes instances where the event or circumstance occurs and instances where it does not.

The substituent "—O—$CH_2$—O—" means that two oxygen atoms in the substituent are linked to two adjacent carbon atoms in the heterocycloalkyl, aryl or heteroaryl, for example:

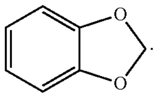

When the number of a linker group is 0, such as $-(CH_2)_0-$, it means that the linker group is a single bond.

When one of the variables is selected from a chemical bond, it means that the two groups linked by this variable are linked directly. For example, when L in X-L-Y represents a chemical bond, it means that the structure is actually X-Y.

The term "membered ring" includes any cyclic structure. The term "membered" refers to the number of backbone atoms that form a ring. For example, cyclohexyl, pyridinyl, pyranyl, and thiopyranyl are six-membered rings, and cyclopentyl, pyrrolyl, furanyl, and thienyl are five-membered rings.

The term "moiety" refers to a specific portion or functional group of a molecule. A chemical moiety is generally considered to be a chemical entity contained in or attached to a molecule. Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ). Unless otherwise stated, a single bond or a double bond is represented by .

Specific Pharmaceutical and Medical Terminology

The term "acceptable", as used herein, means that a formulation component or an active ingredient does not unduly adversely affect a general therapeutic target's health.

The terms "treatment," "treatment course," and "therapy", as used herein, include alleviating, inhibiting, or ameliorating a symptom or condition of a disease; inhibiting the development of complications; ameliorating or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can ameliorate a disease, symptom, or condition, which particularly refers to ameliorating the severity, delaying the onset, slowing the progression, or reducing the duration of the disease. Fixed or temporary administration, or continuous or intermittent administration, may be attributed to or associated with the administration.

"Active ingredient" refers to the compound of general formula (1), and pharmaceutically acceptable inorganic or organic salts of the compound of general formula (1). The compounds of the present invention may contain one or more asymmetric centers (chiral center or axial chirality) and thus occur in the form of a racemate, racemic mixture, single enantiomer, diastereomeric compound, and single diastereomer. Asymmetric centers that may be present depend on the nature of the various substituents on the molecule. Each of these asymmetric centers will independently produce two optical isomers, and all possible optical isomers, diastereomeric mixtures, and pure or partially pure compounds are included within the scope of the present invention. The present invention is meant to include all such isomeric forms of these compounds.

The terms such as "compound", "composition", "agent", or "medicine or medicament" are used interchangeably herein and all refer to a compound or composition that, when administered to an individual (human or animal), is capable of inducing a desired pharmacological and/or physiological response by local and/or systemic action.

The term "administered, administering, or administration" refers herein to the direct administration of the compound or composition, or the administration of a prodrug, derivative, analog, or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range ±10%, 5%, 1%, or 0.5%. Alternatively, the term "about" indicates that the actual numerical value falls within the acceptable standard error of a mean, as considered by those skilled in the art. All ranges, quantities, numerical values, and percentages used herein (e.g., to describe an amount of a material, a length of time, a temperature, an operating condition, a quantitative ratio, and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be understood as the significant digits indicated or the numerical values obtained using conventional rounding rules.

Unless otherwise defined in the specification, the scientific and technical terms used herein have the same meaning as commonly understood by those skilled in the art. Furthermore, nouns in their singular forms used in the specification encompass their plural forms, unless contradicted by context; nouns in their plural forms used also encompass their singular forms.

Therapeutic Use

The present invention provides use of the compound of general formula (1) or the pharmaceutical composition of the present invention in inhibiting Wee1 kinase and, therefore, use in treating one or more disorders associated with Wee1 kinase activity. Therefore, in certain embodiments, the present invention provides a method for treating Wee1 kinase-mediated disorders, the method including the step of administering to a patient in need thereof the compound of the present invention or the pharmaceutically acceptable composition thereof.

In some embodiments, a method for treating cancer is provided, the method including administering to an individual in need thereof an effective amount of any aforementioned pharmaceutical composition including the compound of structural general formula (1). In some embodiments, the compound of general formula (1) can be used in combination with an additional anti-cancer drug. In some embodiments, the compound of general formula (1) can be used in combination with gemcitabine. In some embodiments, the cancer is mediated by Wee1 kinase. In other embodiments, the cancer is a hematologic cancer and a solid tumor, including, but not limited to, hematologic malignancies (leukemias, lymphomas, and myelomas including multiple myeloma, myelodysplastic syndrome and myeloproliferative family syndrome), solid tumors (carcinomas such as prostate, breast, lung, colon, pancreas, kidney, ovary and soft tissue cancers, osteosarcoma, and interstitial tumors), and the like.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment, and other specific conditions of a treated subject.

"Pharmaceutically acceptable excipient or carrier" refers to one or more compatible solid or liquid fillers or gel substances that are suitable for human use and must be of sufficient purity and sufficiently low toxicity. "Compatible" herein means that the components of the composition are capable of intermixing with the compound of the present invention and with each other, without significantly diminishing the pharmaceutical efficacy of the compound. Examples of pharmaceutically acceptable excipients or carriers include cellulose and derivatives thereof (e.g., sodium carboxymethylcellulose, sodium ethylcellulose, or cellulose acetate), gelatin, talc, solid lubricants (e.g., stearic acid or magnesium stearate), calcium sulfate, vegetable oil (e.g., soybean oil, sesame oil, peanut oil, or olive oil), polyols (e.g., propylene glycol, glycerol, mannitol, or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly, or subcutaneously), or topically.

Solid dosage forms for oral administration include capsules, tablets, pills, pulvises, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol, and silicic acid; (b) binders, such as hydroxymethyl cellulose, alginate, gelatin, polyvinylpyrrolidone, sucrose, and acacia; (c) humectants, such as glycerol; (d) disintegrants, such as agar, calcium carbonate, potato or tapioca starch, alginic acid, certain complex silicates, and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets, and pills, the dosage forms may further include buffers.

Solid dosage forms such as tablets, dragees, capsules, pills, and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups, and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil, or mixtures of these substances.

Besides such inert diluents, the composition may further include adjuvants, such as wetting agents, emulsifiers, suspending agents, sweeteners, flavoring agents, and perfuming agents.

In addition to the active compound, suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms for topical administration of the compound of the present invention include ointments, pulvises, patches, sprays, and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose is a pharmaceutically effective dose. For a human of 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent, or similar purpose. Thus, unless otherwise specified, the features disclosed herein are merely general examples of equivalent or similar features.

DETAILED DESCRIPTION

Various specific aspects, features, and advantages of the compounds, methods, and pharmaceutical compositions described above will be set forth in detail in the following description, which will make the content of the present invention very clear. It should be understood that the detailed description and examples below describe specific examples for reference only. After reading the description of the present invention, those skilled in the art can make various changes or modifications to the present invention, and such equivalents also fall within the scope of the present application defined herein.

In all the examples, $^1$H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was a volume ratio.

The following abbreviations are used in the present invention: $(Boc)_2O$ for di-tert-butyl dicarbonate; $CDCl_3$ for deuterated chloroform; EtOAc for ethyl acetate; Hexane for n-hexane; HPLC for high-performance liquid chromatography; MeCN for acetonitrile; DCM for dichloromethane; DIPEA for diisopropylethylamine; Dioxane for 1,4-dioxane; DMF for N,N-dimethylformamide; DMAP for 4-(dimethylamino)pyridine; DMSO for dimethyl sulfoxide; h for hour; IPA for isopropanol; min for minute; $K_2CO_3$ for potassium carbonate; KOAc for potassium acetate; $K_3PO_4$ for potassium phosphate; min for minute; MeOH for methanol; MS for mass spectrometry; MsOH for methanesulfonic acid; m-CPBA for m-chloroperoxybenzoic acid; n-BuLi for n-butyllithium; NMR for nuclear magnetic resonance; Pd/C for palladium carbon; $Pd(PPh_3)_4$ for tetrakis(triphenylphosphine)palladium; $Pd_2(dba)_3$ for tris(dibenzylideneacetone) dipalladium(0); PE for petroleum ether; TFA for trifluoroacetic acid; $T_3P$ for 1-propylphosphonic anhydride; XantPhos for 4,5-bis(diphenylphosphino)-9,9-dimethylxanthene; TLC for thin-layer chromatography; XPhos for 2-dicyclohexylphosphonium-2',4',6'-triisopropylbiphenyl.

Example 1. Synthesis of Compound 1

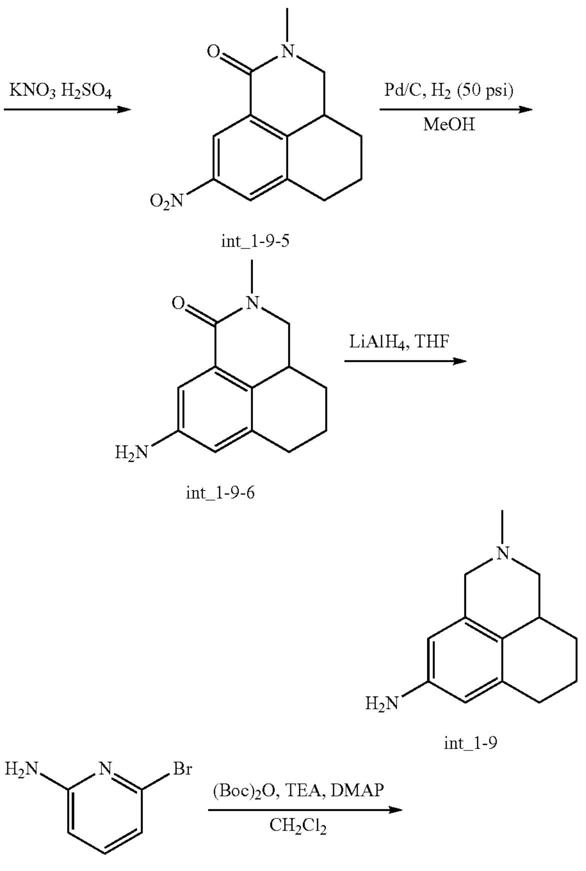

int_1-9-5 int_1-9-6 int_1-9 int_1-1

-continued

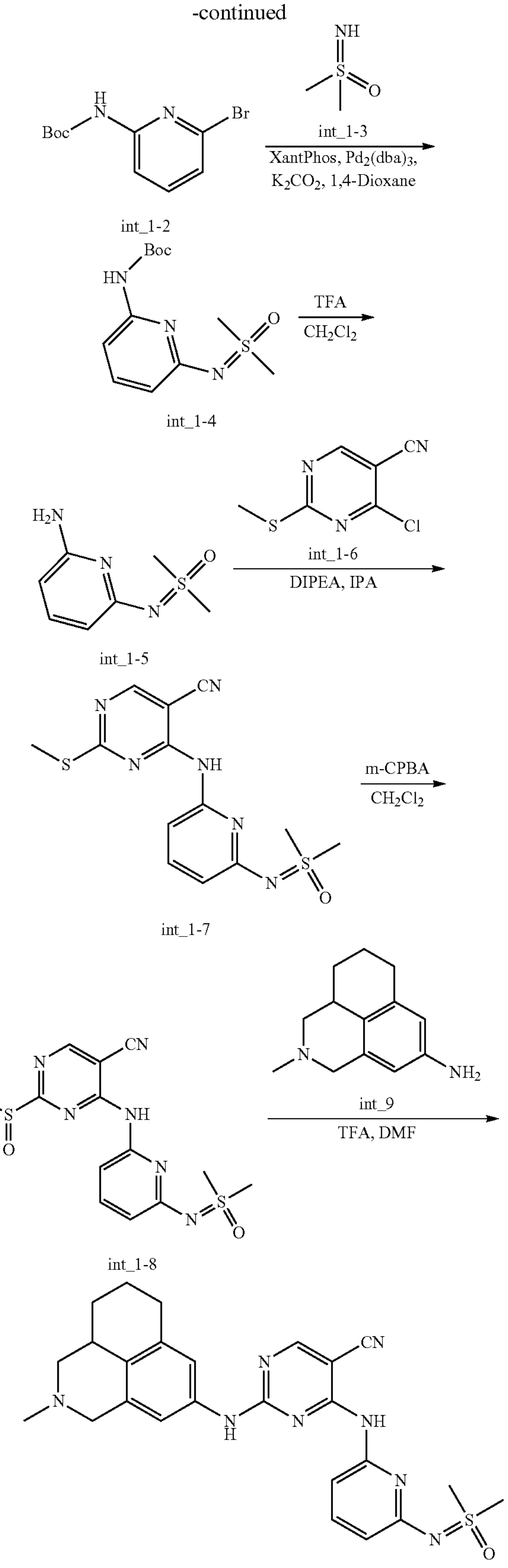

int_1-2 int_1-4 int_1-5 int_1-7 int_1-8

1

Step 1: Synthesis of Compound Int_1-9-2 int_1-9-2

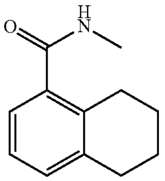

Int_1-9-1 (50 g, 284 mmol), methylamine hydrochloride (57.5 g, 851 mmol) and TEA (144 g, 1.42 mol, 197 mL) were dissolved in acetonitrile (600 mL), and $T_3P$ (217 g, 341 mmol, 203 mL, 50% purity) was added dropwise at room temperature. After the addition, the reaction was heated at 50° C. for 16 h. The reaction mixture was diluted with 1500 mL of ethyl acetate and washed with an aqueous solution of $NaHCO_3$ (400 mL×3). The organic phase was dried over anhydrous sodium sulfate. The organic phase was filtered and distilled under reduced pressure to give a white solid (50 g, 93.1% yield, crude). The crude product was directly used in the next step.

$^1$H NMR: (400 MHz, Chloroform-d) δ 7.12-7.01 (m, 3H), 6.10-5.71 (m, 1H), 2.93 (d, J=4.9 Hz, 3H), 2.83 (br s, 2H), 2.79-2.71 (m, 2H), 1.84-1.65 (m, 4H).

MS (ESI): 190 $[M+H]^+$.

Step 2: Synthesis of Compound Int_1-9-3 int_1-9-3

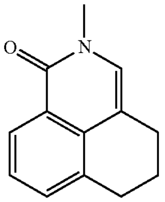

Int_1-9-2 (50 g, 264 mmol) was dissolved in THE (500 mL), and n-BuLi (2.5 M, 275 mL) was slowly added dropwise at −23° C. under nitrogen. Subsequently, DMF (48.3 g, 660 mmol, 50.8 mL) was slowly added dropwise at −23° C. Then a solution of HCl (6 M, 300 mL) was slowly added dropwise at 20° C. The reaction mixture was diluted with 100 mL of water and extracted with ethyl acetate (500 mL×3). The organic phase was dried over anhydrous sodium sulfate. The organic phase was filtered and concentrated under reduced pressure to give a yellow solid (55 g, crude). The crude product was directly used in the next step.

$^1$H NMR: (400 MHz, Chloroform-d) δ 8.36-8.20 (m, 1H), 7.46-7.32 (m, 2H), 6.84 (s, 1H), 3.63-3.52 (m, 3H), 2.99-2.92 (m, 3H), 2.75-2.69 (m, 2H), 2.01-1.90 (m, 2H).

MS (ESI): 200 $[M+H]^+$.

Step 3: Synthesis of Compound Int_1-9-4 int_1-9-4

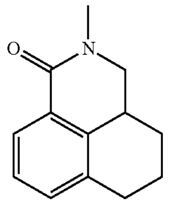

Int_1-9-3 (55 g, 276 mmol) and 20 g of palladium on carbon were suspended in methanol (800 mL), and the suspension was stirred overnight at 30° C. under hydrogen (50 psi). The palladium on carbon was removed by filtration, and the filtrate was concentrated under reduced pressure and purified by column chromatography ($SiO_2$, PE/EtOAc=I/O to 3/1) to give a yellow solid (38.5 g, 69.3% yield).

$^1$H NMR: (400 MHz, DMSO-$d_6$) δ 7.71-7.62 (m, 1H), 7.28-7.20 (m, 2H), 3.42 (dd, J=5.6, 11.9 Hz, 1H), 3.25 (t, J=12.5 Hz, 1H), 3.13-2.99 (m, 4H), 2.87-2.69 (m, 2H), 2.06-1.90 (m, 2H), 1.75-1.61 (m, 1H), 1.41-1.22 (m, 1H).

MS (ESI): 202 $[M+H]^+$.

Step 4: Synthesis of Compound Int_1-9-5 int_1-9-5

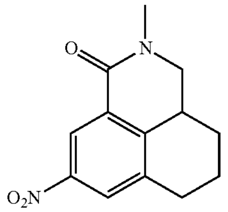

Int_1-9-4 (3.1 g, 19.2 mmol) was dissolved in $H_2SO_4$ (300 mL), and $KNO_3$ (17.9 g, 177 mmol) was slowly added at 0° C. over 3 h. After the addition, the mixture was warmed to room temperature and stirred for 2 h. TLC monitoring showed the reaction was complete. The reaction mixture was diluted with 500 mL of water, and a large amount of solid precipitated. The precipitate was collected by filtration and dried to give a yellow solid (79 g, crude). The crude product was directly used in the next step.

MS (ESI): 247 $[M+H]^+$.

Step 5: Synthesis of Compound Int_1-9-6 int_1-9-6

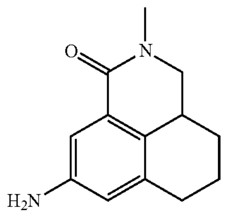

Int_1-9-5 (4.9, 19.9 mmol) and palladium on carbon (2 g, 19.9 mmol, 10% purity) were suspended in methanol (100 mL), and the suspension was left at 25° C. under hydrogen (50 psi) for 16 h. The palladium on carbon was removed by filtration, and the filtrate was concentrated under reduced pressure and purified by column chromatography ($SiO_2$, PE/EtOAc=1/0 to 1/2) to give a yellow solid (1.44 g, 33.5% yield).

$^1H$ NMR: (400 MHz, Chloroform-d) δ 7.24 (d, J=2.3 Hz, 1H), 6.56 (d, J=2.0 Hz, 1H), 3.67 (br s, 2H), 3.32-3.25 (m, 2H), 3.19-3.13 (m, 3H), 3.09-2.97 (m, 1H), 2.81-2.65 (m, 2H), 2.07-1.90 (m, 2H), 1.78-1.62 (m, 1H), 1.37-1.23 (m, 1H).

MS (ESI): 217 $[M+H]^+$.

Step 6: Synthesis of Compound Int_1-9 int_1-9

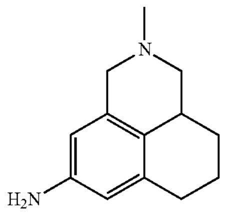

Int_1-9-6 (7 g, 32.4 mmol) was dissolved in anhydrous tetrahydrofuran (300 mL), and $LiAlH_4$ (6.14 g, 162 mmol) was added at 0° C. The mixture was warmed to 25° C. under nitrogen and left for 2 h. Water was slowly added to the reaction mixture to quench the reaction; during the addition, the temperature of the reaction mixture was kept at 0-10° C. The reaction mixture was diluted with 800 mL of ethyl acetate and washed with water (100 mL×3). The organic phase was dried over anhydrous sodium sulfate. The organic phase was filtered and distilled under reduced pressure to give a crude product. The crude product was purified by column chromatography ($SiO_2$, DCM/(MeOH+1% $NH_4OH$)=1/0 to 10/1) to give a yellow oil (6.25 g, 95.5% yield).

$^1H$ NMR: (400 MHz, Chloroform-d) δ 6.31 (s, 1H), 6.21 (s, 1H), 3.88 (d, J=15.1 Hz, 1H), 3.62-3.34 (br s, 2H), 3.26 (d, J=15.1 Hz, 1H), 2.98-2.69 (m, 4H), 2.42 (s, 3H), 2.03 (t, J=10.7 Hz, 1H), 1.92 (tdd, J=3.4, 6.5, 13.1 Hz, 1H), 1.88-1.75 (m, 2H), 1.34-1.17 (m, 1H).

MS (ESI): 203 $[M+H]^+$.

Step 7: Synthesis of Compound Int_1-2 int_1-2

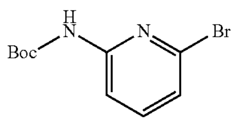

Int_1-1 (3.46 g, 20 mmol) was dissolved in dichloromethane (100 mL), and DIPEA (5.2 g, 40 mmol), DMAP (1.22 g, 10 mmol) and $(Boc)_2O$ (4.8 g, 22 mmol) were added. The mixture was left overnight at room temperature. LC-MS monitoring showed the reaction was complete. The reaction mixture was diluted with dichloromethane (100 mL), washed with water (200 mL), washed with 2 N dilute hydrochloric acid (100 mL), washed with an aqueous solution of sodium bicarbonate (100 mL), washed with water (100 mL), and finally washed with saturated brine (100 mL). The organic phase was dried over anhydrous sodium sulfate. The organic phase was filtered and distilled under reduced pressure to give a pale brown gel (4.0 g, 73% yield, crude). The crude product was directly used in the next step.

ESI-MS m/z: 273 $[M+H]^+$.

Step 8: Synthesis of Compound Int_1-4 int_1-4

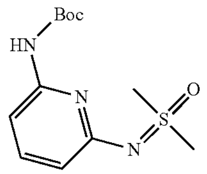

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol) and Xantphos (845 mg, 1.46 mmol) were dissolved in 1,4-dioxane (120 mL), and the mixture was left overnight at 85° C. LC-MS monitoring showed the reaction was complete. The reaction mixture was filtered and distilled under reduced pressure to give a crude product. The crude product was purified by column chromatography ($SiO_2$, DCM:MeOH=100:1 to 30:1) to give a pale yellow solid product (2.7 g, 65% yield).

ESI-MS m/z: 286 $[M+H]^+$.

Step 9: Synthesis of Compound Int_1-5 int_1-5

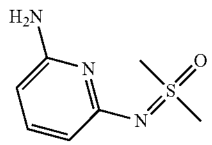

Int_1-4 (2.4 g, 8.41 mmol) was dissolved in dichloromethane (30 mL), and trifluoroacetic acid (10 mL) was added. The mixture was left overnight at room temperature. LC-MS monitoring showed the reaction was complete. The reaction mixture was directly concentrated under reduced pressure to give a grayish yellow solid (1.6 g, 100% yield). The crude product was directly used in the next step.

ESI-MS m/z: 186 $[M+H]^+$.

Step 10: Synthesis of Compound Int_1-7 int_1-7

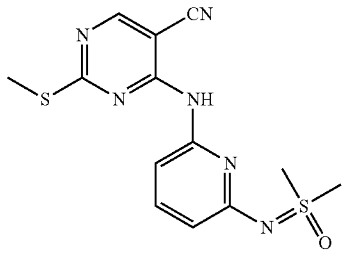

Int_1-6 (2 g, 10.8 mmol) and int_1-5 (3.2 g, 10.8 mmol) were dissolved in isopropanol (5 mL), and DIPEA (5.57 g, 43.1 mmol, 7.51 mL) was added. The reaction mixture was heated to 50° C. and left overnight. LC-MS monitoring showed the reaction was complete. The reaction mixture was cooled to room temperature, and a white solid precipitated. The solid was collected by filtration as the product. The product was dried to give a white solid (1.2 g, 33% yield).

$^1$H NMR: (400 MHz, DMSO-$d_6$). δ 9.80 (s, 1H), 8.70 (s, 1H), 7.58 (t, J=7.9 Hz, 1H), 7.16 (d, J=7.8 Hz, 1H), 6.44 (d, J=7.9 Hz, 1H), 3.41 (s, 6H), 2.49 (s, 3H).

ESI-MS m/z: 335 $[M+H]^+$.

Step 11: Synthesis of Compound Int_1-8 int_1-8

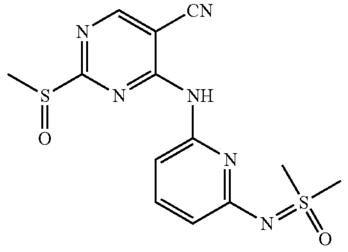

Int_1-7 (334 mg, 1.0 mmol) was dissolved in dichloromethane (40 mL), and m-CPBA (85%, 240 mg, 1.2 mmol) was added at room temperature. The mixture was stirred at room temperature for half an hour. LC-MS monitoring showed the reaction was complete. The reaction mixture was concentrated under reduced pressure to give a crude product (335 mg). The crude product was directly used in the next step.

ESI-MS m/z: 351 $[M+H]^+$.

Step 12: Synthesis of Compound 1

1

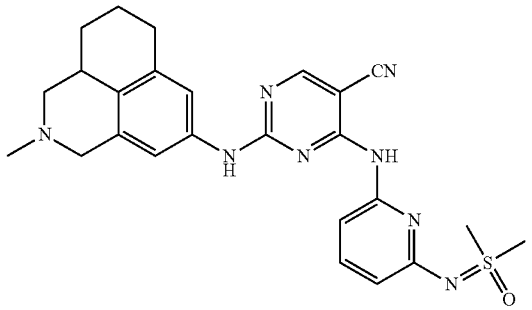

Int_1-8 (335 mg, 0.95 mmol) was dissolved in DMF (20 mL), and int_1-9 (242 mg, 1.2 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative HPLC to give a white solid (160 mg, 34% yield).

$^1$H NMR (400 MHz, Chloroform-d) δ 8.36 (s, 1H), 7.70 (d, J=8.0 Hz, 1H), 7.59 (s, 1H), 7.48 (s, 1H), 7.26 (s, 1H), 7.07 (d, J=8.6 Hz, 2H), 6.57 (dd, J=8.0, 0.7 Hz, 1H), 3.92 (d, J=15.2 Hz, 1H), 3.36 (s, 6H), 3.32 (d, J=15.2 Hz, 1H), 3.05-2.89 (m, 2H), 2.79 (ddt, J=24.3, 17.0, 8.9 Hz, 2H), 2.44 (s, 3H), 2.08 (t, J=10.4 Hz, 1H), 1.99-1.78 (m, 3H), 1.37-1.18 (m, 1H).

LC-MS: 489 $[M+H]^+$.

Preparative HPLC Purification:

Instrument: Agilent 1260 infinity 2

Column: Waters Xbridge Prep C1819×250 mm, 5 μm OBD

Column temperature: 25° C.

Detection wavelengths: 205 nm/254 nm

Mobile phase A: $H_2O$ (0.1% FA)

Mobile phase B: MeCN

Flow rate: 20 mL/min

Gradient: 0.00 min-1.00 min: 5% B→5% B 1.01 min-20.00 min: 5% B→40% B 20.00 min-20.01 min: 40% B→95% B 20.01 min-24.00 min: 95% B→95% B 24.00 min-24.01 min: 95% B→5% B 24.01 min-27.00 min: 5% B→5% B Example 2. Synthesis of Compound 2

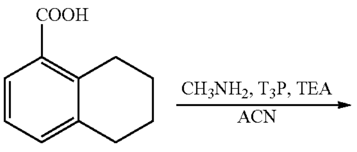

int_1-9-1

-continued
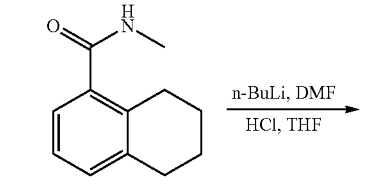
int_1-9-2
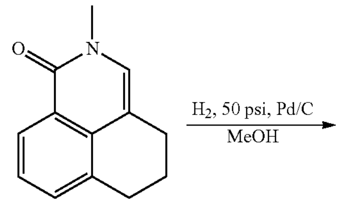
int_1-9-3
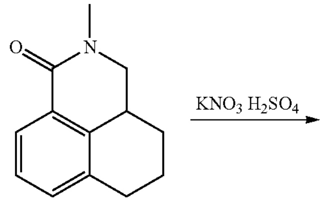
int_1-9-4
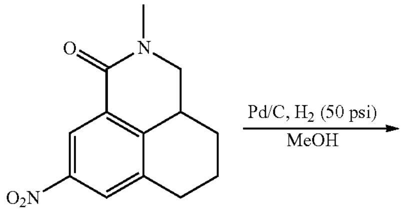
int_1-9-5
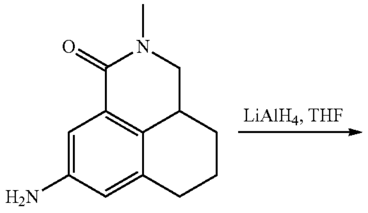
int_1-9-6
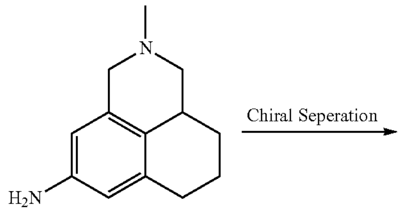
int_1-9
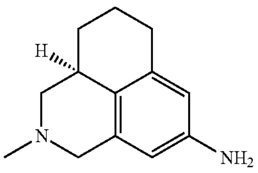
int_1-9A
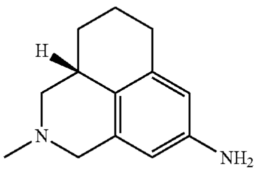
int_1-9B
-continued
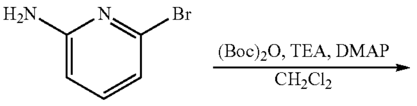
int_1-1
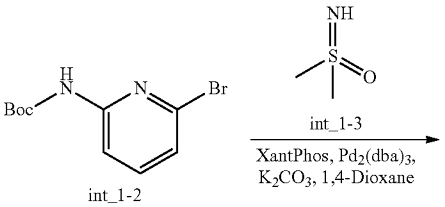
int_1-2
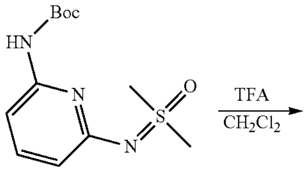
int_1-4
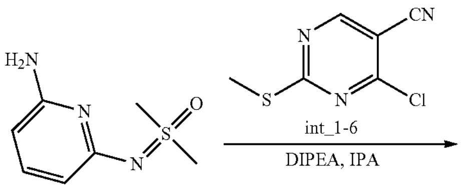
int_1-5
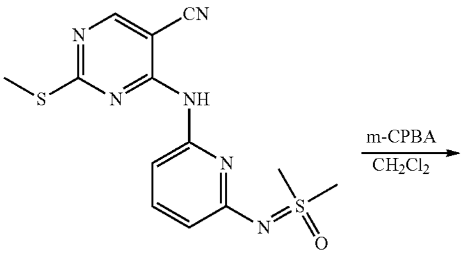
int_1-7
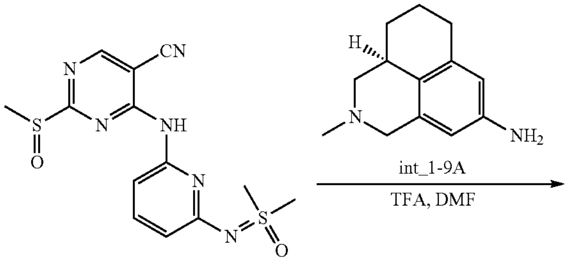
int_1-8
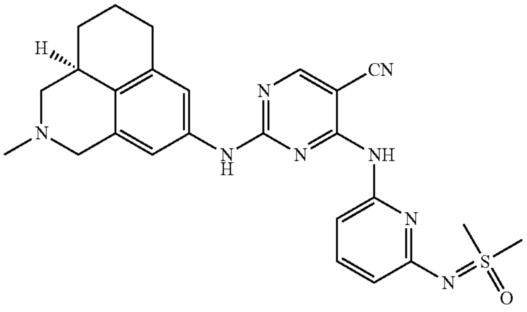
2

Step 1: Synthesis of Compound Int_1-9-2 int_1-9-2

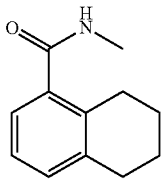

Int_1-9-1 (50 g, 284 mmol), methylamine hydrochloride (57.5 g, 851 mmol) and TEA (144 g, 1.42 mol, 197 mL) were dissolved in acetonitrile (600 mL), and $T_3P$ (217 g, 341 mmol, 203 mL, 50% purity) was added dropwise at room temperature. After the addition, the reaction was heated at 50° C. for 16 h. The reaction mixture was diluted with 1500 mL of ethyl acetate and washed with an aqueous solution of $NaHCO_3$ (400 mL×3). The organic phase was dried over anhydrous sodium sulfate. The organic phase was filtered and distilled under reduced pressure to give a white solid (50 g, 264 mmol, 93.1% yield, crude). The crude product was directly used in the next step.

$^1$H NMR: (400 MHz, Chloroform-d) δ 7.12-7.01 (m, 3H), 6.10-5.71 (m, 1H), 2.93 (d, J=4.9 Hz, 3H), 2.83 (br s, 2H), 2.79-2.71 (m, 2H), 1.84-1.65 (m, 4H).

MS (ESI): 190 $[M+H]^+$.

Step 2: Synthesis of Compound Int_1-9-3 int_1-9-3

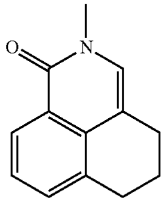

Int_1-9-2 (50 g, 264 mmol) was dissolved in THE (500 mL), and n-BuLi (2.5 M, 275 mL) was slowly added dropwise at −23° C. under nitrogen. Subsequently, DMF (48.3 g, 660 mmol, 50.8 mL) was slowly added dropwise at −23° C. Then a solution of HCl (6 M, 300 mL) was slowly added dropwise at 20° C. The reaction mixture was diluted with 100 mL of water and extracted with ethyl acetate (500 mL×3). The organic phase was dried over anhydrous sodium sulfate. The organic phase was filtered and concentrated under reduced pressure to give a yellow solid (55 g, crude). The crude product was directly used in the next step.

$^1$H NMR: (400 MHz, Chloroform-d) δ 8.36-8.20 (m, 1H), 7.46-7.32 (m, 2H), 6.84 (s, 1H), 3.63-3.52 (m, 3H), 2.99-2.92 (m, 3H), 2.75-2.69 (m, 2H), 2.01-1.90 (m, 2H).

MS (ESI): 200 $[M+H]^+$.

Step 3: Synthesis of Compound Int_1-9-4 int_1-9-4

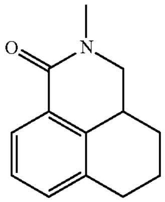

Int_1-9-3 (55 g, 276 mmol) and 20 g of palladium on carbon were suspended in methanol (800 mL), and the suspension was stirred overnight at 30° C. under hydrogen (50 psi). The palladium on carbon was removed by filtration, and the filtrate was concentrated under reduced pressure and purified by column chromatography ($SiO_2$, PE/EtOAc=1/0 to 3/1) to give a yellow solid (38.5 g, 69.3% yield).

$^1$H NMR: (400 MHz, DMSO-$d_6$) δ 7.71-7.62 (m, 1H), 7.28-7.20 (m, 2H), 3.42 (dd, J=5.6, 11.9 Hz, 1H), 3.25 (t, J=12.5 Hz, 1H), 3.13-2.99 (m, 4H), 2.87-2.69 (m, 2H), 2.06-1.90 (m, 2H), 1.75-1.61 (m, 1H), 1.41-1.22 (m, 1H).

MS (ESI): 202 $[M+H]^+$.

Step 4: Synthesis of Compound Int_1-9-5 int_1-9-5

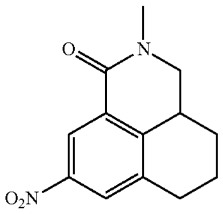

Int_1-9-4 (3.1 g, 19.2 mmol) was dissolved in $H_2SO_4$ (300 mL), and $KNO_3$ (17.9 g, 177 mmol) was slowly added at 0° C. over 3 h. After the addition, the mixture was warmed to room temperature and stirred for 2 h. TLC monitoring showed the reaction was complete. The reaction mixture was diluted with 500 mL of water, and a large amount of solid precipitated. The precipitate was collected by filtration and dried to give a yellow solid (79 g, crude). The crude product was directly used in the next step.

MS (ESI): 247 $[M+H]^+$.

Step 5: Synthesis of Compound Int_1-9-6 int_1-9-6

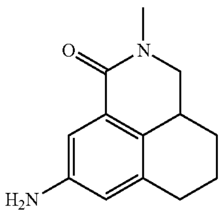

Int_1-9-5 (4.9, 19.9 mmol) and palladium on carbon (2 g, 19.9 mmol, 10% purity) were suspended in methanol (100 mL), and the suspension was left at 25° C. under hydrogen (50 psi) for 16 h. The palladium on carbon was removed by filtration, and the filtrate was concentrated under reduced pressure and purified by column chromatography ($SiO_2$, PE/EtOAc=1/0 to 1/2) to give a yellow solid (1.44 g, 33.5% yield).

$^1H$ NMR: (400 MHz, Chloroform-d) δ 7.24 (d, J=2.3 Hz, 1H), 6.56 (d, J=2.0 Hz, 1H), 3.67 (br s, 2H), 3.32-3.25 (m, 2H), 3.19-3.13 (m, 3H), 3.09-2.97 (m, 1H), 2.81-2.65 (m, 2H), 2.07-1.90 (m, 2H), 1.78-1.62 (m, 1H), 1.37-1.23 (m, 1H).

MS (ESI): 217 $[M+H]^+$.

Step 6: Synthesis of Compound Int_1-9 int_1-9

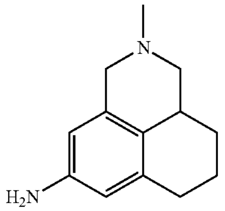

Int_1-9-6 (7 g, 32.4 mmol) was dissolved in anhydrous tetrahydrofuran (300 mL), and $LiAlH_4$ (6.14 g, 162 mmol) was added at 0° C. The mixture was warmed to 25° C. under nitrogen and left for 2 h. Water was slowly added to the reaction mixture to quench the reaction; during the addition, the temperature of the reaction mixture was kept at 0-10° C. The reaction mixture was diluted with 800 mL of ethyl acetate and washed with water (100 mL×3). The organic phase was dried over anhydrous sodium sulfate. The organic phase was filtered and distilled under reduced pressure to give a crude product. The crude product was purified by column chromatography ($SiO_2$, DCM/(MeOH+1% $NH_4OH$)=1/0 to 10/1) to give a yellow oil (6.25 g, 95.5% yield).

$^1H$ NMR: (400 MHz, Chloroform-d) δ 6.31 (s, 1H), 6.21 (s, 1H), 3.88 (d, J=15.1 Hz, 1H), 3.62-3.34 (br s, 2H), 3.26 (d, J=15.1 Hz, 1H), 2.98-2.69 (m, 4H), 2.42 (s, 3H), 2.03 (t, J=10.7 Hz, 1H), 1.92 (tdd, J=3.4, 6.5, 13.1 Hz, 1H), 1.88-1.75 (m, 2H), 1.34-1.17 (m, 1H).

MS (ESI): 203 $[M+H]^+$.

Step 7: Synthesis of Compounds Int_1-9A and Int_1-9B int_1-9A

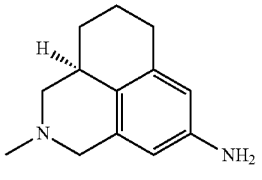

Peak 1

-continued int_1-9B

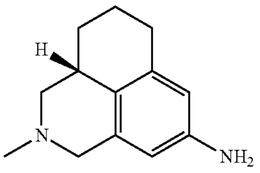

Peak 1

Int_1-9 (1.5 g, 7.41 mmol) was chirally resolved by preparative supercritical fluid chromatography (prep SFC) (SFC chiral resolution conditions: instrument: Waters SFC350; column: DAICEL CHIRALPAK AD (250 mm×50 mm, 10 m); mobile phases: A: $CO_2$, B: IPA (0.1% $NH_3H_2O$); gradient: B %: 50%-50%; flow rate: 200 mL/min; column temperature: 40° C.). The stepwise eluates were concentrated under reduced pressure and lyophilized to give a yellow oil int_1-9A (peak 1, 438 mg, 29.20% yield) and a yellow oil int_1-9B (peak 2, 450 mg, 30.00% yield).

Int_1-9A: $^1H$ NMR: (400 MHz, Chloroform-d) δ 6.32 (s, 1H), 6.22 (s, 1H), 3.88 (d, J=15.1 Hz, 1H), 3.48 (br s, 2H), 3.26 (br d, J=15.1 Hz, 1H), 2.93 (dd, J=4.6, 10.5 Hz, 1H), 2.90-2.80 (m, 1H), 2.79-2.64 (m, 2H), 2.42 (s, 3H), 2.02 (t, J=10.7 Hz, 1H), 1.92 (dtd, J=3.6, 6.5, 9.8 Hz, 1H), 1.87-1.79 (m, 2H), 1.36-1.15 (m, 1H).

MS (ESI): 203 $[M+H]^+$.

Int_1-9B: $^1H$ NMR: (400 MHz, Chloroform-d) δ 6.32 (s, 1H), 6.22 (s, 1H), 3.87 (d, J=15.3 Hz, 1H), 3.47 (br s, 2H), 3.26 (d, J=15.1 Hz, 1H), 2.93 (dd, J=4.8, 10.6 Hz, 1H), 2.89-2.80 (m, 1H), 2.80-2.65 (m, 2H), 2.42 (s, 3H), 2.02 (t, J=10.7 Hz, 1H), 1.97-1.88 (m, 1H), 1.87-1.75 (m, 2H), 1.35-1.17 (m, 1H).

MS (ESI): 203 $[M+H]^+$.

Step 8: Synthesis of Compound Int_1-2 int_1-2

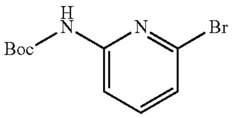

Int_1-1 (3.46 g, 20 mmol) was dissolved in dichloromethane (100 mL), and DIPEA (5.2 g, 40 mmol), DMAP (1.22 g, 10 mmol) and $(Boc)_2O$ (4.8 g, 22 mmol) were added. The mixture was left overnight at room temperature. LC-MS monitoring showed the reaction was complete. The reaction mixture was diluted with dichloromethane (100 mL), washed with water (200 mL), washed with 2 N dilute hydrochloric acid (100 mL), washed with an aqueous solution of sodium bicarbonate (100 mL), washed with water (100 mL), and finally washed with saturated brine (100 mL). The organic phase was dried over anhydrous sodium sulfate. The organic phase was filtered and distilled under reduced pressure to give a pale brown gel (4.0 g, 73% yield, crude). The crude product was directly used in the next step.

ESI-MS m/z: 273 $[M+H]^+$.

Step 9: Synthesis of Compound Int_1-4 int_1-4

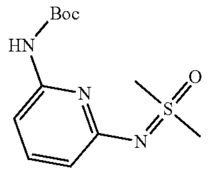

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol) and Xantphos (845 mg, 1.46 mmol) were dissolved in 1,4-dioxane (120 mL), and the mixture was left overnight at 85° C. LC-MS monitoring showed the reaction was complete. The reaction mixture was filtered and distilled under reduced pressure to give a crude product. The crude product was purified by column chromatography ($SiO_2$, DCM:MeOH=100:1 to 30:1) to give a pale yellow solid product (2.7 g, 65% yield).

ESI-MS m/z: 286 $[M+H]^+$.

Step 10: Synthesis of Compound Int_1-5 int_1-5

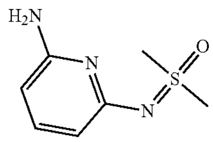

Int_1-4 (2.4 g, 8.41 mmol) was dissolved in dichloromethane (30 mL), and trifluoroacetic acid (10 mL) was added. The mixture was left overnight at room temperature. LC-MS monitoring showed the reaction was complete. The reaction mixture was directly concentrated under reduced pressure to give a grayish yellow solid (1.6 g, 100% yield). The crude product was directly used in the next step.

ESI-MS m/z: 186 $[M+H]^+$.

Step 11: Synthesis of Compound Int_1-7 int_1-7

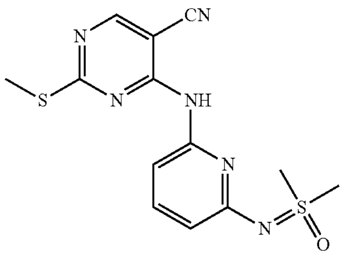

Int_1-6 (2 g, 10.8 mmol) and int_1-5 (3.2 g, 10.8 mmol) were dissolved in isopropanol (5 mL), and DIPEA (5.57 g, 43.1 mmol, 7.51 mL) was added. The reaction mixture was heated to 50° C. and left overnight. LC-MS monitoring showed the reaction was complete. The reaction mixture was cooled to room temperature, and a white solid precipitated. The solid was collected by filtration as the product. The product was dried to give a white solid (1.2 g, 33% yield).

$^1H$ NMR: (400 MHz, DMSO-$d_6$). δ 9.80 (s, 1H), 8.70 (s, 1H), 7.58 (t, J=7.9 Hz, 1H), 7.16 (d, J=7.8 Hz, 1H), 6.44 (d, J=7.9 Hz, 1H), 3.41 (s, 6H), 2.49 (s, 3H).

ESI-MS m/z: 335 $[M+H]^+$.

Step 12: Synthesis of Compound Int_1-8 int_1-8

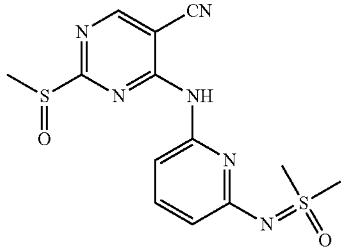

Int_1-7 (334 mg, 1.0 mmol) was dissolved in dichloromethane (40 mL), and m-CPBA (85%, 240 mg, 1.2 mmol) was added at room temperature. The mixture was stirred at room temperature for half an hour. LC-MS monitoring showed the reaction was complete. The reaction mixture was concentrated under reduced pressure to give a crude product (335 mg). The crude product was directly used in the next step.

ESI-MS m/z: 351 $[M+H]^+$.

Step 13: Synthesis of Compound 2

2

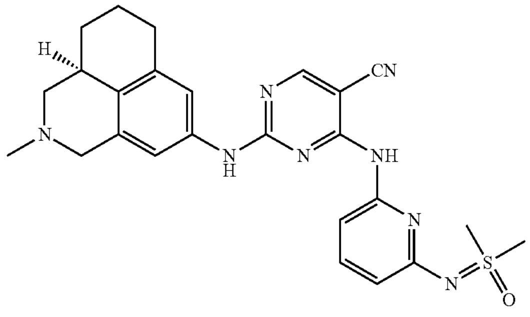

Int_1-8 (100 mg, 0.28 mmol) was dissolved in DMF (5 mL), and int_1-9A (57 mg, 0.28 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by reversed-phase chromatography to give a white solid (70 mg, 50% yield).

$^1H$ NMR (400 MHz, Chloroform-d) δ 8.36 (s, 1H), 7.70 (d, J=8.0 Hz, 1H), 7.59 (s, 1H), 7.48 (s, 1H), 7.26 (s, 1H), 7.07 (d, J=8.6 Hz, 2H), 6.57 (dd, J=8.0, 0.7 Hz, 1H), 3.92 (d, J=15.2 Hz, 1H), 3.36 (s, 6H), 3.32 (d, J=15.2 Hz, 1H), 3.05-2.89 (m, 2H), 2.79 (ddt, J=24.3, 17.0, 8.9 Hz, 2H), 2.44 (s, 3H), 2.08 (t, J=10.4 Hz, 1H), 1.99-1.78 (m, 3H), 1.37-1.18 (m, 1H).

LC-MS: 489 $[M+H]^+$.

Preparative HPLC Purification:

Instrument: Agilent 1260 infinity 2

Column: Waters Xbridge Prep C1819×250 mm, 5 μm OBD

Column temperature: 25° C.

Detection wavelengths: 205 nm/254 nm

Mobile phase A: $H_2O$ (0.1% FA)

Mobile phase B: MeCN

Flow rate: 20 mL/min

Gradient: 0.00 min-1.00 min: 5% B→5% B
1.01 min-20.00 min: 5% B→40% B
20.00 min-20.01 min: 40% B→95% B
20.01 min-24.00 min: 95% B→95% B
24.00 min-24.01 min: 95% B→5% B
24.01 min-27.00 min: 5% B→5% B Example 3. Synthesis of Compound 3

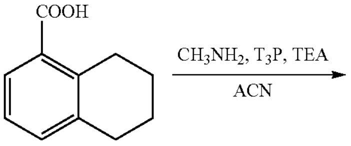

int_1-9-1

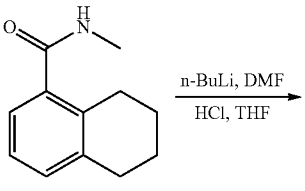

int_1-9-2

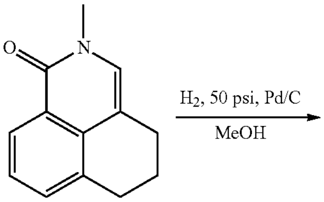

int_1-9-3

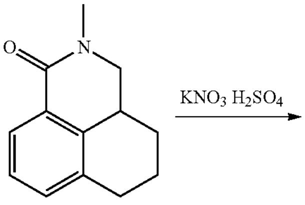

int_1-9-4

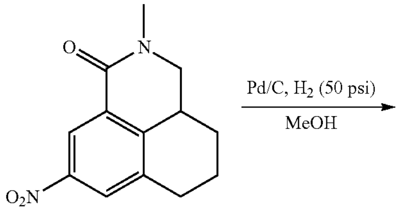

int_1-9-5

-continued

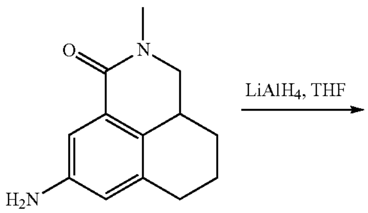

int_1-9-6

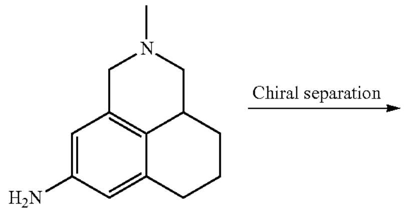

int_1-9

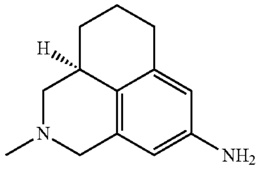

int_1-9A

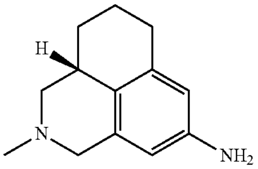

int_1-9B

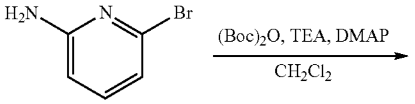

int_1-1

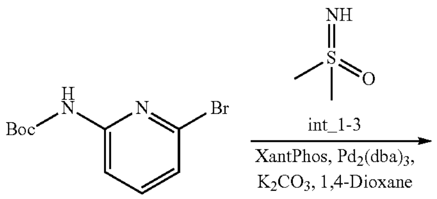

int_1-2

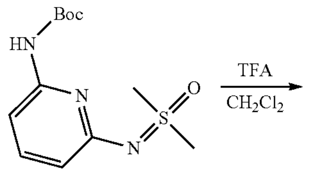

int_1-4

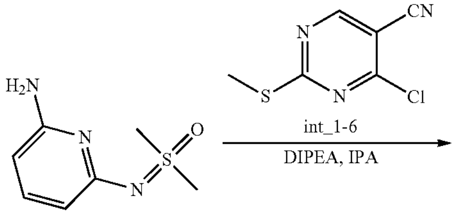

int_1-5

-continued

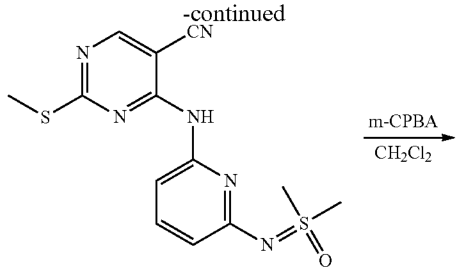

int_1-7

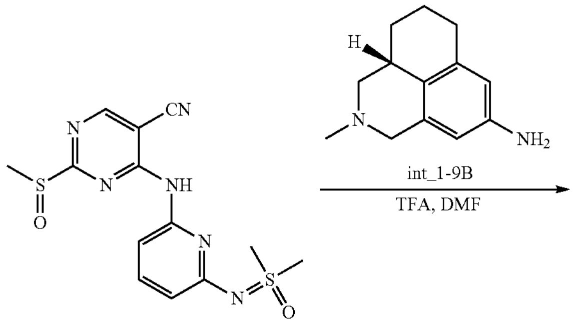

int_1-8

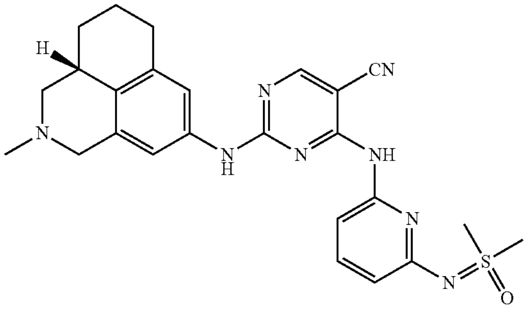

3

Step 1: Synthesis of Compound Int_1-9-2 int_1-9-2

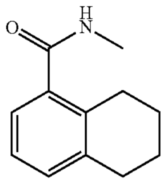

Int_1-9-1 (50 g, 284 mmol), methylamine hydrochloride (57.5 g, 851 mmol) and TEA (144 g, 1.42 mol, 197 mL) were dissolved in acetonitrile (600 mL), and $T_3P$ (217 g, 341 mmol, 203 mL, 50% purity) was added dropwise at room temperature. After the addition, the reaction was heated at 50° C. for 16 h. The reaction mixture was diluted with 1500 mL of ethyl acetate and washed with an aqueous solution of $NaHCO_3$ (400 mL×3). The organic phase was dried over anhydrous sodium sulfate. The organic phase was filtered and distilled under reduced pressure to give a white solid (50 g, 264 mmol, 93.1% yield, crude). The crude product was directly used in the next step.

$^1H$ NMR: (400 MHz, Chloroform-d) δ 7.12-7.01 (m, 3H), 6.10-5.71 (m, 1H), 2.93 (d, J=4.9 Hz, 3H), 2.83 (br s, 2H), 2.79-2.71 (m, 2H), 1.84-1.65 (m, 4H).

MS (ESI): 190 $[M+H]^+$.

Step 2: Synthesis of Compound Int_1-9-3 int_1-9-3

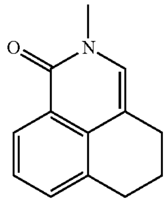

Int_1-9-2 (50 g, 264 mmol) was dissolved in THE (500 mL), and n-BuLi (2.5 M, 275 mL) was slowly added dropwise at −23° C. under nitrogen. Subsequently, DMF (48.3 g, 660 mmol, 50.8 mL) was slowly added dropwise at −23° C. Then a solution of HCl (6 M, 300 mL) was slowly added dropwise at 20° C. The reaction mixture was diluted with 100 mL of water and extracted with ethyl acetate (500 mL×3). The organic phase was dried over anhydrous sodium sulfate. The organic phase was filtered and concentrated under reduced pressure to give a yellow solid (55 g, crude). The crude product was directly used in the next step.

$^1H$ NMR: (400 MHz, Chloroform-d) δ 8.36-8.20 (m, 1H), 7.46-7.32 (m, 2H), 6.84 (s, 1H), 3.63-3.52 (m, 3H), 2.99-2.92 (m, 3H), 2.75-2.69 (m, 2H), 2.01-1.90 (m, 2H).

MS (ESI): 200 $[M+H]^+$.

Step 3: Synthesis of Compound Int_1-9-4 int_1-9-4

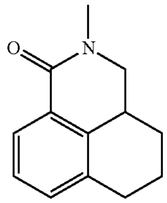

Int_1-9-3 (55 g, 276 mmol) and 20 g of palladium on carbon were suspended in methanol (800 mL), and the suspension was stirred overnight at 30° C. under hydrogen (50 psi). The palladium on carbon was removed by filtration, and the filtrate was concentrated under reduced pressure and purified by column chromatography ($SiO_2$, PE/EtOAc=1/0 to 3/1) to give a yellow solid (38.5 g, 69.3% yield).

$^1H$ NMR: (400 MHz, DMSO-$d_6$) δ 7.71-7.62 (m, 1H), 7.28-7.20 (m, 2H), 3.42 (dd, J=5.6, 11.9 Hz, 1H), 3.25 (t, J=12.5 Hz, 1H), 3.13-2.99 (m, 4H), 2.87-2.69 (m, 2H), 2.06-1.90 (m, 2H), 1.75-1.61 (m, 1H), 1.41-1.22 (m, 1H).

MS (ESI): 202 $[M+H]^+$.

Step 4: Synthesis of Compound Int_1-9-5 int_1-9-5

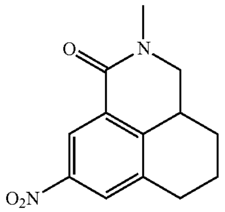

Int_1-9-4 (3.1 g, 19.2 mmol) was dissolved in $H_2SO_4$ (300 mL), and $KNO_3$ (17.9 g, 177 mmol) was slowly added at 0° C. over 3 h. After the addition, the mixture was warmed to room temperature and stirred for 2 h. TLC monitoring showed the reaction was complete. The reaction mixture was diluted with 500 mL of water, and a large amount of solid precipitated. The precipitate was collected by filtration and dried to give a yellow solid (79 g, crude). The crude product was directly used in the next step.

MS (ESI): 247 $[M+H]^+$.

Step 5: Synthesis of Compound Int_1-9-6 int_1-9-6

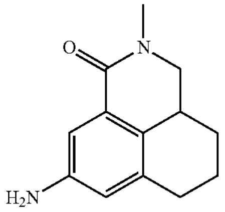

Int_1-9-5 (4.9, 19.9 mmol) and palladium on carbon (2 g, 19.9 mmol, 10% purity) were suspended in methanol (100 mL), and the suspension was left at 25° C. under hydrogen (50 psi) for 16 h. The palladium on carbon was removed by filtration, and the filtrate was concentrated under reduced pressure and purified by column chromatography ($SiO_2$, PE/EtOAc=1/0 to 1/2) to give a yellow solid (1.44 g, 33.5% yield).

$^1$H NMR: (400 MHz, Chloroform-d) δ 7.24 (d, J=2.3 Hz, 1H), 6.56 (d, J=2.0 Hz, 1H), 3.67 (br s, 2H), 3.32-3.25 (m, 2H), 3.19-3.13 (m, 3H), 3.09-2.97 (m, 1H), 2.81-2.65 (m, 2H), 2.07-1.90 (m, 2H), 1.78-1.62 (m, 1H), 1.37-1.23 (m, 1H).

MS (ESI): 217 $[M+H]^+$.

Step 6: Synthesis of Compound Int_1-9 int_1-9

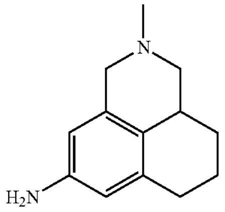

Int_1-9-6 (7 g, 32.4 mmol) was dissolved in anhydrous tetrahydrofuran (300 mL), and $LiAlH_4$ (6.14 g, 162 mmol) was added at 0° C. The mixture was warmed to 25° C. under nitrogen and left for 2 h. Water was slowly added to the reaction mixture to quench the reaction; during the addition, the temperature of the reaction mixture was kept at 0-10° C. The reaction mixture was diluted with 800 mL of ethyl acetate and washed with water (100 mL×3). The organic phase was dried over anhydrous sodium sulfate. The organic phase was filtered and distilled under reduced pressure to give a crude product. The crude product was purified by column chromatography ($SiO_2$, DCM/(MeOH+1% $NH_4OH$)=1/0 to 10/1) to give a yellow oil (6.25 g, 95.5% yield).

$^1$H NMR: (400 MHz, Chloroform-d) δ 6.31 (s, 1H), 6.21 (s, 1H), 3.88 (d, J=15.1 Hz, 1H), 3.62-3.34 (br s, 2H), 3.26 (d, J=15.1 Hz, 1H), 2.98-2.69 (m, 4H), 2.42 (s, 3H), 2.03 (t, J=10.7 Hz, 1H), 1.92 (tdd, J=3.4, 6.5, 13.1 Hz, 1H), 1.88-1.75 (m, 2H), 1.34-1.17 (m, 1H).

MS (ESI): 203 $[M+H]^+$.

Step 7: Synthesis of Compounds Int_1-9A and Int_1-9B int_1-9A

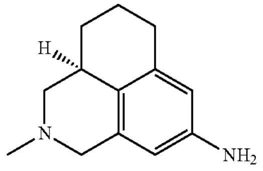

Peak 1 int_1-9B

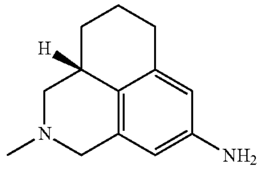

Peak 2

Int_1-9 (1.5 g, 7.41 mmol) was chirally resolved by preparative supercritical fluid chromatography (prep SFC) (SFC chiral resolution conditions: instrument: Waters SFC350; column: DAICEL CHIRALPAK AD (250 mm×50 mm, 10 m); mobile phases: A: $CO_2$, B: IPA (0.1% $NH_3H_2O$); gradient: B %: 50%-50%; flow rate: 200 mL/min; column temperature: 40° C.). The stepwise eluates were concentrated under reduced pressure and lyophilized to give a yellow oil int_1-9A (peak 1, 438 mg, 29.20% yield) and a yellow oil int_1-9B (peak 2, 450 mg, 30.00% yield).

Int_1-9A: $^1$H NMR: (400 MHz, Chloroform-d) δ 6.32 (s, 1H), 6.22 (s, 1H), 3.88 (d, J=15.1 Hz, 1H), 3.48 (br s, 2H), 3.26 (br d, J=15.1 Hz, 1H), 2.93 (dd, J=4.6, 10.5 Hz, 1H), 2.90-2.80 (m, 1H), 2.79-2.64 (m, 2H), 2.42 (s, 3H), 2.02 (t, J=10.7 Hz, 1H), 1.92 (dtd, J=3.6, 6.5, 9.8 Hz, 1H), 1.87-1.79 (m, 2H), 1.36-1.15 (m, 1H).

MS (ESI): 203 $[M+H]^+$.

Int_1-9B: $^1$H NMR: (400 MHz, Chloroform-d) δ 6.32 (s, 1H), 6.22 (s, 1H), 3.87 (d, J=15.3 Hz, 1H), 3.47 (br s, 2H), 3.26 (d, J=15.1 Hz, 1H), 2.93 (dd, J=4.8, 10.6 Hz, 1H), 2.89-2.80 (m, 1H), 2.80-2.65 (m, 2H), 2.42 (s, 3H), 2.02 (t, J=10.7 Hz, 1H), 1.97-1.88 (m, 1H), 1.87-1.75 (m, 2H), 1.35-1.17 (m, 1H).

MS (ESI): 203 $[M+H]^+$.

Step 8: Synthesis of Compound Int_1-2 int_1-2

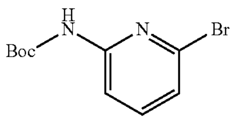

Int_1-1 (3.46 g, 20 mmol) was dissolved in dichloromethane (100 mL), and DIPEA (5.2 g, 40 mmol), DMAP (1.22 g, 10 mmol) and $(Boc)_2O$ (4.8 g, 22 mmol) were added. The mixture was left overnight at room temperature. LC-MS monitoring showed the reaction was complete. The reaction mixture was diluted with dichloromethane (100 mL), washed with water (200 mL), washed with 2 N dilute hydrochloric acid (100 mL), washed with an aqueous solution of sodium bicarbonate (100 mL), washed with water (100 mL), and finally washed with saturated brine (100 mL). The organic phase was dried over anhydrous sodium sulfate. The organic phase was filtered and distilled under reduced pressure to give a pale brown gel (4.0 g, 73% yield, crude). The crude product was directly used in the next step.

ESI-MS m/z: 273 $[M+H]^+$.

Step 9: Synthesis of Compound Int_1-4 int_1-4

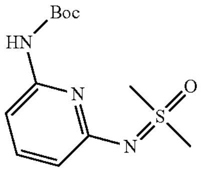

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol) and Xantphos (845 mg, 1.46 mmol) were dissolved in 1,4-dioxane (120 mL), and the mixture was left overnight at 85° C. LC-MS monitoring showed the reaction was complete. The reaction mixture was filtered and distilled under reduced pressure to give a crude product. The crude product was purified by column chromatography ($SiO_2$, DCM:MeOH=100:1 to 30:1) to give a pale yellow solid product (2.7 g, 65% yield).

ESI-MS m/z: 286 $[M+H]^+$.

Step 10: Synthesis of Compound Int_1-5 int_1-5

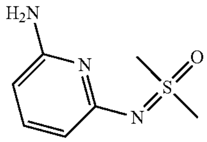

Int_1-4 (2.4 g, 8.41 mmol) was dissolved in dichloromethane (30 mL), and trifluoroacetic acid (10 mL) was added. The mixture was left overnight at room temperature. LC-MS monitoring showed the reaction was complete. The reaction mixture was directly concentrated under reduced pressure to give a grayish yellow solid (1.6 g, 100% yield). The crude product was directly used in the next step.

ESI-MS m/z: 186 $[M+H]^+$.

Step 11: Synthesis of Compound Int_1-7 int_1-7

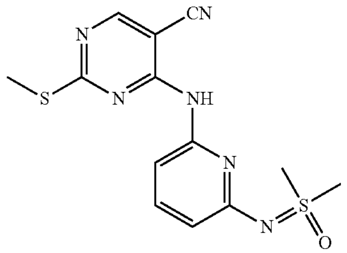

Int_1-6 (2 g, 10.8 mmol) and int_1-5 (3.2 g, 10.8 mmol) were dissolved in isopropanol (5 mL), and DIPEA (5.57 g, 43.1 mmol, 7.51 mL) was added. The reaction mixture was heated to 50° C. and left overnight. LC-MS monitoring showed the reaction was complete. The reaction mixture was cooled to room temperature, and a white solid precipitated. The solid was collected by filtration as the product. The product was dried to give a white solid (1.2 g, 33% yield). $^1H$ NMR: (400 MHz, DMSO-$d_6$). δ 9.80 (s, 1H), 8.70 (s, 1H), 7.58 (t, J=7.9 Hz, 1H), 7.16 (d, J=7.8 Hz, 1H), 6.44 (d, J=7.9 Hz, 1H), 3.41 (s, 6H), 2.49 (s, 3H).

ESI-MS m/z: 335 $[M+H]^+$.

Step 12: Synthesis of Compound Int_1-8 int_1-8

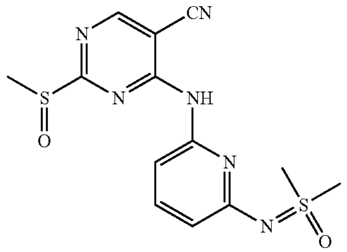

Int_1-7 (334 mg, 1.0 mmol) was dissolved in dichloromethane (40 mL), and m-CPBA (85%, 240 mg, 1.2 mmol) was added at room temperature. The mixture was stirred at room temperature for half an hour. LC-MS monitoring showed the reaction was complete. The reaction mixture was concentrated under reduced pressure to give a crude product (335 mg). The crude product was directly used in the next step.

ESI-MS m/z: 351 $[M+H]^+$.

Step 13: Synthesis of Compound 3

3

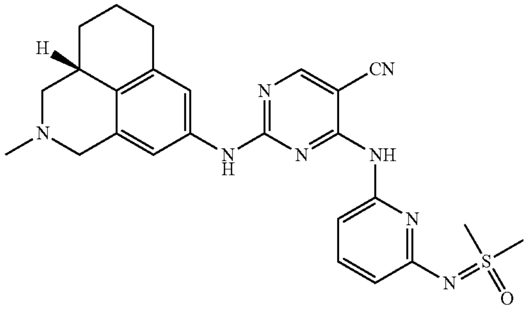

Int_1-8 (100 mg, 0.28 mmol) was dissolved in DMF (5 mL), and int_1-9B (57 mg, 0.28 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative reversed-phase chromatography to give a white solid (75 mg, 55% yield).

$^1$H NMR (400 MHz, Chloroform-d) δ 8.36 (s, 1H), 7.70 (d, J=8.0 Hz, 1H), 7.59 (s, 1H), 7.48 (s, 1H), 7.26 (s, 1H), 7.07 (d, J=8.6 Hz, 2H), 6.57 (dd, J=8.0, 0.7 Hz, 1H), 3.92 (d, J=15.2 Hz, 1H), 3.36 (s, 6H), 3.32 (d, J=15.2 Hz, 1H), 3.05-2.89 (m, 2H), 2.79 (ddt, J=24.3, 17.0, 8.9 Hz, 2H), 2.44 (s, 3H), 2.08 (t, J=10.4 Hz, 1H), 1.99-1.78 (m, 3H), 1.37-1.18 (m, 1H).

LC-MS: 489 $[M+H]^+$.

Preparative HPLC Purification:

- Instrument: Agilent 1260 infinity 2
- Column: Waters Xbridge Prep C1819×250 mm, 5 μm OBD
- Column temperature: 25° C.
- Detection wavelengths: 205 nm/254 nm
- Mobile phase A: $H_2O$ (0.1% FA)
- Mobile phase B: MeCN
- Flow rate: 20 mL/min
- Gradient: 0.00 min-1.00 min: 5% B→5% B
  - 1.01 min-20.00 min: 5% B→40% B
  - 20.00 min-20.01 min: 40% B→95% B
  - 20.01 min-24.00 min: 95% B→95% B
  - 24.00 min-24.01 min: 95% B→5% B
  - 24.01 min-27.00 min: 5% B→5% B Example 4. Synthesis of Compound 64

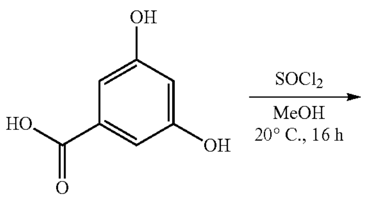

int_64-1-1

-continued

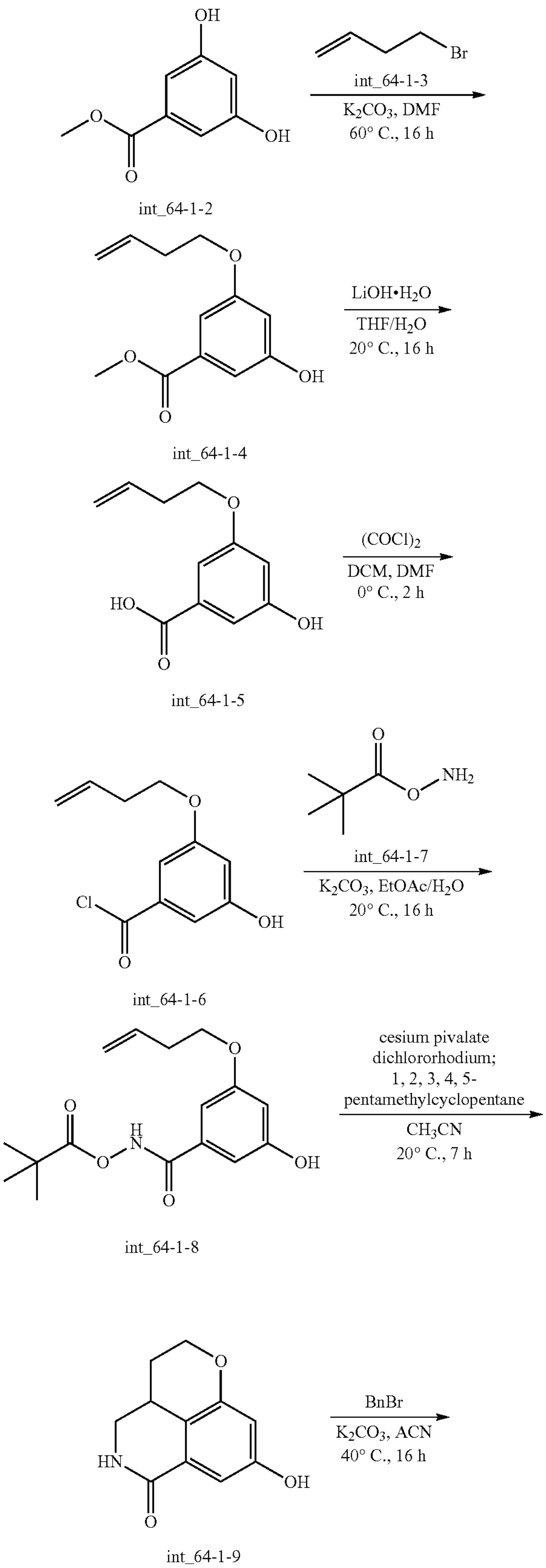

int_64-1-2 int_64-1-4 int_64-1-5 int_64-1-6 int_64-1-8 int_64-1-9

-continued
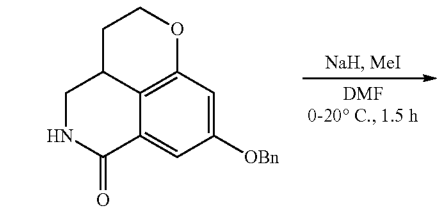
int_64-1-10
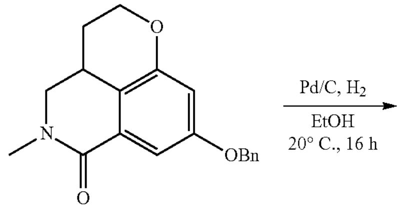
int_64-1-11
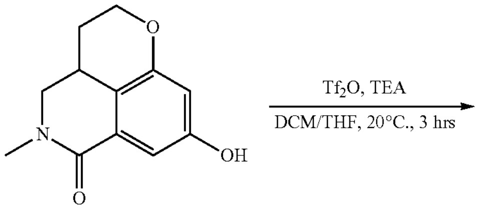
int_64-1-12
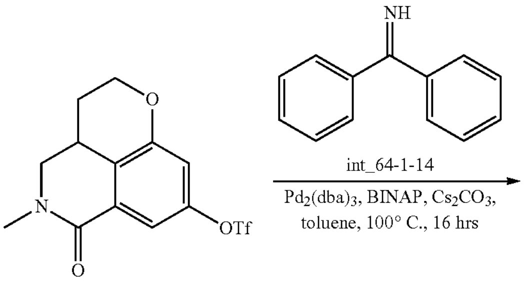
int_64-1-13
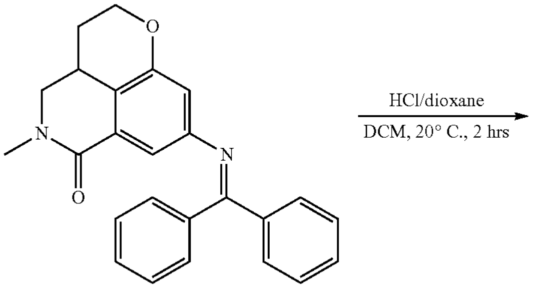
int_64-1-15
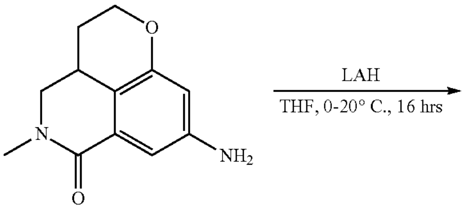
int_64-1-16
-continued
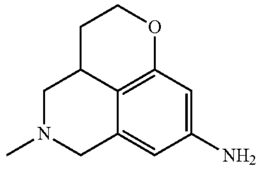
int_64-1
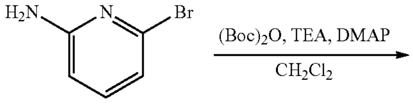
int_1-1
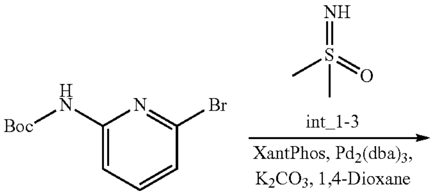
int_1-2
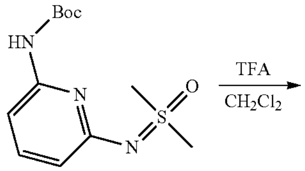
int_1-4
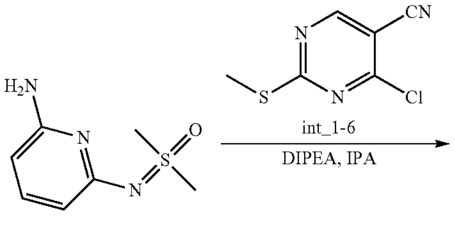
int_1-5
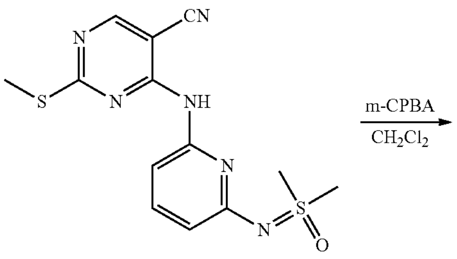
int_1-7
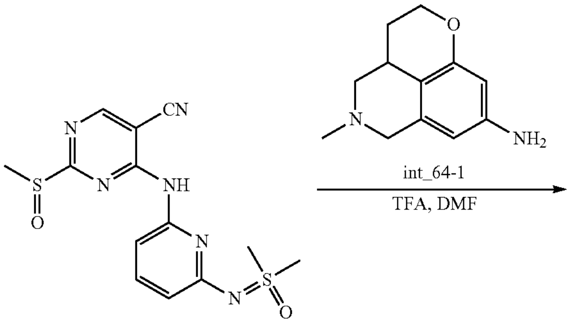
int_1-8

-continued

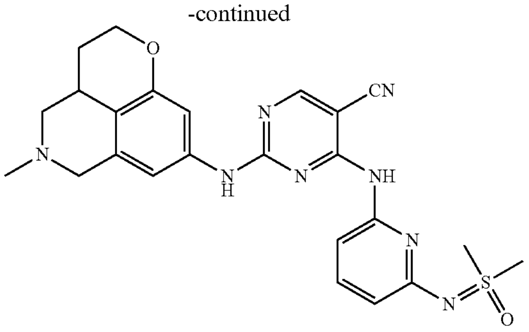

64

Step 1: Synthesis of Compound Int_64-1-2 int_64-1-2

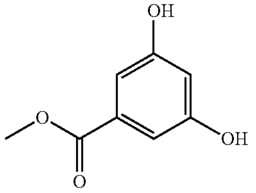

Int_1-9-1 (50 g, 324 mmol) was dissolved in methanol (500 mL), and SOCl2 (77.2 g, 649 mmol, 47.1 mL) was added dropwise at 0° C. After the addition, the mixture was warmed to room temperature and left for 16 h. TLC monitoring showed the reaction was complete. The reaction mixture was concentrated by distillation under reduced pressure to give a white solid (53.4 g, 97.2% yield, crude). The crude product was directly used in the next step.

$^1$H NMR: (400 MHz, METHANOL-d4) δ 6.92 (d, J=2.0 Hz, 2H), 6.47 (t, J=2.3 Hz, 1H), 3.89-3.80 (m, 3H).

Step 2: Synthesis of Compound Int_64-1-4 int_64-1-4

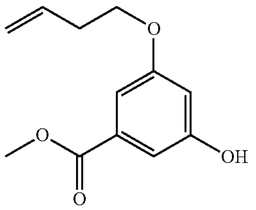

Int_64-1-2 (54.3 g, 315 mmol) was dissolved in DMF (500 mL), and $K_2CO_3$ (87.1 g, 630 mmol) and int_64-1-3 (89.4 g, 662 mmol, 67.2 mL) were added under nitrogen. The mixture was heated to 60° C. and left for 16 h. TLC monitoring showed the reaction was complete. The reaction mixture was diluted with 800 mL of water and extracted with ethyl acetate (800 mL×3). The organic phase was dried over anhydrous sodium sulfate. The organic phase was filtered, concentrated under reduced pressure and purified by column chromatography ($SiO_2$, PE/THF=10/1 to 5/1) to give a yellow solid (23.1 g, 32.3% yield).

$^1$H NMR: (400 MHz, Chloroform-d) δ 7.15 (ddd, J=1.3, 2.2, 6.7 Hz, 2H), 6.62 (t, J=2.3 Hz, 1H), 6.12 (s, 1H), 5.88 (tdd, J=6.7, 10.3, 17.1 Hz, 1H), 5.23-5.04 (m, 2H), 4.02 (t, J=6.7 Hz, 2H), 3.90 (s, 3H), 2.53 (q, J=6.7 Hz, 2H).

Step 3: Synthesis of Compound Int_64-1-5 int_64-1-5

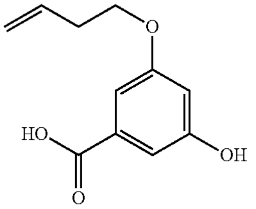

Int_64-1-4 (16 g, 72 mmol) was dissolved in THE (150 mL) and $H_2O$ (37 mL), and LiOH·H2O (15.1 g, 360 mmol) was added at 0° C. The mixture was stirred at 30° C. for 16 h. TLC monitoring showed the reaction was complete. The reaction mixture was diluted with 200 mL of water and 200 mL of ethyl acetate, adjusted to pH 2-3 with a 4 N solution of hydrochloric acid, and extracted with ethyl acetate (100 mL×3). The organic phase was dried over anhydrous sodium sulfate. The organic phase was filtered and concentrated under reduced pressure to give a crude product (12.1 g, 80.7% yield). The crude product was directly used in the next step.

$^1$H NMR: (400 MHz, METHANOL-d4) δ 7.04 (t, J=2.1 Hz, 2H), 6.57 (t, J=2.3 Hz, 1H), 5.92 (tdd, J=6.7, 10.3, 17.1 Hz, 1H), 5.26-5.03 (m, 2H), 4.01 (t, J=6.6 Hz, 2H), 2.51 (q, J=6.5 Hz, 2H).

Step 4: Synthesis of Compound Int_64-1-6 int_64-1-6

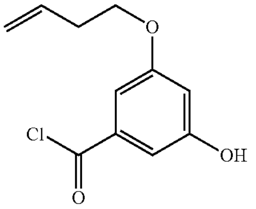

Int_64-1-5 (12 g, 57.6 mmol) was dissolved in DCM (120 mL), and $(COCl)_2$ (11.0 g, 86.5 mmol, 7.57 mL) and two drops of DMF were added slowly at 0° C. The reaction mixture was stirred at 0° C. for 2 h. The reaction mixture was concentrated under reduced pressure to give a yellow solid (16.8 g, crude). The crude product was directly used in the next step.

Step 5: Synthesis of Compound Int_64-1-8 int_64-1-8

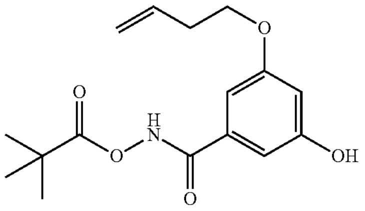

Int_64-1-6 (18.3 g, 68.5 mmol) was dissolved in ethyl acetate (120 mL) and $H_2O$ (60 mL), and $K_2CO_3$ (31.6 g, 228 mmol) was added. The mixture was cooled to 0° C., and a solution of int_64-1-7 (16.8 g, crude) in ethyl acetate (50 mL) was added to the mixture. The reaction mixture was warmed to room temperature and left for 16 h. TLC monitoring showed the reaction was complete. The reaction mixture was diluted with 200 mL of water and extracted with ethyl acetate (100 mL×3). The organic phase was dried over anhydrous sodium sulfate. The organic phase was filtered and concentrated under reduced pressure to give a crude product. The crude product was purified by column chromatography ($SiO_2$, PE/THF=1/0 to 4/1) to give a yellow oil (24 g, 41.1% yield).

The oil was suspended in methanol (100 mL) and left at 25° C. under hydrogen (50 psi) for 16 h. The palladium on carbon was removed by filtration, and the filtrate was concentrated under reduced pressure and purified by column chromatography ($SiO_2$, PE/EtOAc=1/0 to 1/2) to give a yellow solid (1.44 g, 33.5% yield).

MS (ESI): 308 $[M+H]^+$.

Step 6: Synthesis of Compound Int_64-1-9 int_64-1-9

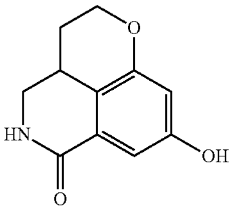

Int_64-1-8 (10.3 g, 13.8 mmol) was dissolved in acetonitrile (180 mL), and cesium pivalate (6.45 g, 27.6 mmol) and dichloropentamethylcyclopentadienylrhodium(III) (216 mg, 345 μmol) were added under nitrogen. The reaction mixture was left at 25° C. under nitrogen for 7 h. LC-MS monitoring showed the reaction was complete. The reaction mixture was filtered and concentrated. The crude product was dissolved in 200 mL of ethyl acetate and 200 mL of water, and the solution was extracted with ethyl acetate (200 mL×3). The organic phase was dried over anhydrous sodium sulfate. The organic phase was filtered and distilled under reduced pressure to give a crude product. The crude product was dissolved in 200 mL of ethyl acetate and filtered. The filter cake was washed with ethyl acetate (20 mL×3), and the filtrate was concentrated to give a crude product. The crude product was diluted by dispersion into 50 mL of dichloromethane, and the dilution was filtered. The filter cake was washed with dichloromethane (5 mL×3) and dried to give a crude product (3.5 g). The product was directly used in the next step.

$^1H$ NMR: (400 MHz, METHANOL-d4) δ 6.91 (d, J=2.4 Hz, 1H), 6.39 (d, J=2.4 Hz, 1H), 4.47-4.34 (m, 1H), 4.17-4.00 (m, 1H), 3.47 (dd, J=4.3, 10.9 Hz, 1H), 3.18-2.99 (m, 2H), 2.10-1.98 (m, 1H), 1.74-1.60 (m, 1H), 1.74-1.60 (m, 1H).

MS (ESI): 206 $[M+H]^+$.

Step 7: Synthesis of Compound Int_64-1-10 int_64-1-10

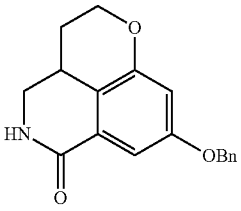

Int_64-1-9 (4.00 g, 19.5 mmol) and $K_2CO_3$ (5.39 g, 39.0 mmol) were dissolved in acetonitrile (40 mL), and benzyl bromide (4.00 g, 23.4 mmol, 2.78 mL) was added. The reaction mixture was left at 40° C. under nitrogen for 16 h. LC-MS monitoring showed the reaction was complete. The reaction mixture was filtered and concentrated. The crude product was dissolved in 200 mL of water, and the solution was extracted with ethyl acetate (200 mL×3). The organic phase was dried over anhydrous sodium sulfate. The organic phase was filtered and distilled under reduced pressure to give a crude product. The crude product was purified by column chromatography ($SiO_2$, PE/EtOAc=1/1 to 1/3) to give a yellow solid (5.2 g, 89.0% yield).

$^1H$ NMR: (400 MHz, Chloroform-d) δ 7.47-7.29 (m, 5H), 6.61 (d, J=2.5 Hz, 1H), 6.52 (br d, J=4.5 Hz, 1H), 5.11-5.03 (m, 2H), 4.49-4.38 (m, 1H), 4.18-4.05 (m, 1H), 3.55-3.43 (m, 1H), 3.26-3.14 (m, 2H), 2.04-1.97 (m, 1H), 1.75 (br dd, J=3.1, 12.2 Hz, 1H).

MS (ESI): 296 $[M+H]^+$.

Step 8: Synthesis of Compound Int_64-1-11 int_64-1-11

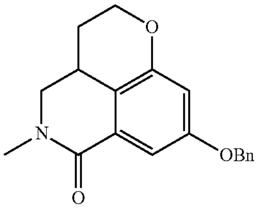

Int_64-1-10 (5.20 g, 17.6 mmol) was dissolved in DMF (50 mL), and sodium hydride (1.06 g, 26.4 mmol, 60% purity) was added at 0° C. under nitrogen. The reaction mixture was left at 0° C. for 0.5 h, and then iodomethane (2.75 g, 19.4 mmol, 1.21 mL) was added. The reaction mixture was warmed to 20° C. and left for 1 h. LC-MS monitoring showed the reaction was complete. The reaction mixture was slowly poured into 100 mL of iced water to quench the reaction, and extracted with ethyl acetate (100 mL×3). The organic phase was dried over anhydrous sodium sulfate. The organic phase was filtered and distilled under reduced pressure to give a crude product. The crude product was purified by column chromatography ($SiO_2$, PE/EtOAc=2/1 to 1/1) to give a product (4.8 g, 88.1% yield).

$^1$H NMR: (400 MHz, Chloroform-d) δ 7.46-7.31 (m, 5H), 7.28 (d, J=2.5 Hz, 1H), 6.57 (d, J=2.6 Hz, 1H), 5.11-5.03 (m, 2H), 4.55-4.33 (m, 1H), 4.23-4.00 (m, 1H), 3.43-3.30 (m, 2H), 3.29-3.19 (m, 1H), 3.15 (s, 3H), 2.04-1.96 (m, 1H), 1.81-1.68 (m, 1H).

MS (ESI): 310 $[M+H]^+$.

Step 9: Synthesis of Compound Int_64-1-12 int_64-1-12

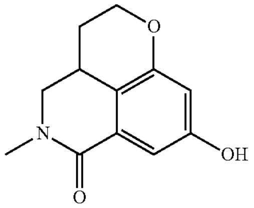

Int_64-1-11 (4.80 g, 15.5 mmol) was dissolved in ethanol (50 mL), and Pd/C (991 mg, 931 μmol, 10% purity) was added. The reaction mixture was left at 20° C. in a hydrogen atmosphere (15 Psi) for 16 h. LC-MS monitoring showed the reaction was complete. The reaction mixture was distilled under reduced pressure to give a product (3.1 g, 89.4% yield).

$^1$H NMR: (400 MHz, METHANOL-d4) δ 6.90 (d, J=2.3 Hz, 1H), 6.36 (d, J=2.5 Hz, 1H), 4.45-4.33 (m, 1H), 4.09 (ddd, J=1.9, 11.0, 12.7 Hz, 1H), 3.56-3.44 (m, 1H), 3.27 (d, J=11.3 Hz, 1H), 3.24-3.15 (m, 1H), 3.12 (s, 3H), 2.04 (tdd, J=2.2, 4.8, 13.4 Hz, 1H), 1.73-1.60 (m, 1H).

MS (ESI): 220 $[M+H]^+$.

Step 10: Synthesis of Compound Int_64-1-13 int_64-1-13

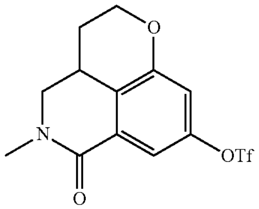

Int_64-1-12 (3 g, 13.7 mmol) and triethylamine (4.15 g, 41.1 mmol, 5.71 mL) were dissolved in dichloromethane (20 mL) and tetrahydrofuran (20 mL), and $Tf_2O$ (4.63 g, 16.42 mmol, 2.71 mL) was added dropwise at 0° C. The reaction mixture was warmed to 20° C. and left for 3 h. LC-MS monitoring showed the reaction was complete. The reaction mixture was slowly poured into 75 mL of iced water to quench the reaction, and extracted with ethyl acetate (100 mL×3). The organic phase was dried over anhydrous sodium sulfate. The organic phase was filtered and distilled under reduced pressure to give a crude product. The crude product was purified by column chromatography (ISCO®; 40 g SepaFlash® Silica Flash Column, Eluent of 0-80% Ethyl acetate/Petroleum ether gradient) to give a product (4 g, 83.2% yield).

$^1$H NMR (400 MHz, Chloroform-d) 6=7.51 (d, J=2.4 Hz, 1H), 6.87 (d, J=2.4 Hz, 1H), 4.59-4.50 (m, 1H), 4.24-4.14 (m, 1H), 3.53-3.27 (m, 4H), 3.18 (s, 4H), 2.15-2.04 (m, 1H), 1.89-1.72 (m, 2H).

MS (ESI): 352 $[M+H]^+$.

Step 11: Synthesis of Compound Int_64-1-15 int_64-1-15

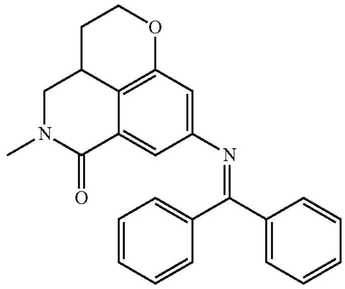

Int_64-1-13 (3 g, 8.54 mmol) and int_64-1-14 (1.86 g, 10.3 mmol, 1.72 mL) were dissolved in toluene (40 mL), and $Pd_2(dba)_3$ (782 mg, 854 μmol), BINAP (532 mg, 854 μmol) and $Cs_2CO_3$ (5.56 g, 17.1 mmol) were added. The reaction mixture was heated to 100° C. under nitrogen and left for 16 h. LC-MS monitoring showed the reaction was complete. The reaction mixture was distilled under reduced pressure to give a crude product. The crude product was purified by column chromatography (ISCO®; 40 g SepaFlash® Silica Flash Column, Eluent of 0-70% Ethyl acetate/Petroleum ether gradient) to give a product (2 g, 61.2% yield).

MS (ESI): 383 $[M+H]^+$.

Step 12: Synthesis of Compound Int_64-1-16 int_64-1-16

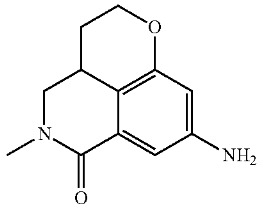

Int_64-1-15 (2 g, 5.23 mmol) was dissolved in dichloromethane (40 mL), and a solution of hydrochloric acid in dioxane (4 M, 1.31 mL) was slowly added dropwise at 0° C. The reaction mixture was warmed to 20° C. under nitrogen and left for 2 h. LC-MS monitoring showed the reaction was complete. The reaction mixture was distilled under reduced pressure to give a crude product. The crude product was purified by column chromatography (ISCO®; 20 g SepaFlash® Silica Flash Column, Eluent of 0-80% Ethyl acetate/Petroleum ether gradient (1% $NH_3 \cdot H_2O$)) to give a product (0.9 g, 78.9% yield).

$^1$H NMR (400 MHz, DMSO-$d_6$) δ=6.68 (d, J=2.2 Hz, 1H), 6.12 (d, J=2.2 Hz, 1H), 5.11 (s, 2H), 4.37-4.28 (m, 1H), 4.07-3.94 (m, 1H), 3.49-3.38 (m, 1H), 3.23-3.03 (m, 3H), 2.99 (s, 3H), 1.99-1.89 (m, 1H), 1.59-1.46 (m, 1H).

MS (ESI): 219 $[M+H]^+$.

Step 13: Synthesis of Compound Int_64-1 int_64-1

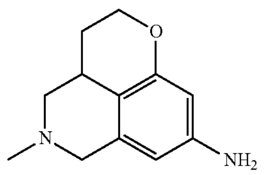

Int_64-1-16 (0.9 g, 4.12 mmol) was dissolved in tetrahydrofuran (30 mL), and lithium aluminum hydride (782 mg, 20.6 mmol) was slowly added at 0° C. The reaction mixture was warmed to 20° C. under nitrogen and left for 16 h. LC-MS monitoring showed the reaction was complete. The reaction mixture was quenched at 0° C. with $Na_2SO_4{\cdot}H_2O$ (50 g) and filtered. The filtrate was concentrated to give a crude product. The crude product was purified by column chromatography (ISCO®; 12 g SepaFlash® Silica Flash Column, Eluent of 0-10% MeOH/DCM (1% $NH_3{\cdot}H_2O$) to give a product (0.7 g, 83.1% yield).

$^1$H NMR (400 MHz, Chloroform-d) δ=6.01 (d, J=2.0 Hz, 1H), 5.98 (d, J=2.0 Hz, 1H), 4.46-4.35 (m, 1H), 4.20 (ddd, J=2.4, 10.6, 12.8 Hz, 1H), 3.91 (d, J=15.4 Hz, 1H), 3.62-3.42 (m, 2H), 3.23 (d, J=15.4 Hz, 1H), 3.10-2.91 (m, 2H), 2.45 (s, 4H), 2.05-1.97 (m, 1H), 1.86 (tdd, J=2.2, 4.2, 12.9 Hz, 1H), 1.72-1.55 (m, 1H).

MS (ESI): 205 $[M+H]^+$.

Step 14: Synthesis of Compound Int_1-2 int_1-2

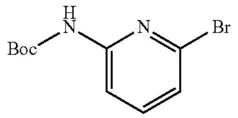

Int_1-1 (3.46 g, 20 mmol) was dissolved in dichloromethane (100 mL), and DIPEA (5.2 g, 40 mmol), DMAP (1.22 g, 10 mmol) and $(Boc)_2O$ (4.8 g, 22 mmol) were added. The mixture was left overnight at room temperature. LC-MS monitoring showed the reaction was complete. The reaction mixture was diluted with dichloromethane (100 mL), washed with water (200 mL), washed with 2 N dilute hydrochloric acid (100 mL), washed with an aqueous solution of sodium bicarbonate (100 mL), washed with water (100 mL), and finally washed with saturated brine (100 mL). The organic phase was dried over anhydrous sodium sulfate. The organic phase was filtered and distilled under reduced pressure to give a pale brown gel (4.0 g, 73% yield, crude).

The crude product was directly used in the next step.

ESI-MS m/z: 273 $[M+H]^+$.

Step 15: Synthesis of Compound Int_1-4 int_1-4

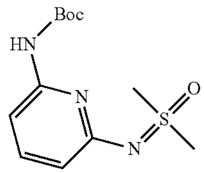

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol) and Xantphos (845 mg, 1.46 mmol) were dissolved in 1,4-dioxane (120 mL), and the mixture was left overnight at 85° C. LC-MS monitoring showed the reaction was complete. The reaction mixture was filtered and distilled under reduced pressure to give a crude product. The crude product was purified by column chromatography ($SiO_2$, DCM:MeOH=100:1 to 30:1) to give a pale yellow solid product (2.7 g, 65% yield).

ESI-MS m/z: 286 $[M+H]^+$.

Step 16: Synthesis of Compound Int_1-5 int_1-5

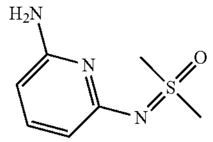

Int_1-4 (2.4 g, 8.41 mmol) was dissolved in dichloromethane (30 mL), and trifluoroacetic acid (10 mL) was added. The mixture was left overnight at room temperature. LC-MS monitoring showed the reaction was complete. The reaction mixture was directly concentrated under reduced pressure to give a grayish yellow solid (1.6 g, 100% yield). The crude product was directly used in the next step.

ESI-MS m/z: 186 $[M+H]^+$.

Step 17: Synthesis of Compound Int_1-7 int_1-7

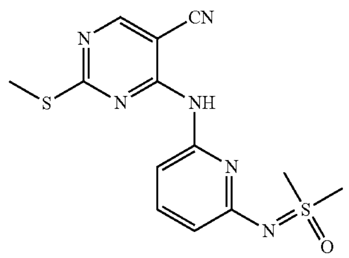

Int_1-6 (2 g, 10.8 mmol) and int_1-5 (3.2 g, 10.8 mmol) were dissolved in isopropanol (5 mL), and DIPEA (5.57 g, 43.1 mmol, 7.51 mL) was added. The reaction mixture was heated to 50° C. and left overnight. LC-MS monitoring showed the reaction was complete. The reaction mixture was cooled to room temperature, and a white solid precipitated.

The solid was collected by filtration as the product. The product was dried to give a white solid (1.2 g, 33% yield). $^1$H NMR: (400 MHz, DMSO-$d_6$). δ 9.80 (s, 1H), 8.70 (s, 1H), 7.58 (t, J=7.9 Hz, 1H), 7.16 (d, J=7.8 Hz, 1H), 6.44 (d, J=7.9 Hz, 1H), 3.41 (s, 6H), 2.49 (s, 3H).

ESI-MS m/z: 335 $[M+H]^+$.

Step 18: Synthesis of Compound Int_1-8 int_1-8

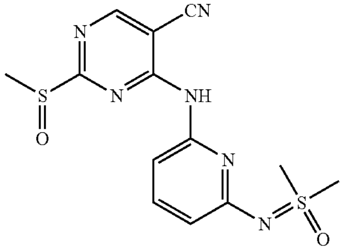

Int_1-7 (334 mg, 1.0 mmol) was dissolved in dichloromethane (40 mL), and m-CPBA (85%, 240 mg, 1.2 mmol) was added at room temperature. The mixture was stirred at room temperature for half an hour. LC-MS monitoring showed the reaction was complete. The reaction mixture was concentrated under reduced pressure to give a crude product (335 mg). The crude product was directly used in the next step.

ESI-MS m/z: 351 $[M+H]^+$.

Step 19: Synthesis of Compound 64

64

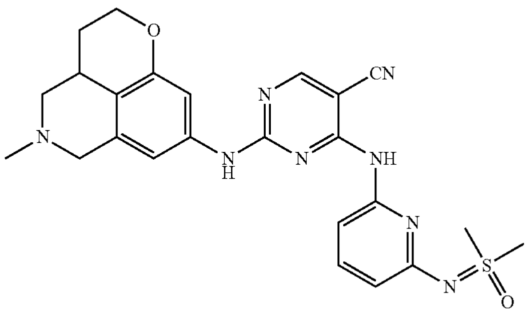

Int_1-8 (335 mg, 0.95 mmol) was dissolved in DMF (20 mL), and int_64-1 (245 mg, 1.2 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative HPLC to give a white solid (165 mg, 35% yield).

$^1$H NMR (400 MHz, Chloroform-d) δ 8.35 (s, 1H), 7.71 (d, J=7.8 Hz, 1H), 7.54 (dd, J=19.7, 11.9 Hz, 2H), 7.40 (s, 1H), 6.84 (d, J=17.9 Hz, 2H), 6.58 (d, J=7.8 Hz, 1H), 4.45 (d, J=10.8 Hz, 1H), 4.23 (t, J=11.7 Hz, 1H), 4.05 (d, J=15.5 Hz, 1H), 3.43 (d, J=33.4 Hz, 1H), 3.36 (s, 6H), 3.16 (d, J=10.3 Hz, 3H), 2.52 (s, 3H), 1.94 (d, J=13.0 Hz, 1H), 1.67 (d, J=12.8 Hz, 1H).

LC-MS: 491 $[M+H]^+$.

Example 5. Synthesis of Compound 95

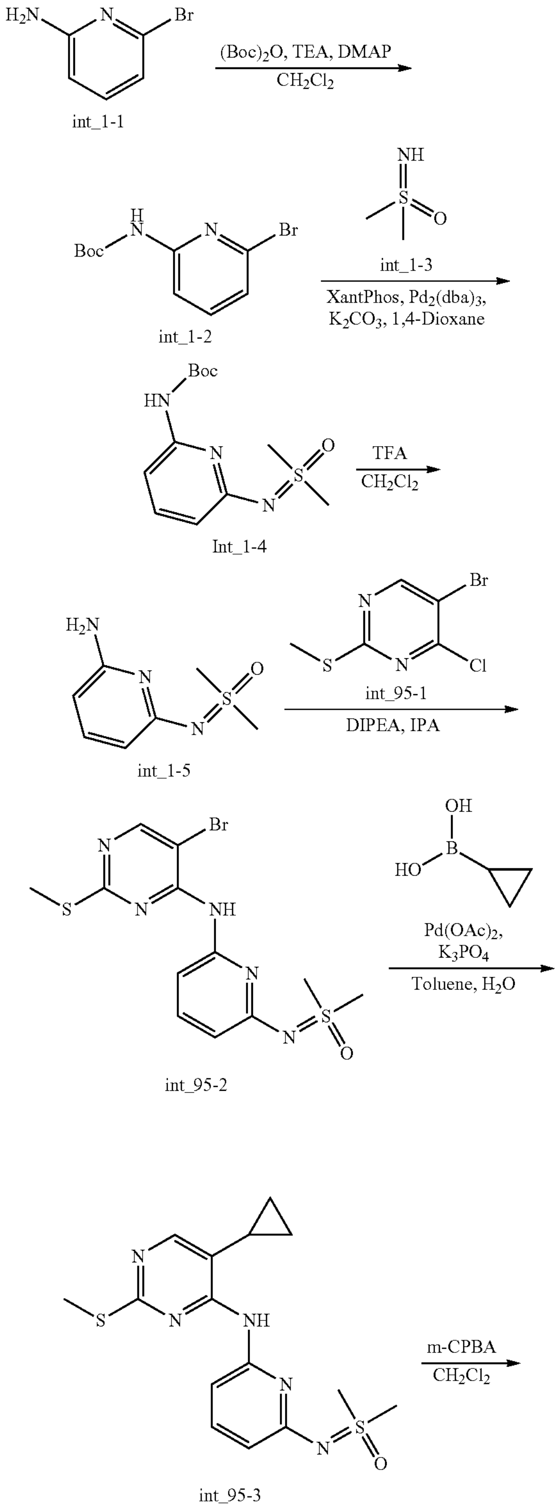

int_1-1
int_1-2
int_1-3
Int_1-4
int_1-5
int_95-1
int_95-2
int_95-3

-continued

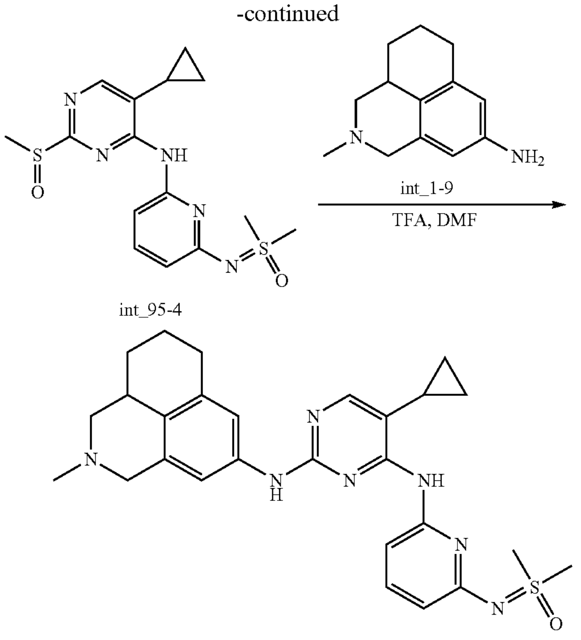

int_95-4

95

Step 1: Synthesis of Compound Int_1-2 int_1-2

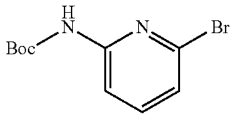

Int_1-1 (3.46 g, 20 mmol) was dissolved in dichloromethane (100 mL), and DIPEA (5.2 g, 40 mmol), DMAP (1.22 g, 10 mmol) and $(Boc)_2O$ (4.8 g, 22 mmol) were added. The mixture was left overnight at room temperature. LC-MS monitoring showed the reaction was complete. The reaction mixture was diluted with dichloromethane (100 mL), washed with water (200 mL), washed with 2 N dilute hydrochloric acid (100 mL), washed with an aqueous solution of sodium bicarbonate (100 mL), washed with water (100 mL), and finally washed with saturated brine (100 mL). The organic phase was dried over anhydrous sodium sulfate. The organic phase was filtered and distilled under reduced pressure to give a pale brown gel (4.0 g, 73% yield, crude). The crude product was directly used in the next step.

ESI-MS m/z: 273 $[M+H]^+$.

Step 2: Synthesis of Compound Int_1-4 int_1-4

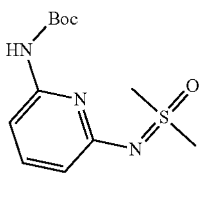

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol) and Xantphos (845 mg, 1.46 mmol) were dissolved in 1,4-dioxane (120 mL), and the mixture was left overnight at 85° C. LC-MS monitoring showed the reaction was complete. The reaction mixture was filtered and distilled under reduced pressure to give a crude product. The crude product was purified by column chromatography ($SiO_2$, DCM:MeOH=100:1 to 30:1) to give a pale yellow solid product (2.7 g, 65% yield).

ESI-MS m/z: 286 $[M+H]^+$.

Step 3: Synthesis of Compound Int_1-5 int-_1-5

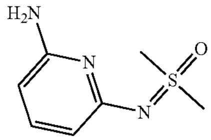

Int_1-4 (2.4 g, 8.41 mmol) was dissolved in dichloromethane (30 mL), and trifluoroacetic acid (10 mL) was added. The mixture was left overnight at room temperature. LC-MS monitoring showed the reaction was complete. The reaction mixture was directly concentrated under reduced pressure to give a grayish yellow solid (1.6 g, 100% yield). The crude product was directly used in the next step.

ESI-MS m/z: 186 $[M+H]^+$.

Step 4: Synthesis of Compound Int_95-2 int_95-2

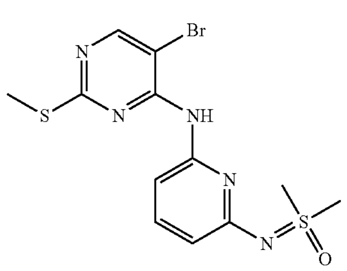

Int_95-1 (2 g, 8.35 mmol) and int_1-5 (1.55 g, 8.35 mmol) were dissolved in isopropanol (5 mL), and DIPEA (4.32 g, 33.4 mmol, 5.83 mL) was added. The reaction mixture was heated to 80° C. and left overnight. LC-MS monitoring showed the reaction was complete. The reaction mixture was cooled to room temperature, concentrated to dryness by rotary evaporation, and purified by column chromatography to give a pale yellow solid (1.5 g, 46.3% yield).

ESI-MS m/z: 388 $[M+H]^+$.

Step 5: Synthesis of Compound Int_95-3 int_95-3

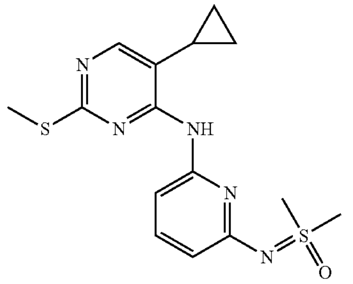

Int_95-2 (100 mg, 0.26 mmol), cyclopropylboronic acid (45 mg, 0.52 mmol) and potassium phosphate (166 mg, 0.78 mmol) were dissolved in a mixed solvent of toluene (7.5 mL) and water (0.5 mL). The solution was purged with argon three times, and palladium acetate (7 mg, 0.03 mmol) and tricyclohexylphosphine (17 mg, 0.06 mmol) were added. The mixture was heated to 100° C. under argon and stirred for 16 h. LC-MS monitoring showed the reaction was complete. The reaction mixture was cooled to room temperature, concentrated to dryness by rotary evaporation, and purified by column chromatography to give a pale yellow solid (61 g, 67.1% yield).

ESI-MS m/z: 350 $[M+H]^+$.

Step 6: Synthesis of Compound Int_95-4 int_95-4

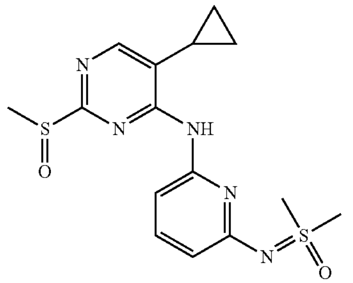

Int_95-3 (500 mg, 1.43 mmol) was dissolved in dichloromethane (40 mL), and m-CPBA (85%, 348.6 mg, 1.72 mmol) was added at room temperature. The mixture was stirred at room temperature for half an hour. LC-MS monitoring showed the reaction was complete. The reaction mixture was concentrated under reduced pressure to give a crude product (335 mg). The crude product was directly used in the next step.

ESI-MS m/z: 366 $[M+H]^+$.

Step 7: Synthesis of Compound 95

95

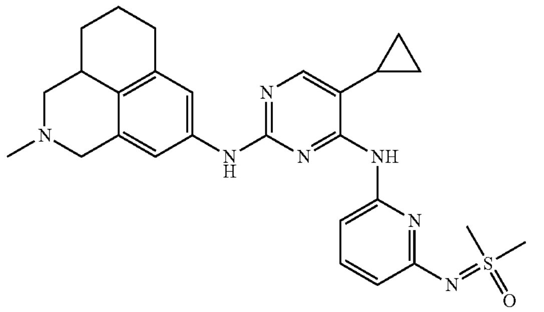

Int_95-4 (100 mg, 0.273 mmol) was dissolved in DMF (5 mL), and int_1-9 (57 mg, 0.28 mmol) and trifluoroacetic acid (456 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative reversed-phase chromatography to give a white solid (75 mg, 55% yield).

ESI-MS m/z: 504 $[M+H]^+$.

Example 6. Synthesis of Compound 137

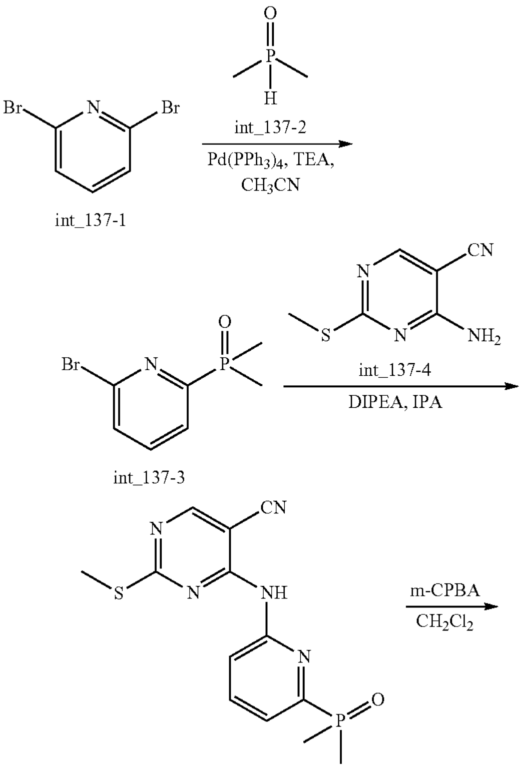

int_137-1 int_137-3 int_137-5

-continued

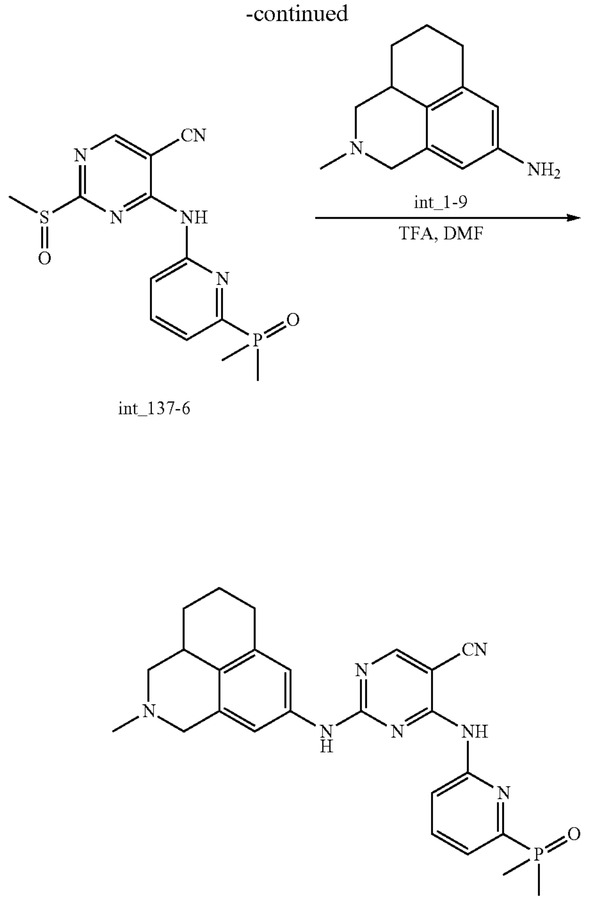

int_137-6

137

Step 1: Synthesis of Compound Int_137-3 int_137-3

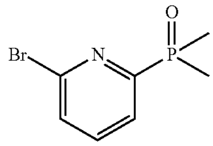

Int_137-1 (3 g, 12.7 mmol), int_137-2 (4.94 g, 63.3 mmol), triethylamine (3.86 g, 38.1 mmol) and $Pd(PPh_3)_4$ (733.8 mg, 0.635 mmol) were dissolved in acetonitrile (100 mL), and the mixture was left overnight at 70° C. LC-MS monitoring showed the reaction was complete. The reaction mixture was filtered and distilled under reduced pressure to give a crude product. The crude product was purified by column chromatography to give a pale yellow solid product (1.8 g, 60% yield).

ESI-MS m/z: 234 $[M+H]^+$.

Step 2: Synthesis of Compound Int_137-5 int_137-5

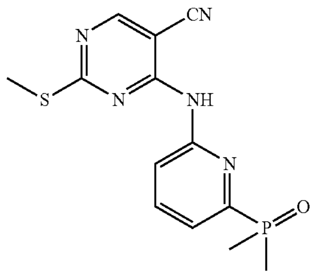

Int_137-3 (2 g, 8.5 mmol) and int_137-4 (1.42 g, 8.5 mmol) were dissolved in isopropanol (5 mL), and DIPEA (4.39 g, 34 mmol, 5.6 mL) was added. The reaction mixture was heated to 50° C. and left overnight. LC-MS monitoring showed the reaction was complete. The reaction mixture was cooled to room temperature, filtered and distilled under reduced pressure to give a crude product. The crude product was purified by column chromatography to give a yellow solid (1.3 g, 48% yield).

ESI-MS m/z: 320 $[M+H]^+$.

Step 3: Synthesis of Compound Int_137-6 int_137-6

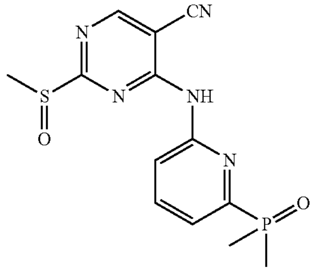

Int_137-5 (500 mg, 1.57 mmol) was dissolved in dichloromethane (40 mL), and m-CPBA (85%, 381.7 mg, 1.88 mmol) was added at room temperature. The mixture was stirred at room temperature for half an hour. LC-MS monitoring showed the reaction was complete. The reaction mixture was concentrated under reduced pressure to give a crude product (500 mg). The crude product was directly used in the next step.

ESI-MS m/z: 336 $[M+H]^+$.

Step 4: Synthesis of Compound 137

137

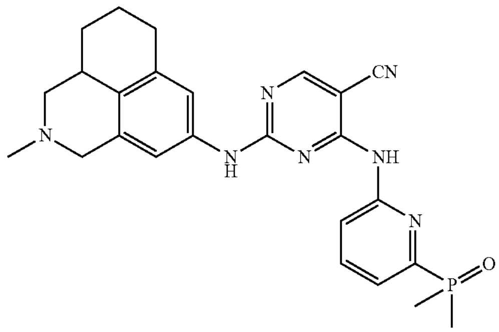

Int_137-6 (100 mg, 0.298 mmol) was dissolved in DMF (5 mL), and int_1-9 (60 mg, 0.298 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative reversed-phase chromatography to give a white solid (65 mg, 46% yield).

$^1$H NMR (400 MHz, DMSO-d6): δ 9.93 (s, 1H), 9.74 (s, 1H), 8.58 (s, 1H), 7.91 (s, 2H), 7.67 (t, J=6.3 Hz, 1H), 7.08 (s, 2H), 3.70 (s, 1H), 3.12 (dd, J=25.9, 9.8 Hz, 1H), 2.88 (dd, J=10.9, 4.8 Hz, 1H), 2.67 (q, J=19.8, 16.3 Hz, 3H), 2.29 (s, 3H), 1.96-1.75 (m, 4H), 1.63 (d, J=13.5 Hz, 6H), 1.28-1.05 (m, 1H).

LC-MS: 474 $[M+H]^+$.

Example 7. Synthesis of Compound 138

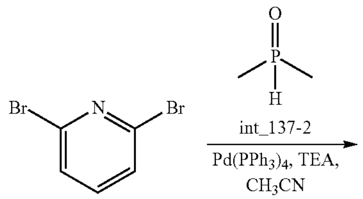

int_137-1

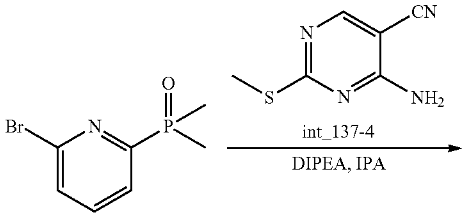

int_137-3

-continued

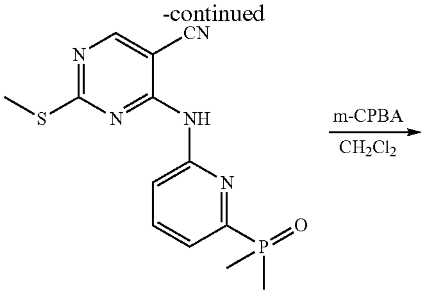

int_137-5

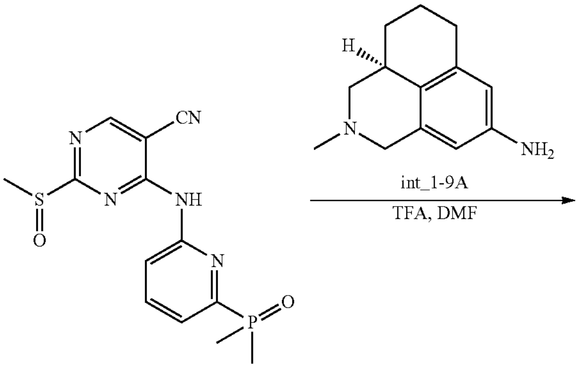

int_137-6

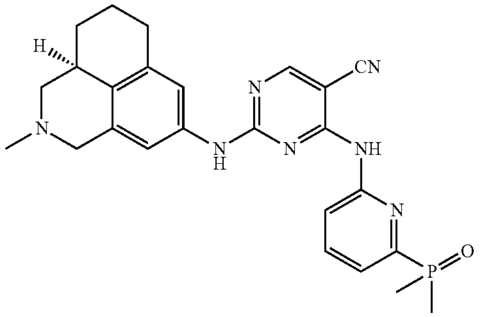

138

Step 1: Synthesis of Compound Int_137-3 int_137-3

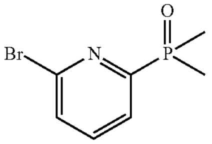

Int_137-1 (3 g, 12.7 mmol), int_137-2 (4.94 g, 63.3 mmol), triethylamine (3.86 g, 38.1 mmol) and $Pd(PPh_3)_4$ (733.8 mg, 0.635 mmol) were dissolved in acetonitrile (100 mL), and the mixture was left overnight at 70° C. LC-MS monitoring showed the reaction was complete. The reaction mixture was filtered and distilled under reduced pressure to give a crude product. The crude product was purified by column chromatography to give a pale yellow solid product (1.8 g, 60% yield).

ESI-MS m/z: 234 $[M+H]^+$.

Step 2: Synthesis of Compound Int_137-5

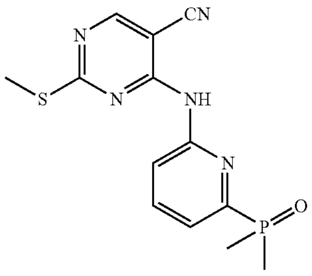

int_137-5

Int_137-3 (2 g, 8.5 mmol) and int_137-4 (1.42 g, 8.5 mmol) were dissolved in isopropanol (5 mL), and DIPEA (4.39 g, 34 mmol, 5.6 mL) was added. The reaction mixture was heated to 50° C. and left overnight. LC-MS monitoring showed the reaction was complete. The reaction mixture was cooled to room temperature, filtered and distilled under reduced pressure to give a crude product. The crude product was purified by column chromatography to give a yellow solid (1.3 g, 48% yield).

ESI-MS m/z: 320 $[M+H]^+$.

Step 3: Synthesis of Compound Int_137-6

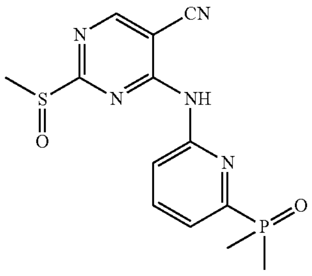

int_137-6

Int_137-5 (500 mg, 1.57 mmol) was dissolved in dichloromethane (40 mL), and m-CPBA (85%, 381.7 mg, 1.88 mmol) was added at room temperature. The mixture was stirred at room temperature for half an hour. LC-MS monitoring showed the reaction was complete. The reaction mixture was concentrated under reduced pressure to give a crude product (500 mg). The crude product was directly used in the next step.

ESI-MS m/z: 336 $[M+H]^+$.

Step 4: Synthesis of Compound 138

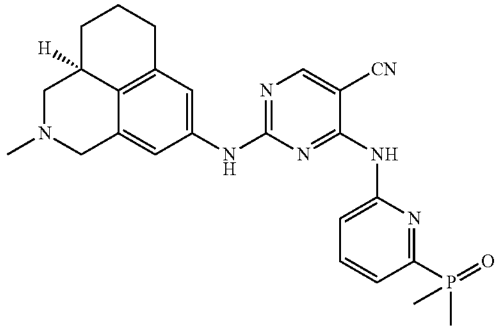

138

Int_137-6 (100 mg, 0.298 mmol) was dissolved in DMF (5 mL), and int_1-9A (60 mg, 0.298 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative reversed-phase chromatography to give a white solid (60 mg, 42.5% yield).

$^1$H NMR (400 MHz, DMSO-$d_6$) δ 9.93 (s, 1H), 9.74 (s, 1H), 8.58 (s, 1H), 7.91 (s, 2H), 7.67 (t, J=6.3 Hz, 1H), 7.08 (s, 2H), 3.70 (s, 1H), 3.12 (dd, J=25.9, 9.8 Hz, 1H), 2.88 (dd, J=10.9, 4.8 Hz, 1H), 2.67 (q, J=19.8, 16.3 Hz, 3H), 2.29 (s, 3H), 1.96-1.75 (m, 4H), 1.63 (d, J=13.5 Hz, 6H), 1.28-1.05 (m, 1H).

LC-MS: 474 $[M+H]^+$.

Example 8. Synthesis of Compound 139

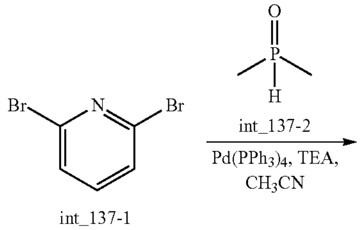

int_137-1

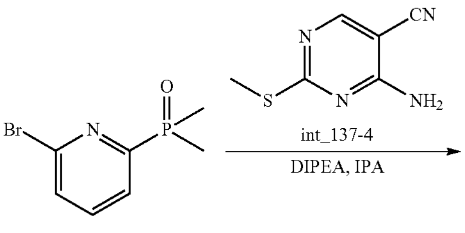

int_137-3

-continued

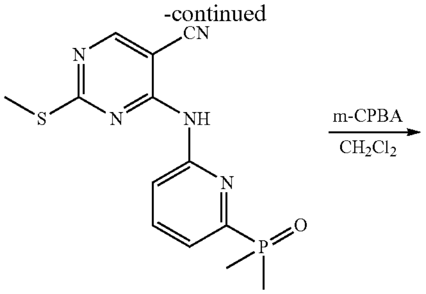

int_137-5

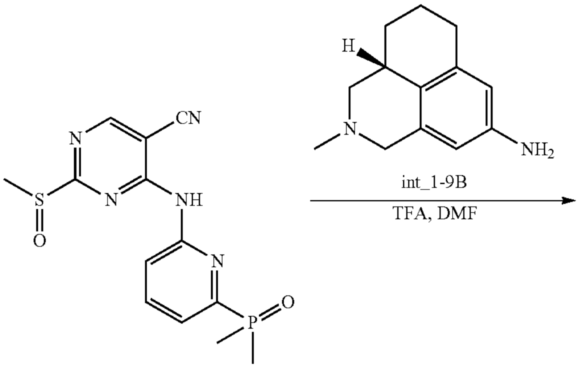

int_137-6

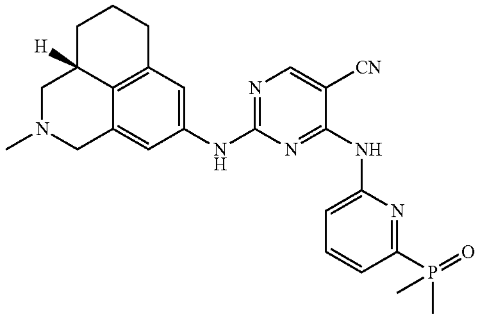

139

Step 1: Synthesis of Compound Int_137-3

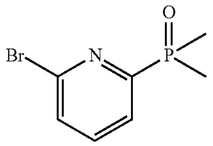

int_137-3

Int_137-1 (3 g, 12.7 mmol), int_137-2 (4.94 g, 63.3 mmol), triethylamine (3.86 g, 38.1 mmol) and $Pd(PPh_3)_4$ (733.8 mg, 0.635 mmol) were dissolved in acetonitrile (100 mL), and the mixture was left overnight at 70° C. LC-MS monitoring showed the reaction was complete. The reaction mixture was filtered and distilled under reduced pressure to give a crude product. The crude product was purified by column chromatography to give a pale yellow solid product (1.8 g, 60% yield).

ESI-MS m/z: 234 $[M+H]^+$.

Step 2: Synthesis of Compound Int_137-5

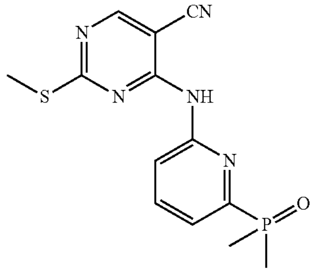

int_137-5

Int_137-3 (2 g, 8.5 mmol) and int_137-4 (1.42 g, 8.5 mmol) were dissolved in isopropanol (5 mL), and DIPEA (4.39 g, 34 mmol, 5.6 mL) was added. The reaction mixture was heated to 50° C. and left overnight. LC-MS monitoring showed the reaction was complete. The reaction mixture was cooled to room temperature, filtered and distilled under reduced pressure to give a crude product. The crude product was purified by column chromatography to give a yellow solid (1.3 g, 48% yield).

ESI-MS m/z: 320 $[M+H]^+$.

Step 3: Synthesis of Compound Int_137-6

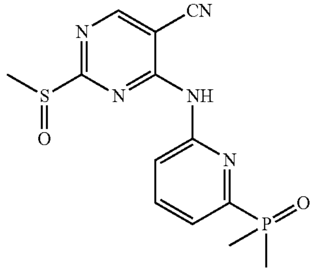

int_137-6

Int_137-5 (500 mg, 1.57 mmol) was dissolved in dichloromethane (40 mL), and m-CPBA (85%, 381.7 mg, 1.88 mmol) was added at room temperature. The mixture was stirred at room temperature for half an hour. LC-MS monitoring showed the reaction was complete. The reaction mixture was concentrated under reduced pressure to give a crude product (500 mg). The crude product was directly used in the next step.

ESI-MS m/z: 336 $[M+H]^+$.

Step 4: Synthesis of Compound 139

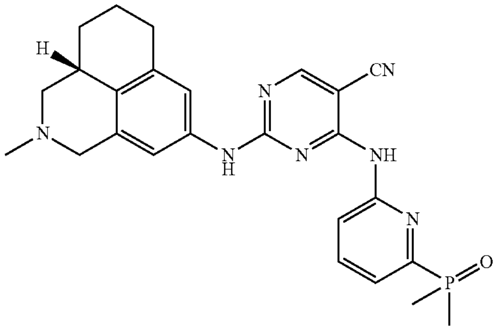

139

Int_137-6 (100 mg, 0.298 mmol) was dissolved in DMF (5 mL), and int_1-9B (60 mg, 0.298 mmol) and trifluoroacetic acid (456.8 mg, 4.0 mmol) were added. The reaction mixture was heated to 80° C. and stirred for 10 h. LC-MS monitoring showed the reaction was complete. The reaction mixture was cooled to room temperature and concentrated under reduced pressure to give a crude product. The crude product was purified by preparative reversed-phase chromatography to give a white solid (70 mg, 50% yield).

$^1$H NMR (400 MHz, DMSO-$d_6$) δ 9.93 (s, 1H), 9.74 (s, 1H), 8.58 (s, 1H), 7.91 (s, 2H), 7.67 (t, J=6.3 Hz, 1H), 7.08

(s, 2H), 3.70 (s, 1H), 3.12 (dd, J=25.9, 9.8 Hz, 1H), 2.88 (dd, J=10.9, 4.8 Hz, 1H), 2.67 (q, J=19.8, 16.3 Hz, 3H), 2.29 (s, 3H), 1.96-1.75 (m, 4H), 1.63 (d, J=13.5 Hz, 6H), 1.28-1.05 (m, 1H).

LC-MS: 474 $[M+H]^+$.

Example 9-296. Synthesis of Compounds 4-63, 65-94, 96-136 and 140-296

The target compounds 4-63, 65-94, 96-136 and 140-296 in Table 1 were obtained by the synthesis methods described above using different starting materials.

LC-MS Analysis:

Instrument: Agilent, LC:1260 InfinityII+MS:G6125B

Column: Welch: Core-shell 2.7 μm, 4.3×50 mm

Temperature: 30° C.

Wavelengths: 254 nm/214 nm

Mobile phase A: H2O (0.1% formic acid)

Mobile phase B: acetonitrile (0.1% formic acid)

Gradient:

| Time (min) | Flow rate (mL/min) | Mobile phase B % | Mobile phase A % |
|---|---|---|---|
| 0 | 2 | 5 | 95 |
| 0.1 | 2 | 5 | 95 |
| 2.2 | 2 | 95 | 5 |
| 2.7 | 2 | 95 | 5 |
| 2.71 | 2 | 5 | 95 |
| 3 | 2 | 5 | 95 |

TABLE 1

| Compound | Compound structure | MS $(M + H)^+$ |
|---|---|---|
| 4 | 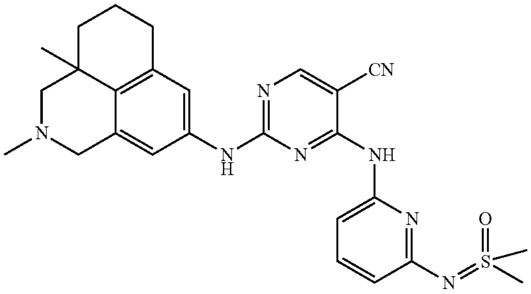 | 503 |
| 5 | 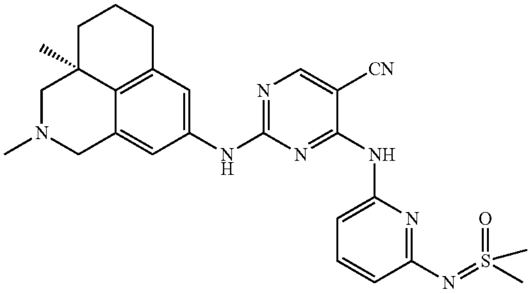 | 503 |

TABLE 1-continued
| Compound | Compound structure | MS (M + H)+ |
|---|---|---|
| 6 | 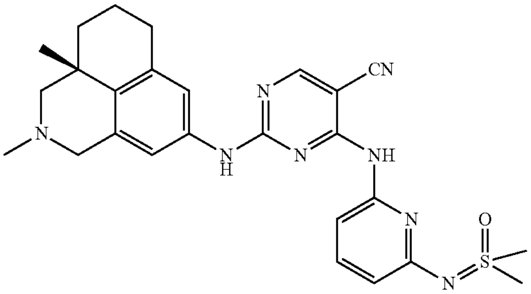 | 503 |
| 7 | 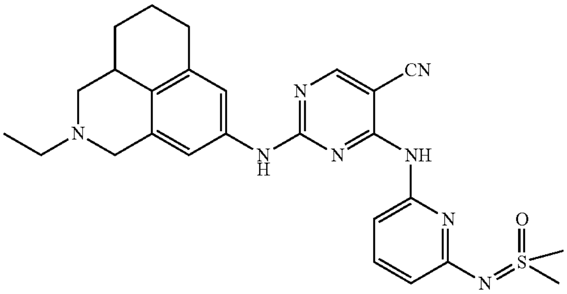 | 503 |
| 8 | 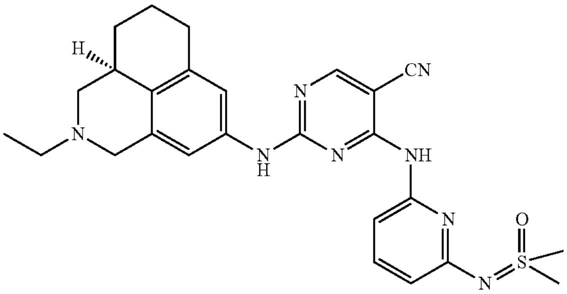 | 503 |
| 9 | 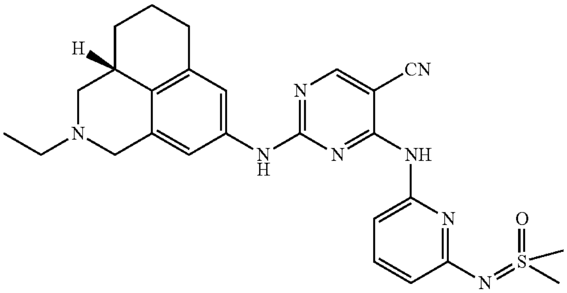 | 503 |
| 10 | 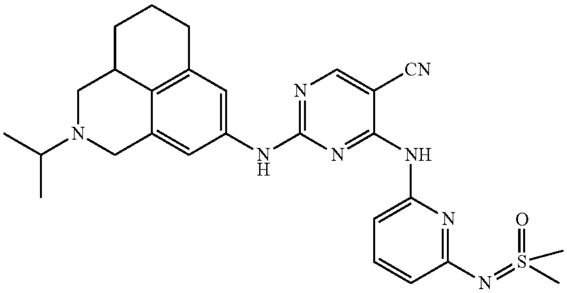 | 517 |

TABLE 1-continued
| Compound | Compound structure | MS (M + H)+ |
|---|---|---|
| 11 | 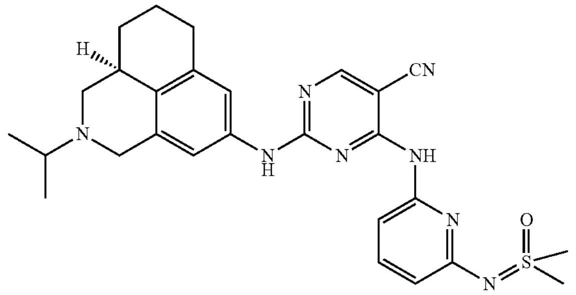 | 517 |
| 12 | 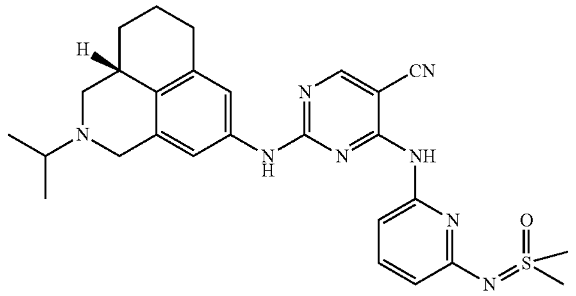 | 517 |
| 13 | 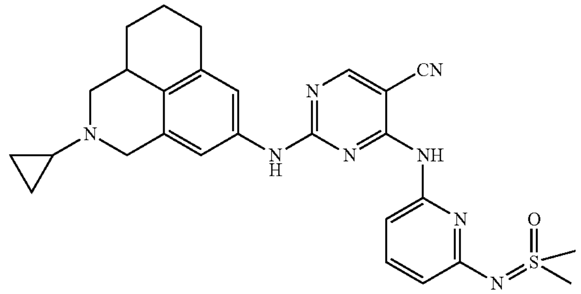 | 515 |
| 14 | 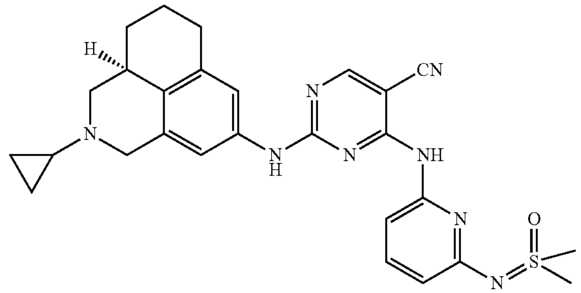 | 515 |
| 15 | 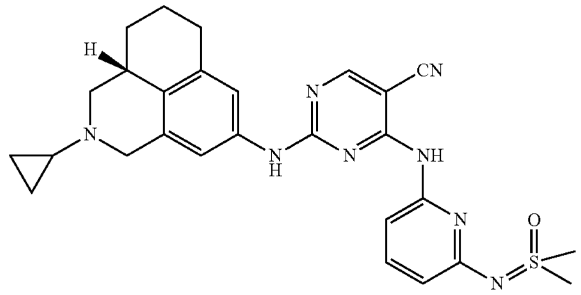 | 515 |

TABLE 1-continued
| Compound | Compound structure | MS (M + H)+ |
| --- | --- | --- |
| 16 | 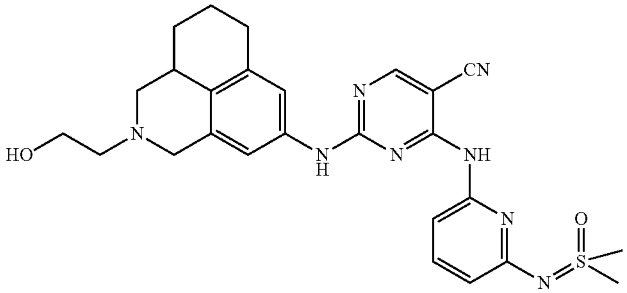 | 519 |
| 17 | 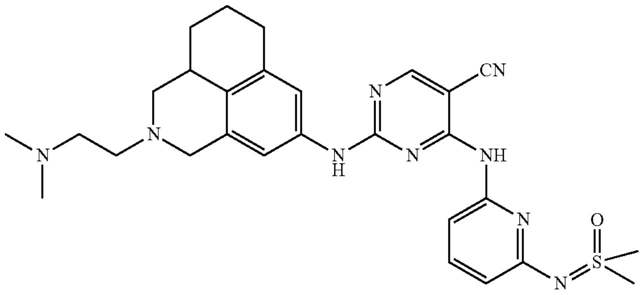 | 546 |
| 18 | 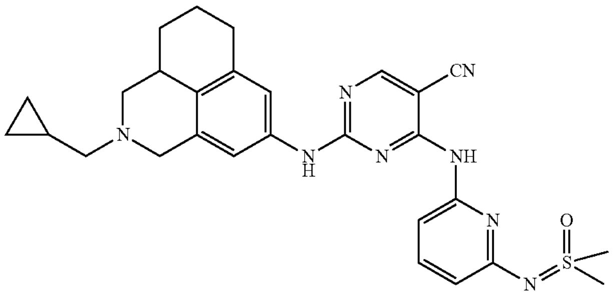 | 529 |
| 19 | 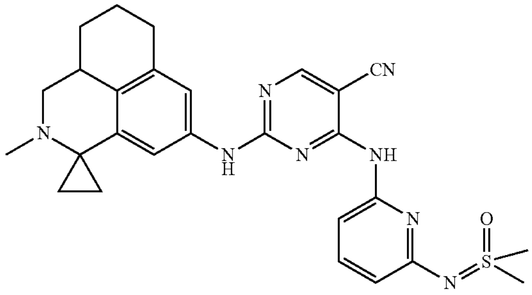 | 515 |
| 20 | 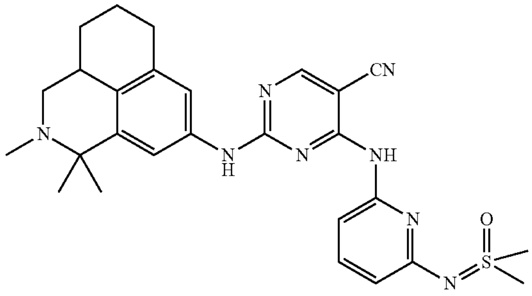 | 517 |

TABLE 1-continued
| Compound | Compound structure | MS (M + H)+ |
|---|---|---|
| 21 | 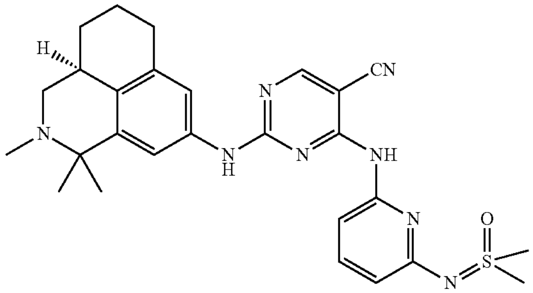 | 517 |
| 22 | 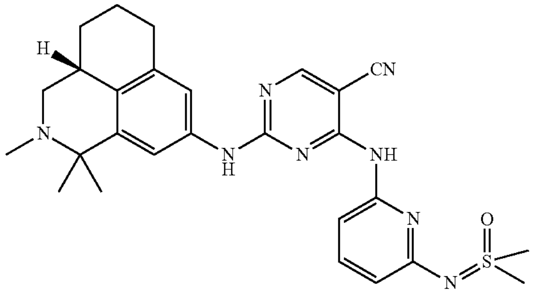 | 517 |
| 23 | 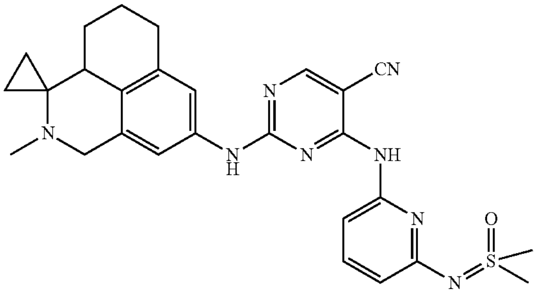 | 515 |
| 24 | 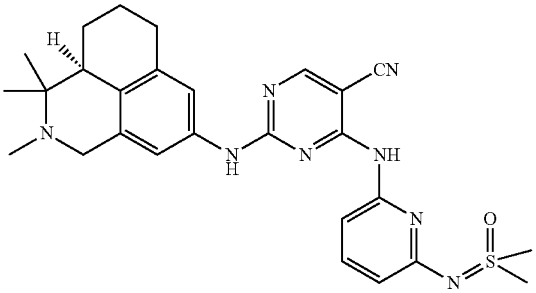 | 517 |
| 25 | 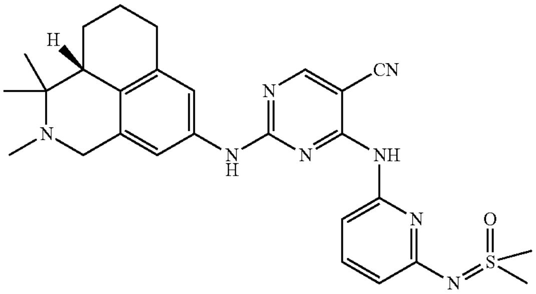 | 517 |

TABLE 1-continued
| Compound | Compound structure | MS (M + H)$^+$ |
| --- | --- | --- |
| 26 | 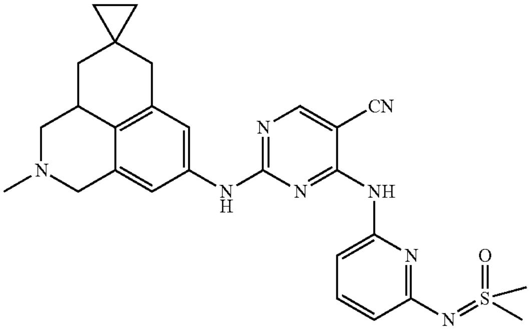 | 515 |
| 27 | 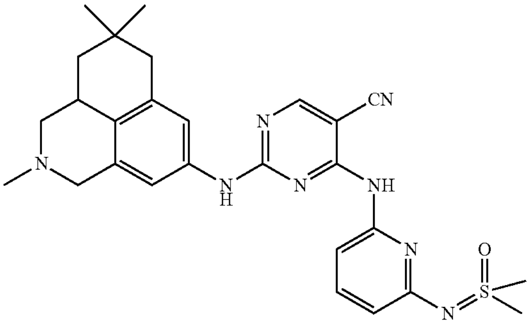 | 517 |
| 28 | 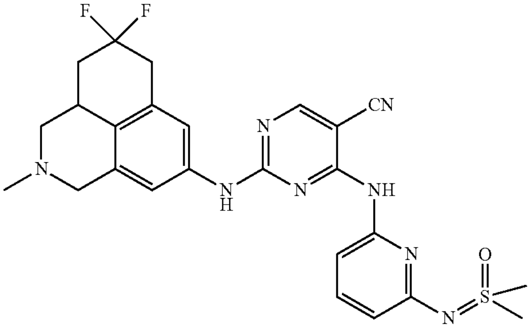 | 525 |
| 29 | 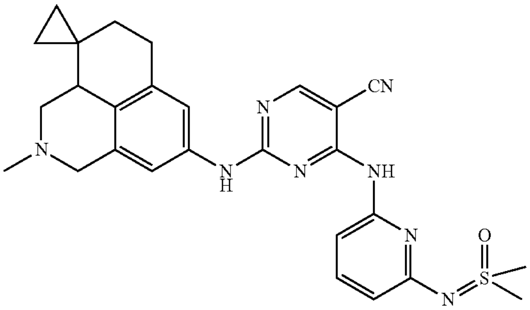 | 515 |

TABLE 1-continued
| Compound | Compound structure | MS (M + H)+ |
| --- | --- | --- |
| 30 | 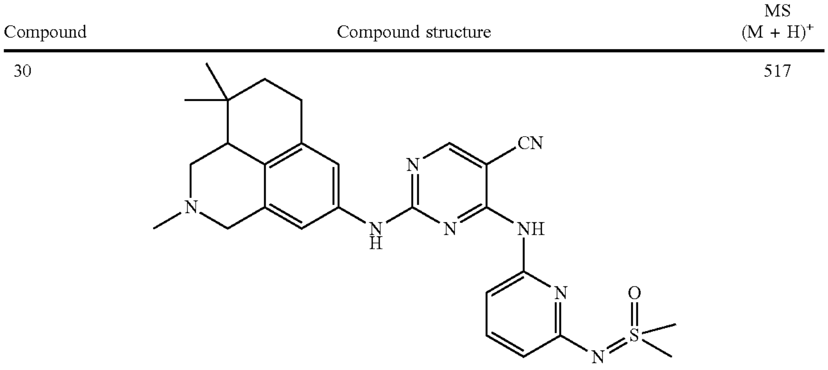 | 517 |
| 31 | 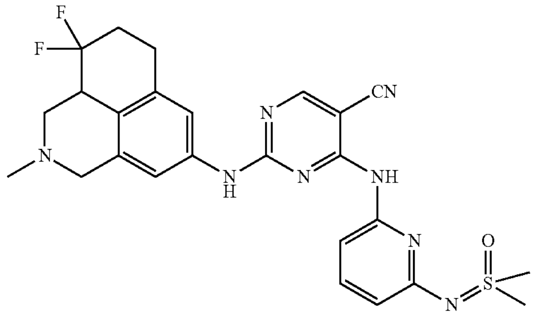 | 525 |
| 32 | 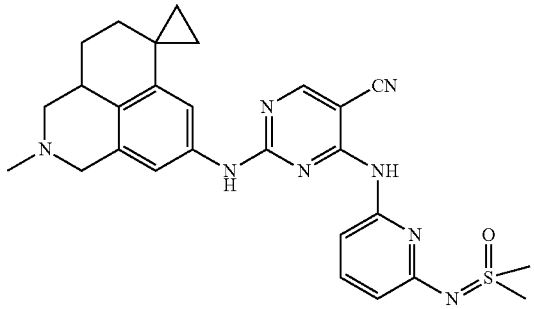 | 515 |
| 33 | 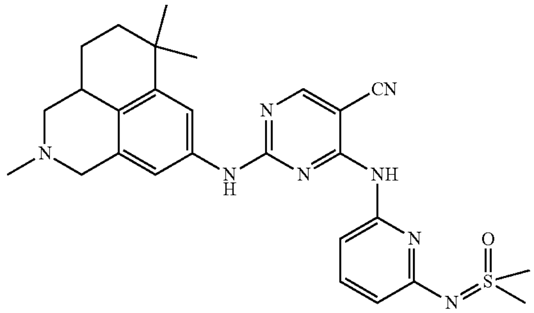 | 517 |
| 34 | 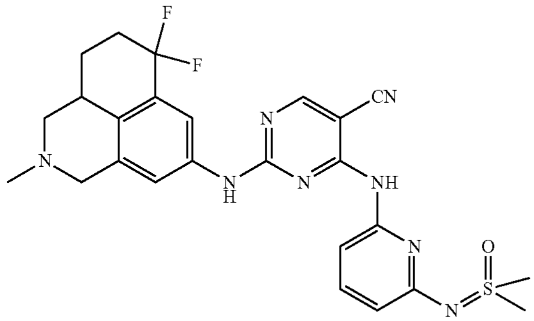 | 525 |

TABLE 1-continued
| Compound | Compound structure | MS (M + H)+ |
|---|---|---|
| 35 | 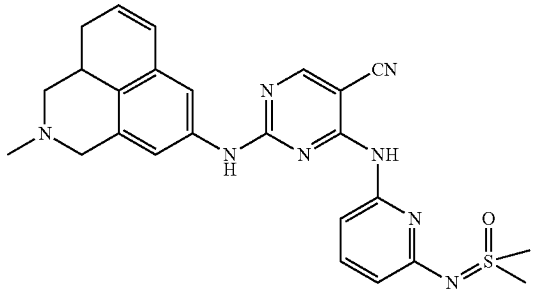 | 487 |
| 36 | 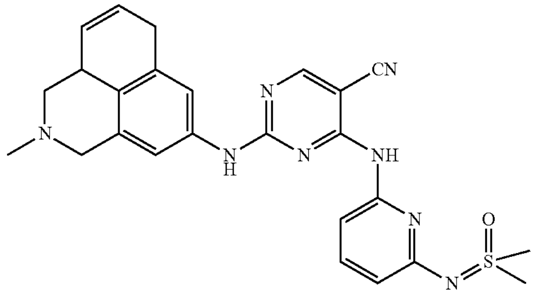 | 487 |
| 37 | 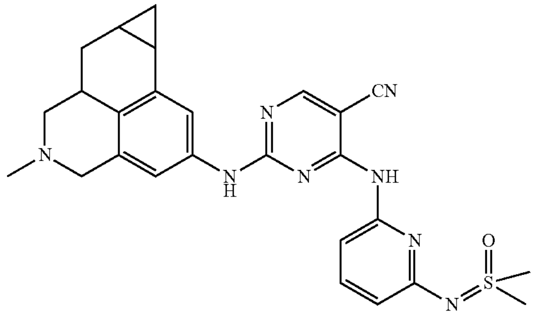 | 501 |
| 38 | 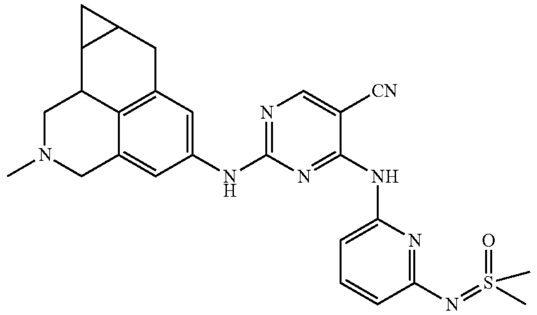 | 501 |
| 39 | 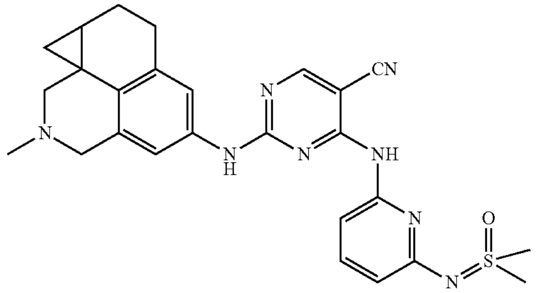 | 501 |

TABLE 1-continued
| Compound | Compound structure | MS (M + H)+ |
|---|---|---|
| 40 | 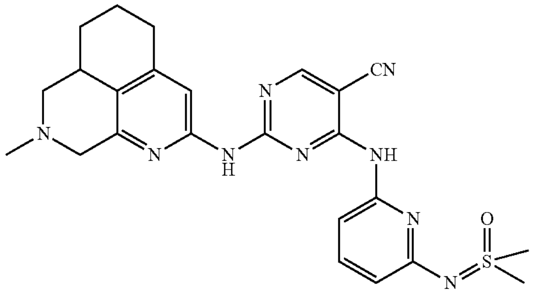 | 490 |
| 41 | 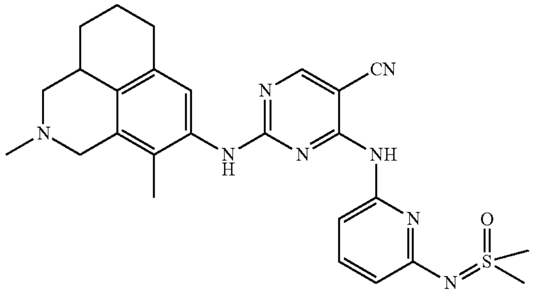 | 503 |
| 42 | 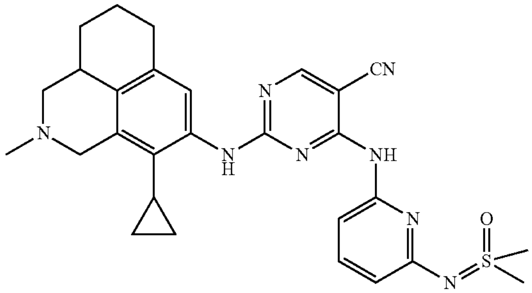 | 529 |
| 43 | 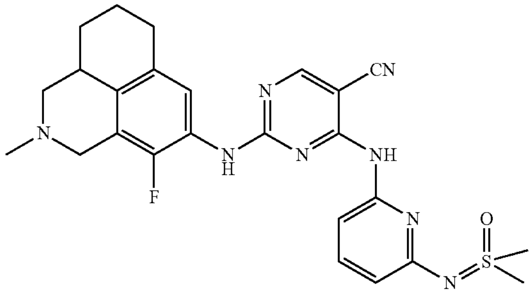 | 507 |
| 44 | 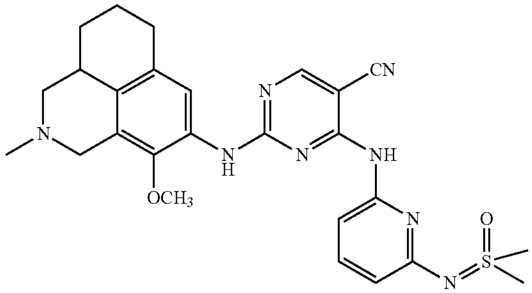 | 519 |

TABLE 1-continued
| Compound | Compound structure | MS $(M + H)^+$ |
| --- | --- | --- |
| 45 | 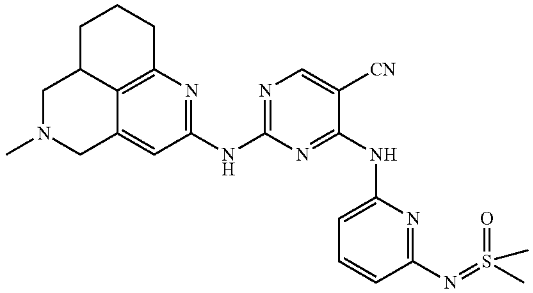 | 490 |
| 46 | 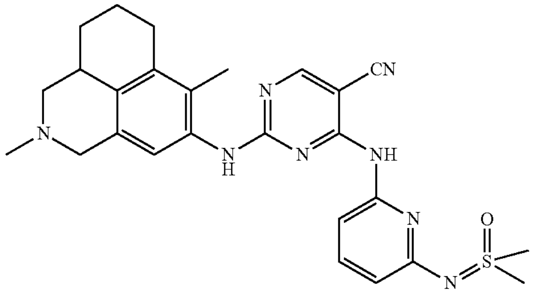 | 503 |
| 47 | 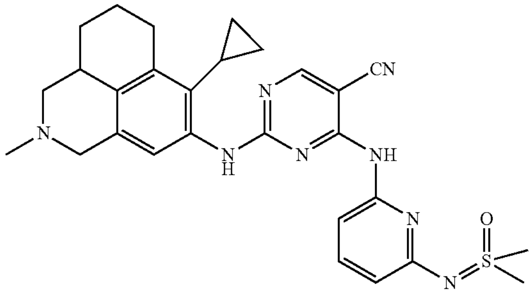 | 529 |
| 48 | 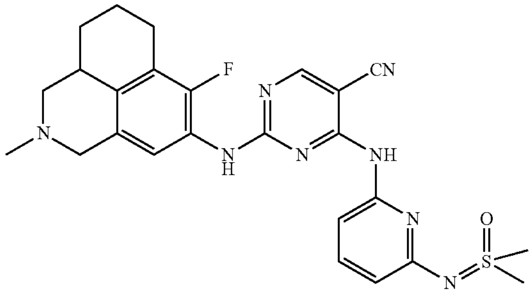 | 507 |
| 49 | 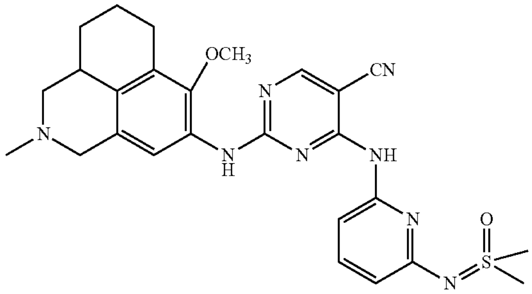 | 519 |

TABLE 1-continued
| Compound | Compound structure | MS (M + H)+ |
|---|---|---|
| 50 | 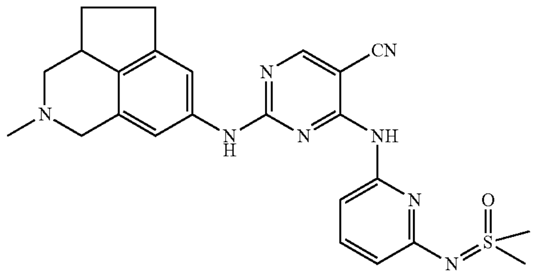 | 475 |
| 51 | 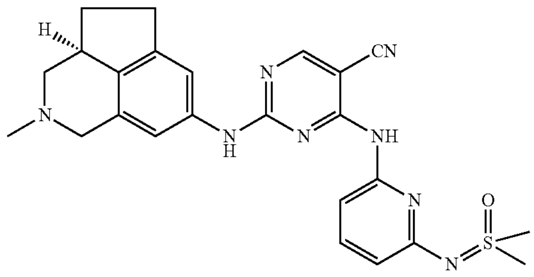 | 475 |
| 52 | 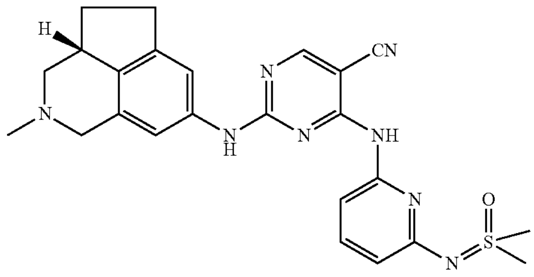 | 475 |
| 53 | 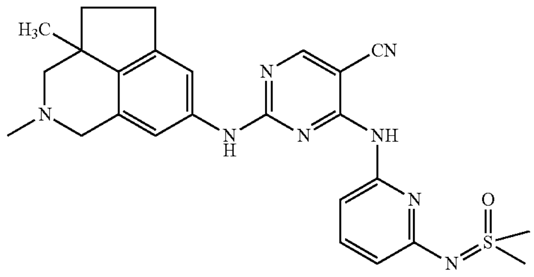 | 489 |
| 54 | 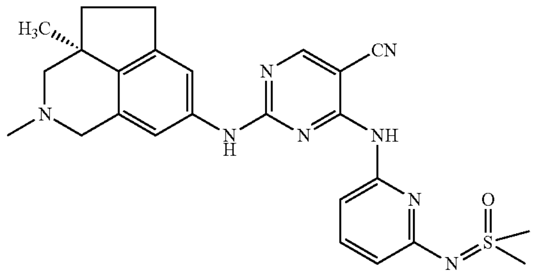 | 489 |

TABLE 1-continued
| Compound | Compound structure | MS (M + H)+ |
| --- | --- | --- |
| 55 | 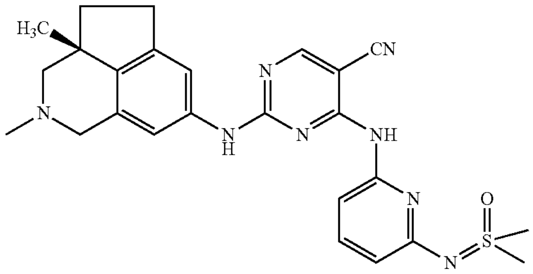 | 489 |
| 56 | 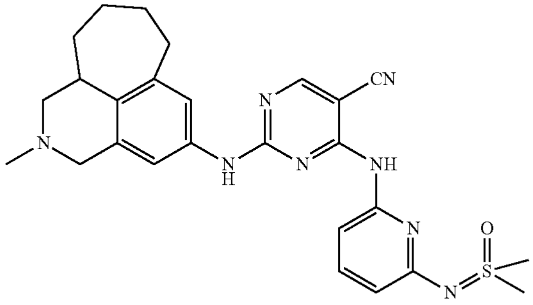 | 503 |
| 57 | 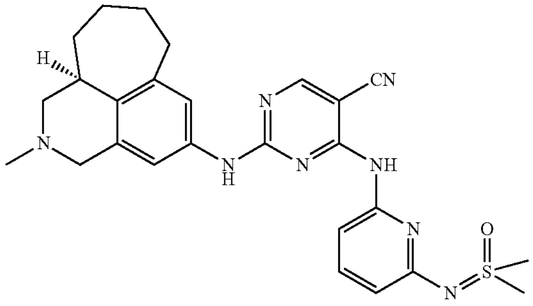 | 503 |
| 58 | 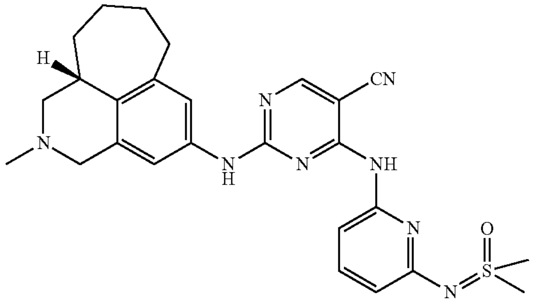 | 503 |
| 59 | 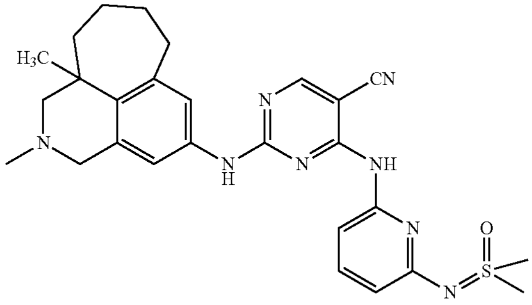 | 517 |

TABLE 1-continued
| Compound | Compound structure | MS (M + H)$^+$ |
|---|---|---|
| 60 | 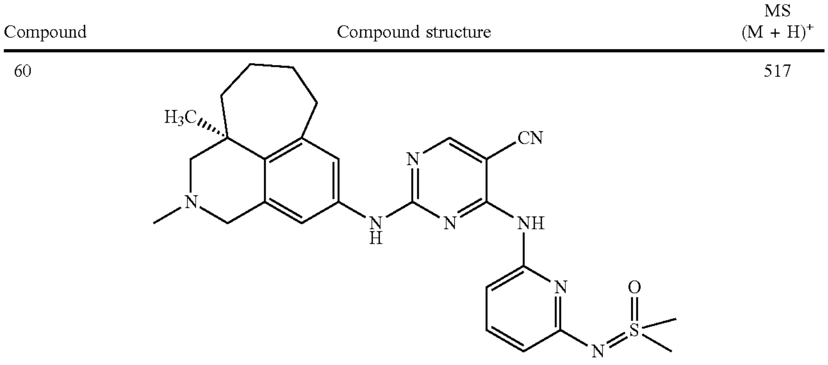 | 517 |
| 61 | 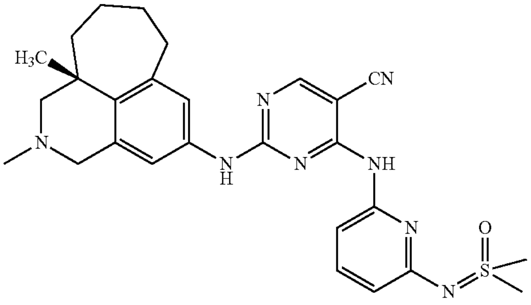 | 517 |
| 62 | 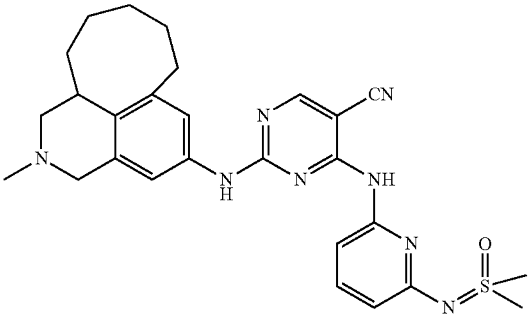 | 517 |
| 63 | 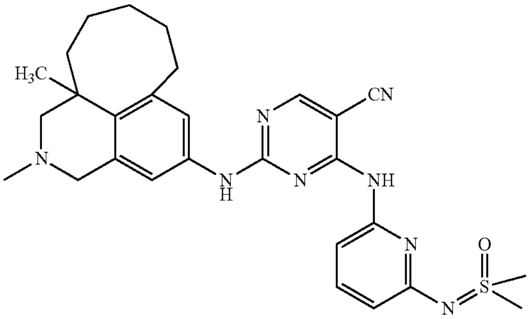 | 530 |
| 64 | 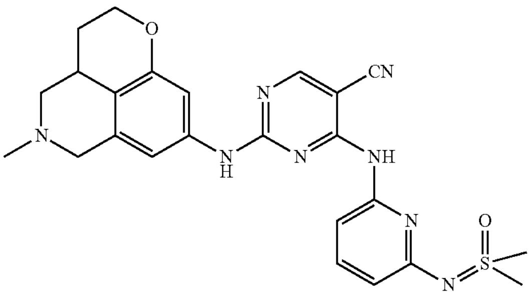 | 491 |

TABLE 1-continued
| Compound | Compound structure | MS (M + H)+ |
|---|---|---|
| 65 | 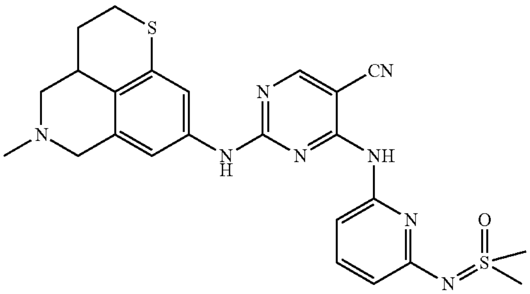 | 507 |
| 66 | 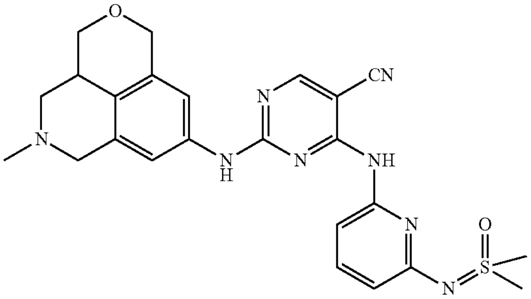 | 491 |
| 67 | 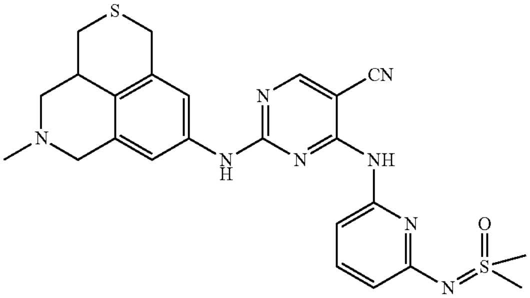 | 507 |
| 68 | 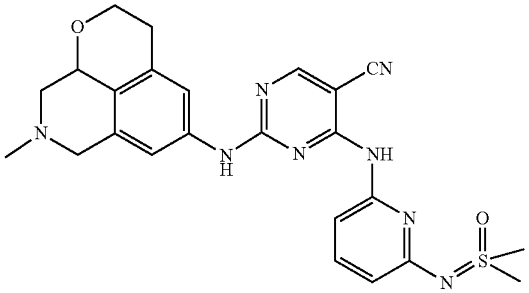 | 491 |
| 69 | 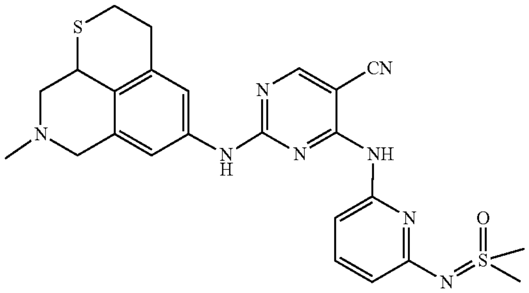 | 507 |

TABLE 1-continued
| Compound | Compound structure | MS (M + H)+ |
|---|---|---|
| 70 | 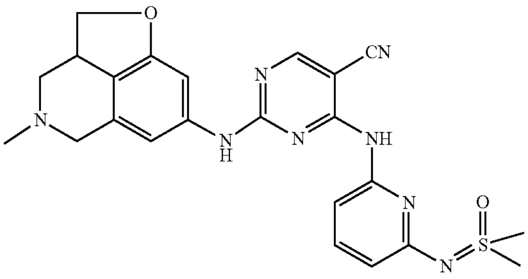 | 477 |
| 71 | 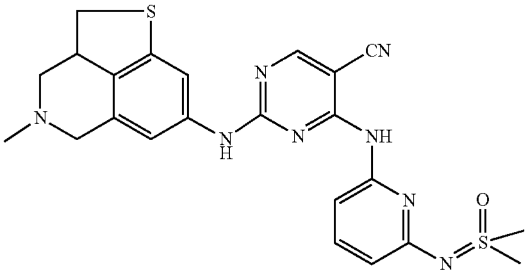 | 493 |
| 72 | 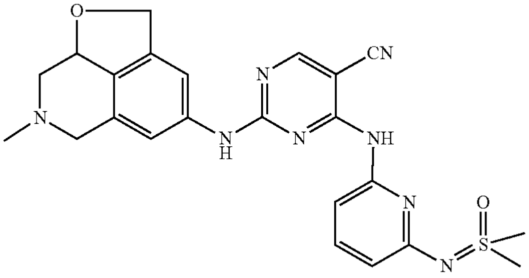 | 477 |
| 73 | 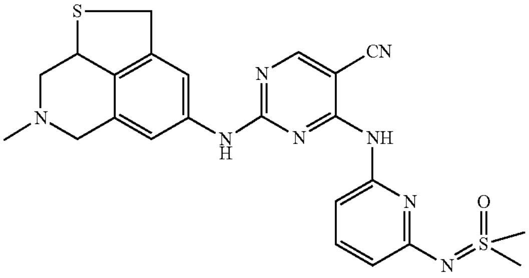 | 493 |
| 74 | 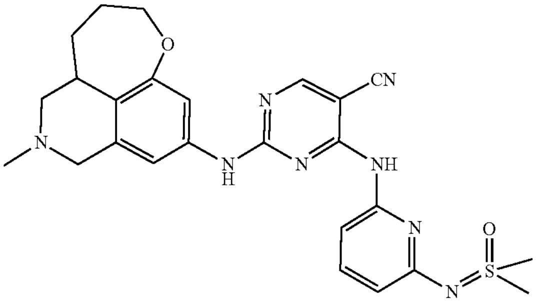 | 505 |

TABLE 1-continued
| Compound | Compound structure | MS (M + H)+ |
|---|---|---|
| 75 | 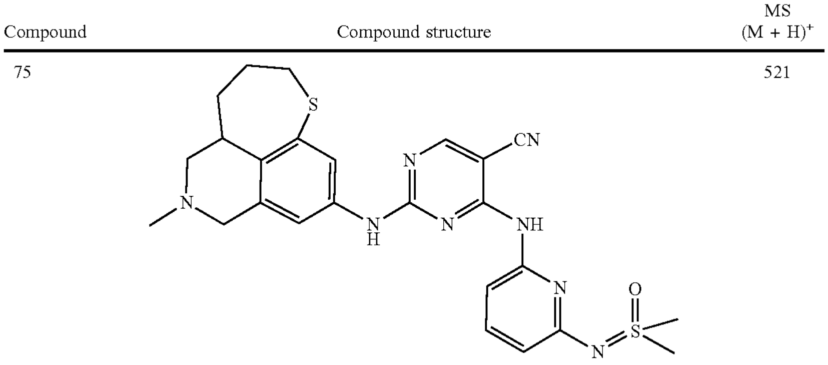 | 521 |
| 76 | 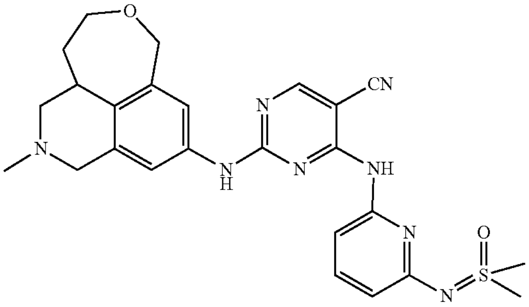 | 505 |
| 77 | 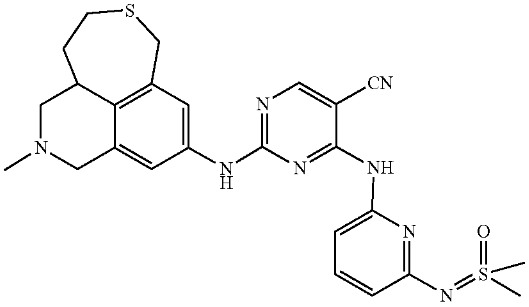 | 521 |
| 78 | 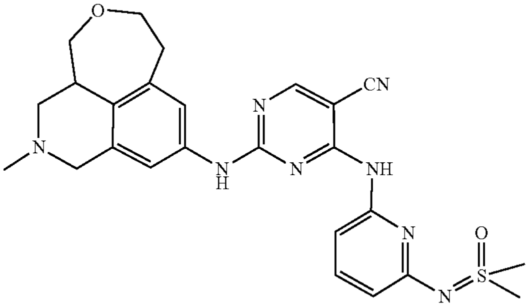 | 505 |
| 79 | 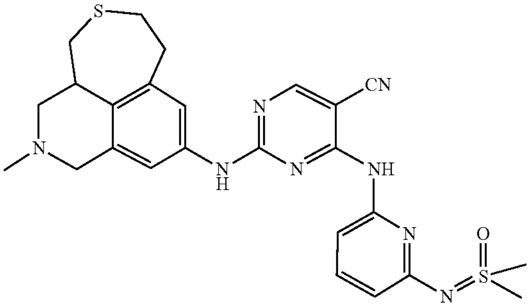 | 521 |

TABLE 1-continued
| Compound | Compound structure | MS (M + H)$^+$ |
|---|---|---|
| 80 | 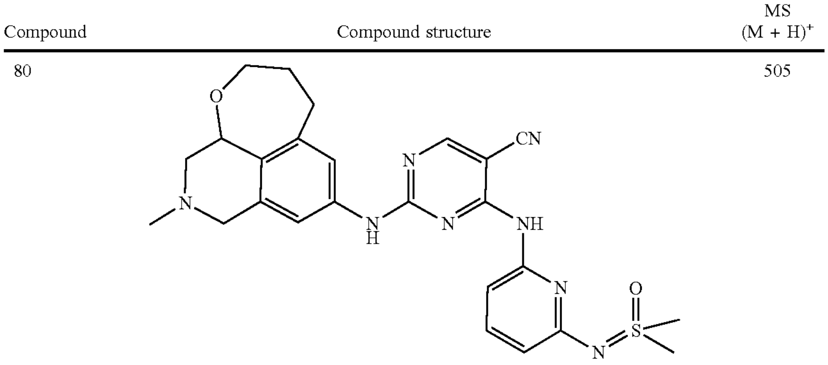 | 505 |
| 81 | 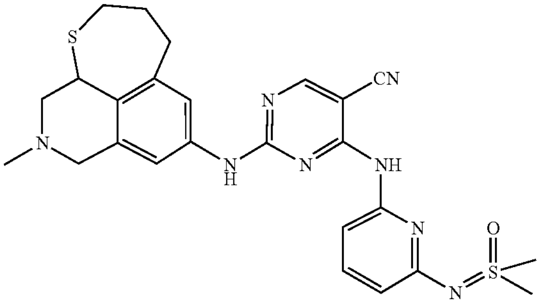 | 521 |
| 82 | 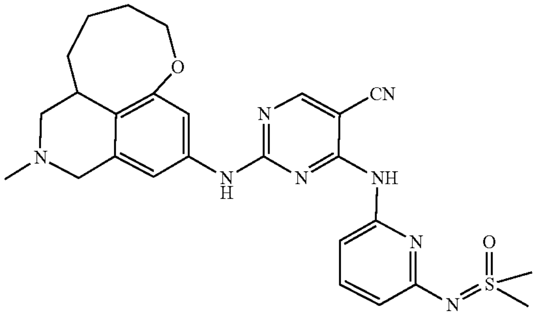 | 519 |
| 83 | 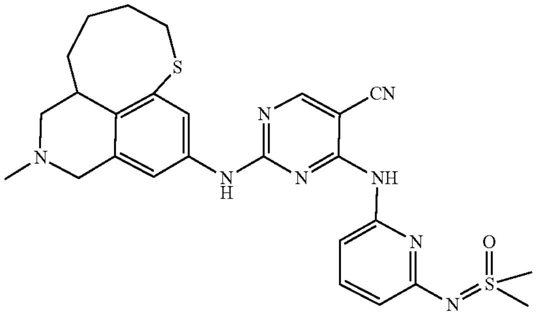 | 535 |
| 84 | 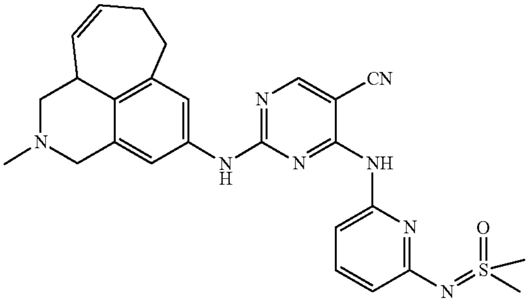 | 501 |

TABLE 1-continued
| Compound | Compound structure | MS (M + H)+ |
| --- | --- | --- |
| 85 | 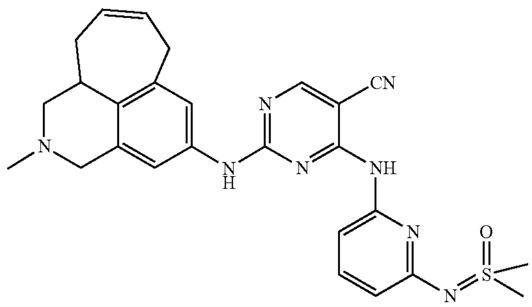 | 501 |
| 86 | 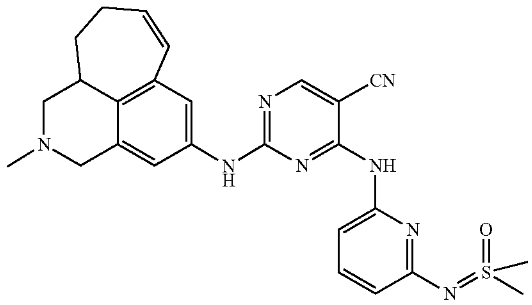 | 501 |
| 87 | 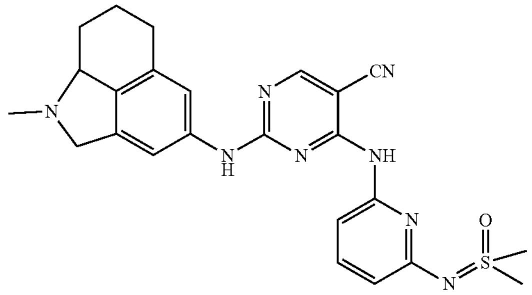 | 475 |
| 88 | 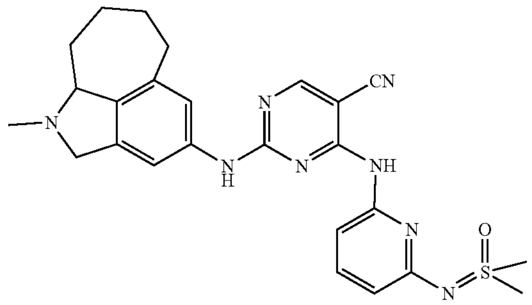 | 489 |
| 89 | 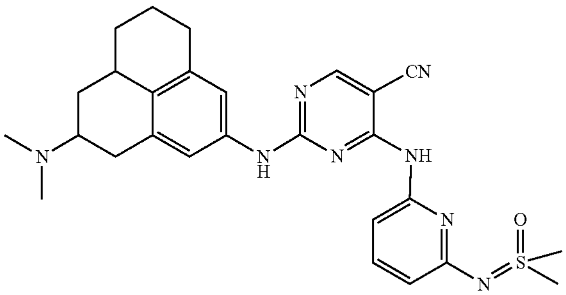 | 517 |

TABLE 1-continued
| Compound | Compound structure | MS (M + H)$^+$ |
|---|---|---|
| 90 | 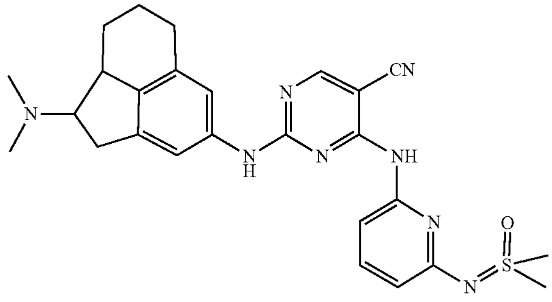 | 503 |
| 91 | 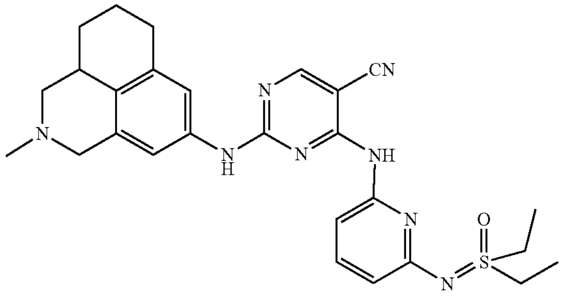 [SMILES: CCS(=O)(CC)=Nc1cccc(Nc2nc(Nc3cc4c5c(c3)CN(C)CC5CCC4)ncc2C#N)n1] | 517 |
| 92 | 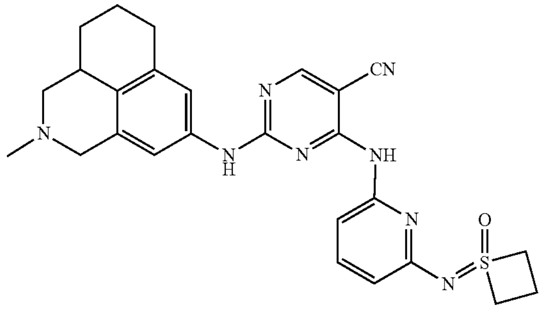 [SMILES: CN1Cc2cc(Nc3ncc(C#N)c(Nc4cccc(N=S5(=O)CCC5)n4)n3)cc3c2C(CCC3)C1] | 501 |
| 93 | 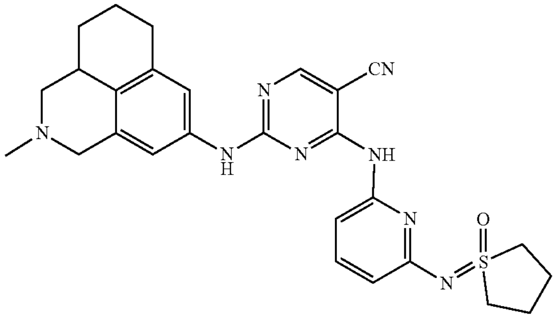 [SMILES: CN1Cc2cc(Nc3ncc(C#N)c(Nc4cccc(N=S5(=O)CCCC5)n4)n3)cc3c2C(CCC3)C1] | 515 |
| 94 | 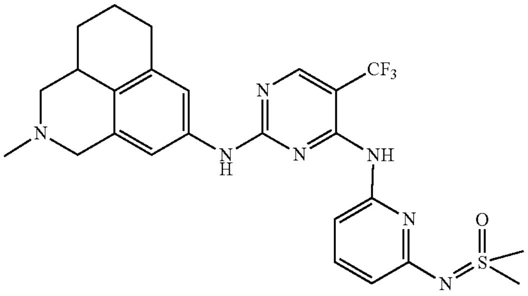 | 532 |

TABLE 1-continued
| Compound | Compound structure | MS $(M + H)^+$ |
| --- | --- | --- |
| 96 | 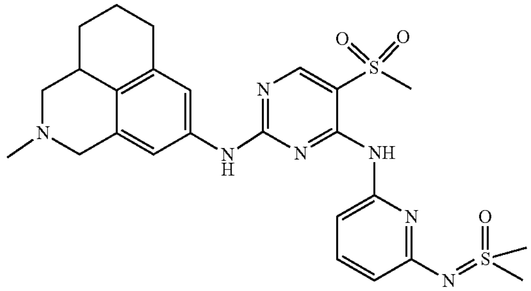 | 540 |
| 97 | 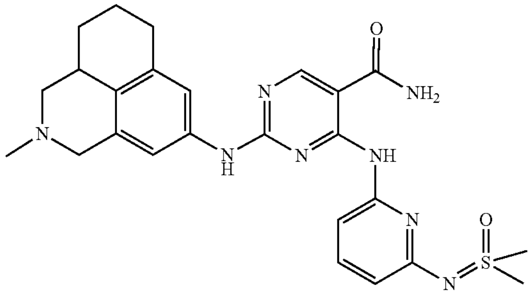 | 542 |
| 98 | 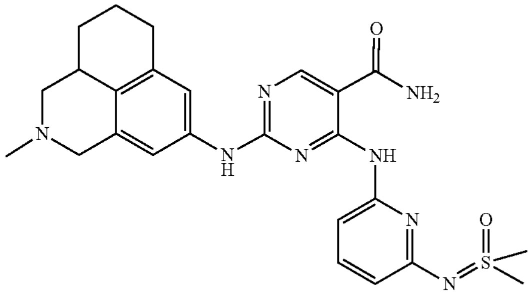 | 507 |
| 99 | 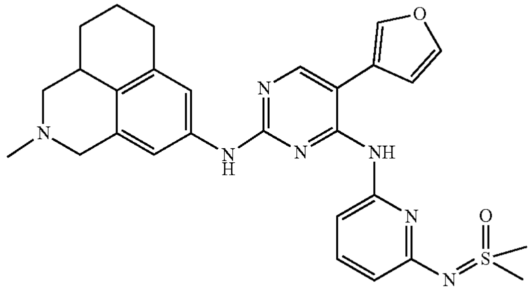 | 530 |
| 100 | 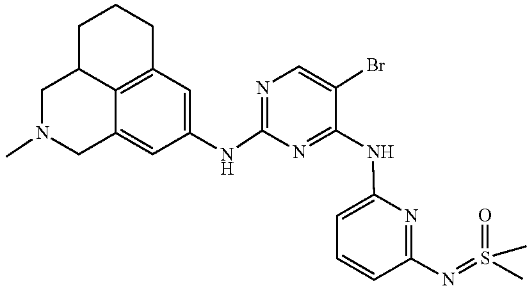 | 542 |

TABLE 1-continued
| Compound | Compound structure | MS (M + H)+ |
|---|---|---|
| 101 | 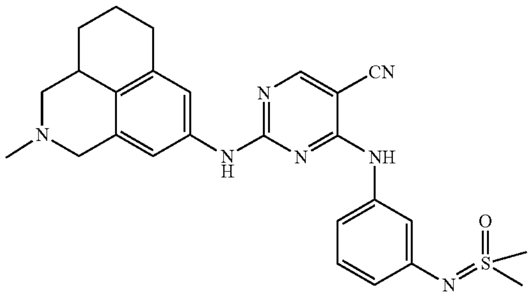 | 488 |
| 102 | 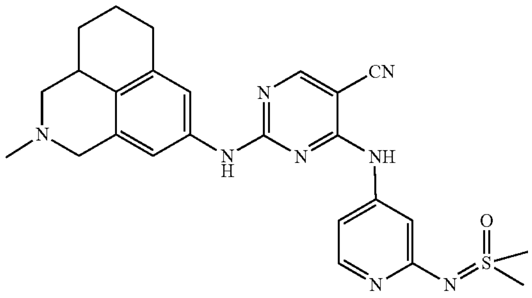 | 489 |
| 103 | 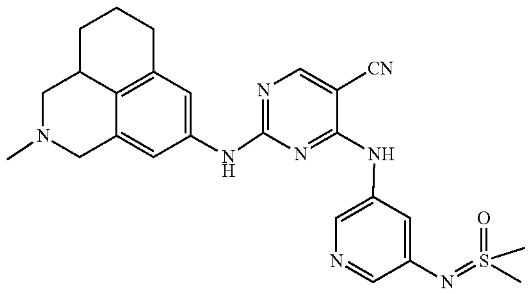 | 489 |
| 104 | 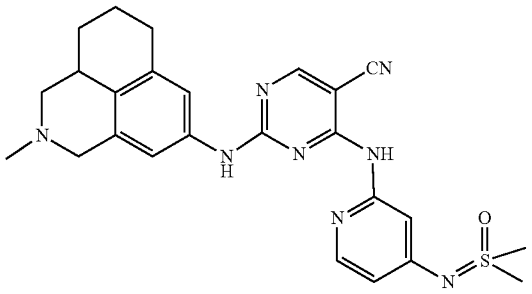 | 489 |
| 105 | 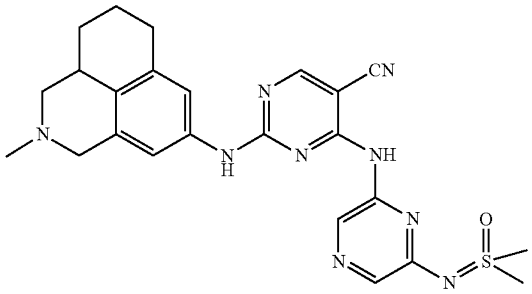 | 490 |

TABLE 1-continued
| Compound | Compound structure | MS (M + H)$^+$ |
|---|---|---|
| 106 | 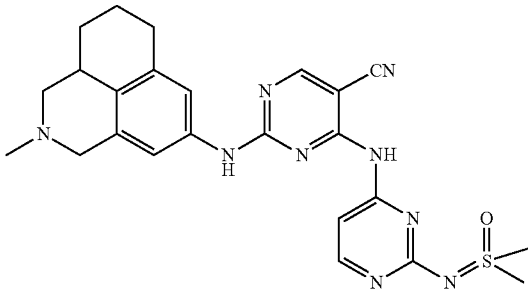 | 490 |
| 107 | 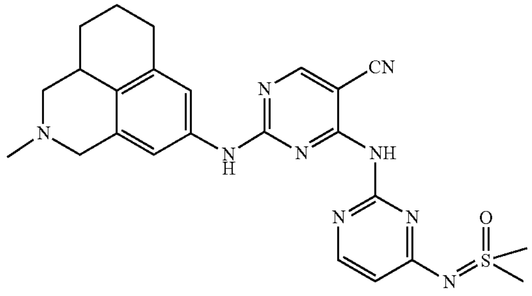 | 490 |
| 108 | 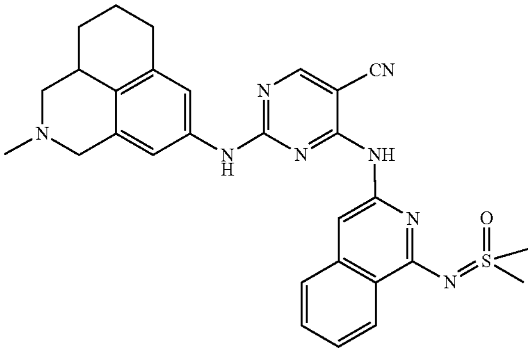 | 539 |
| 109 | 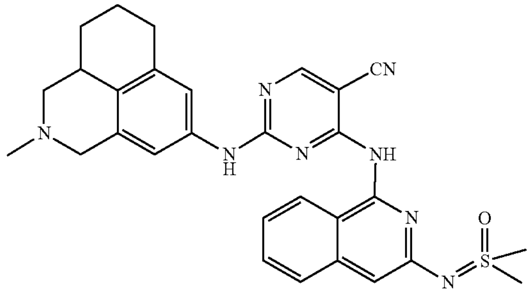 | 539 |
| 110 | 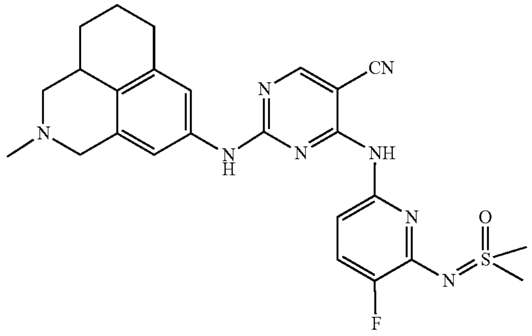 | 507 |

TABLE 1-continued
| Compound | Compound structure | MS $(M + H)^+$ |
|---|---|---|
| 111 | 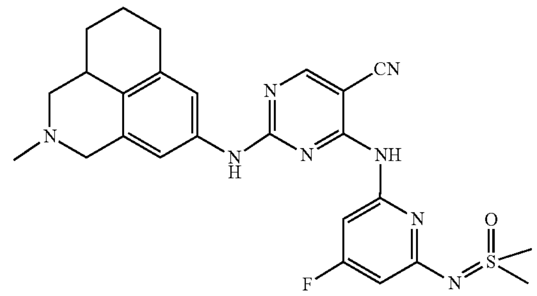 | 507 |
| 112 | 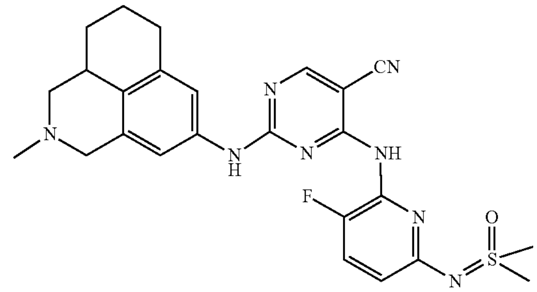 | 507 |
| 113 | 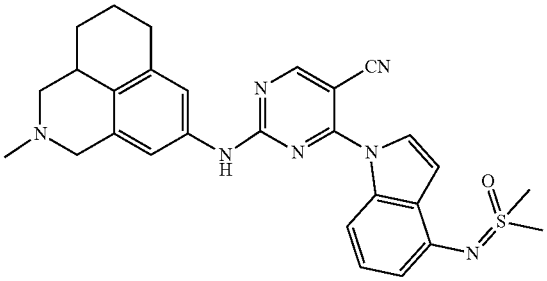 | 512 |
| 114 | 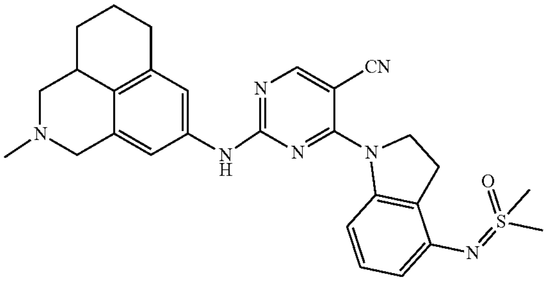 | 514 |
| 115 | 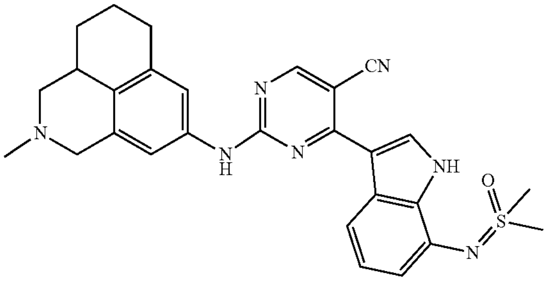 | 512 |

TABLE 1-continued
| Compound | Compound structure | MS (M + H)$^+$ |
|---|---|---|
| 116 | 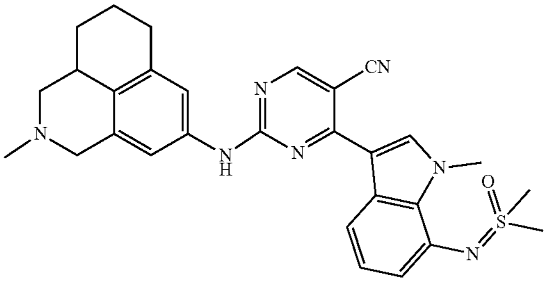 | 526 |
| 117 | 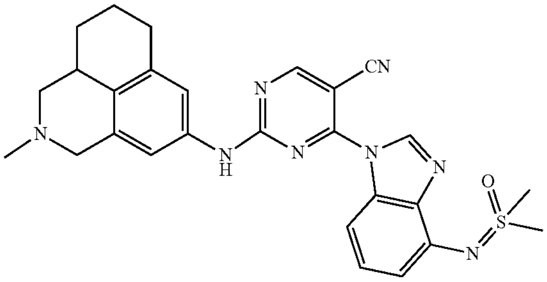 | 513 |
| 118 | 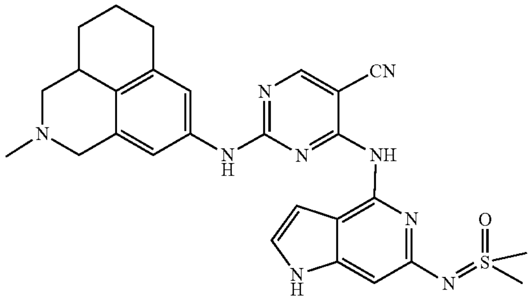 | 528 |
| 119 | 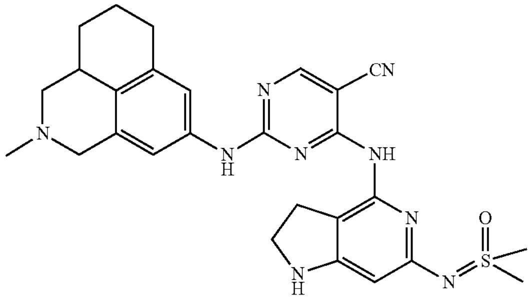 | 530 |
| 120 | 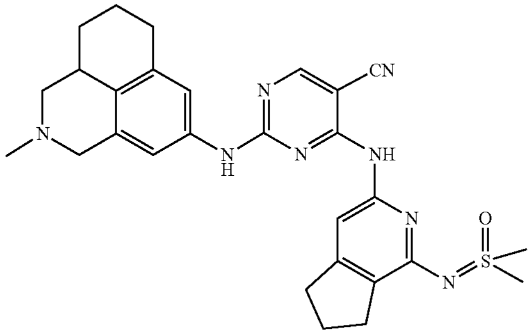 | 529 |

TABLE 1-continued
| Compound | Compound structure | MS (M + H)$^+$ |
|---|---|---|
| 121 | 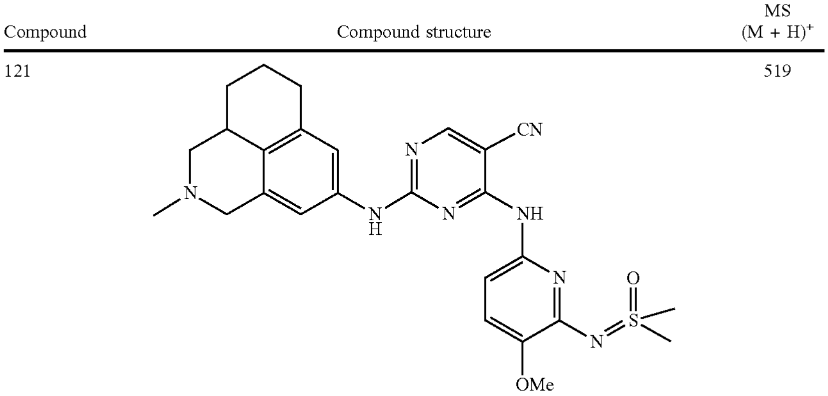 | 519 |
| 122 | 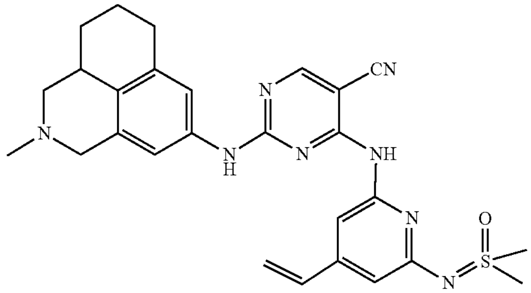 | 515 |
| 123 | 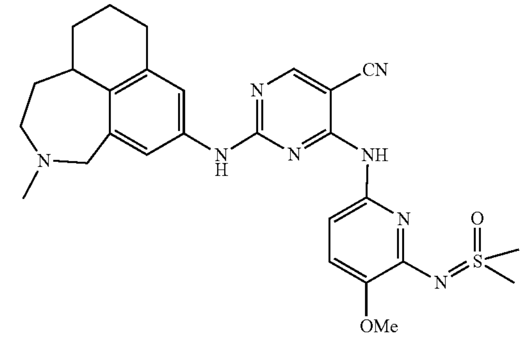 [SMILES: COc1ccc(Nc2nc(Nc3cc4c5c(c3)CN(C)CCC5CCC4)ncc2C#N)nc1N=S(C)(C)=O] | 533 |
| 124 | 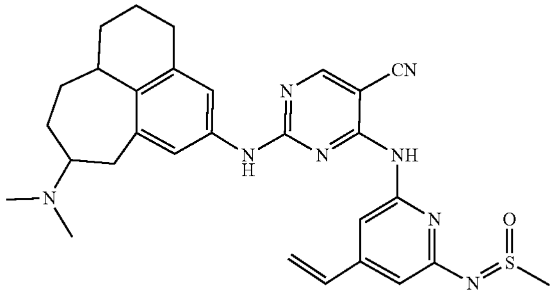 | 557 |
| 125 | 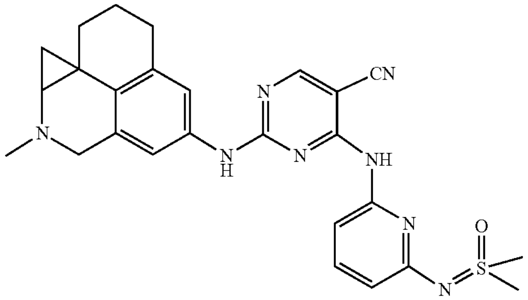 | 501 |

TABLE 1-continued
| Compound | Compound structure | MS (M + H)+ |
|---|---|---|
| 126 | 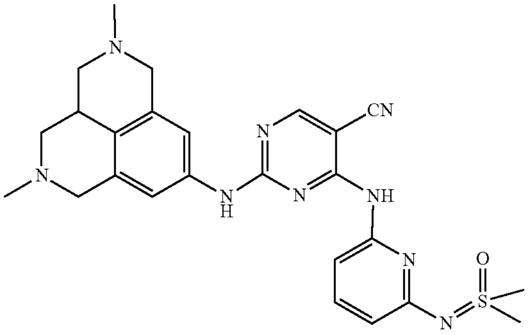 | 504 |
| 127 | 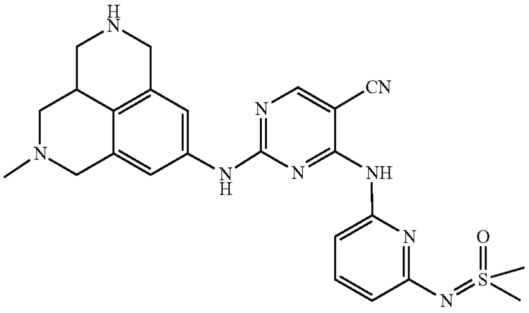 | 490 |
| 128 | 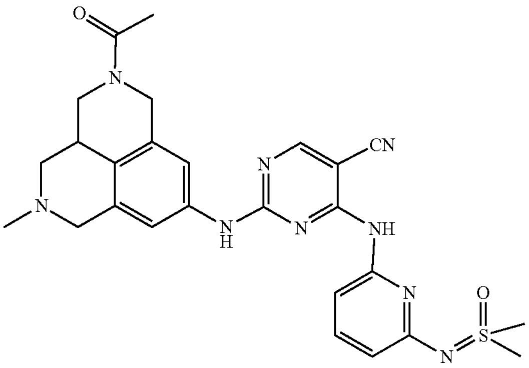 | 532 |
| 129 | 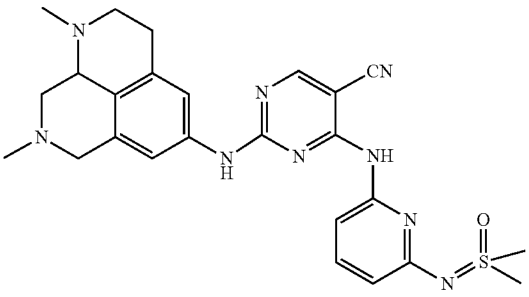 | 504 |

TABLE 1-continued
| Compound | Compound structure | MS $(M + H)^+$ |
| --- | --- | --- |
| 130 | 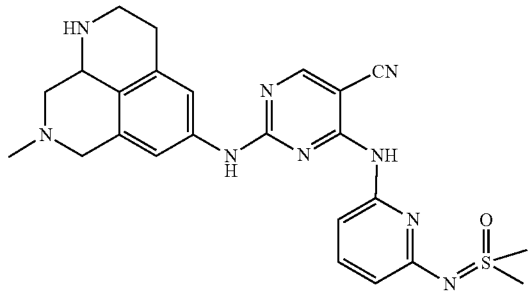 | 490 |
| 131 | 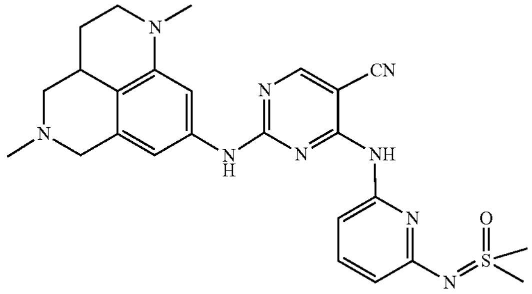 | 504 |
| 132 | 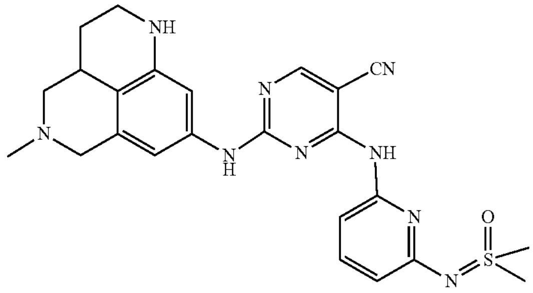 | 490 |
| 133 | 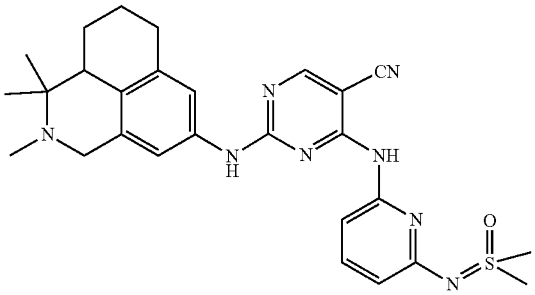 | 517 |
| 134 | 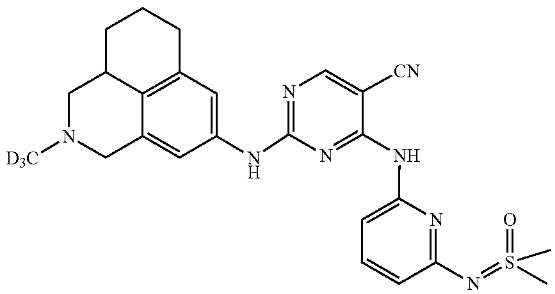 [SMILES: [2H]C([2H])([2H])N1Cc2cc(Nc3ncc(C#N)c(Nc4cccc(N=S(C)(C)=O)n4)n3)cc3c2C(CCC3)C1] | 492 |

TABLE 1-continued
| Compound | Compound structure | MS (M + H)$^+$ |
|---|---|---|
| 135 | 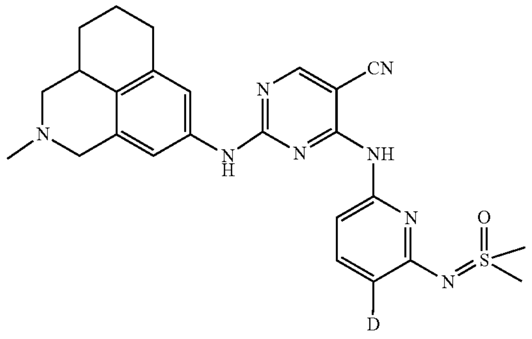 | 490 |
| 136 | 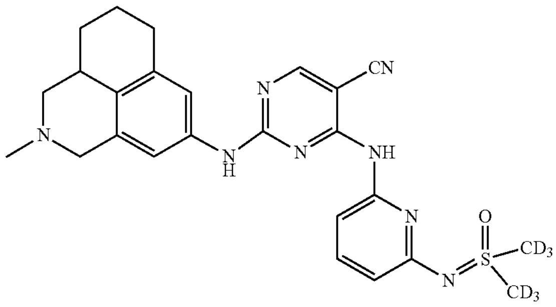 [SMILES: [2H]C([2H])([2H])S(=O)(=Nc1cccc(Nc2nc(Nc3cc4c5c(c3)CN(C)CC5CCC4)ncc2C#N)n1)C([2H])([2H])[2H]] | 495 |
| 140 | 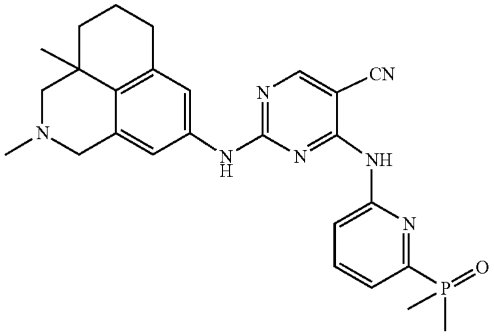 [SMILES: CN1Cc2cc(Nc3ncc(C#N)c(Nc4cccc(P(C)(C)=O)n4)n3)cc3c2C(C)(CCC3)C1] | 488 |
| 141 | 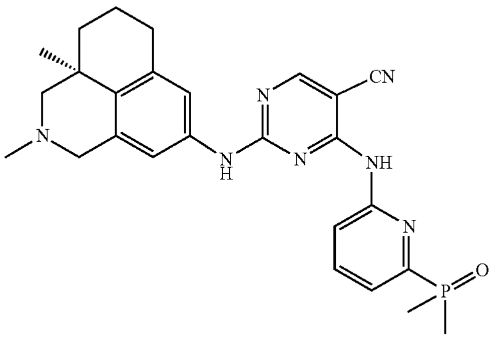 | 488 |

TABLE 1-continued
| Compound | Compound structure | MS (M + H)+ |
| --- | --- | --- |
| 142 | 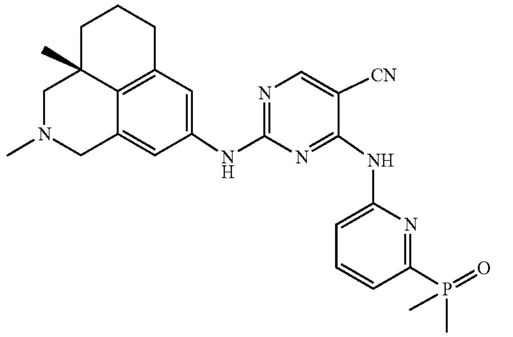 [SMILES: CN1Cc2cc(Nc3ncc(C#N)c(Nc4cccc(P(C)(C)=O)n4)n3)cc3c2[C@@](C)(CCC3)C1] | 488 |
| 143 | 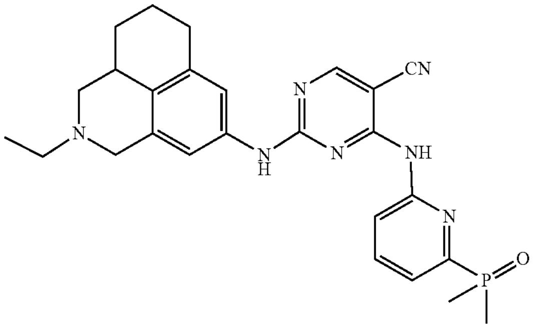 [SMILES: CCN1Cc2cc(Nc3ncc(C#N)c(Nc4cccc(P(C)(C)=O)n4)n3)cc3c2C(CCC3)C1] | 488 |
| 144 | 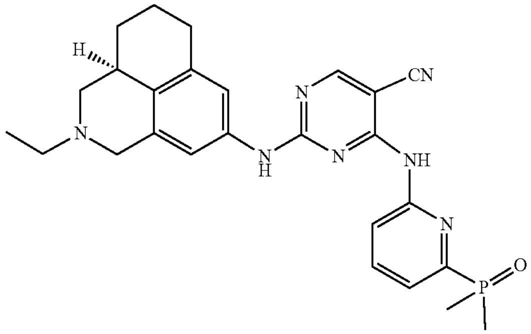 [SMILES: CCN1Cc2cc(Nc3ncc(C#N)c(Nc4cccc(P(C)(C)=O)n4)n3)cc3c2[C@H](CCC3)C1] | 488 |
| 145 | 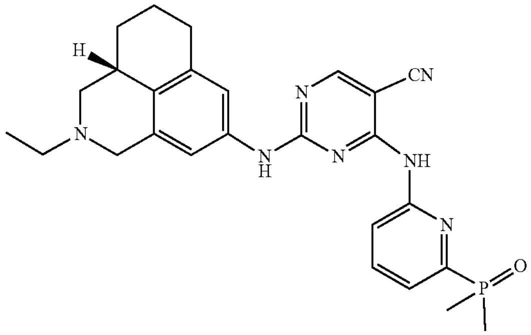 [SMILES: CCN1Cc2cc(Nc3ncc(C#N)c(Nc4cccc(P(C)(C)=O)n4)n3)cc3c2[C@@H](CCC3)C1] | 488 |

TABLE 1-continued
| Compound | Compound structure | MS (M + H)+ |
|---|---|---|
| 146 | 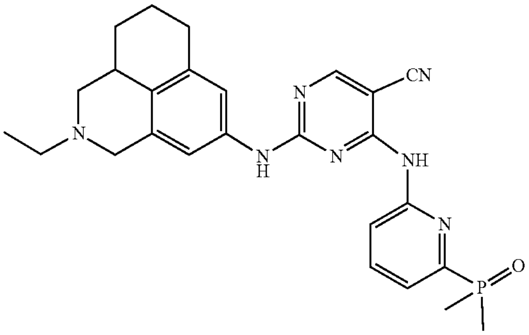 [SMILES: CCN1Cc2cc(Nc3ncc(C#N)c(Nc4cccc(P(C)(C)=O)n4)n3)cc3c2C(CCC3)C1] | 502 |
| 147 | 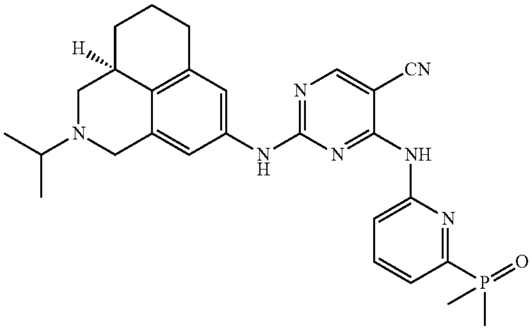 [SMILES: CC(C)N1Cc2cc(Nc3ncc(C#N)c(Nc4cccc(P(C)(C)=O)n4)n3)cc3c2[C@H](CCC3)C1] | 502 |
| 148 | 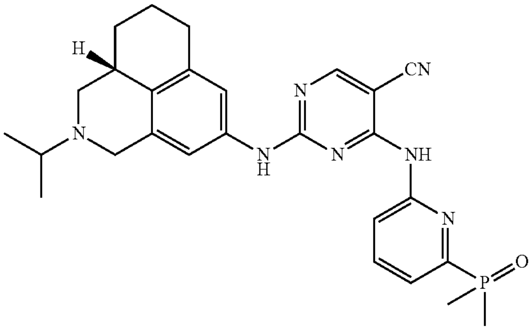 [SMILES: CC(C)N1Cc2cc(Nc3ncc(C#N)c(Nc4cccc(P(C)(C)=O)n4)n3)cc3c2[C@@H](CCC3)C1] | 502 |
| 149 | 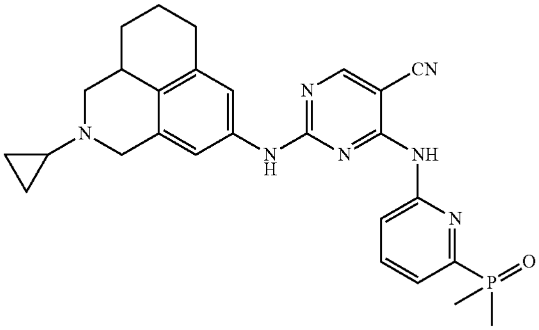 [SMILES: CP(C)(=O)c1cccc(Nc2nc(Nc3cc4c5c(c3)CN(C3CC3)CC5CCC4)ncc2C#N)n1] | 500 |

TABLE 1-continued
| Compound | Compound structure | MS (M + H)+ |
|---|---|---|
| 150 | 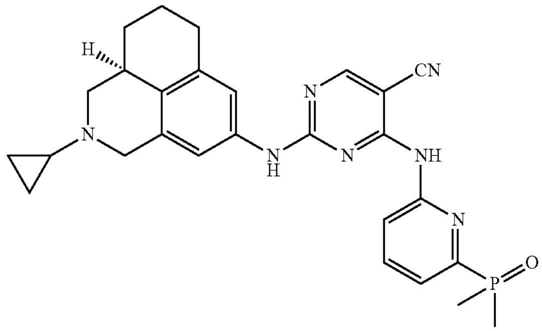 [SMILES: CP(C)(=O)c1cccc(Nc2nc(Nc3cc4c5c(c3)CN(C3CC3)C[C@H]5CCC4)ncc2C#N)n1] | 500 |
| 151 | 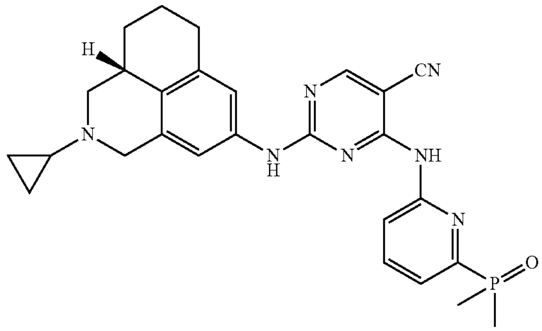 [SMILES: CP(C)(=O)c1cccc(Nc2nc(Nc3cc4c5c(c3)CN(C3CC3)C[C@@H]5CCC4)ncc2C#N)n1] | 500 |
| 152 | 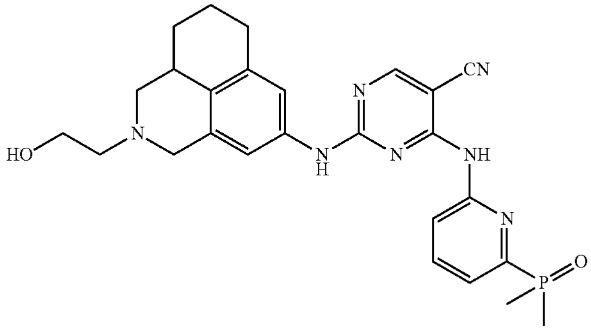 [SMILES: CP(C)(=O)c1cccc(Nc2nc(Nc3cc4c5c(c3)CN(CCO)CC5CCC4)ncc2C#N)n1] | 504 |
| 153 | 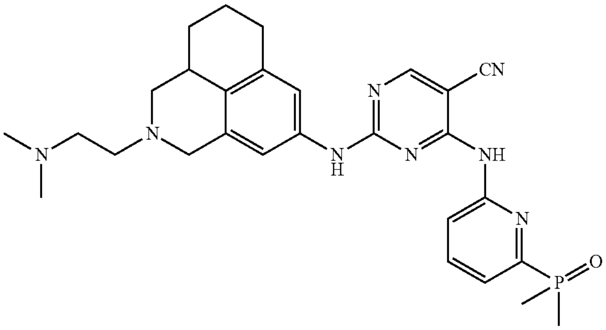 [SMILES: CN(C)CCN1Cc2cc(Nc3ncc(C#N)c(Nc4cccc(P(C)(C)=O)n4)n3)cc3c2C(CCC3)C1] | 531 |

TABLE 1-continued
| Compound | Compound structure | MS (M + H)$^+$ |
| --- | --- | --- |
| 154 | 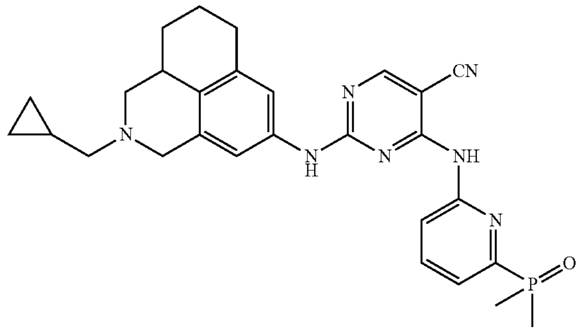 [SMILES: CP(C)(=O)c1cccc(Nc2nc(Nc3cc4c5c(c3)CN(CC3CC3)CC5CCC4)ncc2C#N)n1] | 514 |
| 155 | 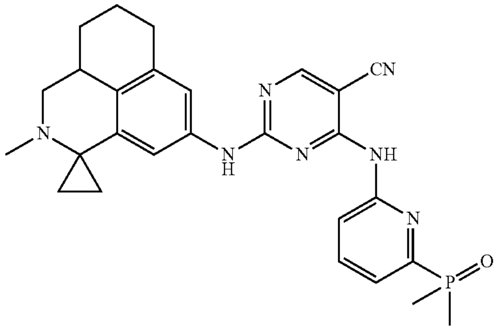 [SMILES: CN1CC2CCCc3cc(Nc4ncc(C#N)c(Nc5cccc(P(C)(C)=O)n5)n4)cc(c32)C12CC2] | 500 |
| 156 | 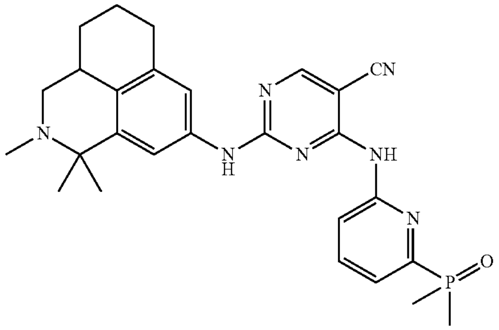 [SMILES: CN1CC2CCCc3cc(Nc4ncc(C#N)c(Nc5cccc(P(C)(C)=O)n5)n4)cc(c32)C1(C)C] | 502 |
| 157 | 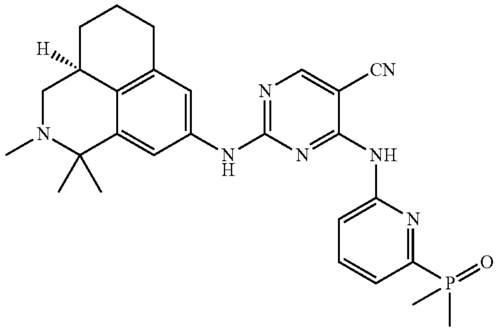 [SMILES: CN1C[C@H]2CCCc3cc(Nc4ncc(C#N)c(Nc5cccc(P(C)(C)=O)n5)n4)cc(c32)C1(C)C] | 502 |

TABLE 1-continued
| Compound | Compound structure | MS (M + H)$^+$ |
| --- | --- | --- |
| 158 | 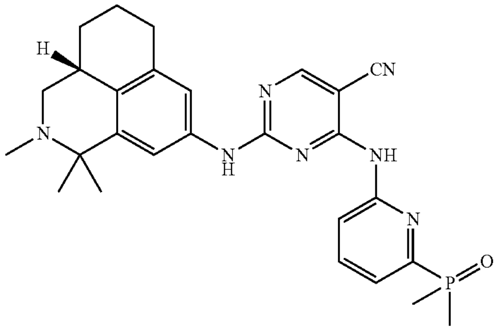 [SMILES: CN1C[C@@H]2CCCc3cc(Nc4ncc(C#N)c(Nc5cccc(P(C)(C)=O)n5)n4)cc(c32)C1(C)C] | 502 |
| 159 | 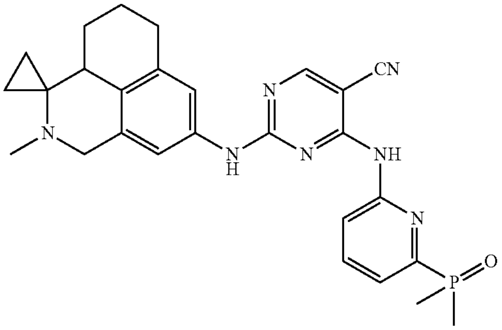 [SMILES: CN1Cc2cc(Nc3ncc(C#N)c(Nc4cccc(P(C)(C)=O)n4)n3)cc3c2C(CCC3)C12CC2] | 500 |
| 160 | 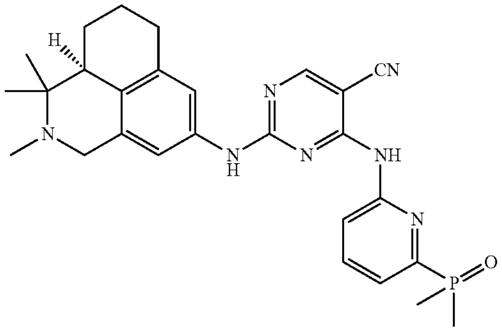 [SMILES: CN1Cc2cc(Nc3ncc(C#N)c(Nc4cccc(P(C)(C)=O)n4)n3)cc3c2[C@H](CCC3)C1(C)C] | 502 |
| 161 | 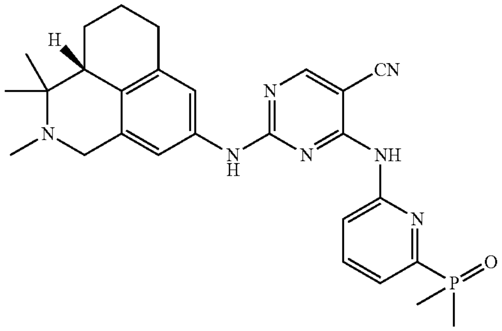 [SMILES: CN1Cc2cc(Nc3ncc(C#N)c(Nc4cccc(P(C)(C)=O)n4)n3)cc3c2[C@@H](CCC3)C1(C)C] | 502 |

TABLE 1-continued
| Compound | Compound structure | MS (M + H)$^+$ |
| --- | --- | --- |
| 162 | 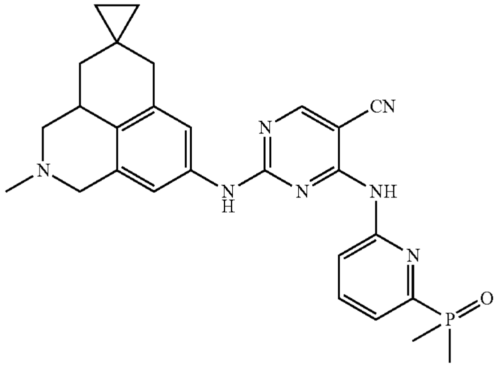 [SMILES: CN1Cc2cc(Nc3ncc(C#N)c(Nc4cccc(P(C)(C)=O)n4)n3)cc3c2C(C1)CC1(CC1)C3] | 500 |
| 163 | 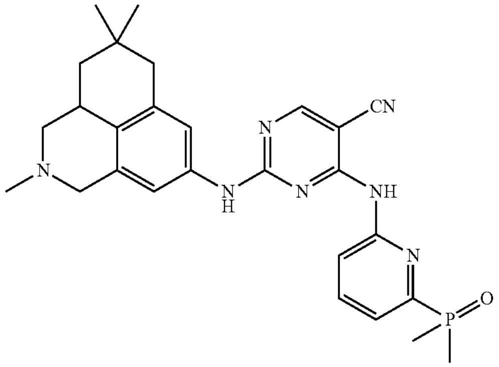 [SMILES: CN1Cc2cc(Nc3ncc(C#N)c(Nc4cccc(P(C)(C)=O)n4)n3)cc3c2C(C1)CC(C)(C)C3] | 502 |
| 164 | 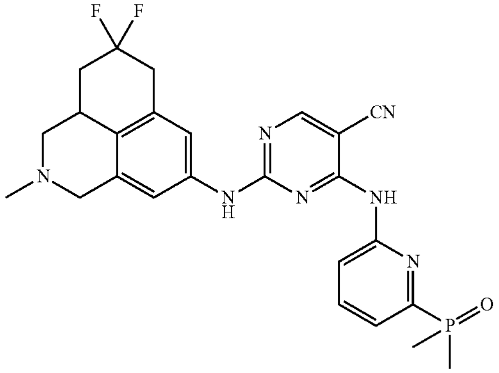 [SMILES: CN1Cc2cc(Nc3ncc(C#N)c(Nc4cccc(P(C)(C)=O)n4)n3)cc3c2C(C1)CC(F)(F)C3] | 510 |
| 165 | 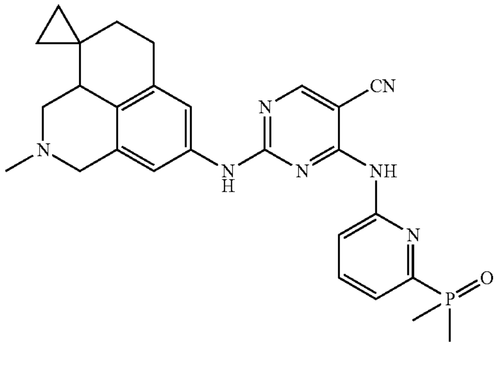 [SMILES: CN1Cc2cc(Nc3ncc(C#N)c(Nc4cccc(P(C)(C)=O)n4)n3)cc3c2C(C1)C1(CC3)CC1] | 500 |

TABLE 1-continued
| Compound | Compound structure | MS (M + H)$^+$ |
|---|---|---|
| 166 | 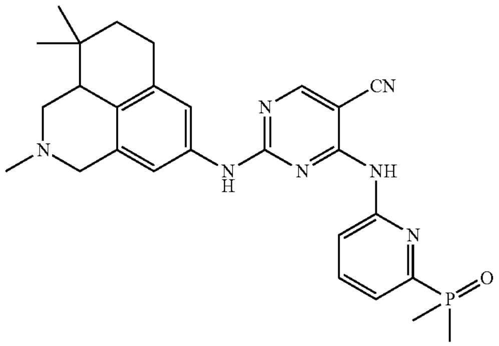 [SMILES: CN1Cc2cc(Nc3ncc(C#N)c(Nc4cccc(P(C)(C)=O)n4)n3)cc3c2C(C1)C(C)(C)CC3] | 502 |
| 167 | 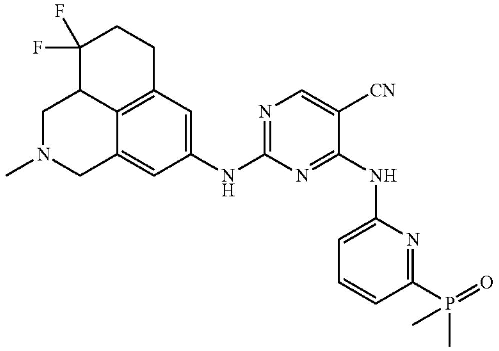 [SMILES: CN1Cc2cc(Nc3ncc(C#N)c(Nc4cccc(P(C)(C)=O)n4)n3)cc3c2C(C1)C(F)(F)CC3] | 510 |
| 168 | 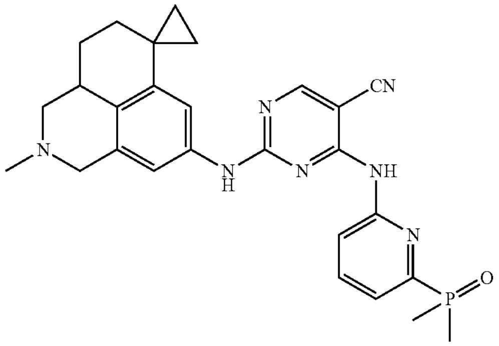 [SMILES: CN1Cc2cc(Nc3ncc(C#N)c(Nc4cccc(P(C)(C)=O)n4)n3)cc3c2C(CCC32CC2)C1] | 500 |
| 169 | 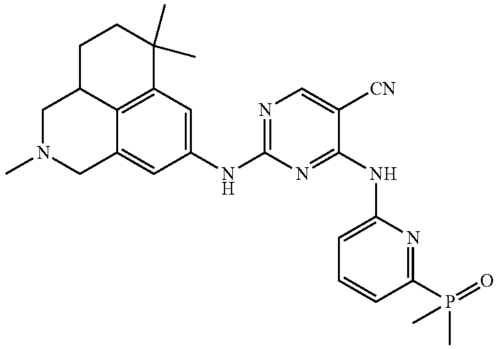 [SMILES: CN1Cc2cc(Nc3ncc(C#N)c(Nc4cccc(P(C)(C)=O)n4)n3)cc3c2C(CCC3(C)C)C1] | 502 |

TABLE 1-continued
| Compound | Compound structure | MS (M + H)+ |
|---|---|---|
| 170 | 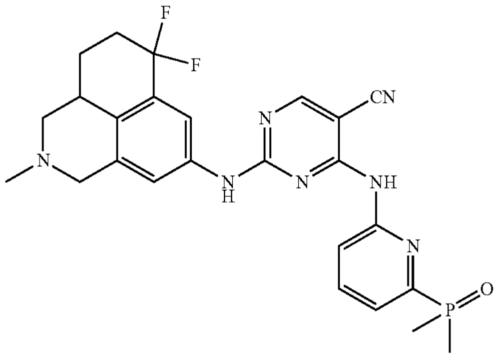 [SMILES: CN1Cc2cc(Nc3ncc(C#N)c(Nc4cccc(P(C)(C)=O)n4)n3)cc3c2C(CCC3(F)F)C1] | 510 |
| 171 | 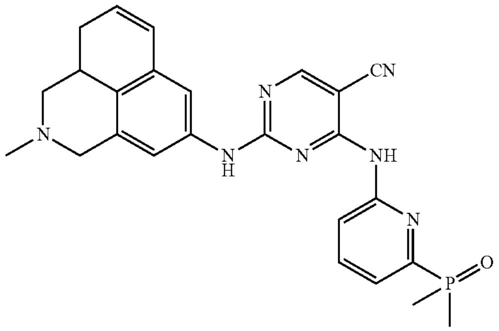 [SMILES: CN1Cc2cc(Nc3ncc(C#N)c(Nc4cccc(P(C)(C)=O)n4)n3)cc3c2C(CC=C3)C1] | 472 |
| 172 | 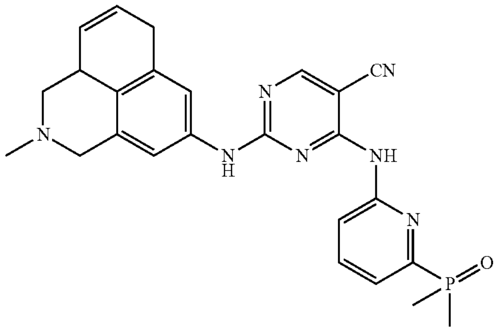 [SMILES: CN1Cc2cc(Nc3ncc(C#N)c(Nc4cccc(P(C)(C)=O)n4)n3)cc3c2C(C=CC3)C1] | 472 |
| 173 | 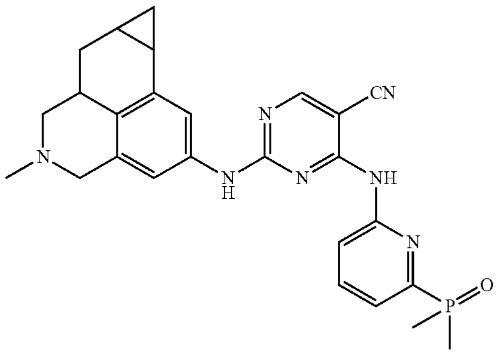 [SMILES: CN1Cc2cc(Nc3ncc(C#N)c(Nc4cccc(P(C)(C)=O)n4)n3)cc3c2C(CC2CC32)C1] | 486 |

TABLE 1-continued
| Compound | Compound structure | MS (M + H)+ |
|---|---|---|
| 174 | 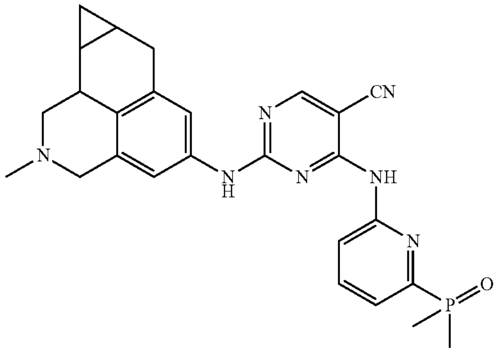 [SMILES: CN1Cc2cc(Nc3ncc(C#N)c(Nc4cccc(P(C)(C)=O)n4)n3)cc3c2C(C1)C1CC1C3] | 486 |
| 175 | 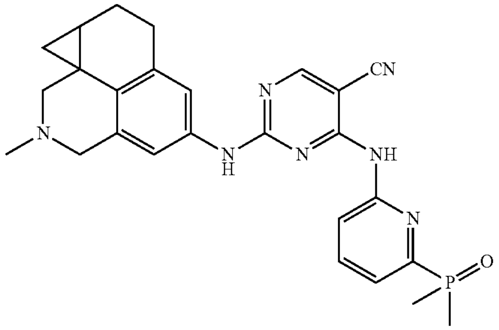 [SMILES: CN1Cc2cc(Nc3ncc(C#N)c(Nc4cccc(P(C)(C)=O)n4)n3)cc3c2C2(CC2CC3)C1] | 486 |
| 176 | 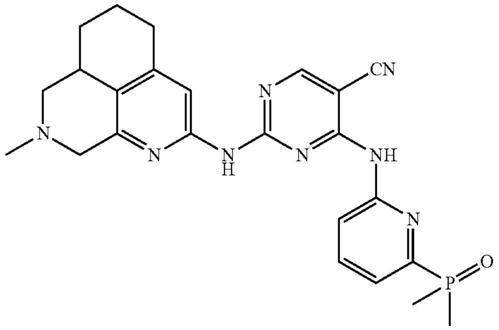 [SMILES: CN1Cc2nc(Nc3ncc(C#N)c(Nc4cccc(P(C)(C)=O)n4)n3)cc3c2C(CCC3)C1] | 475 |
| 177 | 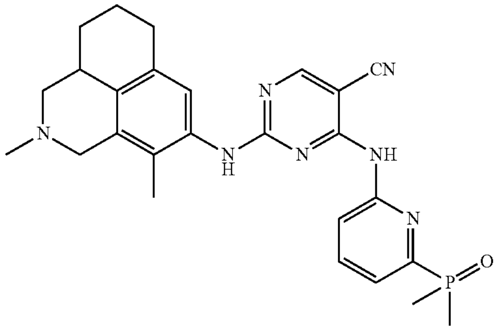 [SMILES: Cc1c(Nc2ncc(C#N)c(Nc3cccc(P(C)(C)=O)n3)n2)cc2c3c1CN(C)CC3CCC2] | 488 |

TABLE 1-continued
| Compound | Compound structure | MS (M + H)$^+$ |
|---|---|---|
| 178 | 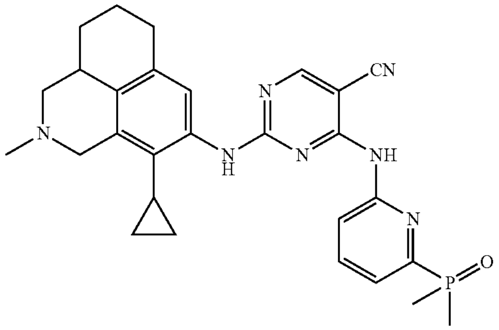 [SMILES: CN1Cc2c3c(cc(Nc4ncc(C#N)c(Nc5cccc(P(C)(C)=O)n5)n4)c2C2CC2)CCCC3C1] | 514 |
| 179 | 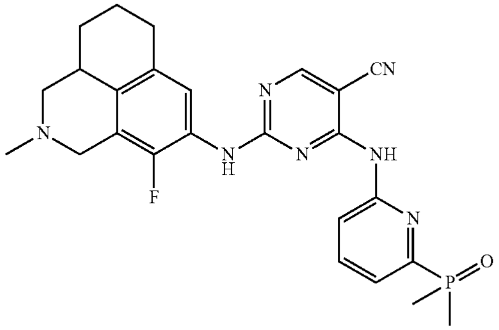 [SMILES: CN1Cc2c(F)c(Nc3ncc(C#N)c(Nc4cccc(P(C)(C)=O)n4)n3)cc3c2C(CCC3)C1] | 492 |
| 180 | 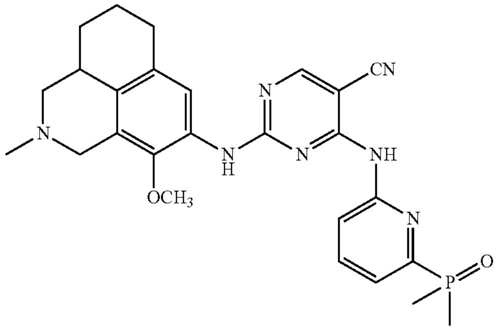 [SMILES: COc1c(Nc2ncc(C#N)c(Nc3cccc(P(C)(C)=O)n3)n2)cc2c3c1CN(C)CC3CCC2] | 504 |
| 181 | 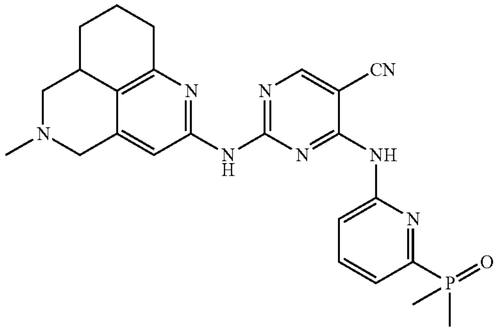 | 475 |

TABLE 1-continued
| Compound | Compound structure | MS $(M + H)^+$ |
|---|---|---|
| 182 | 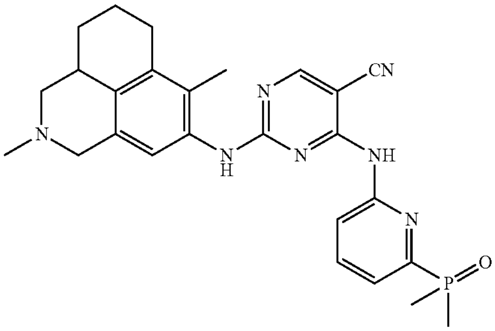 [SMILES: Cc1c(Nc2ncc(C#N)c(Nc3cccc(P(C)(C)=O)n3)n2)cc2c3c1CCCC3CN(C)C2] | 488 |
| 183 | 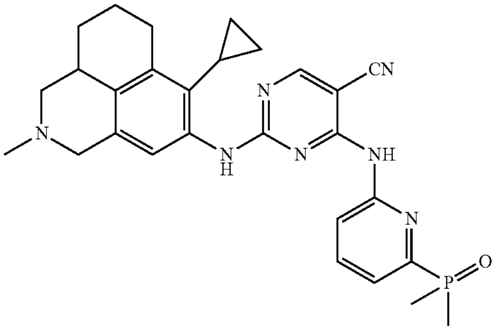 [SMILES: CN1Cc2cc(Nc3ncc(C#N)c(Nc4cccc(P(C)(C)=O)n4)n3)c(C3CC3)c3c2C(CCC3)C1] | 514 |
| 184 | 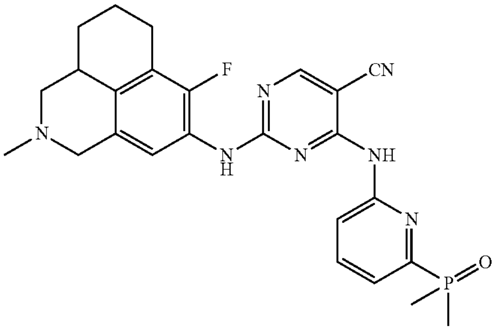 [SMILES: CN1Cc2cc(Nc3ncc(C#N)c(Nc4cccc(P(C)(C)=O)n4)n3)c(F)c3c2C(CCC3)C1] | 492 |
| 185 | 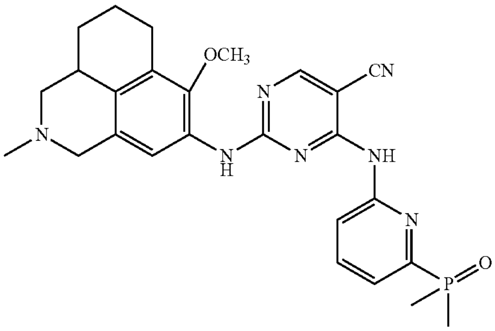 [SMILES: COc1c(Nc2ncc(C#N)c(Nc3cccc(P(C)(C)=O)n3)n2)cc2c3c1CCCC3CN(C)C2] | 504 |

TABLE 1-continued
| Compound | Compound structure | MS (M + H)+ |
| --- | --- | --- |
| 186 | 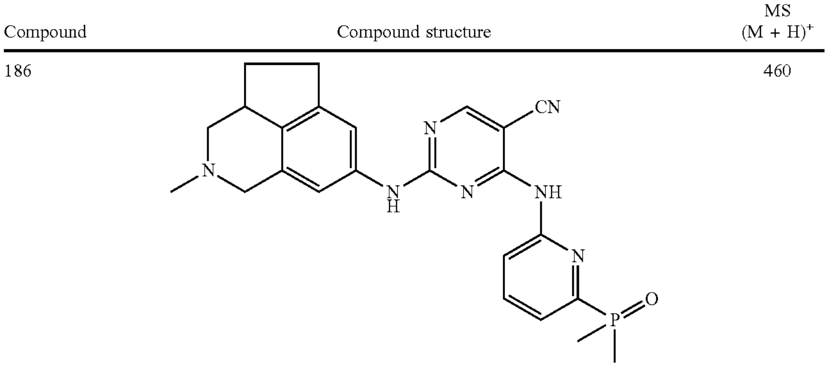 | 460 |
| 187 | 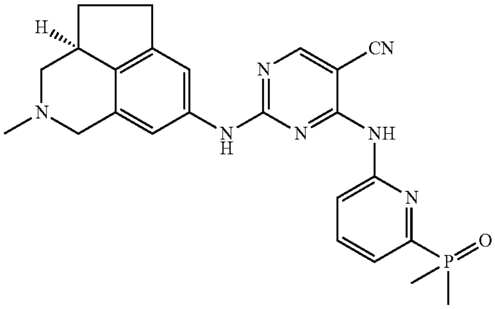 [SMILES: CN1Cc2cc(Nc3ncc(C#N)c(Nc4cccc(P(C)(C)=O)n4)n3)cc3c2[C@H](CC3)C1] | 460 |
| 188 | 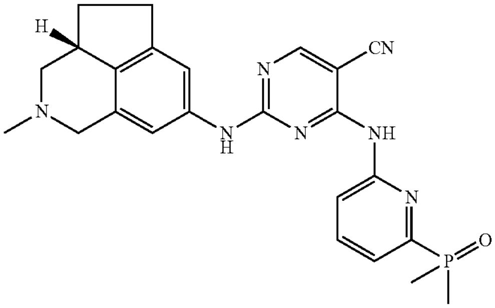 [SMILES: CN1Cc2cc(Nc3ncc(C#N)c(Nc4cccc(P(C)(C)=O)n4)n3)cc3c2[C@@H](CC3)C1] | 460 |
| 189 | 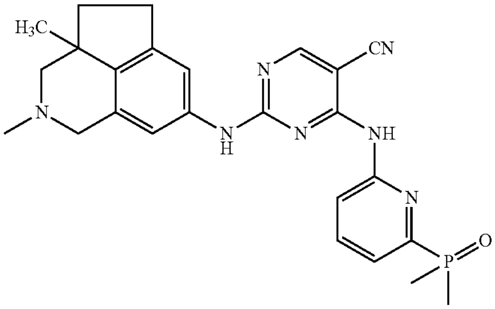 [SMILES: CN1Cc2cc(Nc3ncc(C#N)c(Nc4cccc(P(C)(C)=O)n4)n3)cc3c2C(C)(CC3)C1] | 474 |
| 190 | 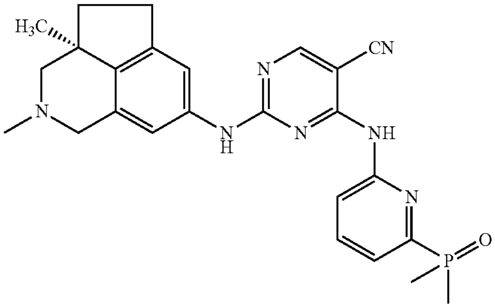 [SMILES: CN1Cc2cc(Nc3ncc(C#N)c(Nc4cccc(P(C)(C)=O)n4)n3)cc3c2[C@](C)(CC3)C1] | 474 |

TABLE 1-continued
| Compound | Compound structure | MS (M + H)+ |
|---|---|---|
| 191 | 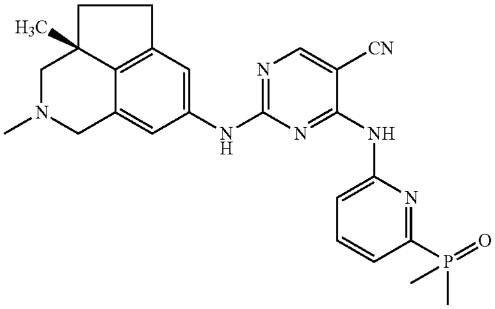 [SMILES: CN1Cc2cc(Nc3ncc(C#N)c(Nc4cccc(P(C)(C)=O)n4)n3)cc3c2[C@@](C)(CC3)C1] | 474 |
| 192 | 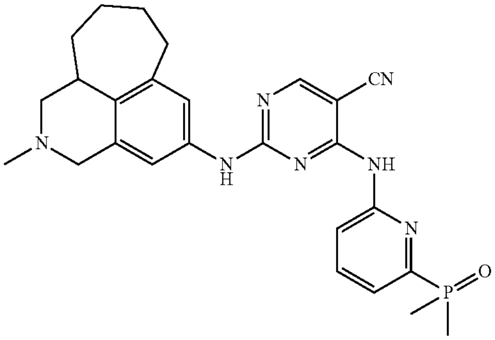 [SMILES: CN1Cc2cc(Nc3ncc(C#N)c(Nc4cccc(P(C)(C)=O)n4)n3)cc3c2C(CCCC3)C1] | 488 |
| 193 | 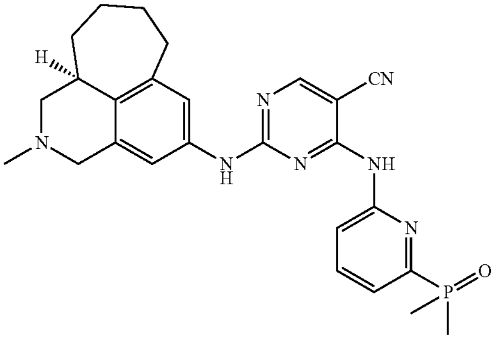 [SMILES: CN1Cc2cc(Nc3ncc(C#N)c(Nc4cccc(P(C)(C)=O)n4)n3)cc3c2[C@H](CCCC3)C1] | 488 |
| 194 | 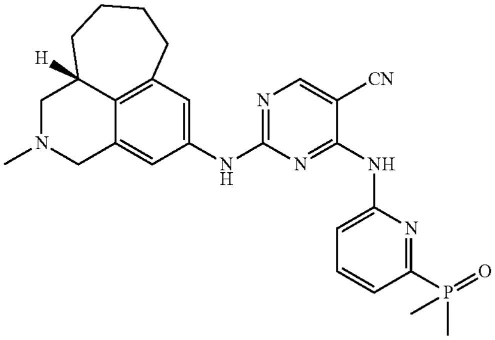 [SMILES: CN1Cc2cc(Nc3ncc(C#N)c(Nc4cccc(P(C)(C)=O)n4)n3)cc3c2[C@@H](CCCC3)C1] | 488 |

TABLE 1-continued
| Compound | Compound structure | MS (M + H)+ |
| --- | --- | --- |
| 195 | 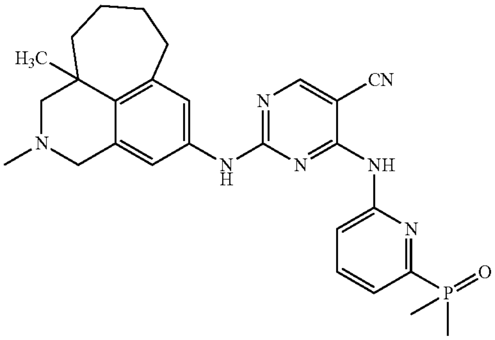 [SMILES: CN1Cc2cc(Nc3ncc(C#N)c(Nc4cccc(P(C)(C)=O)n4)n3)cc3c2C(C)(CCCC3)C1] | 502 |
| 196 | 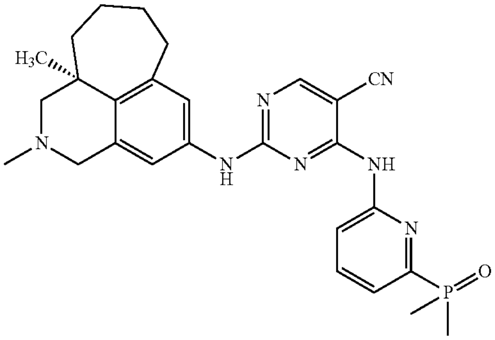 [SMILES: CN1Cc2cc(Nc3ncc(C#N)c(Nc4cccc(P(C)(C)=O)n4)n3)cc3c2[C@](C)(CCCC3)C1] | 502 |
| 197 | 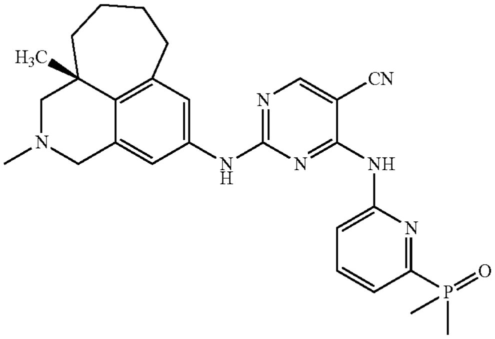 [SMILES: CN1Cc2cc(Nc3ncc(C#N)c(Nc4cccc(P(C)(C)=O)n4)n3)cc3c2[C@@](C)(CCCC3)C1] | 502 |
| 198 | 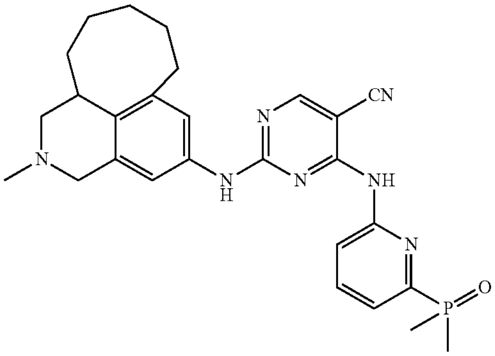 [SMILES: CN1Cc2cc(Nc3ncc(C#N)c(Nc4cccc(P(C)(C)=O)n4)n3)cc3c2C(CCCCC3)C1] | 502 |

TABLE 1-continued
| Compound | Compound structure | MS (M + H)+ |
|---|---|---|
| 199 | 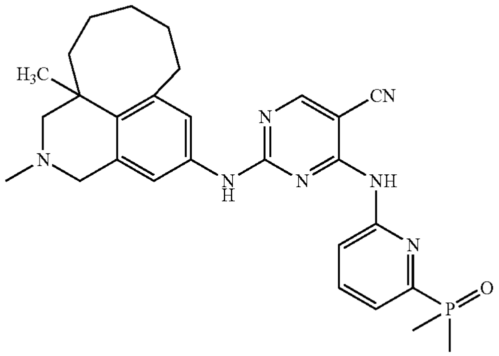 [SMILES: CN1Cc2cc(Nc3ncc(C#N)c(Nc4cccc(P(C)(C)=O)n4)n3)cc3c2C(C)(CCCCC3)C1] | 516 |
| 200 | 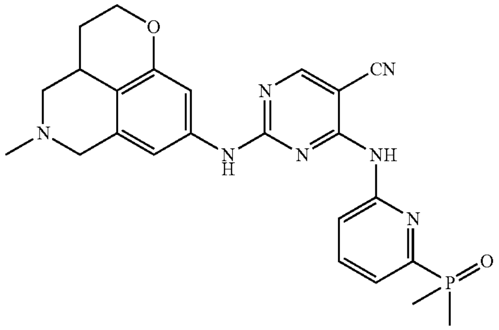 [SMILES: CN1Cc2cc(Nc3ncc(C#N)c(Nc4cccc(P(C)(C)=O)n4)n3)cc3c2C(CCS3)C1] | 476 |
| 201 | 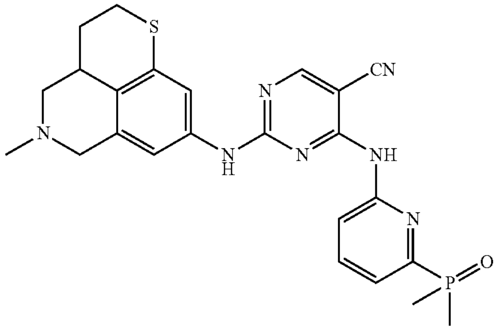 | 492 |
| 202 | 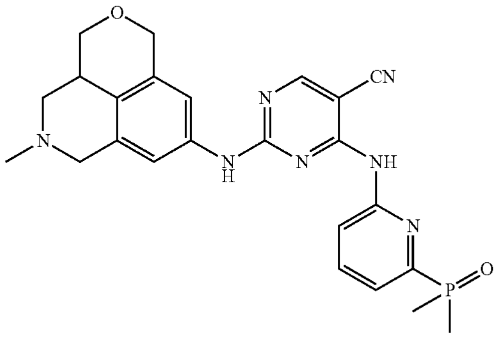 [SMILES: CN1Cc2cc(Nc3ncc(C#N)c(Nc4cccc(P(C)(C)=O)n4)n3)cc3c2C(COC3)C1] | 476 |

TABLE 1-continued
| Compound | Compound structure | MS (M + H)+ |
|---|---|---|
| 203 | 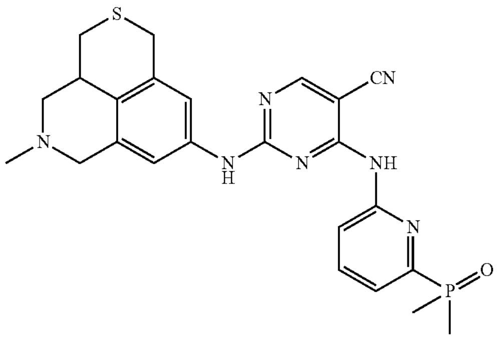 [SMILES: CN1Cc2cc(Nc3ncc(C#N)c(Nc4cccc(P(C)(C)=O)n4)n3)cc3c2C(CSC3)C1] | 492 |
| 204 | 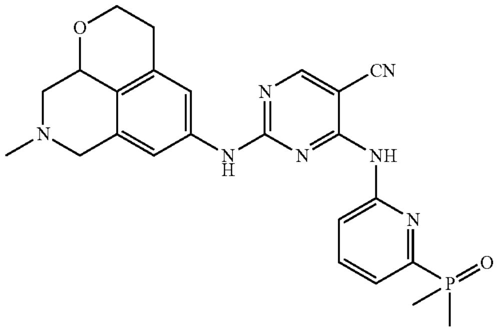 [SMILES: CN1Cc2cc(Nc3ncc(C#N)c(Nc4cccc(P(C)(C)=O)n4)n3)cc3c2C(C1)OCC3] | 476 |
| 205 | 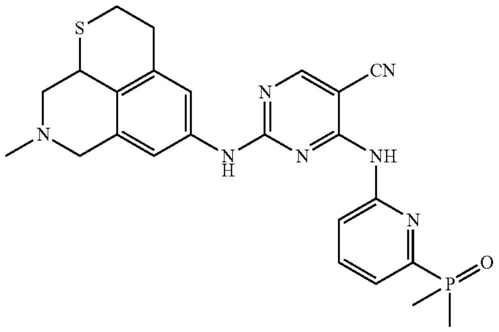 [SMILES: CN1Cc2cc(Nc3ncc(C#N)c(Nc4cccc(P(C)(C)=O)n4)n3)cc3c2C(C1)SCC3] | 492 |
| 206 | 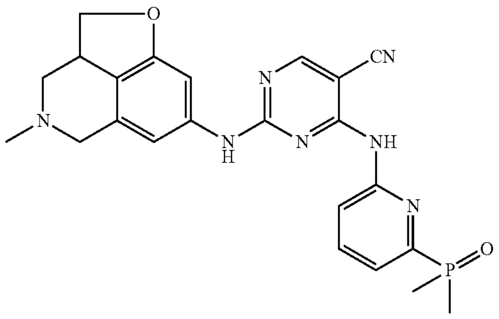 [SMILES: CN1Cc2cc(Nc3ncc(C#N)c(Nc4cccc(P(C)(C)=O)n4)n3)cc3c2C(CO3)C1] | 462 |

TABLE 1-continued
| Compound | Compound structure | MS (M + H)+ |
|---|---|---|
| 207 | 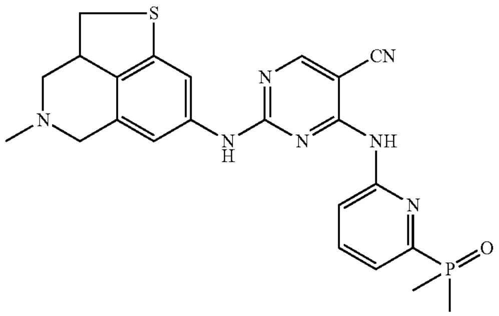 [SMILES: CN1Cc2cc(Nc3ncc(C#N)c(Nc4cccc(P(C)(C)=O)n4)n3)cc3c2C(CS3)C1] | 478 |
| 208 | 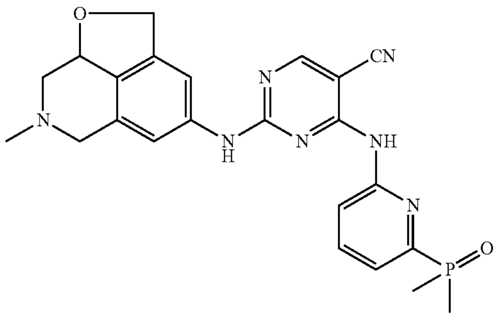 | 462 |
| 209 | 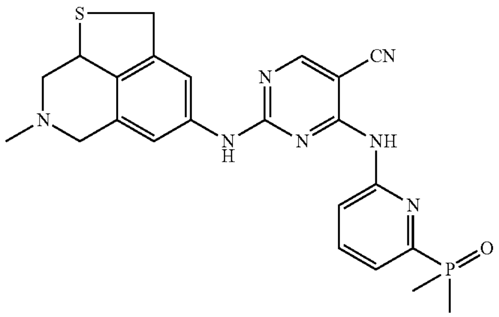 | 478 |
| 210 | 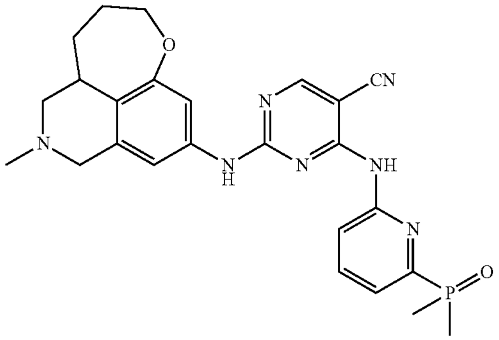 [SMILES: CN1Cc2cc(Nc3ncc(C#N)c(Nc4cccc(P(C)(C)=O)n4)n3)cc3c2C(CCCO3)C1] | 490 |

TABLE 1-continued
| Compound | Compound structure | MS (M + H)+ |
|---|---|---|
| 211 | 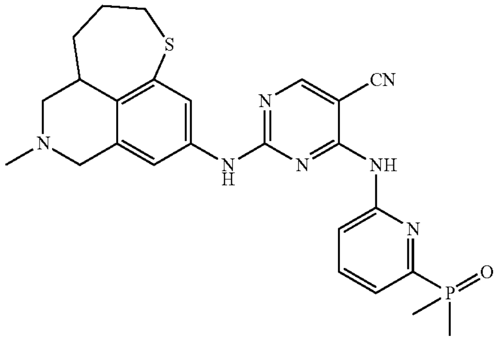 | 506 |
| 212 | 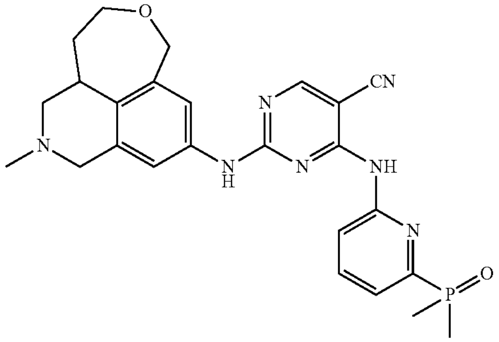 [SMILES: CN1Cc2cc(Nc3ncc(C#N)c(Nc4cccc(P(C)(C)=O)n4)n3)cc3c2C(CCOC3)C1] | 490 |
| 213 | 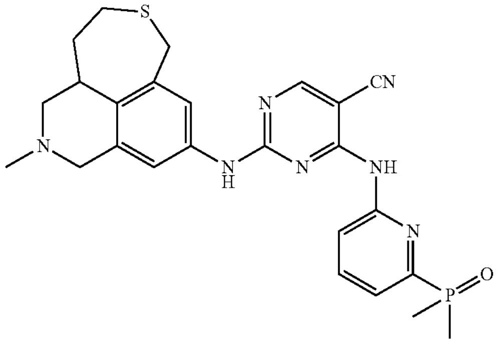 | 506 |
| 214 | 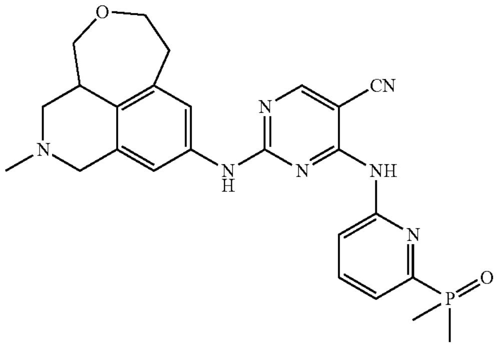 [SMILES: CN1Cc2cc(Nc3ncc(C#N)c(Nc4cccc(P(C)(C)=O)n4)n3)cc3c2C(COCC3)C1] | 490 |

TABLE 1-continued
| Compound | Compound structure | MS (M + H)$^+$ |
|---|---|---|
| 215 | 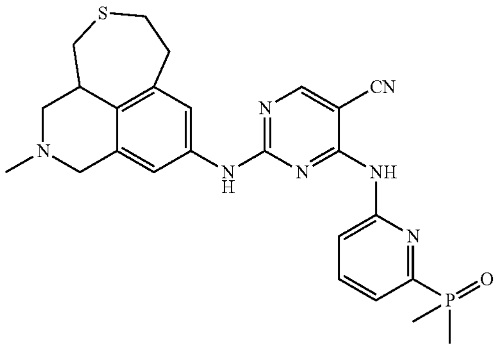 [SMILES: CN1Cc2cc(Nc3ncc(C#N)c(Nc4cccc(P(C)(C)=O)n4)n3)cc3c2C(CSCC3)C1] | 506 |
| 216 | 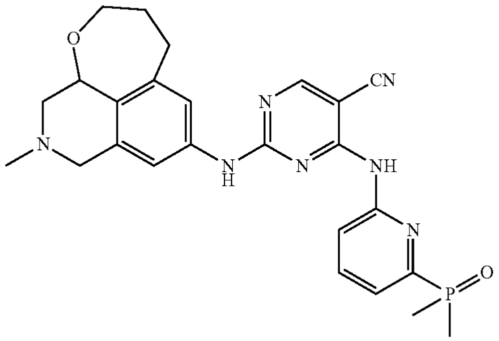 [SMILES: CN1Cc2cc(Nc3ncc(C#N)c(Nc4cccc(P(C)(C)=O)n4)n3)cc3c2C(C1)OCCC3] | 490 |
| 217 | 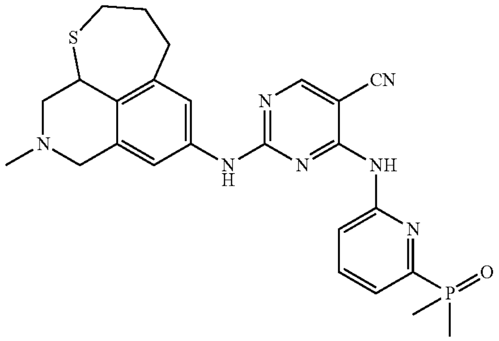 | 506 |
| 218 | 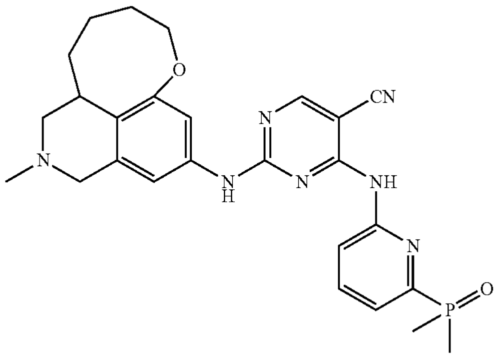 [SMILES: CN1Cc2cc(Nc3ncc(C#N)c(Nc4cccc(P(C)(C)=O)n4)n3)cc3c2C(CCCCO3)C1] | 504 |

TABLE 1-continued
| Compound | Compound structure | MS (M + H)+ |
|---|---|---|
| 219 | 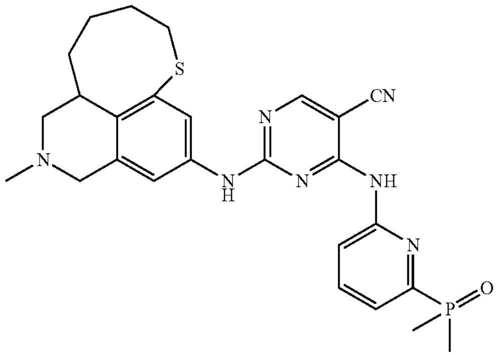 [SMILES: CN1Cc2cc(Nc3ncc(C#N)c(Nc4cccc(P(C)(C)=O)n4)n3)cc3c2C(CCCCS3)C1] | 520 |
| 220 | 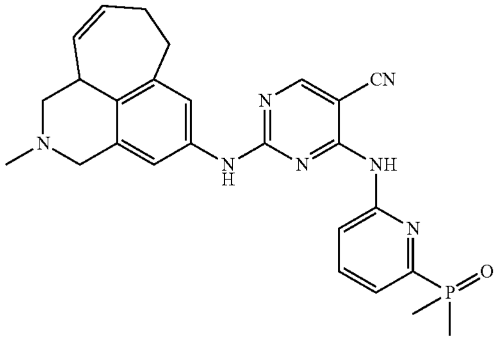 [SMILES: CN1Cc2cc(Nc3ncc(C#N)c(Nc4cccc(P(C)(C)=O)n4)n3)cc3c2C(C=CCC3)C1] | 486 |
| 221 | 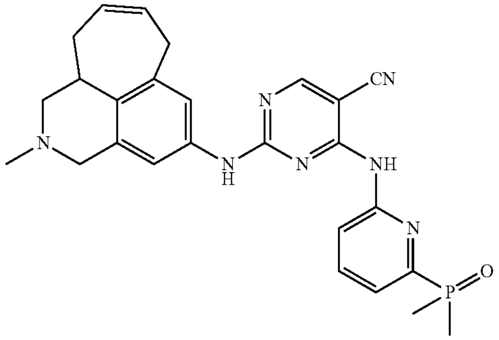 [SMILES: CN1Cc2cc(Nc3ncc(C#N)c(Nc4cccc(P(C)(C)=O)n4)n3)cc3c2C(CC=CC3)C1] | 486 |
| 222 | 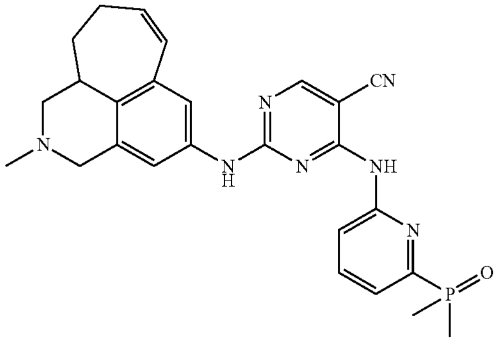 [SMILES: CN1Cc2cc(Nc3ncc(C#N)c(Nc4cccc(P(C)(C)=O)n4)n3)cc3c2C(CCC=C3)C1] | 486 |

TABLE 1-continued
| Compound | Compound structure | MS (M + H)+ |
| --- | --- | --- |
| 223 | 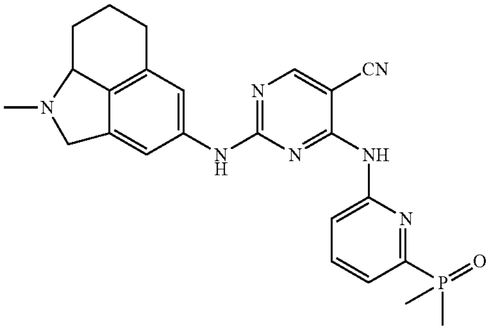 [SMILES: CN1Cc2cc(Nc3ncc(C#N)c(Nc4cccc(P(C)(C)=O)n4)n3)cc3c2C1CCC3] | 460 |
| 224 | 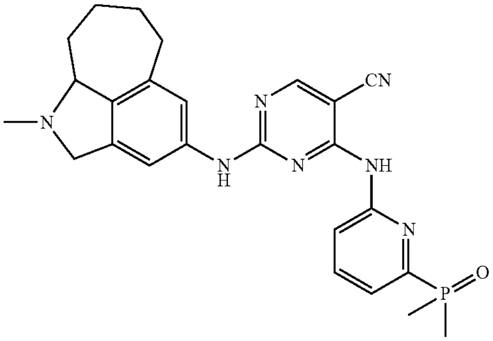 [SMILES: CN1Cc2cc(Nc3ncc(C#N)c(Nc4cccc(P(C)(C)=O)n4)n3)cc3c2C1CCCC3] | 474 |
| 225 | 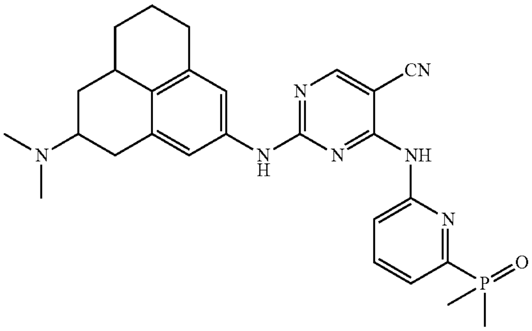 [SMILES: CN(C)C1Cc2cc(Nc3ncc(C#N)c(Nc4cccc(P(C)(C)=O)n4)n3)cc3c2C(CCC3)C1] | 502 |
| 226 | 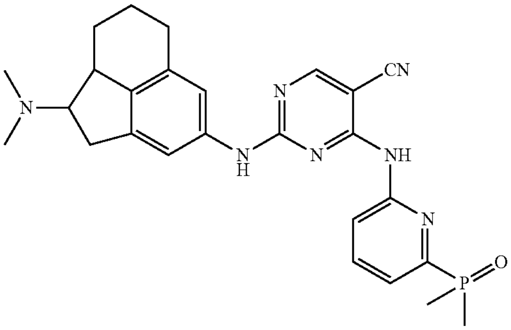 [SMILES: CN(C)C1Cc2cc(Nc3ncc(C#N)c(Nc4cccc(P(C)(C)=O)n4)n3)cc3c2C1CCC3] | 488 |

TABLE 1-continued
| Compound | Compound structure | MS $(M + H)^+$ |
| --- | --- | --- |
| 227 | 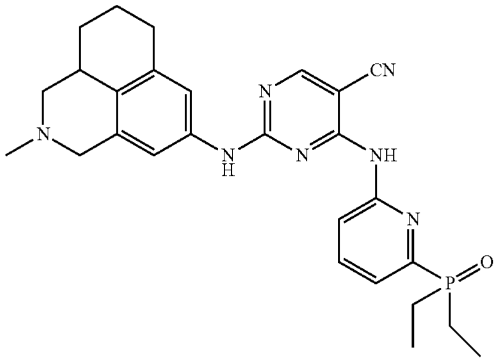 [SMILES: CCP(=O)(CC)c1cccc(Nc2nc(Nc3cc4c5c(c3)CN(C)CC5CCC4)ncc2C#N)n1] | 502 |
| 228 | 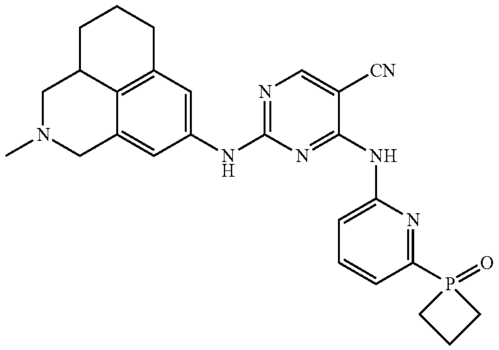 [SMILES: CN1Cc2cc(Nc3ncc(C#N)c(Nc4cccc(P5(=O)CCC5)n4)n3)cc3c2C(CCC3)C1] | 486 |
| 229 | 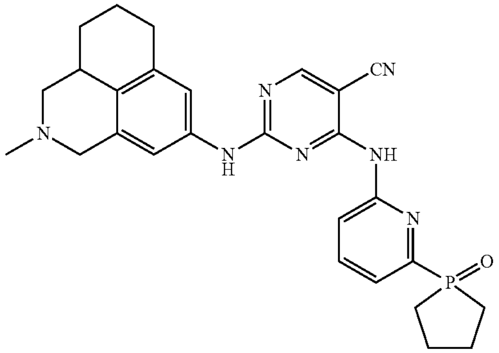 [SMILES: CN1Cc2cc(Nc3ncc(C#N)c(Nc4cccc(P5(=O)CCCC5)n4)n3)cc3c2C(CCC3)C1] | 500 |
| 230 | 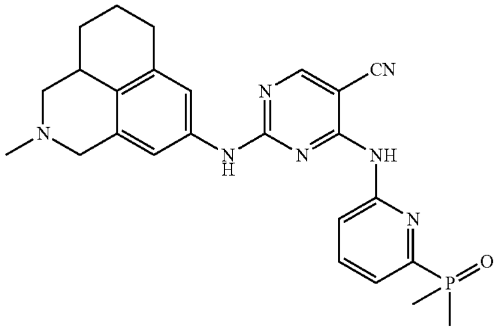 [SMILES: CN1Cc2cc(Nc3ncc(C#N)c(Nc4cccc(P(C)(C)=O)n4)n3)cc3c2C(CCC3)C1] | 517 |

TABLE 1-continued
| Compound | Compound structure | MS (M + H)+ |
|---|---|---|
| 231 | 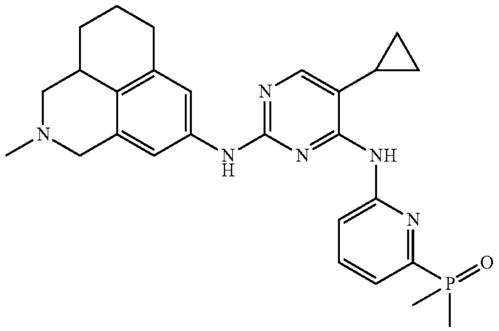 [SMILES: CN1Cc2cc(Nc3ncc(C4CC4)c(Nc4cccc(P(C)(C)=O)n4)n3)cc3c2C(CCC3)C1] | 489 |
| 232 | 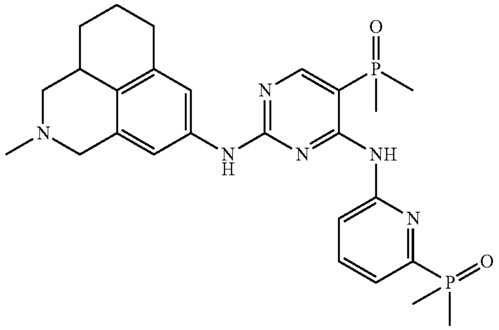 [SMILES: CN1Cc2cc(Nc3ncc(P(C)(C)=O)c(Nc4cccc(P(C)(C)=O)n4)n3)cc3c2C(CCC3)C1] | 525 |
| 233 | 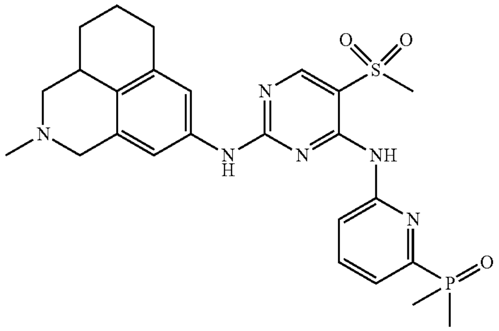 [SMILES: CN1Cc2cc(Nc3ncc(S(C)(=O)=O)c(Nc4cccc(P(C)(C)=O)n4)n3)cc3c2C(CCC3)C1] | 527 |
| 234 | 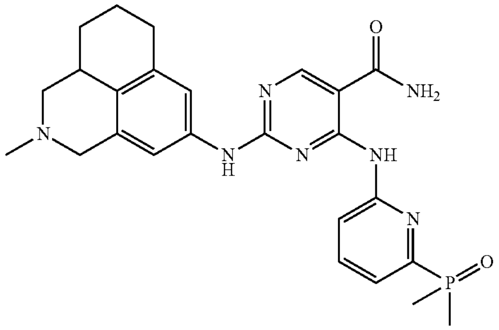 [SMILES: CN1Cc2cc(Nc3ncc(C(N)=O)c(Nc4cccc(P(C)(C)=O)n4)n3)cc3c2C(CCC3)C1] | 492 |

TABLE 1-continued
| Compound | Compound structure | MS (M + H)$^+$ |
|---|---|---|
| 235 | 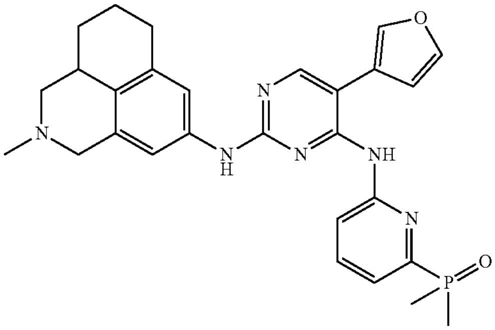 [SMILES: CN1Cc2cc(Nc3ncc(-c4ccoc4)c(Nc4cccc(P(C)(C)=O)n4)n3)cc3c2C(CCC3)C1] | 515 |
| 236 | 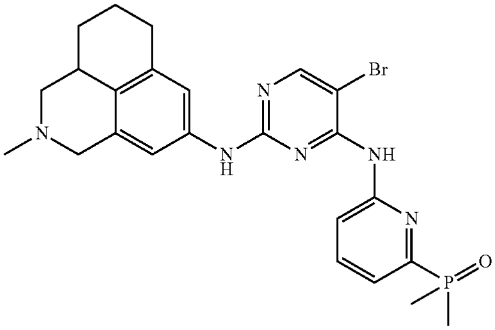 [SMILES: CN1Cc2cc(Nc3ncc(Br)c(Nc4cccc(P(C)(C)=O)n4)n3)cc3c2C(CCC3)C1] | 527 |
| 237 | 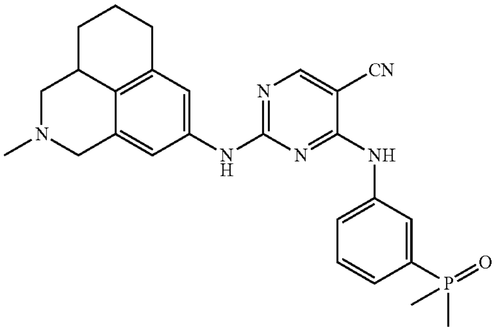 [SMILES: CN1Cc2cc(Nc3ncc(C#N)c(Nc4cccc(P(C)(C)=O)c4)n3)cc3c2C(CCC3)C1] | 473 |
| 238 | 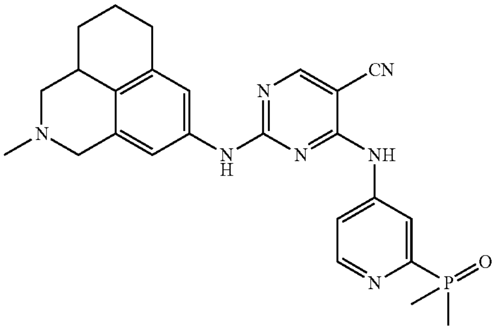 [SMILES: CN1Cc2cc(Nc3ncc(C#N)c(Nc4ccnc(P(C)(C)=O)c4)n3)cc3c2C(CCC3)C1] | 474 |

TABLE 1-continued
| Compound | Compound structure | MS (M + H)+ |
|---|---|---|
| 239 | 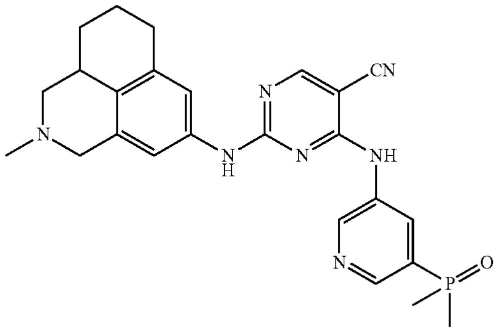 [SMILES: CN1Cc2cc(Nc3ncc(C#N)c(Nc4cncc(P(C)(C)=O)c4)n3)cc3c2C(CCC3)C1] | 474 |
| 240 | 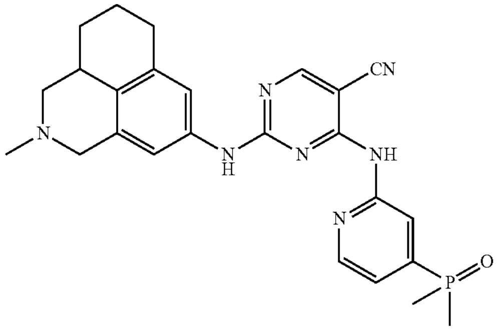 [SMILES: CN1Cc2cc(Nc3ncc(C#N)c(Nc4cc(P(C)(C)=O)ccn4)n3)cc3c2C(CCC3)C1] | 474 |
| 241 | 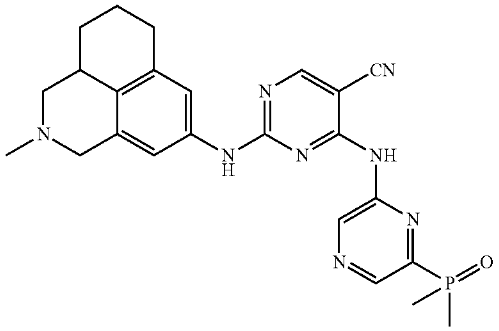 [SMILES: CN1Cc2cc(Nc3ncc(C#N)c(Nc4cncc(P(C)(C)=O)n4)n3)cc3c2C(CCC3)C1] | 475 |
| 242 | 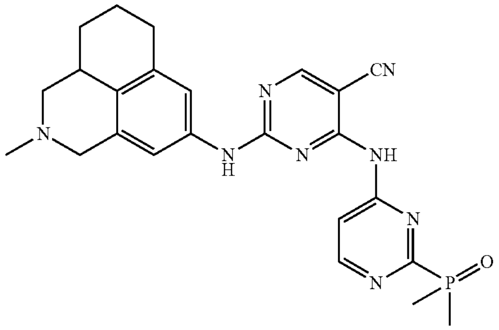 [SMILES: CN1Cc2cc(Nc3ncc(C#N)c(Nc4ccnc(P(C)(C)=O)n4)n3)cc3c2C(CCC3)C1] | 475 |

TABLE 1-continued
| Compound | Compound structure | MS (M + H)$^+$ |
| --- | --- | --- |
| 243 | 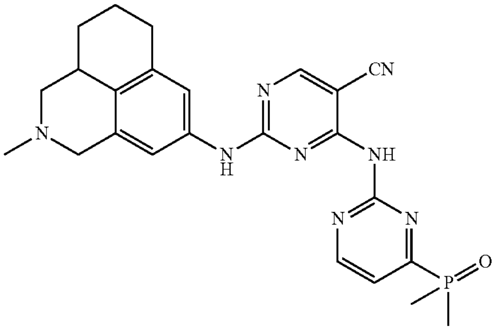 [SMILES: CN1Cc2cc(Nc3ncc(C#N)c(Nc4nccc(P(C)(C)=O)n4)n3)cc3c2C(CCC3)C1] | 475 |
| 244 | 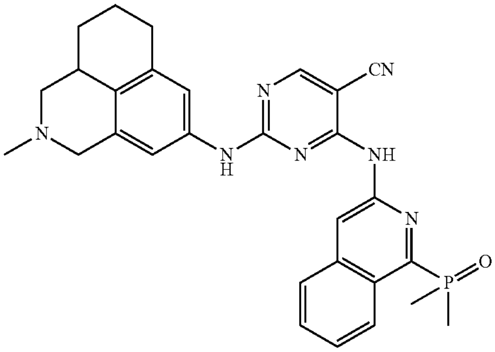 [SMILES: CN1Cc2cc(Nc3ncc(C#N)c(Nc4cc5ccccc5c(P(C)(C)=O)n4)n3)cc3c2C(CCC3)C1] | 524 |
| 245 | 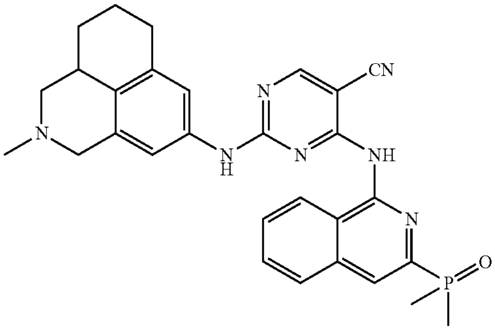 [SMILES: CN1Cc2cc(Nc3ncc(C#N)c(Nc4nc(P(C)(C)=O)cc5ccccc45)n3)cc3c2C(CCC3)C1] | 524 |
| 246 | 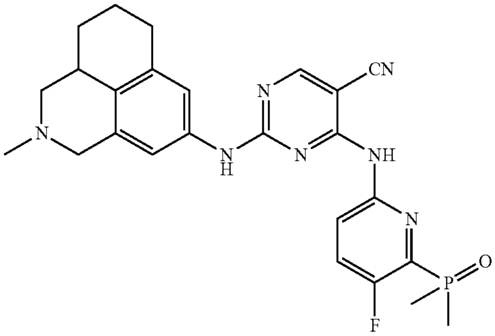 [SMILES: CN1Cc2cc(Nc3ncc(C#N)c(Nc4ccc(F)c(P(C)(C)=O)n4)n3)cc3c2C(CCC3)C1] | 492 |

TABLE 1-continued
| Compound | Compound structure | MS (M + H)+ |
|---|---|---|
| 247 | 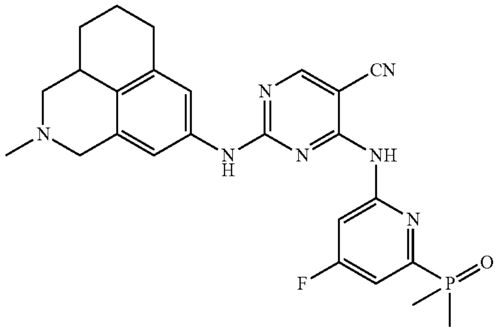 [SMILES: CN1Cc2cc(Nc3ncc(C#N)c(Nc4cc(F)cc(P(C)(C)=O)n4)n3)cc3c2C(CCC3)C1] | 492 |
| 248 | 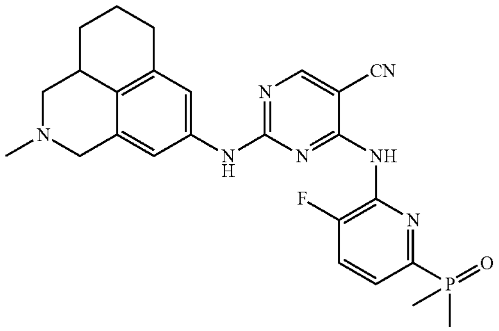 [SMILES: CN1Cc2cc(Nc3ncc(C#N)c(Nc4nc(P(C)(C)=O)ccc4F)n3)cc3c2C(CCC3)C1] | 492 |
| 249 | 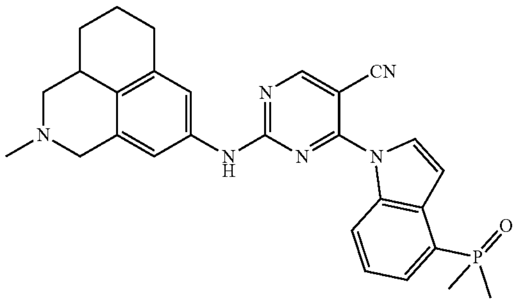 [SMILES: CN1Cc2cc(Nc3ncc(C#N)c(-n4ccc5c(P(C)(C)=O)cccc54)n3)cc3c2C(CCC3)C1] | 497 |
| 250 | 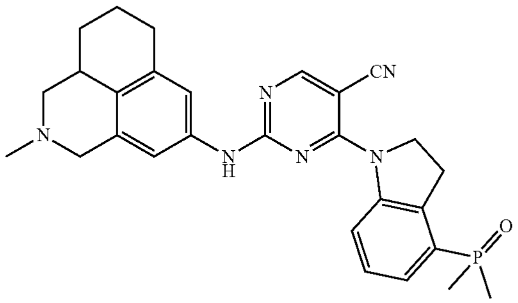 [SMILES: CN1Cc2cc(Nc3ncc(C#N)c(N4CCc5c4cccc5P(C)(C)=O)n3)cc3c2C(CCC3)C1] | 499 |
| 251 | 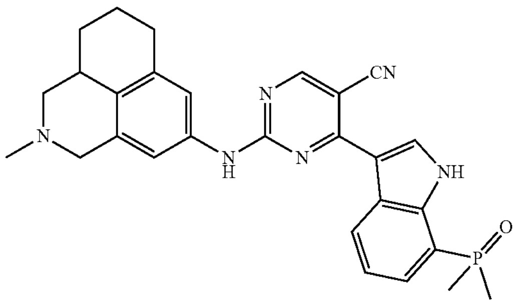 [SMILES: CN1Cc2cc(Nc3ncc(C#N)c(-c4c[nH]c5c(P(C)(C)=O)cccc45)n3)cc3c2C(CCC3)C1] | 497 |

TABLE 1-continued
| Compound | Compound structure | MS (M + H)+ |
| --- | --- | --- |
| 252 | 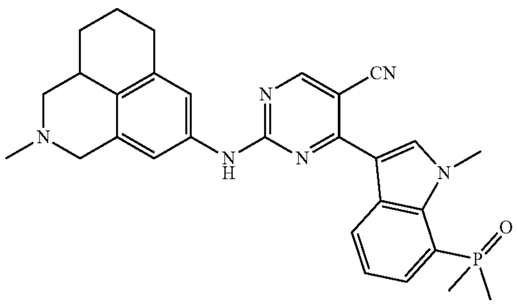 [SMILES: CN1Cc2cc(Nc3ncc(C#N)c(-c4cn(C)c5c(P(C)(C)=O)cccc45)n3)cc3c2C(CCC3)C1] | 511 |
| 253 | 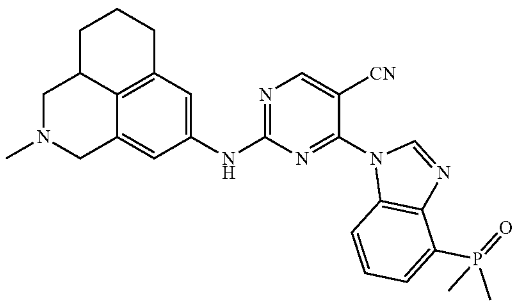 [SMILES: CN1Cc2cc(Nc3ncc(C#N)c(-n4cnc5c(P(C)(C)=O)cccc54)n3)cc3c2C(CCC3)C1] | 498 |
| 254 | 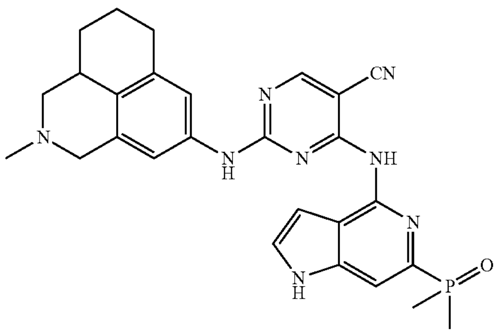 [SMILES: CN1Cc2cc(Nc3ncc(C#N)c(Nc4nc(P(C)(C)=O)cc5[nH]ccc45)n3)cc3c2C(CCC3)C1] | 513 |
| 255 | 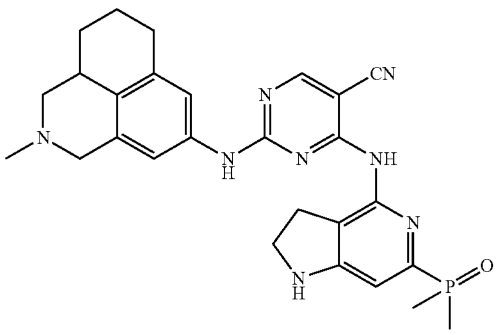 [SMILES: CN1Cc2cc(Nc3ncc(C#N)c(Nc4nc(P(C)(C)=O)cc5c4CCN5)n3)cc3c2C(CCC3)C1] | 515 |

TABLE 1-continued
| Compound | Compound structure | MS (M + H)+ |
|---|---|---|
| 256 | 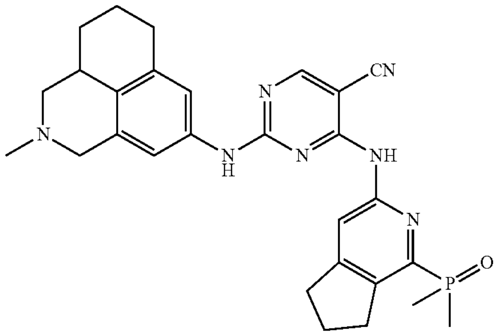 [SMILES: CN1Cc2cc(Nc3ncc(C#N)c(Nc4cc5c(c(P(C)(C)=O)n4)CCC5)n3)cc3c2C(CCC3)C1] | 514 |
| 257 | 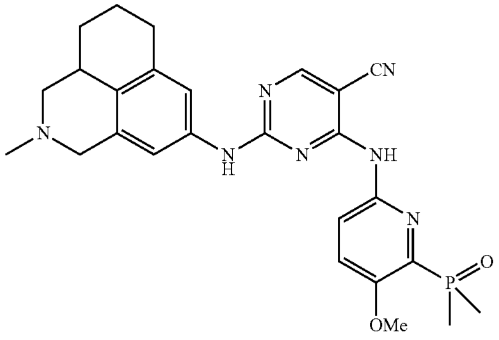 [SMILES: COc1ccc(Nc2nc(Nc3cc4c5c(c3)CN(C)CC5CCC4)ncc2C#N)nc1P(C)(C)=O] | 504 |
| 258 | 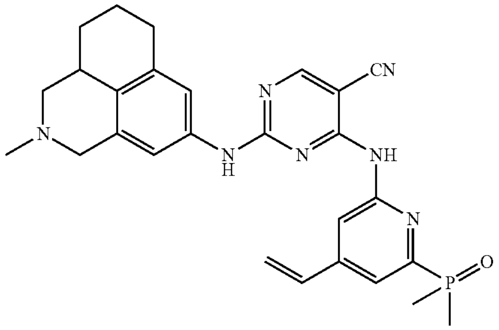 [SMILES: C=Cc1cc(Nc2nc(Nc3cc4c5c(c3)CN(C)CC5CCC4)ncc2C#N)nc(P(C)(C)=O)c1] | 500 |
| 259 | 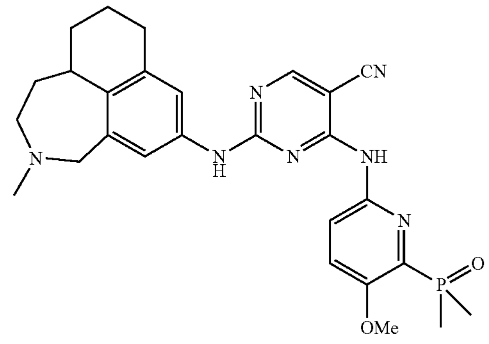 [SMILES: COc1ccc(Nc2nc(Nc3cc4c5c(c3)CN(C)CCC5CCC4)ncc2C#N)nc1P(C)(C)=O] | 518 |

TABLE 1-continued
| Compound | Compound structure | MS (M + H)+ |
|---|---|---|
| 260 | 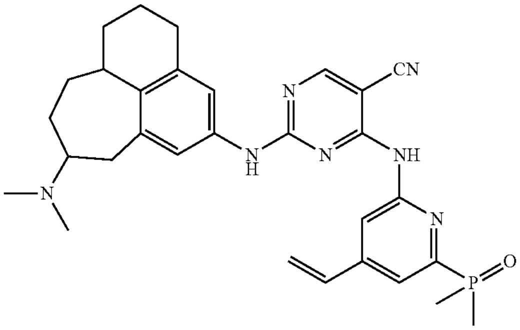 [SMILES: C=Cc1cc(Nc2nc(Nc3cc4c5c(c3)CC(N(C)C)CCC5CCC4)ncc2C#N)nc(P(C)(C)=O)c1] | 542 |
| 261 | 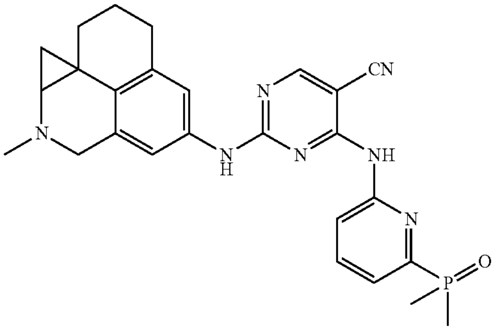 [SMILES: CN1Cc2cc(Nc3ncc(C#N)c(Nc4cccc(P(C)(C)=O)n4)n3)cc3c2C2(CCC3)CC12] | 486 |
| 262 | 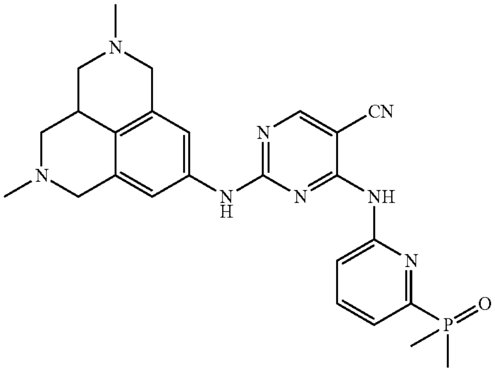 [SMILES: CN1Cc2cc(Nc3ncc(C#N)c(Nc4cccc(P(C)(C)=O)n4)n3)cc3c2C(C1)CN(C)C3] | 489 |
| 263 | 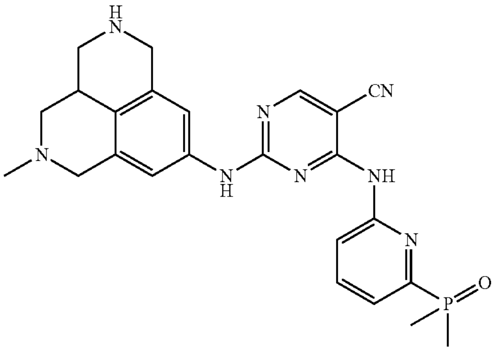 [SMILES: CN1Cc2cc(Nc3ncc(C#N)c(Nc4cccc(P(C)(C)=O)n4)n3)cc3c2C(CNC3)C1] | 475 |

TABLE 1-continued
| Compound | Compound structure | MS (M + H)+ |
|---|---|---|
| 264 | 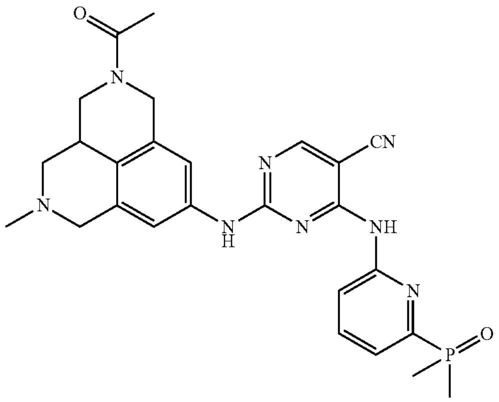 [SMILES: CC(=O)N1Cc2cc(Nc3ncc(C#N)c(Nc4cccc(P(C)(C)=O)n4)n3)cc3c2C(CN(C)C3)C1] | 517 |
| 265 | 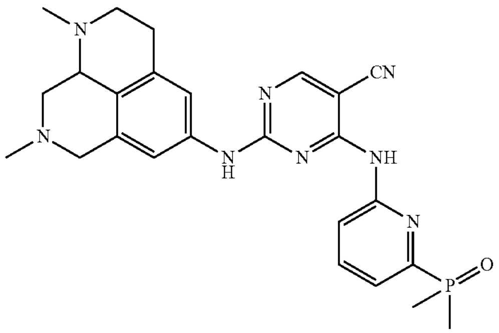 [SMILES: CN1Cc2cc(Nc3ncc(C#N)c(Nc4cccc(P(C)(C)=O)n4)n3)cc3c2C(C1)N(C)CC3] | 489 |
| 266 | 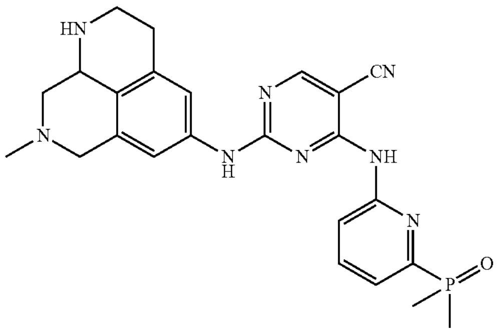 [SMILES: CN1Cc2cc(Nc3ncc(C#N)c(Nc4cccc(P(C)(C)=O)n4)n3)cc3c2C(C1)NCC3] | 475 |
| 267 | 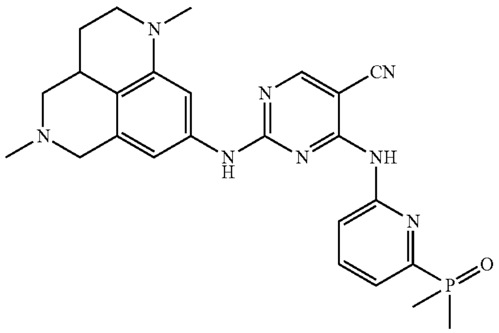 [SMILES: CN1Cc2cc(Nc3ncc(C#N)c(Nc4cccc(P(C)(C)=O)n4)n3)cc3c2C(CCN3C)C1] | 489 |

TABLE 1-continued
| Compound | Compound structure | MS (M + H)+ |
|---|---|---|
| 268 | 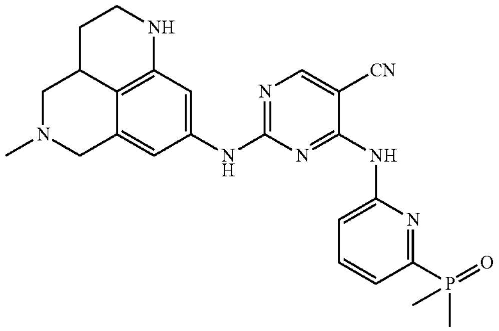 [SMILES: CN1Cc2cc(Nc3ncc(C#N)c(Nc4cccc(P(C)(C)=O)n4)n3)cc3c2C(CCN3)C1] | 475 |
| 269 | 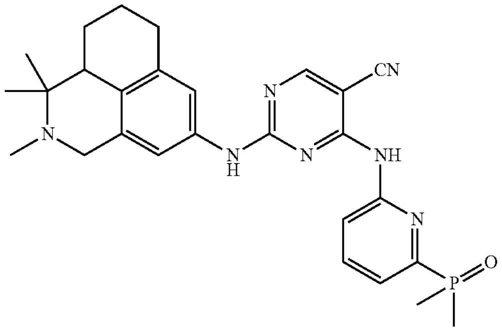 [SMILES: CN1Cc2cc(Nc3ncc(C#N)c(Nc4cccc(P(C)(C)=O)n4)n3)cc3c2C(CCC3)C1(C)C] | 502 |
| 270 | 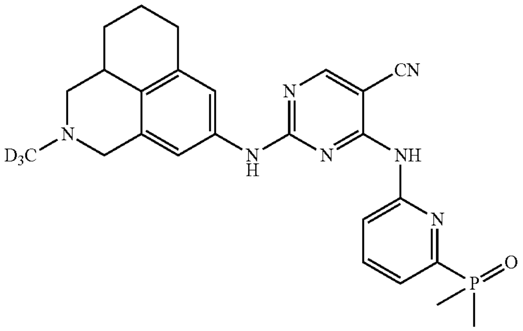 [SMILES: [2H]C([2H])([2H])N1Cc2cc(Nc3ncc(C#N)c(Nc4cccc(P(C)(C)=O)n4)n3)cc3c2C(CCC3)C1] | 477 |
| 271 | 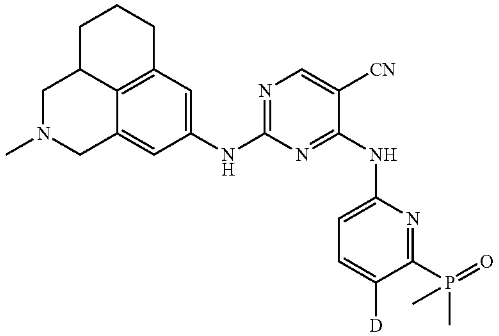 | 475 |

TABLE 1-continued
| Compound | Compound structure | MS (M + H)+ |
| --- | --- | --- |
| 272 | 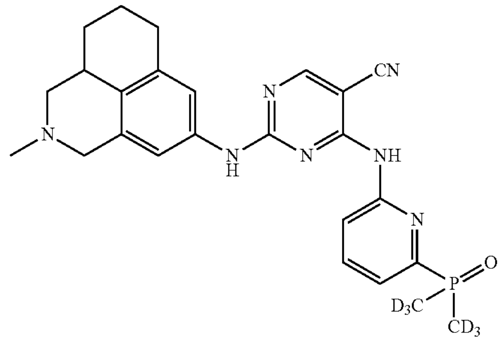 [SMILES: [2H]C([2H])([2H])P(=O)(c1cccc(Nc2nc(Nc3cc4c5c(c3)CN(C)CC5CCC4)ncc2C#N)n1)C([2H])([2H])[2H]] | 480 |
| 273 | 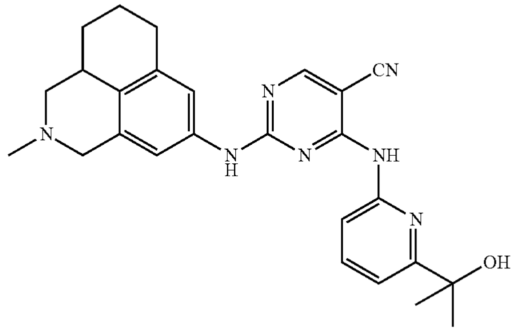 [SMILES: CN1Cc2cc(Nc3ncc(C#N)c(Nc4cccc(C(C)(C)O)n4)n3)cc3c2C(CCC3)C1] | 456 |
| 274 | 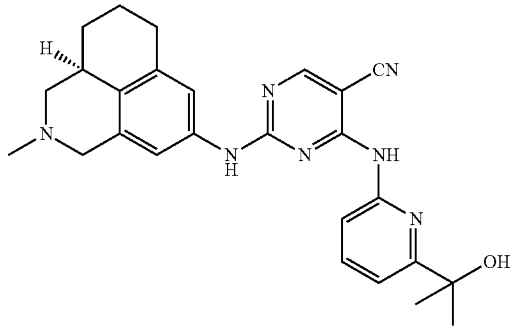 [SMILES: CN1Cc2cc(Nc3ncc(C#N)c(Nc4cccc(C(C)(C)O)n4)n3)cc3c2[C@H](CCC3)C1] | 456 |
| 275 | 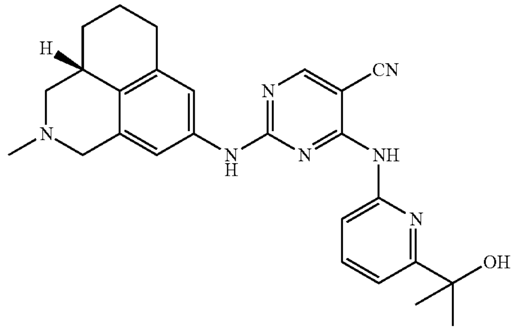 [SMILES: CN1Cc2cc(Nc3ncc(C#N)c(Nc4cccc(C(C)(C)O)n4)n3)cc3c2[C@@H](CCC3)C1] | 456 |

TABLE 1-continued
| Compound | Compound structure | MS (M + H)+ |
|---|---|---|
| 276 | 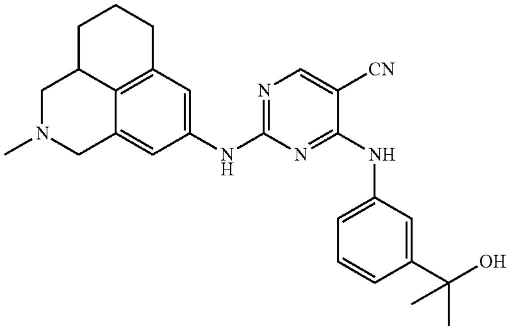 [SMILES: CN1Cc2cc(Nc3ncc(C#N)c(Nc4cccc(C(C)(C)O)c4)n3)cc3c2C(CCC3)C1] | 455 |
| 277 | 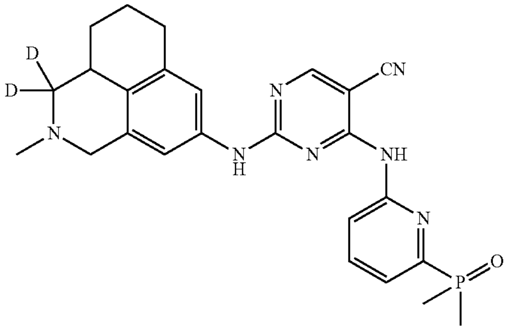 [SMILES: [2H]C1([2H])C2CCCc3cc(Nc4ncc(C#N)c(Nc5cccc(P(C)(C)=O)n5)n4)cc(c32)CN1C] | 476 |
| 278 | 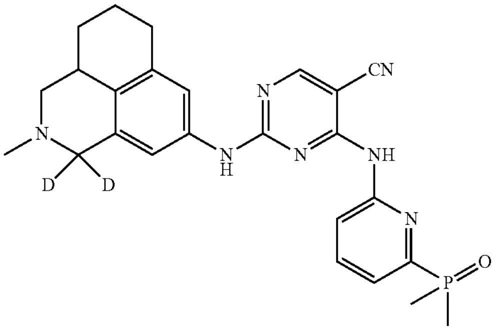 [SMILES: [2H]C1([2H])c2cc(Nc3ncc(C#N)c(Nc4cccc(P(C)(C)=O)n4)n3)cc3c2C(CCC3)CN1C] | 476 |
| 279 | 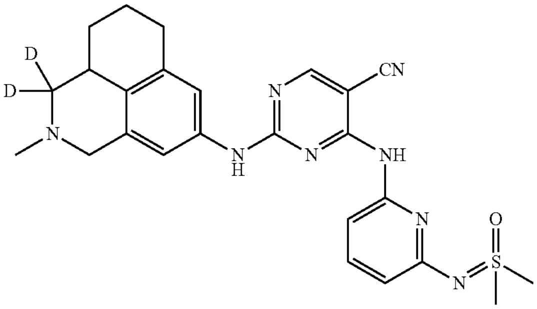 [SMILES: [2H]C1([2H])C2CCCc3cc(Nc4ncc(C#N)c(Nc5cccc(N=S(C)(C)=O)n5)n4)cc(c32)CN1C] | 491 |

TABLE 1-continued
| Compound | Compound structure | MS (M + H)+ |
|---|---|---|
| 280 | 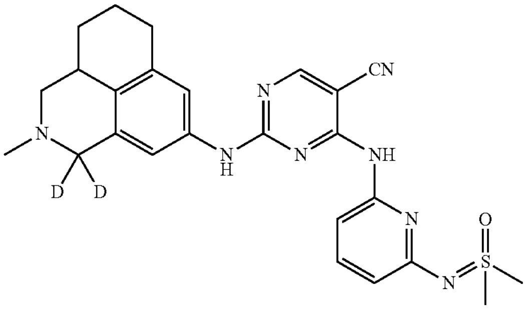 | 491 |
| 281 | 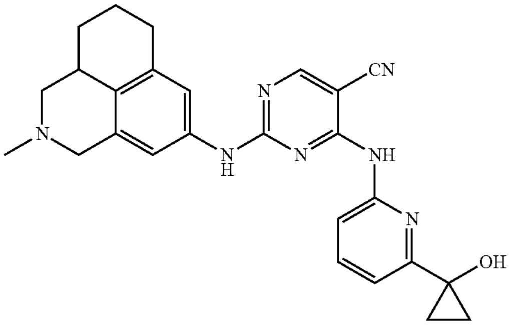 [SMILES: CN1Cc2cc(Nc3ncc(C#N)c(Nc4cccc(C5(O)CC5)n4)n3)cc3c2C(CCC3)C1] | 454 |
| 282 | 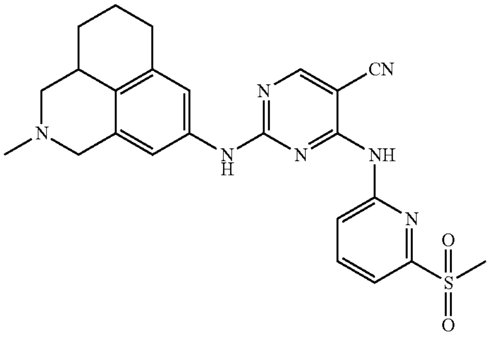 | 476 |
| 283 | 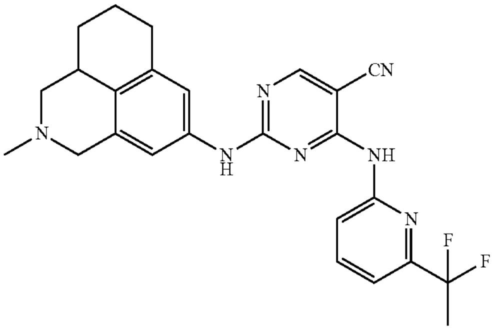 [SMILES: CN1Cc2cc(Nc3ncc(C#N)c(Nc4cccc(C(C)(F)F)n4)n3)cc3c2C(CCC3)C1] | 462 |

TABLE 1-continued
| Compound | Compound structure | MS (M + H)+ |
|---|---|---|
| 284 | 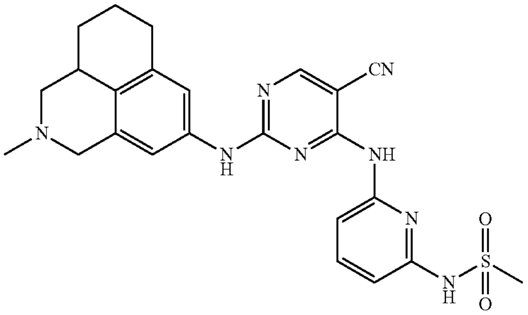 | 491 |
| 285 | 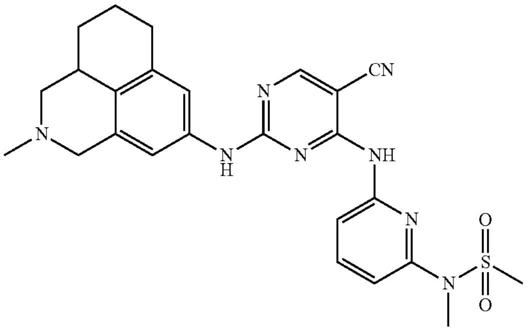 | 505 |
| 286 | 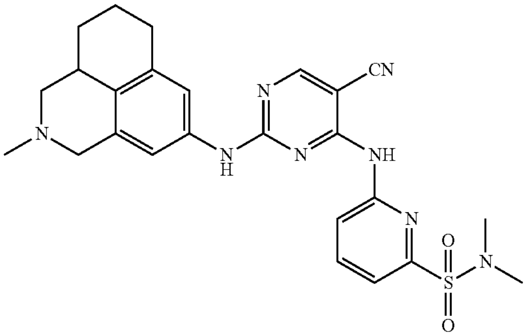 | 505 |
| 287 | 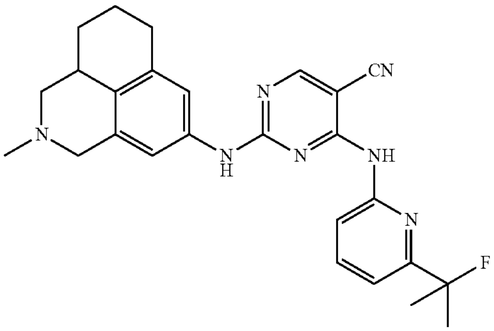 [SMILES: CN1Cc2cc(Nc3ncc(C#N)c(Nc4cccc(C(C)(C)F)n4)n3)cc3c2C(CCC3)C1] | 458 |

TABLE 1-continued
| Compound | Compound structure | MS (M + H)+ |
| --- | --- | --- |
| 288 | 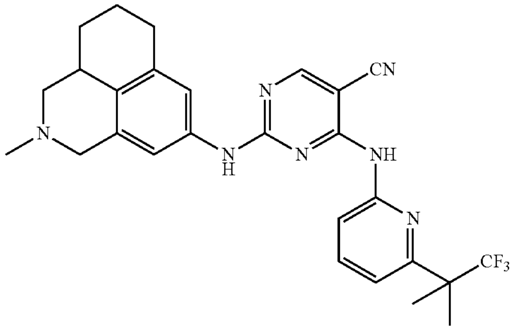 [SMILES: CN1Cc2cc(Nc3ncc(C#N)c(Nc4cccc(C(C)(C)C(F)(F)F)n4)n3)cc3c2C(CCC3)C1] | 508 |
| 289 | 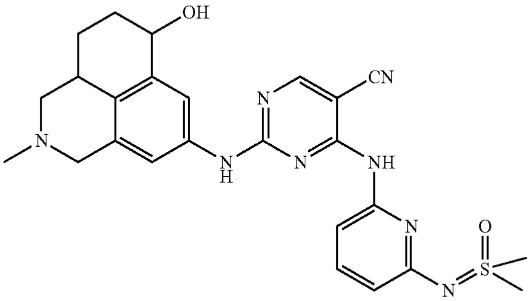 | 505 |
| 290 | 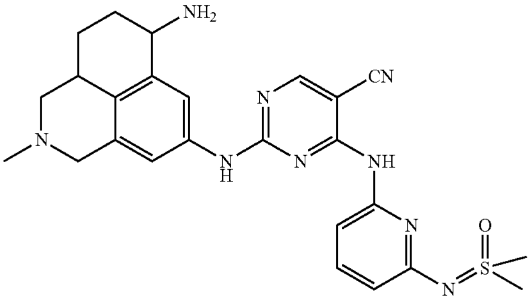 | 504 |
| 291 | 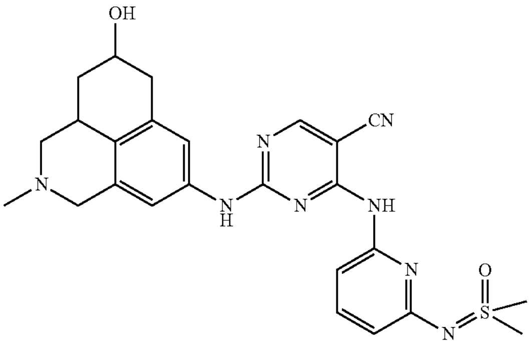 | 505 |

TABLE 1-continued
| Compound | Compound structure | MS (M + H)$^+$ |
| --- | --- | --- |
| 292 | 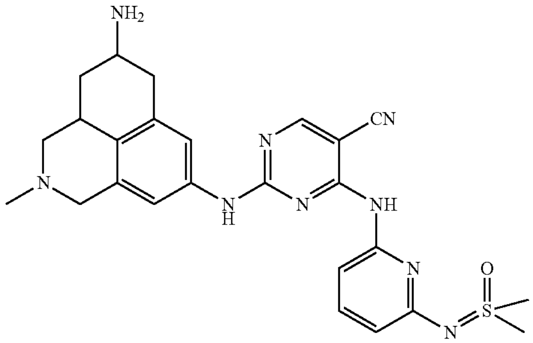 | 504 |
| 293 | 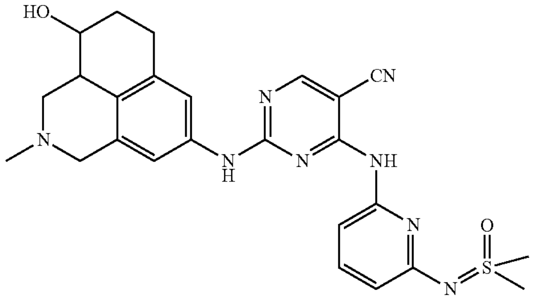 | 505 |
| 294 | 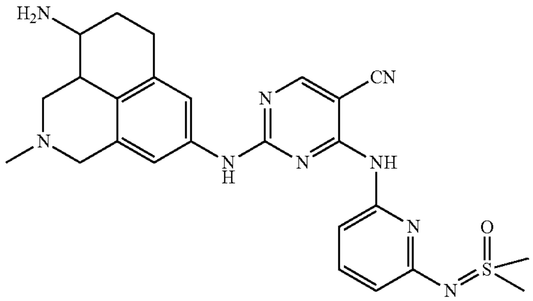 | 504 |
| 295 | 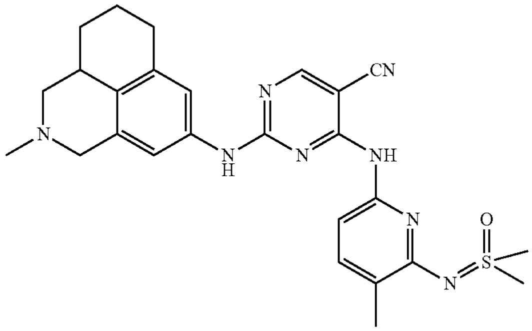 | 503 |

TABLE 1-continued

| Compound | Compound structure | MS (M + H)$^+$ |
|---|---|---|
| 296 | 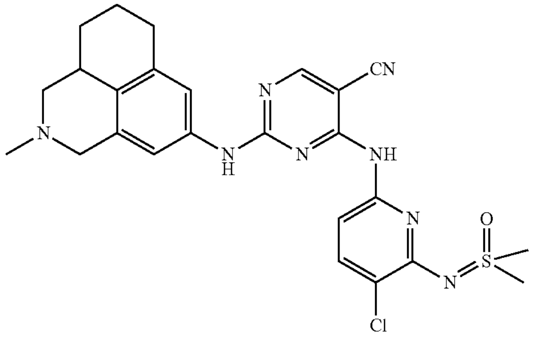 | 523 |

TABLE 2

NMR data and LC-MS retention times of some of the compounds in Table 1

| Compound | NMR | LC-MS retention time (min) |
|---|---|---|
| 4 | $^1$H NMR (400 MHz, Chloroform-d) δ 8.35 (s, 1H), 7.70 (d, J = 7.6 Hz, 2H), 7.47 (s, 1H), 7.32 (s, 1H), 7.04 (d, J = 12.2 Hz, 2H), 6.57 (d, J = 7.8 Hz, 1H), 3.97 (d, J = 15.5 Hz, 1H), 3.36 (s, 6H), 3.23 (d, J = 15.5 Hz, 1H), 2.91 (s, 1H), 2.81-2.56 (m, 2H), 2.41 (s, 3H), 2.15 (d, J = 11.0 Hz, 2H), 1.92-1.80 (m, 1H), 1.61 (d, J = 13.3 Hz, 1H), 1.51-1.41 (m, 1H), 1.35 (s, 3H) | 1.395 |
| 5 | $^1$H NMR (400 MHz, Chloroform-d) δ 8.35 (s, 1H), 7.70 (d, J = 7.6 Hz, 2H), 7.47 (s, 1H), 7.32 (s, 1H), 7.04 (d, J = 12.2 Hz, 2H), 6.57 (d, J = 7.8 Hz, 1H), 3.97 (d, J = 15.5 Hz, 1H), 3.36 (s, 6H), 3.23 (d, J = 15.5 Hz, 1H), 2.91 (s, 1H), 2.81-2.56 (m, 2H), 2.41 (s, 3H), 2.15 (d, J = 11.0 Hz, 2H), 1.92-1.80 (m, 1H), 1.61 (d, J = 13.3 Hz, 1H), 1.51-1.41 (m, 1H), 1.35 (s, 3H) | 1.396 |
| 6 | $^1$H NMR (400 MHz, Chloroform-d) δ 8.35 (s, 1H), 7.70 (d, J = 7.6 Hz, 2H), 7.47 (s, 1H), 7.32 (s, 1H), 7.04 (d, J = 12.2 Hz, 2H), 6.57 (d, J = 7.8 Hz, 1H), 3.97 (d, J = 15.5 Hz, 1H), 3.36 (s, 6H), 3.23 (d, J = 15.5 Hz, 1H), 2.91 (s, 1H), 2.81-2.56 (m, 2H), 2.41 (s, 3H), 2.15 (d, J = 11.0 Hz, 2H), 1.92-1.80 (m, 1H), 1.61 (d, J = 13.3 Hz, 1H), 1.51-1.41 (m, 1H), 1.35 (s, 3H) | 1.395 |
| 7 | $^1$H NMR (400 MHz, cdcl$_3$) δ 8.34 (s, 1H), 7.68 (d, J = 8.2 Hz, 2H), 7.54-7.42 (m, 2H), 7.15-7.09 (m, 1H), 7.07 (s, 1H), 6.56 (d, J = 7.9 Hz, 1H), 4.06 (d, J = 15.4 Hz, 1H), 3.36 (s, 6H), 3.16 (dd, J = 11.1, 4.9 Hz, 1H), 2.98 (d, J = 12.4 Hz, 1H), 2.71 (m, 3H), 2.16 (t, J = 11.0 Hz, 1H), 1.99-1.70 (m, 5H), 1.22 (m, 4H). | 1.393 |
| 49 | $^1$H NMR (400 MHz, Chloroform-d) δ 8.39 (s, 1H), 7.84-7.61 (m, 3H), 7.55 (t, J = 8.0 Hz, 1H), 6.59 (d, J = 7.9 Hz, 1H), 3.87 (d, J = 14.0 Hz, 1H), 3.75 (s, 3H), 3.37 (d, J = 5.2 Hz, 6H), 3.28 (d, J = 15.1 Hz, 1H), 3.04-2.83 (m, 3H), 2.80-2.68 (m, 1H), 2.44 (s, 3H), 2.04 (m, 2H), 1.88 (m, 2H), 1.26 (m, 1H). | 1.322 |
| 50 | $^1$H NMR (400 MHz, Chloroform-d) δ 8.35 (s, 1H), 7.68 (d, J = 7.9 Hz, 1H), 7.57 (s, 1H), 7.44 (s, 2H), 7.23 (s, 1H), 7.04 (s, 1H), 6.56 (d, J = 7.9 Hz, 1H), 3.97 (d, J = 15.6 Hz, 1H), 3.36 (s, 6H), 3.28-3.14 (m, 3H), 2.96 (td, J = 13.8, 11.6, 6.4 Hz, 1H), 2.75 (dd, J = 15.5, 7.8 Hz, 1H), 2.52 (s, 3H), 2.30 (dt, J = 12.0, 6.3 Hz, 1H), 2.09-1.96 (m, 1H), 1.59 (dd, J = 11.7, 8.2 Hz, 1H). | 1.319 |
| 87 | $^1$H NMR (400 MHz, Chloroform-d) δ 8.35 (s, 1H), 7.67 (s, 1H), 7.51 (d, J = 37.1 Hz, 3H), 7.24 (s, 1H), 7.16-7.06 (m, 1H), 6.57 (d, J = 7.9 Hz, 1H), 4.13 (d, J = 12.7 Hz, 1H), 3.66 (s, 1H), 3.36 (s, 7H), 2.78 (dd, J = 17.6, 6.5 Hz, 1H), 2.65 (s, 4H), 2.35-2.22 (m, 1H), 2.13 (s, 1H), 1.75 (dd, J = 13.3, 6.5 Hz, 2H), 1.38 (m, 1H) | 1.280 |
| 105 | $^1$H NMR (400 MHz, cdcl$_3$) δ 9.01 (s, 1H), 8.40 (s, 1H), 7.95 (d, J = 1.7 Hz, 1H), 7.39 (d, J = 27.4 Hz, 2H), 7.06 (d, J = 18.4 Hz, 2H), 3.96 (d, J = 15.3 Hz, 1H), 3.39 (d, J = 1.7 Hz, 6H), 3.34 (s, 1H), 3.01-2.88 (m, 2H), 2.88-2.72 (m, 2H), 2.44 (d, J = 1.8 Hz, 3H), 2.08 (q, J = 12.6, 11.5 Hz, 1H), 1.95 (m, 3H), 1.28 (m, 1H). | 1.729 |
| 108 | $^1$H NMR (400 MHz, cdcl$_3$) δ 8.36 (s, 1H), 8.31 (d, J = 8.3 Hz, 1H), 7.95 (s, 1H), 7.52 (s, 2H), 7.46-7.31 (m, 2H), 7.10 (s, 1H), 7.04 (s, 1H), 3.81 (s, 1H), 3.48 (s, 6H), 3.21 (d, J = 14.7 Hz, 1H), 2.99 (d, J = 8.7 Hz, 2H), 2.68 (s, 2H), 2.35 (s, 3H), 2.16-2.06 (m, 1H), 1.89-1.74 (m, 3H), 1.39-1.21 (m, 1H). | 1.918 |
| 110 | $^1$H NMR (400 MHz, Chloroform-d) δ 8.36 (s, 1H), 7.63 (d, J = 8.4 Hz, 1H), 7.49 (s, 1H), 7.44-7.30 (m, 1H), 7.04 (d, J = 11.0 Hz, 2H), 3.91 (d, | 1.584 |

TABLE 2-continued

| NMR data and LC-MS retention times of some of the compounds in Table 1 | | |
|---|---|---|
| Compound | NMR | LC-MS retention time (min) |
| | J = 15.3 Hz, 1H), 3.42 (s, 6H), 3.31 (d, J = 15.2 Hz, 1H), 3.05-2.89 (m, 2H), 2.78 (d, J = 16.4 Hz, 2H), 2.45 (s, 3H), 2.09 (t, J = 10.5 Hz, 1H), 1.96 (m, 3H), 1.36-1.18 (m, 1H). | |
| 112 | $^1$H NMR (400 MHz, Chloroform-d) δ 8.40 (s, 1H), 7.37 (t, J = 9.0 Hz, 1H), 6.99 (d, J = 30.8 Hz, 2H), 6.62 (s, 1H), 3.87 (s, 1H), 3.48-3.13 (m, 7H), 3.02-2.93 (m, 1H), 2.89 (s, 1H), 2.75 (s, 2H), 2.44 (s, 3H), 2.05 (d, J = 9.6 Hz, 1H), 1.98-1.78 (m, 3H), 1.25 (m, 1H). | 1.848 |
| 121 | $^1$H NMR (400 MHz, Chloroform-d) δ 8.32 (s, 1H), 7.60 (d, J = 8.5 Hz, 1H), 7.50 (s, 1H), 7.41 (s, 1H), 7.14-6.92 (m, 3H), 3.91 (d, J = 15.2 Hz, 1H), 3.85 (d, J = 2.5 Hz, 3H), 3.42 (d, J = 2.5 Hz, 6H), 3.30 (d, J = 15.2 Hz, 1H), 3.04-2.88 (m, 2H), 2.78 (d, J = 15.0 Hz, 2H), 2.43 (d, J = 2.5 Hz, 3H), 2.07 (t, J = 10.4 Hz, 1H), 1.95 (m, 3H), 1.28 (m, 1H). | 1.769 |
| 295 | $^1$H NMR (400 MHz, Chloroform-d) δ 8.33 (s, 1H), 7.68-7.39 (m, 3H), 7.31 (d, J = 7.9 Hz, 1H), 7.06 (d, J = 21.5 Hz, 2H), 3.91 (d, J = 14.8 Hz, 1H), 3.37 (s, 7H), 2.98 (dd, J = 20.8, 11.4 Hz, 2H), 2.77 (d, J = 22.9 Hz, 2H), 2.45 (s, 3H), 2.18 (s, 3H), 2.09 (t, J = 10.3 Hz, 1H), 1.95 (m, 3H), 1.28 (m, 1H). | 1.527 |
| 296 | $^1$H NMR (400 MHz, Chloroform-d) δ 8.37 (s, 1H), 7.63 (d, J = 8.4 Hz, 1H), 7.52 (s, 2H), 7.31 (s, 1H), 7.04 (d, J = 11.8 Hz, 2H), 3.91 (d, J = 15.3 Hz, 1H), 3.42 (d, J = 1.7 Hz, 6H), 3.31 (d, J = 15.3 Hz, 1H), 2.98 (t, J = 15.5 Hz, 2H), 2.78 (d, J = 22.3 Hz, 2H), 2.45 (s, 3H), 2.09 (t, J = 10.5 Hz, 1H), 1.92 (m, 3H), 1.29 (m, 1H). | 1.873 |

Example 297. In-Vitro Assay of the Compounds of the Present Invention for Inhibiting Enzymatic Activity of Recombinant Protein Wee-1

The inhibitory effect of the compounds on the enzyme activity of recombinant protein Wee-1 was determined by HTRF. The procedures are as follows:

After DMSO or serially diluted compounds (up to 200 nM, 1:5 serially diluted) and recombinant proteins were co-incubated in a kinase buffer at 37° C. for 30 min Fluorescein-PolyGAT and ATP were added, and then the reaction was started by the addition of a substrate. After incubation at room temperature for 90 min, an antibody and a detection solution were added, and after further incubation at room temperature for 60 min, fluorescence values were detected (excitation wavelength: 340 nm, emission wavelengths: 495 and 520 nm). The 520 nm/495 nm fluorescence intensity ratio value was calculated, and compared with that of the DMSO group, and then the inhibition percentages and $IC_{50}$ values of the compounds were calculated. The results are shown in Table 3 below.

TABLE 3

Inhibitory activity of the compounds of the present invention against recombinant protein Wee-1

| Compound | ($IC_{50}$) | Compound | ($IC_{50}$) | Compound | ($IC_{50}$) | Compound | ($IC_{50}$) |
|---|---|---|---|---|---|---|---|
| 1 | +++ | 2 | +++ | 3 | +++ | 4 | +++ |
| 5 | +++ | 6 | +++ | 7 | +++ | 8 | +++ |
| 9 | +++ | 10 | +++ | 11 | +++ | 12 | +++ |
| 13 | +++ | 14 | +++ | 15 | +++ | 16 | +++ |
| 17 | +++ | 18 | +++ | 19 | +++ | 20 | +++ |
| 21 | +++ | 22 | +++ | 23 | +++ | 24 | +++ |
| 25 | +++ | 26 | +++ | 27 | +++ | 28 | +++ |
| 29 | +++ | 30 | +++ | 31 | +++ | 32 | +++ |
| 33 | +++ | 34 | +++ | 35 | +++ | 36 | +++ |
| 37 | +++ | 38 | +++ | 39 | +++ | 40 | +++ |
| 41 | +++ | 42 | +++ | 43 | +++ | 44 | +++ |
| 45 | +++ | 46 | +++ | 47 | +++ | 48 | +++ |
| 49 | ++ | 50 | ++ | 51 | ++ | 52 | ++ |
| 53 | ++ | 54 | ++ | 55 | ++ | 56 | ++ |
| 57 | +++ | 58 | +++ | 59 | +++ | 60 | +++ |

TABLE 3-continued

Inhibitory activity of the compounds of the present invention against recombinant protein Wee-1

| Compound | ($IC_{50}$) | Compound | ($IC_{50}$) | Compound | ($IC_{50}$) | Compound | ($IC_{50}$) |
|---|---|---|---|---|---|---|---|
| 61 | +++ | 62 | +++ | 63 | +++ | 64 | +++ |
| 65 | +++ | 66 | +++ | 67 | +++ | 68 | +++ |
| 69 | +++ | 70 | +++ | 71 | +++ | 72 | +++ |
| 73 | +++ | 74 | +++ | 75 | +++ | 76 | +++ |
| 77 | +++ | 78 | +++ | 79 | +++ | 80 | +++ |
| 81 | +++ | 82 | +++ | 83 | +++ | 84 | +++ |
| 85 | +++ | 86 | +++ | 87 | +++ | 88 | +++ |
| 89 | +++ | 90 | +++ | 91 | +++ | 92 | +++ |
| 93 | +++ | 94 | +++ | 95 | +++ | 96 | +++ |
| 97 | +++ | 98 | +++ | 99 | +++ | 100 | +++ |
| 101 | +++ | 102 | +++ | 103 | +++ | 104 | +++ |
| 105 | +++ | 106 | +++ | 107 | +++ | 108 | +++ |
| 111 | +++ | 112 | +++ | 113 | +++ | 114 | +++ |
| 115 | +++ | 116 | +++ | 117 | +++ | 118 | +++ |
| 119 | +++ | 120 | +++ | 121 | +++ | 122 | +++ |
| 123 | +++ | 124 | +++ | 125 | +++ | 126 | +++ |
| 127 | +++ | 128 | +++ | 129 | +++ | 130 | +++ |
| 131 | +++ | 132 | +++ | 133 | +++ | 134 | +++ |
| 135 | +++ | 136 | +++ | 137 | +++ | 138 | +++ |
| 139 | +++ | 279 | +++ | 280 | +++ | 289 | +++ |
| 290 | +++ | 291 | +++ | 292 | +++ | 293 | +++ |
| 294 | +++ | 295 | +++ | 296 | +++ | | |

+++ means that $IC_{50}$ is less than or equal to 10 nM
++ means that $IC_{50}$ is 10 nM to 50 nM
+ means that $IC_{50}$ is greater than 50 nM.

As can be seen from the data in Table 3, the compounds of the present invention have good inhibitory activity against the enzymatic activity of recombinant protein Wee-1.

Example 298. In-Vitro Anti-Proliferative Activity of the Compounds of the Present Invention on MIA PaCa-2 Cells MIA PaCa-2 cells were seeded on a 384-well plate at 3000 cells/well. After overnight adherence culture, DMSO or the compounds serially diluted 1:5 from 5 μM were added. The viability was assessed 72 h after dosing by measuring the intracellular ATP content. The inhibition percentage of viable cells by the compounds was calculated by comparing with the DMSO group, and the $IC_{50}$ value was calculated. The results are shown in Table 4 below.

TABLE 4

Anti-proliferative activity of the compounds of the present invention against MIA PaCa-2 cells

| Compound | $IC_{50}$ (nM) | Compound | $IC_{50}$ (nM) |
|---|---|---|---|
| 1 | 236 | 2 | 259 |
| 3 | 1090 | 4 | 968 |
| 5 | 1180 | 6 | 910 |
| 49 | >5000 | 50 | 148 |
| 64 | 400 | 87 | 184 |
| 105 | 441 | 108 | 225 |
| 110 | 186 | 112 | >5000 |
| 121 | 89 | 137 | >5000 |
| 295 | 72 | 296 | 161 |

As can be seen from the data in Table 4, the compounds of the present invention have strong anti-proliferative activity against MIA PaCa-2 cells.

Example 299. In-Vitro Anti-Proliferative Activity of the Compounds of the Present Invention in Combination with Gemcitabine on MIA PaCa-2 Cells MIA PaCa-2 cells were seeded on a 384-well plate at 3000 cells/well, and 20 nM gemcitabine was added. After overnight adherence culture, DMSO or the compounds serially diluted 1:5 from 100 nM were added. The viability was assessed 72 h after dosing by measuring the intracellular ATP content. The inhibition percentage of viable cells by the compounds was calculated by comparing with the DMSO group, and the $IC_{50}$ value was calculated. The results are shown in Table 5 below.

TABLE 5

In-vitro anti-proliferative activity of the compounds of the present invention in combination with gemcitabine on MIA PaCa-2 cells

| Compound | $IC_{50}$ (nM) | Compound | $IC_{50}$ (nM) |
|---|---|---|---|
| 1 | 1.9 | 2 | 0.245 |
| 3 | 6.4 | 4 | 2.4 |
| 5 | 2.1 | 6 | 5.3 |
| 49 | >100 | 50 | >100 |
| 64 | 3.5 | 87 | 1.6 |
| 105 | 2.1 | 108 | 11 |
| 110 | 1.1 | 112 | 29 |
| 121 | 1.4 | 137 | 26 |
| 295 | 1.5 | 296 | 3.1 |

As can be seen from the data in Table 5, the compounds of the present invention, in combination with gemcitabine, have strong anti-proliferative activity against MIA PaCa-2 cells in vitro.

Example 300. In-Vivo Pharmacodynamic Study—Mouse HT29 Subcutaneous Xenograft Tumor Model HT29 is a colon cancer cell. Each nude mouse was grafted subcutaneously with $5\times10^6$ HT29 cells. When the tumor grew to 100-200 $mm^3$, the compound was administered orally once a day alone or in combination with 15 mg/kg of gemcitabine injected intraperitoneally once a week, and the tumor volume was measured twice a week and at the end of treatment. Tumor growth inhibition of the compound was calculated according to the following equation: tumor growth inhibition (TGI)=1−(tumor volume on day 18 in treatment group−tumor volume on day 1 in treatment group)/(tumor volume on day 18 in vehicle control group−tumor volume on day 1 in treatment group). The results are shown in Tables 6 and 7.

TABLE 6

Growth inhibition in mouse HT29 subcutaneous xenograft tumor - monotherapy

| Compound | Dose | Tumor volume on day 1 of treatment ($mm^3$) | Tumor volume on day 18 of treatment ($mm^3$) | TGI |
|---|---|---|---|---|
| Control | Not applicable | 112 | 1126 | Not applicable |
| Gemcitabine | 15 mg/kg | 112 | 539 | 57% |
| Compound 2 | 30 mg/kg | 112 | 115 | 99% |

TABLE 7

Growth inhibition in mouse HT29 subcutaneous xenograft tumor - in combination with 15 mg/kg of gemcitabine

| Compound | Dose | Tumor volume on day 1 of treatment ($mm^3$) | Tumor volume on day 18 of treatment ($mm^3$) | TGI |
|---|---|---|---|---|
| Control | Not applicable | 112 | 1126 | Not applicable |
| Gemcitabine | 15 mg/kg | 112 | 539 | 57% |
| Compound 2 | 30 mg/kg | 112 | 11 | 109% |

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1) or a stereoisomer, a crystalline form, a pharmaceutically acceptable salt, a hydrate or a solvate thereof:

(1)

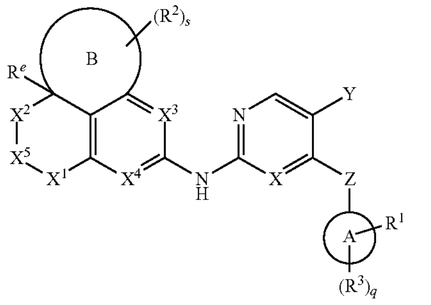

wherein in general formula (1):

X is CH or N;

Y is —H, a halogen, —CN, $—S(O)_2R^6$, $—P(O)(R^7)_2$, $—C(O)NR^8R^9$, (C1-C6) alkyl, (C1-C6) haloalkyl, (C2-C6) alkynyl, (C3-C14) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkynyl, (C3-C14) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)$~$OR^8$—, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

Z is a chemical bond, —$CH_2$—, —O— or —NH—;

ring A is (C6-C14) aryl, (5-14 membered) heteroaryl or (3-14 membered) heterocycloalkyl;

$R^1$ is

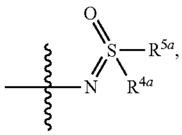,
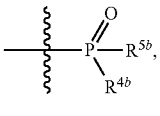,
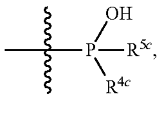,
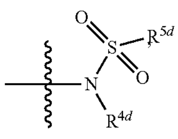
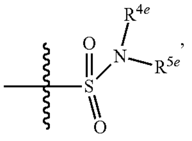,
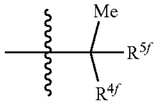 or 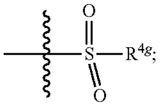;

$R^{4a}$ and $R^{5a}$ are each independently (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4a}$ and $R^{5a}$, together with the S atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4b}$ and $R^{5b}$ are each independently (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4b}$ and $R^{5b}$, together with the P atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4c}$ and $R^{5c}$ are each independently —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4c}$ and $R^{5c}$, together with the carbon atom to which they are attached, can form (3-7 membered) cycloalkyl, wherein the (3-7 membered) cycloalkyl may be optionally substituted with 1, 2, 3 or 4 of the following groups: —H, halogen, $R^8$, —$OR^8$, —$NR^8R^9$ and —CN;

$R^{4d}$ is —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; and $R^{5d}$ is (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl, or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4d}$ and $R^{5d}$, together with the atoms to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4e}$ and $R^{5e}$ are each independently —H, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4e}$ and $R^{5e}$, together with the N atom to which they are attached, can form (4-7 membered) heterocycloalkyl, wherein the (4-7 membered) heterocycloalkyl may be optionally substituted with 1, 2, 3 or 4 of the following groups: —H, halogen, $R^8$, —$OR^8$, —$NR^8R^9$ and —CN;

$R^{4f}$ and $R^{5f}$ are each independently —H, a halogen, (C1-C6) alkyl, (C1-C6) haloalkyl, (C2-C6) alkenyl or (C3-C6) cycloalkyl, wherein the (C1-C6) alkyl, (C1-C6) haloalkyl, (C2-C6) alkenyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^{4f}$ and $R^{5f}$ together with the carbon atom to which they are attached, can form (3-7 membered) cycloalkyl, wherein the (3-7 membered) cycloalkyl may be optionally substituted with 1, 2, 3 or 4 of the following groups: —H, halogen, $R^8$, —$OR^8$, —$NR^8R^9$ and —CN;

$R^{4g}$ is (C1-C3) alkyl or (C3-C6) cycloalkyl, wherein the (C1-C3) alkyl or (C3-C6) cycloalkyl may be each independently and optionally substituted with 1, 2, 3 or 4 of the following groups: —H, -D, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

each $R^3$ is independently —H, -D, a halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or 2 adjacent $R^3$, together with the atoms to which they are attached, can form (5-9 membered) heterocycloalkyl or (C5-C9) cycloalkyl, wherein the (5-9 membered) heterocycloalkyl or (C5-C9) cycloalkyl may be optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

ring B is (C5-C11) partially unsaturated cycloalkyl or (5-11 membered) partially unsaturated heterocycloalkyl;

$X^1$ is

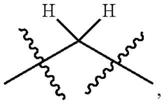, 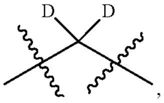, 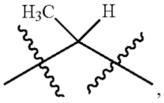,
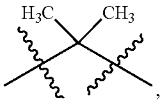, 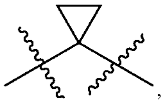, 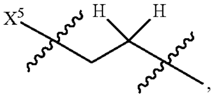,
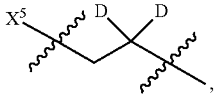, 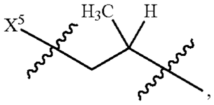,
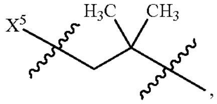, 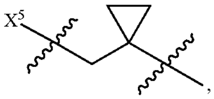,
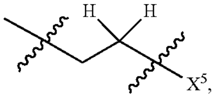, 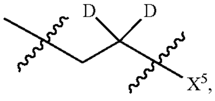,
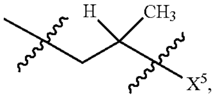, 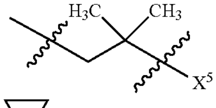 or
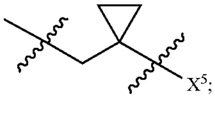;

$X^2$ is a chemical bond,

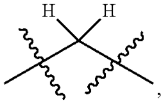, 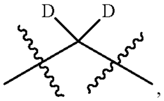, 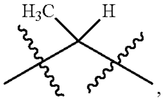,

-continued

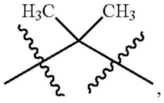, 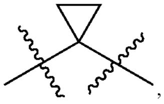, 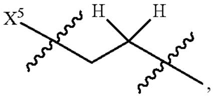,
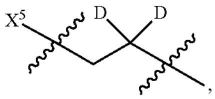, 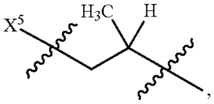,
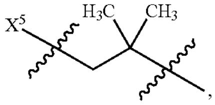, 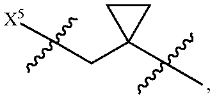,
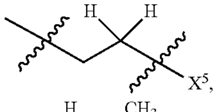, 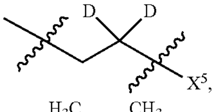,
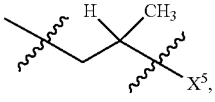, 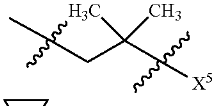 or
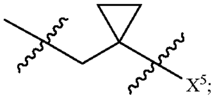;

$X^3$ is CH, N or C—$R^c$;

$X^4$ is CH, N or C—$R^d$;

$X^5$ is N—Ra or CH—$R^b$;

each $R^2$ is independently —H, -D, a halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or 2 adjacent $R^2$, together with the atoms to which they are attached, can form (5-7 membered) heterocycloalkyl or (C3-C9) cycloalkyl, wherein the (5-7 membered) heterocycloalkyl or (C3-C9) cycloalkyl may be optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or 2 $R^2$ on the same carbon atom of ring B, together with the carbon atom to which they are attached, can form (4-7 membered) heterocycloalkyl or (C3-C6) cycloalkyl, wherein the (4-7 membered) heterocycloalkyl or (C3-C6) cycloalkyl may be optionally substituted with 1, 2, 3 or 4 of the following groups: —H, halogen, $R^8$, —OH, —$(CH_2)_nOR^8$, —$(CH_2)_nNR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$; or $R^2$ and an adjacent $R^e$, together with the atoms to which they are attached, can form (5-7 membered) heterocycloalkyl or (C3-C9) cycloalkyl, wherein the (5-7 membered) heterocycloalkyl or (C3-C9) cycloalkyl may be optionally substituted with 1, 2, 3 or 4 of the following groups: —H, halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^a$ is —H, $R^8$, —$(CH_2)_m$$OR^8$, —$(CH_2)_m$$NR^8R^9$, (C1-C6) alkyl, (C1-C6) haloalkyl, (C3-C14) cycloalkyl or (3-15 membered) heterocycloalkyl, wherein the (C1-C6) alkyl, (C1-C6) haloalkyl, (C3-C14) cycloalkyl or (3-15 membered) heterocycloalkyl may be optionally substituted with 1, 2, 3 or 4 of the following groups: —H, -D, halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^b$ is —H, $R^8$, —$(CH_2)_n$$OR^8$, —$(CH_2)_n$$NR^8R^9$, (C1-C6) alkyl, (C1-C6) haloalkyl, (C3-C14) cycloalkyl or (3-15 membered) heterocycloalkyl, wherein the $R^8$, $R^9$, (C1-C6) alkyl, (C1-C6) haloalkyl, (C3-C14) cycloalkyl or (3-15 membered) heterocycloalkyl may be optionally substituted with 1, 2, 3 or 4 of the following groups: —H, -D, halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^c$ and $R^d$ are each independently —H, a halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^e$ is —H, -D, (C1-C6) alkyl, (C1-C6) haloalkyl, (C2-C6) alkenyl, (C2-C6) alkynyl, (C1-C6) alkoxy, (C1-C6) haloalkoxy, (C3-C9) cycloalkyl, (C6-C14) aryl, (3-11 membered) heterocycloalkyl or (5-11 membered) heteroaryl, wherein the (C1-C6) alkyl, (C1-C6) haloalkyl, (C2-C6) alkenyl, (C2-C6) alkynyl, (C1-C6) alkoxy, (C1-C6) haloalkoxy, (C3-C9) cycloalkyl, (C6-C14) aryl, (3-11 membered) heterocycloalkyl or (5-11 membered) heteroaryl may be each independently and optionally substituted with 1, 2, 3 or 4 of the following groups: —H, halogen, $R^8$, —OH, —$(CH_2)_n$$OR^8$, —$(CH_2)_n$$NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$ and —$S(O)_2NR^8R^9$;

$R^6$ is (C1-C3) alkyl or (C3-C6) cycloalkyl;

$R^7$ is (C1-C3) alkyl;

$R^8$ and $R^9$ are each independently —H, (C1-C6) alkyl or (C3-C14) cycloalkyl, or $R^8$ and $R^9$ on the same nitrogen atom, together with the N atom to which they are attached, can form (3-11 membered) heterocycloalkyl, wherein the (3-11 membered) heterocycloalkyl may be optionally substituted with 1, 2, 3 or 4 of the following groups: —H, halogen, $R^{10}$ and —$OR^{10}$;

$R^{10}$ is —H, (C1-C6) alkyl or (C3-C14) cycloalkyl;

$R^{11}$ and $R^{12}$ are each independently —H, (C1-C3) alkyl, (C1-C3) haloalkyl or (C3-C6) cycloalkyl, or $R^{11}$ and $R^{12}$ on the same nitrogen atom, together with the N atom to which they are attached, can form (4-6 membered) heterocycloalkyl;

p is an integer of 0, 1 or 2;

q is an integer of 1, 2, 3 or 4;

s is an integer of 1, 2, 3 or 4;

n is an integer of 0, 1, 2 or 3; and and m is an integer of 1, 2 or 3.

2. The compound or the stereoisomer, the crystalline form, the pharmaceutically acceptable salt, the hydrate or the solvate thereof according to claim 1, wherein in general formula (1), Y is —H, —F, —Cl, —Br, —I, —CN, —$S(O)_2CH_3$, —$P(O)(CH_3)_2$, —$C(O)NH_2$, (C1-C3) alkyl, (C1-C3) haloalkyl, (C3-C5) cycloalkyl, (C2-C3) alkynyl or (5-6 membered) heteroaryl, wherein the (5-6 membered) heteroaryl may be each independently and optionally substituted with 1, 2, 3 or 4 of the following groups: —H, —F, —CN, —$CH_3$ and —$OCH_3$; or in general formula (1), Y is: —H, —F, —Cl, —Br, —I, —CN, —$S(O)_2CH_3$, —P(O)$(CH_3)_2$, —$C(O)NH_2$, —$CH_3$, —$CF_3$,

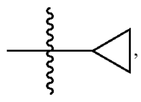, 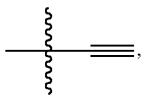, 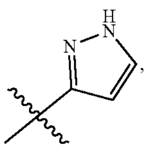,

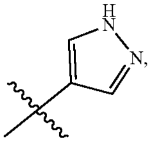, 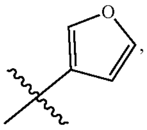, 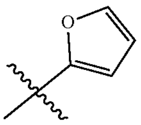 or

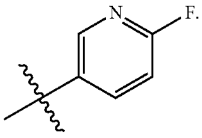

3. The compound or the stereoisomer, the crystalline form, the pharmaceutically acceptable salt, the hydrate or the solvate thereof according to claim 1, wherein in general formula (1), ring A is (C6-C10) aryl, (5-10 membered) heteroaryl or (5-10 membered) heterocycloalkyl; or in general formula (1), ring A is:

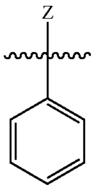, 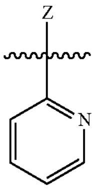, 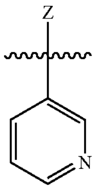, 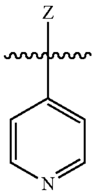,

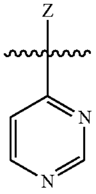, 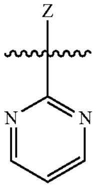, 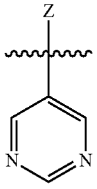, 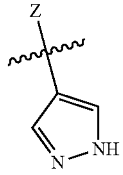,

-continued

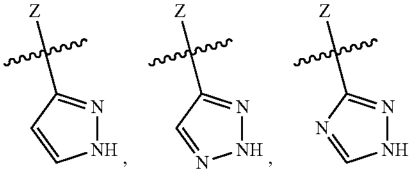,

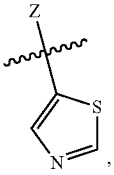, 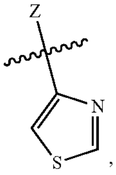, 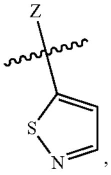, 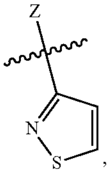,

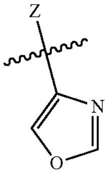, 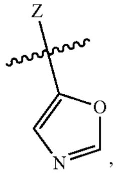, 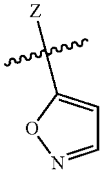, 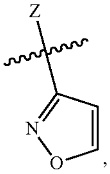,

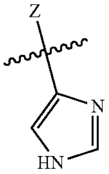, 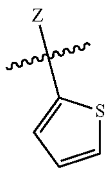, 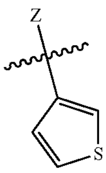, 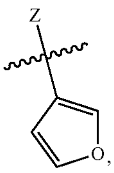,

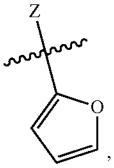, 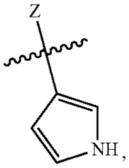, 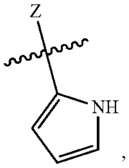, 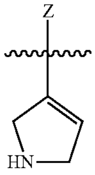,

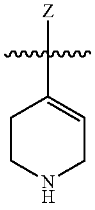, 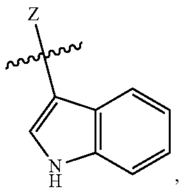, 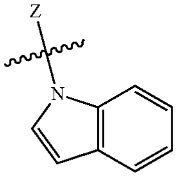,

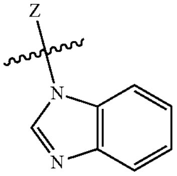, 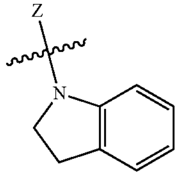,

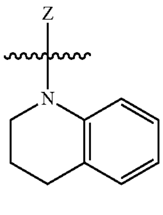, 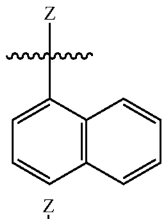,

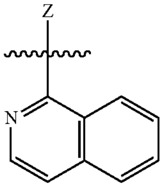, 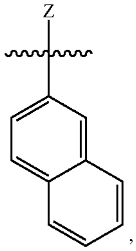, 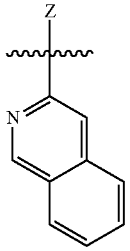,

-continued

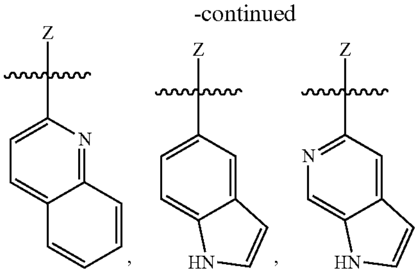,

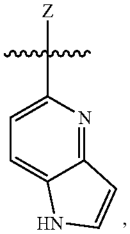, 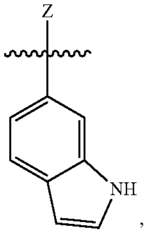, 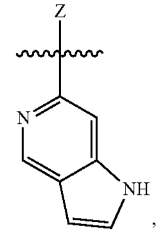,

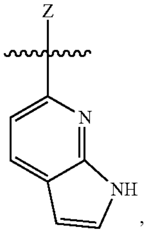, 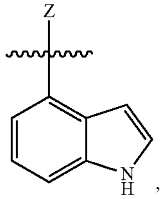, 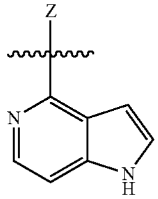,

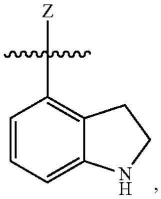, 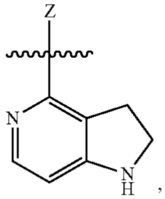, 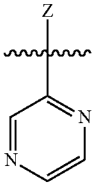 or

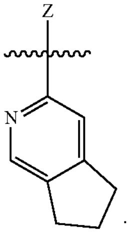.

4. The compound or the stereoisomer, the crystalline form, the pharmaceutically acceptable salt, the hydrate or the solvate thereof according to claim 1, wherein in general formula (1), when $R^1$ is

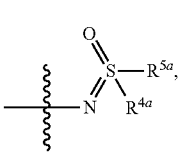

$R^{4a}$ and $R^{5a}$ are each independently (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4a}$ and $R^{5a}$, together with the S atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$OCH_3$, —$N(CH_3)_2$ and —CN; or in general formula (1), when $R^1$ is

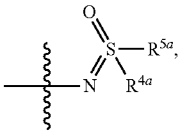

the structural unit is:

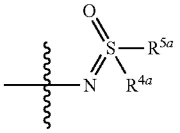

is:

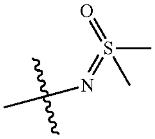

,

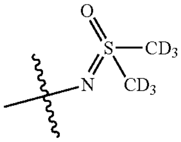

,

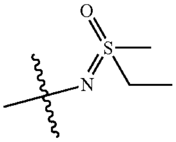

,

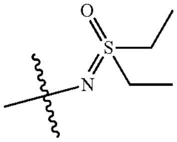

,

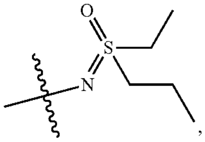

,

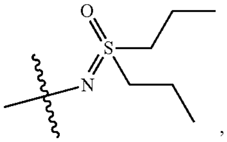

,

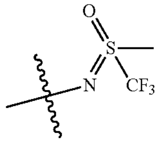

,

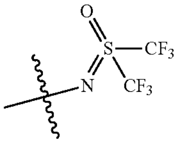

,

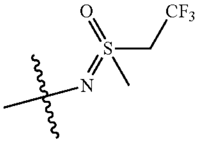

,

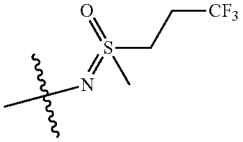

,

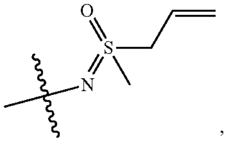

,

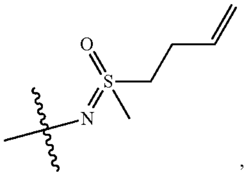

,

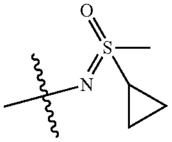

,

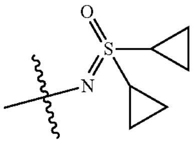

,

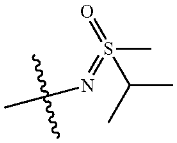

,

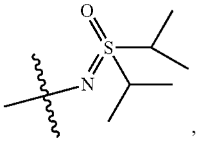

,

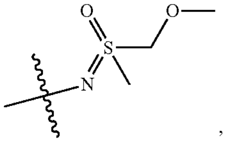

,

-continued

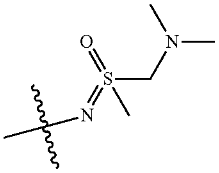

,

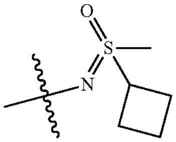

,

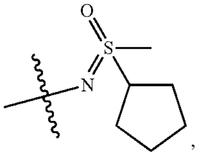

,

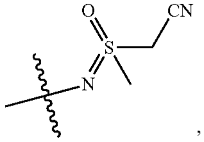

,

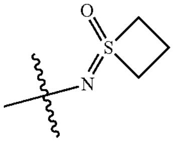

,

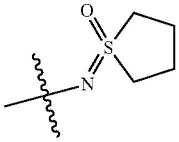

or

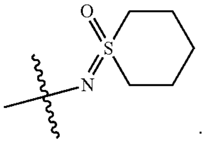

.

5. The compound or the stereoisomer, the crystalline form, the pharmaceutically acceptable salt, the hydrate or the solvate thereof according to claim 1, wherein in general formula (1), when $R^1$ is

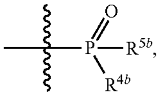

$R^{4b}$ and $R^{5b}$ are each independently (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4b}$ and $R^{5b}$, together with the P atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$OCH_3$, —$N(CH_3)_2$ and —CN; or in general formula (1), when $R^1$ is

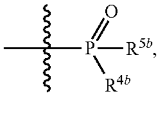

the structural unit

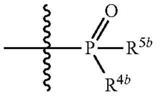

is:

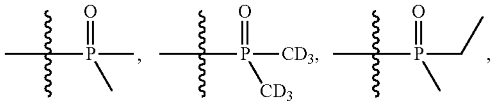
, , ,

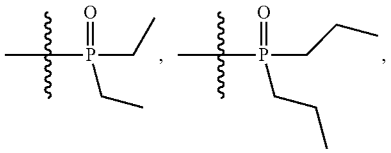
, ,

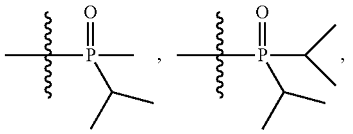
, ,

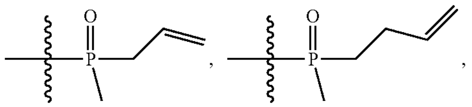
, ,

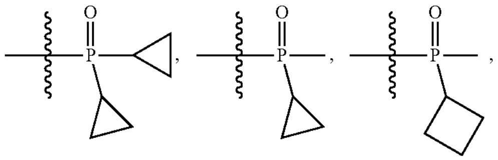
, , ,

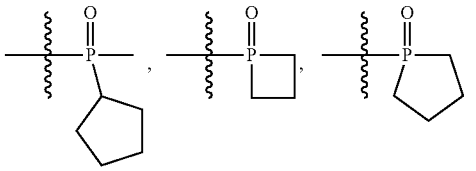
, , or

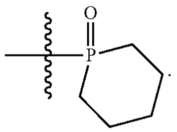
.

6. The compound or the stereoisomer, the crystalline form, the pharmaceutically acceptable salt, the hydrate or the solvate thereof according to claim 1, wherein in general formula (1), when $R^1$ is

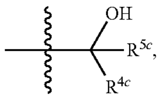
, $R^{4c}$ and $R^{5c}$ are each independently —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4c}$ and $R^{5c}$, together with the carbon atom to which they are attached, can form (3-6 membered) cycloalkyl, wherein the (3-6 membered) cycloalkyl may be optionally substituted with 1, 2, 3 or 4 of the following groups: —H, —F, —Cl, —Br, —I, —$CH_3$, —OH, —$OCH_3$, —$N(CH_3)_2$ and —CN; or in general formula (1), when $R^1$ is

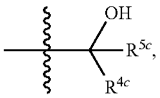
, the structural unit

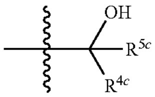

is:

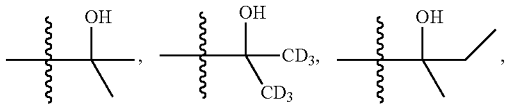
, , ,

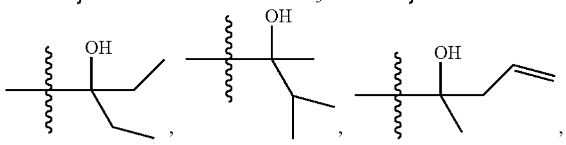
, , ,

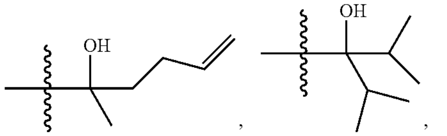
, ,

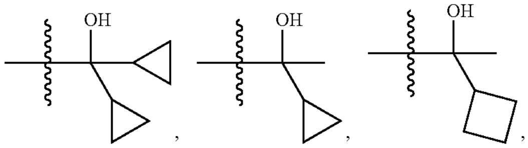
, , ,

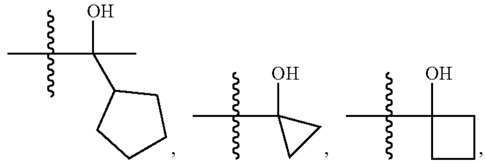
, , ,

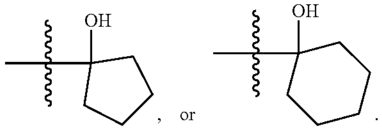
, or .

7. The compound or the stereoisomer, the crystalline form, the pharmaceutically acceptable salt, the hydrate or the solvate thereof according to claim 1, wherein in general formula (1), when $R^1$ is

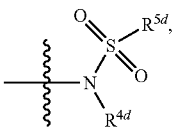
, $R^{4d}$ is —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; and $R^{5d}$ is (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4d}$ and $R^{5d}$, together with the atoms to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$OCH_3$, —$N(CH_3)_2$ and —CN; or in general formula (1), when $R^1$ is

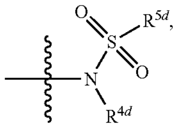

the structural unit

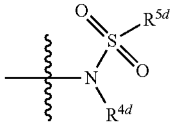

is:

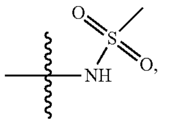 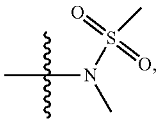 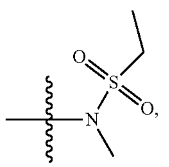

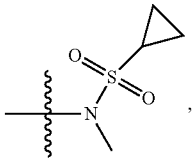 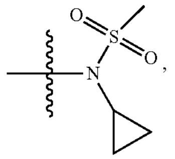

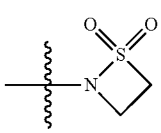 or 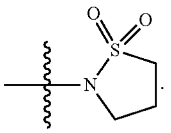

8. The compound or the stereoisomer, the crystalline form, the pharmaceutically acceptable salt, the hydrate or the solvate thereof according to claim 1, wherein in general formula (1), when $R^1$ is

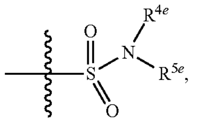

$R^{4e}$ and $R^{5e}$ are each independently —H, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$ and —CN; or $R^{4e}$ and $R^{5e}$, together with the N atom to which they are attached, can form (4-6 membered) heterocycloalkyl, wherein the (4-6 membered) heterocycloalkyl may be optionally substituted with 1, 2, 3 or 4 of the following groups: —H, —F, —Cl, —Br, —I, —$CH_3$, —OH, —$OCH_3$, —$N(CH_3)_2$ and —CN; or in general formula (1), when $R^1$ is

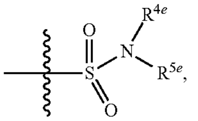

the structural unit

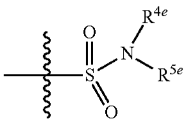

is:

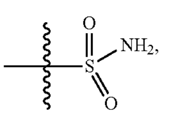 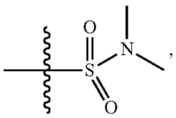

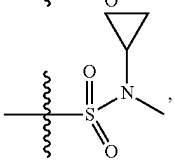 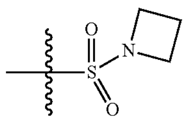 or

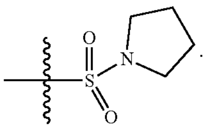

9. The compound or the stereoisomer, the crystalline form, the pharmaceutically acceptable salt, the hydrate or the solvate thereof according to claim 1, wherein in general formula (1), when $R^1$ is

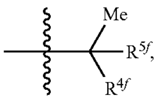

$R^{4f}$ and $R^{5f}$ are each independently —H, a halogen, (C1-C3) alkyl, (C1-C3) haloalkyl, (C2-C4) alkenyl or (C3-C5) cycloalkyl, wherein the (C1-C3) alkyl, (C1-C3) haloalkyl, (C2-C4) alkenyl or (C3-C5) cycloalkyl may be each independently and optionally substituted with 1, 2, 3 or 4 of the following groups: —H, -D, —F, —Cl, —Br, —I, —$CH_3$, —OH, —$OCH_3$, —$N(CH_3)_2$ and —CN; or $R^{4f}$ and $R^{5f}$ together with the carbon atom to which they are attached, can form (3-6 membered) cycloalkyl, wherein the (3-6 membered) cycloalkyl may be optionally substituted with 1, 2, 3 or 4 of the B following groups: —H, —F, —Cl, —Br, —I, —$CH_3$, —OH, —$OCH_3$, —$N(CH_3)_2$ and —CN; or in general formula (1), when $R^1$ is

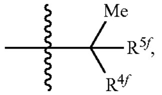

the structural unit

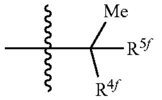

is:

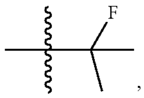
,
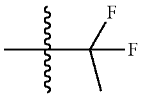
or
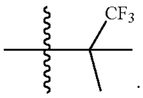
.

10. The compound or the stereoisomer, the crystalline form, the pharmaceutically acceptable salt, the hydrate or the solvate thereof according to claim 1, wherein in general formula (1), when $R^1$ is

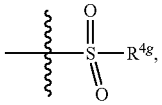

$R^{4g}$ is (C1-C3) alkyl or (C3-C5) cycloalkyl, wherein the (C1-C3) alkyl or (C3-C5) cycloalkyl may be each independently and optionally substituted with 1, 2, 3 or 4 of the following groups: —H, —F, —Cl, —Br, —I, —$CH_3$, —OH, —$CH_2CH_3$, —$CH_2N(CH_3)_2$, —$OCH_3$, —$N(CH_3)_2$ and —CN; or in general formula (1), when $R^1$ is

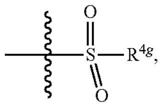

the structural unit

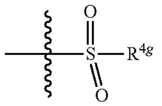

is:

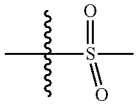
or
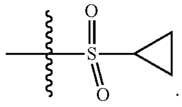
.

11. The compound or the i-ene stereoisomer, the crystalline form, the pharmaceutically acceptable salt, the hydrate or the solvate thereof according to claim 1, wherein in general formula (1), each $R^3$ is independently —H, -D, —F, —Cl, —Br, —I, —OH, —$CH_2OR^{11}$, —$CH_2NR^{11}R^{12}$, —$OR^{11}$, —$NR^{11}R^{12}$, —CN, —$C(O)NR^{11}R^{12}$, —$NR^{12}C(O)R^{11}$, —$NR^{12}S(O)_2R^{11}$, —$SR^{11}$, —$S(O)_2R^{11}$, —$S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl, wherein the (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl may be each independently and optionally substituted with 1, 2, 3 or 4 of the following groups: —H, —F, —Cl, —Br, —I, —OH, —$OCH_3$, —$N(CH_3)_2$ and —CN; or 2 adjacent $R^3$, together with the atoms to which they are attached, can form (5-7 membered) heterocycloalkyl or (C5-C7) cycloalkyl, wherein the (5-7 membered) heterocycloalkyl or (C5-C7) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or in general formula (1), each $R^3$ is independently: —H, -D, —F, —Cl, —Br, —I, —OH, —$CH_2OCH_3$, —$CH_2N(CH_3)_2$, —$OCH_3$, —$OCF_3$, —$N(CH_3)_2$, —CN, —$C(O)NH_2$, —$C(O)NH(CH_3)$, —$C(O)N(CH_3)_2$, —$NHC(O)CH_3$, —$N(CH_3)$—$C(O)CH_3$, —$NHS(O)_2CH_3$, —$NCH_3S(O)_2CH_3$, —$SCH_3$, —$S(O)_2CH_3$, —$S(O)_2NH_2$, —$S(O)_2NH(CH_3)$, —$S(O)_2N(CH_3)_2$,

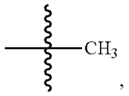
,
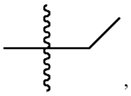
,
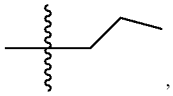
,
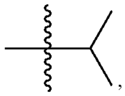
,
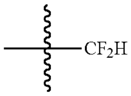
,
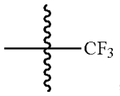
,
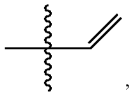
,
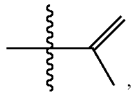
,
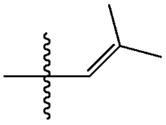
,
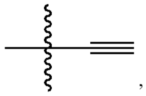
,
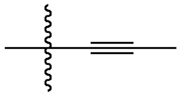
,
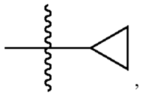
,
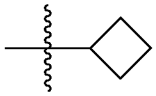
,
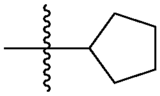
,
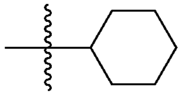
,
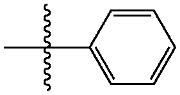
,
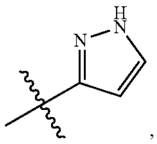
,
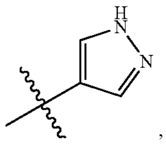
,
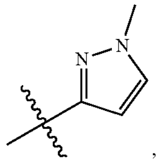
, -continued
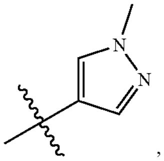, 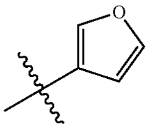, 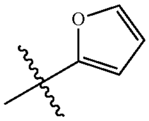,
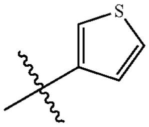, 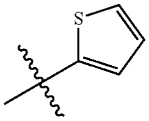, 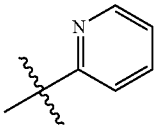,
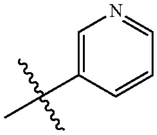, 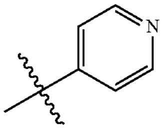,
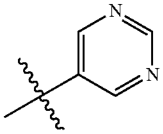, 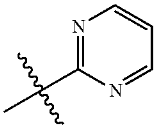, 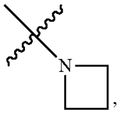,
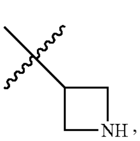, 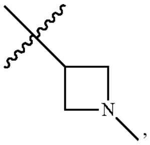, 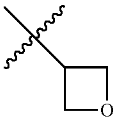,
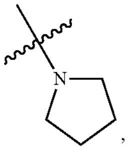, 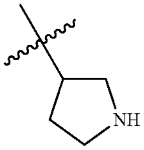, 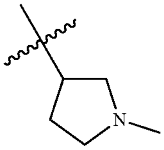,
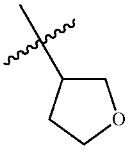, 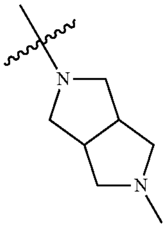, 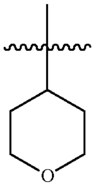,
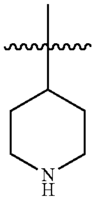, 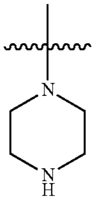, 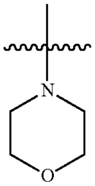, 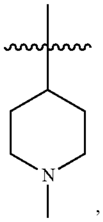,
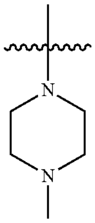 or 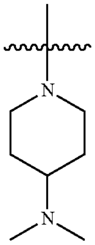.
12. The compound or the stereoisomer, the crystalline form, the pharmaceutically acceptable salt, the hydrate or the solvate thereof according to claim 1, wherein in general formula (1), the structural unit
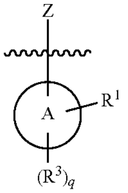
is
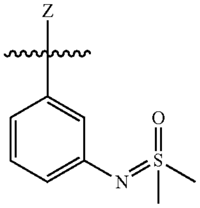, 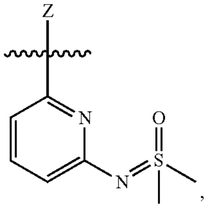,
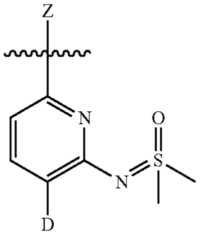, 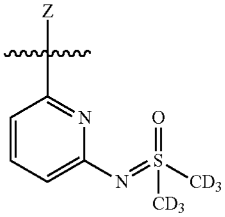,
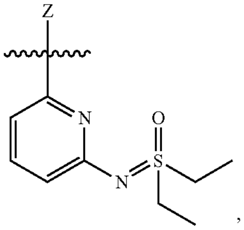,
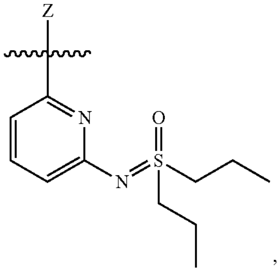,
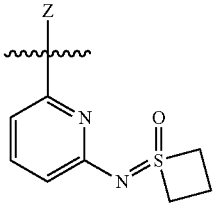, 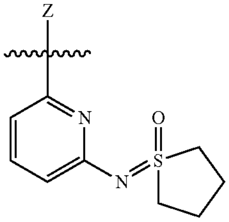,
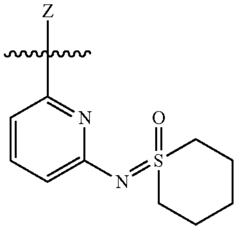, 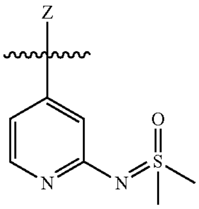, -continued
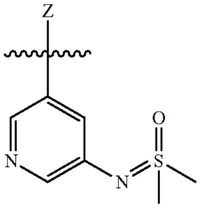,
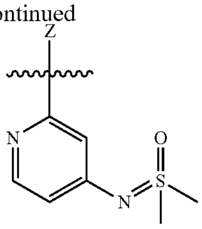,
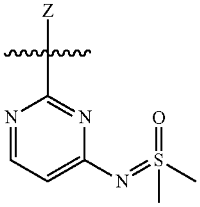,
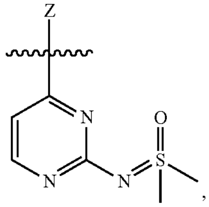,
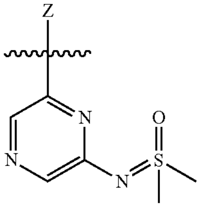,
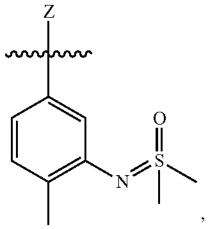,
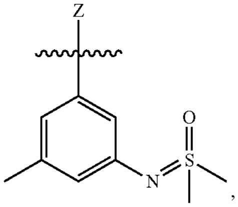,
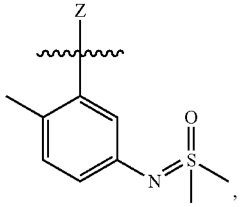,
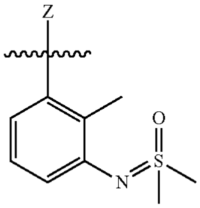,
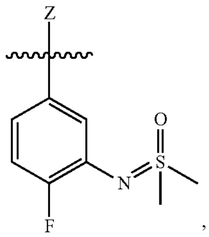,
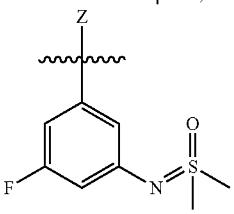,
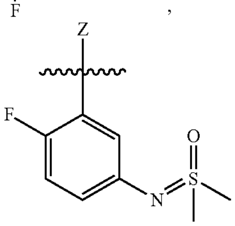,
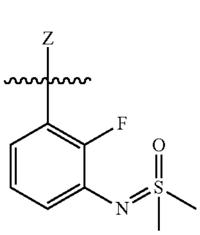,
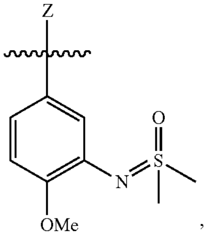,
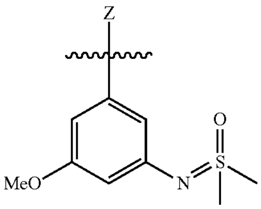,
-continued
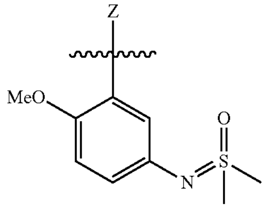,
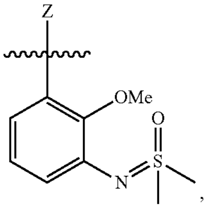,
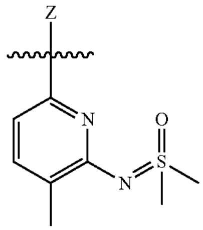,
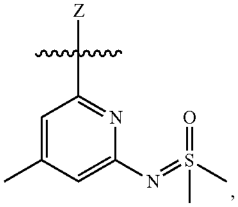,
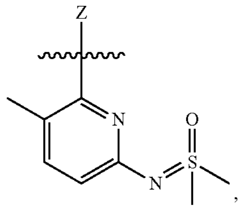,
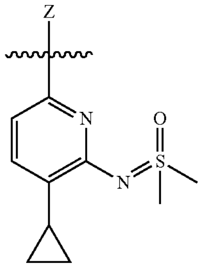,
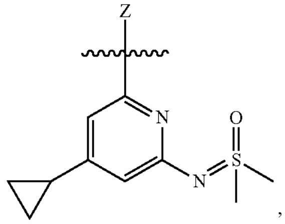,
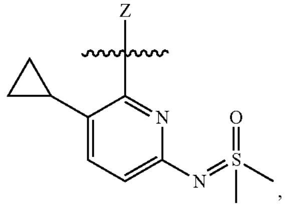,
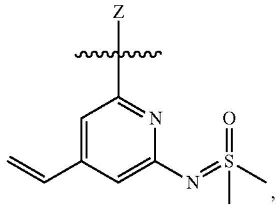,
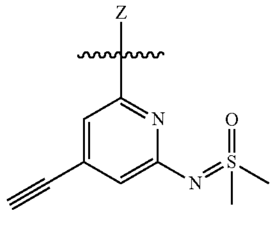,
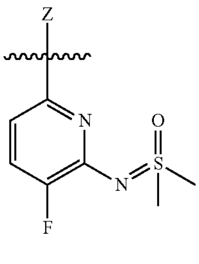, -continued
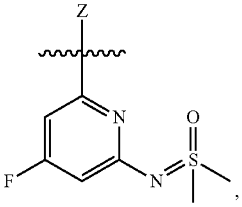,
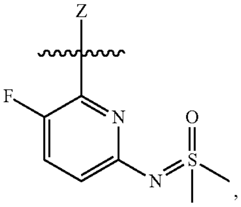,
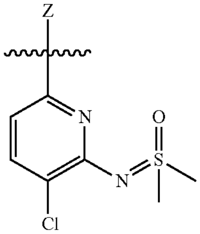,
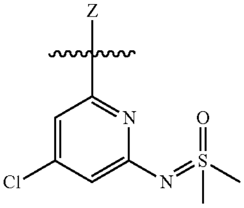,
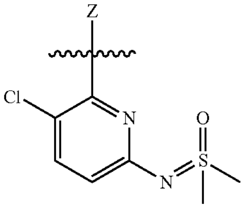,
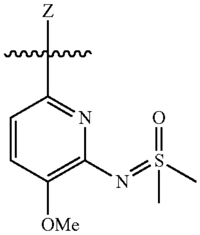,
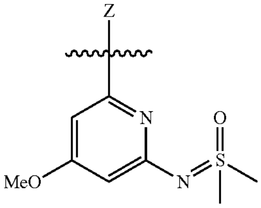,
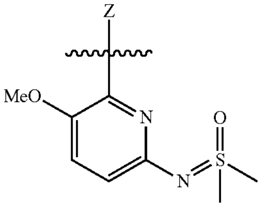,
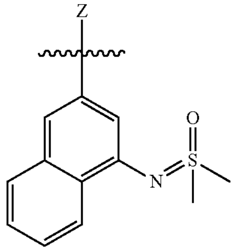,
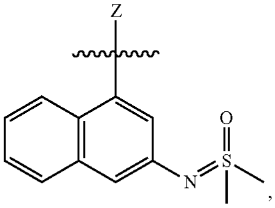,
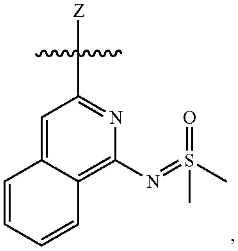,
-continued
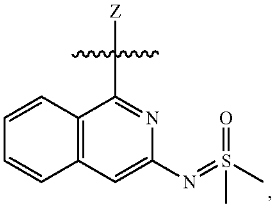,
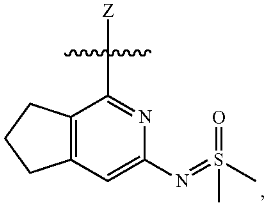,
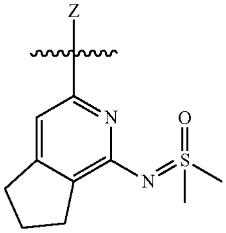,
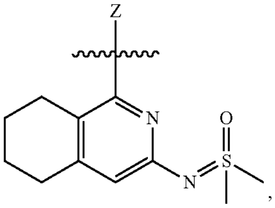,
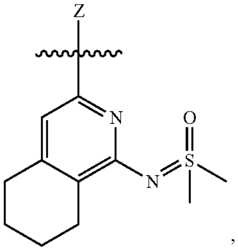,
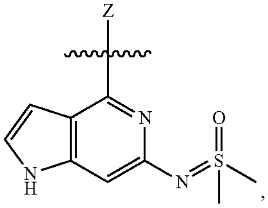,
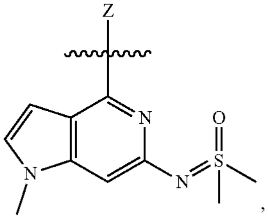,
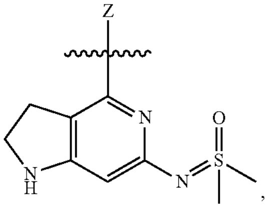, -continued
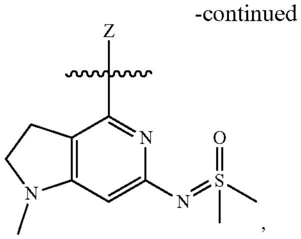
,
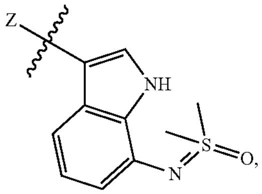
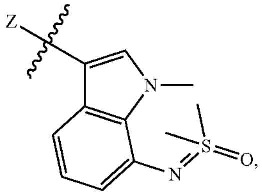
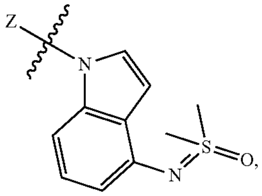
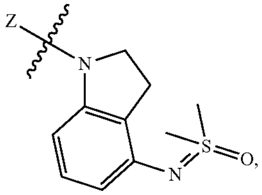
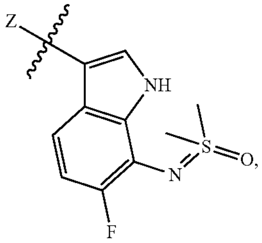
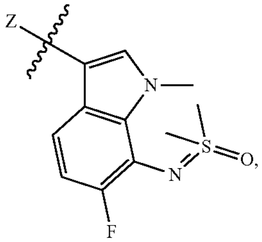
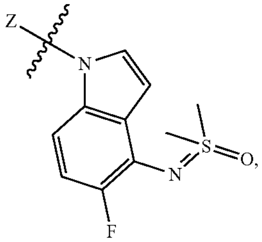
-continued
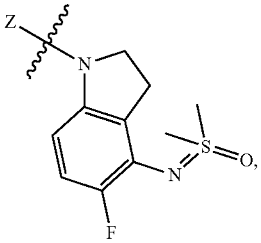
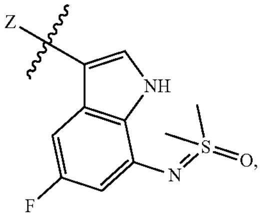
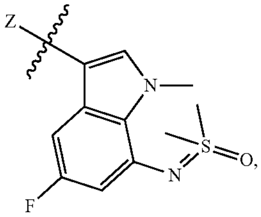
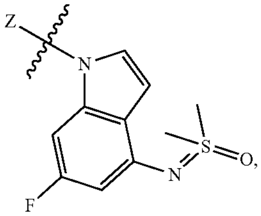
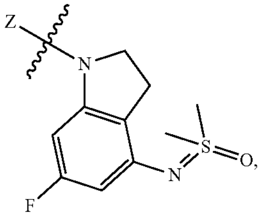
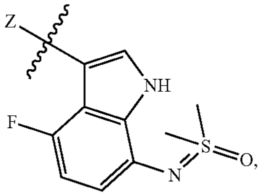
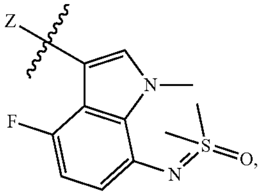
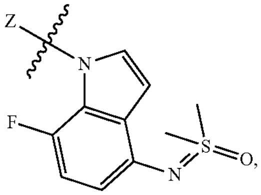

-continued
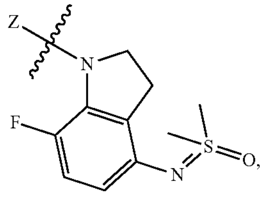
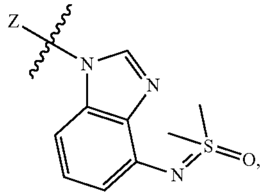
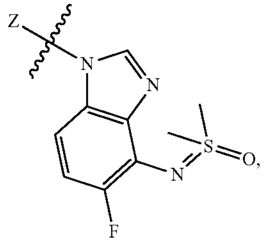
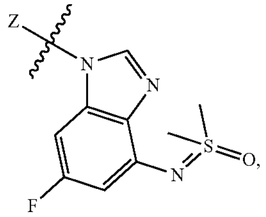
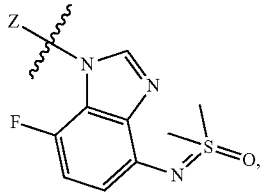
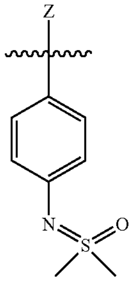 ,
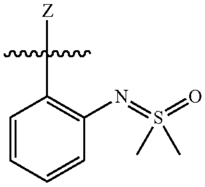 ,
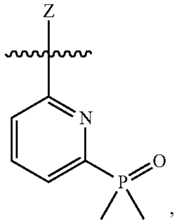 ,
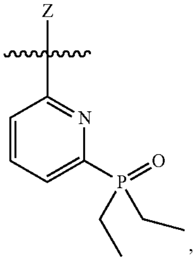 ,
-continued
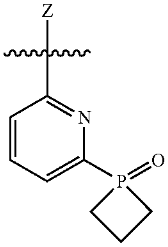 ,
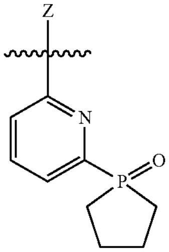 ,
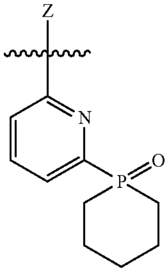 ,
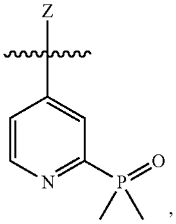 ,
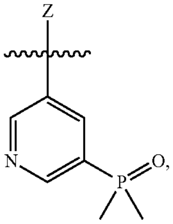
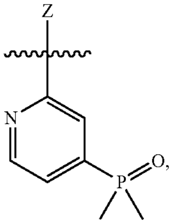
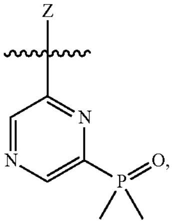
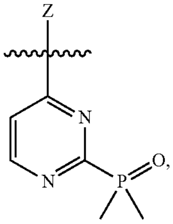
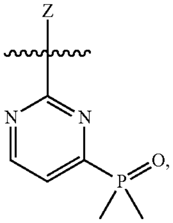
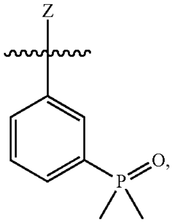
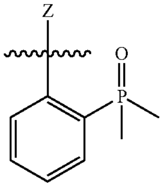 ,
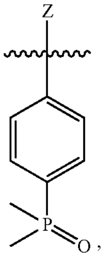
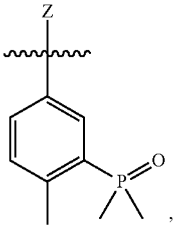 ,
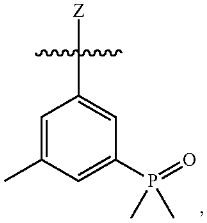 ,
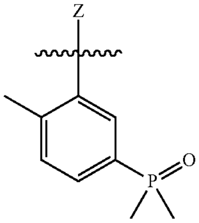 , -continued
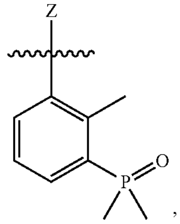,
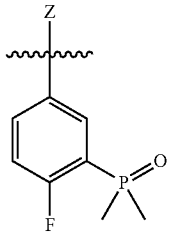,
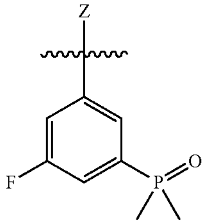,
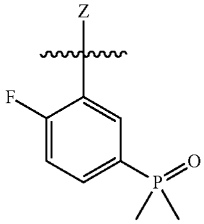,
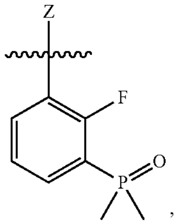,
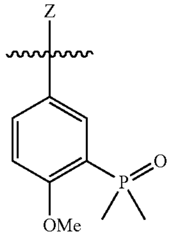,
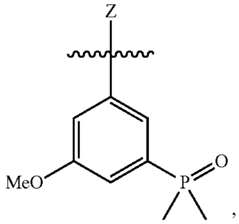,
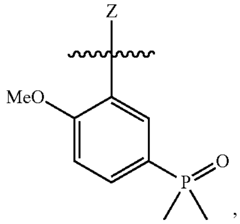,
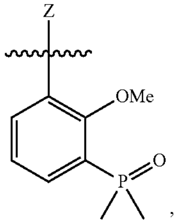,
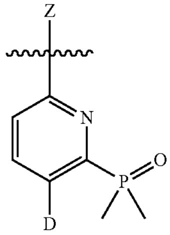,
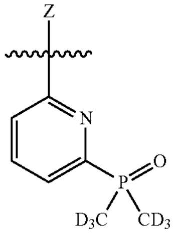,
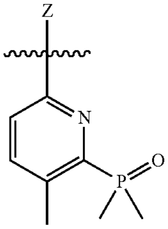,
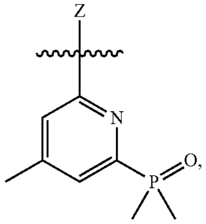
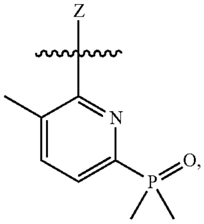
-continued
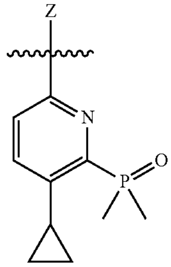,
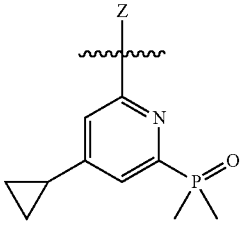,
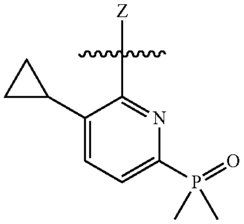,
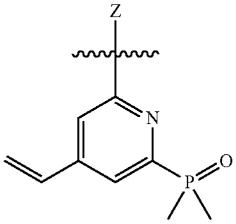,
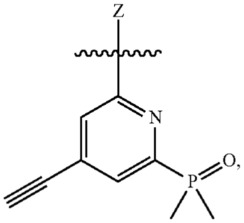
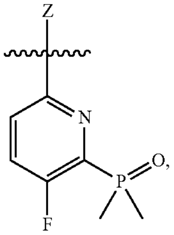
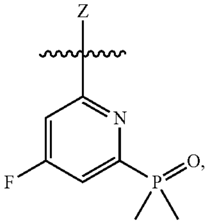
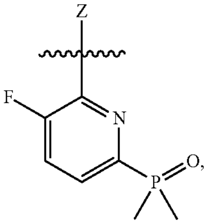
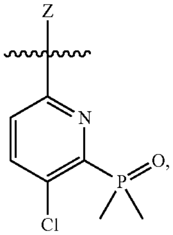
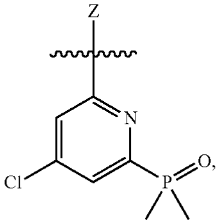
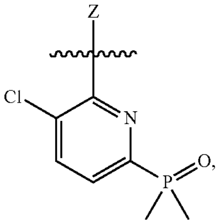
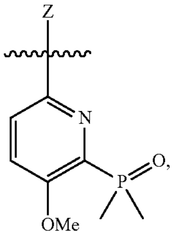
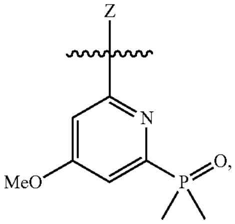
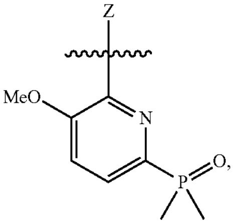

-continued
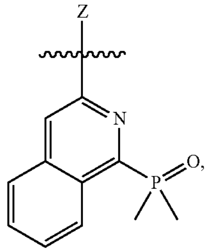
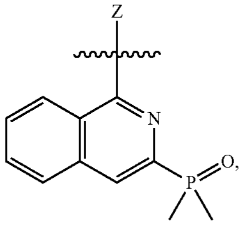
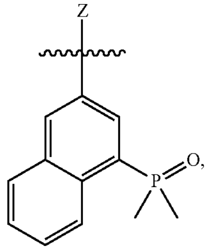
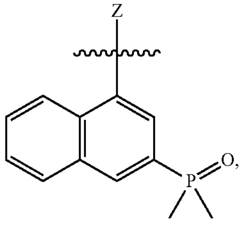
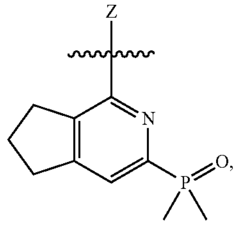
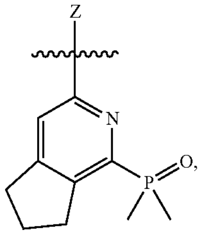
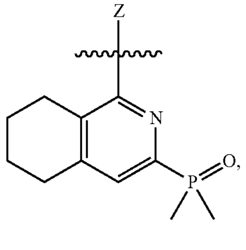
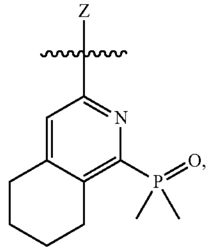
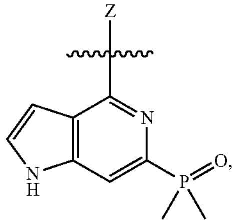
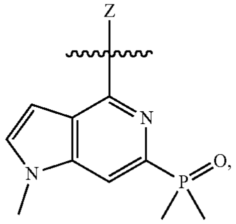
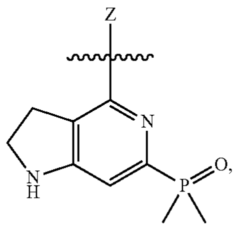
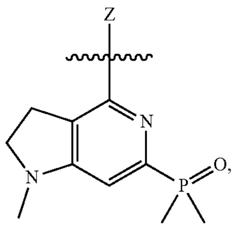
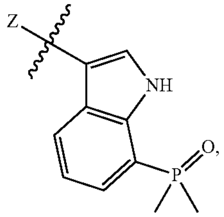
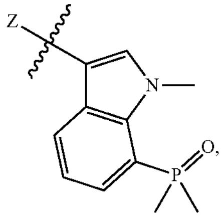
-continued
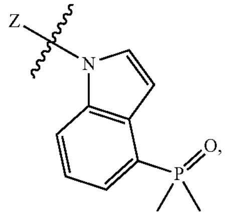
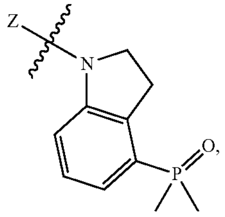
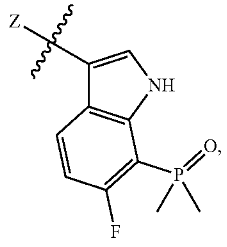
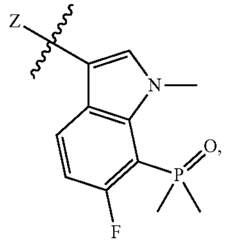
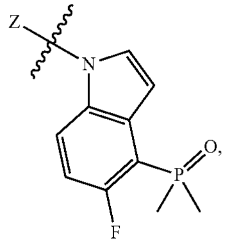
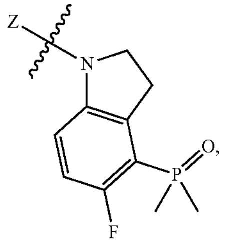
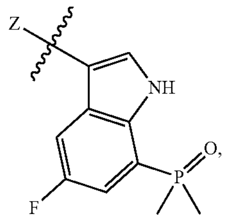
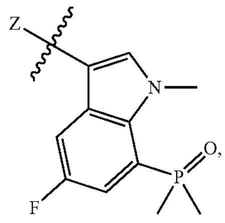
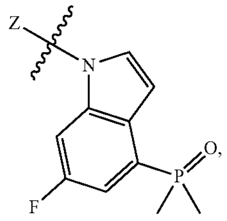
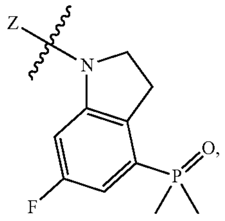
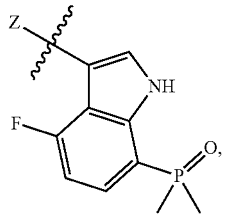
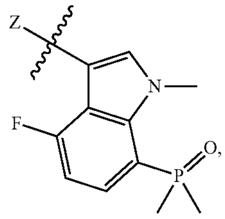
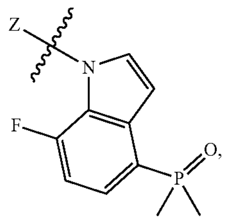
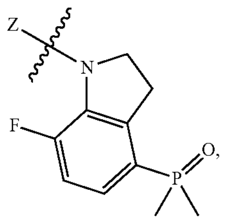

-continued

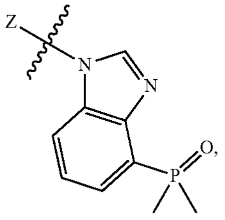
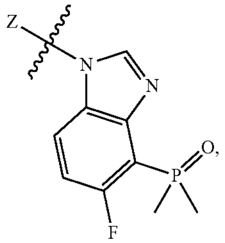
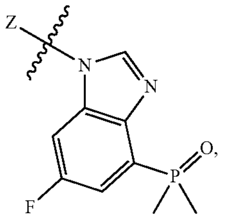
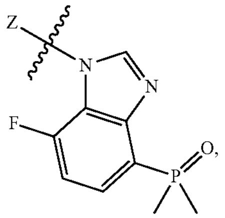
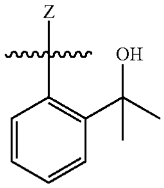
,
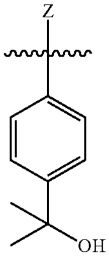
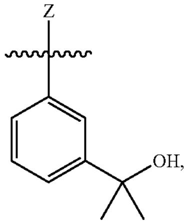
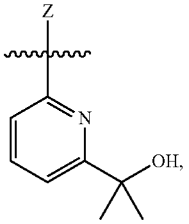
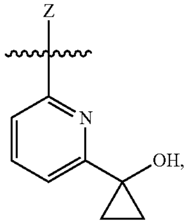
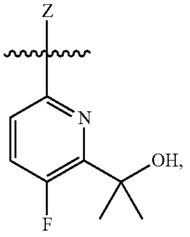
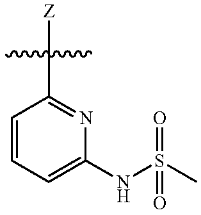
,
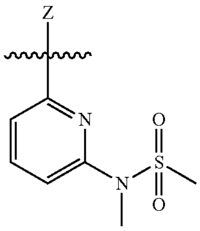
,
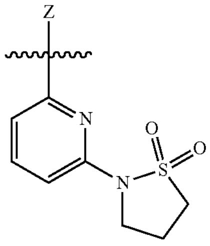
,
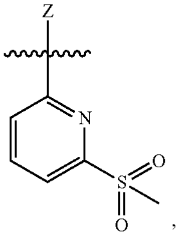
, -continued

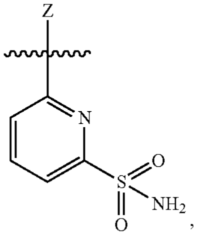
,
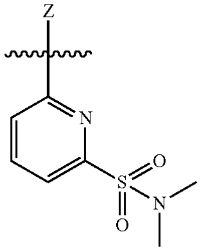
,
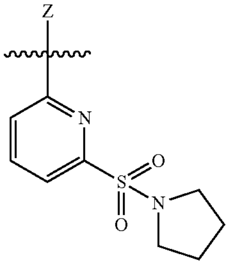
,
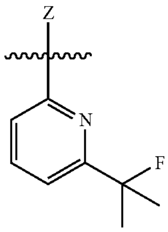
,
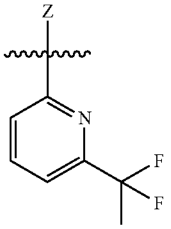
or
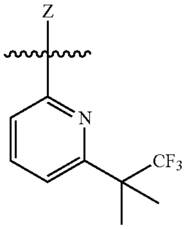
.

13. The compound or the stereoisomer, the crystalline form, the pharmaceutically acceptable salt, the hydrate or the solvate thereof according to claim 1, wherein in general formula (1), ring B is (C5-C8) partially unsaturated cycloalkyl or (5-8 membered) partially unsaturated heterocycloalkyl; and $R^e$ is: —H, -D, —$CH_3$, —$OCH_3$ or —$CH_2CH_3$.

14. The compound or the stereoisomer, the crystalline form, the pharmaceutically acceptable salt, the hydrate or the solvate thereof according to claim 13, wherein in general formula (1), the structural unit

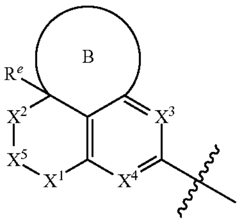
is:

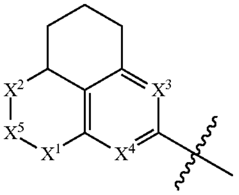
,
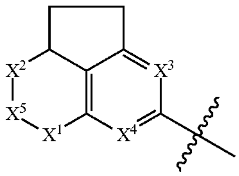
,
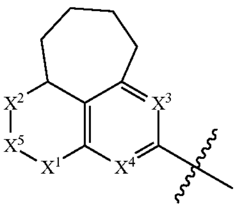
,
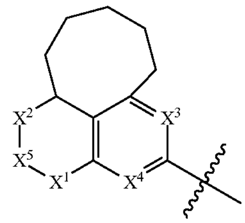
,

-continued
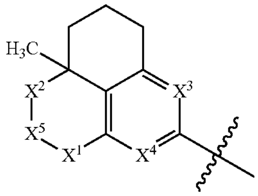
,
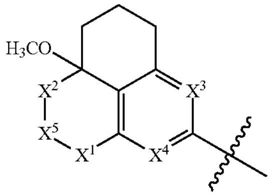
,
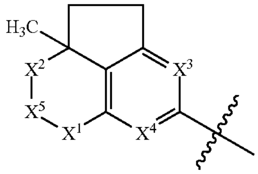
,
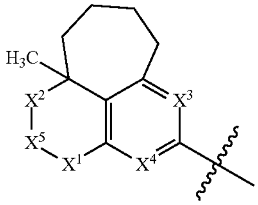
,
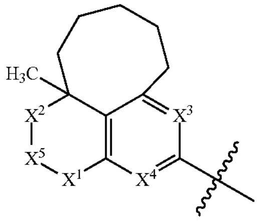
,
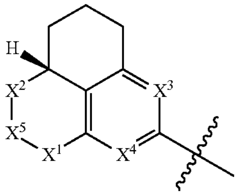
,
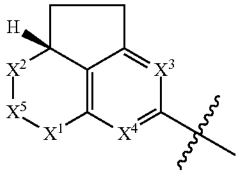
,
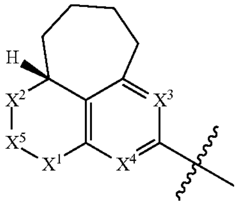
,
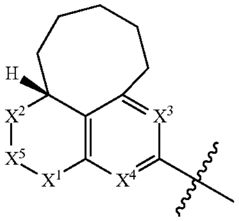
,
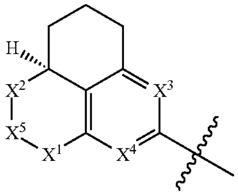
,
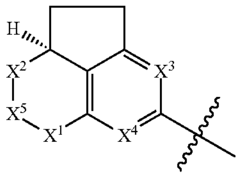
,
-continued
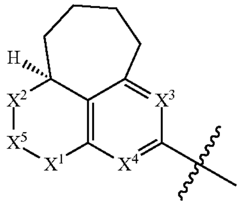
,
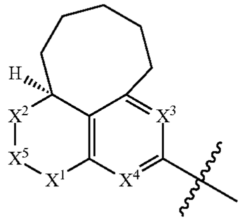
,
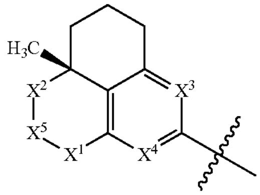
,
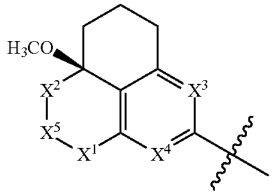
,
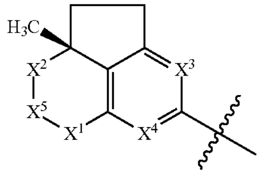
,
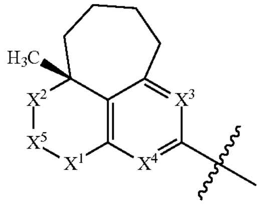
,
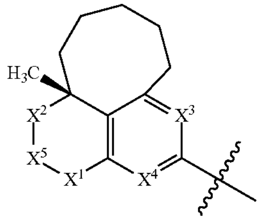
,
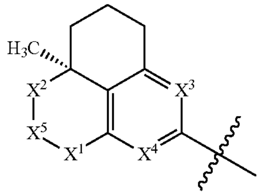
,
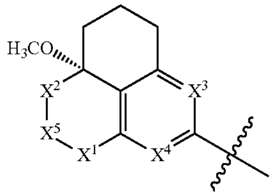
, -continued
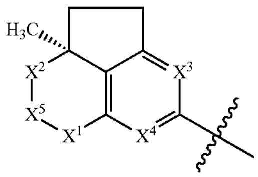,
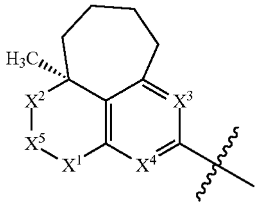,
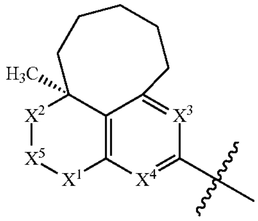,
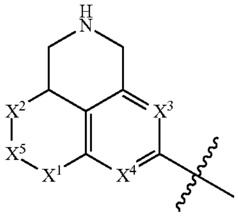,
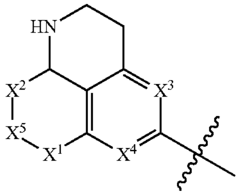,
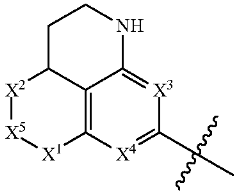,
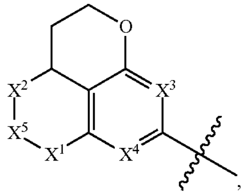,
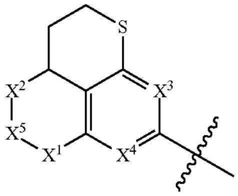,
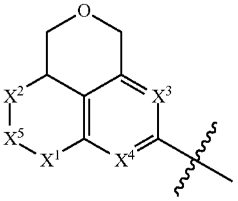,
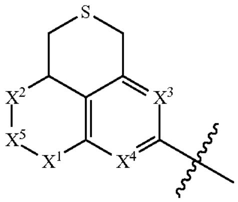,
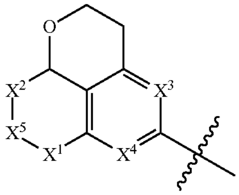,
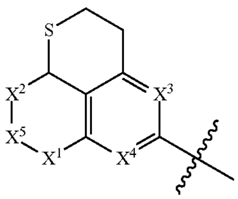,
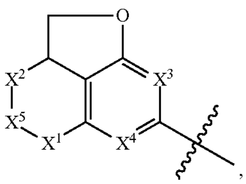,
-continued
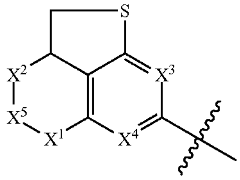,
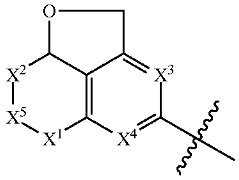,
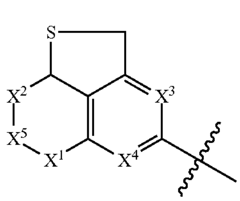,
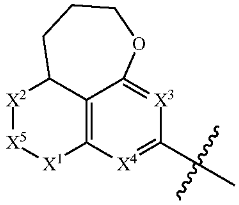,
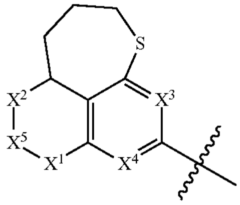,
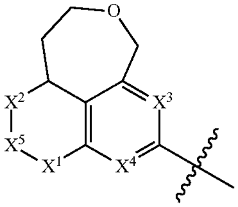,
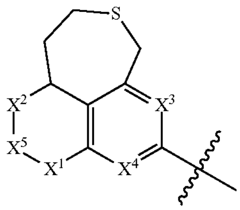,
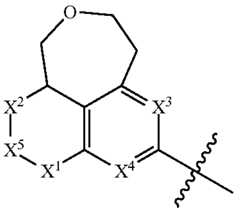,
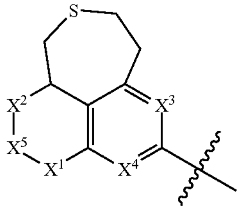,
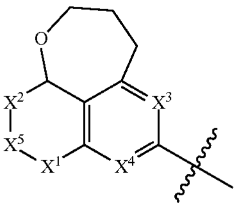,
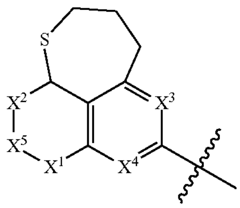,
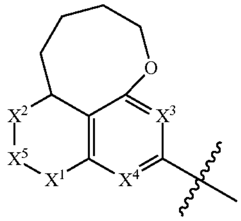,
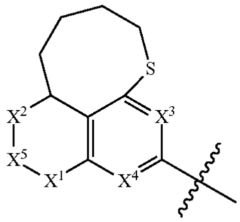,
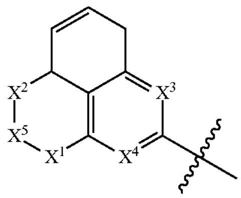,
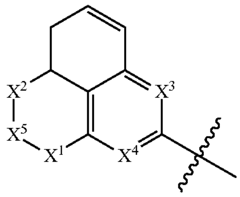,
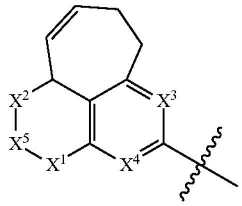

-continued

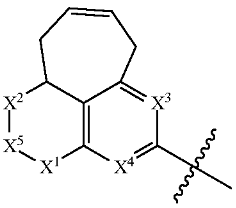

or

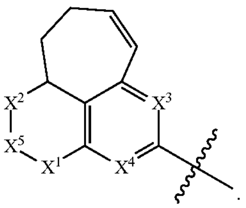

.

15. The compound or the stereoisomer, the crystalline form, the pharmaceutically acceptable salt, the hydrate or the solvate thereof according to claim 1, wherein in general formula (1), when $X^5$ is N—$R^a$, $R^a$ is —H, —$(CH_2)_2OR^{11}$, —$(CH_2)_2NR^{11}R^{12}$, (C1-C3) alkyl, (C1-C3) haloalkyl, (C3-C6) cycloalkyl or (4-7 membered) heterocycloalkyl, wherein the (C1-C3) alkyl, (C1-C3) haloalkyl, (C3-C6) cycloalkyl or (4-7 membered) heterocycloalkyl may be optionally substituted with 1, 2, 3 or 4 of the following groups: —H, -D, —F, —OH, —$CH_3$, —$CH_2OCH_3$, —$(CH_2)_2OCH_3$, —$OCH_3$, —$OCH_2CH_3$, —$OCH(CH_3)_2$,

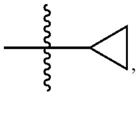

,

—$OCF_3$, —$CH_2N(CH_3)_2$, —$(CH_2)_2N(CH_3)_2$, —$N(CH_3)_2$ and —CN; or in general formula (1), when $X^5$ is N—$R^a$, $R^a$ is: —H, —$(CH_2)_2OCH_3$, —$(CH_2)_2OH$, —$(CH_2)_2N(CH_3)_2$,

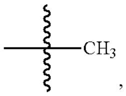

,

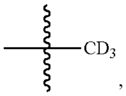

,

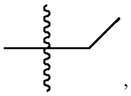

,

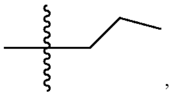

,

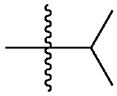

,

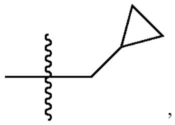

,

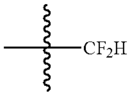

,

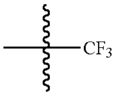

,

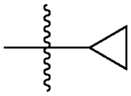

,

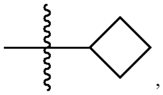

,

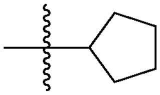

,

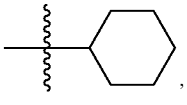

,

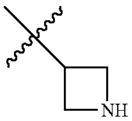

,

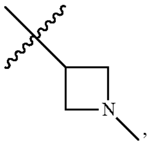

,

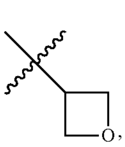

,

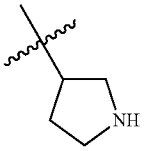

,

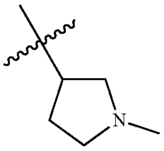

,

-continued

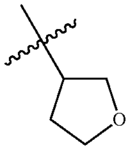

,

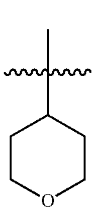

,

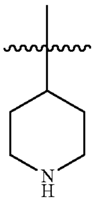

or

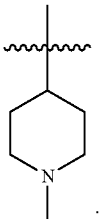

.

16. The compound or the stereoisomer, the crystalline form, the pharmaceutically acceptable salt, the hydrate or the solvate thereof according to claim 1, wherein in general formula (1), when $X^5$ is CH—$R^b$, $R^b$ is —H, —$(CH_2)_2OR^{11}$, —$NR^{11}R^{12}$, —$(CH_2)_2NR^{11}R^{12}$, (C1-C3) alkyl, (C1-C3) haloalkyl, (C3-C6) cycloalkyl or (4-7 membered) heterocycloalkyl, wherein the $R^{11}$, $R^{12}$, (C1-C3) alkyl, (C1-C3) haloalkyl, (C3-C6) cycloalkyl or (4-7 membered) heterocycloalkyl may be optionally substituted with 1, 2, 3 or 4 of the following groups: —H, -D, —F, —OH, —$CH_3$, —$CH_2OCH_3$, —$(CH_2)_2OCH_3$, —$OCH_3$, —$OCH_2CH_3$, —$OCH(CH_3)_2$,

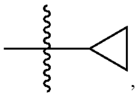 [SMILES: *C1CC1]

,

—$OCF_3$, —$CH_2N(CH_3)_2$, —$(CH_2)_2N(CH_3)_2$, —$N(CH_3)_2$ and —CN; or in general formula (1), when $X^5$ is CH—$R^b$, $R^b$ is: —H, —$N(CH_3)_2$, —$N(CD_3)_2$, —$(CH_2)_2OCH_3$, —$(CH_2)_2OH$, —$(CH_2)_2N(CH_3)_2$,

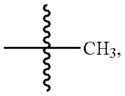

,

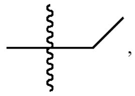

,

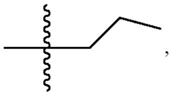

,

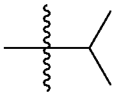

,

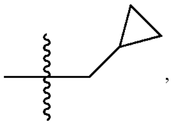

,

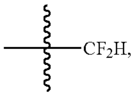

,

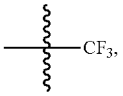

,

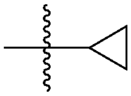

,

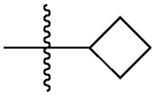

,

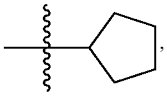

,

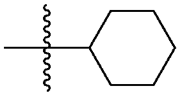

,

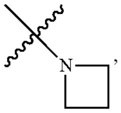

,

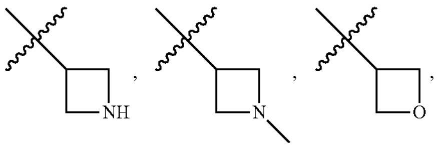

,

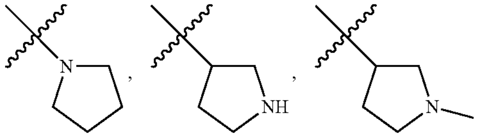

,

-continued

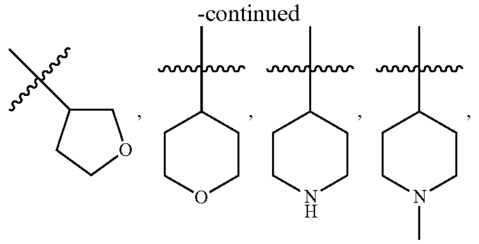

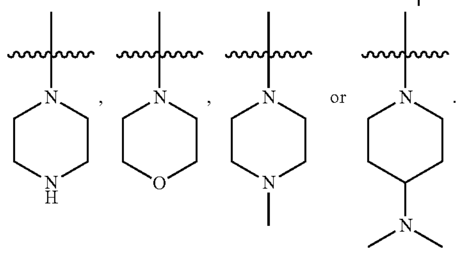

17. The compound or the stereoisomer, the crystalline form, the pharmaceutically acceptable salt, the hydrate or the solvate thereof according to claim 1, wherein in general formula (1), $X^3$ is: CH, N or C—$R^c$, wherein the $R^c$ is: —H, —F, —Cl, —Br, —I, —OH, —$CH_3$, —$CH_2OCH_3$,

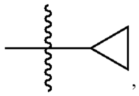

—$(CH_2)_2OCH_3$, —$OCH_3$, —$OCH_2CH_3$, —$OCH(CH_3)_2$, —$OCF_3$, —$CH_2N(CH_3)_2$, —$(CH_2)_2N(CH_3)_2$, —$N(CH_3)_2$ or —CN; in general formula (1), $X^4$ is: CH, N or C—$R^d$, wherein the $R^d$ is: —H, —F, —Cl, —Br, —I, —OH, —$CH_3$, —$CH_2OCH_3$,

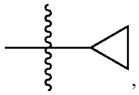

—$(CH_2)_2OCH_3$, —$OCH_3$, —$OCH_2CH_3$, —$OCH(CH_3)_2$, —$OCF_3$, —$CH_2N(CH_3)_2$, —$(CH_2)_2N(CH_3)_2$, —$N(CH_3)_2$ or —CN; and in general formula (1), each $R^2$ is independently —H, -D, —F, —Cl, —Br, —I, —OH, —$CH_2OR^{11}$, —$CH_2NR^{11}R^{12}$, —$OR^{11}$, —$NR^{11}R^{12}$, —CN, —C(O)$NR^{11}R^{12}$, —$NR^{12}C(O)R^{11}$, —$NR^{12}S(O)_2R^{11}$, —$SR^{11}$, —$S(O)_2R^{11}$, —$S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl, wherein the (C1-C3) alkyl, (C1-C3) haloalkyl, (C2-C4) alkenyl, (C2-C4) alkynyl, (C3-C6) cycloalkyl, phenyl, (4-8 membered) heterocycloalkyl or (5-6 membered) heteroaryl may be each independently and optionally substituted with 1, 2, 3 or 4 of the following groups: —H, —F, —Cl, —Br, —I, —$CH_3$, —OH, —$OCH_3$, —$N(CH_3)_2$ and —CN; or 2 adjacent $R^2$, together with the atoms to which they are attached, can form (5-7 membered) heterocycloalkyl or (C3-C6) cycloalkyl, wherein the (5-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or 2 $R^2$ on the same carbon atom of ring B, together with the carbon atom to which they are attached, can form (4-7 membered) heterocycloalkyl or (C3-C6) cycloalkyl, wherein the (4-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or $R^2$ and an adjacent $R^e$, together with the atoms to which they are attached, can form (5-7 membered) heterocycloalkyl or (C3-C6) cycloalkyl, wherein the (5-7 membered) heterocycloalkyl or (C3-C6) cycloalkyl may be optionally substituted with 1, 2, 3 or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$ and —CN; or in general formula (1), each $R^2$ is independently: —H, -D, —F, —Cl, —Br, —I, —OH, —$CH_2OCH_3$, —$CH_2N(CH_3)_2$, —$OCH_3$, —$OCF_3$, —$N(CH_3)_2$, —CN, —$C(O)NH_2$, —$C(O)NH(CH_3)$, —$C(O)N(CH_3)_2$, —NHC(O)$CH_3$, —$N(CH_3)$—C(O)$CH_3$, —$NHS(O)_2CH_3$, —$NCH_3S(O)_2CH_3$, —$S(O)_2CH_3$, —$S(O)_2NH_2$, —$S(O)_2NH(CH_3)$, —$S(O)_2N(CH_3)_2$,

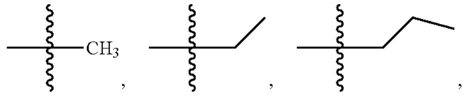

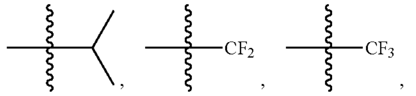

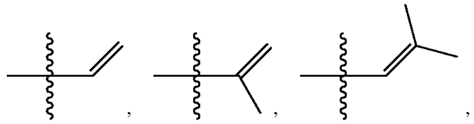

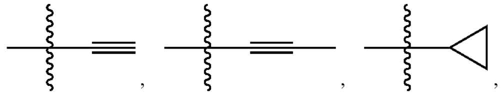

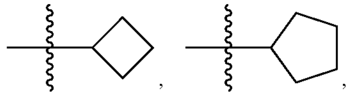

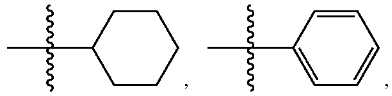

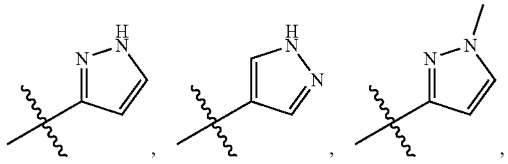

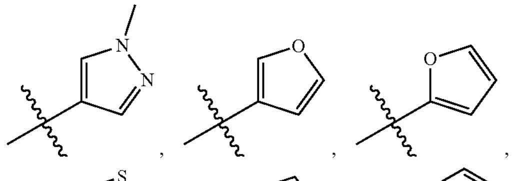

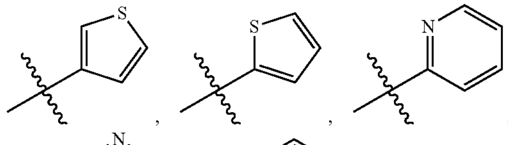

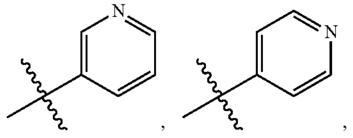

-continued
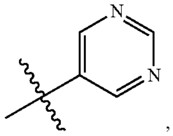,
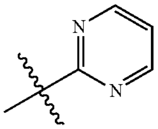,
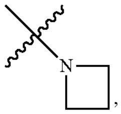,
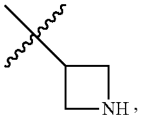,
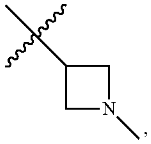,
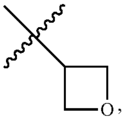,
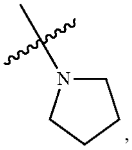,
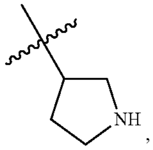,
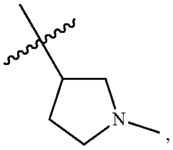,
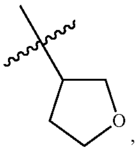,
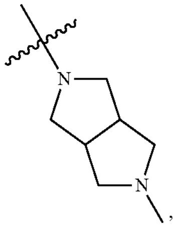,
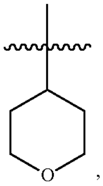,
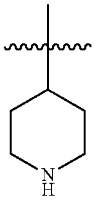,
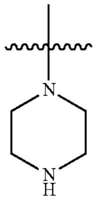,
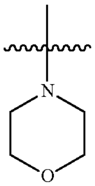,
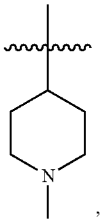,
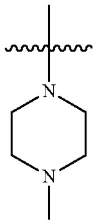, or
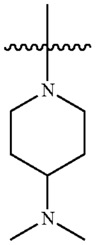.
18. The compound or the stereoisomer, the crystalline form, the pharmaceutically acceptable salt, the hydrate or the solvate thereof according to claim 1, wherein in general formula (1), the structural unit
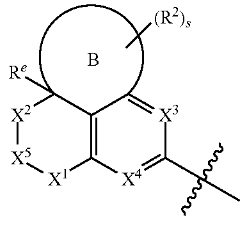
is:
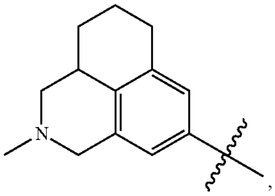,
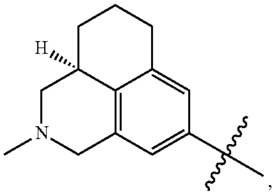,
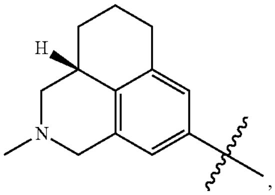,
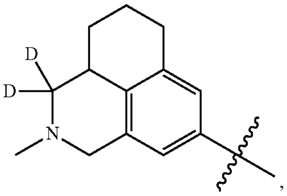,
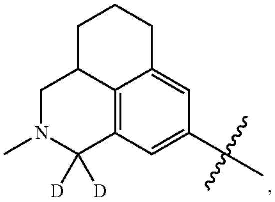,
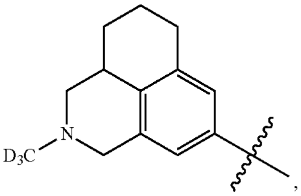,
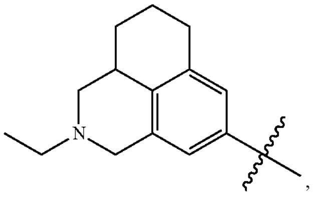,
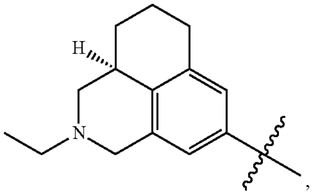, -continued
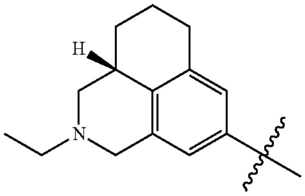
,
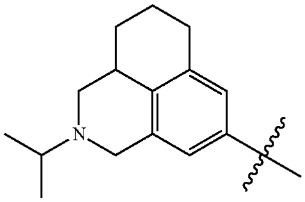
,
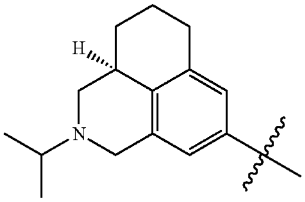
,
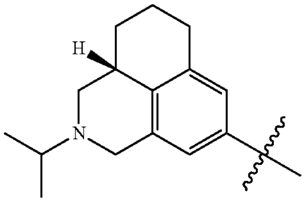
,
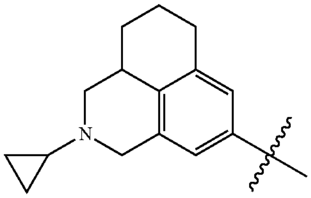
,
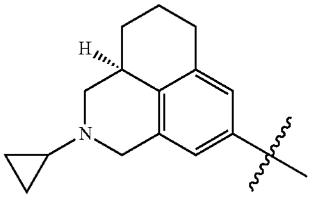
,
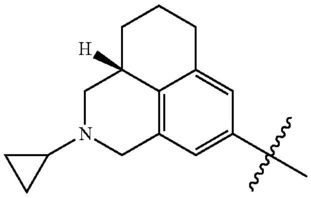
,
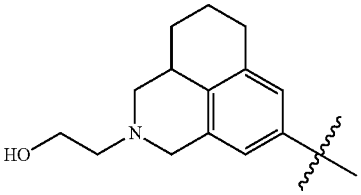
,
-continued
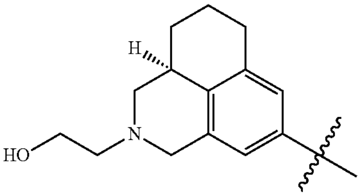
,
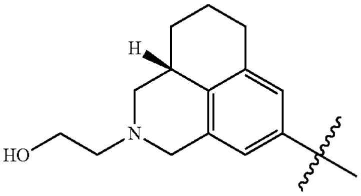
,
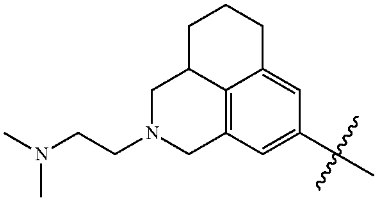
,
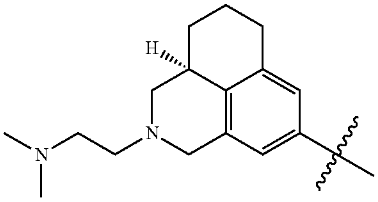
,
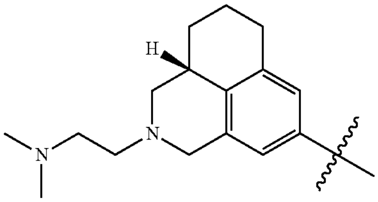
,
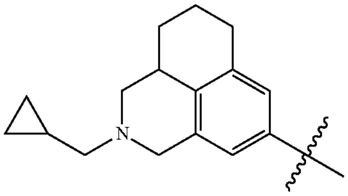
,
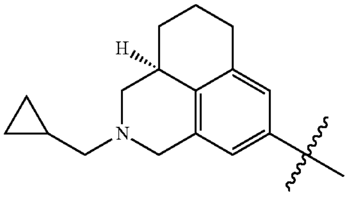
,
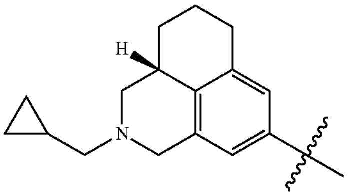
, -continued
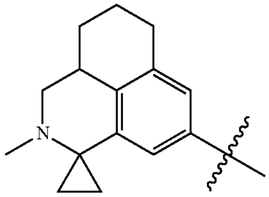
,
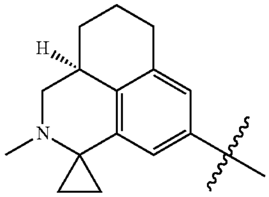
,
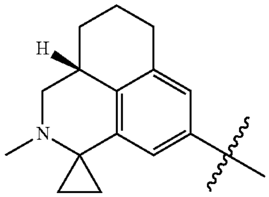
,
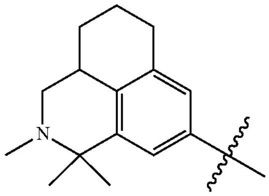
,
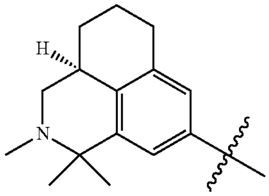
,
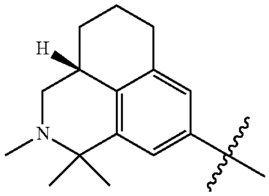
,
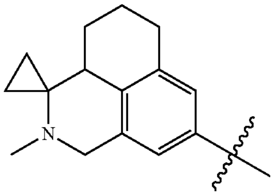
,
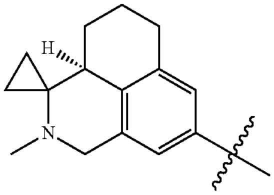
,
-continued
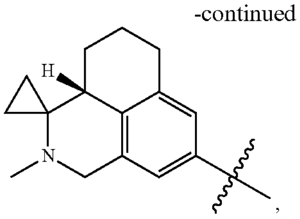
,
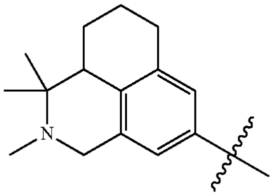
,
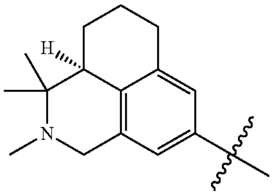
,
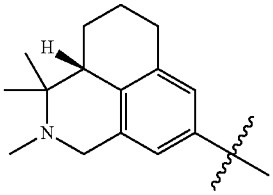
,
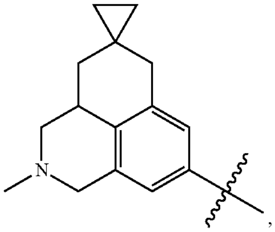
,
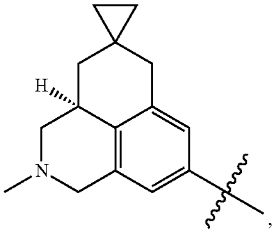
,
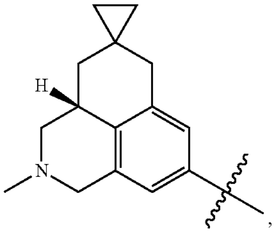
,
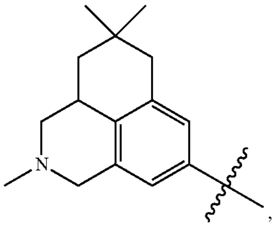
, -continued
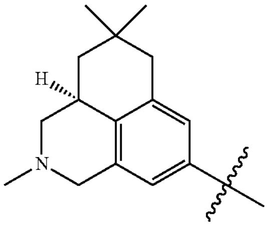
,
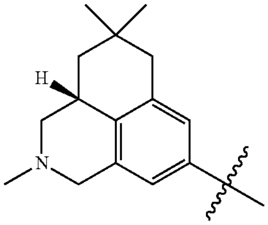
,
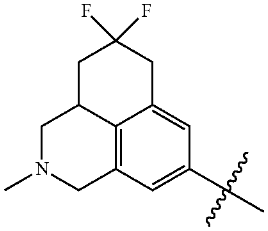
,
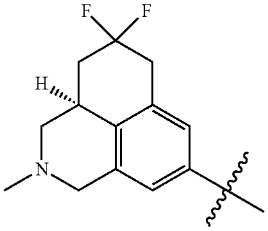
,
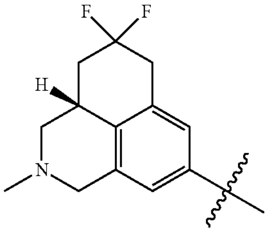
,
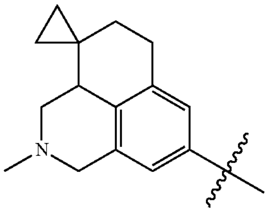
,
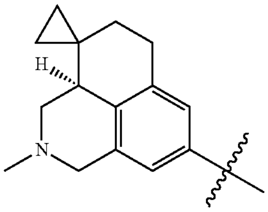
,
-continued
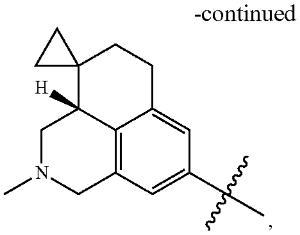
,
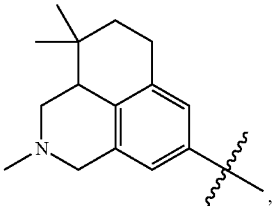
,
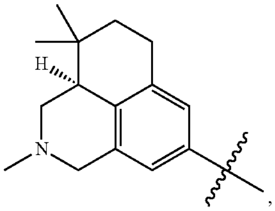
,
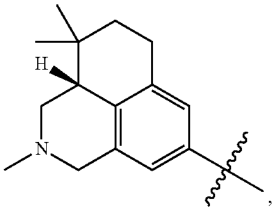
,
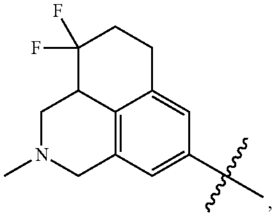
,
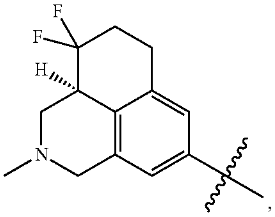
,
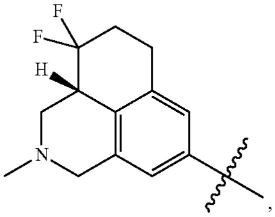
,
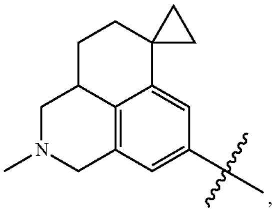
, -continued
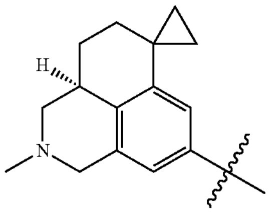
,
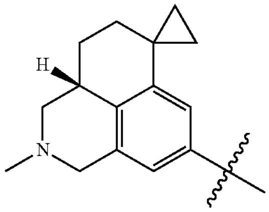
,
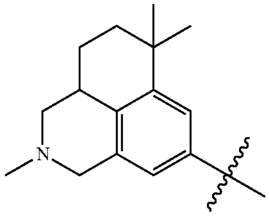
,
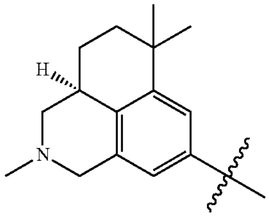
,
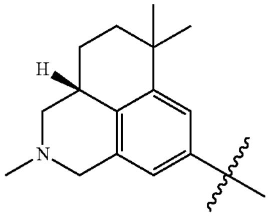
,
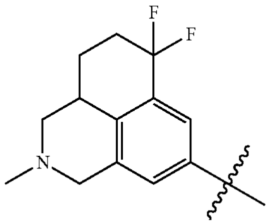
,
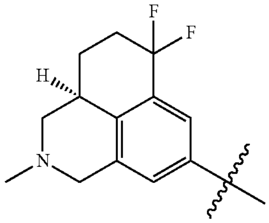
,
-continued
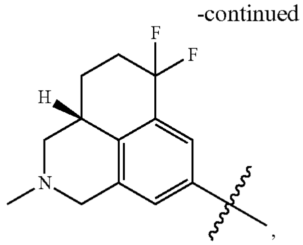
,
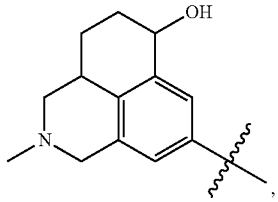
,
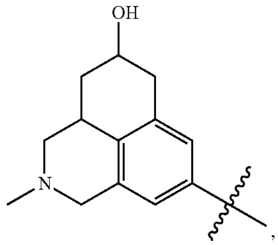
,
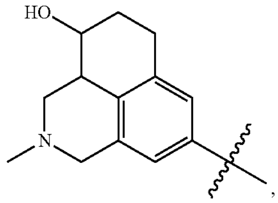
,
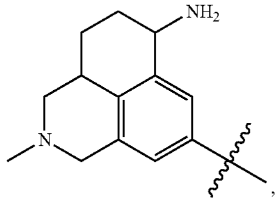
,
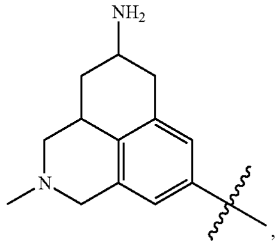
,
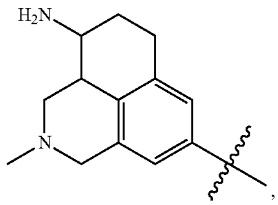
,
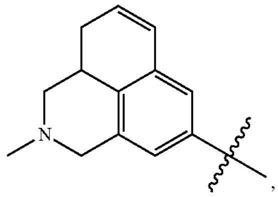
, -continued
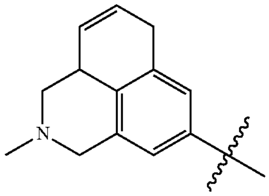
,
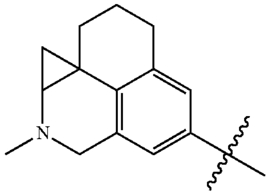
,
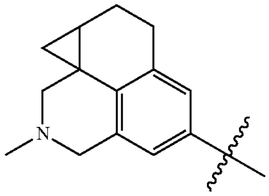
,
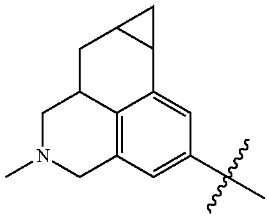
,
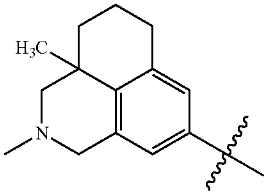
,
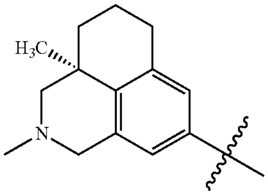
,
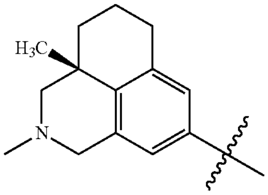
,
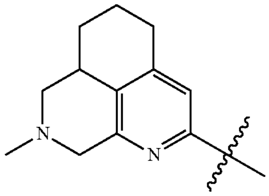
,
-continued
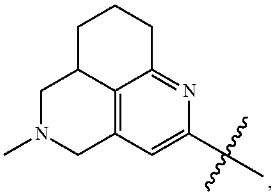
,
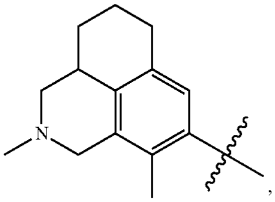
,
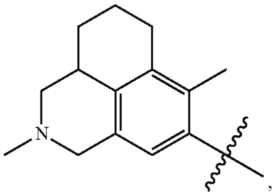
,
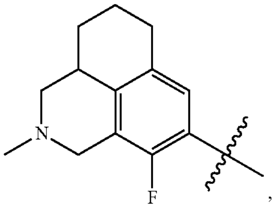
,
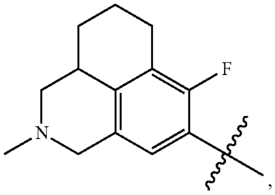
,
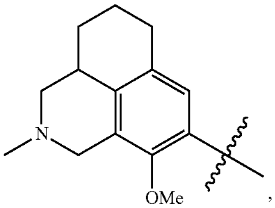
,
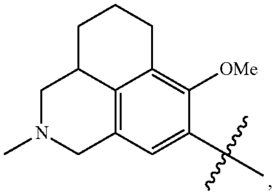
,
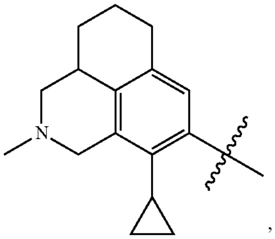
, -continued
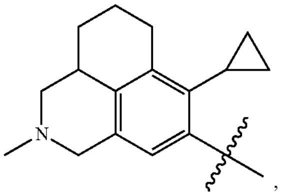
,
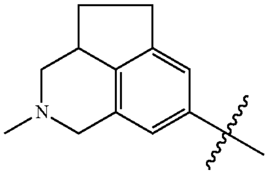
,
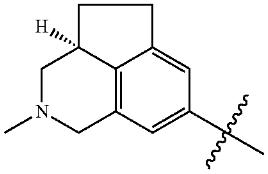
,
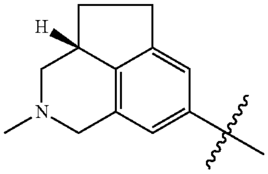
,
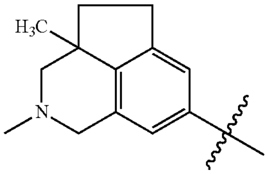
,
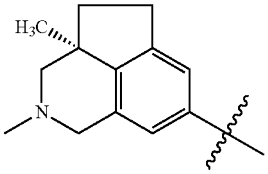
,
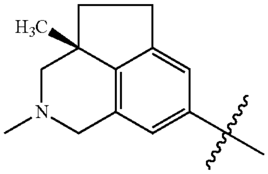
,
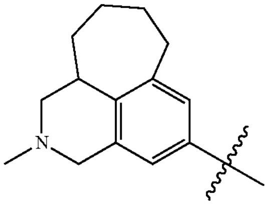
,
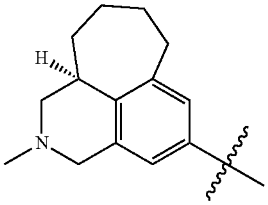
,
-continued
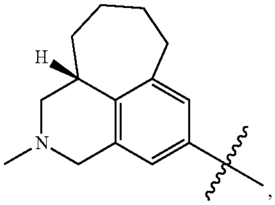
,
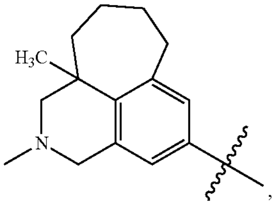
,
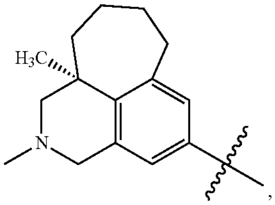
,
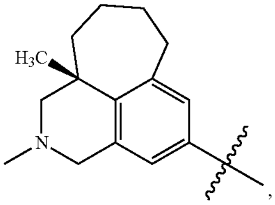
,
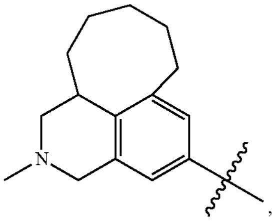
,
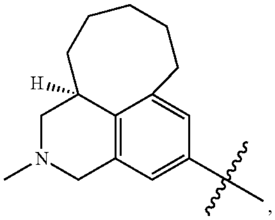
,
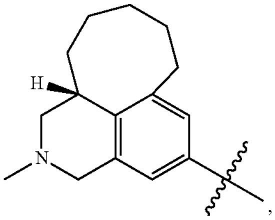
,
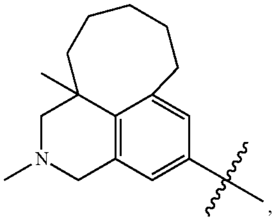
,

419
-continued
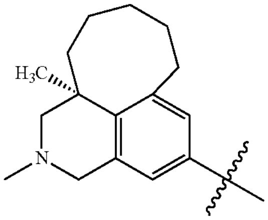
,
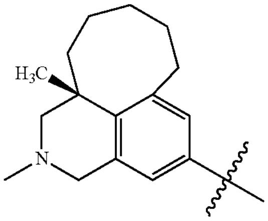
,
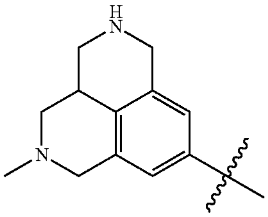
,
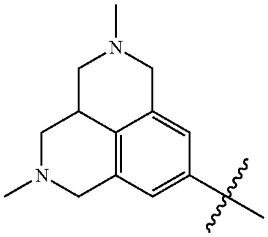
,
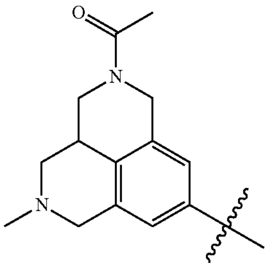
,
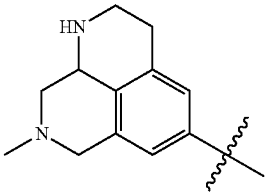
,
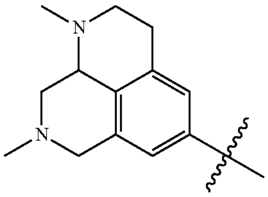
,
420
-continued
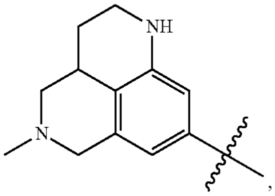
,
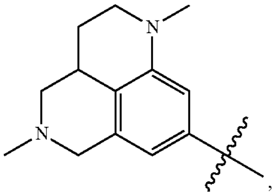
,
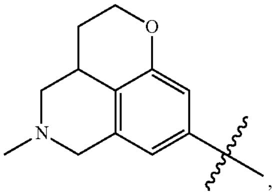
,
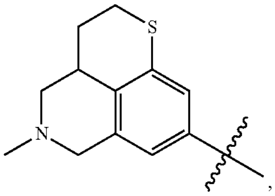
,
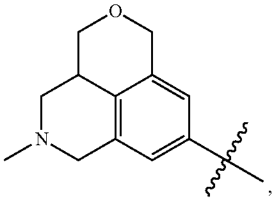
,
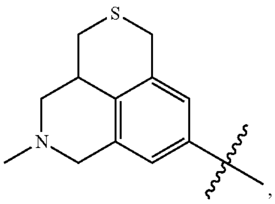
,
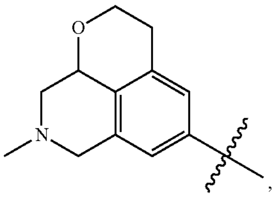
,
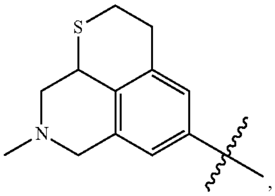
, -continued
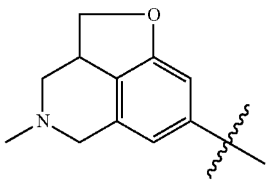,
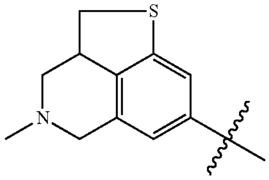,
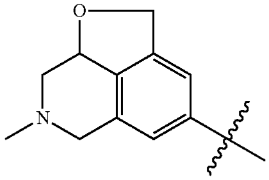,
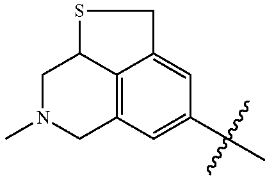,
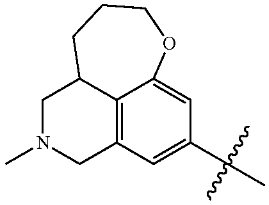,
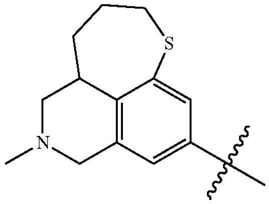,
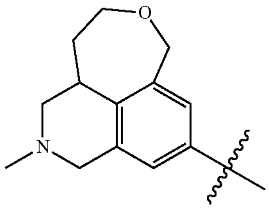,
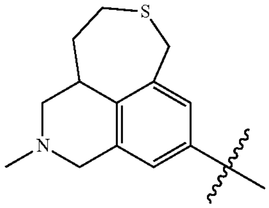,
-continued
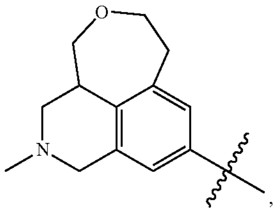,
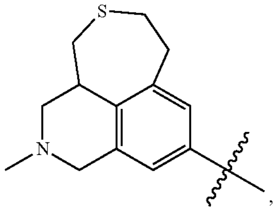,
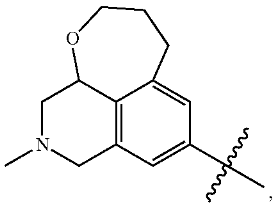,
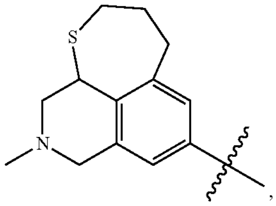,
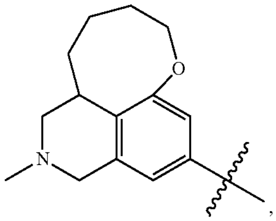,
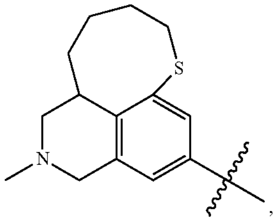,
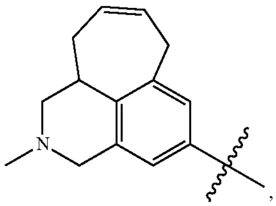,
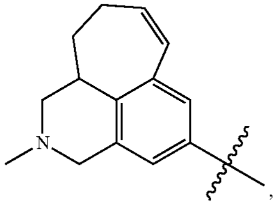,

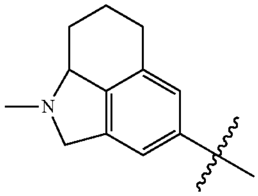
,
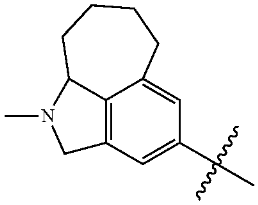
,
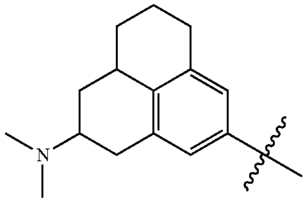
,
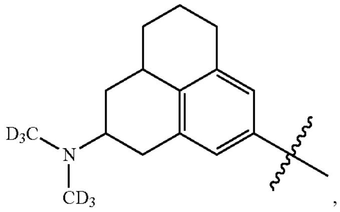
,
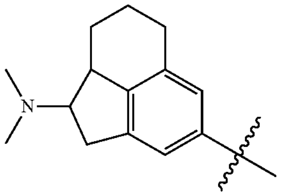
,
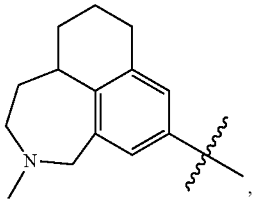
,
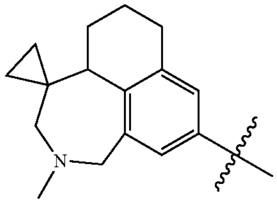
,
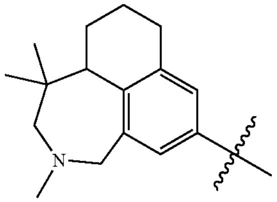
,
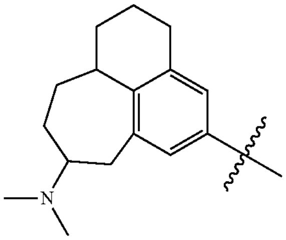
,
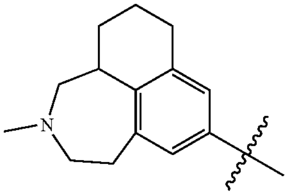
,
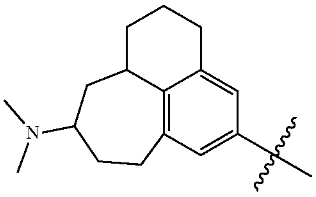
,
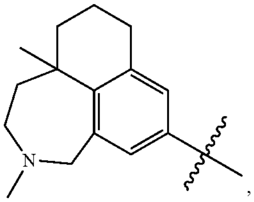
,
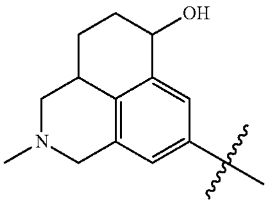
,
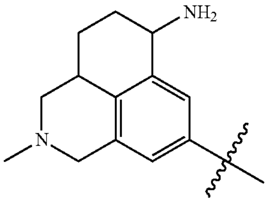
,
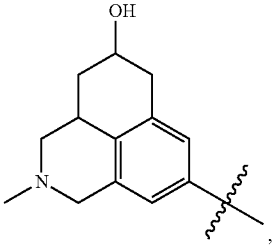
, -continued
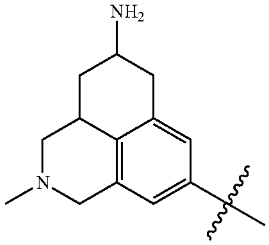
,
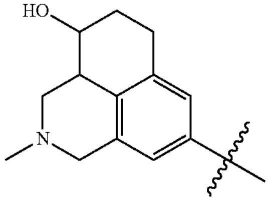
or
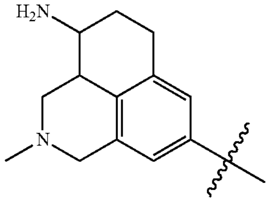
.
19. The compound or the stereoisomer, the crystalline form, the pharmaceutically acceptable salt, the hydrate or the solvate thereof according to claim 1, wherein the compound is selected from the group consisting of:
1
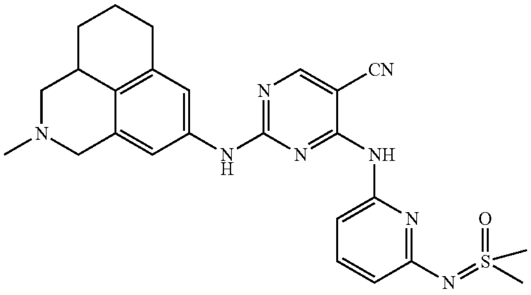
2
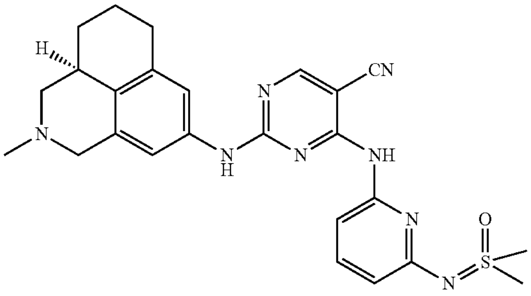
-continued
3
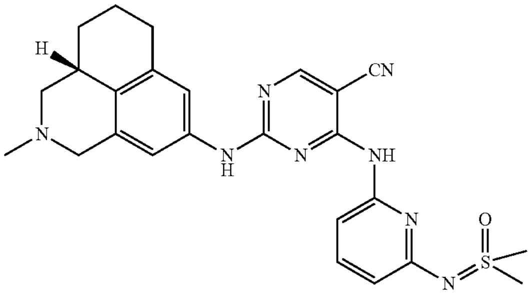
4
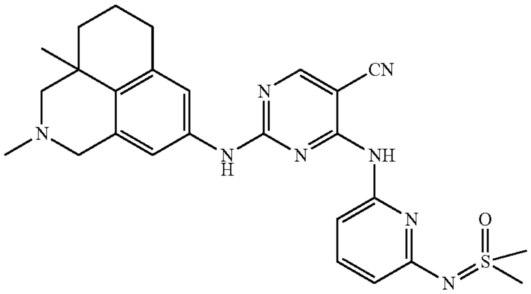
5
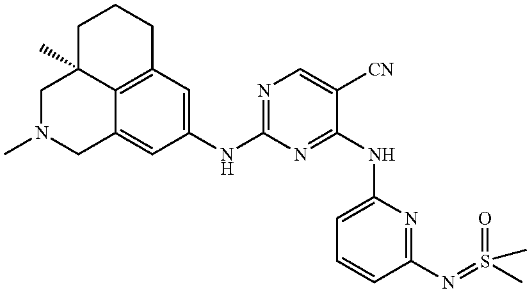
6
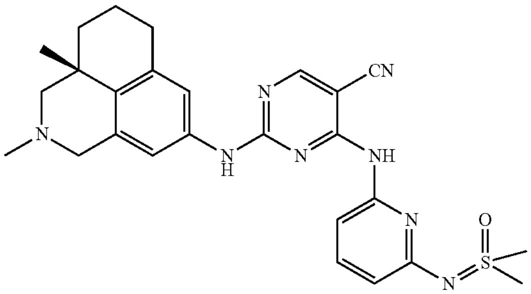
7
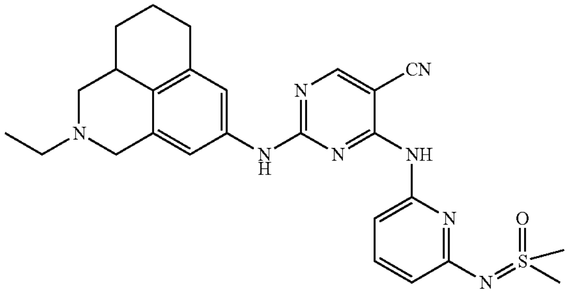

-continued
8
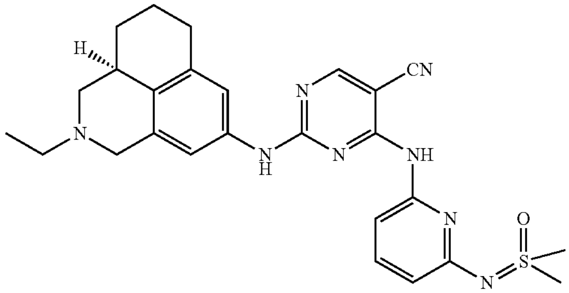
9
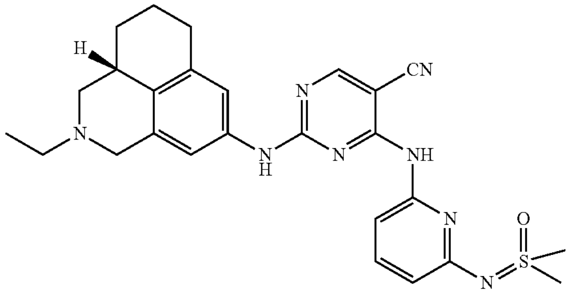
10
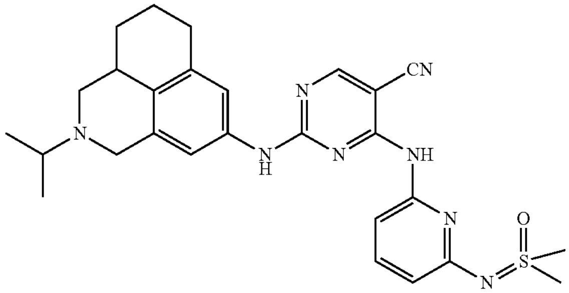
11
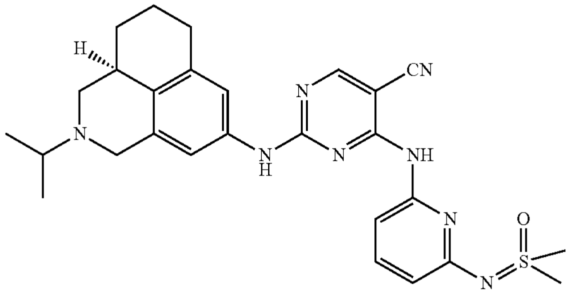
12
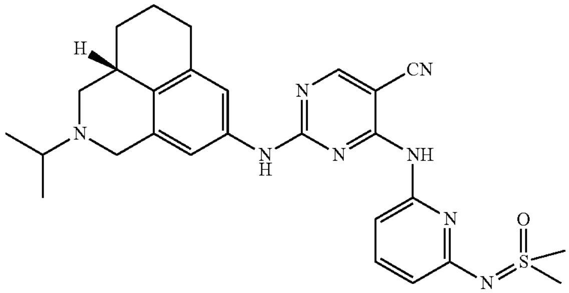
-continued
13
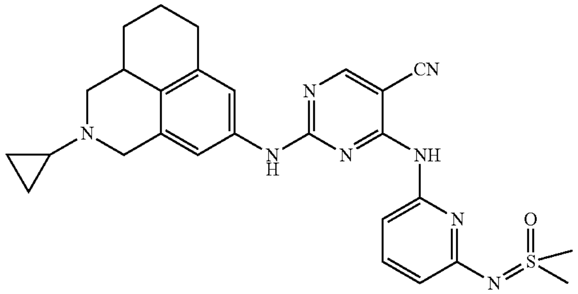
14
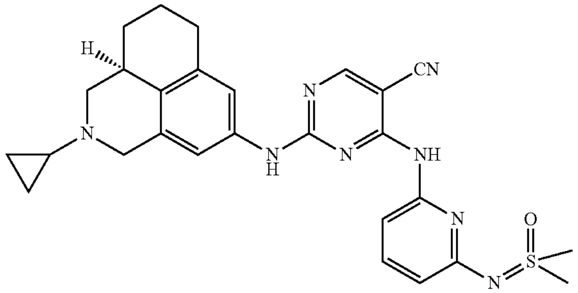
15
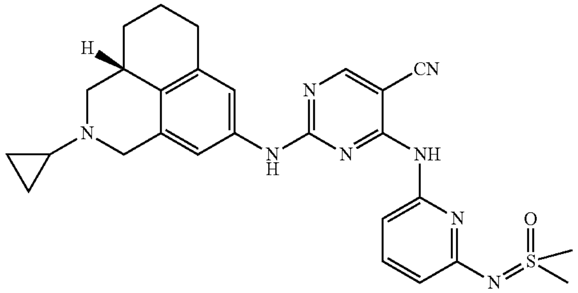
16
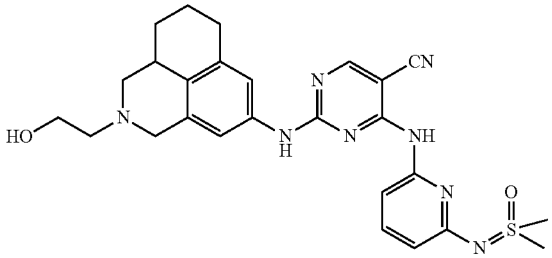
17
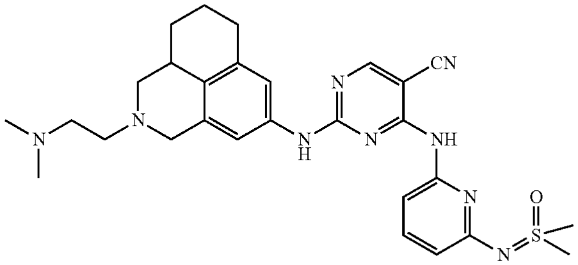

-continued
18
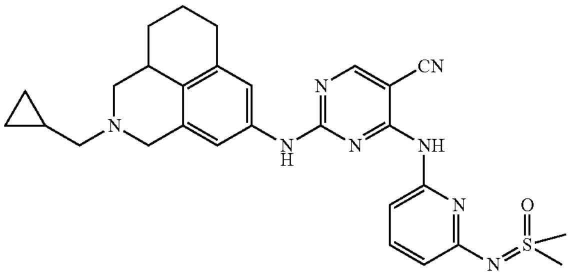
19
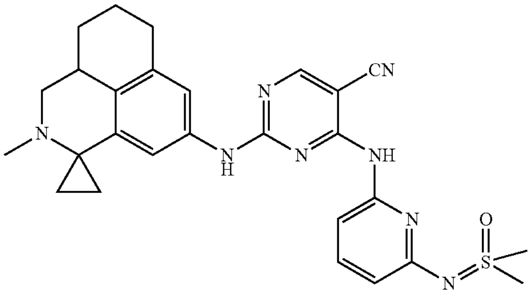
20
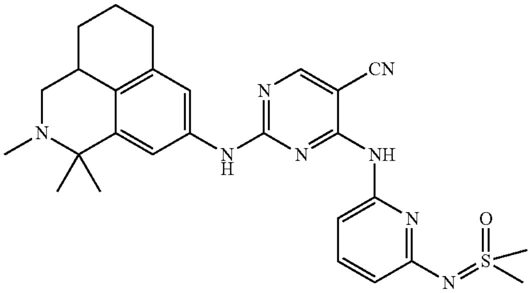
21
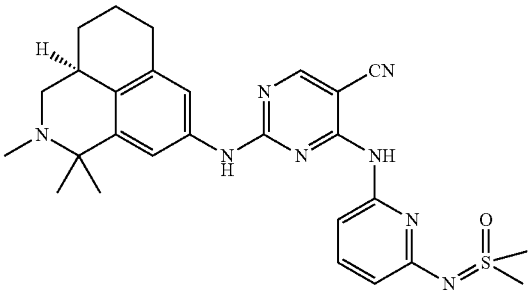
22
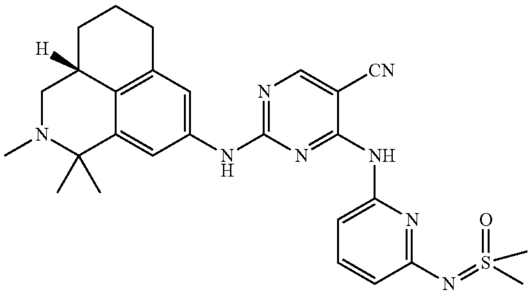
-continued
23
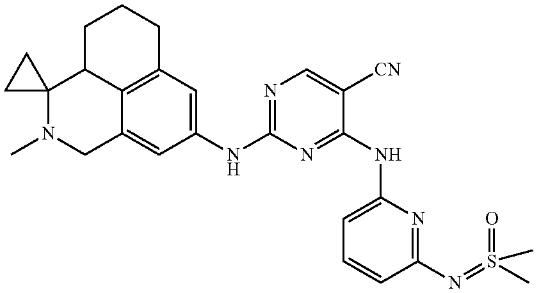
24
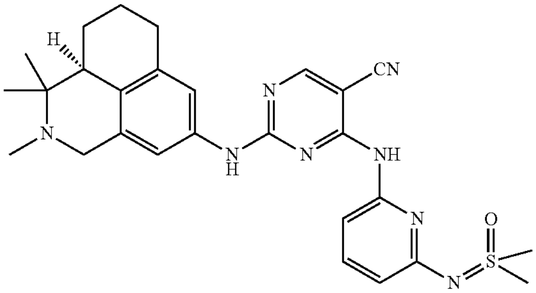
25
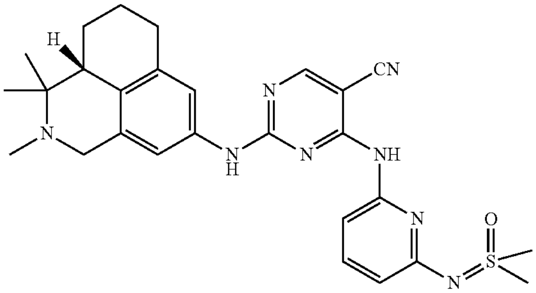
26
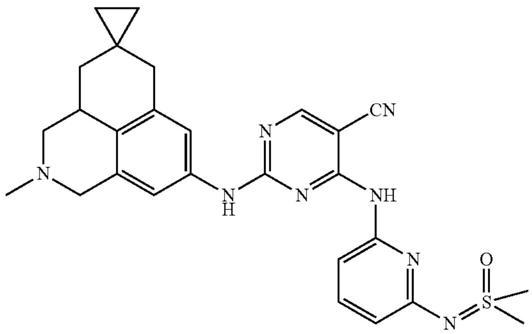

-continued
27
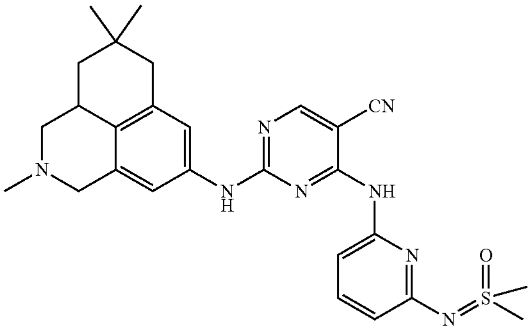
28
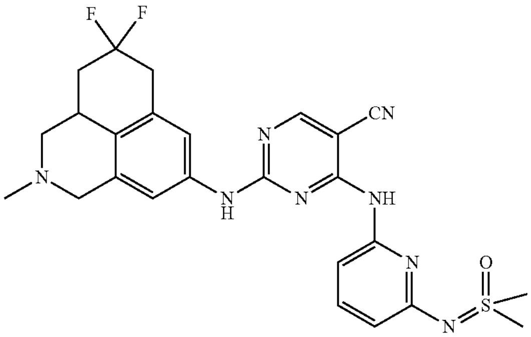
29
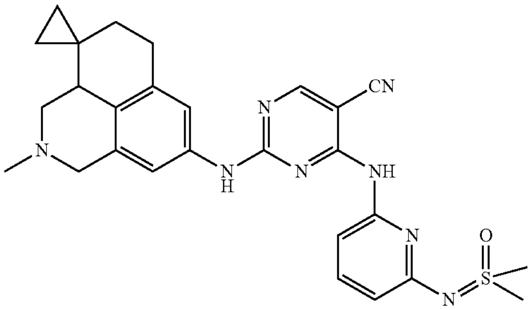
30
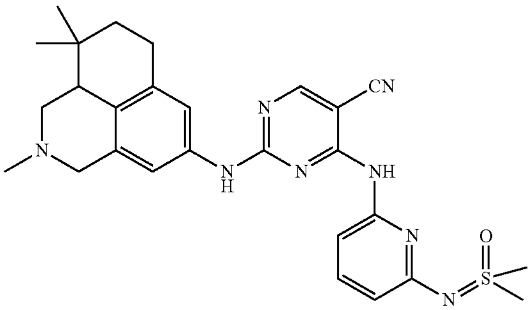
-continued
31
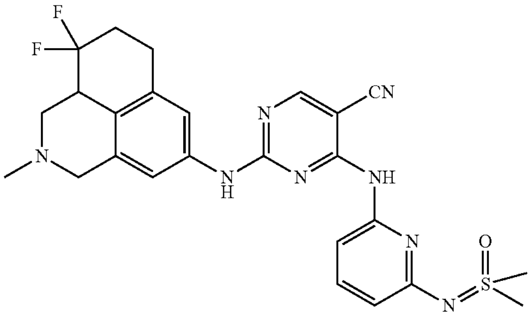
32
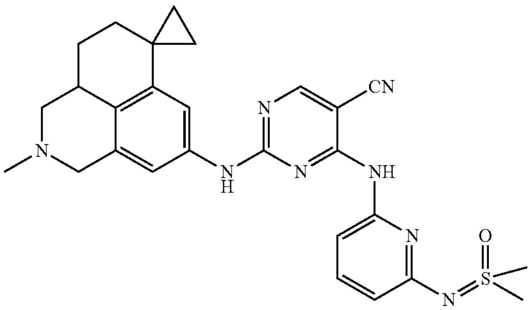
33
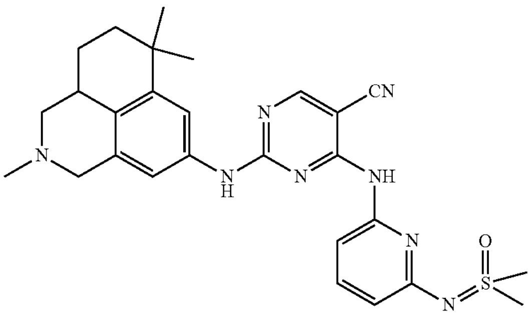
34
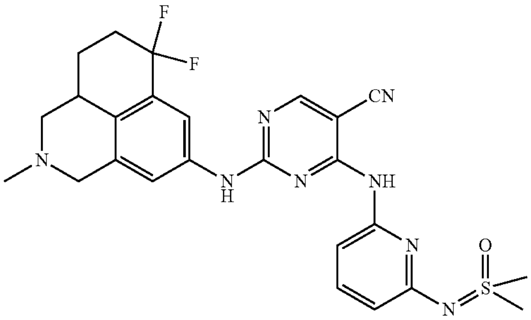

-continued
35
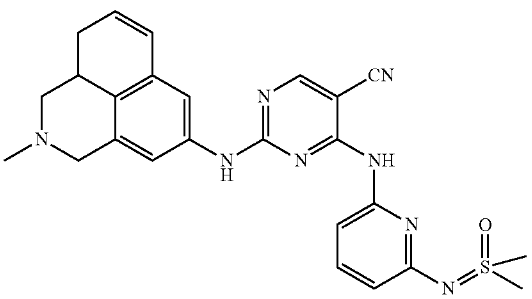
36
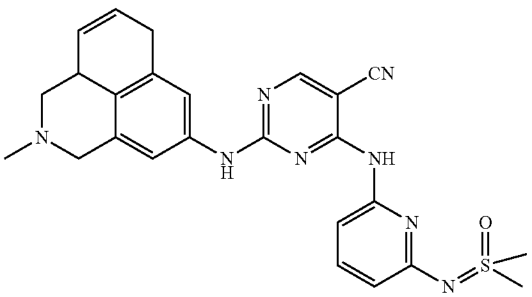
37
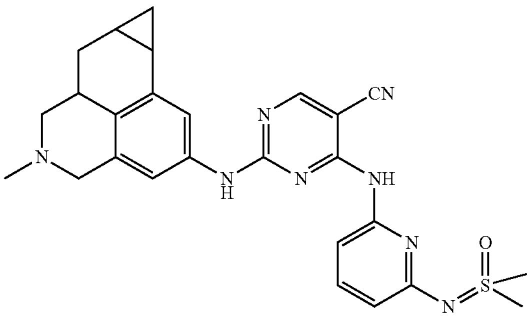
38
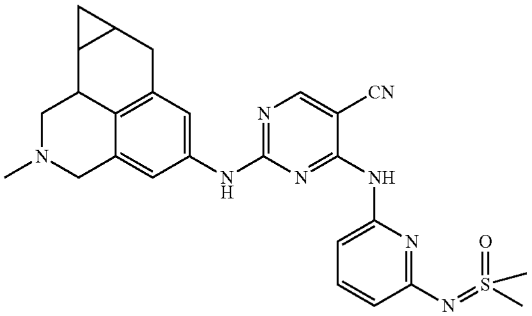
39
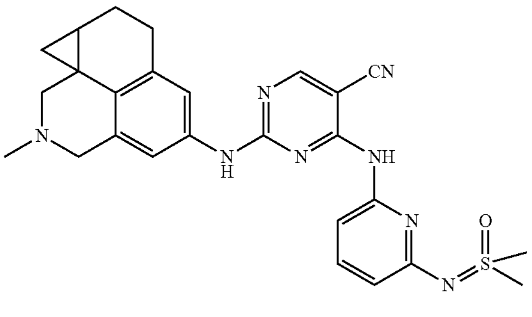
-continued
40
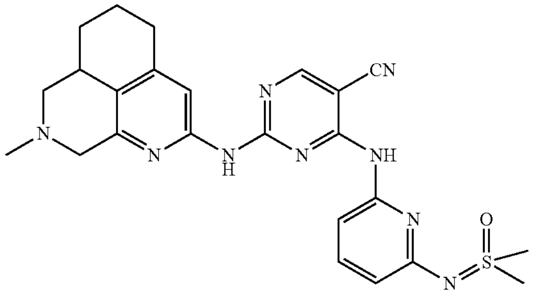
41
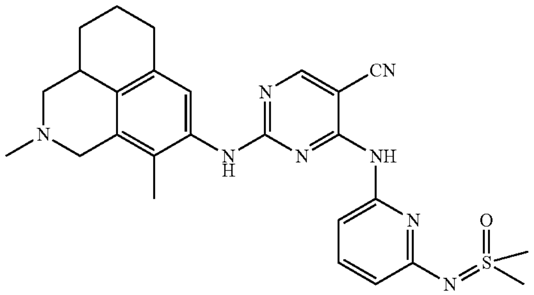
42
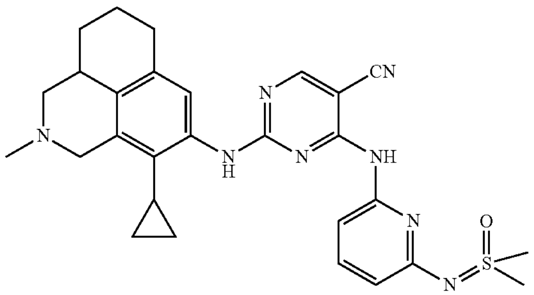
43
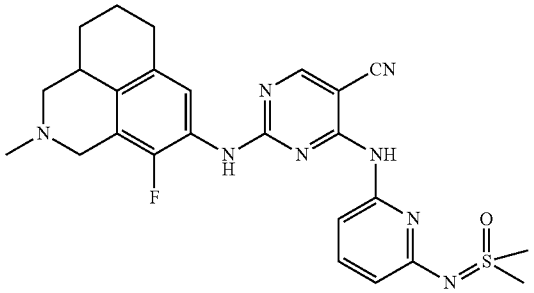
44
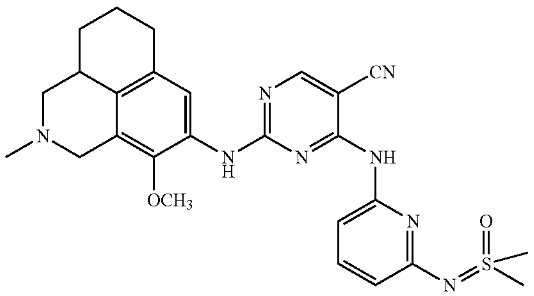

-continued
45
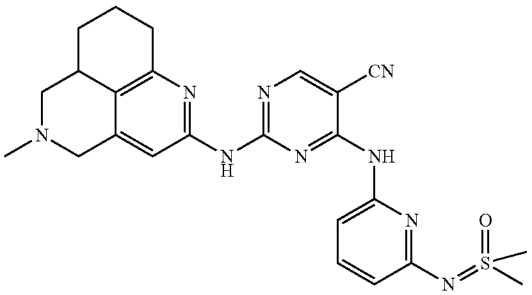
46
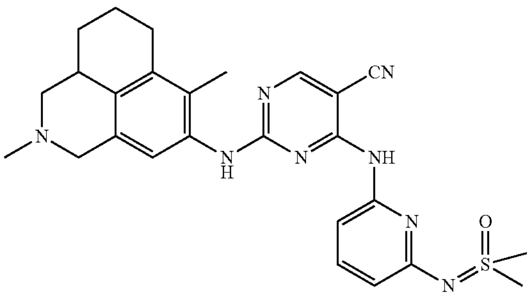
47
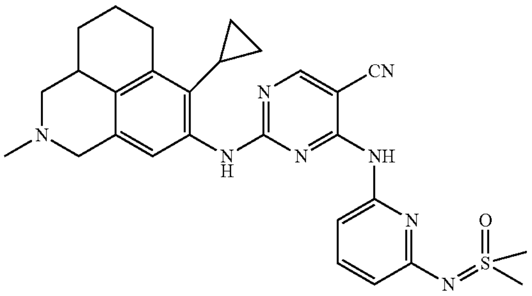
48
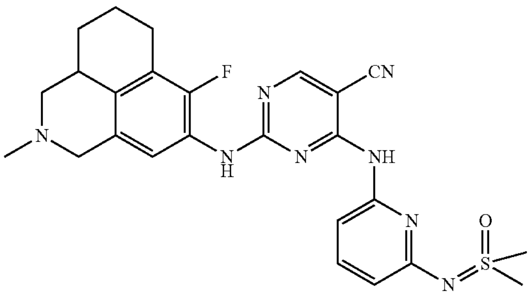
49
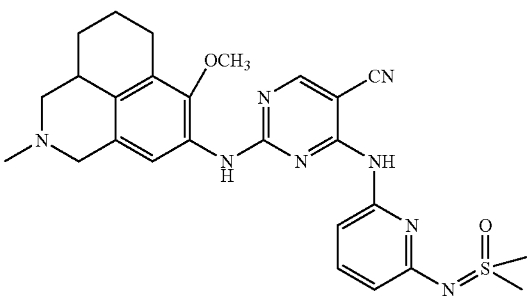
-continued
50
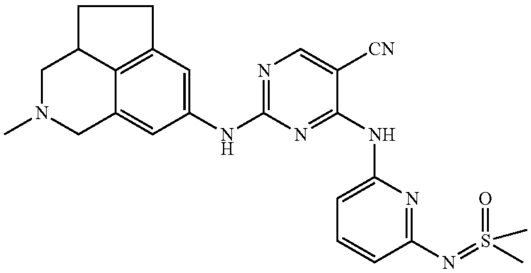
51
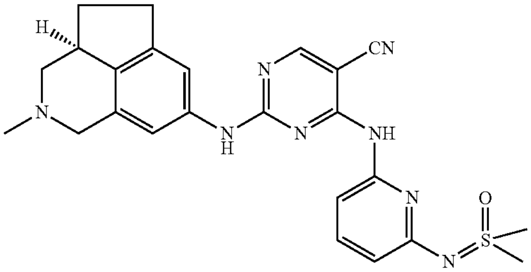
52
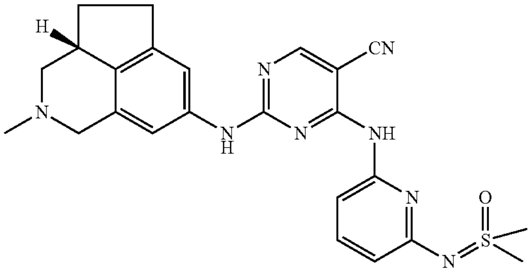
53
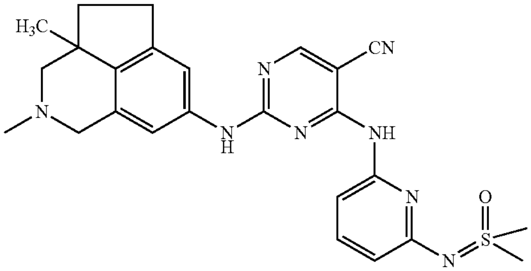
54
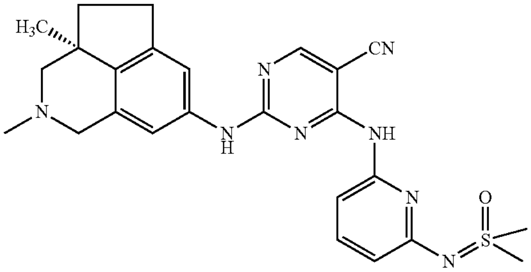

-continued
55
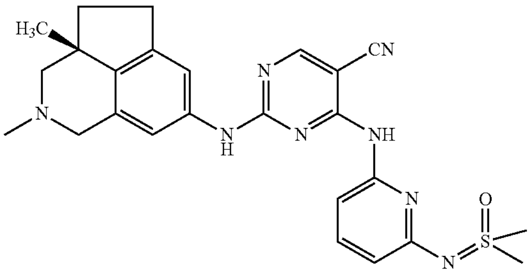
56
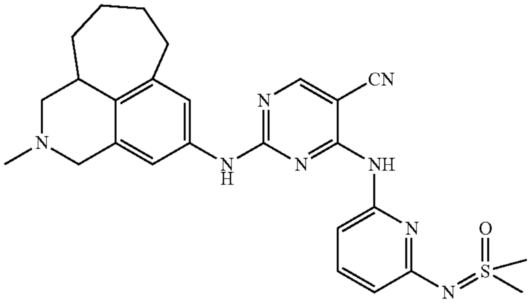
57
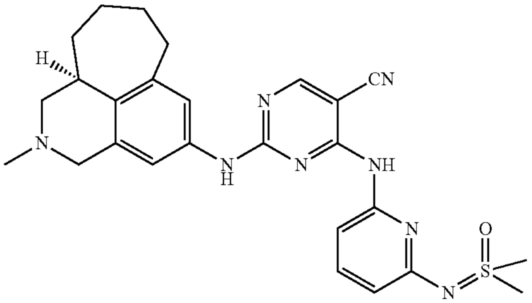
58
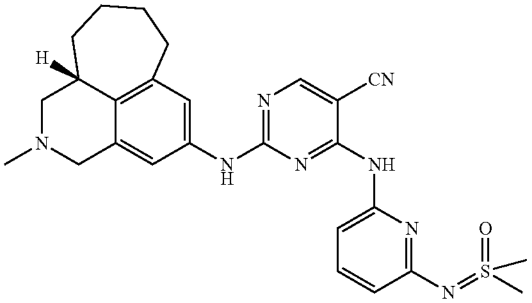
59
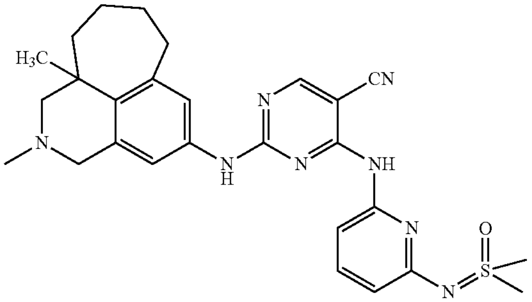
-continued
60
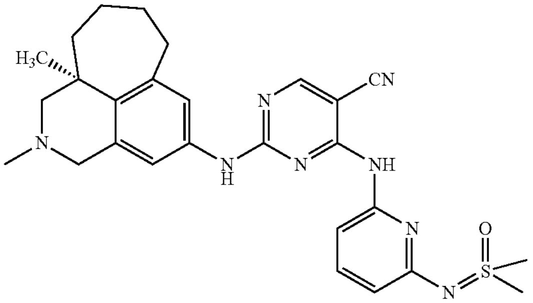
61
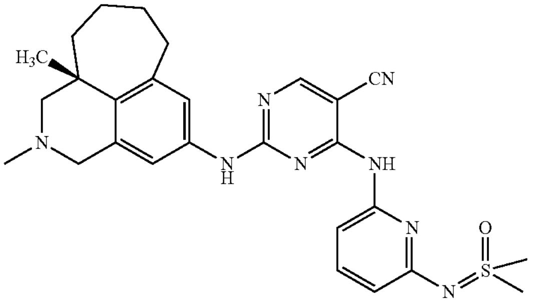
62
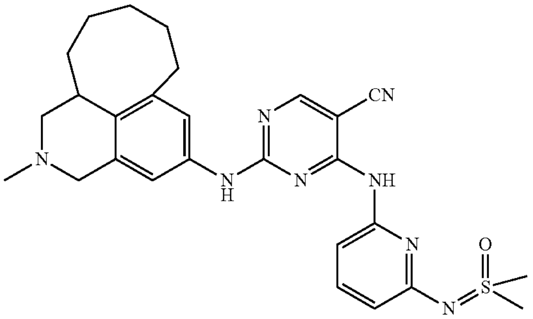
63
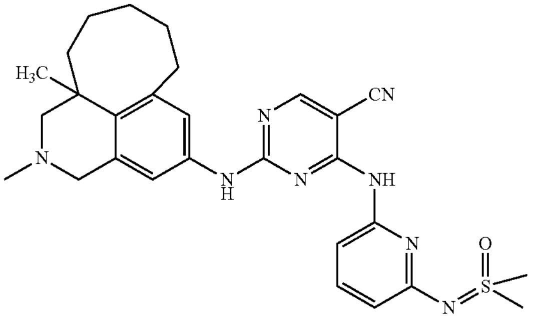

-continued
64
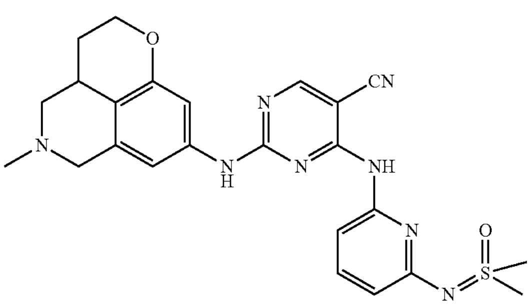
65
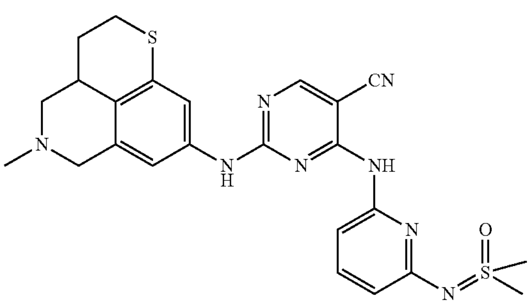
66
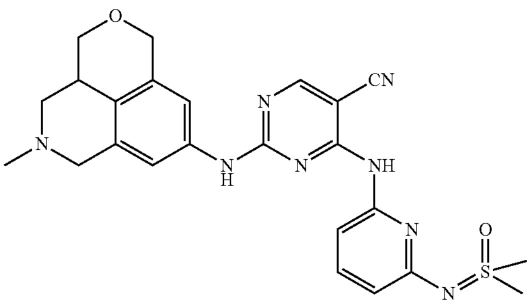
67
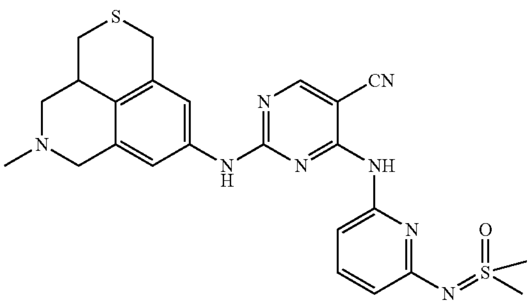
68
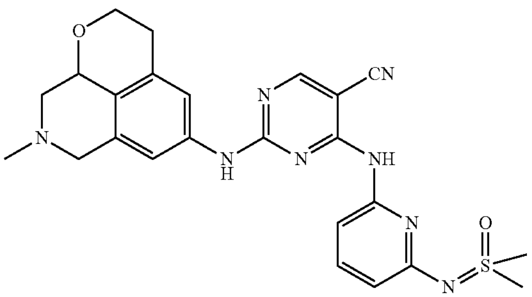
-continued
69
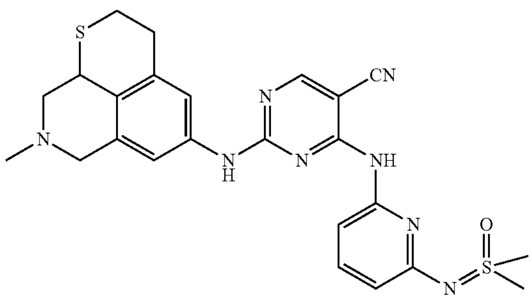
70
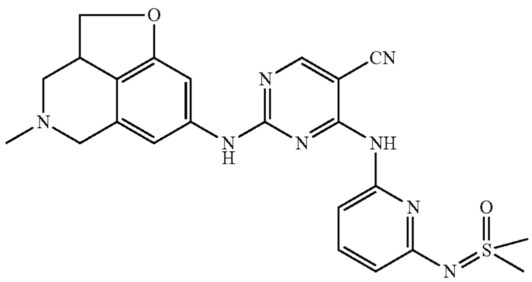
71
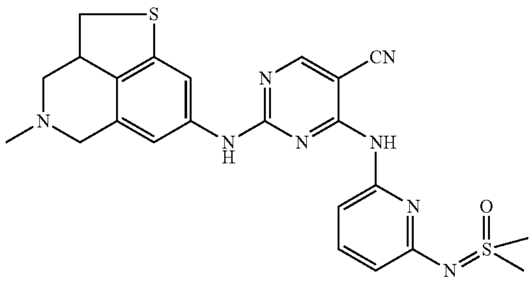
72
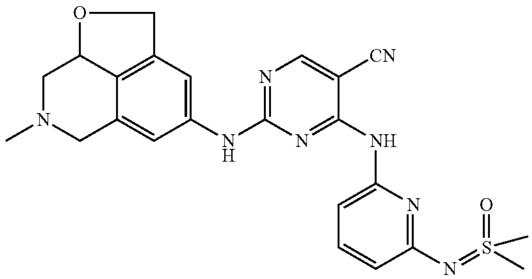
73
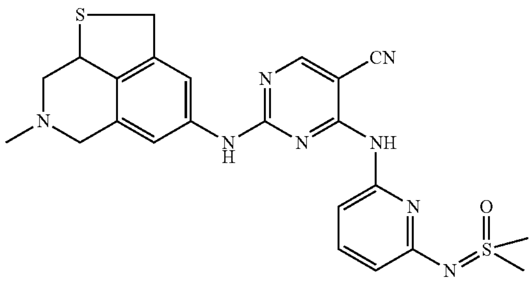

-continued
74
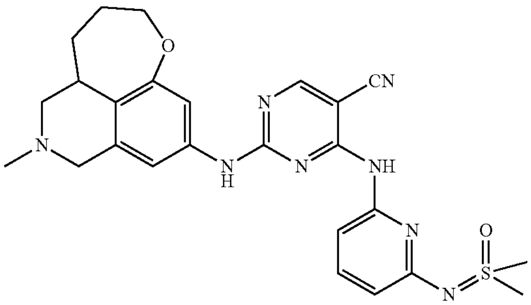
75
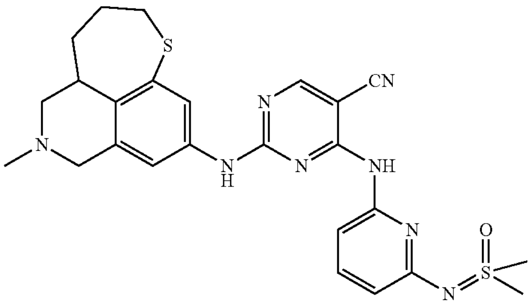
76
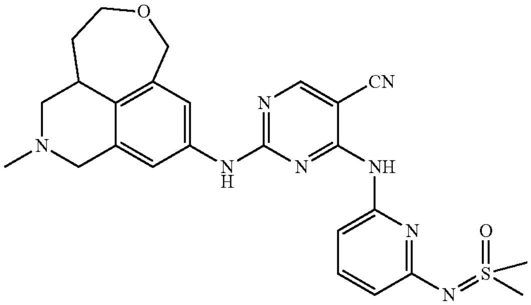
77
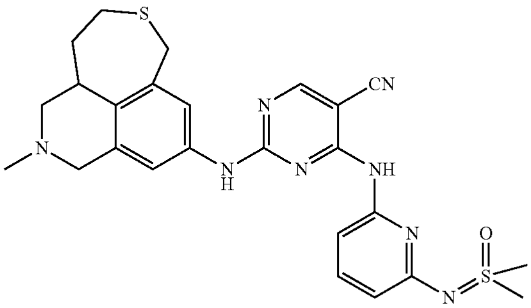
78
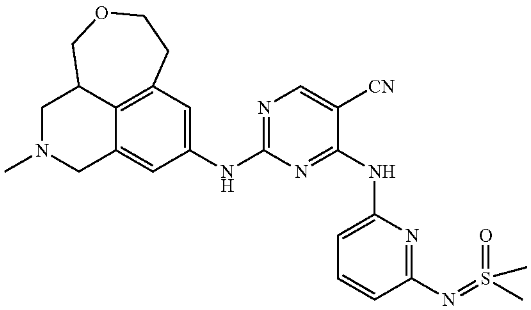
-continued
79
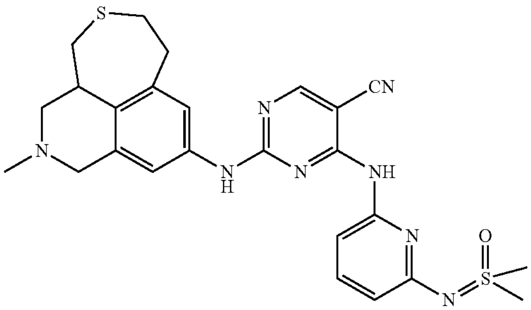
80
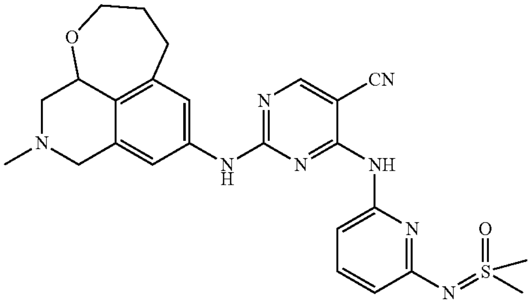
81
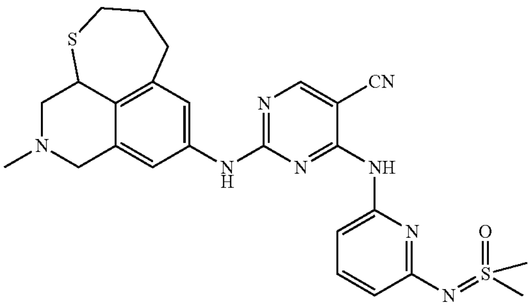
82
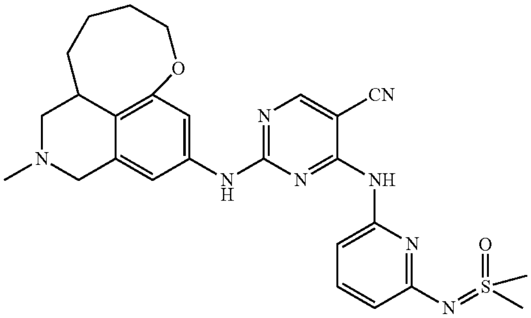

-continued
83
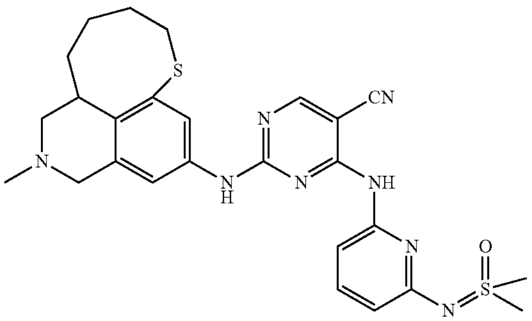
84
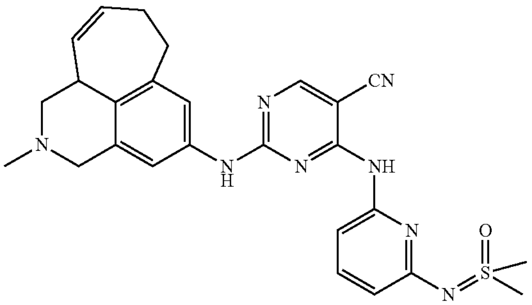
85
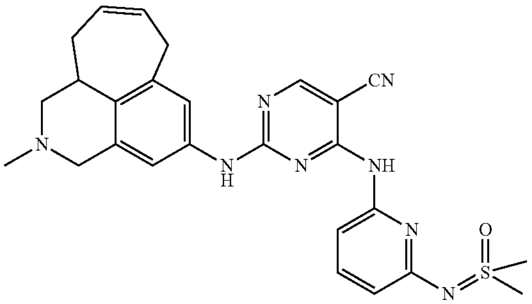
86
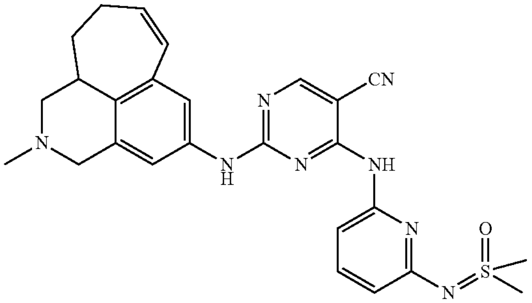
87
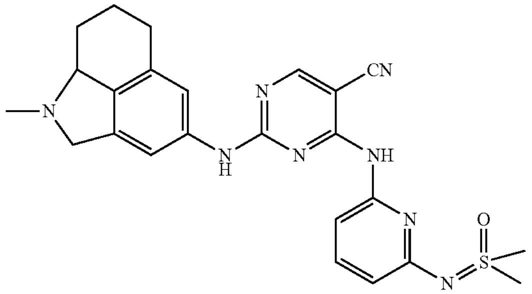
-continued
88
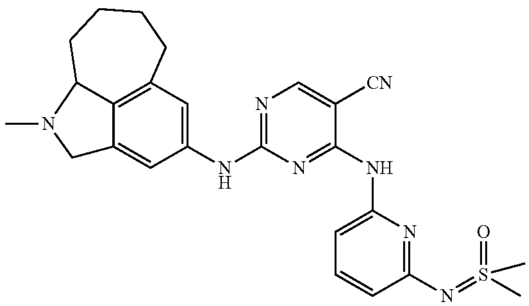
89
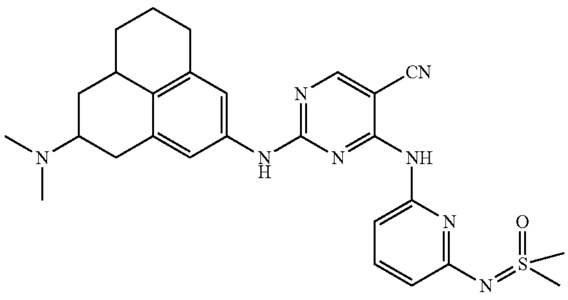
90
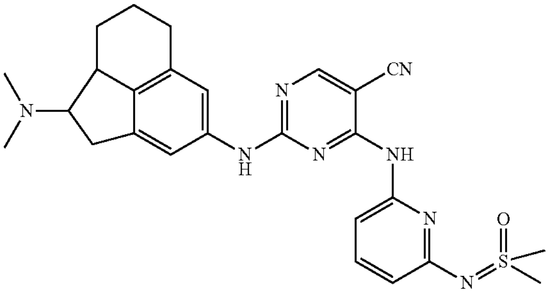
91
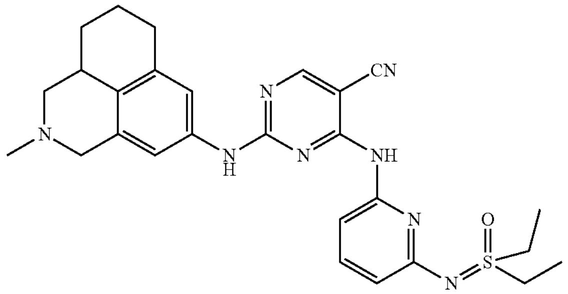
92
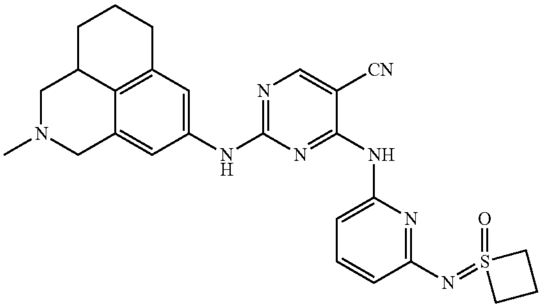

-continued
93
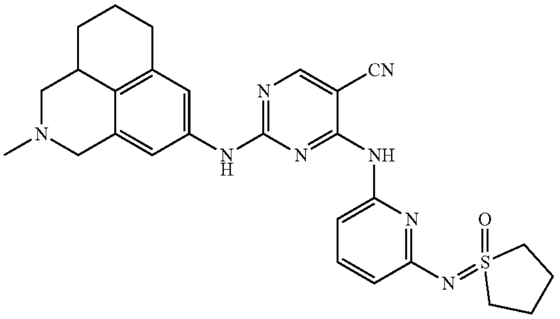
94
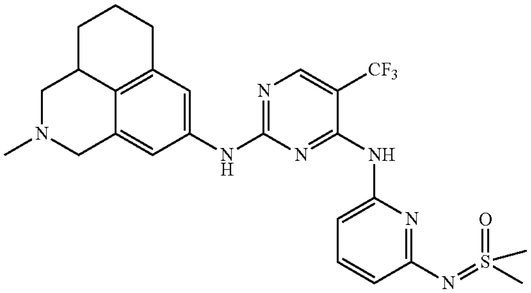
95
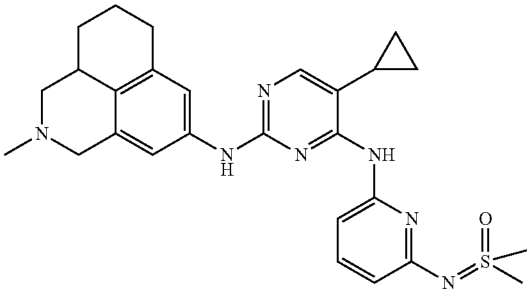
96
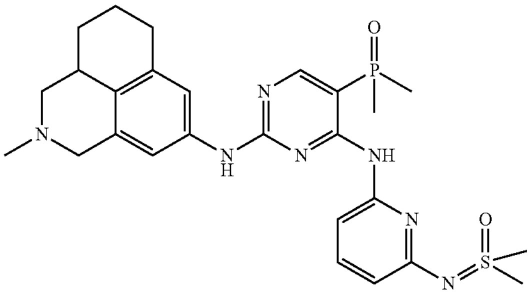
97
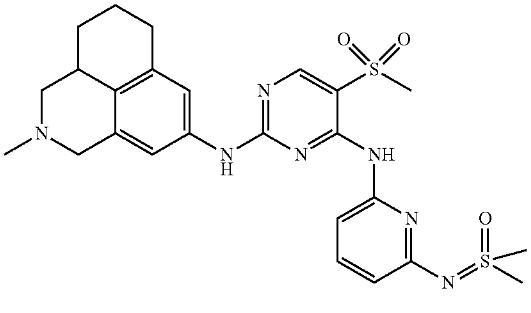
-continued
98
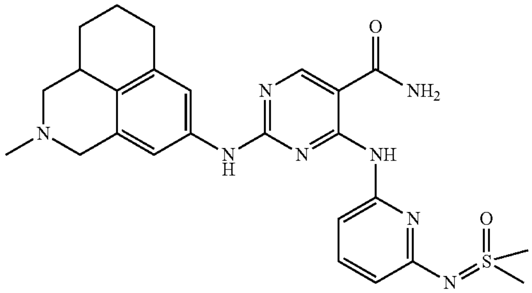
99
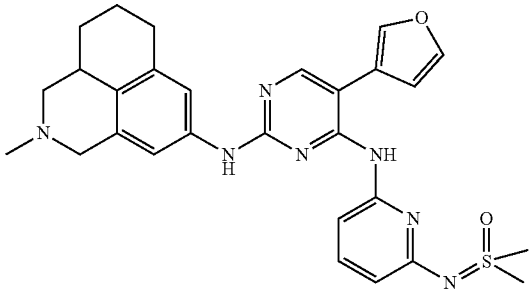
100
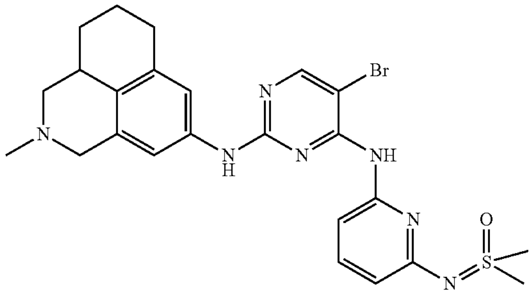
101
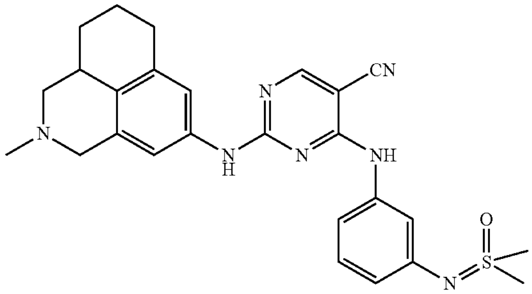
102
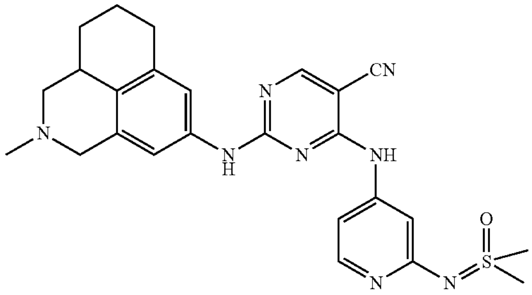

-continued
103
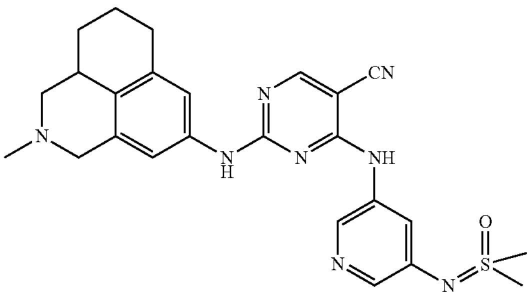
104
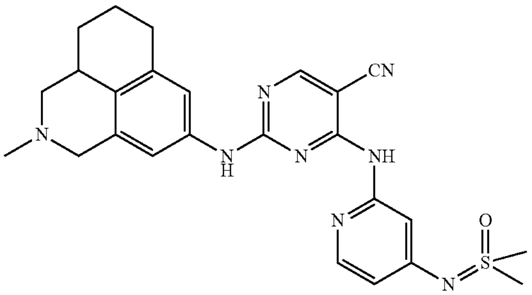
105
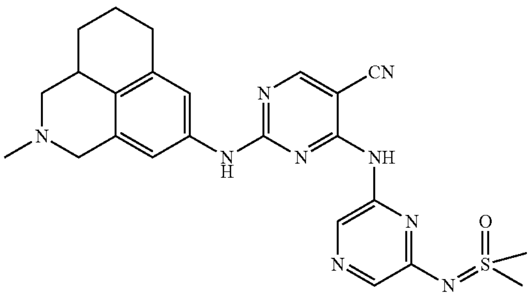
106
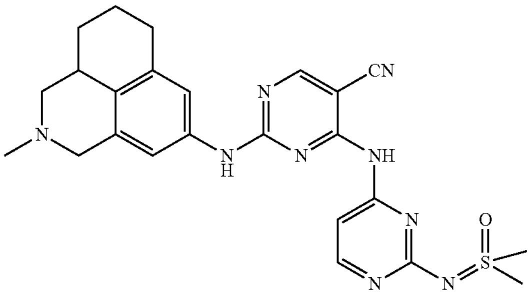
107
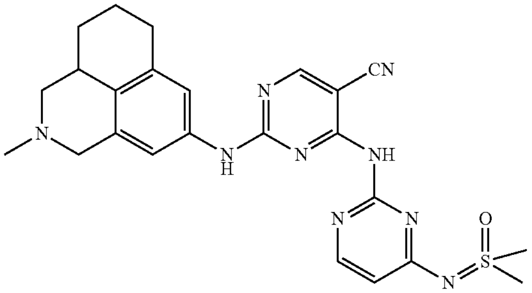
-continued
108
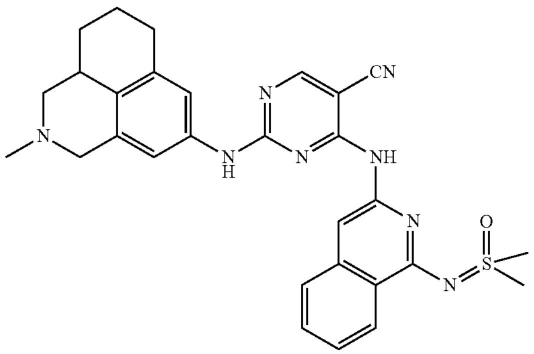
109
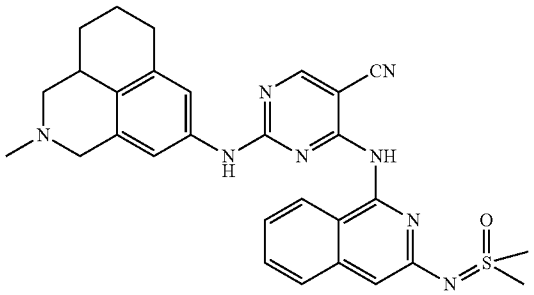
110
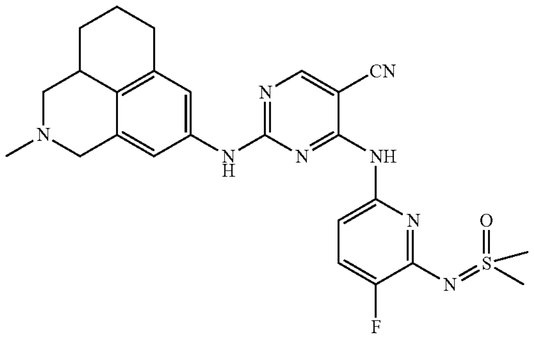
111
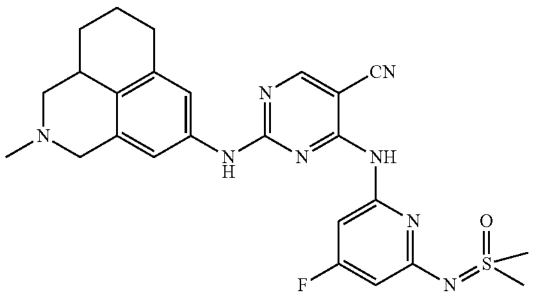

-continued
112
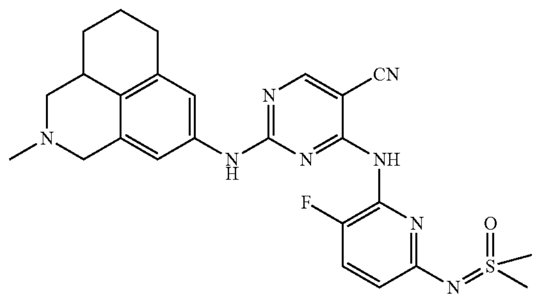
113
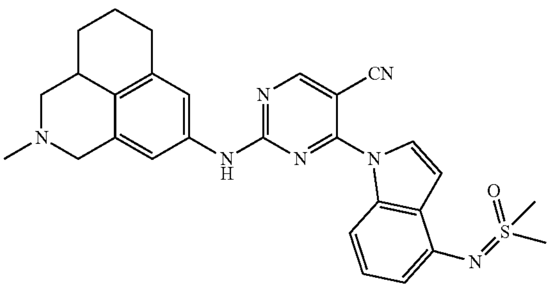
114
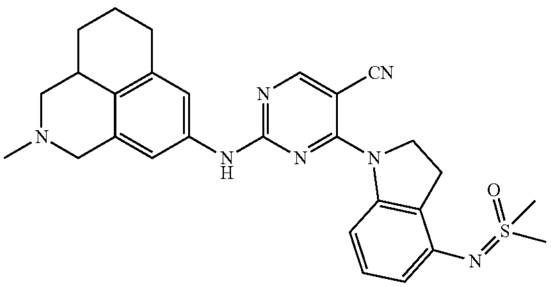
115
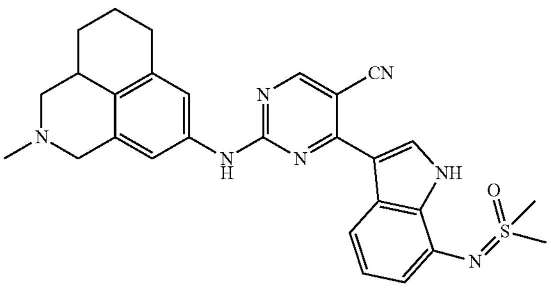
116
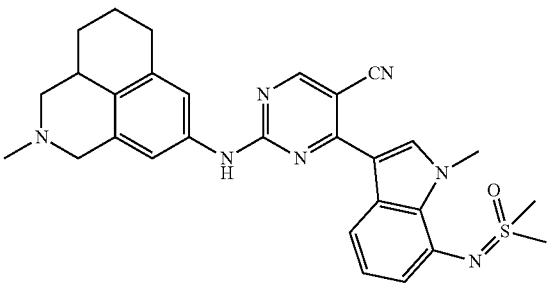
-continued
117
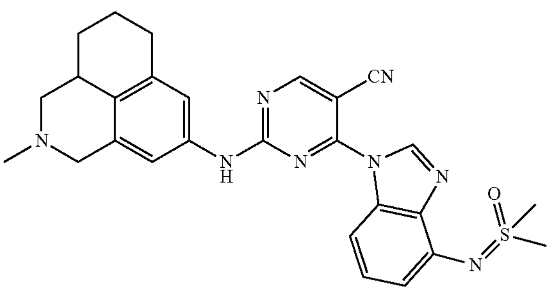
118
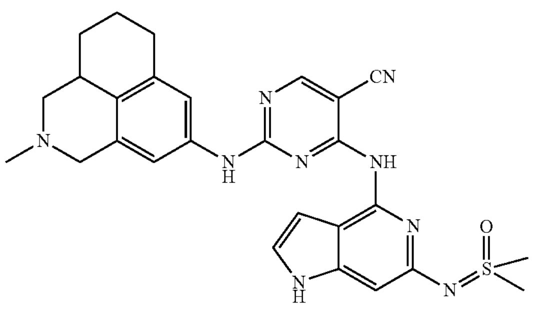
119
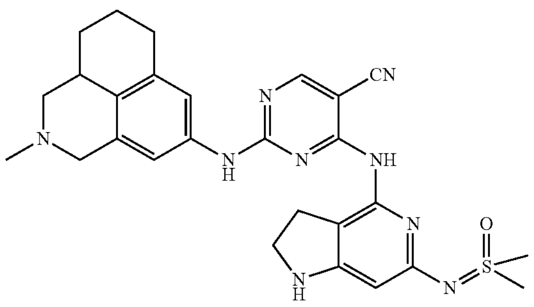
120
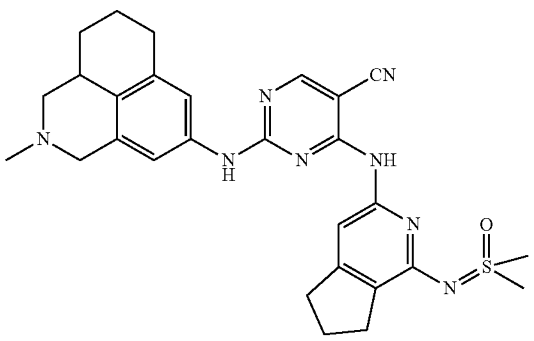

-continued
121
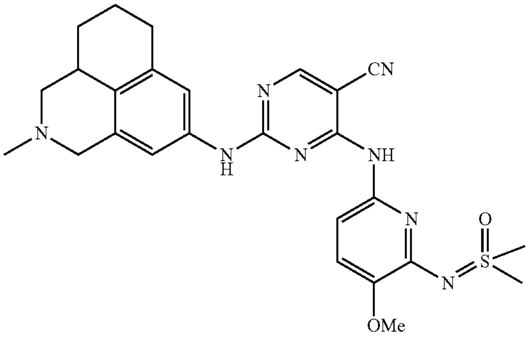
122
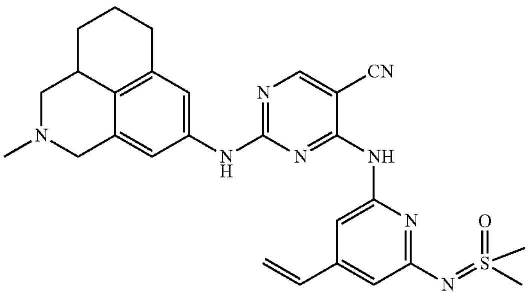
123
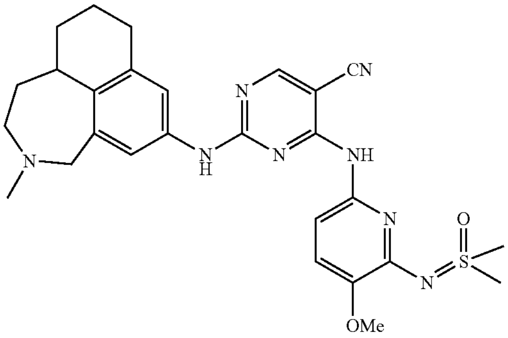
124
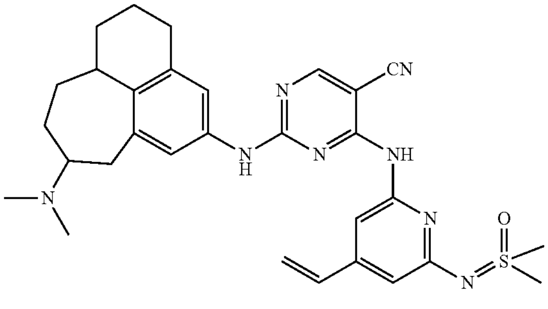
126
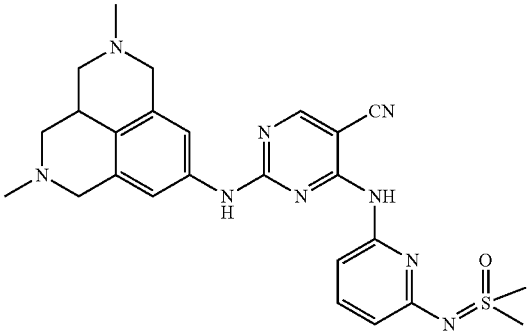
127
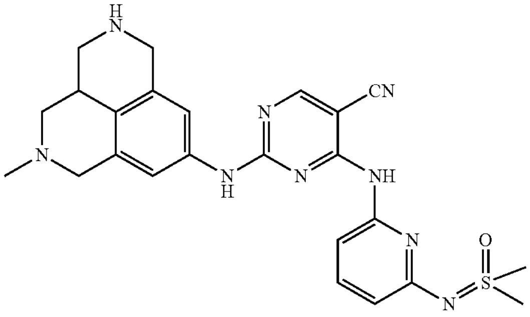
128
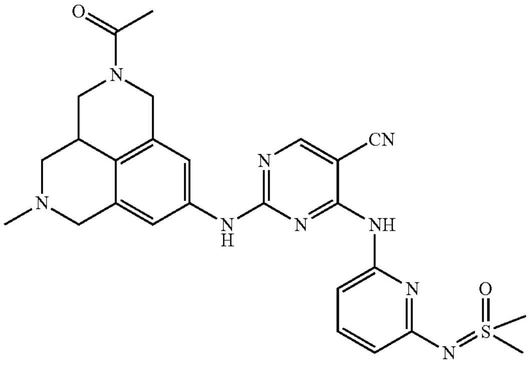
129
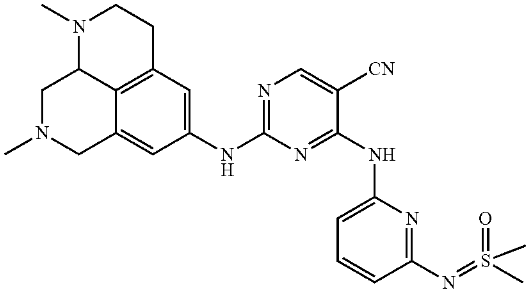

-continued
130
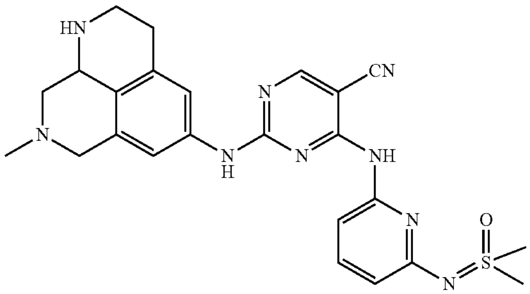
131
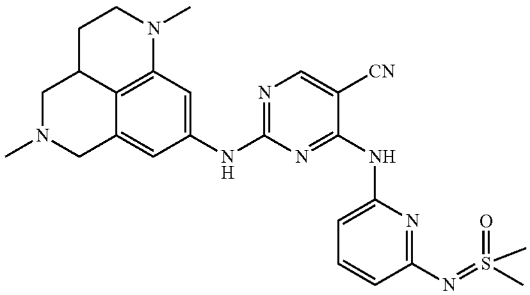
132
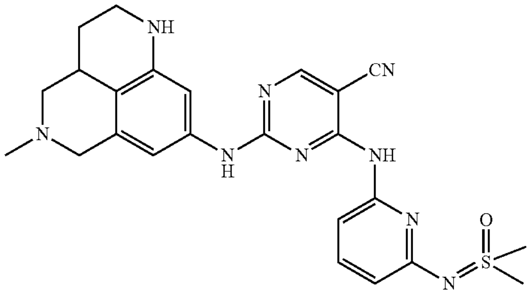
133
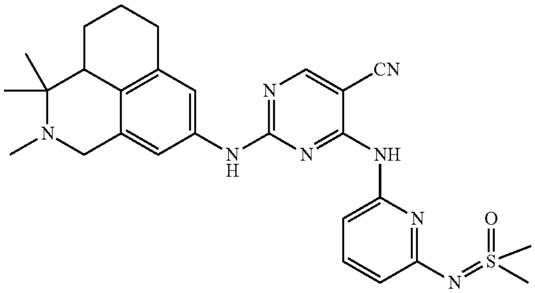
134
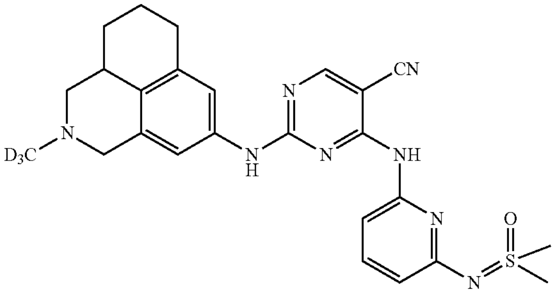
-continued
135
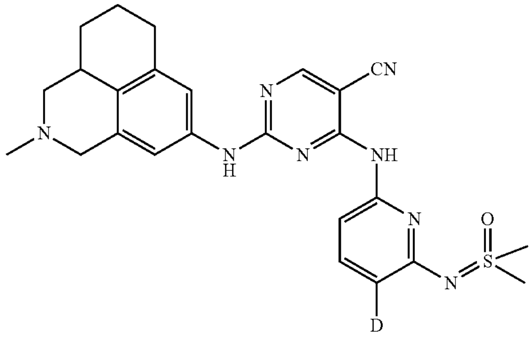
136
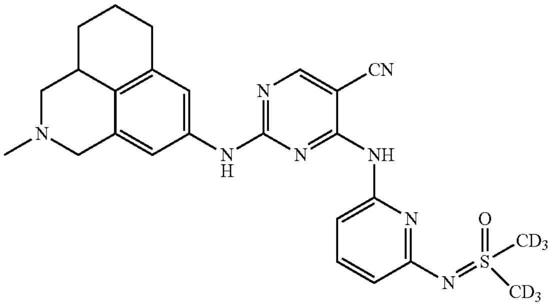
137
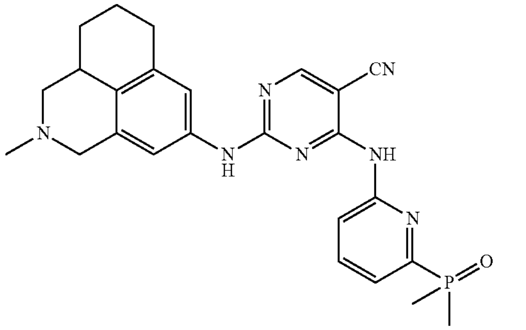
138
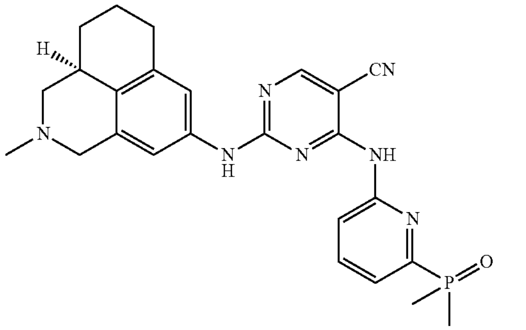

-continued
139
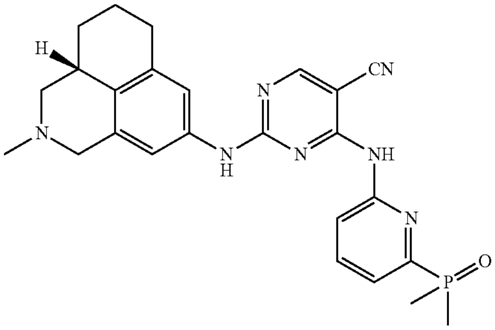
140
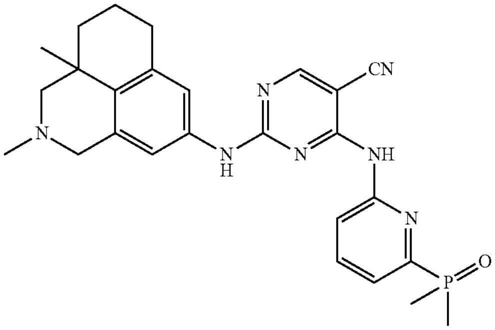
141
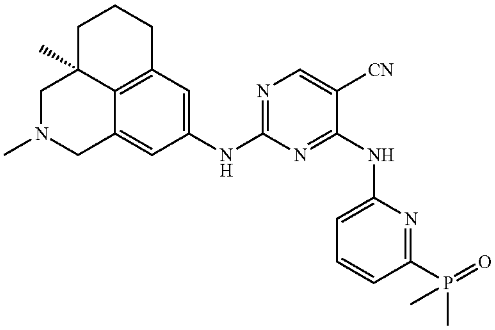
142
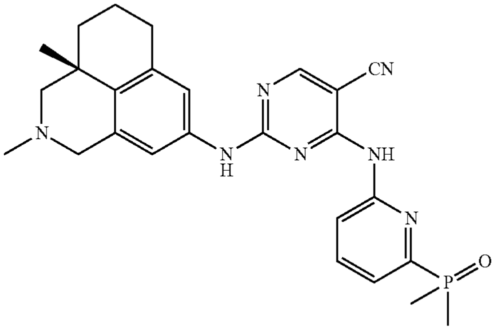
-continued
143
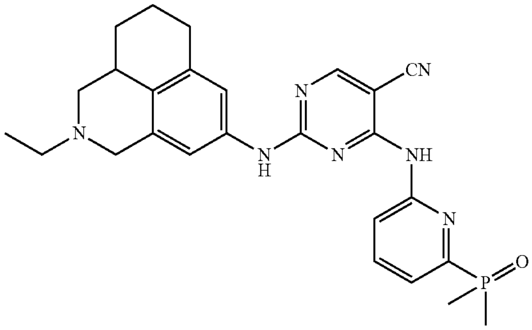
144
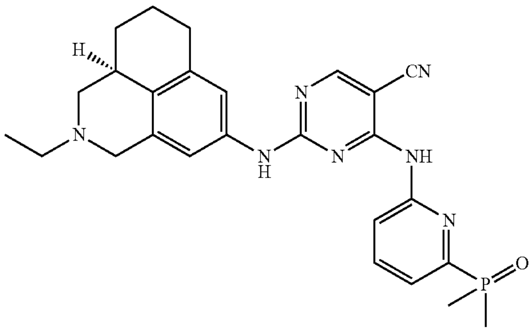
145
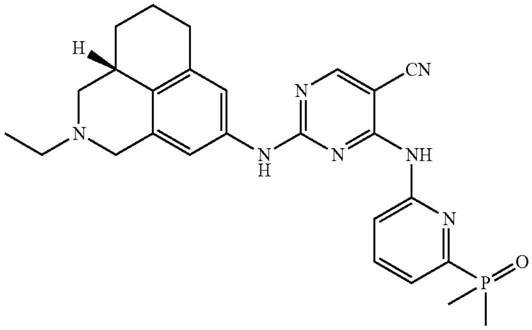
146
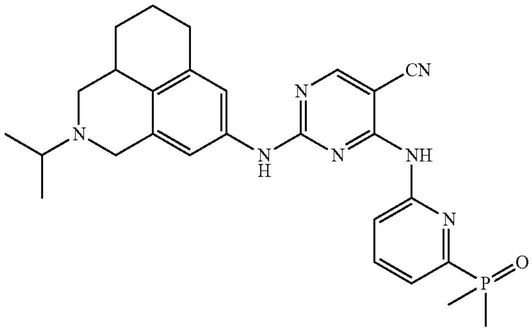

-continued
147
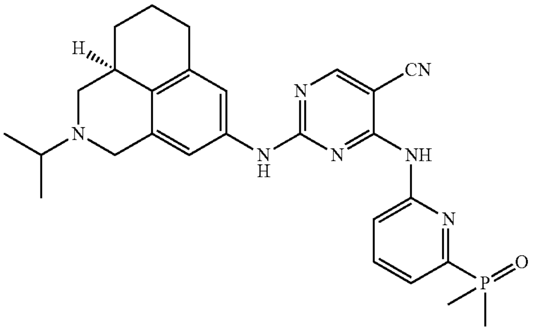
148
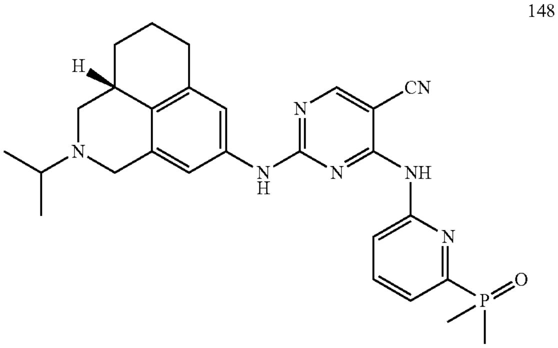
149
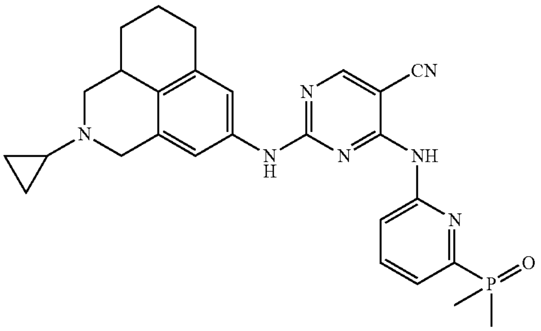
150
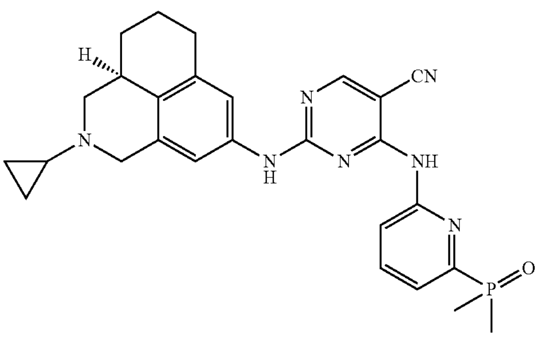
-continued
151
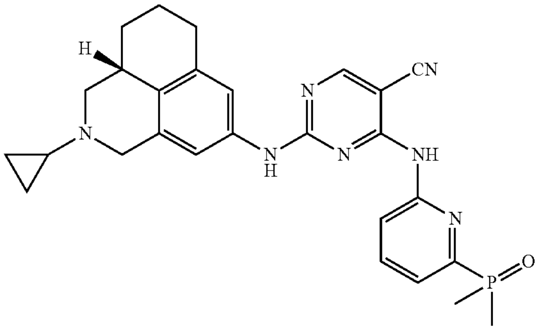
152
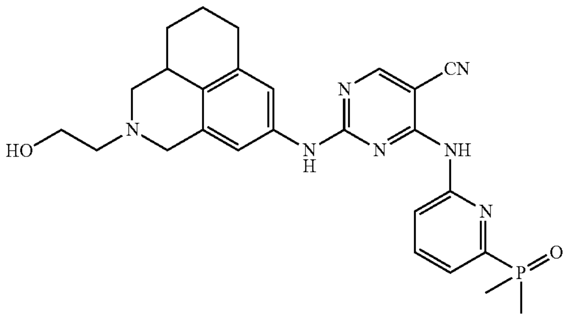
153
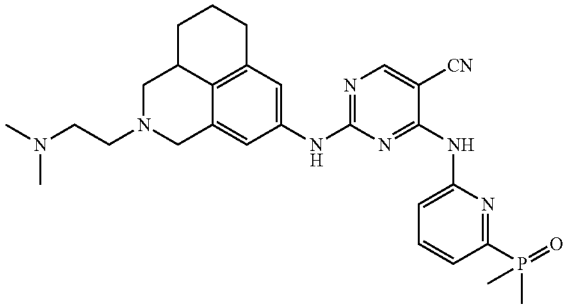
154
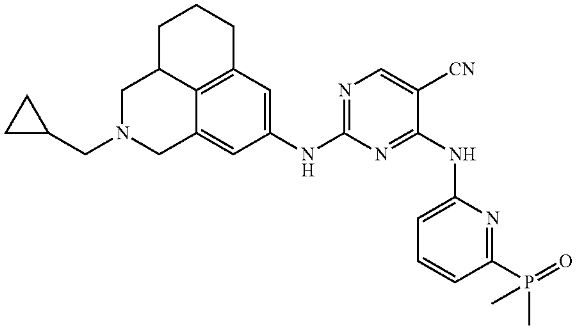

-continued
155
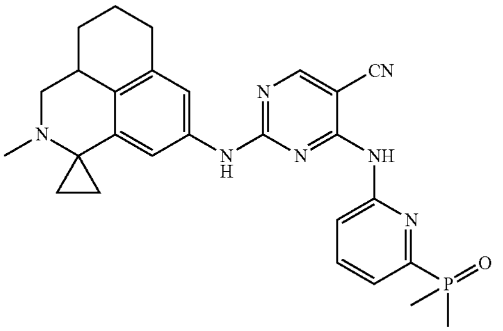
156
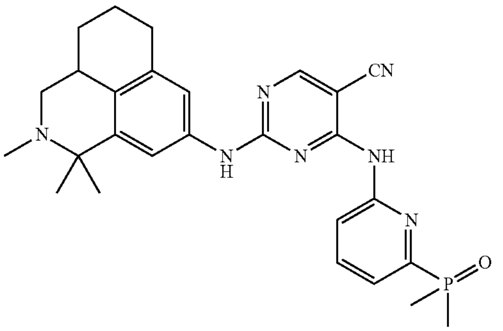
157
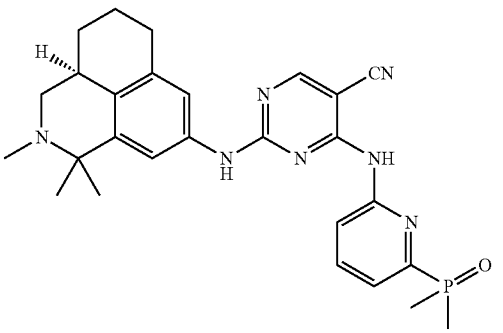
158
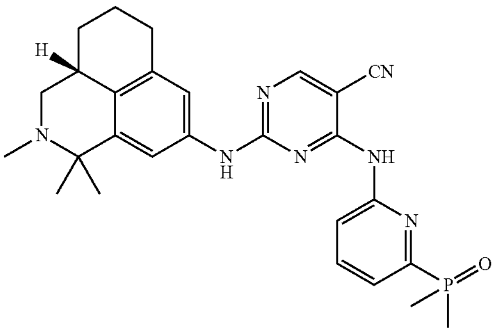
-continued
159
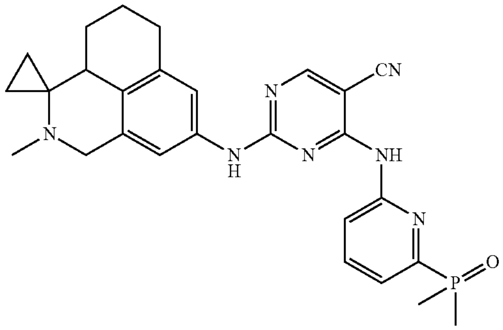
160
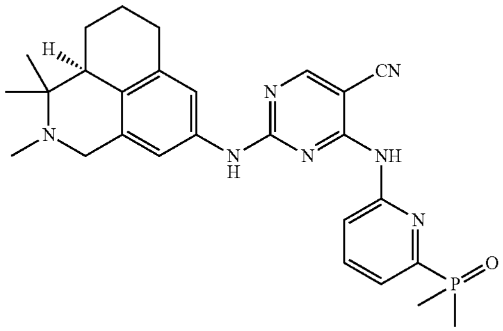
161
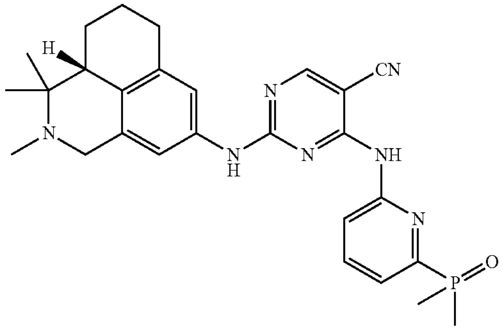
162
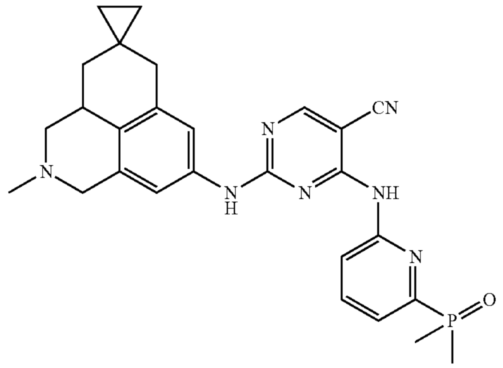

-continued
163
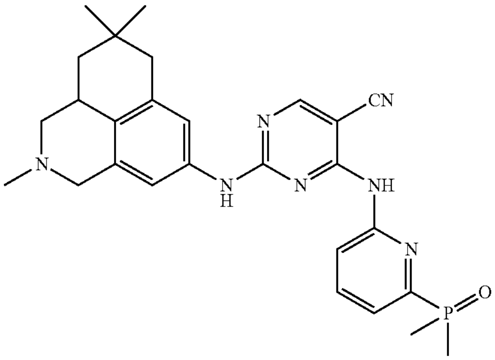
164
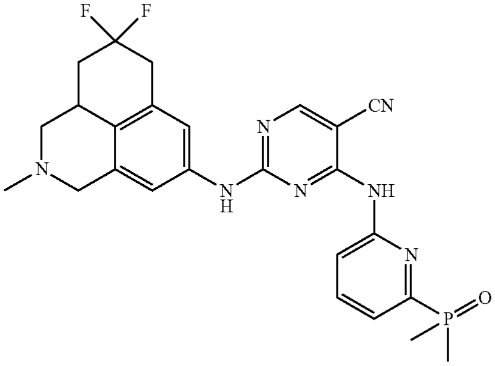
165
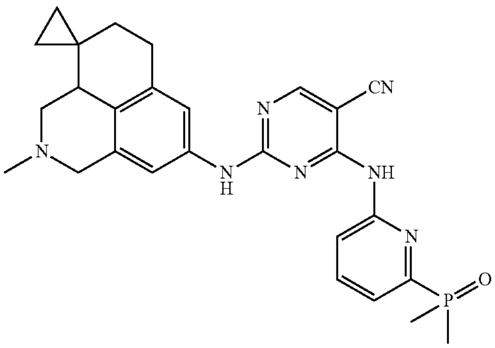
166
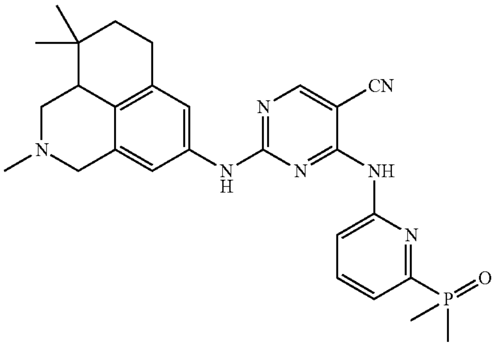
-continued
167
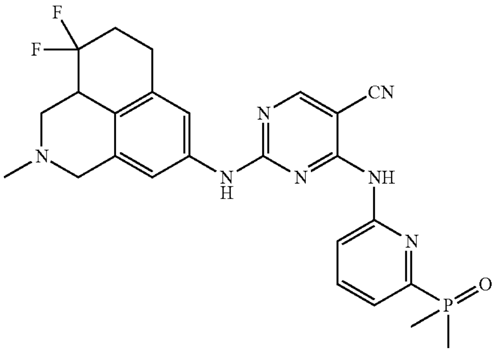
168
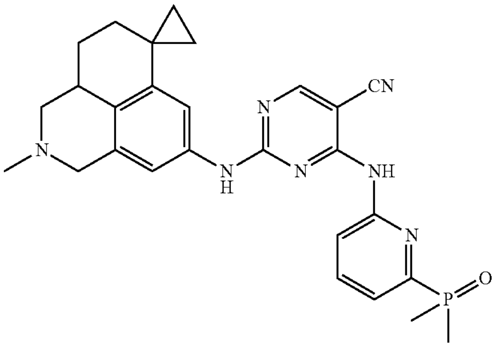
169
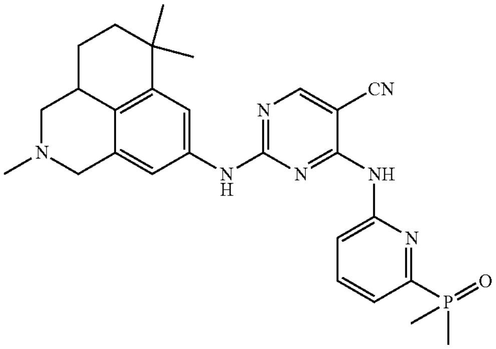
170
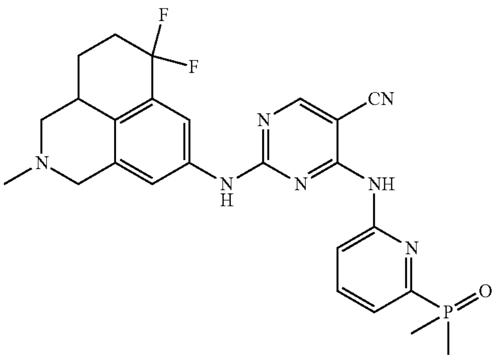

-continued
171
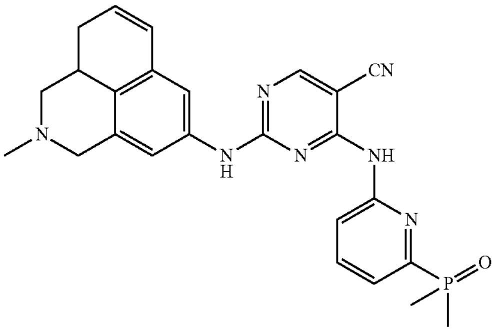
172
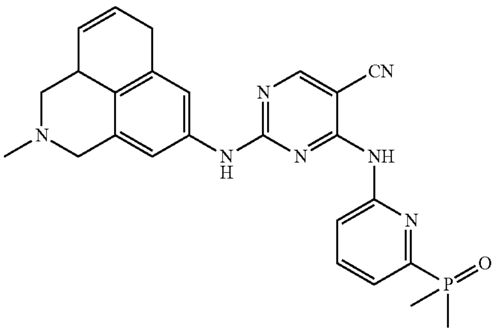
173
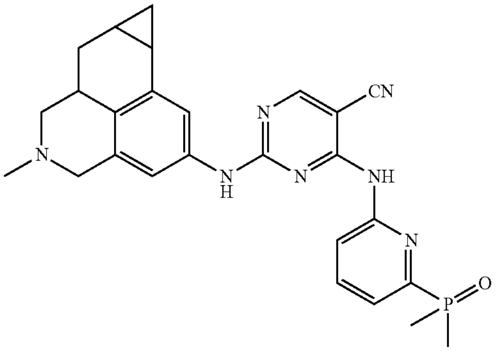
174
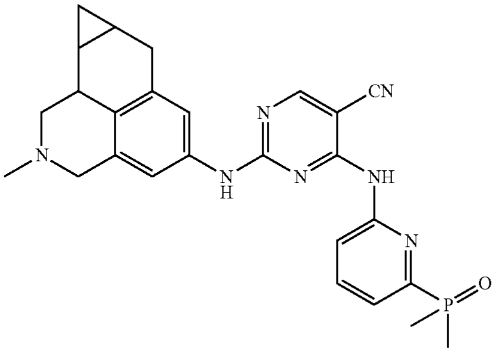
-continued
175
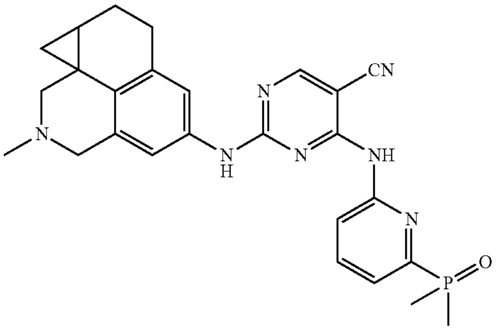
176
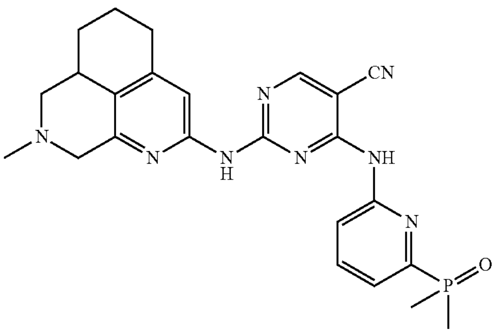
177
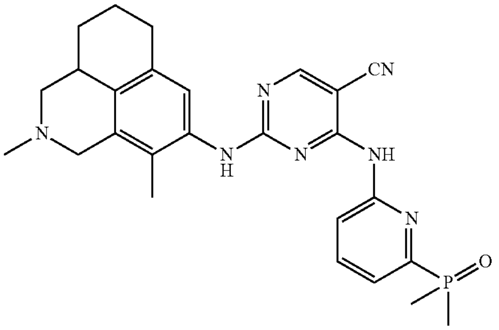
178
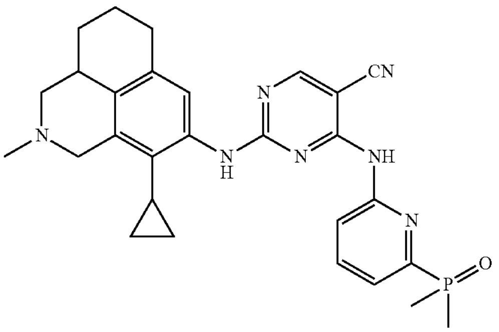

-continued
179
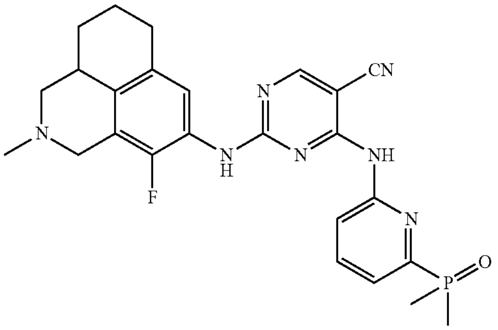
180
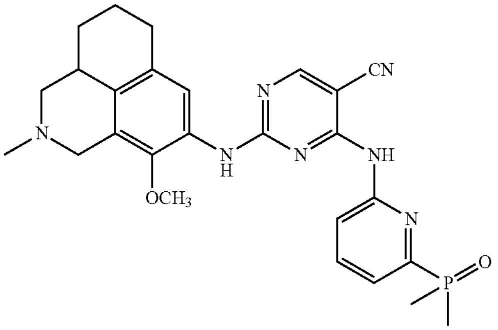
181
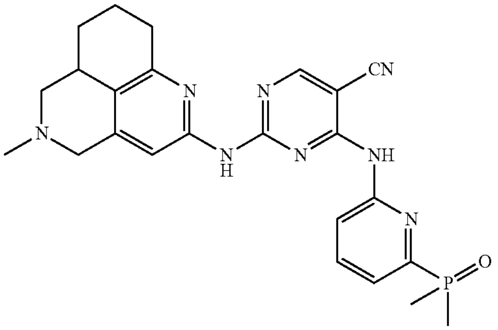
182
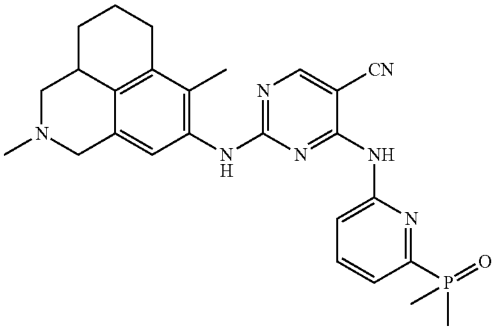
-continued
183
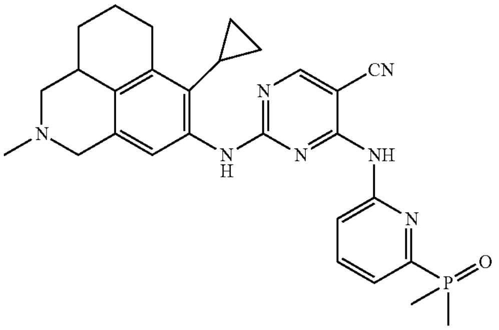
184
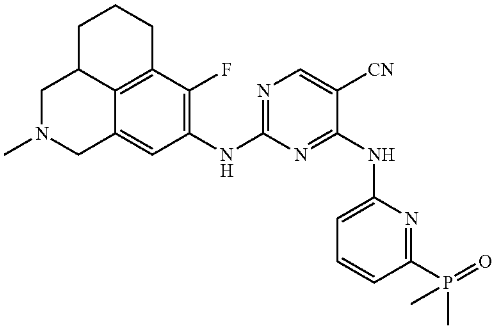
185
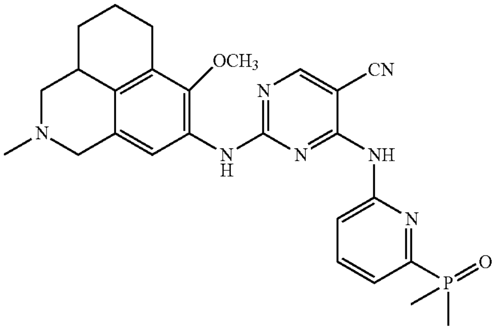
186
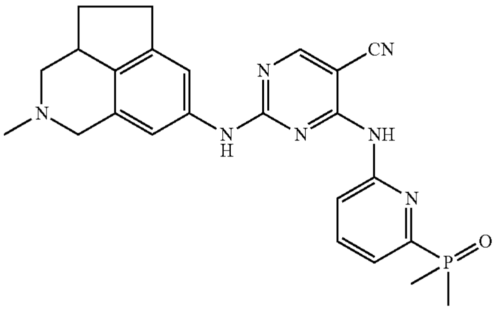

187
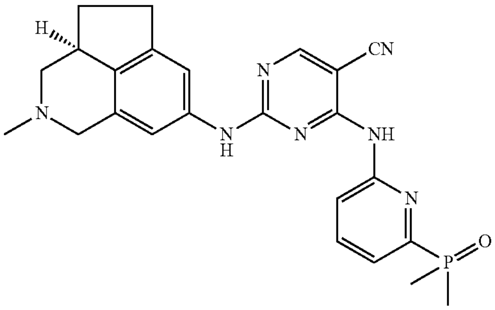
188
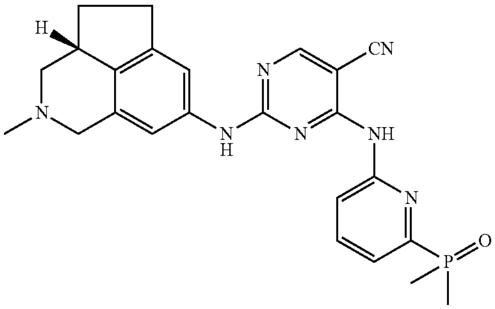
189
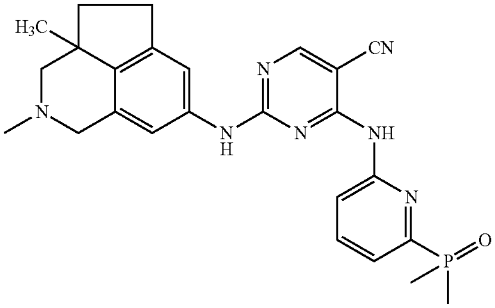
190
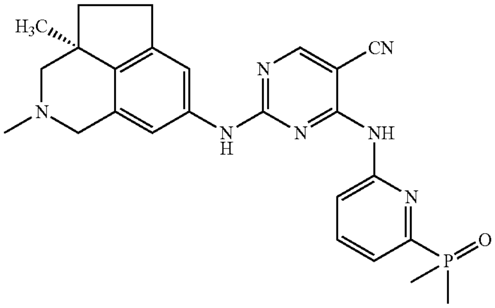
191
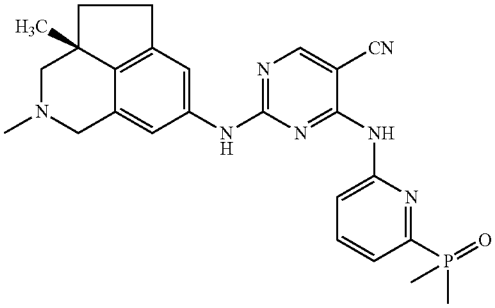
192
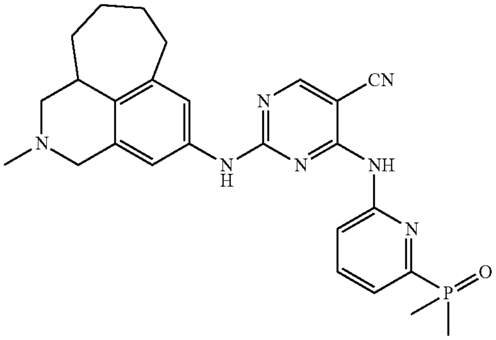
193
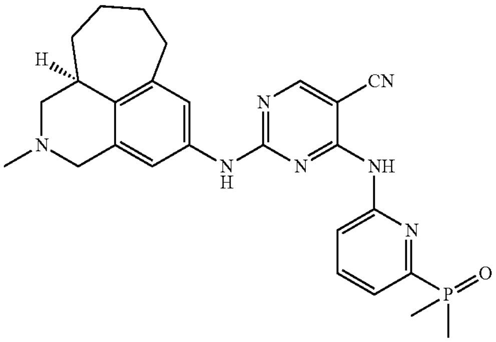
194
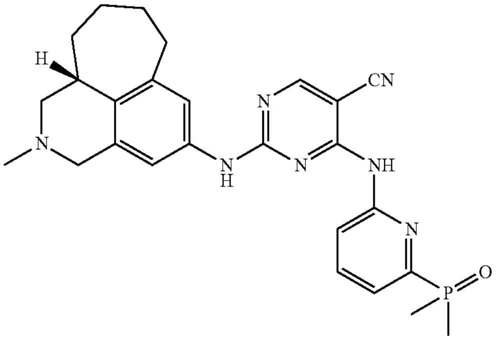
195
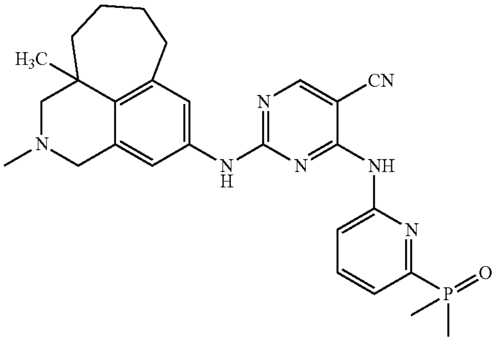

-continued
196
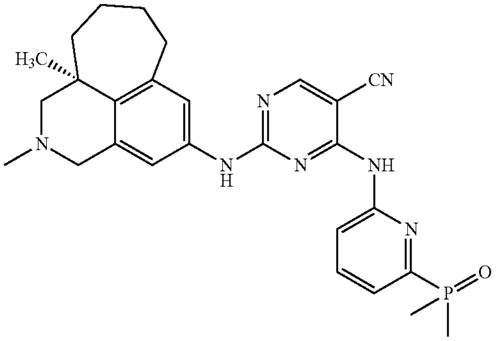
197
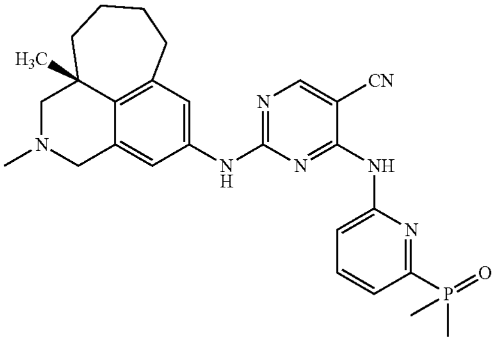
198
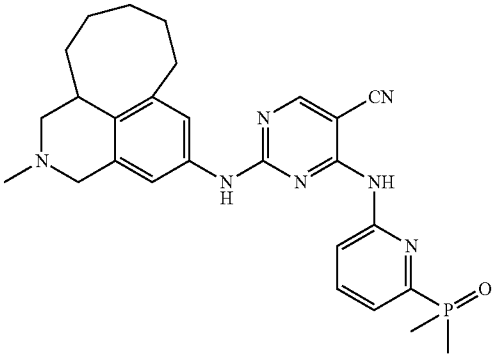
199
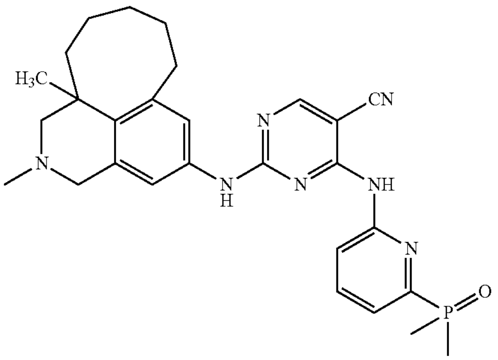
-continued
200
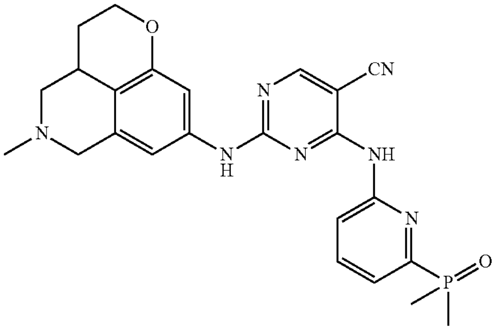
201
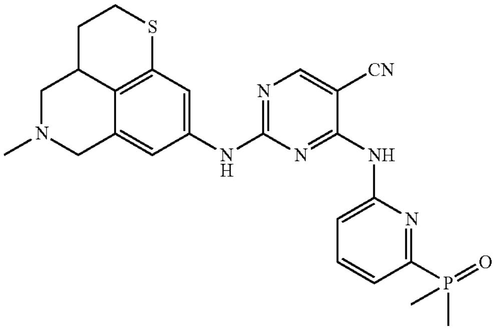
202
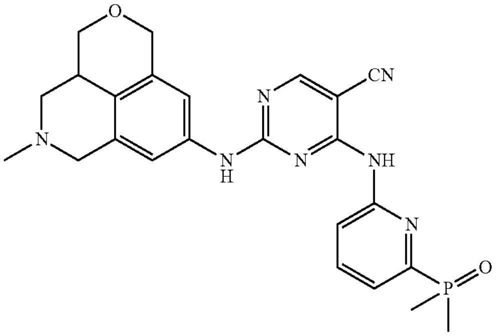
203
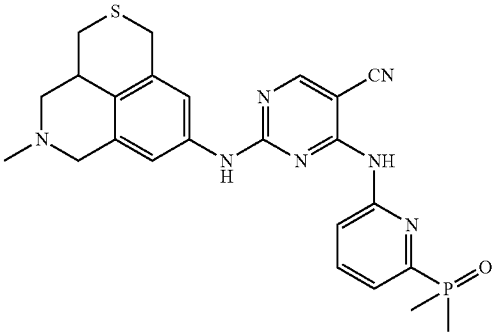

-continued
204
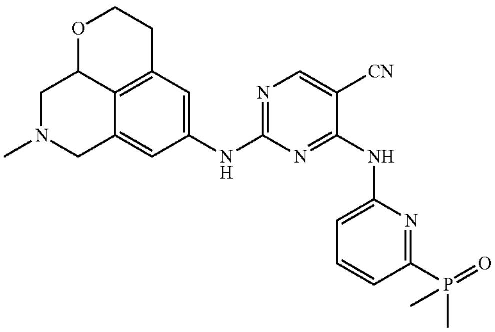
205
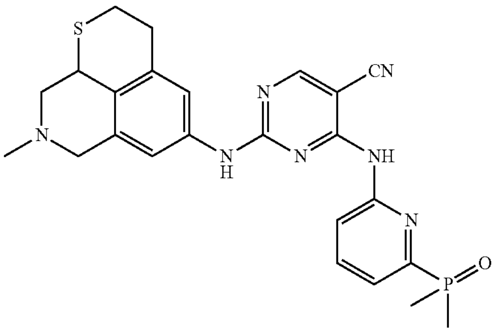
206
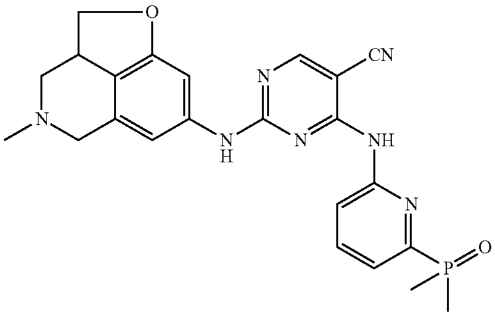
207
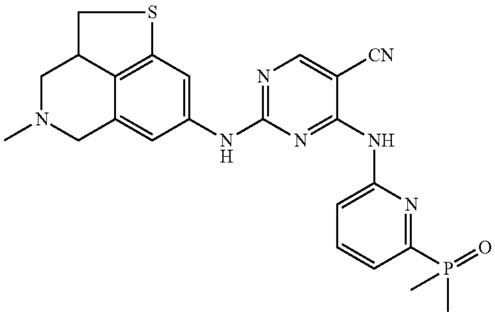
208
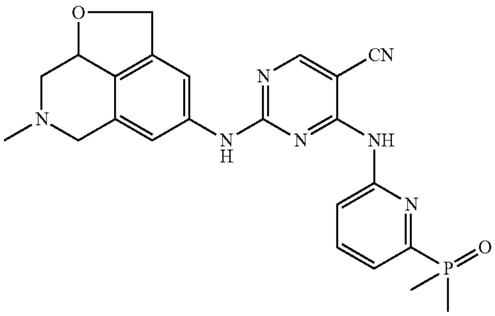
-continued
209
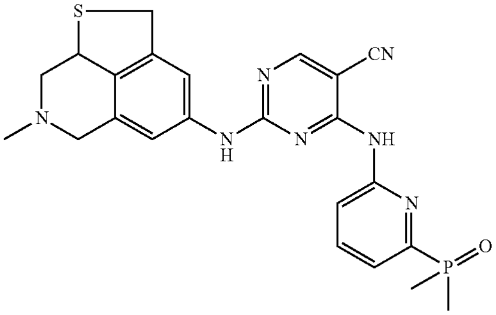
210
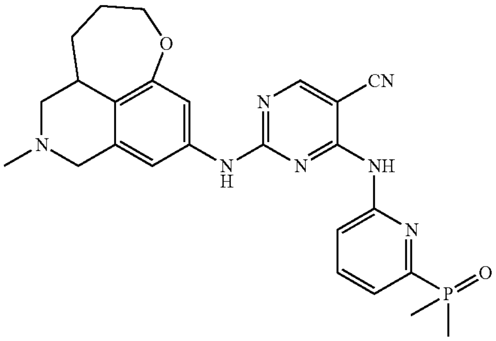
211
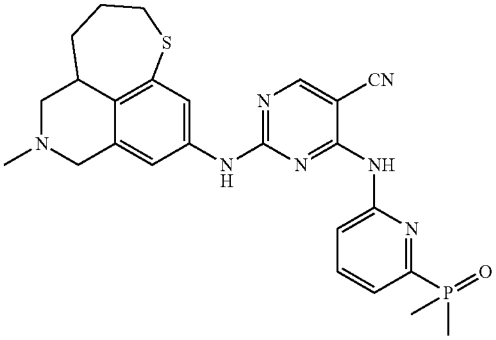
212
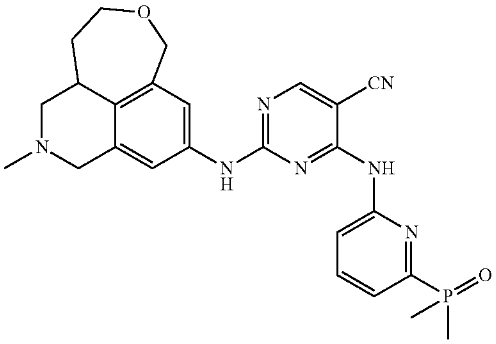

-continued
213
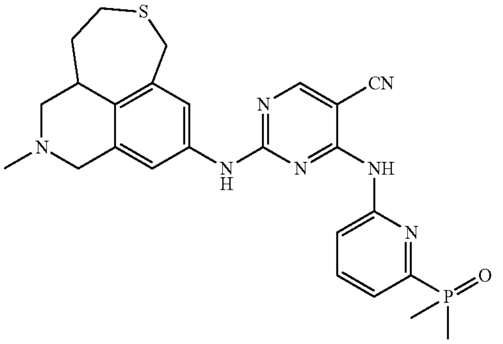
214
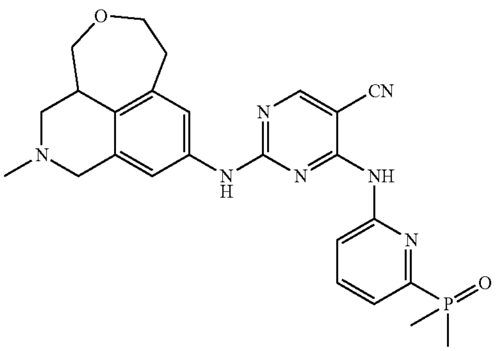
215
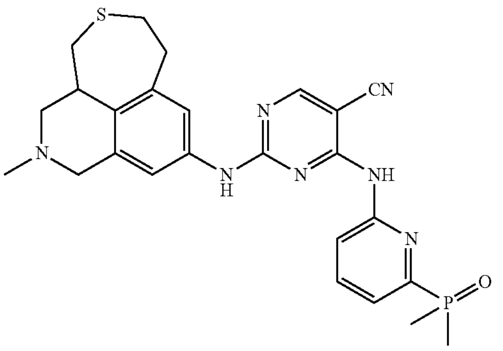
216
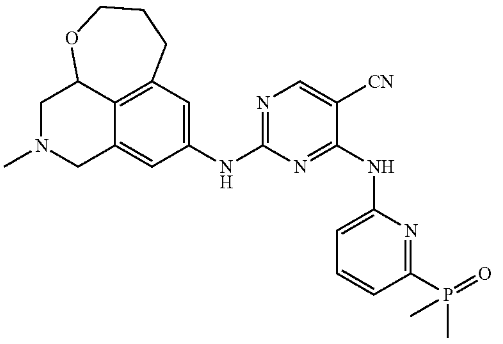
217
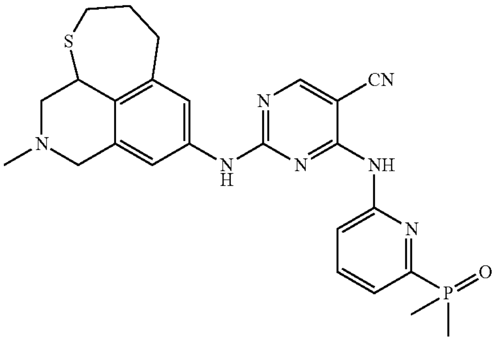
218
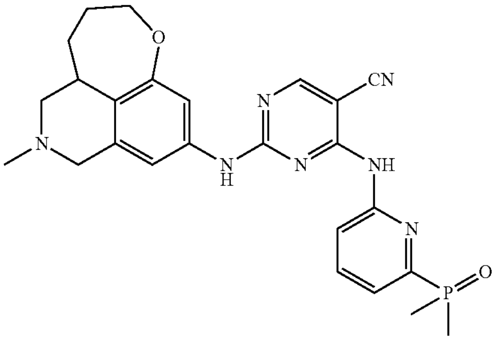
219
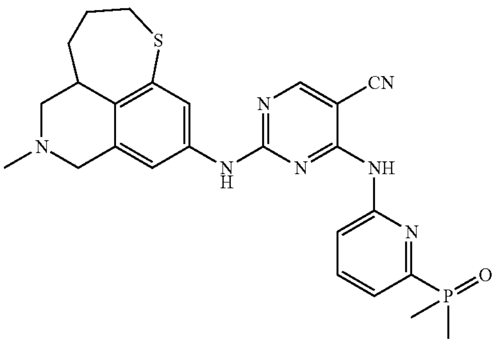
220
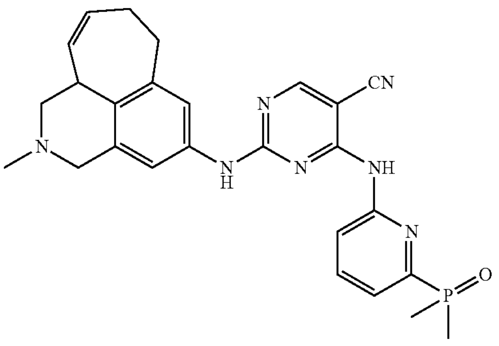

-continued
221
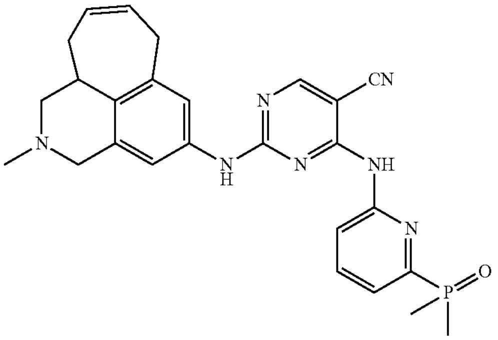
222
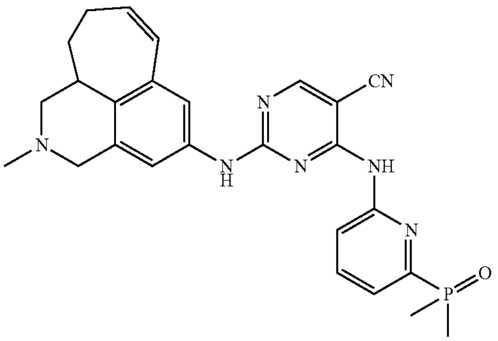
223
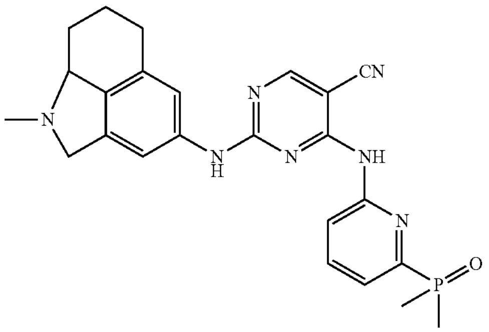
224
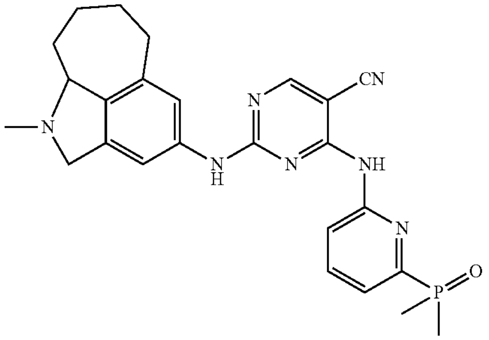
-continued
225
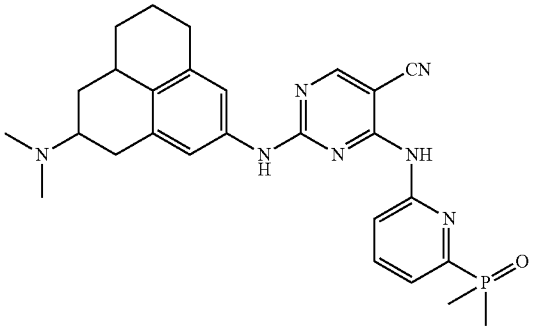
226
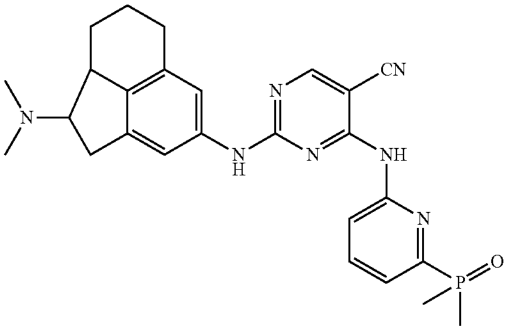
227
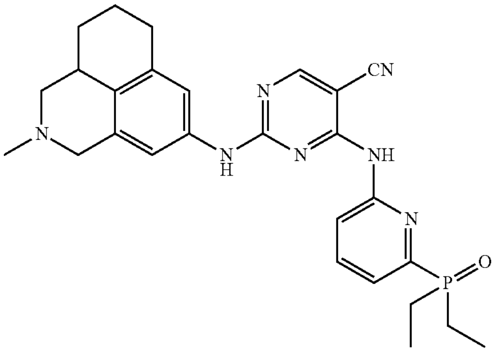
228
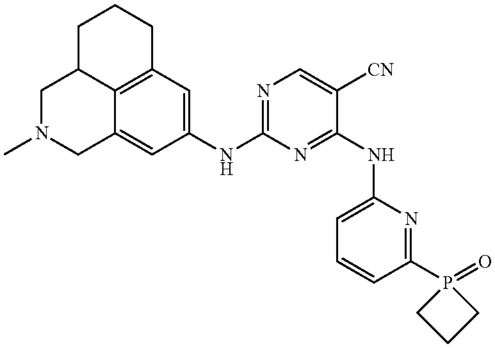

-continued
229
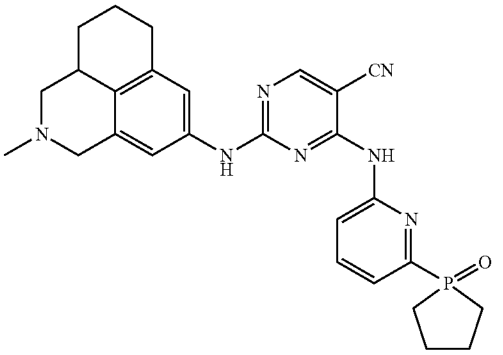
230
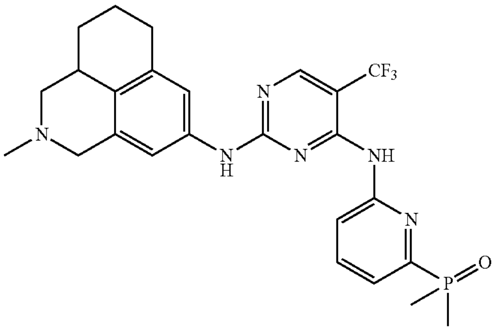
231
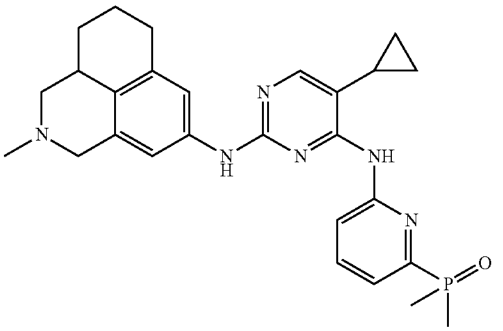
232
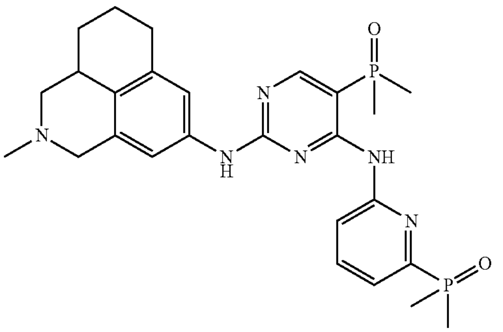
-continued
233
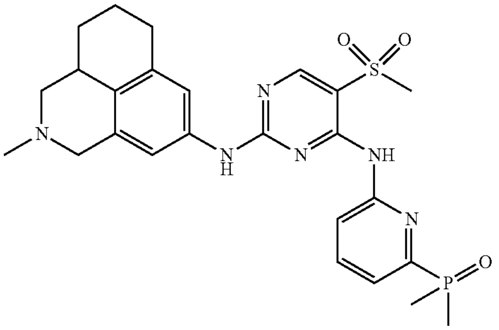
234
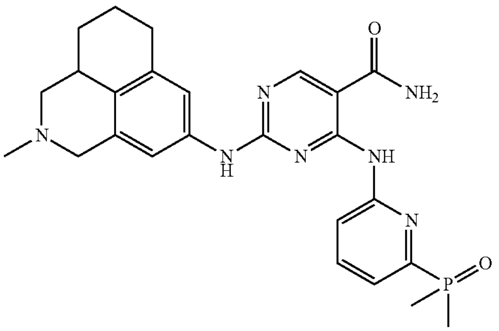
235
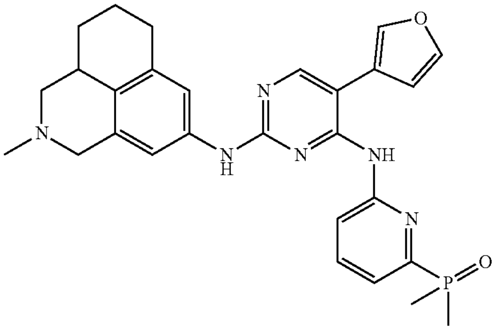
236
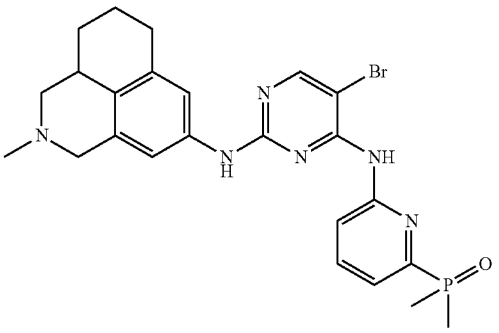

-continued
237
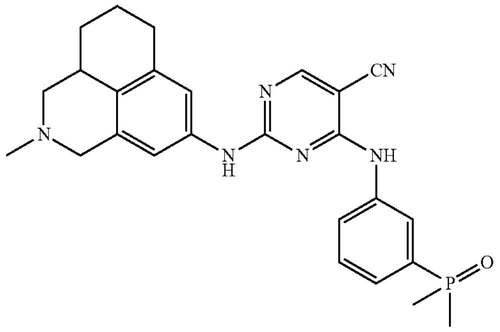
238
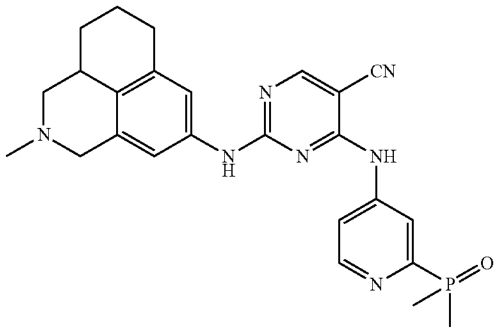
239
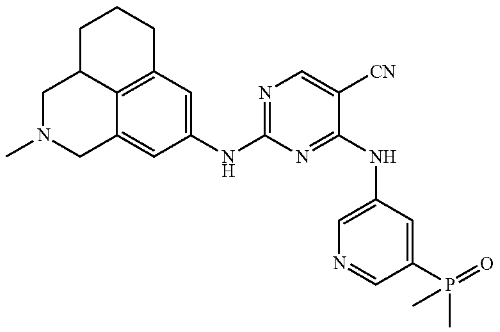
240
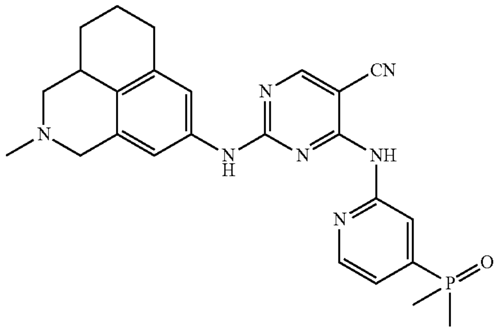
-continued
241
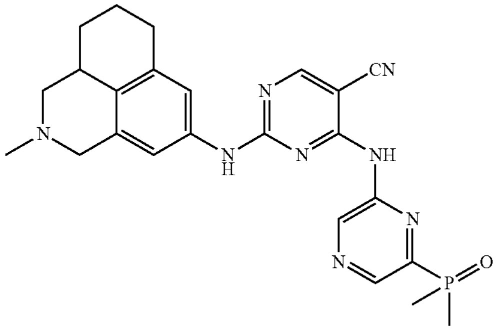
242
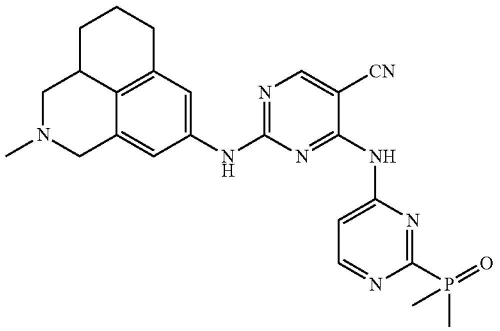
243
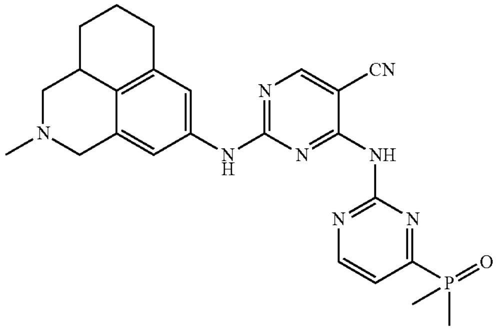
244
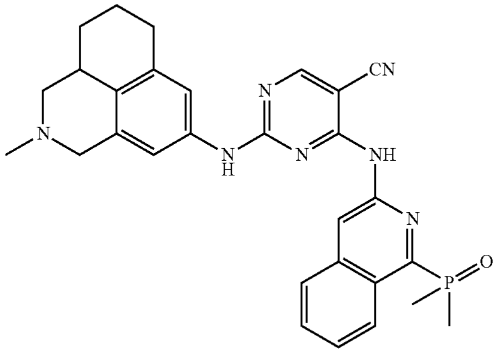

-continued
245
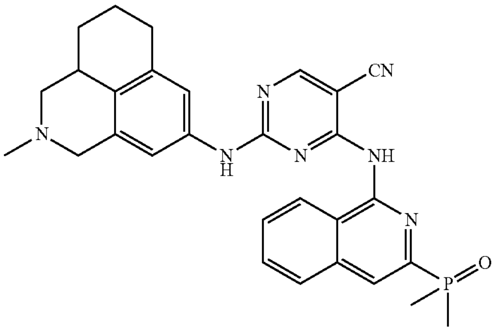
246
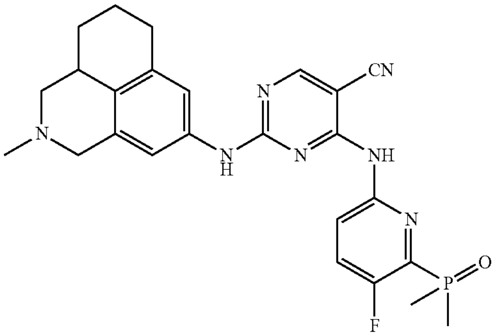
247
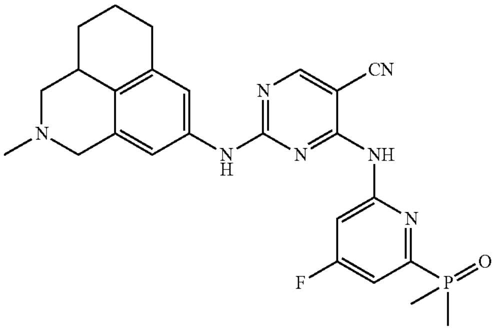
248
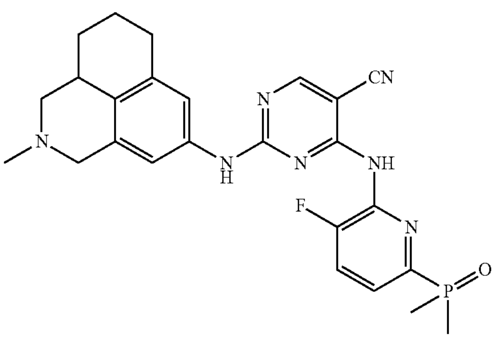
-continued
249
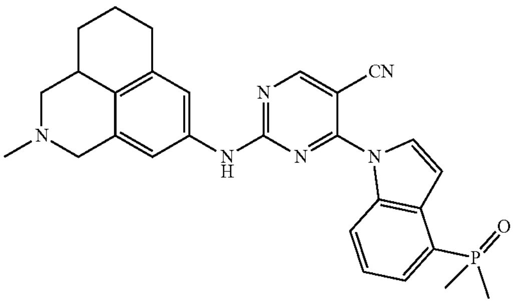
250
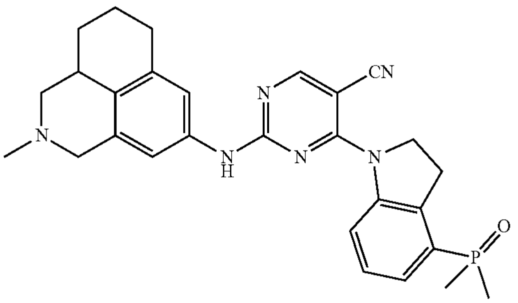
251
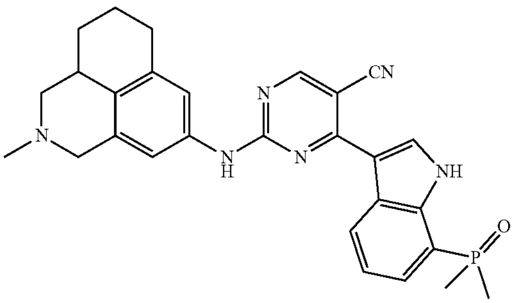
252
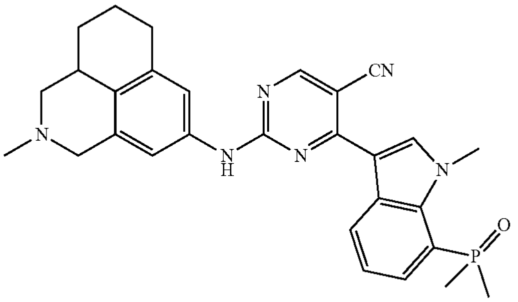
253
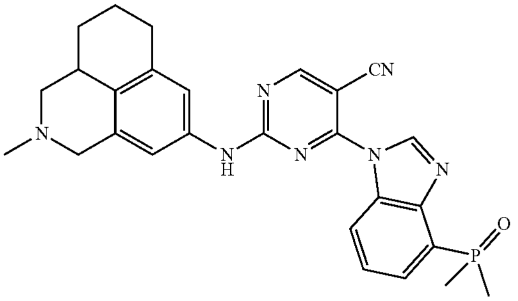

-continued
254
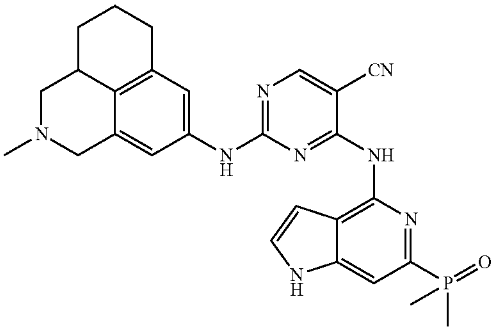
255
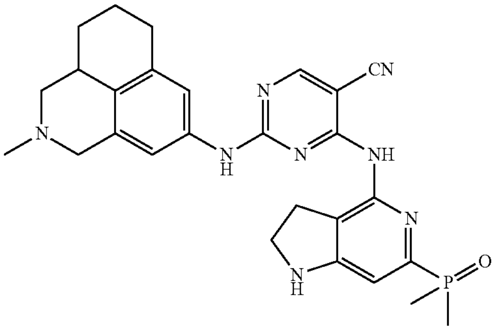
256
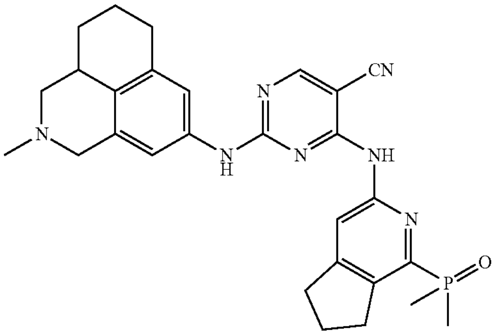
257
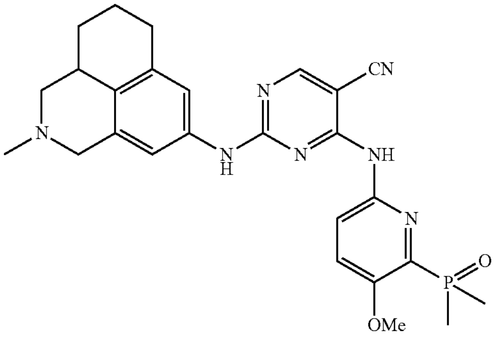
-continued
258
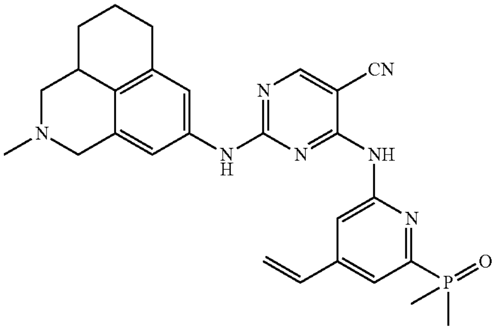
259
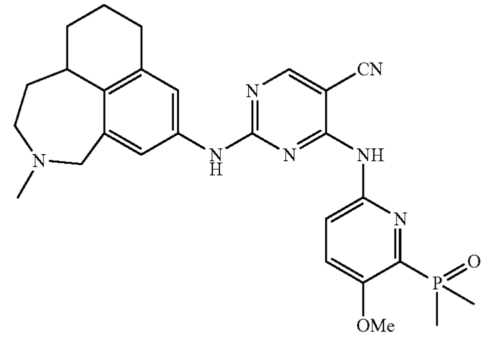
260
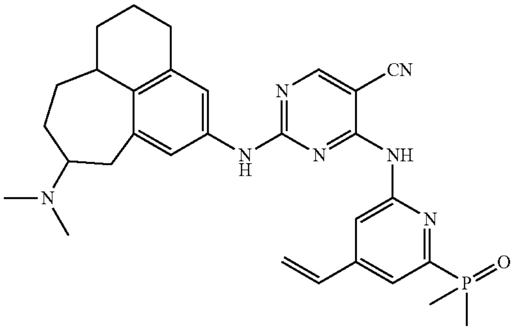
261
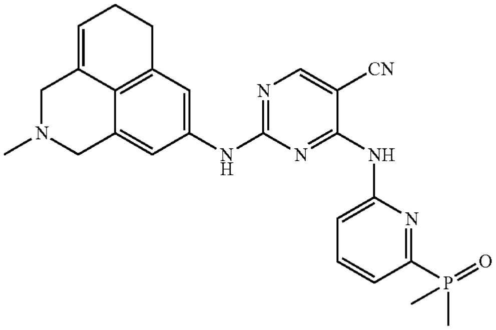

-continued
262
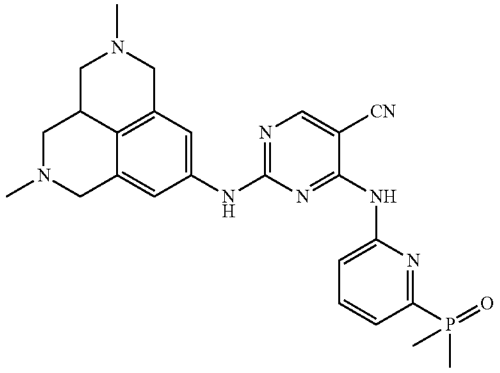
263
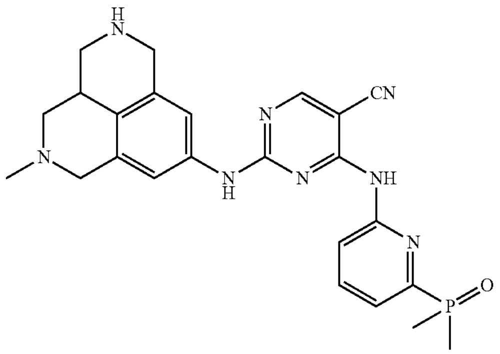
264
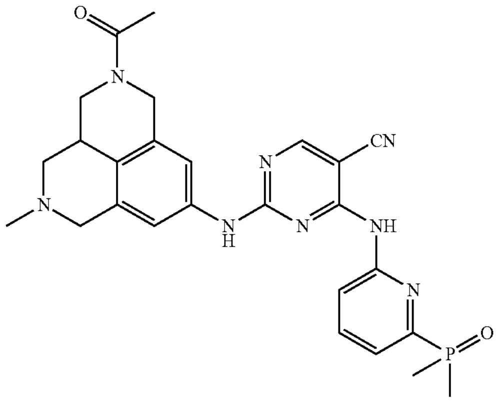
273
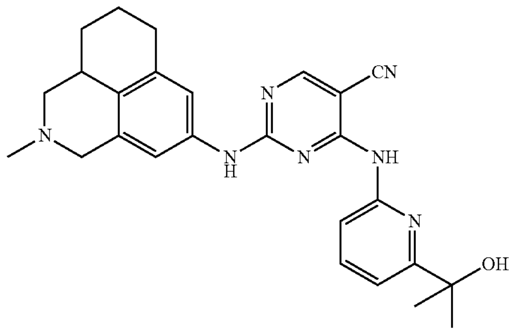
-continued
274
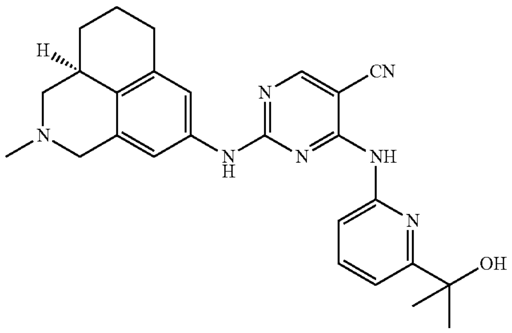
275
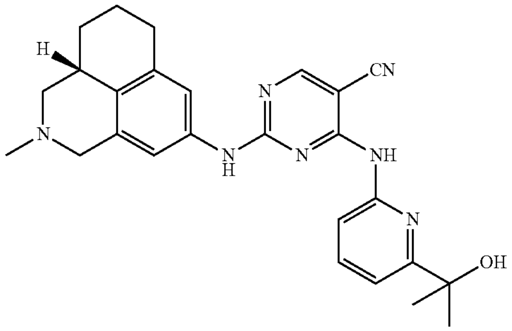
276
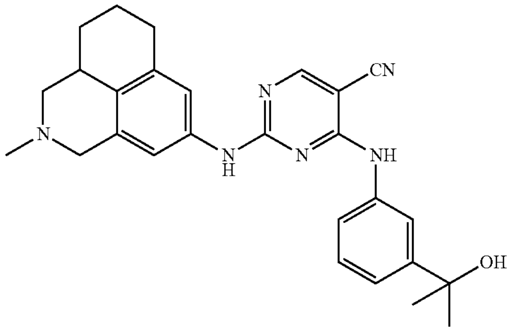
277
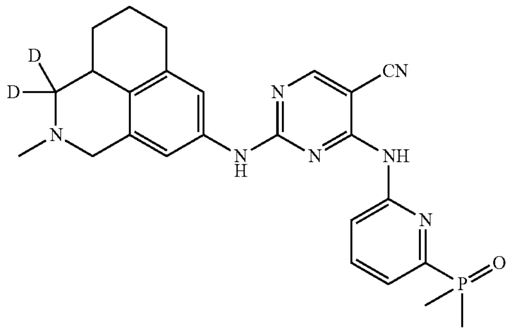

-continued
278
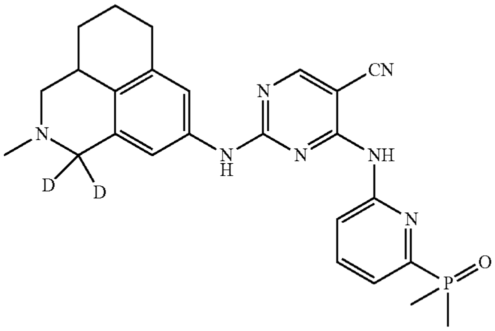
279
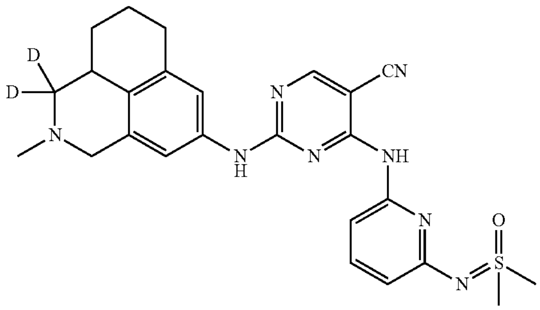
280
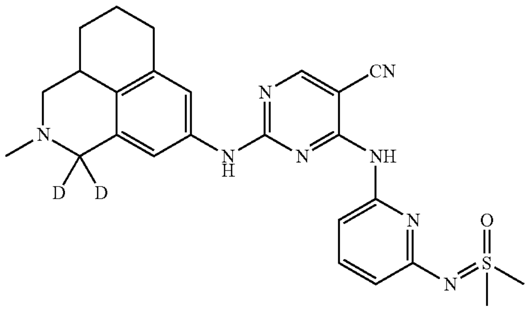
281
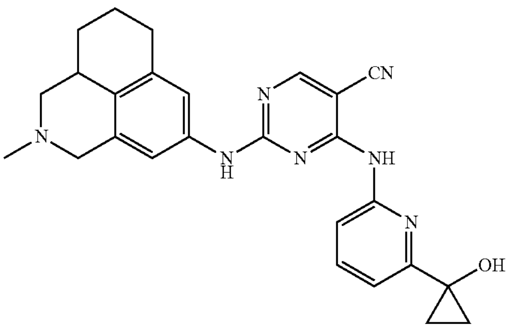
-continued
282
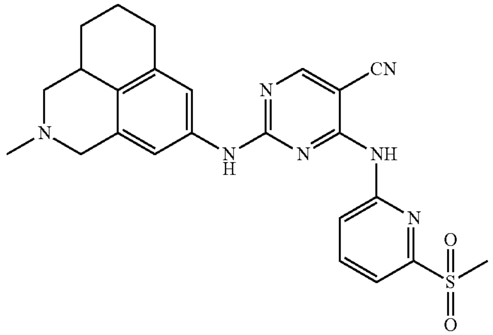
283
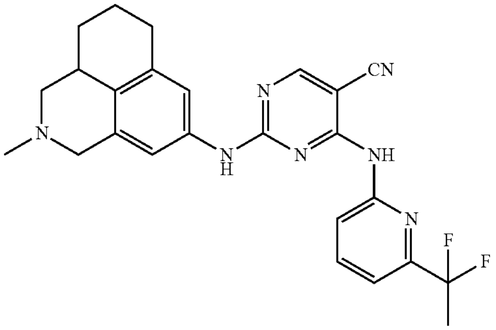
284
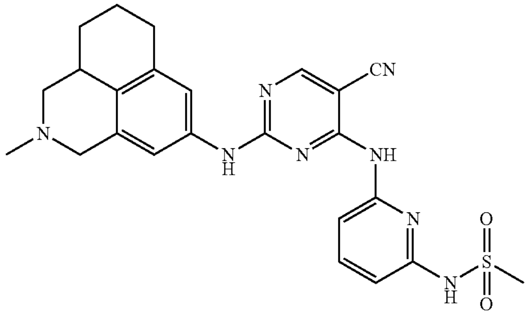
285
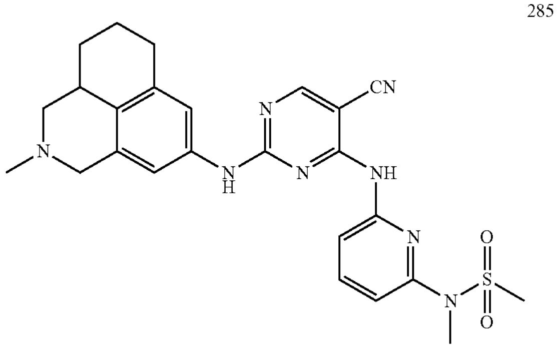

-continued
286
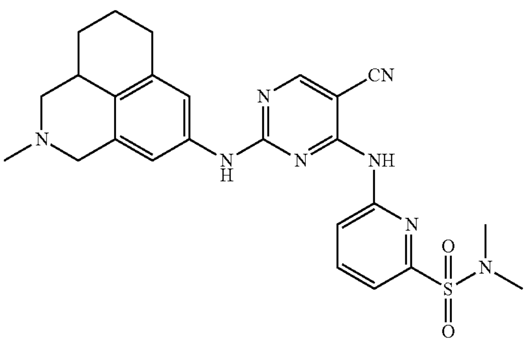
287
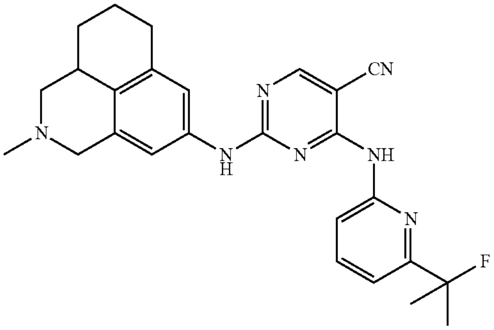
288
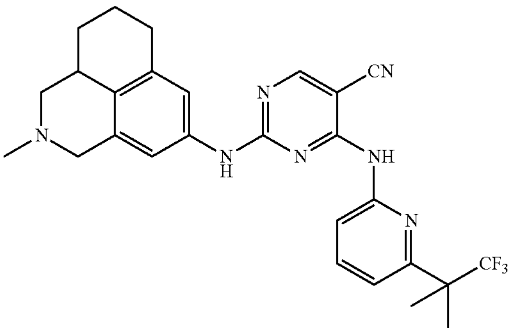
289
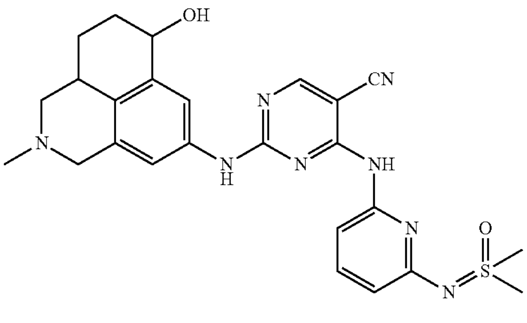
-continued
290
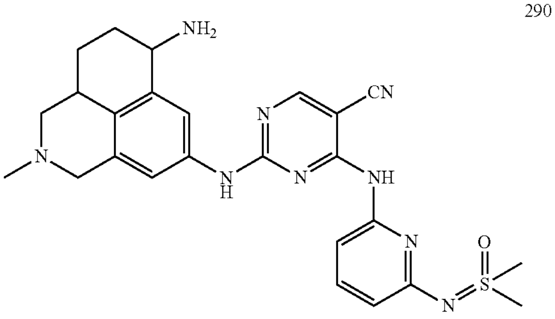
291
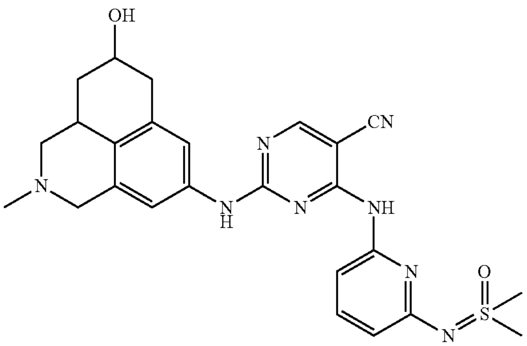
292
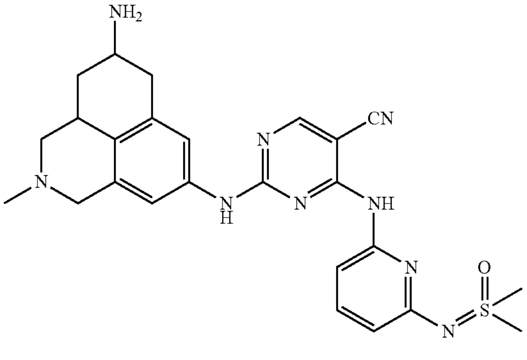

-continued
293
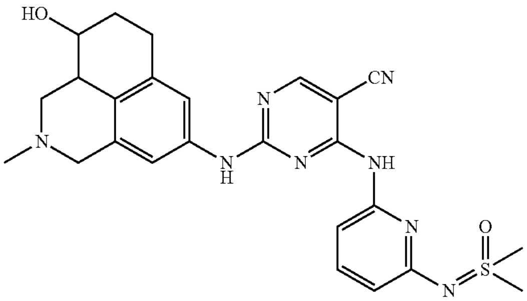
294
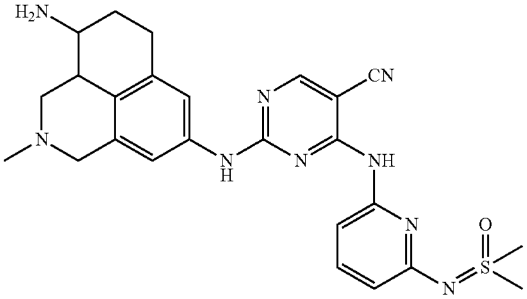
-continued
295
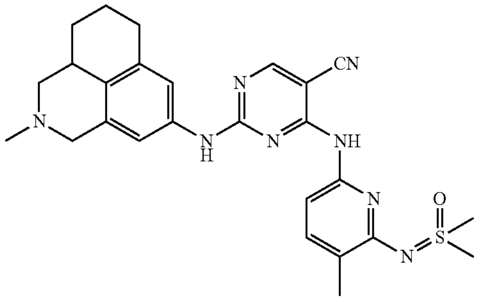
and
296
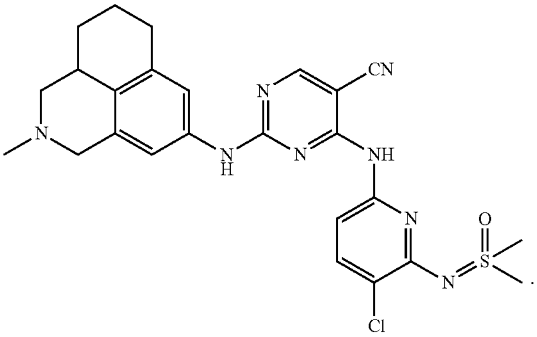
.
* * * * *